(12) United States Patent
Lotvin et al.

(10) Patent No.: US 8,247,211 B2
(45) Date of Patent: Aug. 21, 2012

(54) GLYCOPEPTIDE ANTIBIOTICS

(75) Inventors: Jason Arnold Lotvin, Union, NJ (US); Mark Edward Ruppen, Garnerville, NY (US)

(73) Assignees: American Cyanamid Company, Madison, NJ (US); Wyeth Holdings Corporation, Madison, NJ (US)

(*) Notice: Subject to any disclaimer, the term of this patent is extended or adjusted under 35 U.S.C. 154(b) by 0 days.

(21) Appl. No.: 13/022,764

(22) Filed: Feb. 8, 2011

(65) Prior Publication Data

US 2011/0151546 A1 Jun. 23, 2011

Related U.S. Application Data

(60) Continuation of application No. 11/116,149, filed on Apr. 27, 2005, now abandoned, which is a division of application No. 10/131,847, filed on Apr. 25, 2002, now Pat. No. 6,964,860.

(60) Provisional application No. 60/286,396, filed on Apr. 25, 2001, provisional application No. 60/286,249, filed on Apr. 25, 2001, provisional application No. 60/286,244, filed on Apr. 25, 2001.

(51) Int. Cl.
*C12N 1/20* (2006.01)

(52) U.S. Cl. .................. 435/252.35; 435/253.5

(58) Field of Classification Search .............. 435/252.35, 435/253.5
See application file for complete search history.

(56) References Cited

U.S. PATENT DOCUMENTS

| 3,495,004 | A | 2/1970 | De Voe et al. |
| 6,521,429 | B2 | 2/2003 | Honma et al. |
| 6,713,448 | B2 | 3/2004 | Carter et al. |
| 6,964,860 | B2 | 11/2005 | Abbanat et al. |

OTHER PUBLICATIONS

Berge et al., "Pharmaceutical Salts", Journal of Pharmaceutical Sciences, 66(1):1-19, 1977.
Zabriskie et al., Traders' Guide to Fermentation Media Formulation, 1980, Cottonseed Flour, Traders Oil Mill Co., Fort Worth, TX, pp. 50-51.
Cote et al., "ATCC Agar Medium #172", ATCC Media Handbook, First edition, American Type Culture Collection, Rockville, MD, 1984.
Larock, "6. From Nitro Compounds", Comprehensive Organic Transformations, VCH Publishers, pp. 411-415, 1989.
CDC (1993). "Nosocomial Enterococci Resistant to Vancomycin—United States, 1989-1993." MMWR (Morbidity and Mortality Weekly Report), 42(30):597-599. Centers for Disease Control and Prevention.
Handwerger et al., "Nosocomial Outbreak Due to *Enterococcus faecium* Highly Resistant to Vancomycin, Penicillin, and Gentamicin", Clinical Infectious Diseases, 16(6):750-755, 1993.
Boyle et al., "Epidemiologic Analysis and Genotypic Characterization of a Nosocomial Outbreak of Vancomycin-Resistant Enterococci", Journal of Clinical Microbiology, 31(5):1280-1285, 1993.
de Meijere and Meyer, "Fine Feathers Make Fine Birds: The Heck Reaction in Modern Garb", Angew. Chem. Int. Ed. Engl., 33:2379-2411, 1994.
Miyaura and Suzuki, "Palladium-Catalyzed Cross-Coupling Reactions of Organoboron Compounds", Chem. Rev., 95:2457-2483, 1995.
Farina and Roth, "Recent Advances in the Stille Reaction", Advances in Metal-Organic Chemistry, 5:1-53, 1996.
Smith et al., "Emergence of Vancomycin Resistance in *Staphylococcus aureus*", The New England Journal of Medicine, 340(7):493-501, 1999.
Waldvogel, "Editorials—New Resistance in *Staphylococcus aureus*", The New England Journal of Medicine, 340 (7):556-557, 1999.
Cetinkaya et al., "Vancomycin-Resistant Enterococci", Clinical Microbiology Reviews, 13(4):686-707, 2000.
Murray, "Vancomycin-Resistant Enterococcal Infections", The New England Journal of Medicine, 342(10):710-721, 2000.
National Committee for Clinical Laboratory Standards (NCCLS), "Methods for Dilution Antimicrobial Susceptibility Tests for Bacteria that Grow Aerobically—second edition"; Approved Standard, NCCLS Document M7-A2, Villanova, PA, vol. 10, No. 8, 1990.
PCT International Search Report, PCT/US02/13108, mailed Aug. 22, 2002.

*Primary Examiner* — Herbert J Lilling
(74) *Attorney, Agent, or Firm* — Martha A. Gammill

(57) ABSTRACT

The invention provides compounds of formula

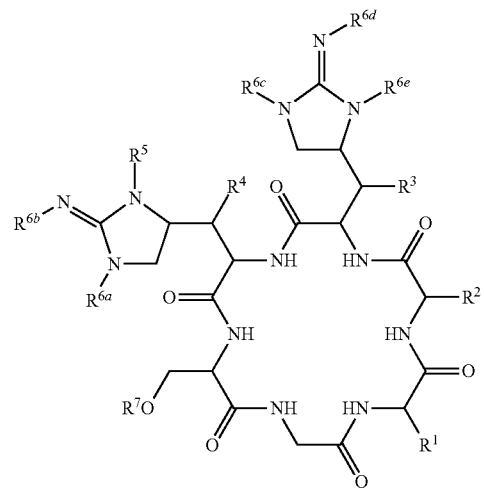

Wherein $R^1$, $R^2$, $R^3$, $R^4$, $R^5$, $R^{6a}$, $R^{6b}$, $R^{6c}$, $R^{6d}$, $R^{6e}$ and $R^7$ are defined in the specification. These compounds are useful as antibiotic agents.

17 Claims, No Drawings

GLYCOPEPTIDE ANTIBIOTICS

CROSS REFERENCE TO RELATED APPLICATIONS

This application is a continuation of U.S. Ser. No. 11/116,149 filed Apr. 27, 2005, which is a divisional of U.S. Ser. No. 10/131,847 filed Apr. 25, 2002, now U.S. Pat. No. 6,964,860 granted Nov. 15, 2005, which claims priority from provisional application Ser. No. 60/286,396 filed on Apr. 25, 2001, provisional application Ser. No. 60/286,249 filed on April 25, 2001 and provisional application Ser. No. 60/286,244 filed on Apr. 25, 2001 all incorporated herein by reference.

FIELD OF THE INVENTION

The present invention relates to novel glycopeptides, which are useful as antibiotics.

BACKGROUND OF THE INVENTION

New improved antibiotics are continually in demand, for the treatment of human diseases. Antibiotic resistant organisms are continually a problem, particularly in hospitals. Vancomycin has been the last defense. However, especially in hospitals, isolates which are vancomycin resistant are becoming more'common. A recent survey found 7.9% of Enterococci in United States hospitals are now vancomycin resistant. "Nosocomial Enterococci Resistant to Vancomycin" Morbidity and Mortality Weekly Report 42(30):597-598 (1993). Further resistance of Vancomycin and other antibiotics to *Enterococcus faecium* is reported, Handwergers. et al., Clin. Infect. Dis. 1993(16), 750-755. Additional resistance to enterococci is reported, Boyle, J F, Clin. Microbiol. 1993(31), 1280-1285. Vancomycin resistance has been reported against *Staphylococcus aureus*, F. A. Waldvogel, The New England Journal of Medicine, 340(7), 1999. Additional reports include: Murry, B. E. The New England Journal of Medicine, 342(10), 710-721 (2000) and Y. Cetinkaya et al, Clinical Microbiology Reviews, 13(4) 686-707 (2000). Clearly, antibiotic resistance is a growing public health problem. Having new antibiotics available could provide additional options for physicians in treatment regimens.

The search for new antibiotics which exhibit improved antibacterial activity against vancomycin-resistant isolates and having structures which are not derivatives of vancomycin are particularly appealing targets for screening and synthetic efforts. Structural similarity to existing antibiotics could facilitate the emergence of resistance.

The AC98-antibiotic complex isolated as an unseparated mixture of compounds of undetermined structure produced from cultures of *Streptomyces hygroscopicus* (strain NRRL 3085) is described in U.S. Pat. No. 3,495,004. It is an object of this invention to provide a novel family of glycopeptide antibiotics which are shown to possess antibacterial activity, especially against vancomycin resistant bacterial isolates and in particular having chemical structures unlike vancomycin.

SUMMARY OF THE INVENTION

This invention is concerned with novel glycopeptides which have antibacterial activity; with methods of treating infectious disease in mammals employing these novel glycopeptides; with pharmaceutical preparations containing these glycopeptides and processes for the production of glycopeptides of the invention. More particularly, this invention is concerned with glycopeptides which have enhanced antibacterial activity against vancomycin, penicillin and methicillin resistant strains. Compounds according to the invention comprise compounds of the formula:

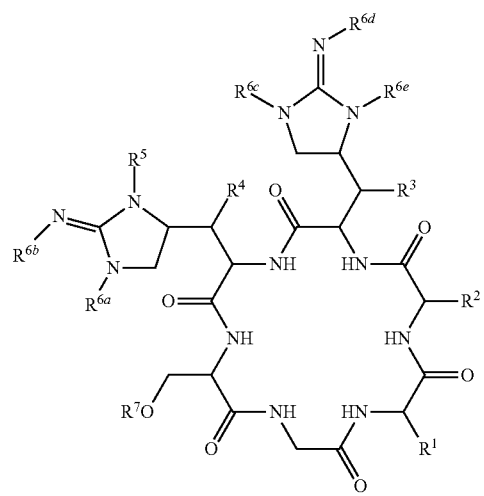

wherein:
$R^1$ is a moiety selected from:

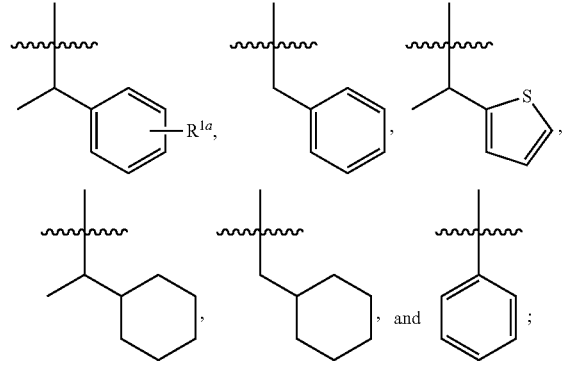

$R^{1a}$ is H or halogen;
$R^2$ is a moiety selected from:

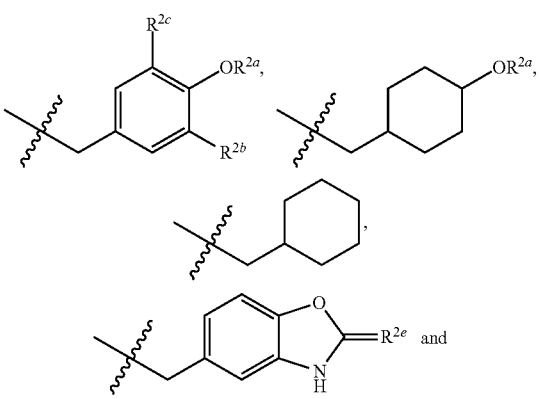

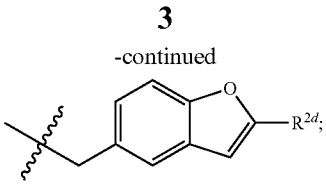

provided when R² is selected from the moieties:

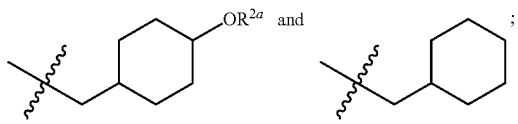

that R¹ is selected from the moieties:

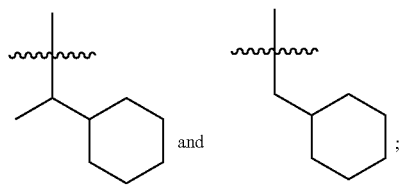

$R^{2a}$ is selected from H, alkyl($C_1$-$C_{20}$), cycloalkyl($C_3$-$C_{20}$), alkenyl($C_3$-$C_{20}$), alkynyl($C_3$-$C_{20}$), the group —C(O)—Y—Z, and a moiety selected from:

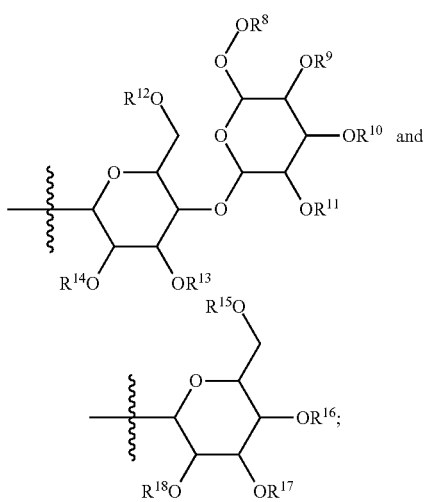

Y is selected from a single bond, —O— and —$NR^{8a}$—;

Z is selected from alkyl($C_1$-$C_{20}$), cycloalkyl($C_3$-$C_{20}$), alkenyl($C_3$-$C_{20}$), alkynyl($C_3$-$C_{20}$), aryl and heteroaryl;

and when Y is a single bond then Z is also selected from H, alkenyl($C_2$-$C_{20}$) and alkynyl ($C_2$-$C_{20}$);

$R^{2b}$ and $R^{2c}$ are independently selected from H, halogen, alkyl($C_1$-$C_{20}$), cycloalkyl($C_3$-$C_{20}$), alkenyl($C_2$-$C_{20}$), alkynyl($C_2$—$C_{20}$), aryl, heteroaryl, —$NH_2$, —$NR^{2f}R^{2g}$, and —$NO_2$, provided when $R^{2b}$ is —$NO_2$, that $R^{2c}$ must be H;

$R^{2d}$ is selected from alkyl ($C_1$-$C_{20}$), alkenyl($C_2$-$C_{20}$), alkynyl ($C_2$-$C_{20}$), aryl, heteroaryl, and when R² is

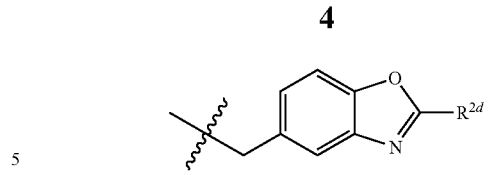

$R^{2d}$ may also be the group L-M, wherein;

L is selected from —NH—, —S—, —$SCH_2C(O)$—, and a group of the formula:

M is selected from alkyl($C_1$-$C_{20}$), cycloalkyl($C_3$-$C_{20}$), alkenyl($C_3$-$C_{20}$) and alkynyl($C_3$-$C_{20}$);

and when:

a) L is not —S—, M may also be aryl or heteroaryl;
b) L is —$SCH_2C(O)$—, M may also be H, alkenyl($C_2$-$C_{20}$) or alkynyl($C_2$-$C_{20}$); or
c) L is —NH— or a group of the formula:

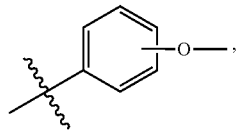

M may also be a moiety of the formula:

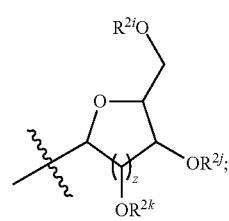

z is an integer of 1 or 2;

$R^{2i}$, $R^{2j}$ and $R^{2k}$ are independently selected from H, alkyl($C_1$-$C_{20}$), cycloalkyl($C_3$-$C_{20}$), alkenyl($C_3$-$C_{20}$), alkynyl($C_3$-$C_{20}$), acyl, —Si(alkyl($C_1$-$C_{20}$))$_3$, —Si(alkyl($C_1$-$C_{20}$))$_2$(aryl), —Si(alkyl($C_1$-$C_{20}$))(aryl)$_2$, —Si(aryl)$_3$, and aroyl;

$R^{2e}$ is S or O;

$R^{2f}$ is selected from H, alkyl($C_1$-$C_{20}$), cycloalkyl($C_3$-$C_{20}$), alkenyl($C_3$-$C_{20}$), alkynyl($C_3$-$C_{20}$), aryl and heteroaryl;

$R^{2g}$ is H, alkyl($C_1$-$C_{20}$), cycloalkyl($C_3$-$C_{20}$), alkenyl($C_3$-$C_{20}$), alkynyl($C_3$-$C_{20}$), aryl and heteroaryl, and the group D-E-G, wherein;

D is selected from —C(O)—, —C(S)— and —$S(O)_2$—;

E is selected from a single bond, and, when D is —C(O)— or —C(S)—, E is also selected from —O— and —$NR^{2h}$—;

G is selected from alkyl($C_1$-$C_{20}$), cycloalkyl($C_3$-$C_{20}$), alkenyl($C_3$-$C_{20}$), alkynyl($C_3$-$C_{20}$), aryl and heteroaryl; and when:

a) E is a single bond, then G may also be alkenyl($C_2$-$C_{20}$) or alkynyl($C_2$-$C_{20}$); or
b) D is —C(O)— or —C(S)— and E is a single bond, then G may also be H;

$R^{2f}$ and $R^{2g}$ may optionally when taken together with the nitrogen atom to which each is attached form a monocyclic ring having three to seven atoms independently selected from the elements C, N, O and S where said monocyclic ring optionally contains up to three nitrogen atoms, up to two oxygen atoms and up to two sulfur atoms provided said monocyclic ring does not contain —O—O—, —S—S— or —S—O— bonds;

$R^{2h}$ is selected from H, alkyl($C_1$-$C_{20}$), cycloalkyl($C_3$-$C_{20}$), alkenyl($C_3$-$C_{20}$), alkynyl($C_3$-$C_{20}$), aryl and heteroaryl;

$R^{2h}$ and G may optionally when taken together with the nitrogen atom to which each is attached form a monocyclic ring having three to seven atoms independently selected from the elements C, N, O and S where said monocyclic ring optionally contains up to three nitrogen atoms, up to two oxygen atoms and up to two sulfur atoms provided said monocyclic ring does not contain —O—O—, —S—S— or —S—O— bonds;

$R^3$ and $R^4$ are independently H, OH, —Si(alkyl($C_1$-$C_{20}$))$_3$, —Si(alkyl($C_1$-$C_{20}$))$_2$(aryl), —Si(alkyl($C_1$-$C_{20}$)(aryl)$_2$, —Si(aryl)$_3$ or the group —C(O)—Y—Z;

$R^5$ is selected from H, alkyl($C_1$-$C_{20}$), cycloalkyl($C_3$-$C_{20}$), alkenyl($C_3$-$C_{20}$), alkynyl($C_3$-$C_{20}$), the group —C(O)—Y—Z and moieties of the formulae;

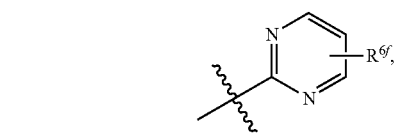

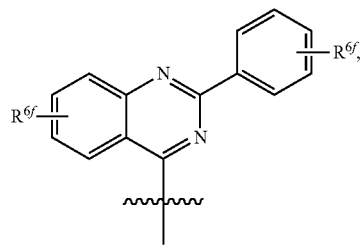

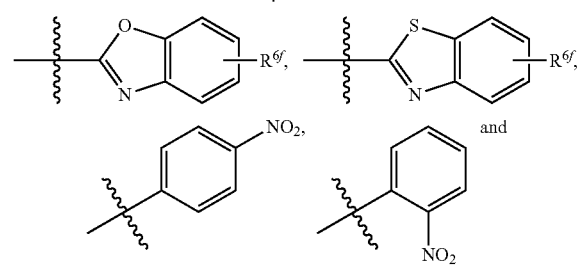

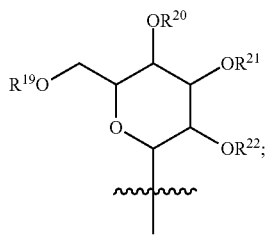

$R^{6a}, R^{6b}, R^{6c}, R^{6d}$ and $R^{6e}$ are independently selected from H, alkyl($C_1$-$C_{20}$), cycloalkyl($C_3$-$C_{20}$), alkenyl($C_3$-$C_{20}$), alkynyl($C_3$-$C_{20}$), the group —C(O)—Y—Z and moieties of the formulae;

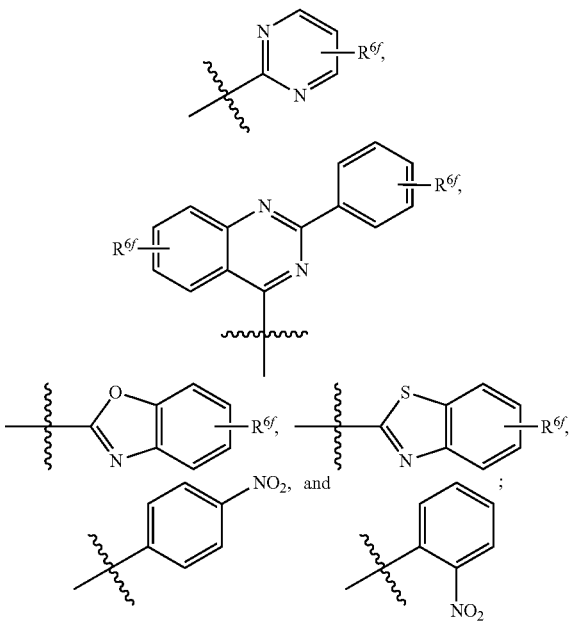

$R^{6f}$ is selected from H, alkyl($C_1$-$C_{20}$), cycloalkyl($C_3$-$C_{20}$), alkenyl($C_3$-$C_{20}$), alkynyl($C_3$-$C_{20}$), aryl, heteroaryl, halogen, hydroxy, alkoxy($C_1$-$C_{20}$), aryloxy, amino, monoalkyl ($C_1$-$C_{20}$)amino, dialkyl($C_1$-$C_{20}$)amino, carboxy, carboxyalkyl($C_1$-$C_{20}$), carboxyaryl and carboxyamido;

$R^7$ is selected from H, allyl($C_1$-$C_{20}$), cycloalkyl($C_3$-$C_{20}$), alkenyl($C_3$-$C_{20}$), alkynyl($C_3$-$C_{20}$), —Si (alkyl ($C_1$-$C_{20}$))$_3$, —Si (alkyl ($C_1$-$C_{20}$))$_2$(aryl), —Si(alkyl($C_1$-$C_{20}$)(aryl)$_2$, —Si(aryl)$_3$ and the group —C(O)—Y—Z;

$R^8, R^9, R^{10}, R^{11}, R^{12}, R^{13}, R^{14}, R^{15}, R^{16}, R^{17}, R^{18}, R^{19}, R^{20}, R^{21}$ and $R^{22}$ are independently selected from H, alkyl($C_1$-$C_{20}$), cycloalkyl($C_3$-$C_{20}$), alkenyl($C_3$-$C_{20}$), alkynyl($C_3$-$C_{20}$), —Si(alkyl($C_1$-$C_{20}$))$_3$, —Si(alkyl($C_1$-$C_{20}$))$_2$(aryl), —Si(alkyl($C_1$-$C_{20}$))(aryl)$_2$, —Si(aryl)$_3$ and the group —C(O)—Y—Z or, optionally, $R^8$ and $R^9$, $R^9$ and $R^{10}$, $R^{10}$ and $R^{11}$, $R^{13}$ and $R^{14}$, $R^{15}$ and $R^{16}$, $R^{16}$ and $R^{17}$, $R^{17}$ and $R^{18}$, $R^{19}$ and $R^{20}$, $R^{20}$ and $R^{21}$ or $R^{21}$ and $R^{22}$ may independently be taken together forming moieties of the formulae:

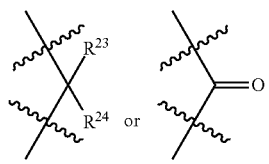

provided when;
a) $R^8$ and $R^9$ are so joined, $R^9$ and $R^{10}$ may not be so joined;
b) $R^9$ and $R^{10}$ are so joined, $R^8$ and $R^9$ and $R^{10}$ and $R^{11}$ may not be so joined;
c) $R^{15}$ and $R^{16}$ are so joined, $R^{16}$ and $R^{17}$ may not be so joined;
d) $R^{16}$ and $R^{17}$ are so joined, $R^{15}$ and $R^{16}$, $R^{17}$ and $R^{18}$ may not be so joined;
e) $R^{19}$ and $R^{20}$ are so joined, $R^{20}$ and $R^{21}$ may not be so joined;
f) $R^{20}$ and $R^{21}$ are so joined, $R^{19}$ and $R^{20}$, and $R^{21}$ and $R^{22}$ may not be so joined;

$R^{8a}$ is selected from H, alkyl($C_1$-$C_{20}$), cycloalkyl($C_3$-$C_{20}$), alkenyl($C_3$-$C_{20}$), alkynyl($C_3$-$C_{20}$), aryl and heteroaryl;

$R^{8a}$ and Z may optionally when taken together with the nitrogen atom to which each is attached form a monocyclic ring having three to seven atoms independently selected from the elements C, N, O and S where said monocyclic ring optionally contains up to three nitrogen atoms, up to two oxygen atoms and up to two sulfur atoms provided said monocyclic ring does not contain —O—O—, —S—S— or —S—O— bonds;

$R^{23}$ and $R^{24}$ are independently selected from H, alkyl($C_1$-$C_{20}$), cycloalkyl($C_3$-$C_{20}$), alkenyl($C_2$-$C_{20}$), alkynyl($C_2$-$C_{20}$), aryl, and heteroaryl;

$R^{23}$ and $R^{24}$ may optionally when taken together with the carbon atom to which each is attached form carbocyclic, monocyclic, fused, bridged, spirocyclic or polycyclic rings from three to twenty ring atoms optionally selected from the elements C, N, O and S where said monocyclic ring optionally contains up to three nitrogen atoms, up to two oxygen atoms and up to two sulfur atoms provided said monocyclic ring does not contain —O—O—, —S—S— or —S—O— bonds;

provided when:

$R^1$ is

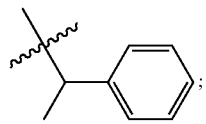

$R^3$ and $R^4$ are —OH;

$R^5$ is

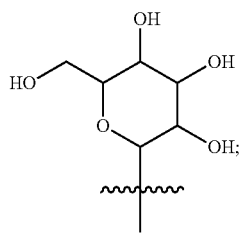

and $R^{2b}$, $R^{2c}$, $R^{6a}$, $R^{6b}$, $R^{6c}$, $R^{6d}$, $R^{6e}$, $R^7$, are H;

that:

$R^{2a}$ is not H or moieties selected from the formulae:

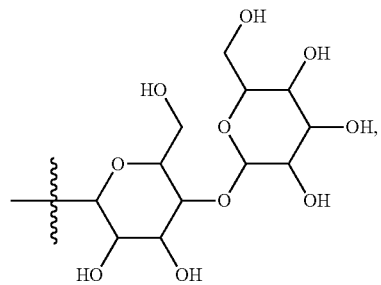

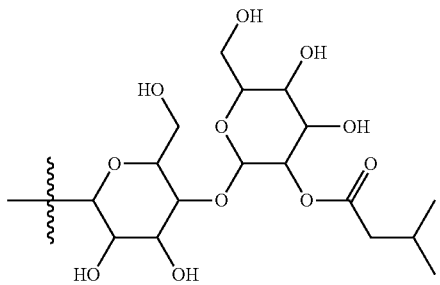

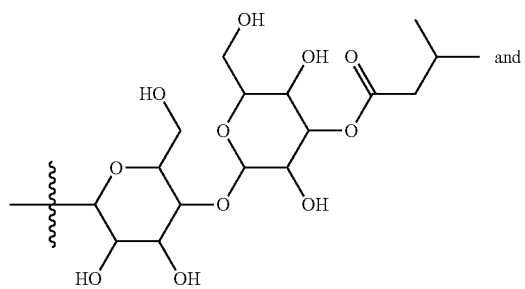

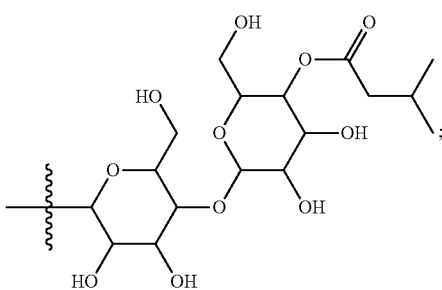

or a pharmaceutically acceptable salt thereof.

Among the preferred groups of compounds of this invention including pharmaceutically acceptable salts thereof are those in the subgroups below, wherein other variables are as defined above:

a)

$R_1$ is a moiety selected from the group:

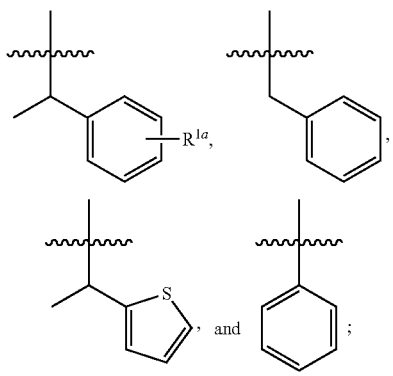

b)
 R$^1$ is a moiety of the formula:

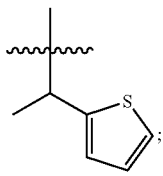

c)
 R$^1$ is a moiety selected from the group:

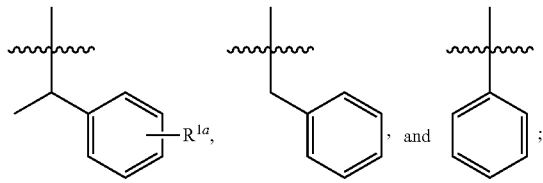

d)
 R$^1$ is a moiety selected from the group:

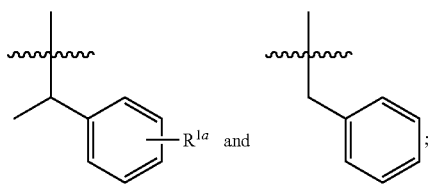

or
e)
 R$^1$ is a moiety selected from the group:

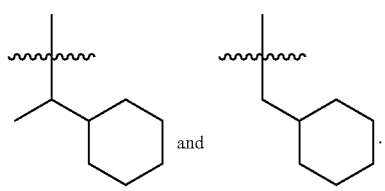

Also among the preferred groups of compounds of this invention including pharmaceutically acceptable salts thereof are those in the subgroups below, wherein other variables are as defined above:
a)
 R$^2$ is a moiety of the formula:

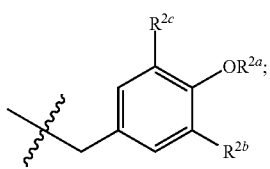

b)
 R$^2$ is a moiety of the formula:

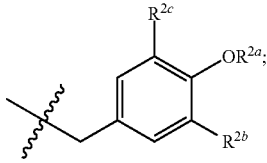

R$^{2b}$ is selected from —NH$_2$, and —NR$^{2f}$R$^{2g}$; and R$^{2c}$ is H;

c)
 R$^2$ is a moiety of the formula:

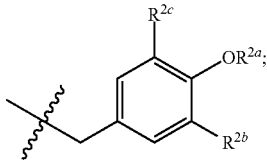

R$^{2a}$ is H;
R$^{2b}$ is selected from —NH$_2$, and —NR$^{2f}$R$^{2g}$; and R$^{2c}$ is H;

d)
 R$^2$ is a moiety of the formula:

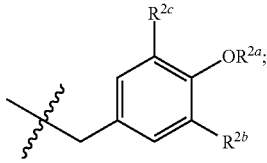

and
 R$^{2b}$ and R$^{2c}$ are independently selected from H, halogen, alkyl(C$_1$-C$_{20}$), cycloalkyl(C$_3$-C$_{20}$), alkenyl(C$_2$-C$_{20}$), alkynyl (C$_2$-C$_{20}$), aryl and heteroaryl;

e)
 R$^2$ is a moiety of the formula:

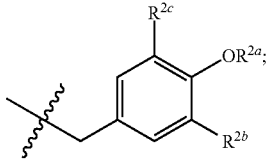

and
 R$^{2b}$ and R$^{2c}$ are independently selected from H and halogen;

f)
 R$^2$ is a moiety of the formula:

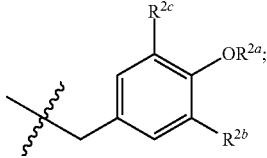

$R^{2a}$ is a moiety of the formula:

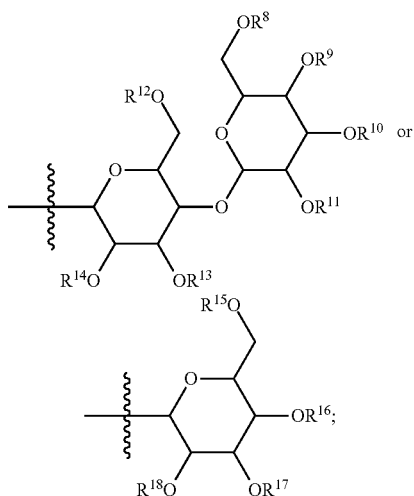

and $R^{2b}$ and $R^{2c}$ are independently selected from H and halogen;

g)

$R^2$ is a moiety selected from the group:

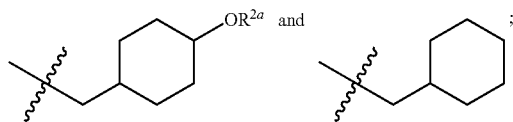

h)

$R^2$ is a moiety of the formula:

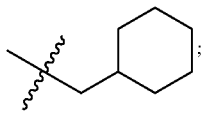

or i)

$R^2$ is a moiety selected from the group:

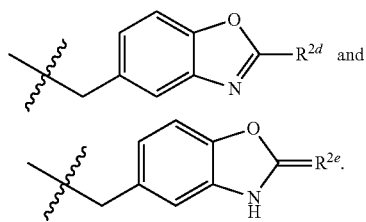

Additionally preferred groups of compounds of this invention including pharmaceutically acceptable salts thereof are those in the subgroups below, wherein other variables are as defined above:

a)
$R^3$ and $R^4$ are independently selected from H and OH; or b)
$R^3$ and $R^4$ are OH.

Another preferred group of compounds of this invention including pharmaceutically acceptable salts thereof are those in the subgroup below, wherein other variables are as defined above:

$R^5$ is selected from H or a moiety of the formula:

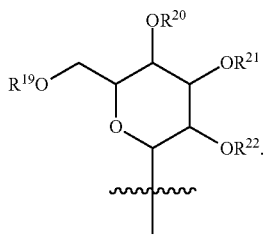

Also among the preferred groups of compounds of this invention including pharmaceutically acceptable salts thereof are those in the subgroups below, wherein other variables are as defined above:

a)
$R^{6a}$, $R^{6b}$, $R^{6c}$, $R^{6d}$ and $R^{6e}$ are independently selected from H, alkyl($C_1$-$C_{20}$), cycloalkyl($C_3$-$C_{20}$), alkenyl($C_3$-$C_{20}$) and alkynyl($C_3$-$C_{20}$);

b)
$R^{6a}$, $R^{6b}$, $R^{6c}$, $R^{6d}$ and $R^{6e}$ are independently selected from H and moieties of the formulae:

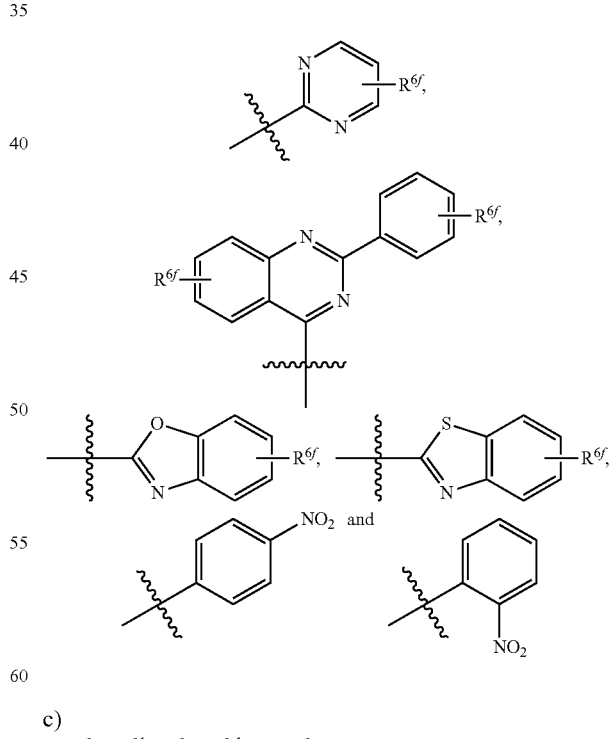

c)
$R^{6a}$, $R^{6b}$, $R^{6c}$, $R^{6d}$ and $R^{6e}$ are H.

Preferred groups of compounds of this invention including pharmaceutically acceptable salts thereof are those in the subgroups below, wherein other variables are as defined above:

a)
  $R^7$ is H; and/or
b)
  $R^7$ is —C(O)—Y—Z; and/or
c)
  $R^7$ is alkyl($C_1$-$C_{20}$), cycloalkyl($C_3$-$C_{20}$), alkenyl($C_3$-$C_{20}$) and alkynyl($C_3$-$C_{20}$).

Also among the preferred groups of compounds of this invention including pharmaceutically acceptable salts thereof are those in the subgroups below, wherein other variables are as defined above:

a)
  $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are independently selected from H and —C(O)—Y—Z;

b)
  $R^{13}$, $R^{14}$, $R_{19}$, $R^{20}$, $R^{21}$ and $R^{22}$ are H;
  $R^8$, $R^9$, $R^{10}$, $R^{11}$, $R^{12}$, $R^{15}$, $R^{16}$, $R^{17}$ and $R^{18}$ are independently selected from H and —C(O)—Y—Z;

c)
  $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are independently selected from H, allyl($C_1$-$C_{20}$), cycloalkyl($C_3$-$C_{20}$), alkenyl($C_3$-$C_{20}$) and alkynyl($C_3$-$C_{20}$);

d)
  $R^{13}$, $R^{14}$, $R^{19}$, $R^{20}$, $R^{21}$ and $R^{22}$ are H;
  $R^8$, $R^9$, $R^{10}$, $R^{11}$, $R^{12}$, $R^{15}$, $R^{16}$, $R^{17}$ and $R^{18}$ are independently selected from H, alkyl($C_1$-$C_{20}$), cycloalkyl($C_3$-$C_{20}$), alkenyl($C_3$-$C_{20}$) and alkynyl($C_3$-$C_{20}$);

e)
  $R^8$ and $R^9$, $R^9$ and $R^{10}$, $R^{10}$ and $R^{11}$, $R^{13}$ and $R^{14}$, $R^{15}$ and $R^{16}$, $R^{16}$ and $R^{17}$, $R^{17}$ and $R^{18}$, $R^{19}$ and $R^{20}$, $R^{20}$ and $R^{21}$ or $R^{21}$ and $R^{22}$ may independently be joined forming a moiety of the formula:

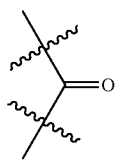

provided when;
  i) $R^8$ and $R^9$ are so joined, $R^9$ and $R^{10}$ may not be so joined;
  ii) $R^9$ and $R^{10}$ are so joined, $R^{10}$ and $R^{11}$ and $R^8$ and $R^9$ may not be so joined;
  iii) $R^{15}$ and $R^{16}$ are so joined, $R^{16}$ and $R^{17}$ may not be so joined;
  iv) $R^{16}$ and $R^{17}$ are so joined, $R^{15}$ and $R^{16}$ and $R^{17}$ and $R^{18}$ may not be so joined;
  v) $R^{19}$ and $R^{20}$ are so joined, $R^{20}$ and $R^{21}$ may not be so joined;
  vi) $R^{20}$ and $R^{21}$ are so joined, $R^{19}$ and $R^{20}$ and $R^{21}$ and $R^{22}$ may not be so joined;

f)
  $R^{12}$, $R^{13}$, $R^{14}$, $R^{19}$, $R^{20}$, $R^{21}$, and $R^{22}$ are H;
  $R^8$ and $R^9$, $R^9$ and $R^{10}$, $R^{10}$ and $R^{11}$, $R^{15}$ and $R^{16}$, $R^{16}$ and $R^{17}$ or $R^{17}$ and $R^{18}$ may independently be joined forming a moiety of the formula:

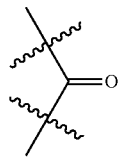

provided when;
  i) $R^8$ and $R^9$ are so joined, $R^9$ and $R^{10}$ may not be so joined;
  ii) $R^9$ and $R^{10}$ are so joined, $R^8$ and $R^9$ and $R^{10}$ and $R^{11}$ may not be so joined;
  iii) $R^{15}$ and $R^{16}$ are so joined, $R^{16}$ and $R^{17}$ may not be so joined;
  iv) $R^{16}$ and $R^{17}$ are so joined, $R^{15}$ and $R^{16}$ and $R^{17}$ and $R^{18}$ may not be so joined;

g)
  $R^8$ and $R^9$, $R^9$ and $R^{10}$, $R^{10}$ and $R^{11}$, $R^{13}$ and $R^{14}$, $R^{15}$ and $R^{16}$, $R^{16}$ and $R^{17}$, $R^{17}$ and $R^{18}$, $R^{19}$ and $R^{20}$, $R^{20}$ and $R^{21}$ or $R^{21}$ and $R^{22}$ may independently be joined forming a moiety of the formula:

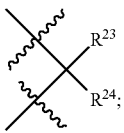

provided when;
  i) $R^8$ and $R^9$ are so joined, $R^9$ and $R^{10}$ may not be so joined;
  ii) $R^9$ and $R^{10}$ are so joined, $R^8$ and $R^9$ and $R^{10}$ and $R^{11}$ may not be so joined;
  iii) $R^{15}$ and $R^{16}$ are so joined, $R^{16}$ and $R^{17}$ may not be so joined;
  iv) $R^{16}$ and $R^{17}$ are so joined, $R^{15}$ and $R^{16}$ and $R^{17}$ and $R^{18}$ may not be so joined;
  v) $R^{19}$ and $R^{20}$ are so joined, $R^{20}$ and $R^{21}$ may not be so joined;
  vi) $R^{20}$ and $R^{21}$ are so joined, $R^{19}$ and $R^{20}$ and $R^{21}$ and $R^{22}$ may not be so joined;

h)
  $R^{12}$, $R^{13}$, $R^{14}$, $R^{19}$, $R^{20}$, $R^{21}$, and $R^{22}$ are H;
  $R^8$ and $R^9$, $R^9$ and $R^{10}$, $R^{10}$ and $R^{11}$, $R^{15}$ and $R^{16}$, $R^{16}$ and $R^{17}$ or $R^{17}$ and $R^{18}$ may independently be joined forming a moiety of the formula:

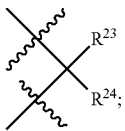

provided when;
  i) $R^8$ and $R^9$ are so joined, $R^9$ and $R^{10}$ may not be so joined;
  ii) $R^9$ and $R^{10}$ are so joined, $R^8$ and $R^9$ and $R^{10}$ and $R^{11}$ may not be so joined;
  iii) $R^{15}$ and $R^{16}$ are so joined, $R^{16}$ and $R^{17}$ may not be so joined;
  iv) $R^{16}$ and $R^{17}$ are so joined, $R^{15}$ and $R^{16}$ and $R^{17}$ and $R^{18}$ may not be so joined;
  and i)
  $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are H;

$R^8$ and $R^9$, $R^9$ and $R^{10}$ or $R^{10}$ and $R^{11}$ may independently be joined forming a moiety of the formula:

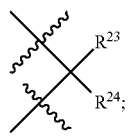

provided when;
i) $R^8$ and $R^9$ are so joined, $R^9$ and $R^{10}$ may not be so joined;
ii) $R^9$ and $R^{10}$ are so joined, $R^8$ and $R^9$ and $R^{10}$ and $R^{11}$ may not be so joined;

Among the most preferred groups of compounds of this invention including pharmaceutically acceptable salts thereof are those in the subgroups below, wherein other variables are as defined above:

a)
$R^1$ is a moiety selected from the group:

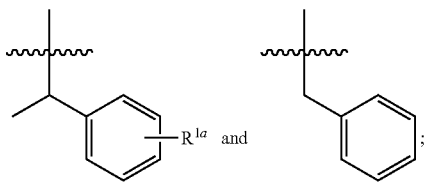

$R^2$ is a moiety of the formula:

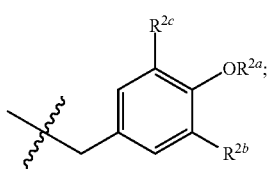

$R^{2a}$ is a moiety of the formula:

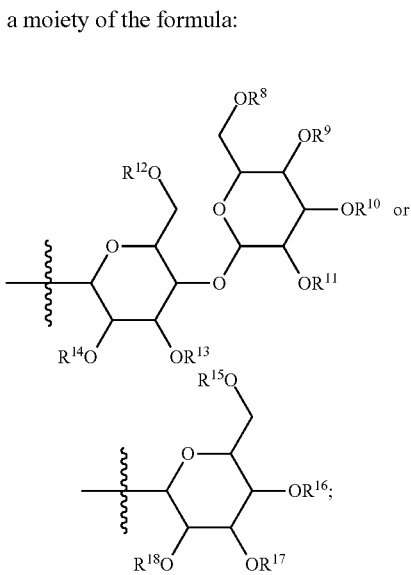

$R^{2b}$ and $R^{2c}$ are H;
$R^3$ and $R^4$ are independently H or OH;
$R^5$ is a moiety of the formula:

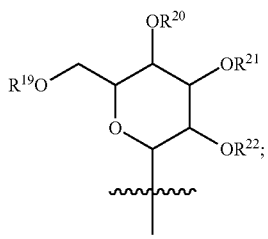

$R^{6a}$, $R^{6b}$, $R^{6c}$, $R^{6d}$ and $R^{6e}$ are H;
$R^7$ is H;
$R^{13}$, $R^{14}$, $R^{19}$, $R^{20}$, $R^{21}$ and $R^{22}$ are H; and
$R^8$; $R^9$, $R^{10}$, $R^{11}$; $R^{12}$, $R^{15}$, $R^{16}$, $R^{17}$ and $R^{18}$ are independently selected from H and —C(O)—Y—Z;

b)
$R^1$ is a moiety selected from the group:

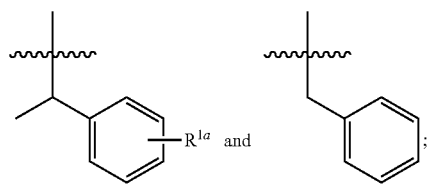

$R^2$ is a moiety of the formula:

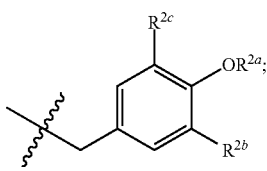

$R^{2a}$ is a moiety of the formula:

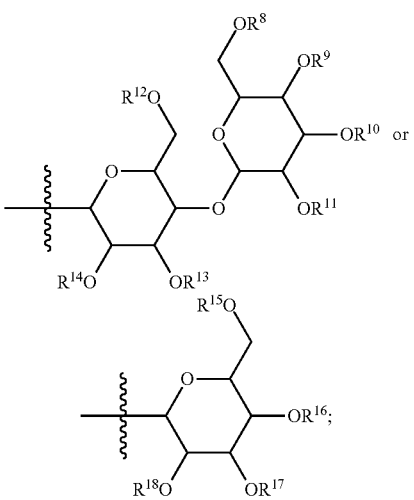

$R^{2b}$ and $R^{2c}$ are H;
$R^3$ and $R^4$ are independently H or OH;
$R^5$ is a moiety of the formula:

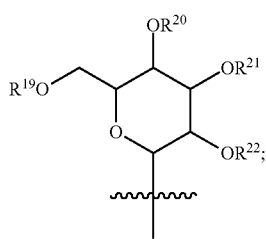

$R^{6a}$, $R^{6b}$, $R^{6c}$, $R^{6d}$ and $R^{6e}$ are H;
$R^7$ is H;
$R^{13}$, $R^{14}$, $R^{19}$, $R^{20}$, $R^{21}$ and $R^{22}$ are H; and
$R^8$, $R^9$, $R^{10}$, $R^{11}$, $R^{12}$, $R^{15}$, $R^{16}$, $R^{17}$ and $R^{18}$ are independently selected from H, alkyl($C_1$-$C_{20}$), cycloalkyl($C_3$-$C_{20}$), alkenyl($C_3$-$C_{20}$) and alkynyl($C_3$-$C_{20}$);

c)
$R^1$ is a moiety selected from the group:

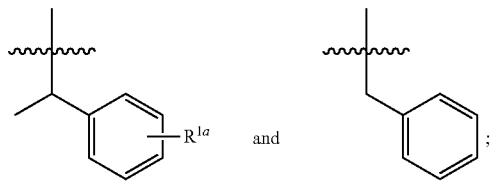

$R^2$ is a moiety of the formula:

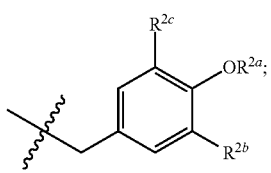

$R^{2a}$ is a moiety of the formula:

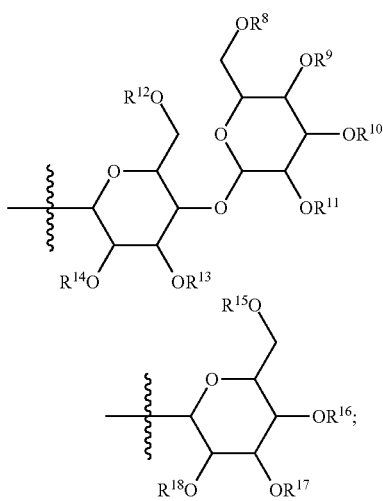

$R^{2b}$ and $R^{2c}$ are H;
$R^3$ and $R^4$ are independently H or OH;

$R^5$ is a moiety of the formula:

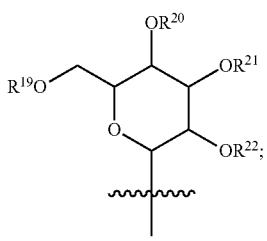

$R^{6a}$, $R^{6b}$, $R^{6c}$, $R^{6d}$ and $R^{6e}$ are H;
$R^7$ is H;
$R^{12}$, $R^{13}$, $R^{14}$, $R^{19}$, $R^{20}$, $R^{21}$ and $R^{22}$ are H;
$R^8$ and $R^9$, $R^9$ and $R^{10}$, $R^{10}$ and $R^{11}$, $R^{15}$ and $R^{16}$, $R^{16}$ and $R^{17}$ or $R^{17}$ and $R^{18}$ may independently be joined forming a moiety of the formula:

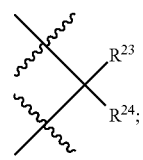

provided when;
i) $R^8$ and $R^9$ are so joined, $R^9$ and $R^{10}$ may not be so joined;
ii) $R^9$ and $R^{10}$ are so joined, $R^8$ and $R^9$ and $R^{10}$ and $R^{11}$ may not be so joined;
iii) $R^{15}$ and $R^{16}$ are so joined, $R^{16}$ and $R^{17}$ may not be so joined;
iv) $R^{16}$ and $R^{17}$ are so joined, $R^{15}$ and $R^{16}$ and $R^{17}$ and $R^{18}$ may not be so joined;

d)
$R^1$ is a moiety selected from the group:

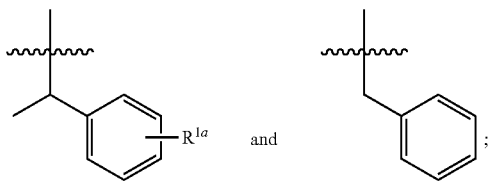

$R^2$ is a moiety of the formula:

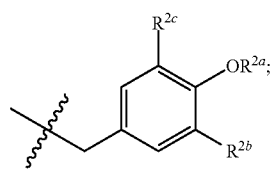

19

$R^{2a}$ is a moiety of the formula:

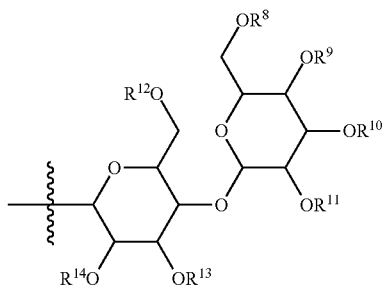

$R^{2b}$ and $R^{2c}$ are H;
$R^3$ and $R^4$ are independently H or OH;
$R^5$ is a moiety of the formula:

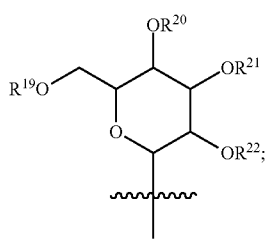

$R^{6a}$, $R^{6b}$, $R^{6c}$, $R^{6d}$ and $R^{6e}$ are H;
$R^7$ is H;
$R^{12}$, $R^{13}$, $R^{14}$, $R^{19}$, $R^{20}$, $R^{21}$ and $R^{22}$ are H;
$R^8$ and $R^9$, $R^9$ and $R^{10}$ or $R^{10}$ and $R^{11}$ may independently be joined forming a moiety of the forla:

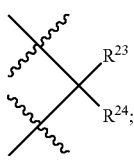

provided when;
i) $R^8$ and $R^9$ are so joined, $R^9$ and $R^{10}$ may not be so joined;
ii) $R^9$ and $R^{10}$ are so joined, $R^8$ and $R^9$ and $R^{10}$ and $R^{11}$ may not be so joined;
e)
$R^1$ is a moiety selected from the group:

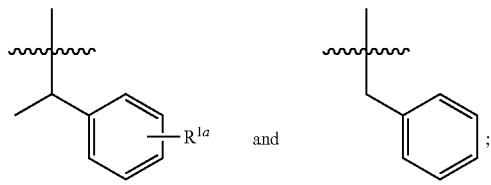

20

$R^2$ is a moiety of the formula:

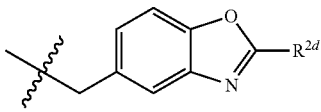

$R^3$ and $R^4$ are independently H or OH;
$R^5$ is H or a moiety of the formula:

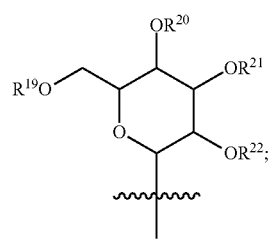

$R^{19}$, $R^{20}$, $R^{21}$ and $R^{22}$ are H;
f)
$R^1$ is a moiety selected from the group:

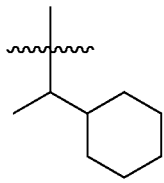 and 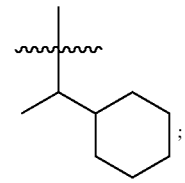;

$R^2$ is a moiety of the formula:

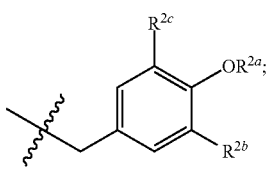

$R^{2a}$ is a moiety of the formula:

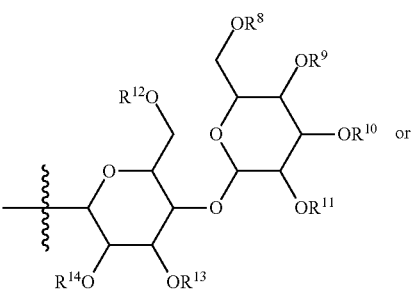

-continued

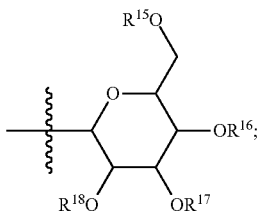

$R^{2b}$ and $R^{2c}$ are H;
$R^3$ and $R^4$ are independently H or OH;
$R^5$ is a moiety of the formula:

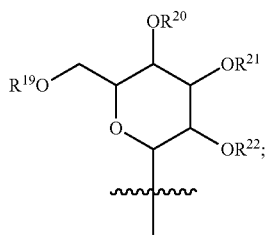

$R^{6a}$, $R^{6b}$, $R^{6c}$, $R^{6d}$ and $R^{6e}$ are H;
$R^7$ is H;
$R^{13}$, $R^{14}$, $R^{19}$, $R^{20}$, $R^{21}$ and $R^{22}$ are H; and
$R^8$, $R^9$, $R^{10}$ $R^{11}$, $R^{12}$, $R^{15}$, $R^{16}$, $R^{17}$ and $R^{18}$ are independently selected from H and —C(O)—Y—Z;

g)
$R^1$ is a moiety selected from the group:

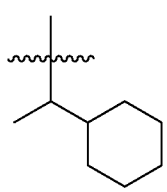 and 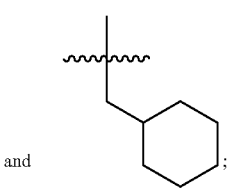;

$R^2$ is a moiety of the formula:

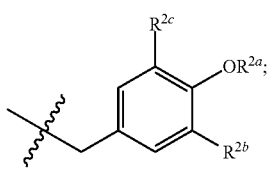

$R^{2a}$ is a moiety of the formula:

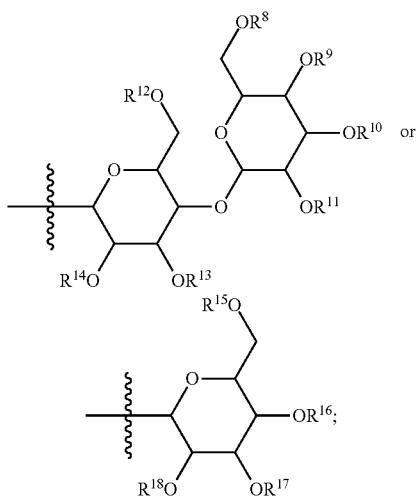

$R^{2b}$ and $R^{2c}$ are H;
$R^3$ and $R^4$ are independently H or OH;
$R^5$ is a moiety of the formula:

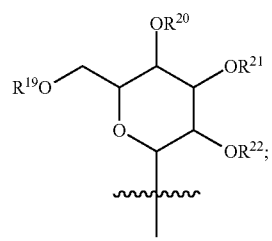

$R^{6a}$, $R^{6b}$, $R^{6c}$, $R^{6d}$ and $R^{6e}$ are H;
$R^7$ is H;
$R^{13}$, $R^{14}$, $R^{19}$, $R^{20}$, $R^{21}$ and $R^{22}$ are H; and
$R^8$, $R^9$, $R^{10}$, $R^{11}$, $R^{12}$, $R^{15}$, $R^{16}$, $R^{17}$ and $R^{18}$ are independently selected from H, alkyl($C_1$-$C_{20}$), cycloalkyl($C_3$-$C_{20}$), alkenyl($C_3$-$C_{20}$) and alkynyl($C_3$-$C_{20}$);

h)
$R^1$ is a moiety selected from the group:

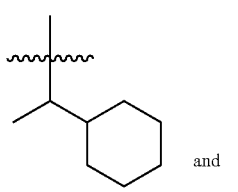 and 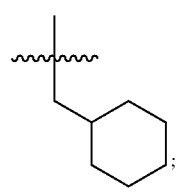;

$R^2$ is a moiety of the formula:

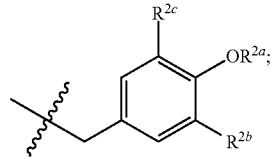

$R^{2a}$ is a moiety of the formula:

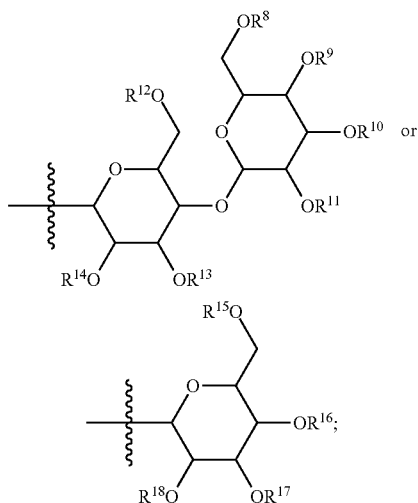

$R^{2b}$ and $R^{2c}$ are H;
$R^3$ and $R^4$ are independently H or OH;
$R^5$ is a moiety of the formula:

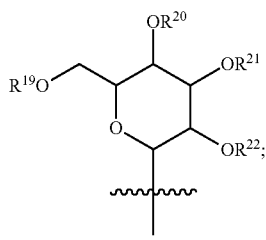

$R^{6a}$, $R^{6b}$, $R^{6c}$, $R^{6d}$ and $R^{6e}$ are H;
$R^7$ is H;
$R^{12}$, $R^{13}$, $R^{14}$, $R^{19}$, $R^{20}$, $R^{21}$ and $R^{22}$ are H;
$R^8$ and $R^9$, $R^9$ and $R^{10}$, $R^{10}$ and $R^{11}$, $R^{15}$ and $R^{16}$, $R^{16}$ and $R^{17}$ or $R^{17}$ and $R^{18}$ may independently be joined forming a moiety of the formula:

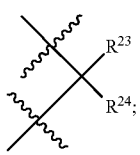

provided when;
i) $R^8$ and $R^9$ are so joined, $R^9$ and $R^{10}$ may not be so joined;
ii) $R^9$ and $R^{10}$ are so joined, $R^8$ and $R^9$ and $R^{10}$ and $R^{11}$ may not be so joined;
iii) $R^{15}$ and $R^{16}$ are so joined, $R^{16}$ and $R^{17}$ may not be so joined;
iv) $R^{16}$ and $R^{17}$ are so joined, $R^{15}$ and $R^{16}$ and $R^{17}$ and $R^{18}$ may not be so joined;

i)
$R^1$ is a moiety selected from the group:

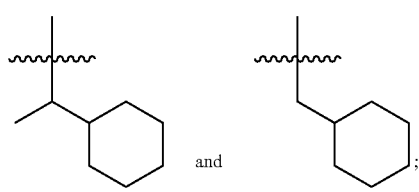

$R^2$ is a moiety of the formula:

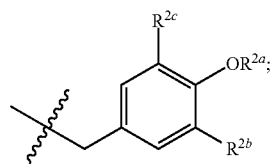

$R^{2a}$ is a moiety of the formula:

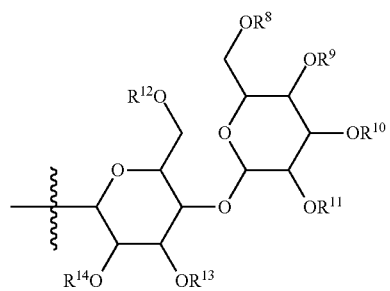

$R^{2b}$ and $R^{2c}$ are H;
$R^3$ and $R^4$ are independently H or OH;
$R^5$ is a moiety of the formula:

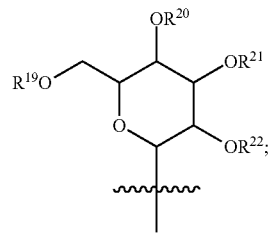

$R^{6a}$, $R^{6b}$, $R^{6c}$, $R^{6d}$ and $R^{6e}$ are H;
$R^7$ is H;
$R^{12}$, $R^{13}$, $R^{14}$, $R^{19}$, $R^{20}$, $R^{21}$, and $R^{22}$ are H;
$R^8$ and $R^9$, $R^9$ and $R^{10}$ or $R^{10}$ and $R^{11}$ may independently be joined forming a moiety of the formula:

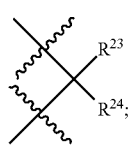

provided when;
i) $R^8$ and $R^9$ are so joined, $R^9$ and $R^{10}$ may not be so joined;
ii) $R^9$ and $R^{10}$ are so joined, $R^8$ and $R^9$ and $R^{10}$ and $R^{11}$ may not be so joined;

j)
$R^1$ is a moiety selected from the group:

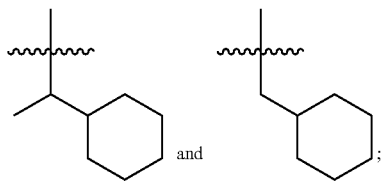

$R^2$ is a moiety of the formula:

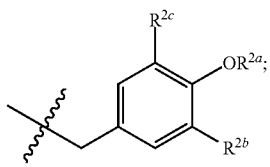

$R^{2a}$ is a moiety of the formula:

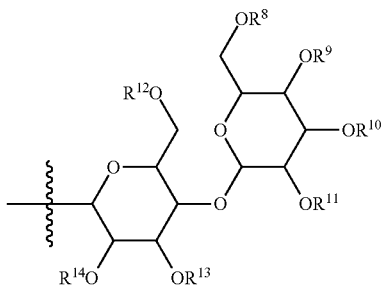

$R^{2b}$ $R^{2c}$ are H;
$R^3$ and $R^4$ are independently H or OH;
$R^5$ is a moiety of the formula:

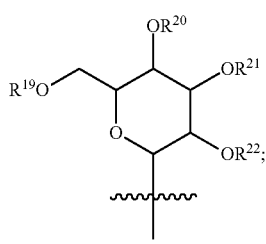

$R^{6a}$, $R^{6b}$, $R^{6c}$, $R^{6d}$ and $R^{6e}$ are H;
$R^7$ is H;
$R^{12}$, $R^{13}$, $R^{14}$, $R^{19}$, $R^{20}$, $R^{21}$, and $R^{22}$ are H;
$R^8$ and $R^9$, $R^9$ and $R^{10}$ or $R^{10}$ and $R^{11}$ may independently be joined forming a moiety of the formula:

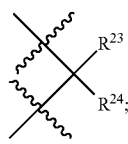

provided when;
i) $R^8$ and $R^9$ are so joined, $R^9$ and $R^{10}$ may not be so joined;
ii) $R^9$ and $R^{10}$ are so joined, $R^8$ and $R^9$ and $R^{10}$ and $R^{11}$ may not be so joined;
$R^{23}$ and $R^{24}$ when taken together with the carbon atom to which each is attached may optionally form carbocyclic, monocyclic, fused, bridged, spirocyclic or polycyclic rings of from three to twenty ring atoms;
provided when;
i) $R^8$ and $R^9$ are so joined, $R^9$ and $R^{10}$ may not be so joined;
ii) $R^9$ and $R^{10}$ are so joined, $R^8$ and $R^9$ and $R^{10}$ and $R^{11}$ may not be so joined;

k)
$R^1$ is a moiety selected from the group:

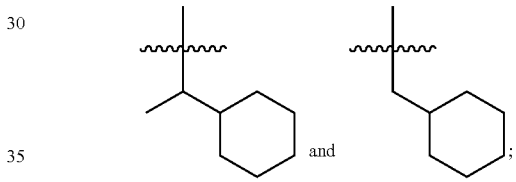

$R^2$ is a moiety of the formula:

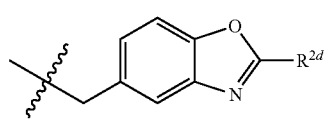

$R^3$ and $R^4$ are independently H or OH;
$R^5$ is H or a moiety of the formula:

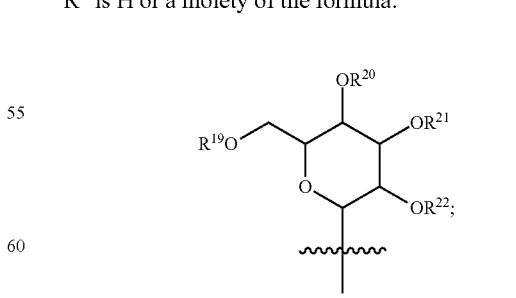

and
$R^{19}$, $R^{20}$, $R^{21}$ and $R^{22}$ are H;
and

1)
$R^1$ is a moiety selected from the group:

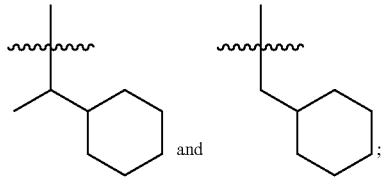

and ;

$R^2$ is a moiety of the formula:

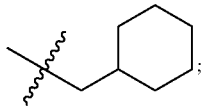

;

$R^3$ and $R^4$ are independently H or OH;
$R^5$ is H or a moiety of the formula:

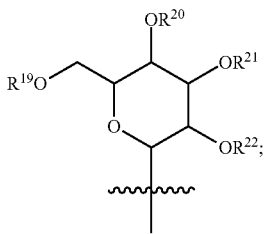

;

and
$R^{19}$, $R^{20}$, $R^{21}$ and $R^{22}$ are H.

Specifically preferred compounds of the invention are the following compounds or a pharmaceutically acceptable salt thereof:

Cyclo[glycyl-(S)-β-methyl-L-phenylalanyl-3-bromo-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-bromo-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-bromo-D-tyrosyl-3-(2-iminoimidazolidin-4-yl)-L-seryl-3-(2-imino-3α-mannopyranosylimidazolidin-4-yl)-D-seryl-L-seryl];

Cyclo[glycyl-β-methylphenylalanyl-3-bromotyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3,5-dibromo-D-tyrosyl-3-(2-iminoimidazolidin-4-yl)-L-seryl-3-(2-imino-3α-mannopyranosylimidazolidin-4-yl)-D-seryl-L-seryl];

Cyclo[glycyl-β-methylphenylalanyl-3,5-dibromotyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3,5-dibromo-D-tyrosyl-3-(2-iminoimidazolidin-4-yl)-L-seryl-3-(2-iminoimidazolidin-4-yl)-D-seryl-L-seryl];

Cyclo[glycyl-β-methylphenylalanyl-3,5-dibromotyrosyl-3-(2-iminoimidazolidin-4-yl)seryl-3-(2-iminoimidazolidin-4-yl)serylseryl];

Cyclo[glycyl-(S)-β-methyl-L-phenylalanyl-3-iodo-D-tyrosyl-3-(2-iminoimidazolidin-4-yl)-L-seryl-3-(2-imino-3α-mannopyranosylimidazolidin-4-yl)-D-seryl-L-seryl];

Cyclo[glycyl-β-methylphenylalanyl-3-iodotyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-iodo-O-(4-O-α-D-mannopyranosyl-α-D-mannopyranosyl)-D-tyrosyl-3-(2-iminoixnidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-(4-O-hexopyranosylhexopyranosyl)-3-iodo-tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3,5-diiodo-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-(4-O-hexopyranosylhexopyranosyl)-3,5-diiodo-tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-nitro-D-tyrosyl-3-(2-iminoimidazolidin-4-yl)-L-seryl-3-(2-imino-3α-mannopyranosylimidazolidin-4-yl)-D-seryl-L-seryl];

Cyclo[glycyl-β-methylphenylalanyl-3-nitrotyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-nitro-D-tyrosyl-3-(2-iminoimidazolidin-4-yl)-L-seryl-3-(2-iminoimidazolidin-4-yl)-D-seryl-L-seryl];

Cyclo[glycyl-β-methylphenylalanyl-3-nitrotyrosyl-3-(2-iminoimidazolidin-4-yl)seryl-3-(2-iminoimidazolidin-4-yl)serylseryl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-3-nitro-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-3-nitrotyrosyl];

Cyclo[glycyl-(S)-β-methyl-L-phenyl alanyl-3-amino-D-tyrosyl-3-(2-iminoimidazolidin-4-yl)-L-seryl-3-(2-imino-3α-mannopyranosylimidazolidin-4-yl)-D-seryl-L-seryl];

Cyclo[glycyl-β-methylphenylalanyl-3-aminotyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-(dimethylamino)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-(dimethylamino)tyrosyl-3-(2-iminoimidazolidin-4-yl)-seryl-3-(3-hexopyranosyl-2-iminoimidazolidin-4-yl)serylseryl];

Cyclo[glycyl-(S)-β-methyl-L-phenylalanyl-3-acetamido-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-acetamidotyrosyl-3-(2-iminoimidazolidin-4-yl)seryl-3-(3-hexopyranosyl-2-iminoimidazolodin-4-yl)serylseryl];

Cyclo[glycyl-(S)-β-methyl-L-phenylalanyl-3-(propanamido)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-(propanamido)tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-(2-methylpropanamido)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-(2-methylpropanamido)tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-(heptanamido)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-(heptanamido)tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-(benzamido)-D-tyrosyl-3-(2-iminoimidazoliclin-4-yl)-L-seryl-3-(2-imino-3-α-D-mannopyranosylimidazolidin-4-yl)-D-seryl-L-seryl];

Cyclo[glycyl-β-methylphenylalanyl-3-(benzamido)tyrosyl-3-(2-iminoimidazolidin-4-yl)seryl-3-(3-hexopyranosyl-2-iminoimidazolichn-4-yl)serylseryl];

Cyclo[glycyl-(S)-β-methyl-L-phenylalanyl-3-formamido-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-formamidotyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-[[(4-methylphenoxy)carbonyl]amino]-D-tyrosyl-3-(2-iminoimidazoliclin-4-yl)-L-seryl-3-(2-imino-3-α-D-mannopyranosylimidazolidin-4-yl)-D-seryl-L-seryl];

Cyclo[glycyl-β-methylphenylalanyl-3-[[(4-methylphenoxy)carbonyl]amino]tyrosyl-3-(2-iminoimidazolidin-4-yl)seryl-3-(3-hexopyranosyl-2-iminoimidazoliclin-4-yl)serylseryl];

Cyclo[glycyl-(S)-β-methyl-L-phenylalanyl-3-[(methoxycarbonyl)amino]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-[(methoxycarbonyl)amino)tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-[(phenylmethoxycarbonyl)amino]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-[(phenylmethoxycarbonyl)amino]tyrosyl-3-(2-iminoimidazolidin-4-yl)seryl-3-(3-hexopyranosyl-2-iminoimidazolidin-4-yl)serylseryl];

Cyclo[3-(2,3-dihydro-2-oxo-1,3-benzoxazol-5-yl)-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-(2,3-dihydro-2-oxo-1,3-benzoxazol-5-yl)alanyl-3-(2-iminoimidazolidin-4-yl)seryl-3-(3-hexopyranosyl-2-iminoimidazolidin-4-yl)serylserylglycyl-β-methylphenylalanyl];

Cyclo[3-(2,3-dihydro-2-thio-1,3-benzoxazol-5-yl)-D-alanyl-3-(2-iminoimidazolidin-4-yl)-L-seryl-3-(2-imino-3-α-D-mannopyranosylimidazolidin-4-yl)-D-seryl-L-serylglycyl-(S)-[1-methyl-L-phenylalanyl];

Cyclo[3-(2,3-dihydro-2-thio-1,3-benzoxazol-5-yl)alanyl-3-(2-iminoimidazolidin-4-yl)seryl-3-(3-hexopyranosyl-2-iminoimidazolidin-4-yl)serylserylglycyl-β-methylphenylalanyl];

Cyclo[glycyl-(S)-β-methyl-L-phenylalanyl-3-[[[3,5-bis(trifluoromethyl)phenyl]carbamothioyl]-amino]D-tyrosyl-3-(2-iminoimidazolidin-4-yl)-L-seryl-3-(2-imino-3-α-D-mannopyranosyl-imidazolidin-4-yl)-D-seryl-L-seryl];

Cyclo[glycyl-β-methylphenylalanyl-3-[[[3,5-bis(trifluoromethyl)phenyl]carbamothioyl]amino]-tyrosyl-3-(2-iminoimidazolidin-4-yl)seryl-3-(3-hexopyranosyl-2-iminoimidazolidin-4-yl)-serylseryl];

Cyclo[3-[2-(4-carboxyphenyl)-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-(4-carboxyphenyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl];

Cyclo[3-[2-(3-nitrophenyl)-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-(3-nitrophenyl)-1,3-benzoxazol-5-yl]alanyl-3-(2-iminoimidazolidin-4-yl)seryl-3-(3-hexopyranosyl-2-iminoimidazoliciin-4-yl)serylserylglycyl-β-methylphenylalanyl];

Cyclo[3-[2-(4-bromophenyl)-1,3-benzoxazol-5-yl]-D-alanyl-3-(2-iminoimirlazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-(4-bromophenyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl];

Cyclo[3-[2-β-(4-methylphenoxy)phen yl]-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-[3-(4-methylphenoxy)phenyl]-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenyl-alanyl];

Cyclo[3-[2-[4-(dimethylamino)phenyl]-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-[4-(dimethylamino)phenyl)-1,3-benzoxazol-5-yl]alanyl-3-(2-iminoimidazolidin-4-yl)-seryl-3-(3-hexopyranosyl-2-iminoimidazolidin-4-yl)serylserylglycyl-β-methylphenyl-alanyl];

Cyclo[3-[2-(3-fluorophenyl)-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-(3-fluorophenyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl];

Cyclo[3-[2-[4-(phen ylmethoxy)phen yl]-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-seryl glycyl-(S)-β-methyl-L-phenylalanyl];

Cyclo[3-[2-[4-(phenylmethoxy)phenyl]-1,3-benzoxazol-5-yl]alanyl-3-(2-iminoimidazolidin-4-yl)seryl-3-(3-hexopyranosyl-2-iminoimidazolidin-4-yl)serylserylglycyl-β-methyl-phenyl alanyl];

Cyclo[3-[2-(4-tert-butylphenyl)-1,3-benzoxazol-5-yl)-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-(4-tert-butyl phen yl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl];

Cyclo[3-[2-([1,1-biphenyl]-4-yl)-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-([1,1-biphenyl]-4-yl)-1,3-benzoxazol-5-yl]alanyl-3-(2-iminoimidazolidin-4-yl)-seryl-3-(3-hexopyranosyl-2-iminoimidazolidin-4-yl)serylserylglycyl-β-methylphenylalanyl];

Cyclo[3-[2-(3,4,5-trimethoxyphenyl)-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-(3,4,5-trimethoxyphenyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenyl-alanyl];

Cyclo[3-[2-β-(4-methoxyphenoxy)phenyl]-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(5)-β-methyl-L-phenylalanyl];

Cyclo[3-[2-β-(4-methoxyphenoxy)phenyl]-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenyl-alanyl];

Cyclo[3-[2-[2-(α-D-glucopyranosyloxy)phenyl]-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-[2-(hexopyranosyloxy)phenyl]-1,3-benzoxazol-5-yl]alanyl-3-(2-iminoimidazolidin-4-yl)seryl-3-(3-hexopyranosyl-2-iminoimidazolidin-4-yl)serylserylglycyl-β-methyl-phenylalanyl];

Cyclo[3-[2-(9H-fluororen-2-yl)-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-(9H-fluoren-2-yl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl];

Cyclo[3-[2-(3-furyl)-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-(3-furyl)-1,3-benzoxazol-5-y]lalanyl-3-(2-iminoimidazolidin-4-yl)seryl-3-(3-hexopyranosyl-2-iminoimidazolidin-4-yl)serylserylglycyl-β-methylphenylalanyl];

Cyclo[3-[2-(2,2-diphenylethenyl)-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-(2,2-diphenylethenyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl];

Cyclo[3-[2-(2-methylprop-1-en-1-yl)-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-(2-methylprop-1-en-1-yl)-1,3-benzoxazol-5-yl]alanyl-3-(2-iminoimidazoliclin-4-yl)seryl-3-(3-hexopyranosyl-2-iminoimidazolidin-4-yl)serylserylglycyl-β-methylphenyl-alanyl];

Cyclo[3-[2-β-(4-methylphenoxy)phenyl]-1,3-benzoxazol-5-yl]-D-alanyl-3-(2-iminoimidazolidin-4-yl)-L-seryl-3-(2-iminoimidazoliclin-4-yl)-D-seryl-L-serylglycyl-(S)-β-methyl-L-phenyl-alanyl];

Cyclo[3-[2-[4-(3-methylphenoxy)phenyl]benzoxazol-5-yl)alanyl-3-(2-iminoimidazolichn-4-yl)-seryl-3-(2-iminoimidazolidin-4-yl)serylserylglycyl-β-methylphenylalanyl];

Cyclo[3-[2-(9H-fluoren-2-yl)-1,3-benzoxazol-5-yl]-D-alanyl-3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl];

Cyclo[3-[2-(9H-fluoren-2-yl)-1,3-benzoxazol-5-yl]alanyl-3-(2-iminoimidazolidin-4-yl)alanyl-3-(3-hexopyranosyl-2-iminoimidazolidin-4-yl)alanylserylglycyl-β-methylphenylalanyl];

Cyclo[3-[2-(6-methoxynaphth-2-yl)-1,3-benzoxazol-5-A-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-(6-methoxynaphth-2-yl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl];

Cyclo[3-[[2-(2,3,4,6-tetra-O-benzoyl-glucopyranosyl)amino]-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl);

Cyclo[3-[[2-(2,3,4,6-tetra-O-benzoylhexopyranosyl)amino]-1,3-benzoxazol-5-yl]alanyl-3-(2-iminoimidazolidin-4-yl)seryl-3-(3-hexopyranosyl-2-iminoimidazolidin-4-yl)seryl-serylglycyl-β-methylphenylalanyl];

Cyclo[3-[2-(benzylthio)-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[312-(benzylthio)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl];

Cyclo[3-[2-[(2-naphthylmethyl)thio]-1,3-benzoxazol-5-yl]-D-alanyl-3-(2-iminoimidazolidin-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-[(naphthylmethyl)thio]-1,3-benzoxazol-5-yl]alanyl-3-(2-iminoimidazolidin-4-yl)-seryl-3-(3-hexopyranosyl-2-iminoimidazolidin-4-yl)serylserylglycyl-β-methylphenylalanyl];

Cyclo[3-[2-[(4-phenylbenzyl)thio]-1,3-benzoxazol-5-yl)-D-alanyl-3-(2-iminoimidazolichn-4-yl)-L-seryl-3-(2-imino-3-α-D-mannopyranosylimidazolidin-4-yl)-D-seryl-L-serylglycyl-(S)-β-methyl-L-phenylalanyl];

Cyclo[3-[2-[(4-phenylbenzyl)thio]-1,3-benzoxazol-5-yl]
    alanyl-3-(2-iminoimidazolidin-4-yl)seryl-3-(3-hexopyra-
    nosyl-2-iminoimidazolidin-4-yl)serylserylglycyl-β-meth-
    ylphenylalanyl];
Cyclo[3-[2-[(2-oxo-2-phenylethyl)thio]-1,3-benzoxazol-5-
    yl]-D-alanyl-3-(2-iminoimidazoliciin-4-yl)-L-seryl-3-(2-
    imino-3-α-D-mannopyranosylimidazolidin-4-yl)-D-
    seryl-L-serylglycyl-(S)-β-methyl-L-phenylalanyl];
Cyclo[3-[2-[(2-oxo-2-phenylethyl)thio]-1,3-benzoxazol-5-
    yl]alanyl-3-(2-iminoimidazolidin-4-yl)-seryl-3-(3-hex-
    opyranosyl-2-iminoimidazolidin-4-yl)serylserylglycyl-β-
    methylphenyl-alanyl];
Cyclo[3-[2-[[2-(4-chlorophenyl)-2-oxoethyl]thio]-1,3-ben-
    zoxazol-5-yl]-D-alanyl-3-(2-iminoimidazolidin-4-yl)-L-
    seryl-3-(2-imino-3-α-D-mannopyranosylimidazolidin-4-
    yl)-D-seryl-L-serylglycyl-(S)-β-methyl-L-phenylalanyl];
Cyclo[3-[2-[[2-(4-chlorophenyl)-2-oxoethyl]thio]-1,3-ben-
    zoxazol-5-yl]alanyl-3-(2-iminoimidazolidin-4-yl)seryl-3-
    (3-hexopyranosyl-2-iminoimidazolidin-4-yl)serylsery-
    lycyl-β-methylphenylalanyl];
Cyclo[3-cyclohex yl-L-alanyl-O-(4-O-α-D-mannopyrano-
    syl-α-D-mannopyranosyl)-D-tyrosyl-3-(2-iminoimidazo-
    lidin-4-yl)-L-seryl-3-(2-imino-3-α-D-mannopyrano-
    sylimidazolidin-4-yl)-D-seryl-L-serylglycyl];
Cyclo[3-cyclohexylalanyl-O-(4-O-hexopyranosylhexopyra-
    nosyl)tyrosyl-3-(2-iminoimidazolidin-4-yl)seryl-3-(3-
    hexopyranosyl-2-iminoimidazolidin-4-yl)serylserylgly-
    cyl];
Cyclo[(3S)-3-cyclohexyl-L-2-aminobutanoyl-O-(4-O-α-D-
    mannopyranosyl-α-D-mannopyranosyl)-D-tyrosyl-3-(2-
    iminoimidazolidin-4-yl)-L-seryl-3-(2-imino-3-α-D-man-
    nopyranosylimidazolidin-4-yl)-D-seryl-L-serylglycyl];
Cyclo[3-cyclohexyl-2-aminobutanoyl-O-(4-O-hexopyrano-
    sylhexopyranosyl)tyrosyl-3-(2-iminoimidazolidin-4-yl)
    seryl-3-(3-hexopyranosyl-2-iminoimidazoliciin-4-yl)-ser-
    ylserylglycyl];
Cyclo[3-cyclohexyl-L-alanyl-3-cyclohexyl-D-alanyl-3-(2-
    iminoimidazolidin-4-yl)-L-seryl-3-(2-imino-3-α-D-man-
    nopyranosylimidazolidin-4-yl)-D-seryl-L-serylglycyl];
Cyclo[3-cyclohexylalanyl-3-cyclohexylalanyl-3-(2-imi-
    noimidazolidin-4-yl)seryl-3-(3-hexopyranosyl-2-imi-
    noimidazolidin-4-yl)serylserylglycyl];
Cyclo[3-cyclohexyl-L-alanyl-3-[4-[(4-O-α-D-mannopyra-
    nosyl-α-D-mannopyranosyl)oxy]cyclohexyl]-D-alanyl-
    3-(2-iminoimidazolidin-4-yl)-L-seryl-3-(2-imino-3-α-D-
    mannopyranosylimidazolidin-4-yl)-D-seryl-L-
    serylglycyl];
Cyclo[3-cyclohexylalanyl-3-[4-[(4-O-hexopyranosylhex-
    opyranosyl)oxy]cyclohexyl]alanyl-3-(2-iminoimidazoli-
    din-4-yl)seryl-3-(3-hexopyranosyl-2-iminoimidazolidin-
    4-yl)serylserylglycyl];
Cyclo[3-cyclohex yl-L-alanyl-3-[4-[(4-O-α-D-mannopyra-
    nosyl-α-D-mannopyranosyl)oxy]cyclohexyl]-D-alanyl-
    3-(2-iminoimidazolidin-4-yl)-L-seryl-3-(2-imino-3-α-D-
    mannopyranosylimidazolidin-4-yl)-D-seryl-L-
    serylglycyl);
Cyclo[3-cyclohexylalanyl-3-[4-[(4-O-hexopyranosylhex-
    opyranosyl)oxy]cyclohexyl]alanyl-3-(2-iminoimidazoli-
    din-4-yl)seryl-3-(3-hexopyranosyl-2-iminoimidazolidin-
    4-yl)serylserylglycyl];
Cyclo[3-cyclohexyl-D-alanyl-3-(2-iminoimidazolidin-4-
    yl)-L-seryl-3-(2-imino-3-α-D-mannopyranosylimidazoli-
    din-4-yl)-D-seryl-L-serylglycyl-(3S)-3-cyclohexyl-L-2-
    aminobutanoyl]
Cyclo[3-cyclohexylalanyl-3-(2-iminoimidazolidin-4-yl)
    seryl-3-(3-hexopyranosyl-2-iminoimidazolidin-4-yl)ser-
    ylserylglycyl-3-cyclohexyl-2-aminobutanoyl];
Cyclo[3-[4-[(4-O-α-D-mannopyranosyl-α-D-mannopyra-
    nosyl)oxy)cyclohexyl]-D-alanyl-3-(2-iminoimidazolidin-
    4-yl)-L-seryl-3-(2-imino-3-α-D-mannopyranosylimida-
    zolidin-4-yl)-D-seryl-L-serylglycyl-(3S)-3-cyclohexyl-L-
    2-aminobutanoyl];
Cyclo[344-[(4-O-hexopyranosylhexopyranosyl)oxy]cyclo-
    hexyl]alanyl-3-(2-iminoimidazolidin-4-yl)seryl-3-(3-hex-
    opyranosyl-2-iminoimidazolidin-4-yl)serylserylglycyl-3-
    cyclohexyl-2-aminobutanoyl];
Cyclo[3-(syn-4-hydroxycyclohexyl)-D-alanyl-3-(2-imi-
    noimidazolidin-4-yl)-L-seryl-3-(2-imino-3-α-D-man-
    nopyranosylimidazolidin-4-yl)-D-seryl-L-serylglycyl-
    (3S)-3-cyclohexyl-L-2-aminobutanoyl];
Cyclo[3-(syn-4-hydroxycyclohex yl)alanyl-3-(2-iminoimi-
    dazolidin-4-yl)seryl-3-(3-hexopyranosyl-2-iminoimida-
    zolidin-4-yl)serylserylglycyl-3-cyclohexyl-2-aminobu-
    tanoyl];
Cyclo[3-(anti-4-hydroxycyclohexyl)-D-alanyl-3-(2-imi-
    noimidazolidin-4-yl)-L-seryl-3-(2-imino-3-α-D-man-
    nopyranosylimidazolidin-4-yl)-D-seryl-L-serylglycyl-
    (3S)-3-cyclohexyl-L-2-aminobutanoyl];
Cyclo[3-(anti-4-hydroxycyclohexyl)alanyl-3-(2-iminoimi-
    dazolidin-4-yl)seryl-3-(3-hexopyranosyl-2-iminoimida-
    zolidin-4-yl)serylserylglycyl-3-cyclohexyl-2-aminobu-
    tanoyl];
Cyclo[glycyl-(S)-β-methyl-L-phenylalanyl-D-tyrosyl-3-(2-
    iminoimidazolidin-4-yl)-L-seryl-3-(2-imino-3-α-D-man-
    nopyranosylimidazolidin-4-yl)-D-seryl-L-seryl];
Cyclo[glycyl-β-methylphenylalanyltyrosyl-3-(2-iminoimi-
    dazolidin-4-yl)seryl-3-(3-hexopyranosyl-2-iminoimida-
    zolidin-4-yl)serylseryl];
Cyclo[glycyl-L-phenylalanyl-D-tyrosyl-3-(2-iminoimidazo-
    lidin-4-yl)-L-seryl-3-(2-imino-3-α-D-mannopyrano-
    sylimidazolidin-4-yl)-D-seryl-L-seryl];
Cyclo[glycylphenylalanyltyrosyl-3-(2-iminoimidazolidin-
    4-yl)seryl-3-(3-hexopyranosyl-2-iminoimidazolidin-4-yl)
    serylseryl];
Cyclo[glycyl-(S)-β-methyl-L-phenylalanyl-D-tyrosyl-3-(2-
    iminoimidazolidin-4-yl)-L-seryl-3-(2-iminoimidazolidin-
    4-yl)-D-seryl-L-seryl];
Cyclo[glycyl-β-methylphenylalanyltyrosyl-3-(2-iminoimi-
    dazolidin-4-yl)seryl-3-(2-iminoimidazolidin-4-yl)ser-
    ylseryl];
Cyclo[3-cyclohexyl-L-alanyl-3-cyclohexyl-D-alanyl-3-(2-
    iminoimidazolidin-4-yl)-L-seryl-3-(2-iminoimidazolidin-
    4-yl)-D-seryl-L-serylglycyl];
Cyclo[3-cyclohexylalanyl-3-cyclohexylalanyl-3-(2-imi-
    noimidazolidin-4-yl)seryl-3-(2-iminoimidazolidin-4-yl)-
    serylserylglycyl];
Cyclo[glycyl-(S)-β-methyl-L-phenylalanyl-O-(4-O-α-D-
    mannopyranosyl-α-D-mannopyranosyl)-D-tyrosyl-3-(2-
    iminoimidazolidin-4-yl)-L-seryl-3-[1-benzyl-2-imino-3-
    α-D-mannopyranosyl-imidazolidin-4-yl]-D-seryl-L-
    seryl];
Cyclo[glycyl-β-methylphenylalanyl-O-(4-O-hexopyrano-
    sylhexopyranosyl)tyrosyl-(2-iminoimidazolidin-4-yl)
    seryl-3-(1-benzyl-3-hexopyranosyl-2-iminoimidazolidin-
    4-yl]serylseryl];
Cyclo[glycyl-(S)-β-methyl-L-phenylalanyl-O-(4-O-α-D-
    mannopyranosyl-α-D-mannopyranosyl)-D-tyrosyl-3-(2-
    iminoimidazolidin-4-yl)-L-seryl-3-[1-(4-tert-butylben-
    zyl)-2-imino-3-α-D-mannopyranosylimidazolidin-4-yl]-
    D-seryl-L-seryl];
Cyclo[glycyl-β-methylphenylalanyl-O-(4-O-hexopyrano-
    sylhexopyranosyl)tyrosyl-(2-iminoimidazolidin-4-yl)
    seryl-3-[1-(4-tert-butylbenzyl)-3-hexopyranosyl-2-imi-
    noimidazolidin-4-yl]-serylseryl];

Di-N-(4-tert-butylbenzyl)-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Di-N-(4-tert-butylbenzyl)-cyclo[glycyl-O-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-[1-(12-hydroxydodecyl)-2-imino-3-α-D-mannopyranosylimidazolidin-4-yl]-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-β-hexopyranosyl-1-(12-hydroxydodecyl)-2-iminoimidazolidin-4-yl]-serylseryl];

Cyclo[glycyl-(S)-β-methyl-L-phenylalanyl-O-(4-O-α-D-mannopyranosyl-α-D-mannopyranosyl)-D-tyrosyl-3-[1,3-dibenzyl-2-(benzylimino)imidazolidin-4-yl]-L-seryl-3-[1-benzyl-2-(benzyl-imino)-3-α-D-mannopyranosylimidazolidin-4-yl)-D-seryl-L-seryl];

Cyclo[glycyl-β-methylphenylalanyl-O-(4-O-hexopyranosylhexopyranosyl)tyrosyl-3-[1,3-dibenzyl-2-(benzylimino)imidazolidin-4-yl]seryl-3-[1-benzyl-2-(benzylimino)-3-hexopyranosyl]midazolidin-4-yl]serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-[1-butyl-2-imino-3-α-D-mannopyranosyl-imidazolidin-4-yl]-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-[1-butyl-3-hexopyranosyl-2-iminoimidazolidin-4-yl]serylseryl];

Cyclo[glycyl-(S)-β-methyl-L-phenylalanyl-O-(4-O-α-D-mannopyranosyl-α-D-mannopyranosyl)-D-tyrosyl-3-[1,3-dimethyl-2-(methylimino)imidazolidin-4-yl]-L-seryl-3-β-α-D-mannopyranosyl-1-methyl-2-(methylimino)imidazolidin-4-yl]-D-seryl-L-seryl]bis-methiodide Cyclo[glycyl-β-methylphenylalanyl-O-(4-O-hexopyranosylhexopyranosyl)tyrosyl-3-(1,3-dimethyl-2-(methylimino)imidazolidin-4-yl)seryl-3-β-hexopyranosyl-1-methyl-2-(methylimino)imidazolidin-4-yl]serylseryl]bis-methiodide Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-[2-imino-3-α-D-mannopyranosyl-1-(2-phenylbenzyl)-imidazolidin-4-yl]-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl]-3-β-hexopyranosyl-2-imino-1-(2-phenylbenzyl)-imidazolidin-4-yl]-serylseryl];

Cyclo[glycyl-(S)-β-methyl-L-phenylalanyl-O-(4-O-α-D-mannopyranosyl-α-D-mannopyranosyl)-D-tyrosyl-3-β-(4-phenylbenzyl)-2-[(4-phenylbenzyl)imino]imidazolidin-4-yl]-L-seryl-3,2-imino-3-α-D-mannopyranosyl-1-(4-phenylbenzyl)-imidazolidin-4-yl]-D-seryl-L-seryl];

Cyclo[glycyl-β-methylphenylalanyl-O-(4-O-hexopyranosylhexopyranosyl)tyrosyl-3-β-(4-phenylbenzyl)-2-[(4-phenylbenzyl)imino]imidazolidin-4-yl]seryl-3-β-hexopyranosyl-2-imino-1-(4-phenylbenzyl)-imidazolidin-4-yl]serylseryl];

Cyclo[glycyl-β-methyl-L-phenylalanyl-O-(4-O-α-D-mannopyranosyl-α-D-mannopyranosyl)-D-tyrosyl-3-(2-iminoimidazolidin-4-yl)-L-seryl-3-[2-imino-3-α-D-mannopyranosyl-1-(4-phenylbenzyl)-imidazolidin-4-yl]-D-seryl-L-seryl);

Cyclo[glycyl-β-methylphenylalanyl-O-(4-O-hexopyranosylhexopyranosyl)tyrosyl-3-(2-iminoimidazolidin-4-yl)seryl]-3-β-hexopyranosyl-2-imino-1-(4-phenylbenzyl)-imidazolidin-4-yl]-serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-[2-imino-3-α-D-mannopyranosyl-1-(2-naphthylmethyl)-imidazolidin-4-yl]-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl]-3-β-hexopyranosyl-2-imino-1-(2-naphthylmethyl)-imidazolidin-4-yl]-serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-[2-imino-3-α-D-mannopyranosyl-1-(4-trifluoromethylbenzyl)-imidazolidin-4-yl]-D-seryl-L-seryl);

Cyclo[glycyl-β-methylphenylalanyl-O-(4-O-hexopyranosylhexopyranosyl)tyrosyl-3-(2-iminoimidazolidin-4-yl)seryl]-3-β-hexopyranosyl-2-imino-1-(4-trifluoromethylbenzyl)-imidazolidin-4-A-serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-[1-(4-carboxybenzyl)-2-imino-3-α-D-mannopyranosylimidazolidin-4-yl]-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl]-3-[1-(4-carboxybenzyl)-2-imino-3-hexopyranosyl]midazolidin-4-A-serylseryl];

Di-N-(4-carboxybenzyl)-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Di-N-(4-carboxybenzyl)-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

Tri-N-(4-carboxybenzyl)-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl]

Tri-N-(4-carboxybenzyl)-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]

Cyclo[glycyl-(S)-β-methyl-L-phenylalanyl-O-(4-O-α-D-mannopyranosyl-α-D-mannopyranosyl)-D-tyrosyl-3-(2-iminoimidazoliclin-4-yl)-L-seryl-3-[2-imino-3-α-D-mannopyranosyl-1-(3-methyl-but-2-enyl)-imidazolidin-4-yl]-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl]-3-β-hexopyranosyl-2-imino-1-(3-methyl-but-2-enyl)imidazolidin-4-yl]serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-[1-heptyl-2-imino-3-α-D-mannopyranosyl-imidazolidin-4-yl]-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-[1-heptyl-3-hexopyranosyl-2-iminoimidazolidin-4-yl]serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-[1-(10-carboxydecyl)-2-imino-3-α-D-mannopyranosylimidazolidin-4-yl]-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-[1-(10-carboxydecyl)-3-hexopyranosyl-2-iminoimidazolidin-4-yl]serylseryl];

Di-N-(10-carboxydecyl)-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Di-N-(10-carboxydecyl)-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

Cyclo[3-[1,3-dibenzyl-2-(benzylimino)imidazolidin-4-yl]-L-alanyl-3-[1-benzyl-2-(benzylimino)-3-α-D-mannopyranosylimidazolidin-4-yl]-D-alanyl-L-serylglycyl-(S)-β-methyl-L-phenylalanyl-O-(4-O-α-D-mannopyranosyl-α-D-mannopyranosyl)-D-tyrosyl];

Cyclo[3-[1,3-benzyl-2-(benzylimino)imidazolidin-4-yl]alanyl-3-[1-benzyl-2-(benzylimino)-3-hexopyranosyl]midazolidin-4-yl]alanylserylglycyl-β-methylphenylalanyl-O-(4-O-hexopyranosylhexopyranosyl)tyrosyl];

Cyclo[3-[1,3-dimethyl-2-(methylimino)imidazolidin-4-yl]-L-alanyl-3-β-α-D-mannopyranosyl-1-methyl-2-(methylimino)imidazolidin-4-yl]-D-alanyl-L-serylglycyl-(S)-β-methyl-L-phenylalanyl-O-(4-O-α-D-mannopyranosyl-α-D-mannopyranosyl)-D-tyrosyl) bis-methiodide Cyclo[3-[1,3-dimethyl-2-(methylimino)imidazolidin-4-yl]alanyl-3-β-hexopyranosyl-1-methyl-2-(methylimino)imidazolidin-4-yl]alanylserylglycyl-β-methylphenylalanyl-O-(4-O-hexopyranosylhexopyranosyl)tyrosyl]bis-methiodide Cyclo[glycyl-(S)-β-methyl-L-phenylalanyl-O-methyl-D-tyrosyl-3-[1,3-dimethyl-2-(methylimino)imidazolidin-4-yl]-L-seryl-3,3-α-D-mannopyranosyl-1-methyl-2-(methylimino)imidazolidin-4-yl]-D-seryl-L-seryl]bis-methiodide Cyclo[glycyl-β-methylphenylalanyl-O-(methyl)tyrosyl-3-(1,3-dimethyl-2-(methylimino)imidazolidin-4-yl)seryl-3,3-hexopyranosyl-1-methyl-2-(methylimino)imidazolidin-4-yl]serylseryl]bis-methiodide Cyclo[glycyl-(S)-β-methyl-L-phenylalanyl-O-(4-O-[4,6-O-(2-adamantylidene)-α-D-mannopyranosyl]-α-D-mannopyranosyl]-D-tyrosyl-3-(2-iminoimidazolidin-4-yl)-L-seryl-3-[1-benzyl-2-imino-3-α-D-mannopyranosyl-imidazolin-4-yl]-D-seryl-L-seryl]

Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-[1-benzyl-3-hexopyranosyl-2-iminoimidazolidin-4-yl]serylseryl]

Cyclo[glycyl-(S)-β-methyl-L-phenylalanyl-O-[4-O-[4,6-O-(2-adamantylidene)-α-D-mannopyranosyl]-α-D-mannopyranosyl]-D-tyrosyl-3-(2-iminoimidazolidin-4-yl)-L-seryl-3-[1-(4-tert-butylbenzyl)-2-imino-3-α-D-mannopyranosylimidazolidin-4-yl]-D-seryl-L-seryl]

Cyclo[glycyl-β-methylphenylalanyl-O-4-O-[4,6-O-(2-adamantylidene)hexopyranosyl]hexopyranosyl]tyrosyl-3-(2-iminoimidazolidin-4-yl)seryl-3-[2-[1-(4-tert-butylbenzyl)-3-hexopyranosyl-2-iminoimidazolidin-4-yl]serylseryl)

Cyclo[glycyl-(S)-β-methyl-L-phenylalanyl-O-(4-O-[4,6-O-(2-adamantylidene)-α-D-mannopyranosyl]-α-D-mannopyranosyl]-D-tyrosyl-3-(2-iminoimidazolidin-4-yl)-L-seryl-3-[2-imino-3-α-D-mannopyranosyl-1-(2-naphthylmethyl)-imidazolidin-4-yl]-D-seryl-L-seryl)

Cyclo[glycyl-β-methylphenylalanyl-O-4-O-[4,6-O-(2-adamantylidene)hexopyranosyl]hexopyranosyl]tyrosyl-3-(2-iminoimidazolidin-4-yl)seryl-3-β-hexopyranosyl-2-imino-1-(2-naphthylmethyl)-imidazolidin-4-yl]serylseryl]

Cyclo[glycyl-(S)-β-methyl-L-phenylalanyl-O-4-O-[4,6-O-(2-adamantylidene)-α-D-mannopyranosyl]-α-D-mannopyranosyl)-D-tyrosyl-3-[1,3-dibenzyl-2-(benzylimino)imidazolidin-4-yl]-L-seryl-3-[1-benzyl-2-(benzylimino)-3-α-D-mannopyranosylimidazolidin-4-yl]-D-seryl-L-seryl];

Cyclo[glycyl-β-methylphenylalanyl-O-[4-O-[4,6-O-(2-adamantylidene)hexopyranosyl]hexopyranosyl]tyrosyl-3-[1,3-dibenzyl-2-(benzylimino)imidazolidin-4-yl]seryl-3-[1-benzyl-2-(benzylimino)-3-hexopyranosyl]midazolidin-4-yl]serylseryl];

Cyclo[3-(2-iminoimidazolidin-4-yl)-L-alanyl-3-(1-benzyl-2-imino-3-α-D-mannopyranosyl-imidazolidin-4-yl)-D-alanyl-L-serylglycyl-(S)-β-methyl-L-phenylalanyl-O-[4-O-[4,6-O-(2-adamantylidene)-α-D-mannopyranosyl]-α-D-mannopyranosyl]-D-tyrosyl];

Cyclo[3-(2-iminoimidazolidin-4-yl)alanyl-3-(1-benzyl-3-hexopyranosyl-2-iminoimidazolidin-4-yl)alanylserylglycyl-β-methylphenylalanyl-O-4-O-[4,6-O-(2-adamantylidene)hexopyranosyl]hexopyranosyl]tyrosyl];

Cyclo[glycyl-(S)-β-methyl-L-phenylalanyl-O-[4-O-4,6-O-(2-adamantylidene)-α-D-mannopyranosyl]-α-D-mannopyranosyl]-tyrosyl-3-[1,3-dimethyl-2-(methylimino)imidazolidin-4-yl]-L-seryl-3-β-α-D-mannopyranosyl-1-methyl-2-(methylimino)imidazolidin-4-yl]-D-seryl-L-seryl]bis-methiodide Cyclo[glycyl-β-methylphenylalanyl-O-[4-O-[4,6-O-(2-adamantylidene)hexopyranosyl]hexopyranosyl]tyrosyl-3-[1,3-dimethyl-2-(methylimino)imidazolidin-4-yl]seryl-3-β-hexopyranosyl-1-methyl-2-(methylimino)imidazolidin-4-yl]serylseryl]bis-methiodide Cyclo[glycyl-(S)-β-methyl-L-phenylalanyl-O-[4-O-[4,6-(2-adamantylidene)-α-D-mannopyranosyl]-α-D-mannopyranosyl]-D-tyrosyl-3-(2-iminoimidazolidin-4-yl)-L-seryl-3-[1-[(2E)-3,7-dimethylocta-2,6-dien-1-yl]-2-imino-3-α-D-mannopyranosylimidazolidin-4-yl]-D-seryl-L-seryl]

Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-[1-(3,7-dimethylocta-2,6-dien-1-yl)-3-hexopyranosyl-2-iminoimidazolidin-4-yl]serylseryl]

Cyclo[glycyl-(S)-β-methyl-L-phenylalanyl-O-[4-O-[4,6-O-(2-adamantylidene)-α-D-mannopyranosyl]-α-D-mannopyranosyl]-D-tyrosyl-3-(2-iminoimidazolidin-4-yl)-L-seryl-3-[1-heptyl-2-imino-3-α-D-mannopyranosyl-imidazolidin-4-yl]-D-seryl-L-seryl]

Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-[1-heptyl-3-hexopyranosyl-2-iminoimidazolidin-4-yl]serylseryl]

Cyclo[glycyl-(S)-β-methyl-L-phenylalanyl-O-(4-O-[4,6-O-(2-adamantylidene)-α-D-mannopyranosyl]-α-D-mannopyranosyl]-D-tyrosyl-3-(2-iminoimidazolidin-4-yl)-L- seryl-3-[1-hexyl-2-imino-3-α-D-mannopyranosylimidazolidin-4-yl]-D-seryl-L-seryl]

Cyclo[glycyl-β-methylphenylalanyl-O-[4-O-[4,6-O-(2-adamantylidene)hexopyranosyl]-hexopyranosyl]tyrosyl-3-(2-iminoimidazolidin-4-yl)seryl-3-β-hexopyranosyl-1-hexyl-2-iminoimidazolidin-4-yl]serylseryl]

Cyclo[3-[2-[2-(α-D-glucopyranosyloxy)phenyl]-1,3-benzoxazol-5-yl]-D-alanyl-3-(2-iminoimidazolidin-4-yl)-L-seryl-3-(1-benzyl-2-imino-3-α-D-mannopyranosylimidazolidin-4-yl)-D-seryl-L-serylglycyl-(S)-β-methyl-L-phenylalanyl);

Cyclo[3-[2-[2-(hexopyranosyloxy)phenyl]-1,3-benzoxazol-5-yl]alanyl-3-(2-iminoimidazolidin-4-yl)seryl-3-(1-benzyl-3-hexopyranosyl-2-iminoimidazolidin-4-yl)serylserylglycyl-β-methyl-phenylalanyl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-decanoylimino-3-α-D-mannopyranosylimidazolidin-4-yl)-D-seryl-L-seryl);

Cyclo[glycyl-β-methylphenylalanyl-O-(4-O-hexopyranosylhexopyranosyl)tyrosyl-3-(2-iminoimidazolidin-4-yl)seryl-3-(2-decanoylimino-3-hexopyranosyl]midazolidin-4-yl)serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(3-α-D-mannopyranosyl-2-(3-methyl-butyrylimino)-imidazolidin-4-yl)-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-(3-methyl-butyrylimino)-imidazolidin-4-yl)serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-(2-ethyl-butyrylimino)-3-α-D-mannopyranosylimidazolidin-4-yl)-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-(2-(2-ethyl-butyrylimino)-3-hexopyranosyl]midazolidin-4-yl)serylseryl];

Tri-N-[(phenylmethoxy)carbonyl]-cyclo[glycyl-(S)-β-methyl-L-phenylalanyl-D-tyrosyl-3-(2-iminoimidazolidin-4-yl)-L-seryl-3-(2-imino-3-α-D-mannopyranosylimidazolidin-4-yl)-D-seryl-L-seryl];

Tri-N-((phenylmethoxy)carbonyl]-cyclo[glycyl-β-methylphenylalanyltyrosyl-3-(2-iminoimidazolidin-4-yl)seryl-3-(3-hexopyranosyl-2-iminoimidazolidin-4-yl)serylseryl];

N-[(Phenylmethoxy)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

N-[(Phenylmethoxy)carbonyl]-cyclo[glycyl-O-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl);

Tri-N-[(phenylmethoxy)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Tri-N-[(phenylmethoxy)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

Cyclo[glycyl-(S)-(3-methyl-L-phenylalanyl-O-(4-O-α-D-mannopyranosyl-α-D-mannopyranosyl)-D-tyrosyl-3-[2-(pyrimidin-2-ylimino)imidazolidin-4-yl]-L-seryl-3-β-α-D-mannopyranosyl-2-imino-1-(pyrimidin-2-yl)imidazolidin-4-yl]-D-seryl-L-seryl);

Cyclo[glycyl-β-methylphenylalanyl-O-(4-O-hexopyranosylhexopyranosyl)tyrosyl-3-[2-(pyrimidin-2-ylimino)imidazolidin-4-yl]seryl-3-β-hexopyranosyl-2-imino-1-(pyrimidin-2-yl)imidazolidin-4-yl]serylseryl];

Cyclo[glycyl-(S)-β-methyl-L-phenylalanyl-O-(4-O-α-D-mannopyranosyl-α-D-mannopyranosyl)-D-tyrosyl-3-[2-(1,3-benzoxazol-2-ylimino)imidazolidin-4-yl]-L-seryl-3-[1-(1,3-benzoxazol-2-yl)-2-imino-3-α-D-mannopyranosylimidazolidin-4-yl]-D-seryl-L-seryl];

Cyclo[glycyl-β-methylphenylalanyl-O-(4-O-hexopyranosylhexopyranosyl)tyrosyl-3-[2-(1,3-benzoxazol-2-ylimino)imidazolidin-4-yl]seryl-3-[1-(1,3-benzoxaxol-2-yl)-3-hexopyranosyl-2-iminoimidazolidin-4-yl]serylseryl];

Cyclo[glycyl-(S)-β-methyl-L-phenylalanyl-O-(4-O-α-D-mannopyranosyl-α-D-mannopyranosyl)-D-tyrosyl-3-[2-(1,3-benzothiazol-2-ylimino)imidazolidin-4-A-L-seryl-3-[1-(1,3-benzothiazol-2-yl-3-α-D-mannopyranosyl)-2-iminoimidazolidin-4-yl]-D-seryl-L-seryl];

Cyclo[glycyl-β-methylphenylalanyl-O-(4-O-hexopyranosylhexopyranosyl)tyrosyl-3-[2-(1,3-benzothiazol-2-ylimino)imidazolidin-4-yl]seryl-3-[1-(1,3-benzo-thiazol-2-yl)-2-imino-3-hexopyranosyl]midazolidin-4-yl]serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-β-(6-O-hexanoyl-α-D-mannopyranosyl)-2-iminoimidazolidin-4-A-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-β-(6-O-hexanoylhexopyranosyl)-2-iminoimidazolidin-4-yl]serylseryl];

Cyclo[glycyl-(S)-β-methyl-L-phenylalanyl-O-6-O-hexanoyl-4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-(6-O-hexanoyl-4-O-hexopyranosylhexopyranosyl)-tyrosyl-3-(2-iminoimidazolidin-4-yl)seryl-3-(3-hexopyranosyl-2-iminoimidazolidin-4-yl)-serylseryl);

Cyclo[glycyl-(S)-β-methyl-L-phenylalanyl-O-[4-O-(6-O-hexanoyl-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(6-O-hexanoylhexopyranosyl)hexopyranosyl]-tyrosyl-3-(2-iminoimidazolidin-4-yl)seryl-3-(3-hexopyranosyl-2-iminoimidazolidin-4-yl)-serylseryl];

Cyclo[glycyl-(S)-β-methyl-L-phenylalanyl-O-4-O-[6-O-(diphenylacetyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl);

Cyclo[glycyl-β-methylphenylalanyl-O-[4-O-[6-O-(diphenylacetyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-β-[6-O-(diphenylacetyl)-α-D-mannopyranosyl]-2-iminoimidazolidin-4-yl)-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-[3-[6-O-(diphenylacetyl)hexopyranosyl]-2-iminoimidazolidin-4-yl]-serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-O-(diphenylacetyl)-L-seryl];

Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolichn-4-yl)seryl-O-(diphenylacetyl)-seryl];

Cyclo[glycyl-(S)-β-methyl-L-phenylalanyl-O-[6-O-(diphenylacetyl)-4-O-α-D-mannopyranosyl-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[6-O-(diphenylacetyl)-4-O-hexopyranosylhexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-β-(6-O-heptanoyl-α-D-mannopyranosyl)-2-iminoimidazolidin-4-yl]-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-β-(6-O-heptanoylhexopyranosyl)-2-iminoimidazolidin-4-yl]seryl-seryl];

Cyclo[glycyl-(S)-β-methyl-L-phenylalanyl-O-(6-O-heptanoyl-4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-(6-O-heptanoyl-4-O-hexopyranosylhexopyranosyl)-tyrosyl-3-(2-iminoimidazolidin-4-yl)seryl-3-(3-hexopyranosyl-2-iminoimidazoliclin-4-yl)-serylseryl];

Cyclo[glycyl-(S)-β-methyl-L-phenylalanyl-O-[4-O-(6-O-heptanoyl-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(6-O-heptanoylhexopyranosyl)hexopyranosyl]-tyrosyl-3-(2-iminoimidazolidin-4-yl)seryl-3-(3-hexopyranosyl-2-iminoimidazolidin-4-yl)-serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-(6-O-(phenylacetyl)-α-D-mannopyranosylimidazolidin-4-yl)-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-(3-(6-O-(phenylacetyl)hexopyranosyl-2-iminoimidazolidin-4-yl-serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-O-(phenyacetyl)-L-seryl);

Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl-seryl-O-(phenylacetyl)seryl];

Cyclo[glycyl-(S)-β-methyl-L-phenylalanyl-O-4-O-α-D-mannopyranosyl-6-O-(phenylacetyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-4-O-hexopyranosyl-6-O-(phenylacetyl)hexopyranosyl]-tyrosyl-3-(2-iminoimidazolidin-4-yl)seryl-3-(3-hexopyranosyl-2-iminoimidazolidin-4-yl-serylseryl];

Cyclo[glycyl-(S)-β-methyl-L-phenylalanyl-O-4-O-[6-O-(phenylacetyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-(phenylacetyl)hexopyranosyl]hexopyranosyl]-tyrosyl-3-(2-iminoimidazolidin-4-yl)seryl-3-(3-hexopyranosyl-2-iminoimidazolidin-4-yl)-serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-[6-O-(2-propylpentanoyl)-α-D-mannopyranosyl]-imidazolidin-4-yl)-D-seryl-L-seryl];

Cyclo[glycyl-β-methylphenylalanyl-O-[4-O-[6-O-(2-propylpentanoyl)hexopyranosyl]-hexopyranosyl]tyrosyl-3-(2-iminoimidazolidin-4-yl)seryl-3,3-(6-O-(2-propylpentanoyl)-hexopyranosyl)-2-iminoimidazolidin-4-yl]serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-O-(2-propylpentanoyl)-L-seryl];

Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)seryl-0-(2-propylpentanoyl)-seryl];

Cyclo[glycyl-(S)-β-methyl-L-phenylalanyl-O-[4-O-α-D-mannopyranosyl-6-O-(2-propyl-pentanoyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-hexopyranosyl-6-O-(2-propylpentanoyl)hexopyranosyl]tyrosyl-3-(2-iminoimidazolidin-4-yl)seryl-3-(3-hexopyranosyl-2-iminoimidazolidin-4-yl)serylseryl);

Cyclo[glycyl-(S)-β-methyl-L-phenylalanyl-O-[4-O-6-O-(2-propylpentanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-(2-propylpentanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-[2-imino-3-(6-O-(3-cyclopentylpropanoyl)-α-D-mannopyranosyl)-imidazolidin-4-yl]-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-β-(6-O-(3-cyclopentylpropanoyl)-hexopyranosyl)-2-iminoimidazolidin-4-yl]serylseryl);

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-O-(3-cyclopentylpropanoyl)-L-seryl];

Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)seryl-O-(3-cyclopentylpropanoyl)seryl];

Cyclo[glycyl-(S)-β-methyl-L-phenylalanyl-O-[6-O-(3-cyclopentylpropanoyl)-4-O-α-D-mannopyranosyl-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[6-O-(3-cyclopentylpropanoyl)-4-O-hexopyranosyl-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-(3-cyclopentylpropanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-(3-cyclopentylpropanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-α-D-mannopyranosyl-6-O-[(phenylmethoxy)-carbonyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-hexopyranosyl-6-O-[(phenylmethoxy)carbonyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-[(phenylmethoxy)carbonyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O—[(phenylmethoxy)carbonyl]hexopyranosyl)-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-4-O-(4,6-O-phenethylidene-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-4-O-(4,6-O-phenethylidenehexopyranosyl)-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-methoxyphenethylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-⊕-methylphenylalanyl-O-[4-O-[4,6-O-(4-methoxyphenethylidene)hexopyranosyl]-hexopyranosyl)tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O[4-O-(4,6-O-benzylidene-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(4,6-O-benzylidenehexopyranosyl)hexopyranosyl]-tyrosyl-3-(2-iminoimidazolidin-4-yl)seryl-3-(3-hexopyranosyl-2-iminoimidazolidin-4-yl)-serylseryl];

Cyclo[glycyl-(S)-β-methyl-L-phenylalanyl-O-4-O-(2,3-O-benzylidene-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-4-O-(2,3-O-benzylidenehexopyranosyl)hexopyranosyl]-tyrosyl-3-(2-iminoimidazoliciin-4-yl)seryl-3-(3-hexopyranosyl-2-iminoimidazolidin-4-yl)-serylseryl];

Cyclo[glycyl-(S)-β-methyl-L-phenylalanyl-O-[4-O-(2,3-O-benzylidene-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(2,3-O-benzylidenehexopyranosyl)hexopyranosyl]-tyrosyl-3-(2-iminoimidazolidin-4-yl)seryl-3-(3-hexopyranosyl-2-iminoimidazolidin-4-yl)-serylseryl];

Cyclo[glycyl-(S)-β-methyl-L-phenylalanyl-O-4-O-[4,6-O-(2-adamantylidene)-α-D-mannopyranosyl]-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl);

Cyclo[glycyl-β-methylphenylalanyl-O-4-O-[4,6-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[3-cyclohexyl-L-alanyl-O-[4-O-[4,6-O-(2-adamantylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexylalanyl-O-[4-O-[4,6-O-(2-adamantylidene)hexopyranosyl]hexopyranosyl]tyrosyl-3-(2-iminoimirlazolidin-4-yl)seryl-3-(3-hexopyranosyl-2-iminoimidazolidin-4-yl)-serylserylglycyl];

Cyclo[3-cyclohexyl-L-alanyl-O-[4-O-[2,3-O-(2-adamantylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexylalanyl-O-[4-O-[2,3-O-(2-adamantylidene)hexopyranosyl]hexopyranosyl]-tyrosyl-3-(2-iminoimidazolidin-4-yl)seryl-3-(3-hexopyranosyl-2-iminoimidazolidin-4-yl)-serylserylglycyl];

Cyclo[3-cyclohexyl-L-alanyl-O-[4-O-[2,3:4,6-di-O-(2-adamantylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexylalanyl-O-[4-O-[2,3:4,6-di-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)-serylserylglycyl];

Cyclo[glycyl-(S)-β-methyl-L-phenylalanyl-O-[4-O-[4,6-O-(3-methylbutylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-methylbutylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(4,6-O-hex ylidene-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl);

Cyclo[glycyl-β-methylphenylalanyl-0,4-O-(4,6-O-hexylidenehexopyranosyl)hexopyranosyl]tyrosyl-3-(2-iminoimidazolidin-4-yl)seryl-3-(3-hexopyranosyl-2-iminoimidazolidin-4-yl)-serylseryl];

Cyclo[glycyl-(S)-β-methyl-L-phenylalanyl-O-[4-O-(4,6-O-octylidene-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl);

Cyclo[glycyl-β-methylphenylalanyl-O-4-O-(4,6-O-octylidenehexopyranosyl)hexopyranosyl]-tyrosyl-3-(2-iminoimidazolidin-4-yl)seryl-3-(3-hexopyranosyl-2-iminoimidazolidin-4-yl)-serylseryl];

Cyclo[glycyl-(S)-β-methyl-L-phenylalanyl-O-[4-O-[4,6-O-(3,3-dimethylbutylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl);

Cyclo[glycyl-β-methylphenylalanyl-O-4-O-[4,6-O-(3,3-dimethylbutylidene)hexopyranosyl]hexopyranosyl]tyrosyl-3-(2-iminoimidazolidin-4-yl)seryl-3-(3-hexopyranosyl-2-iminoimidazolidin-4-yl)serylseryl);

Cyclo[glycyl-(S)-β-methyl-L-phenylalanyl-O-[4-O-[4,6-O-(2-methylpentylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-4-O-[4,6-O-(2-methylpentylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(cyclohexylmethylene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(cyclohexylmethylene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(4,6-O-[2-[1-[(phenylmethoxy)carbonyl]-piperidin-4-yl]ethylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(2-[1-[(phenylmethoxy)carbonyl]piperidin-4-yl]ethylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-butoxy-4-oxobutylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-butoxy-4-oxobutylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(cyclohex-3-en-1-ylmethylene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-4,6-O-(cyclohex-3-en-1-ylmethylene)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(2-ethylbutylidene)-α-D-mannopyranosyl]-α-D-mannopyranosyf]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(2-ethylbutylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(cyclopentylmethylene)α-mannopyranosyl]α-mannopyranosyl]-tyrosyl-3-(2-iminoimidazolidin-4-yl)-seryl-3-(2-imino-3αDmannopyranosylimidazolidin-4-yl)-seryl-seryl];

Cyclo[glycyl-β-methylphenylalanyl-O-[4-O-[4,6-O-(cyclopentylmethylene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-bromophenethylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-4-O-[4,6-O-(4-bromopheneihylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-methylphenethylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-methylphenethylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-chlorophenethylidene)-α-D-mannopyranosyl]-α-D-mannopyranosyl]-D-tyrosyl-3-(2-iminoimidazoliclin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-chlorophenethylidene)hexopyranosyl)-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-fluorophenethylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenyl alanyl-O-[4-O-[4,6-O-(4-fluorophenethylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(2-cyclohexylethylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl);

Cyclo[glycyl-β-methylphenylalanyl-O-[4-O-[4,6-O-(2-cyclohexyletylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(5-methylhex-4-en-1-ylidene),α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(5-methylhex-4-en-1-ylidene)hexopyranosyl]hexopyranosyl]tyrosyl-3-(2-iminoimidazoliciin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(3-phenylpropylidene)-α-D-mannopyranosyl]-α-D-mannopyranosyl]-D-tyrosyl-3-(2-iminoimidazoliclin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-phenylpropylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[2,6-di methylhept-5-en-1-ylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(2,6-dimethylhept-5-en-1-yidene)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(3,7-dimethyloct-6-en-1-ylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3,7-dimethyloct-6-en-1-ylidene)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(4,6-O-(1-adaxnantylmethylene)-α-D-mannopyranosyl]-α-D-mannopyranosyl]-D-tyros yl-3-(2-iminoimidazolidin-4-yl)-L-seryl-3-(2-imino-3-α-D-mannopyranosylimidazoldin-4-yl)-D-seryl-L-seryl];

Cyclo[glycyl-β-methylphenylalanyl-O-[4-O-[4,6-O-(1-adamantyl methylene)hexopyranos yl]-hexopyranosyl)tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[2,3-O-[2-(1-adamantyl)ethylidene]-α-D-mannopyranosyl]-α-D-mannopyranosyl]-1]-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[2,3-O-[2-(1-adamantyl)ethylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(4,6-O-[2-(1-adamantyl)ethylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[2-(1-adamantyl)ethylidene]hexopyranosyl]hexopyranosyl]tyrosyl-3-(2-iminoimidazoliclin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(3α-methoxy-5(3-cholan-24-ylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-methoxycholan-24-ylidene)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(4,6-O-(4-phenylbenzylidene)-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(4,6-O-(4-phenylbenzylidene)-hexopyranosyl)hexopyranosyl)-tyrosyl-3-(2-iminoimidazolidin-4-yl)seryl-3-(3-hexopyranosyl-2-iminoimidazolidin-4-yl)-serylseryl];

Cyclo[glycyl-(S)-β-methyl-L-phenylalanyl-O-[4-O-[4,6-O-(2-thienylmethylene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(2-thienylmethylene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(3-thienylmethylene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-thienylmethylene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-methylbenzylidene)-α-D-mannopyranosyl]-α-D-mannopyranosyl]-D-tyrosyl-3-(2-iminoimidazolidin-4-54)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-methylbenzylidene)hexopyranosyl]-hexopyranosyl]-tyrosyl-3-(2-iminoimidazolidin-4-yl)seryl-3-(3-hexopyranosyl-2-iminoimidazolidin-4-yl)-serylseryl];

Cyclo[glycyl-(S)-β-methyl-L-phenylalanyl-O-[4-O-[4,6-O-(3-methylbenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-methylbenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(3-hydroxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-hydroxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(3-methoxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-methoxybenzylidene)hexopyranosyl]-hexopyranosyl]tyrosyl-3-(2-iminoimidazolidin-4-yl)seryl-3-(3-hexopyranosyl-2-iminoimidazoliciin-4-yl)serylseryl];

Cyclo[glycyl-(S)-β-methyl-L-phenylalanyl-O-[4-O-[2,3-O-(3-methoxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[2,3-O-(3-methoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl);

Cyclo[glycyl-(S)-β-methyl-L-phenylalanyl-O-[4-O-[2,3-O-(3-methoxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[2,3-O-(3-methoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-4,6-O-(3-chlorobenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-chlorobenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-isopropylbenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-isopropylbenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-propylbenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl);

Cyclo[glycyl-β-methylphenylalanyl-O-[4-O-[4,6-O-(4-propylbenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-carboxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-carboxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-ethoxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-ethoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(1,3-benzodioxol-5-ylmethylene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl);

Cyclo[glycyl-β-methylphenylalanyl-O-[4-O-[4,6-O-(1,3-benzodioxol-5-ylmethylene)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[4-(methylthio)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[4-(methylthio)benzylidene)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(2-naphthylmethylene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-4,6-O-(2-naphthylmethylene)hexopyranosyl]-hexopyranosyl]tyrosyl-3-(2-iminoimidazolidin-4-yl)seryl-3-(3-hexopyranosyl-2-iminoimidazoliclin-4-yl)serylseryl];

Cyclo[glycyl-(S)-β-methyl-L-phenylalanyl-O-[4-O-[4,6-o-[3-(2-methylprop-1-en-1-yl)-benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-β-(2-methylprop-1-en-1-yl)benzylidene]-hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-tert-butylbenzylidene)-α-D-mannopyranosyl]-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-tert-butylbenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-4,6-O-(4-propyloxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-propyloxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[(2,3-dihydro-1,4-benzodioxan-6-yl)-methylene]-α-D-mannopyranosyl]-α-D-mannopyranosyl]-D-tyrosyl-3-(2- iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[(2,3-dihydro-1,4-benzodioxan-6-yl)-methylene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(3,5-dimethoxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3,5-dimethoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[2,3-O-(3,5-dimethoxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[2,3-O-(3,5-dimethoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(3-methyl-4-nitrobenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-methyl-4-nitrobenzylidene)hexopyranosyl]hexopyranosyl]tyrosyl-3-(2-iminoimidazolidin-4-yl)seryl-3-(3-hexopyranosyl-2-iminoimidazoliciin-4-yl)serylseryl];

Cyclo[glycyl-(S)-β-methyl-L-phenylalanyl-O-[4-O-[4,6-O-(3-ethoxy-4-methoxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-(4-O-[4,6-O-(3-ethoxy-4-methoxybenzylidene)hexopyranosyl]hexopyranosyl]tyrosyl-3-(2-iminoimidazoliciin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(3-methoxy-4-nitrobenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-methoxy-4-nitrobenzylidene)hexopyranosyl]hexopyranosyl]tyrosyl-3-(2-iminoimidazolidin-4-yl)seryl-3-(3-hexopyranosyl-2-iminoimidazolidin-4-yl)serylseryl];

cyclo[glycyl-(S)-β-methyl-L-phenylalanyl-O-[4-O-[4,6-O-(3-phenylbenzylidene)-α-D-mannopyranosyl]-α-D-mannopyranosyl]-D-tyrosyl-3-(2-iminoimidazoliciin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-phenylbenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-(4-O-α-D-mannopyranosyl-α-D-mannopyranosyl)-D-tyrosyl-3-[2-[(2,2-dimethylpropanoyl)imino]imidazolidin-4-yl]-L-seryl-3-(2-imino-3-α-D-mannopyranosylimidazolidin-4-yl)-D-seryl-L-seryl];

Cyclo[glycyl-β-methylphenylalanyl-O-(4-O-hexopyranosylhexopyranosyl)tyrosyl-3-[2-[(2,2-dimethylpropanoyl)imino]imidazolidin-4-yl]seryl-3-(3-hexopyranosyl-2-iminoimidazolidin-4-yl)serylseryl];

Cyclo[glycyl-(S)-β-methyl-L-phenylalanyl-O-[4-O-[4,6-O-β-(3-pyridyl)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-β-(3-pyridyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[4-(methylsulfonyl)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[4-(methylsulfonyl)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[(6-chloro-1,3-benzodioxol-5-yl)-methylene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[(6-chloro-1,3-benzodioxol-5-yl)-methylene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[(6-methoxy-2-naphthyl)-methylene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[(6-methoxy-2-naphthyl)-methylene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-(3-methyl-L-phenylalanyl-O-[4-O-[2,3-O-[(6-methoxy-2-naphthyl)-methylene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[2,3-O-[(6-methoxy-2-naphthyl)-methylene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[(1-acetylindol-3-yl)methylene]-α-D-mannopyranosyl]-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[1-(acetylindol-3-yl)methylene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-β-(3-thienyl)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-β-(3-thienyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[4-(2-thienyl)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[4-(2-thienyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[4-(3-thienyl)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[4-(3-thienyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[2,3-O-[4-(3-thienyl)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[2,3-O-[4-(3-thienyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-β-[(3-methylbut-2-en-1-yl)oxy]-benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-β-[(3-methylbut-2-en-1-yl)oxy]-benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-β-(carboxymethoxy)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-β-(carboxymethoxy)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(3-ethoxy-4-nitrobenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-ethoxy-4-nitrobenzylidene)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O[4-O-[4,6-O-[4-(methylthio)-3-nitrobenzylidene]-α-D-mannopyranosyl]-α-D-mannopyranosyl]-D-tyrosyl-3-(2-iminoimidazoliciin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[4-(methylthio)-3-nitrobenzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-hydroxy-3-methoxy-5-nitro-benzylidene)-α-D-mannopyranosyl]-α-D-mannopyranosyl]-D-tyrosyl-3-(2-iminoimidazoliciin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-hydroxy-3-methoxy-4-nitro-benzylidene)hexopyranosyl]hexopyranosyl]tyrosyl-3-(2-iminoimidazolidin-4-yl)seryl-3-(3-hexopyranosyl-2-iminoimidazoliclin-4-yl)serylseryl];

Cyclo[glycyl-(S)-β-methyl-L-phenylalanyl-O-[4-O-[4,6-O-(3-phenoxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(3-phenoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(4-phenoxybenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-phenoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[4-[(E)-2-phenylethenyl]benzylidene]-α-D-mannopyranosyl]-α-D-mannopyranosyl]-D-tyrosyl-mannopyranosylimidazolidin-4-yl)-D-seryl-L-seryl];

Cyclo[glycyl-β-methylphenylalanyl-O-[4-O-[4,6-O-[4-(2-phenylethenyl)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-4-O-[4,6-O-(4-benzoylbenzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(4-benzoylbenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[4-(4-methylphenoxy)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[4-(4-methylphenoxy)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-β-(phenylmethoxy)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-β-(phenylmethoxy)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[4-(phenylmethoxy)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(4,6-O-[4-(phenylmethoxy)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-4,6-O-β-(4-chlorophenyl)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-β-(4-chlorophenyl)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-(3-methyl-L-phenylalanyl-O-[4-O-[4,6-O-[4-(4-chlorophenyl)benzylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[4-(4-chlorophenyl)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-β-(1,1,2,2-tetrafluoroethoxy)-benzylidene]-α-D-mannopyranosyl]-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-β-(1,1,2,2-tetrafluoroethoxy)benzylidene]-hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-β-(4-methoxyphenoxy)benzylidene)-α-D-mannopyranosyl]-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-β-(4-methoxyphenoxy)benzylidene]hexopyranosyl]hexopyranosyl]tyrosyl-3-(2-iminoimidazolidin-4-yl)seryl-3-(3-hexopyranosyl-2-iminoimidazolichn-4-yl)serylseryl];

Cyclo[glycyl-(S)-β-methyl-L-phenylalanyl-O-[4-O-[4,6-O-[4-(4-tert-butylphenoxy)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[4-(4-tert-butylphenoxy)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl]

Cyclo[glycyl-(S)-β-methyl-L-phenylalanyl-O-[4-O-(4,6-O-[3-[(4-nitrophenyl)methoxy]benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-β-[(4-nitrophenyl)methoxy]benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[[4-[(2E)-3,7-dimethylocta-2,6-dien-1-yl]-oxy]benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[4-[(3,7-dimethylocta-2,6-dien-1-yl)oxy]-benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-β-β-(trifluoromethyl)phenoxy]-benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-β-β-(trifluoromethyl)phenoxy]-benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[[3-[(2E,6E)-3,7,11-trimethyldodeca-2,6,10-tri en-1-yl]oxy]benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-(3-methylphenylalanyl-O-[4-O-[4,6-O-[[3-(3,7,11-trimethyldodeca-2,6,10-tri en-1-yl)oxy]benzylidene]hexopyranosyl]hexopyranosyl]tyrosyl-3-(2-iminoimidazolidin-4-yl)-seryl-3-(3-hexopyranosyl-2-iminoimidazolidin-4-yl)serylseryl];

Cyclo[glycyl-(S)-β-methyl-L-phenylalanyl-O-[4-O-[4,6-O-[4-(4-iodobenzoyl)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[4-(4-iodobenzoyl)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-[4-(3,4,5-triiodobenzoyl)benz-ylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[4-(3,4,5-triiodobenzoyl)benzylidene]-hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(3,3-diphenylprop-2-enylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalany]-O-[4-O-[4,6-O-(3,3-diphenylprop-2-enylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl);

Cyclo[glycyl-(S)-β-methyl-L-phenylalanyl-O-[4-O-[4,6-O-(prop-2-enylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(prop-2-enylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-4,6-O-[(6-methoxy-2-naphtypmethylene)-α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-(4-O-[4,6-O-[(6-methoxy-2-naphthyl)-methylene]hexopyranosyl]hexopyranosyl]tyrosyl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-[4,6-O-[4-(phenylmethoxy)-benzylidene]-α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazoliclin-4-yl)-alanylserylglycyl-β-methylphenylalanyl-O-[4-O-[4,6-O-[4-(phenylmethoxy)benzylidene]hexopyranosyl]hexopyranosyl]tyrosyl);

Cyclo[3-(2-iminoimidazolidin-4-yl)-D-alanyl-3-(2-imino-3-α-D-mannopyranosylimidazolidin-4-yl)-D-alanyl-L-serylglycyl-(S)-β-methyl-L-phenyl alanyl-O-[4-O-[4,6-O-β-(4-methoxy-phenoxy)benzylidene]-α-D-mannopyranosyl]-α-D-mannopyranosyl]-D-tyrosyl];

Cyclo[3-(2-iminoimidazoliclin-4-yl)alanyl-3-(3-hexopyranosyl-2-iminoimidazolidin-4-yl)-alanylserylglycyl-β-methylphenylalanyl-O-[4-O-[4,6-O-β-(4-methoxyphenoxy)benzylidene]-hexopyranosyl]hexopyranosyl]tyrosyl];

Cyclo[glycyl-(S)-4-chloro-β-methyl-L-phenylalanyl-O-[4-O-4,6-O-(cyclohexyhnothylene)-α-mannopyranosyl]α-mannopyranosyl]-D-tyrosyl-3-(2-iminoimidazolidin-4-yl)-L-seryl-3-(2-imino-3α-mannopyranosylimidazolidin-4-yl)-D-seryl-L-seryl];

Cyclo[glycyl-4-chloro-β-methylphenylalanyl-O-[4-O-[4,6-O-(cyclohexylmethylene)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-4-chloro-β-methyl-L-phenylalanyl-O-[4-O-[4,6-O-(2-methylpentylidene)-α-mannopyranosyl]α-mannopyranosyl]-D-tyrosyl-3-(2-iminoimidazolidin-4-yl)-L-seryl-3-(2-imino-3α-mannopyranosylimidazolidin-4-yl)-D-seryl-L-seryl];

Cyclo[glycyl-4-chloro-β-methylphenylalanyl-O-[4-O-4,6-O-(2-methylpentylidene)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-4-chloro-β-methyl-L-phenylalanyl-O-[4-O-(4,6-O-benzylidene-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-4-chloro-β-methylphenylalanyl-O-[4-O-(4,6-O-benzyhdenehexopyranosyl)-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(4,6-O-benzylidene-α-D-mannopyranosyl)-α-D-mannopyranosyl]-3-iodo-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(4,6-O-benzylidenehexopyranosyl)hexopyranosyl]-3-iodotyrosyl-3-(2-iminoimidazolidin-4-yl)seryl-3-(3-hexopyranosyl-2-iminoimidazolidin-4-yl)-serylseryl];

Cyclo[glycyl-(S)-β-methyl-L-phenylalanyl-O-[4-O-[4,6-O-[3-(4-methylphenoxy)benzylidene]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-[3-(4-methylphenoxy)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[3-cyclohexyl-L-alanyl-O-[4-O-[4,6-O-(3-phenylpropylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexylalanyl-O-[4-O-[4,6-O-(3-phenylpropylidene)hexopyranosyl]hexopyranosyl]tyrosyl-3-(2-iminoimidazolidin-4-yl)seryl-3-(3-hexopyranosyl-2-iminoimidazolidin-4-yl)serylserylglycyl];

Cyclo[3-cyclohexyl-L-alanyl-O-[4-O-(4,6-O-benzylidene-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexylalanyl-O-[4-O-(4,6-O-benzyhdenehexopyranosyl)hexopyranosyl]tyrosyl-3-(2-iminoimidazolidin-4-yl)seryl-3-(3-hexopyranosyl-2-iminoimidazolidin-4-yl)-seryl-serylglycyl];

Cyclo[3-cyclohexyl-L-alanyl-O-[4-O-[4,6-O-phenethylidene-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexylalanyl-O-[4-O-[4,6-O-phenethylidenehexopyranosyl]hexopyranosyl]tyrosyl-3-(2-iminoimidazolidin-4-yl)seryl-3-(3-hexopyranosyl-2-iminoimidazolidin-4-yl)serylserylglycyl];

Cyclo[(3S)-3-cyclohexyl-L-2-aminobutanoyl-O-[4-O-[4,6-O-benzylidene-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexyl-2-aminobutanoyl-O-[4-O-[4,6-O-benzylidenehexopyranosyl]hexopyranosyl]tyrosyl-3-(2-iminoimidazolidin-4-yl)seryl-3-(3-hexopyranosyl-2-iminoimidazolidin-4-yl)serylserylglycyl];

Cyclo[glycyl-(S)-4-chloro-β-methyl-L-phenylalanyl-O-[4-O-(4,6-O-cyclopentylidene-α-D-mannopyranosyl)-α-D-mannopyranosyl]-D-tyrosyl-3-(2-iminoimidazoliciin-4-yl)-L-seryl-3-(2-imino-3-α-D-mannopyranosylimidazolidin-4-yl)-D-seryl-L-seryl];

Cyclo[glycyl-4-chloro-β-methylphenylalanyl-O-[4-O-(4,6-O-cyclopentylidenehexopyranosyl)-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(4,6-O-cyclohexylidene-α-D-mamopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylpthenylalanyl-O-[4-O-(4,6-O-cyclohexylidene-4-O-hexopyranosyl)hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(3S)-β-methyl-L-phenylalanyl-O-[4-O-[4,6-O-(2-methylcyclohexylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4,6-O-(2-methylcyclohexylidene)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4,6-O-(2,2-dimethylcyclohexylidene)-α-D-mannopyranosyl]-α-D-mannopyranosyl]-D-tyrosyl-3-(2-iminoimidazolidin- 4-yl)-L-seryl-3-(2-imino-3-α-D-
mannopyranosylimidazolidin-4-yl)-D-seryl-L-seryl];
Cyclo[glycyl-β-methylphenylalanyl-O-[4-O-[4,6-O-(2,2-
dimethylcyclohexylidene)hexopyranosyl]hexopyranosyl]
tyrosyl-3-(2-iminoimidazolidin-4-yl)seryl-3-(3-hexopy-
ranosyl-2-iminoimidazolidin-4-yl)serylseryl];
Cyclo[glycyl-(S)-β-methyl-L-phenylalanyl-O-[4-O-[4,6-O-
(2,6-dimethylcyclohexylidene)-α-D-mannopyranosyl]-α-
D-mannopyranosyl]-D-tyrosyl-3-(2-iminoimidazolidin-
4-yl)-L-seryl-3-(2-imino-3-α-D-
mannopyranosylimidazolidin-4-yl)-D-seryl-L-seryl];
Cyclo[glycyl-β-methylphenylalanyl-O-[4-O-[4,6-O-(2,6-
dimethylcyclohexylidene)hexopyranosyl]hexopyranosyl]
tyrosyl-3-(2-iminoimidazolidin-4-yl)seryl-3-(3-hexopy-
ranosyl-2-iminoimidazolidin-4-yl)serylseryl];
Cyclo[glycyl-(S)-β-methyl-L-phenylalanyl-O-[4-O-[4,6-O-
(3,3,5,5-tetramethylcyclohex ylidene)-α-D-mannopyra-
nosyl]-α-D-mannopyranosyl]-D-tyrosyl-3-(2-iminoimi-
dazolidin-4-yl)-L-seryl-3-(2-imino-3-α-D-
mannopyranosylimidazolidin-4-yl)-D-seryl-L-seryl];
Cyclo[glycyl-β-methylphenylalanyl-O-[4-O-[4,6-O-(3,3,5,
5-tetramethylcyclohexylidene)hexopyranosyl]hexopyra-
nosyl]tyrosyl-3-(2-iminoimidazolidin-4-yl)seryl-3-(3-
hexopyranosyl-2-iminoimidazolidin-4-yl)serylseryl];
Cyclo[glycyl-(S)-(3-methyl-L-phenylalanyl-O-[4-O-[4,6-
O-(4-tert-butylcyclohex ylidene)-α-D-mannopyranosyl]-
α-D-mannopyranosyl]-D-tyrosyl-3-(2-iminoimidazoli-
din-4-yl)-L-seryl-3-(2-imino-3-α-D-
mannopyranosylimidazolidin-4-yl)-D-seryl-L-seryl];
Cyclo[glycyl-β-methylphenylalanyl-O-[4-O-[4,6-O-(4-tert-
butylcyclohexylidene)hexopyranosyl]hexopyranosyl]ty-
rosyl-3-(2-iminoimidazolidin-4-yl)seryl-3-(3-hexopyra-
nosyl-2-iminoimidazolidin-4-yl)serylseryl];
Cyclo[glycyl-(S)-(3-methyl-L-phenylalanyl-O-[4-O-(4,6-
O-cyclododecylidene-α-D-mannopyranosyl)-α-D-man-
nopyranosyl]-D-tyrosyl-3-(2-iminoimidazolidin-4-yl)-L-
seryl-3-(2-imino-3-α-D-mannopyranosylimidazolidin-4-
yl)-D-seryl-L-seryl];
Cyclo[glycyl-β-methylphenylalanyl-O-[4-O-(4,6-O-cy-
clododecylidenehexopyranosyl)-hexopyranosyl]tyrosyl-
3-(2-iminoimidazolidin-4-yl)seryl-3-(3-hexopyranosyl-2-
iminoimidazolidin-4-yl)serylseryl];
Cyclo[glycyl-(S)-β-methyl-L-phenylalanyl-O-[4-O-(4,6-O-
cyclotridecylidene-α-D-mannopyranosyl)-α-D-man-
nopyranosyl]-D-tyrosyl-3-(2-iminoimidazolidin-4-yl)-L-
seryl-3-(2-imino-3-α-D-mannopyranosylimidazolidin-4-
yl)-D-seryl-L-seryl];
Cyclo[glycyl-β-methylphenylalanyl-O-[4-O-(4,6-O-cyclot-
ridecylidene)hexopyranosyl]hexopyranosyl]tyrosyl-3-(2-
iminoimidazolidin-4-yl)seryl-3-(3-hexopyranosyl-2-imi-
noimidazolidin-4-yl)serylseryl];
Cyclo[glycyl-(S)-β-methyl-L-phenylalanyl-O-[4-O-(2,3-O-
cyclotridec ylidene-α-D-mannopyranosyl)-α-D-man-
nopyranosyl]-D-tyrosyl-3-(2-iminoimidazolidin-4-yl)-L-
seryl-3-(2-imino-3-α-D-mannopyranosylimidazolidin-4-
yl)-D-seryl-L-seryl];
Cyclo[glycyl-β-methylphenylalanyl-O-[4-O-(2,3-O-cyclot-
ridecylidenehexopyranosyl)hexopyranosyl]tyrosyl-3-(2-
iminoimidazolidin-4-yl)seryl-3-(3-hexopyranosyl-2-imi-
noimidazolidin-4-yl)serylseryl];
Cyclo[glycyl-(S)-β-methyl-L-phenylalanyl-O-[4-O-[4,6-O-
(bicylo-[3.2.1]oct-2-ylidene)-α-D-mannopyranosyl]-α-
D-mannopyranosyl]-D-tyrosyl-3-(2-iminoimidazolidin-
4-yl)-L-seryl-3-(2-imino-3-α-D-
mannopyranosylimidazolidin-4-yl)-D-seryl-L-seryl];
Cyclo[glycyl-β-methylphenylalanyl-O-[4-O-[4,6-O-(bi-
cylo-[3.2.1]oct-2-ylidene)-hexopyranosyl]hexopyrano-
syl]tyrosyl-3-(2-iminoimidazolidin-4-yl)seryl-3-(3-hex-
opyranosyl-2-iminoimidazolidin-4-yl)serylseryl];
Cyclo[glycyl-(S)-β-methyl-L-phenylalanyl-O-[4-O-(4,6-O-
bicyclo[3.3.1]non-9-ylidene-α-D-mannopyranosyl)-α-D-
mannopyranosyl]-D-tyrosyl-3-(2-iminoimidazolidin-4-
yl)-L-seryl-3-(2-imino-3-α-D-
mannopyranosylimidazolidin-4-yl)-D-seryl-L-seryl];
Cyclo[glycyl-β-methylphenylalanyl-O-[4-O-(4,6-O-bicyclo
[3.3.1]non-9-ylidenehexopyranosyl)hexopyranosyl]ty-
rosyl-3-(2-iminoimidazolidin-4-yl)seryl-3-(3-hexopyra-
nosyl-2-iminoimidazolidin-4-yl)serylseryl];
Cyclo[glycyl-(S)-β-methyl-L-phenylalanyl-O-[4-O-(4,6-O-
tricyclo[5.2.1.0(2,6)]decan-2-ylidene-α-D-mannopyrano-
syl)-α-D-mannopyranosyl]-D-tyrosyl-3-(2-iminoimida-
zolidin-4-yl)-L-seryl-3-(2-imino-3-α-D-
mannopyranosylimidazolidin-4-yl)-D-seryl-L-seryl];
Cyclo[glycyl-β-methylphenylalanyl-O-[4-O-(4,6-O-tricyclo
[5.2.1.0(2,6)]decan-2-ylidenehexopyranosyl)hexopyrano-
syl]tyrosyl-3-(2-iminoimidazolidin-4-yl)seryl-3-(3-hex-
opyranosyl-2-iminoimidazolidin-4-yl)serylseryl];
Cyclo[glycyl-(S)-β-methyl-L-phenylalanyl-O-[4-O-[4,6-O-
[(1R,4R)-1,7,7-trimethylbicyclo[2.2.1]hept-2-ylidene)-α-
D-mannopyranosyl]-α-D-mannopyranosyl]-D-tyrosyl-3-
(2-iminoimidazolidin-4-yl)-L-seryl-3-(2-imino-3-α-D-
mannopyranosylimidazolidin-4-yl)-D-seryl-L-seryl];
Cyclo[glycyl-β-methylphenylalanyl-O-[4-O-4,6-O-(1,7,7-
trimethylbicyclo[2.2.1]hept-2-ylidene)hexopyranosyl]
hexopyranosyl]tyrosyl-3-(2-iminoimidazolidin-4-yl)
seryl-3-(3-hexopyranosyl-2-iminoimidazolidin-4-yl)
serylseryl];
Cyclo[glycyl-(S)-β-methyl-L-phenylalanyl-O-[4-O-[4,6-O-
[(1S,4S)-1,7,7-trimethylbicyclo[2.2.1]hept-2-ylidene]-α-
D-mannopyranosyl]-α-D-mannopyranosyl]-D-tyrosyl-3-
(2-iminoimidazolidin-4-yl)-L-seryl-3-(2-imino-3-α-D-
mannopyranosylimidazolidin-4-yl)-D-seryl-L-seryl];
Cyclo[glycyl-β-methylphenylalanyl-O-[4-O-[4,6-O-(1,7,7-
trimethylbicyclo[2.2.1]hept-2-ylidene)hexopyranosyl]
hexopyranosyl]tyrosyl-3-(2-iminoimidazolidin-4-yl)
seryl-3-(3-hexopyranosyl-2-iminoimidazolidin-4-yl)
serylseryl];
Cyclo[glycyl-(S)-β-methyl-L-phenylalanyl-O-[4-O-[4,6-O-
(4-fluoro-α-methylbenzylidene)-α-D-mannopyranosyl]-
α-D-mannopyranosyl]-D-tyrosyl-3-(2-iminoimidazoli-
din-4-yl)-L-seryl-3-(2-imino-3-α-D-
mannopyranosylimidazolidin-4-yl)-D-seryl-L-seryl];
Cyclo[glycyl-β-methylphenylalanyl-O-[4-O-[4,6-O-(4-
fluoro-α-methylbenzylidene)hexopyranosyl]hexopyrano-
syl]tyrosyl-3-(2-iminoimidazolidin-4-yl)seryl-3-(3-hex-
opyranosyl-2-iminoimidazolidin-4-yl)serylseryl];
Cyclo[glycyl-(S)-β-methyl-L-phenylalanyl-O-[4-O-[4,6-O-
(tetrahydrothiopyran-4-ylidene)-α-D-mannopyranosyl]-
α-D-mannopyranosyl]-D-tyrosyl-3-(2-iminoimidazoli-
din-4-yl)-L-seryl-3-(2-imino-3-α-D-
mannopyranosylimidazolidin-4-yl)-D-seryl-L-seryl];
Cyclo[glycyl-β-methylphenylalanyl-O-[4-O-4,6-O-(tet-
rahydrothiopyran-4-ylidene)hexopyranosyl]hexopyrano-
syl]tyrosyl-3-(2-iminoimidazolidin-4-yl)seryl-3-(3-hex-
opyranosyl-2-iminoimidazolidin-4-yl)serylseryl];
Cyclo[glycyl-(S)-β-methyl-L-phenylalanyl-O-[4-O-[4,6-O-
(2-adamantylidene)-3-O-(3-methyl-butanoyl)-α-D-man-
nopyranosyl]-α-D-mannopyranosyl)-D-tyrosyl-3-(2-imi-
noimidazolidin-4-yl)-L-seryl-3-(2-imino-3-α-D-
mannopyranosylimidazolidin-4-yl)-D-seryl-L-seryl];
Cyclo[glycyl-β-methylphenylalanyl-O-[4-O-[4,6-O-(2-ada-
mantylidene)-3-O-(3-methyl-butanoyl)-hexopyranosyl]

hexopyranosyl]tyrosyl-3-(2-iminoimidazolidin-4-yl)-seryl-3-(3-hexopyranosyl-2-iminoimidazolidin-4-yl)serylseryl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-[4,6-O-(2-adamantylidene)-α-D-mannopyranosyl]-α-D-mannopyranosyl)-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[4,6-O-(2-adamantylidene)hexopyranosyl]-hexopyranosyl]tyrosyl];

Cyclo[glycyl-L-phenylalanyl-O-[4-O-[4,6-O-(2-adamantylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycylphenylalanyl-O-[4-O-[4,6-O-(2-adamantylidene)hexopyranosyl]hexopyranosyl]-tyrosyl-3-(2-iminoimidazolidin-4-yl)seryl-3-(3-hexopyranosyl-2-iminoimidazolidin-4-yl)-serylseryl];

Cyclo[(3S)-3-cyclohexyl-L-2-aminobutanoyl-O-[4-O-[4,6-O-(2-adamantylidene)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexyl-2-aminobutanoyl-O-[4-O-4,6-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)serylserylglycyl];

Cyclo[3-cyclohexyl-L-alanyl-3-[cis-4-[[4-O-[4,6-O-(2-adamantylidene)-α-D-mannopyranosyl]-α-D-mannopyranosyl]oxy]cyclohexyl]-D-alanyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexylalanyl-3-[4-[[4-O-[4,6-O-(2-adamantylidene)hexopyranosyl]hexopyranosyl]oxy]cyclohexyl]alanyl-3-(2-iminoimidazolidin-4-yl)seryl-3-(3-hexopyranosyl-2-iminoimidazolidin-4-yl)serylserylglycyl];

Cyclo[3-cyclohexyl-L-alanyl-3-[trans-4-[[4-O-[4,6-O-(2-adamantylidene)-α-D-mannopyranosyl]-α-D-mannopyranosyl]oxy]cyclohexyl]-D-alanyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexylalanyl-3-[4-[[4-O-[4,6-O-(2-adamantylidene)hexopyranosyl]hexopyranosyl]oxy]cyclohexyl]alanyl-3-(2-iminoimidazolidin-4-yl)seryl-3-(3-hexopyranosyl-2-iminoimidazolidin-4-yl)serylserylglycyl];

Cyclo[glycyl-(S)-β-methyl-L-phenylalanyl-O-[4-O-[4,6-O-(2-adamantylidene)-α-D-mannopyranosyl]-α-D-mannopyranosyl]-D-tyrosyl-3-(2-iminoimidazolidin-4-yl)-L-seryl-3-(1-butyl-2-imino-3-α-D-mannopyranosylimidazolidin-4-yl)-D-seryl-L-seryl];

Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-(1-butyl-3-hexopyranosyl-2-iminoimidazolidin-4-yl)serylseryl];

Cyclo[glycyl-(S)-β-methyl-L-phenylalanyl-O-[4-O-[4,6-O-(2-adamantylidene)-α-D-mannopyranosyl]-α-D-mannopyranosyl]-D-tyrosyl-3-(2-iminoimidazolidin-4-yl)-4-seryl-3-[2-imino-3-α-D-mannopyranosyl-1-(3-methylbut-2-en-1-yl)imidazolidin-4-yl]-D-seryl-L-seryl];

Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-β-hexopyranosyl-2-imino-1-(3-methylbut-2-en-1-yl)imidazolidin-4-yl]serylseryl];

Cyclo[glycyl-(S)-β-methyl-L-phenylalanyl-O-[4-O-4,6-O-(2-adamantylidene)-α-D-mannopyranosyl]-α-D-mannopyranosyl]-D-tyrosyl-3-(2-iminoimidazolidin-4-yl)-1-seryl-3,2-imino-3-α-D-mannopyranosyl-1-[4-(trifluoromethyl)benzyl]imidazolidin-4-yl]-D-seryl-L-seryl]

Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-β-hexopyranosyl-2-imino-1-[4-(trifluoromethyl)benzyl]imidazolidin-4-yl]serylseryl]

Di-N-(2-(1,3-benzoxazolyl))-cyclo[glycyl-(S)-β-methyl-L-phenylalanyl-O-[4-O-[4,6-O-(2-adamantylidene)-α-D-mannopyranosyl]-α-D-mannopyranosyl]-D-tyrosyl-3-[2-iminoimidazolidin-4-yl]-L-seryl-3-[2-imino-3-α-D-mannopyranosylimidazolidin-4-yl]-D-seryl-L-seryl]

Di-N-(2-(1,3-benzoxazolyl))-cyclo[glycyl-α-methylphenylalanyl-O-[4-O-[4,6-O-(2-adamantylidene)hexopyranosyl]hexopyranosyl]tyrosyl-3-[2-iminoimidazolidin-4-yl]seryl-3-β-hexopyranosyl-2-iminoimidazolidin-4-yl]serylseryl]

Di-N-(2-pyrimidinyl)-cyclo[glycyl-(S)-β-methyl-L-phenylalanyl-O-[4-O-[4,6-O-(2-adamantylidene)-α-D-mannopyranosyl]-α-D-mannopyranosyl]-D-tyrosyl-3-[2-iminoimidazolidin-4-yl]-L-seryl-3-[2-imino-3-α-D-mannopyranosyl-imidazolidin-4-yl]-D-seryl-L-seryl]

Di-N-(2-pyrimidinyl)-cyclo[glycyl-β-methylphenylalanyl-O-[4-O-[4,6-O-(2-adamantylidene)hexopyranosyl]hexopyranosyl]tyrosyl-3,2-iminoimidazolidin-4-yl]seryl-3-β-hexopyranosyl-2-iminoimidazolidin-4-yl]serylseryl]

Cyclo[glycyl-(S)-β-methyl-L-phenylalanyl-O-(2,3-O-isopropylidene-4-O-α-D-mannopyranosyl-α-D-mannopyranosyl)-D-tyrosyl-3-(2-iminoimidazolidin-4-yl)-L-seryl-3-[2-imino-3-(2,3-O-isopropylidene-α-D-mannopyranosyl)imidazolidin-4-yl]-D-seryl-L-seryl];

Cyclo[glycyl-β-methylphenylalanyl-O-(2,3-O-isopropylidene-4-O-hexopyranosylhexopyranosyl)tyrosyl-3-(2-iminoimidazolidin-4-yl)seryl-3-[2-imino-(2,3-O-isopropylidene-hexopyranosyl)imidazolidin-4-yl]serylseryl];

Cyclo[glycyl-(S)-β-methyl-L-phenylalanyl-O-[2,3-O-isopropylidene-4-O-(2,3-isopropylidene-α-D-mannopyranosyl)-α-D-mannopyranosyl]-D-tyrosyl-3-(2-iminoimidazolidin-4-yl)-L-seryl-3-[2-imino-3-(2,3-O-isopropylidene-α-D-mannopyranosyl)imidazolidin-4-A-D-seryl-L-seryl];

Cyclo[glycyl-β-methylphenylalanyl-O-[2,3-O-isopropylidene-4-O-(2,3-isopropylidenehexopyranosyl)hexopyranosyl]tyrosyl-3-(2-iminoimidazolidin-4-yl)seryl-3-[2-imino-3-(2,3-O-isopropylidenehexopyranosyl)imidazolidin-4-yl]serylseryl];

Cyclo[glycyl-(S)-β-methyl-L-phenylalanyl-O-[2,3-O-isopropylidene-4-O-(2,3:4,6-di-O-iso-propylidene-α-D-mannopyranosyl)-α-D-mannopyranosyl]-D-tyrosyl-3-(2-iminoimidazolidin-4-yl)-L-seryl-3-[2-imino-3-(2,3-O-isopropylidene-α-D-mannopyranosyl)imidazolidin-4-yl]-D-seryl-L-seryl];

Cyclo[glycyl-β-methylphenylalanyl-O-[2,3-O-isopropylidene-4-O-(2,3:4,6-di-O-isopropylidene-hexopyranosyl)hexopyranosyl]tyrosyl-3-(2-iminoimidazolidin-4-yl)seryl-3-[2-imino-(2,3-O-isopropylidenehexopyranosyl)imidazolidin-4-yl]serylseryl];

Cyclo[glycyl-(S)-β-methyl-L-phenylalanyl-O-4-O-[6-O-[(6-methoxy-2-naphthyl)methyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-[(6-methoxy-2-naphthyl)methyl]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4-O-[(6-methoxy-2-naphthyl)methyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4-O-[(6-methoxy-2-naphthyl)methyl]hexopyranosylpexopyranosyl]tyrosyl-3-(2-iminoimidazolidin-4-yl)seryl-3-(3-hexopyranosyl-2-iminoimidazoliclin-4-yl)serylseryl];

Cyclo[glycyl-(S)-β-methyl-L-phenylalanyl-O-[4-O-[3-O-[(6-methoxy-2-naphthyl)methyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[3-O-[(6-methoxy-2-naphthyl)methyl]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[2-O-[(6-methoxy-2-naphthyl)methyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[2-O-[(6-methoxy-2-naphthyl)methyl]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-[4-(phenylmethoxy)benzyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-[4-(phenylmethoxy)benzyl]hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4-O-[4-(phenylmethoxy)benzyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4-O-[4-(phenylmethoxy)benzyl]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[2-O-[4-(phenylmethoxy)benzyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[2-O-[4-(phenylmethoxy)benzyl]hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[3-O-[4-(phenylmethoxy)benzyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[3-O-[4-(phenylmethoxy)benzyl]hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-(4-methoxybenzyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-(4-methoxybenzyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-(4-ethoxybenzyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-O-methylphenylalanyl-O-[4-O-[6-O-(4-ethoxybenzyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-(4-methylbenzyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-(4-methylbenzyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-(4-propoxybenzyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-(4-propoxybenzyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-(4-phenoxybenzyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-(4-phenoxybenzyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-(3-fluoro-4-methoxybenzyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-(3-fluoro-4-methoxybenzyl)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-(3-ethoxy-4-methoxybenzyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-(3-ethoxy-4-methoxybenzyl)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-[4-methoxy-3-(phenylmethoxy)-benzyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-[4-methoxy-3-(phenylmethoxy)benzyl]-hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4-O-[4-methoxy-3-(phenylmethoxy)-benzyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4-O-[4-methoxy-3-(phenylmethoxy)benzyl]-hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-[(4-methoxy-1-naphthyl)methyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-[(4-methoxy-1-naphthyl)methyl]hexo-pyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4-O-[(4-methoxy-1-naphthyl)methyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4-O-[(4-methoxy-1-naphthyl)methyl]hexo-pyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[2-O-[(4-methoxy-1-naphthyl)methyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[2-O-[(4-methoxy-1-naphthyl)methyl]hexo-pyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-(3,3-diphenylprop-2-en-1-yl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-(3,3-diphenylprop-2-en-1-yl)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4-O-(3,3-diphenylprop-2-en-1-yl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4-O-(3,3-diphenylprop-2-en-1-yl)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-[(2E)-3-phenylprop-2-en-1-yl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-(3-phenylprop-2-en-1-yl)hexopyranosyl]-hexopyranosyl)tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-[3-[4-(dimethylamino)phenyl](2E)-prop-2-en-1-yl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-[3-[4-(dimethylamino)phenyl]prop-2-en-1-yl]hexopyranosyl]hexopyranosyl]tyrosyl (3-hexopyranosyl-2-iminoimidazolidin-4-yl)serylseryl];

Cyclo[glycyl-(S)-β-methyl-L-phenylalanyl-O-[4-O-[4-O-[3-[4-(dimethylamino)phenyl](2E)-prop-2-en-1-yl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4-O-[3-[4-(dimethylamino)phen yl]prop-2-en-1-yl]hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-(2-thienylmethyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-[2-thienylmethyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-[6-O-[(6-methoxy-2-naphthyl)methyl]-α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[6-O-[(6-methoxy-2-naphthyl)methyl]-hexopyranosyl]hexopyranosyl]tyrosyl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-[4-O-[(6-methoxy-2-naphthyl)methyl]-α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[4-O-[(6-methoxy-2-naphthyl)methyl]-hexopyranosyl]hexopyranosyl]tyrosyl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-[3-O-[(6-methoxy-2-naphthyl)methyl]-α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[3-O-[(6-methoxy-2-naphthyl)methyl]-hexopyranosyl]hexopyranosyl]tyrosyl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-[2-O-[(6-methoxy-2-naphthyl)methyl]-α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[2-O-[(6-methoxy-2-naphthyl)methyl]-hexopyranosyl]hexopyranosyl]tyrosyl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-[6-O-[4-(phenylmethoxy)-benzyl]-α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[6-O-[4-(phenylmethoxy)benzyl]hexopyranosyl]hexopyranosyl]tyrosyl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-[4-O-[4-(phenylmethoxy)-benzyl]-α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[4-O-[4-(phenylmethoxy)benzyl]hexopyranosyl]hexopyranosyl]tyrosyl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-[3-O-[4-(phenylmethoxy)-benzyl]-α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[3-O-[4-(phenylmethoxy)benzyl]hexopyranosyl]hexopyranosyl]tyrosyl];

Cyclo[3-(2-iminoimidazolidin-4-yl)-L-alanyl-3-(2-imino-3-α-D-mannopyranosylimidazolidin-4-yl)-D-alanyl-L-serylglycyl-(5)-(3-methyl-L-phenylalanyl-O-[4-O-[2-O-[4-(phenylmethoxy)-benzyl]-α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[2-O-[4-(phenylmethoxy)benzyl]hexopyranosyl]hexopyranosyl]tyrosyl];

Cyclo[glycyl-(S)-β-methyl-L-phenylalanyl-D-tyrosyl-3-(2-iminoimidazolidin-4-yl)-L-seryl-3-(2,3:4,6-diisopropylidene-α-D-mannopyranosyl)-2-iminoimidazolidin-4-yl-D-seryl-L-seryl];

Cyclo[glycyl-β-methylphenylalanyltyrosyl-3-(2-iminoimidazolidin-4-yl)seryl-3-(2,3:4,6-diisopropylidenehexopyranosyl)-2-iminoimidazolidin-4-ylseryl];

Cyclo[glycyl-(S)-β-methyl-L-phenylalanyl-D-tyrosyl-3-(2-iminoimidazolidin-4-yl)-L-seryl-3-β-(2,3:4,6-di-O-isopropylidene-α-D-mannopyranosyl)-2-iminoimidazolidin-4-yl]-D-seryl-O-(tert-butyldimethylsilyl)-L-seryl];

Cyclo[glycyl-β-methylphenylalanyltyrosyl-3-(2-iminoimidazolidin-4-yl)seryl-3-β-(2,3:4,6-di-O-isopropylidenehexopyranosyl)-2-iminoimidazolidin-4-yl]seryl-O-(tert-butyldimethylsilyl)seryl];

Tri-N-[(phenylmethoxy)carbonyl]-cyclo[glycyl-(S)-β-methyl-L-phenylalanyl-D-tyrosyl-3-(2-iminoimidazolidin-4-yl)-L-seryl-3-β-(2,3:4,6-di-O-isopropylidene-α-D-mannopyranosyl)-2-iminoimidazolidin-4-yl]-D-seryl-O-(tert-butyldimethylsilyl)-L-seryl];

Tri-N-[(phenylmethoxy)carbonyl)-cyclo[glycyl-β-methylphenylalanyltyrosyl-3-(2-iminoimidazolidin-4-yl)seryl-3-β-(2,3:4,6-di-O-isopropylidenehexopyranosyl)-2-iminoimidazolidin-4-yl]seryl-O-(tert-butyldimethylsilyl)seryl];

Tetra-N-[(phenylmethoxy)carbonyl]-cyclo[glycyl-(S)-β-methyl-L-phenylalanyl-D-tyrosyl-3-(2-iminoimidazolidin-4-yl)-L-seryl-3-(2-iminoimidazolidin-4-yl)-D-seryl-O-(tert-butyldimethylsilyl)-L-seryl];

Tetra-N-[(phenylmethoxy)carbonyl]cyclo[glycyl-β-methylphenylalanyltyrosyl-3-(2-iminoimidazolidin-4-yl)seryl-3-(2-iminoimidazolidin-4-yl)seryl-O-(tert-butyldimethylsilyl)seryl];

α-O-[(Pentylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

α-O-[(Pentylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

β-O-[(Pentylamino)carbonyl]-Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

β-O-[(Pentylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

γ-O-[(Pentylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

γ-O-[(Pentylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

α-O-[(Butylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

α-O-[(Butylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

α-O-[(Butylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

β-O-[(Butylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazoliclin-4-yl)serylseryl];

α-O-[(Heptylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

α-O-[(Heptylamino)carbonyl]-cyclo[glycyl-β-methylphenylalanyl-O-(4-O-hexopyrartosylhexopyranosyl)tyrosyl-3-(2-iminoimidazolidin-4-yl)seryl-3-(3-hexopyranosyl-2-iminoimidazolidin-4-yl)serylseryl];

β-O-[(Heptylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

β-O-[(Heptylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

γ-O-[(Heptylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

γ-O-[(Heptylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

α-O-[(Dodecylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

α-O-[(Dodecylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

β-O-[(Dodecylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

β-O-[(Dodecylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

γ-O-[(Dodecylamino)carbonyl]-cyclo[glycyl-(S)-(3-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

γ-O-[(Dodecylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

α-O-[(N-Methyl-2-methylpropylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

α-O-[(N-Methyl-2-methylpropylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

β-O-[(N-Methyl-2-methylpropylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyrartosylimidazolidin-4-yl)-D-seryl-L-seryl];

β-O-[(N-Methyl-2-methylpropylamino)carbonyl]-cyclo[glycyl-β-methylphenylalanyl-0-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

α-O-[(Cyclohexylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

α-O-[(Cyclohexylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

β-O-[(Cyclohexylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

β-O-[(Cyclohexylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

α-O-[(Benzylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

α-O-[(Benzylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl);

β-O-[(Benzylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

β-O-[(Benzylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl);

γ-O-[(Benzylamino)carbonyl]-cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl);

γ-O-[(Benzylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl);

Cyclo[glycyl-(S)-4-fluoro-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-4-fluoro-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl)

Cyclo[glycyl-(S)-4-fluoro-β-methyl-L-phenylalanyl-O-(4-O-(2-O-(3-methylbutanoyl)-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-4-fluoro-β-methylphenylalanyl-O-[4-O-[2-O-(3-methylbutanoyl)hexopyranosyl]-hexopyranosyl]tyrosyl-3-(2-iminoimidazolidin-4-yl)seryl-3-(3-hexopyranosyl-2-imino-imidazolidin-4-yl)serylseryl]

Cyclo[glycyl-(S)-4-fluoro-β-methyl-L-phenylalanyl-O-[4-O-[3-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-4-fluoro-β-methylphenylalanyl-O-[4-O-[3-O-(3-methylbutanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl]

Cyclo[glycyl-(S)-4-chloro-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-4-chloro-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

Cyclo[glycyl-(S)-4-chloro-β-methyl-L-phenylalanyl-O-[4-O-[3-O-(3-methylbutanoyl)α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-4-chloro-β-methylphenylalanyl-O-[4-O-[3-O-(3-methylbutanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-4-chloro-β-methyl-L-phenylalanyl-O-[4-O-[2-O-(3-methylbutanoyl)α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-4-chloro-β-methylphenylalanyl-O-[4-O-[2-O-(3-methylbutanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[3-cyclohexyl-L-alanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylserylglycyl]

Cyclo[glycyl-(S)-3-fluoro-β-methyl-L-phenylalanyl-O-[4-O-[2-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-3-fluoro-β-methylphenylalanyl-O-[4-O-[2-O-(3-methylbutanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl]

Cyclo[glycyl-(S)-3-fluoro-β-methyl-L-phenylalanyl-O-[4-O-[3-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-3-fluoro-β-methylphenylalanyl-O-[4-O-[3-O-(3-methylbutanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl]

Cyclo[glycyl-(S)-3-fluoro-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-3-fluoro-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]

Cyclo[(3R)-3-(2-thienyl)-L-2-aminobutanoyl-O-[4-O-[2-O-(3-methylbutanoyl)α-D-mannopyranosyl]-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[3-(2-thienyl)-2-aminobutanoyl-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylserylglycyl];

Cyclo[(3R)-3-(2-thienyl)-L-2-aminobutanoyl-O-[4-O-[3-O-(3-methylbutanoyl)α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl);

Cyclo[3-(2-thienyl)-2-aminobutanoyl-O-[4-O-[3-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylserylglycyl]

Cyclo[(3R)-3-(2-thienyl)-L-2-aminobutanoyl-O-[4-O-α-D-mannopyranosyl-α-D-mannopyranosyl)-D-tyrosyl-3-(2-iminoimidazoliclin-4-yl)-L-seryl-3-(2-imino-3-α-D-mannopyranosylimidazolidin-4-yl)-D-seryl-L-seryl];

Cyclo[3-(2-thienyl)-2-aminobutanoyl-O-(4-O-hexopyranosylhexopyranosyl)tyrosyl-3-(2-iminoimidazolidin-4-yl)seryl-3-(3-hexopyranosyl-2-iminoimidazoliclin-4-yl)serylserylglycyl];

Cyclo[glycyl-(S)-β-methyl-L-phenylalanyl-3-fluoro-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-fluoro-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]

Cyclo[glycyl-(S)-β-methyl-L-phenylalanyl-3-fluoro-O-[4-O-[2-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-fluoro-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-fluoro-O-[4-O-[3-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-fluoro-O-[4-O-[3-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-amino-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-amino-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenyl alanyl-3-amino-O-[4-O-[2-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-amino-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-3-amino-O-[4-O-[3-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-3-amino-O-[4-O-[3-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-L-phenylglycyl-O-[4-O-[2-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-phenylglycyl-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-2-chloro-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-2-chloro-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

Cyclo[glycyl-(S)-2-chloro-β-methyl-L-phenylalanyl-O-[4-O-[2-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-2-chloro-β-methylphenylalanyl-O-[4-O-[2-O-(3-methylbutanoyl)hexopyranosyl]hexopyranosyl)tyrosyl-3-(2-iminoimidazolidin-4-yl)seryl-3-(3-hexopyranosyl-2-iminoimidazolidin-4-yl)serylseryl];

Cyclo[glycyl-(S)-2-chloro-β-methyl-L-phenylalanyl-O-[4-O-[3-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-2-chloro-β-methylphenylalanyl-O-[4-O-[3-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[2-O-(4-methylpentanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[2-O-(4-methylpentanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-acetyl-3-O-(4-methylpentanoyl)-α-D-mannopyranosyl]-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-acetyl-3-O-(4-methylpentanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[4-O-(4-methylpentanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4-O-(4-methylpentanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[3-O-(3-methylpentanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[3-O-(3-methylpentanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-acetyl-3-O-(3-methylpentanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-acetyl-3-O-(3-methylpentanoyl)hexopyranosyl]hexopyranosyl]tyrosyl-3-(2-iminoimidazoliclin-4-yl)seryl-3-(3-hexopyranosyl-2-iminoimidazolidin-4-yl)serylseryl);

Cyclo[glycyl-(S)-β-methyl-L-phenylalanyl-O-[4-O-[4-O-(3-methylpentanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4-O-(3-methylpentanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(2-O-butanoyl-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(2-O-butanoyl-hexopyranosyl)-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(3-O-butanoyl-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(3-O-butanoyl-hexopyranosyl)-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(2-O-hexanoyl-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(2-O-hexanoyl-hexopyranosyl)-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(3-O-hexanoyl-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(3-O-hexanoyl-hexopyranosyl)-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(2-O-heptanoyl-α-D-mannopyranosyl)-α-D-mannopyranosyl]-

D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(2-O-heptanoyl-hexopyranosyl)-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-(3-O-heptanoyl-α-D-mannopyranosyl)-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-(3-O-heptanoyl-hexopyranosyl)-hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-acetyl-3-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-acetyl-3-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-acetyl-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl]

Cyclo[glycyl-β-methylphenylalanyl-O-[4-O-[6-O-acetyl-hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[6-O-acetyl-2-O-(3-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[6-O-acetyl-2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-(4-O-α-D-mannopyranosyl-α-D-mannopyranosyl)-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-(4-O-hexopyranosylhexopyranosyl)tyrosyl];

Cyclo[3-(2-iminoimidazoliclin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-[2-O-(3-methylbutanoyl)α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-4-O-[2-O-(3-methylbutanoyl)hexopyranosyl]-hexopyranosyl]tyrosyl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-O-[4-O-[3-O-(3-methylbutanoyl)α-D-mannopyranosyl]-α-D-mannopyranosyl]-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[3-O-(3-methylbutanoyl)hexopyranosyl]-hexopyranosyl]tyrosyl];

Cyclo[glycyl-(S)-β-methyl-L-phenylalanyl-O-[α-D-mannopyranosyl]-D-tyrosyl-3-(2-iminoimidazolidin-4-yl)-L-seryl-3-(2-iminoimidazolidin-4-yl)-D-seryl-L-seryl];

Cyclo[glycyl-β-methylphenylalanyl-O-hexopyranosyltyrosyl-3-(2-iminoimidazoliclin-4-yl)-seryl-3-(2-iminoimidazolidin-4-yl)serylseryl];

Cyclo[glycyl-(S)-β-methyl-L-phenylalanyl-O-[4-O-[4-O-[(2E)-2-methylbut-2-enoyl]-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-(4-O-[4-O-(2-methylbut-2-enoyl)hexopyranosyl]-hexopyranosyl]tyrosyl-3-(2-iminoimidazolidin-4-yl)seryl-3-(3-hexopyranosyl-2-imino-imidazolidin-4-yl)serylseryl];

Cyclo[glycyl-(S)-β-methyl-L-phenylalanyl-O-[4-O-[4-O-(2-methylbutanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-O-[4-O-[4-O-(2-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[4-O-[3-O-(4-methylpentanoyl)-α-D-mannopyranosyl]-α-D-mannopyranosyl]-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl(3-methylphenylalanyl-O-[4-O-[3-O-(4-methylpentanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-L-phenylalanyl-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycylphenylalanyltyrosyl-3-(2-iminoimidazolidin-4-yl)seryl-3-(3-hexopyranosyl-2-iminoimidazolidin-4-yl)serylseryl];

Cyclo[glycyl-L-phenylalanyl-D-tyrosyl-3-(2-iminoimidazoliclin-4-yl)-L-seryl-3-(2-iminoimidazolidin-4-yl)-D-seryl-L-seryl];

Cyclo[glycylphenylalanyltyrosyl-3-(2-iminoimidazolidin-4-yl)seryl-3-(2-iminoimidazolidin-4-yl)serylseryl];

Cyclo[glycyl-(S)-β-methyl-L-phenylalanyl-D-tyrosyl-3-(2-iminoimidazolidin-4-yl)-L-seryl-3-(2-iminoimidazolidin-4-yl)-D-seryl-L-seryl];

Cyclo[glycyl-β-methylphenylalanyltyrosyl-3-(2-iminoimidazolidin-4-yl)seryl-3-(2-iminoimidazolidin-4-yl)serylseryl];

Cyclo[glycyl-L-phenylalanyl-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

Cyclo[glycyl-L-phenylalanyl-O-(4-O-(6-O-(2-methylpropanoyl)-α-D-mannopyranosyl]-α-D-mannopyranosyl)-D-tyros seryl-3-(2-imino-3-α-D-mannopyranosylimidazolidin-4-yl)-D-seryl-L-seryl];

Cyclo[glycylphenylalanyl-O-[4-O-[6-O-(2-methylpropanoyl)-hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-L-phenylalanyl-O-[4-O-[3-O-(2-methylpropanoyl)-α-D-mannopyranosyl]-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycylphenylalanyl-O-[4-O-[3-O-(2-methylpropanoyl)-hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-L-phenylalanyl-O-(4-O-[6-O-(3-methylbutanoyl)-α-D-mannopyranosyl)-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycylphenylalanyl-O-[4-O-[6-O-(3-methylbutanoyl)-hexopyranosyl]hexopyranosyl]tyrosyl-3-(2-iminoimidazolidin-4-yl)seryl-3-(3-hexopyranosyl-2-iminoimidazoliclin-4-yl)serylseryl];

Cyclo[3-(2-iminoimidazolidin-4-yl)-L-alanyl-3-(2-imino-3-α-D-mannopyranosylimidazolidin-4-yl)-D-seryl-L-serylglycyl-(S)-β-methyl-L-phenylalanyl-O-(4-O-α-D-mannopyranosyl-α-D-mannopyranosyl)-D-tyrosyl);

Cyclo[3-(2-iminoimidazolidin-4-yl)alanyl-3-(3-hexopyranosyl-2-iminoimidazolidin-4-yl)-serylserylglycyl-1-methylphenylalanyl-O-(4-O-hexopyranosylhexopyranosyl)tyrosyl];

Cyclo[3-(2-imino-3-α-D-mannopyranosylimidazolidin-4-yl)-D-alanyl-L-serylglycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl];

Cyclo[3-(3-hexopyranosyl-2-iminoimidazolidin-4-yl)-alanylserylglycyl-O-methylphenylalanyl-O-(4-O-hexopyranosylhexopyranosyl)tyrosyl-3-(2-iminoimidazolidin-4-yl)seryl];

Cyclo[3-(2-iminoimidazolidin-4-yl)-L-alanyl-3-(2-imino-3-α-D-mannopyranosylimidazolidin-4-yl)-D-alanyl-L-serylglycyl-L-phenylalanyl-O-(4-O-α-D-mannopyranosyl-α-D-mannopyranosyl)-D-tyrosyl];

Cyclo[3-(2-iminoimidazolidin-4-yl)alanyl-3-(3-hexopyranosyl-2-iminoimidazolidin-4-yl)-alanylserylglycylphenylalanyl-O-(4-O-hexopyranosylhexopyranosyl)tyrosyl]

Cyclo[glycyl-L-phenylalanyl-O-(4-O-[2-O-(3-methylbutanoyl]-α-D-mannopyranosyl]-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycylphenylalanyl-O-[4-O-[2-O-(3-methylbutanoyl)-hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-L-phenylalanyl-O-(4-O-[3-O-(3-methylbutanoyl]-α-D-mannopyranosyl]-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycylphenylalanyl-O-[4-O-[3-O-(3-methylbutanoyl)-hexopyranosyl]hexopyranosyl]tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-2-amino-O-(4-O-α-D-mannopyranosyl-α-D-mannopyranosyl)-D-tyrosyl-3-(2-iminoimidazolidin-4-yl)-L-seryl-3-(2-imino-3-α-D-mannopyranosylimidazolidin-4-yl)-D-seryl-L-seryl];

Cyclo[glycyl-β-methylphenylalanyl-2-amino-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl];

Cyclo[glycyl-(S)-β-methyl-L-phenylalanyl-O-[α-D-mannopyranosyl]-D-tyrosyl-3-(2-iminoimidazoliclin-4-yl)-L-seryl-3-(2-imino-3-α-D-mannopyranosylimidazolidin-4-yl)-D-seryl-L-seryl];

Cyclo[glycyl-β-methylphenylalanyl-O-hexopyranosyltyrosyl-3-(2-iminoimidazolidin-4-yl)-seryl-3-(3-hexopyranosyl-2-iminoimidazolidin-4-yl)serylseryl];

Cyclo[3-cyclohexyl-L-alanyl-D-tyrosyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexylalanyltyrosyl-3-(2-iminoimidazolidin-4-yl)seryl-3-(3-hexopyranosyl-2-iminoimidazolidin-4-yl)serylserylglycyl];

Cyclo[3-(2-iminoimidazolidin-4-yl)-L-alanyl-3-(2-imino-3-α-D-mannopyranosylimidazolidin-4-yl)-D-alanyl-L-serylglycyl-(S)-β-methyl-L-phenylalanyl-D-tyrosyl];

Cyclo[3-(2-iminoimidazolidin-4-yl)alanyl-3-(3-hexopyranosyl-2-iminoimidazolidin-4-yl)-alanylserylglycyl-β-methylphenylalanyhyrosyl];

Cyclo[(3S)-3-cyclohexyl-L-2-aminobutanoyl-D-tyrosyl-3-(2-iminoimidazolidin-4-yl)-L-seryl-3-(2-imino-3-α-D-mannopyranosylimidazolidin-4-yl)-D-seryl-L-serylglycyl];

Cyclo[3-cyclohexyl-2-aminobutanoyl-tyrosyl-3-(2-iminoimidazolidin-4-yl)seryl-3-(3-hexopyranosyl-2-iminoimidazolidin-4-yl)-serylserylglycyl];

Cyclo[glycyl-(S)-β-methyl-L-phenylalanyl-O-(2,3-O-isopropylidene-α-D-mannopyranosyl)-D-tyrosyl-3-(2-iminoimidazolidin-4-yl)-L-seryl-3-[2-imino-3-(2,3-O-isopropylidene-α-D-mannopyranosyl)imidazolidin-4-yl]-D-seryl-L-seryl];

Cyclo[glycyl-β-methylphenylalanyl-O-(2,3-O-isopropylidene-hexopyranosyl)tyrosyl-3-(2-iminoimidazolidin-4-yl)seryl-3-[2-imino-(2,3-O-isopropylidene-hexopyranosyl)imidazolidin-4-yl]serylseryl];

Cyclo[glycyl-L-phenylalanyl-O-(4-O-α-D-mannopyranosyl-α-D-mannopyranosyl)-D-tyrosyl-3-(2-iminoimidazoliclin-4-yl)-L-seryl-3-(2-iminoimidazolidin-4-yl)-D-seryl-L-seryl];

Cyclo[glycylphenylalanyl-O-(4-O-hexopyranosylhexopyranosyl)tyrosyl-3-(2-iminoimidazolidin-4-yl)seryl-3-(2-iminoimidazolidin-4-yl)serylseryl]

Cyclo[glycyl-(S)-β-methyl-L-phenylalanyl-O-(4-O-α-D-mannopyranosyl-α-D-mannopyranosyl)-D-tyrosyl-3-(2-iminoimidazolidin-4-yl)-L-seryl-3-(2-iminoimidazolidin-4-yl)-D-seryl-L-seryl];

Cyclo[glycyl-β-methylphenylalanyl-O-(4-O-hexopyranosylhexopyranosyl)tyrosyl-3-(2-iminoimidazolidin-4-yl)seryl-3-(2-iminoimidazolidin-4-yl)serylseryl].

An aspect of the invention is a process for producing a compound of the formula:

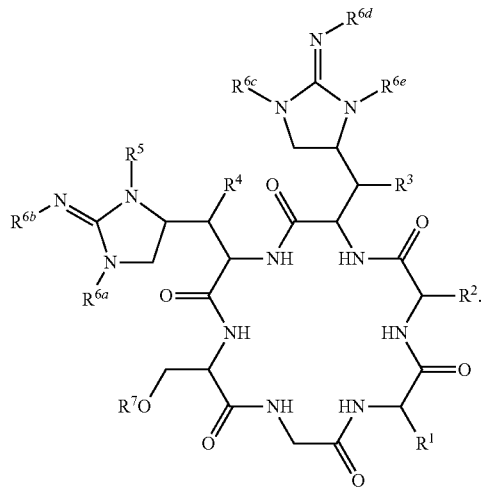

wherein:

R$^1$ is selected from:

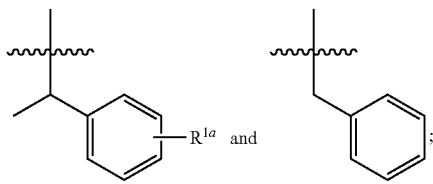

R$^{1a}$ is H;
R$^2$ is a moiety

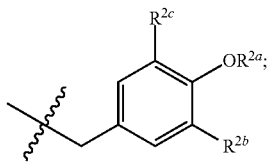

R$^{2a}$ is selected from

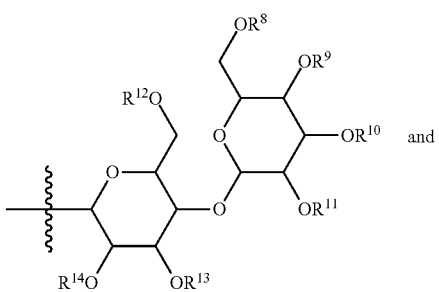

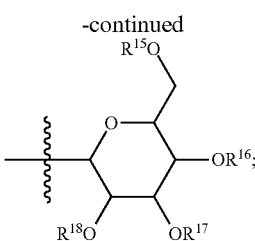

R$^{2b}$ is H;
R$^{2c}$ is H;
R$^3$ and R$^4$ are independently H or OH;
R$^5$ is H or

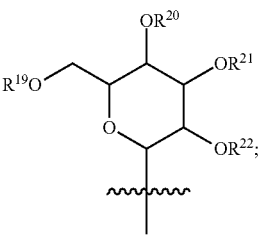

R$^{6a}$, R$^{6b}$, R$^{6c}$; R$^{6d}$, R$^{6e}$ are H;
R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$ and R$^{22}$ are independently
H, or —C(O)—Y—Z;
Y is a single bond;
Z is straight or branched chain alkyl(C$_1$-C$_{20}$) or straight or branched chain alkenyl(C$_2$-C$_{20}$);

which process comprises:

cultivating a glycopeptide antibiotic producing strain of *Streptomyces hygroscopicus* selected from the group LL4600, LL4614, LL4666, LL4690, LL4728, LL4741, LL4742, LL4744, LL4773, LL4779, LL4783, LL4902, BD2, BD20 and BD70 or a mutant thereof under aerobic conditions, in a suitable culture medium until a recoverable amount of said antibiotic is formed in said medium and recovering said antibiotic therefrom. Preferred aspects of the process include:

a.) R$^7$, R$^{12}$, R$^{13}$, R$^{14}$, R$^{15}$, R$^{16}$, R$^{17}$, R$^{18}$, R$^{19}$, R$^{20}$, R$^{21}$ and R$^{22}$ are H; and Z is straight or branched chain alkyl(C$_1$-C$_9$) or straight or branched chain alkenyl(C$_2$-C$_{10}$);

b.) R$^7$, R$^{12}$, R$^{13}$, R$^{14}$, R$^{15}$, R$^{16}$, R$^{17}$, R$^{18}$, R$^{19}$, R$^{20}$, R$^{21}$ and R$^{22}$ are H;

Z is straight or branched chain alkyl(C$_1$-C$_9$) or straight or branched chain alkenyl(C$_2$-C$_{10}$);

R$^3$ and R$^4$ are H;

c.) R$^7$, R$^{12}$, R$^{13}$, R$^{14}$, R$^{15}$, R$^{16}$, R$^{17}$, R$^{18}$, R$^{19}$, R$^{20}$, R$^{21}$ and R$^{22}$ are H;

Z is straight or branched chain alkyl(C$_1$-C$_9$) or straight or branched chain alkenyl(C$_2$-C$_{10}$); and R$^3$ and R$^4$ are OH; and d.) the glycopeptide antibiotic produced has the structure selected from the group

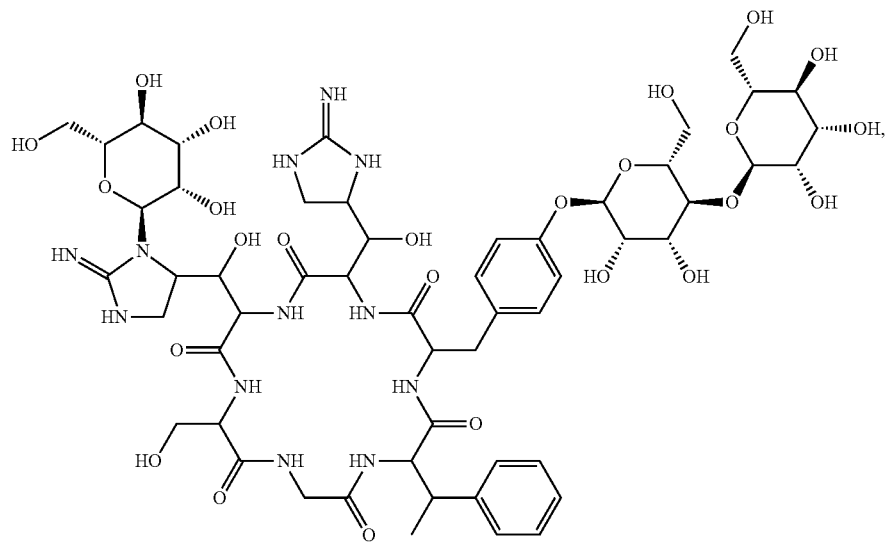
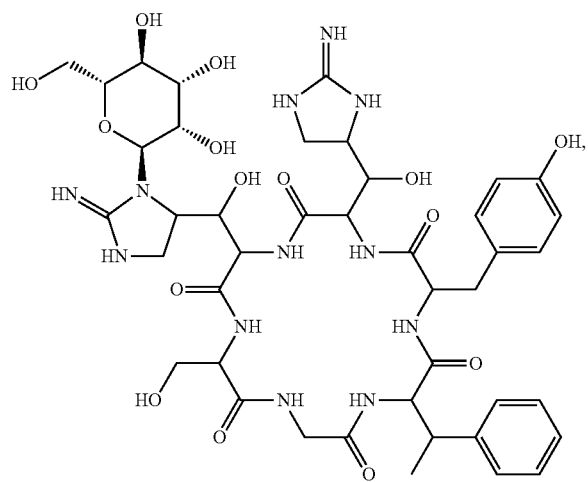
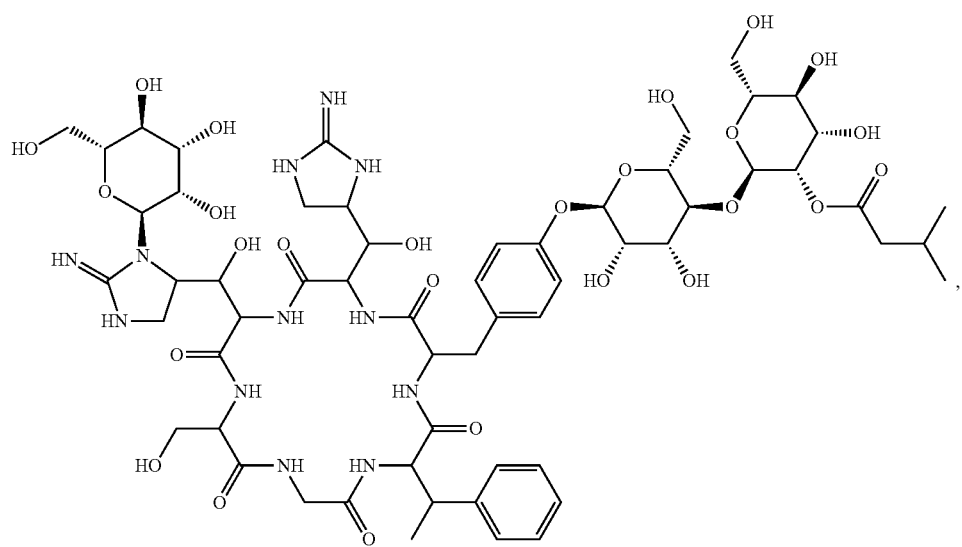

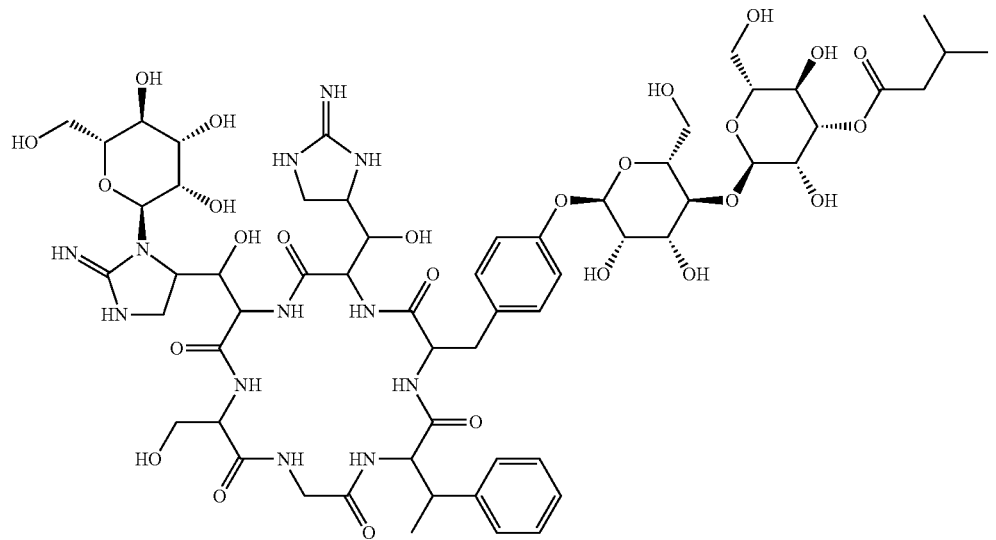
and
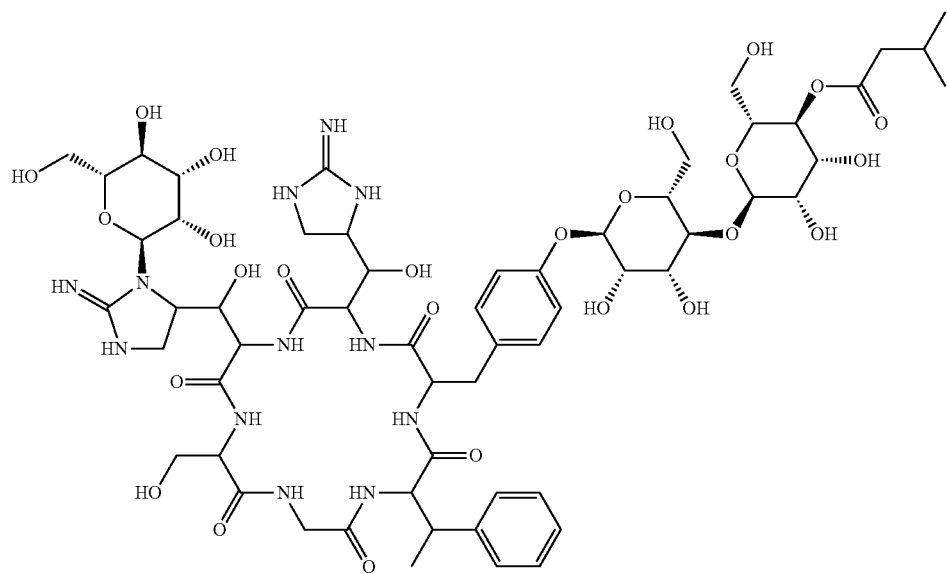

Another aspect of the invention is the preparation by fermentation means in a liquid media using modified strains of *Streptomyces hygroscopicus* selected from the group LL4600, LL4614, LL4666, LL4690, LL4728, LL4741, LL4742, LL4744, LL4773, LL4779, LL4783, LL4902, BD2, BD20 and BD70 or mutats thereof glycopeptide antibiotics of the formula

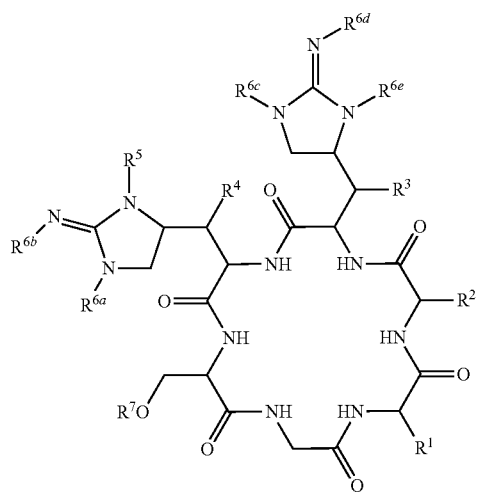

wherein:
$R^1$ is selected from:

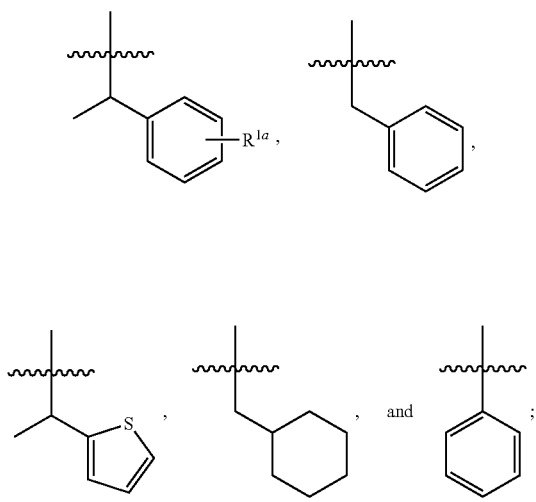

$R^{1a}$ is H or halogen;
$R^2$ is a moiety

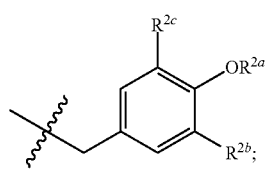

$R^{2a}$ is selected from
H,

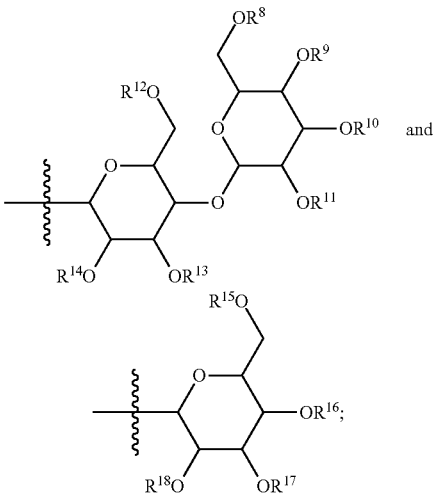

$R^{2b}$ is H, F, or $NH_2$;
$R^{2c}$ is H;
$R^3$ and $R^4$ are independently H or OH;
$R^5$ is H or $R^{6a}$, $R^{6b}$, $R^{6c}$, $R^{6d}$,
$R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are independently H, or —C(O)—Y—Z;
Y is a single bond;
Z is straight or branched chain alkyl($C_1$-$C_{20}$) or straight or branched chain alkenyl($C_2$-$C_{20}$);
by the addition of substrates of the formulae:
straight or branched chain alkyl($C_1$-$C_{20}$)$CO_2H$, straight or branched chain alkenyl($C_2$-$C_{20}$)$CO_2H$,

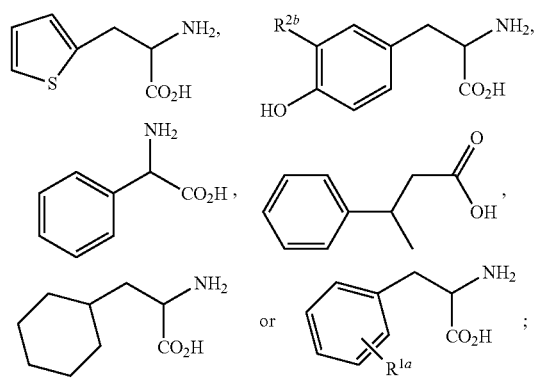

and detecting and/or recovering the antibiotic. In an additional aspect of the process multiple substrates may optionally be added. For example, straight or branched chain alkyl $(C_1\text{-}C_{20})CO_2H$ and

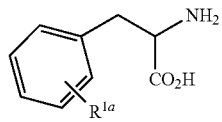

may optionally be added.

Preferred aspects of the process include:

a.) $R^7, R^{12}, R^{13}, R^{14}, R^{15}, R^{16}, R^{17}, R^{18}, R^{19}, R^{20}, R^{21}$ and $R^{22}$ are H; and Z is straight or branched chain alkyl$(C_1\text{-}C_9)$ or straight or branched chain alkenyl$(C_2\text{-}C_{10})$;

b.) $R^7, R^{12}, R^{13}, R^{14}, R^{15}, R^{16}, R^{17}, R^{18}, R^{19}, R^{20}, R^{21}$ and $R^{22}$ are H;

Z is straight or branched chain alkyl$(C_1\text{-}C_9)$ or straight or branched chain alkenyl$(C_2\text{-}C_{10})$; and $R^3$ and $R^4$ are H; or c.) $R^7, R^{12}, R^{13}, R^{14}, R^{15}, R^{16}, R^{17}, R^{18}, R^{19}, R^{20}, R^{21}$ and $R^{22}$ are H;

Z is straight or branched chain alkyl$(C_1\text{-}C_9)$ or straight or branched chain alkenyl$(C_2\text{-}C_{10})$; and $R^3$ and $R^4$ are OH.

A further aspect of the invention is the preparation by fermentation means in a liquid media using modified strains of *Streptomyces hygroscopicus* selected from the group LL4600, LL4614, LL4666, LL4690, LL4728, LL4741, LL4742, LL4744, LL4773, LL4779, LL4783, LL4902, BD2, BD20 and BD70 or mutants thereof glycopeptide antibiotics of the formula

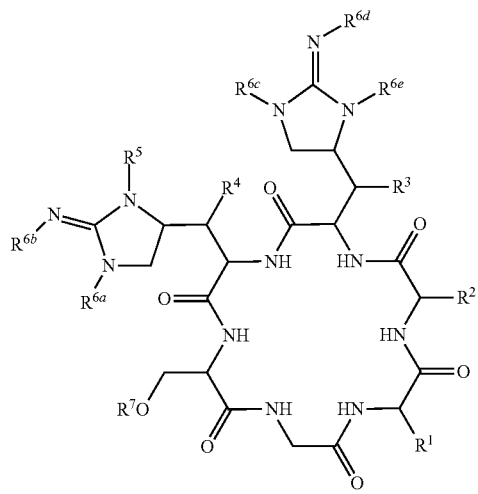

wherein:

$R^1$ is selected from:

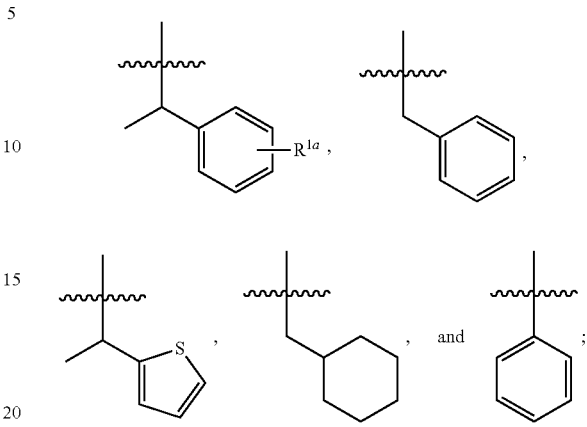

$R^{1a}$ is H or halogen;

$R^2$ is a moiety

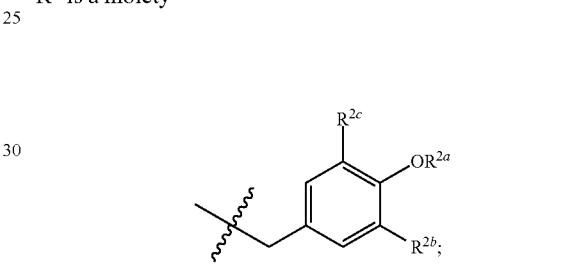

$R^{2a}$ is selected from H,

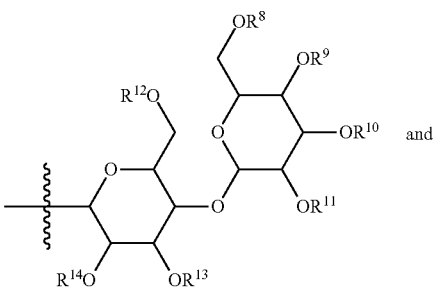

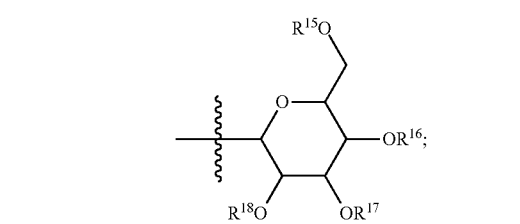

$R^{2b}$ is H, F, or $NH_2$;

$R^{2c}$ is H;

$R^3$ and $R^4$ are independently H or OH;

$R^5$ is H or

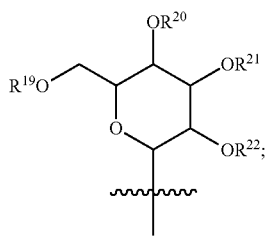

$R^{6a}$, $R^{6b}$, $R^{6c}$, $R^{6d}$, or $R^{6e}$ are H;

$R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are independently H, or —C(O)—Y—Z;

Y is a single bond;

Z is straight or branched chain alkyl($C_1$-$C_{20}$) or straight or branched chain alkenyl($C_2$-$C_{20}$);

by the addition of suitable substrates of the formulae:

straight or branched chain alkyl($C_1$-$C_{20}$)$CO_2H$, straight or branched chain alkenyl($C_2$-$C_{20}$)$CO_2H$,

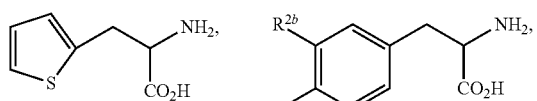

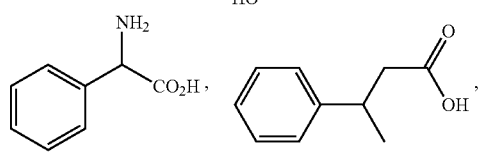

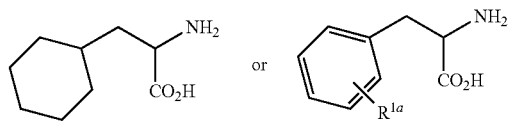

and detecting and/or recovering the antibiotic.

It is understood herein that when a compound of the invention contains asymmetric carbons, that they encompass all possible regioisomers, stereoisomers and mixtures thereof. In particular, the definitions encompass any optical isomers and diastereomers, as well as the racemic and resolved, enantiomerically pure R and S stereoisomers, as well as other mixtures of the R and S stereoisomers and pharmaceutically acceptable salts thereof. Optical isomers may be obtained in pure form by standard separation techniques.

Glycopeptide compounds of the formula according to the invention may contain mobile hydrogen atoms and consequently be present in different tautomeric forms. One skilled in the art will recognize that said tautomers often exist in equilibrium with each other. As these tautomers interconvert under physiological conditions, they provide the same useful antibacterial effects. The present invention includes mixtures of such tautomers as well as the individual tautomers of compounds of the invention.

Compounds of Formula I where $R^5$, $R^{6a}$, $R^{6b}$, $R^{6c}$, $R^{6d}$, or $R^{6e}$ are not H may form regioisomeric products which are represented by the formulae:

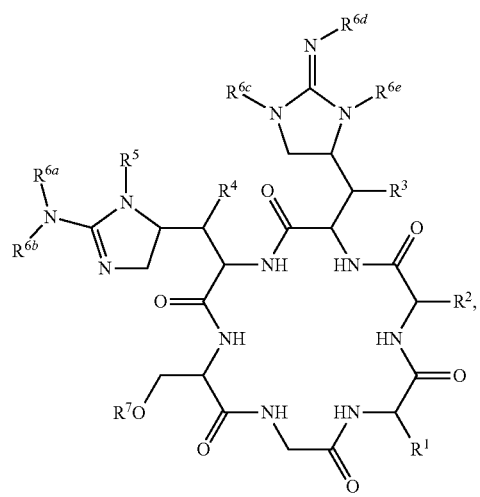

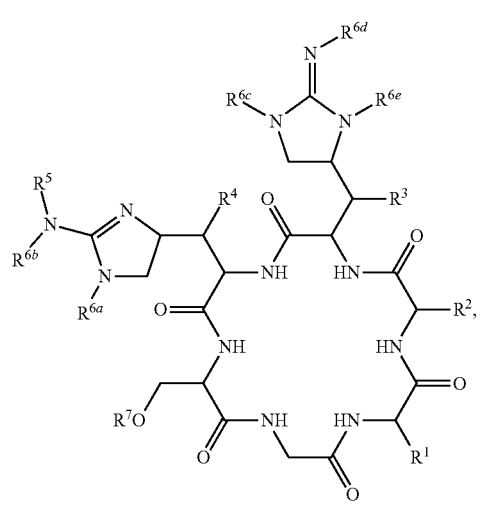

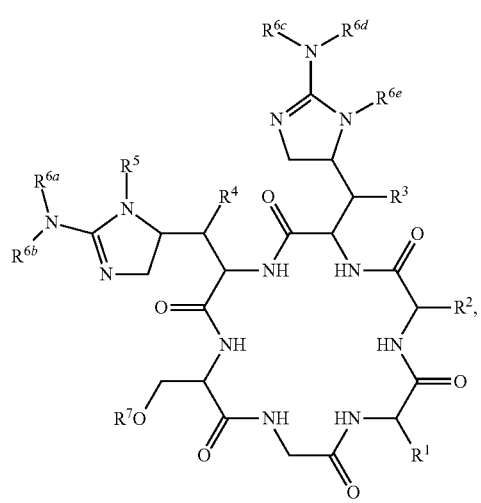

-continued

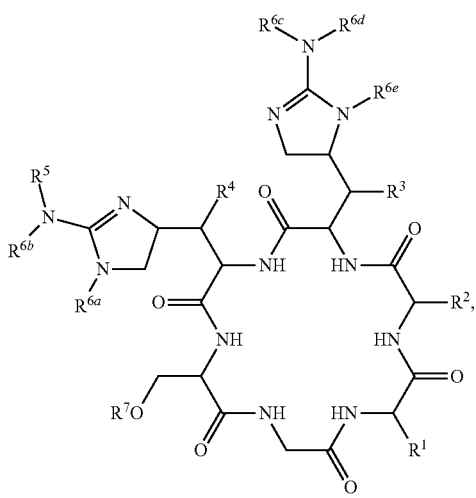

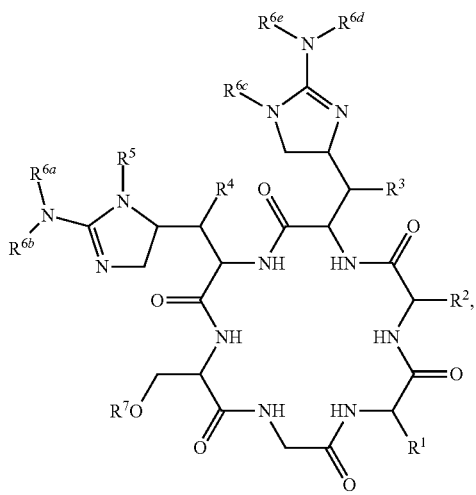

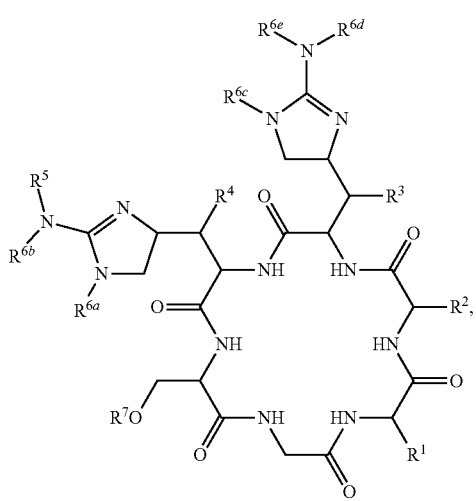

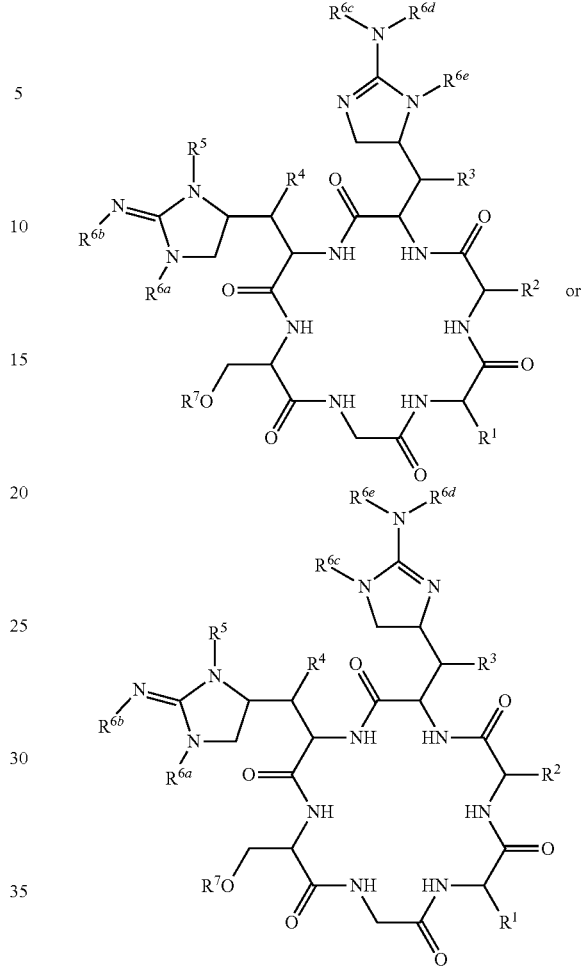

In the same regard, any substituents $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ and $R^{29}$ of the compounds of the invention above and below, may be represented by their alternative tautomeric forms, where appropriate, as is known to those skilled in the art.

For the compounds of the invention defined above and referred to herein, unless otherwise noted, the following terms are defined:

Halogen, as used herein means fluoro, chloro, bromo and/or iodo.

Alkyl as used herein means a branched or straight chain radical having from 1 to 20 (preferably 1 to 6) carbon atoms optionally substituted with one or more groups selected from halogen, cyano, nitro, hydroxy, sulfhydryl, amino, alkylamino, dialkylamino, alkoxy, aryloxy, thioalkyl, thioaryl, acyl, aroyl, acyloxy, acylamino, carboxy, carboxyalkyl, carboxyaryl, carboxamido, carboxamidoalkyl, carboxamidodialkyl, alkylsulfonamido, arylsulfonamido, aryl, and heteroaryl. Exemplary alkyl groups include but are not limited to methyl, ethyl, propyl, isopropyl, butyl, isobutyl, t-butyl, pentyl and hexyl, also optionally substituted, as well as perfluoroalkyl.

Alkenyl as used herein means a branched or straight chain radical having from 2 to 20 (preferably 2 to 6) carbon atoms optionally substituted with one or more groups selected from halogen, cyano, nitro, hydroxy, sulfhydryl, amino, alkylamino, dialkylamino, alkoxy, aryloxy, thioalkyl, thioaryl, acyl, aroyl, acyloxy, acylamino, carboxy, carboxyalkyl, carboxyaryl, carboxamido, carboxamidoalkyl, carboxamidodialkyl, alkylsulfonarilido, arylsulfonamido, aryl, and heteroaryl, with the chain containing at least one carbon-carbon double bond. Alkenyl, may be used synonymously with the term olefin and includes alkylidenes. Exemplary alkenyl groups include but are not limited to ethylene, propylene and isobutylene.

Alkynyl as used herein means a branched or straight chain radical having from 2 to 20 (preferably 3 to 10) carbon atoms optionally substituted with one or more groups selected from halogen, cyano, nitro, hydroxy, sulfhydryl, amino, alkylamino, dialkylamino, alkoxy, aryloxy, thioalkyl, thioaryl, acyl, aroyl, acyloxy, acylamino, carboxy, carboxyalkyl, carboxyaryl, carboxamido, carboxamidoalkyl, carboxamidodialkyl, alkylsulfonamido, arylsulfonamido, aryl, and heteroaryl. The chain contains at least one carbon-carbon triple bond.

Cycloalkyl as used herein means a saturated monocyclic or polycyclic fused, bridged, or spirocyclic ring system having from 3 to 20 carbon atoms. Exemplary cycloalkyl rings include but are not limited to cyclopropyl, cyclobutyl, cyclopentyl, cyclohexyl, [2.2.1]-bicycloheptanyl, [2.2.2]-bicyclooctanyl, adamantyl, [3.3.1]-bicyclononanyl, spiro-[4.4]-nonanyl, spiro-[4.5)-decanyl, spiro-[5.5]-undecanyl, and the like.

Aryl as used herein means a homocyclic or polycyclic aromatic radical, fused or catenated, having 6 to 20 carbon atoms independently substituted with one to three substituents selected from the group of alkyl, halogen, cyano, nitro, hydroxy, sulfhydryl, amino, alkylamino, dialkylamino, alkoxy, aryloxy, thioalkyl, thioaryl, acyl, aroyl, acyloxy, acylamino, carboxy, carboxyalkyl, carboxyaryl, carboxamido, carboxamidoalkyl, carboxamidodialkyl, alkylsulfonamido, arylsulfonamido, aryl, or heteroaryl. Examples include, but are not limited to, phenyl, biphenyl, naphthyl, fluorenyl, and anthracenyl, optionally substituted with one to three substituents.

Alkoxy as used herein means an alkyl-O— group in which the alkyl group is as previously described. Exemplary alkoxy groups include but are not limited to methoxy, ethoxy, n-propoxy, i-propoxy, n-butoxy, and t-butoxy.

Aryloxy as used herein means an aryl-O— group in which the aryl group is as previously described.

Thioalkyl as used herein means an alkyl-S— group in which the alkyl group is as previously described.

Thioaryl as used herein means an aryl-S— group in which the aryl group is as previously described.

Acyl as used herein means an alkyl-C(O)— group in which the alkyl group is as previously described.

Aroyl as used herein refers to an aryl-C(O)— group in which the aryl group is as previously defined. Examples include but are not limited to benzoyl and naphthoyl.

Acyloxy as used herein means an alkyl-C(O)O— group or an aryl-C(O)O— group in which the alkyl or aryl group is as previously described.

Acylamino as used herein means an alkyl-C(O)N= group or an aryl-C(O)N= group in which the alkyl or aryl group is as previously described.

Carboxyalkyl as used herein means an alkyl-OC(O)— group in which the alkyl group is as previously defined.

Carboxyaryl as used herein means an aryl-OC(O)— group in which the aryl group is as previously defined.

Carboxyamido as used herein means a $NH_2C(O)$— group.

Carboxyamidoalkyl as used herein means an alkyl-NHC(O)— group in which the alkyl group is as previously defined.

Carboxyamidodialkyl as used herein means a dialkyl-NC(O)— group in which the alkyl groups are as previously defined.

Alkylsulfondamido as used herein means an alkyl-$S(O)_2$—N= group in which the alkyl group is as previously defined.

Arylsulfonamido as used herein means an aryl-$S(O)_2$—N= group in which the aryl group is as previously defined.

Heteroaryl denotes a 5- or 6-membered heterocyclic ring, which may be fused to another 5- or 6-membered heterocyclic ring or non-heterocyclic ring, especially heteroaromatic rings which contain 1 to 3 heteroatoms which may be'the same or different. Nitrogen, oxygen and sulfur are the preferred heteroatoms provided that the heterocyclic ring does not contain —O—O—, —S—S— and —S—O— bonds. A heteroaryl group may be optionally substituted with 1 to 3 substituents selected from the group halogen, cyano, nitro, hydroxy, sulfhydryl, amino, alkylamino, dialkylamino, alkoxy, aryloxy, thioalkyl, thioaryl, acyl, aroyl, acyloxy, acylamino, carboxy, carboxyalkyl, carboxyaryl, carboxamido, carboxamidoalkyl, carboxamidodialkyl, alkylsulfonamido, arylsulfonamido, aryl, and heteroaryl. Exemplary heteroaryl groups include but are not limited to furan, thiophene, pyrrole, oxazole, thiazole, imidazole, isoxazole, isothiazole, pyridine, pyrimidine, pyrazine, pyridazine, indole, quinoline, isoquinoline, benzimidazole, quinazoline, and the like.

Where terms are used in combination, the definition for each individual part of the combination applies unless defined otherwise. For instance, aralkyl refers to an aryl group, and alkyl refers to the alkyl group as defined above.

The compounds of the invention may be obtained as inorganic or organic salts using methods known to those skilled in the art (Richard C. Larock, Comprehensive Organic Transformations, VCH publishers, 411-415, 1989). It is well known to one skilled in the art that an appropriate salt form is chosen based on physical and chemical stability, flowability, hydroscopicity and solubility.

Pharmaceutically acceptable salts of the compounds of the invention include basic salts of inorganic and organic acids, including but not limited to hydrochloric acid, hydrobromic acid, sulphuric acid, phosphoric acid, nitric acid, methanesulfonic acid, ethanesulfonic acid, benzenesulfonic acid, toluenesulfonic acid, napthalenesulfonic acid, camphorsulfonic acid, malic acid, acetic acid, trifluoroacetic acid, oxalic acid, malonic acid, tartaric acid, citric acid, lactic acid, fumaric acid, succinic acid, maleic acid, salycylic acid, benzoic acid, phenylacetic acid, mandelic acid and the like.

When compounds of the invention include an acidic function such as a carboxy then suitable pharmaceutically acceptable salts of the compounds of the invention with an acidic moiety can be formed from organic and inorganic bases. Such includes but is not limited to salts formed with alkali metals or alkaline earth metals such as sodium, potassium, lithium, calcium, or magnesium or organic bases such as triethylamine, N,N-diethylmethylamine, N,N-diethylethylenediamine, and N-tetraalkylammonium salts such as N-tetrabutylammonium salts. For additional examples of "pharmaceutically acceptable salts" see Berge et al, J. Pharm. Sci. 66, 1 (1977).

The compounds can also be used in the form of esters, carbonates, carbamates and other conventional prodrug forms, which when administered in such form, convert to the active moiety in vivo.

DESCRIPTION OF THE PREFERRED EMBODIMENTS

This invention uses as starting materials for the preparation of certain compounds of the invention, a variety of glycopeptide antibiotics prepared by fermentation. In particular, using the fermentation conditions described in U.S. Pat. No. 3,495,004 a complex of antibiotics is isolated. Optionally, using hereindescribed fermentation conditions, with *Streptomyces hygroscopicus* strain LL4600, the complex may also be prepared. Further separation of the complex of antibiotics by HPLC into individual components AC-98-1, AC-98-2, AC-98-3, AC-98-4 and AC-98-5 and determination of the chemical structures by spectroscopy is described in copending provisional patent application No. 60/286,249, filed Apr. 25, 2001. The structures of the individual components are shown below.

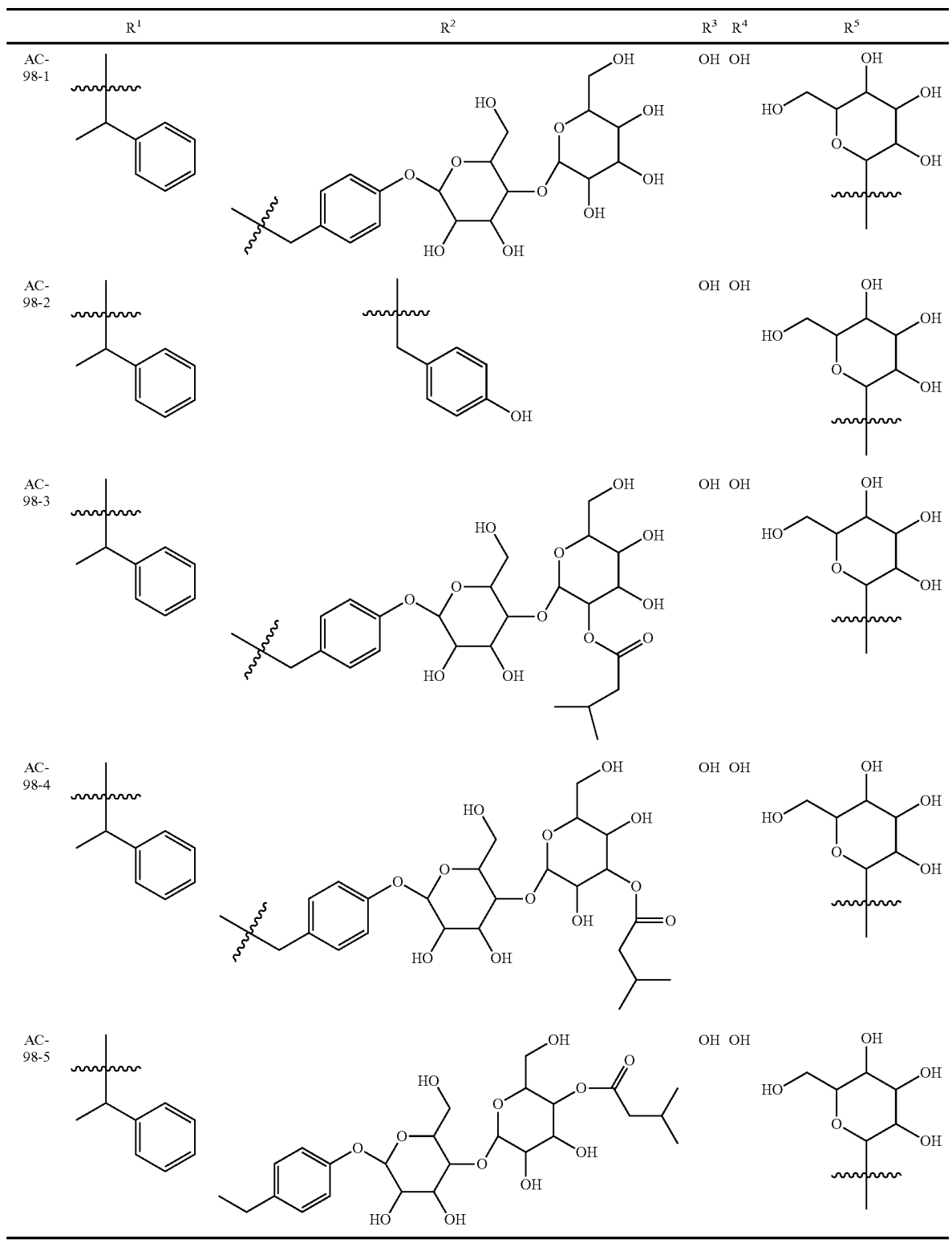

Certain compounds of the invention are prepared by fermentation means using modified strains of *Streptomyces hygroscopicus* selected from the group LL4600, LL4614, LL4666, LL4690, LL4728, LL4741, LL4742, LL4744, LL4773, LL4779, LL4783, LL4902, BD2, BD20 and BD70 and mutants thereof and include those of the formula

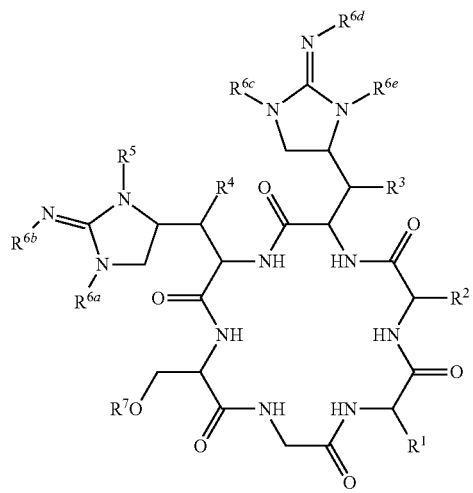

wherein:
$R^1$ is selected from:

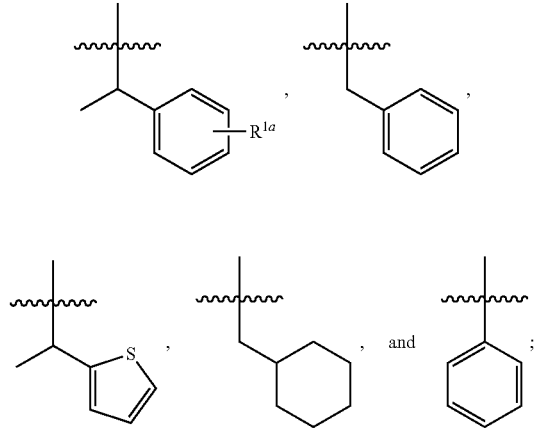

$R^{1a}$ is H or halogen;
$R^2$ is a moiety

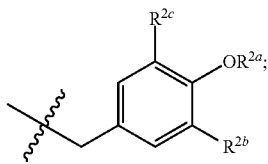

$R^{2a}$ is selected from
H,

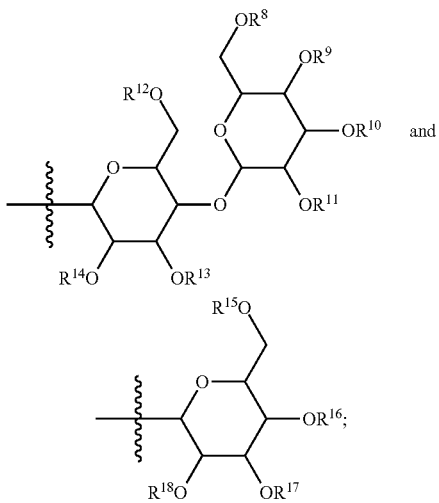

$R^{2b}$ is H, F or $NH_2$;
$R^{2c}$ is H;
$R^3$ and $R^4$ are independently H or OH;
$R^5$ is H or

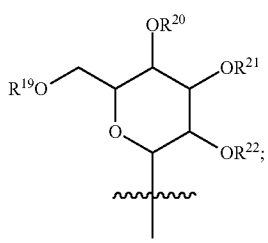

$R^{6a}$, $R^{6b}$, $R^{6c}$, $R^{6d}$, or $R^{6e}$ are H;
$R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are independently H, or —C(O)—Y—Z;
Y is a single bond;
Z is straight or branched chain alkyl($C_1$-$C_{20}$) or straight or branched chain alkenyl($C_2$-$C_{20}$);
by directed biosynthetic fermentations through the addition of substrates of the formulae:
straight or branched chain alkyl($C_1$-$C_{20}$)$CO_2H$, straight or branched chain alkenyl($C_2$-$C_{20}$)$CO_2H$,

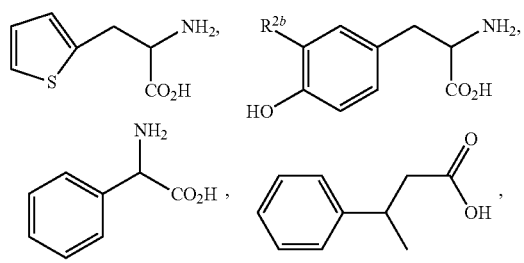

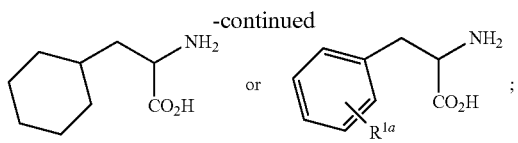

using controlled conditions in a suitable media, optionally containing mannose, under aerobic conditions and isolating the antibiotics which optionally may be further chemically modified. Multiple substrates may optionally be added.

For example cultivating *streptomyces hygroscopicus* LL4614 in the presence of p-chloro-DL-phenylalanine affords recoverable quantities of glycopeptide antibiotics cyclo(glycyl-4-chloro-β-methylphenylalanyl-O-[4-O-[3-O-β-methylbutanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl] and cyclo[glycyl-4-chloro-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl].

A further aspect of the invention is to recover glycopeptide antibiotics of the invention wherein $R^7, R^8, R^9, R^{10}, R^{11}, R^{12}, R^{13}, R^{14}, R^{15}, R^{16}, R^{17}, R^{18}, R^{19}, R^{20}, R^{21}$ and $R^{22}$ are H by hydrolysis of mixtures where $R^7, R^8, R^9, R^{10}, R^{11}, R^{12}, R^{13}, R^{14}, R^{15}, R^{16}, R^{17}, R^{18}, R^{19}, R^{20}, R^{21}$ and $R^{22}$ are H or esters (—C(O)—Y—Z) by adding base which includes sodium hydroxide and the like or (3-[cyclohexylamino]-1-propanesulfonic acid)to the medium at about 0° to about 25° C., preferred is about 0° to about 4° C. at a pH of about 8.0 to about 13.5, preferred about 11.5 to about 13.5 and recovering said antibiotic at a pH of about 1.8 to about 6.5 preferred is about 4.0 to about 6.0. The pH is adjusted from about 8.0 to about 13.5 to about 1.8 to about 6.5 with acids which include hydrochloric acid, acetic acid, propanoic acid and (3-[N-morpholino]propanesulfonic acid). Preferably the acid adjusted pH is about 4.0 to about 5.0. Optionally buffers may also be used to adjust pH. Optionally, mixtures where $R^7, R^8, R^9, R^{10}, R^{11}, R^{12}, R^{13}, R^{14}, R^{15}, R^{16}, R^{17}, R^{18}, R^{19}, R^{20}, R^{21}$ and $R^{22}$ are H or esters (—C(O)—Y—Z) may first be isolated from the medium and then hydrolyzed as described hereinabove.

Certain of the glycopeptide antibiotics of the invention are produced by fermentation of mutant derivative strains of *Streptomyces hygroscopicus* LL4600. These microorganisms listed in Table 1 are maintained in the culture collection of American Home Products, Wyeth-Ayerst Discovery, Pearl River, N.Y. as culture numbers LL4600, LL4614, LL4666, LL4690, LL4728, LL4741, LL4742, LL4744, LL4773, LL4779, LL4780, LL4783, LL4902, BD2, BD20 and BD70. A viable culture of these new microorganisms is deposited under the Budapest Treaty with the Patent Culture Collection Laboratory, Northern Regional Research Center, U.S. Department of Agriculture, Peoria, Ill. 61604, and added to its permanent collection.

TABLE 1

| Wyeth-Ayerst culture collection # | NRRL culture collection |
|---|---|
| LL4600 | NRRL 30439 |
| LL4614 | NRRL 30440 |
| LL4666 | NRRL 30441 |
| LL4690 | NRRL 30442 |
| LL4728 | NRRL 30443 |

TABLE 1-continued

| Wyeth-Ayerst culture collection # | NRRL culture collection |
|---|---|
| LL4741 | NRRL 30444 |
| LL4742 | NRRL 30445 |
| LL4744 | NRRL 30446 |
| LL4773 | NRRL 30447 |
| LL4779 | NRRL 30448 |
| LL4780 | NRRL 30449 |
| LL4783 | NRRL 30450 |
| LL4902 | NRRL 30451 |
| BD2 | NRRL 30452 |
| BD20 | NRRL 30453 |
| BD70 | NRRL 30454 |

It is to be understood that the production of certain glycopeptide antibiotics of the invention by fermentation is not limited to the particular mutants defined above which are for illustrative purposes only. In fact, it is desired and intended to include the use of mutants as described herein and those produced by additional exposure of the above defined mutants to X-radiation, ultraviolet radiation, N'-methyl-N'-nitro-N-nitrosoguanidine, ethyl-methane sulfonate and the like. Strains presented are all derivatives of NRRL 3085. A culture stock designated LL4600 is derived from NRRL 3085 by colony purification and served as the starting point for the work described. Mutants accumulating biosynthetic intermediates, shunt metabolites or compounds not detected in LL4600 are derived by NTG mutagenesis of LL4600 or various industrial derivatives of LL4600.

Mutagenesis

The described strains are obtained via N-methyl-N'-nitro-N-nitrosoguanidine (NTG) mutagenesis. Cells are grown in TSBG (Tryptic soy broth [Difco]supplemented with 20 g/L glucose) for 24-48 hours and then are sonicated for 5-40" to disperse mycelial pellets to variably-sized mycelial fragments. The sonicated suspension is pelleted, resuspended in fresh TSBG containing 50-1000 µg/mL NTG and dosed for 10-260 min at 30° C. with shaking. The dosed cells are then pelleted, resuspended in fresh TSBG and grown overnight at 30° C. The overnight cells are then sonicated for 6-20" to disrupt mycelial pellets. The mutagenized cells are stored as a 20% glycerol stock at –70° C.

Cultivation

Cultivation of mutant strains of *Streptomyces hygroscopicus* designated above may be carried out in a wide variety of liquid culture media. Media which are useful for the production of glycopeptide antibiotics include an assimilable source of carbon, such as dextrin, dextrose, sucrose, molasses, starch, glycerol, etc; an assimilable source of nitrogen such as protein, protein hydrolysate, polypeptides, amino acids, corn steep liquor, etc; and inorganic anions and cations, such as potassium, sodium, ammonium, calcium, sulfate, carbonate, phosphate, chloride, etc. Trace elements such as zinc, cobalt, iron, boron, molybdenum, copper, etc., are supplied as impurities of other constituents of the media. Aeration in tanks and bottles is supplied by forcing sterile air through or onto the surface of the fermenting medium. Aeration provides for aerobic fermentations. Further agitation in tanks is provided by a mechanical impeller. An antifoam agent such as polypropylene glycol may be added as needed.

Culture Preservation

Strains are preserved as frozen whole cells (frozen vegetative mycelia, FVM) prepared from cells grown for 24-48 hours in TSBG (Tryptic soy broth [Difco] supplemented with 20 g/L glucose). Glycerol is added to 20% and the cells are frozen at −70° C.

Inoculum Development Fermentation In Suitable Culture Media and Conditions

Composition of suitable culture media used in the examples presented is as follows:

| Composition of fermentation media | | | | | | |
|---|---|---|---|---|---|---|
| Component | BPM17 | BPM17stat | BPM17stat gal | BPM17stat man | BPM27 | BPM27- man |
| Pharmamedia (Traders) | 10 g/L | 20 g/L | 20 g/L | 20 g/L | 20 g/L | 20 g/L |
| Glucose | 40 g/L | 60 g/L | 60 g/L | 60 g/L | 60 g/L | 60 g/L |
| Galactose | — | — | 20 g/L | — | — | — |
| Mannose | — | — | — | 2 g/L | 2 g/L | — |
| CaCO$_3$ (Mississippi Lime) | 5 g/L | 5 g/L | 5 g/L | 5 g/L | — | — |
| CaCO$_3$ (Gamaco) | — | — | — | — | 15 g/L | 15 g/L |

Fermentations are inoculated from cells grown in TSBG medium at 30° C. for 24-48 hr with shaking on a gyrorotary shaker. Shake-flask fermentations are performed at 30° C. for 3-5 days on a gyro-rotary shaker operating at 250 rpm (2″ stroke). Ten-liter fermentations are performed at 30° C. for 3-5 days at 30° C., at 400-800 rpm with 1 vvm airflow. Fermentation at 300 liters is similarly performed with agitation at 170-200 rpm. Antifoam, such as Macol P2000 is added to fermentor medium at 0.2-2.0%. Three hundred-liter fermentations with medium BPM17statgal employ galactose at 8 g/L. The strains described may be fermented in any of the media listed above beyond the specific examples herein described.

Biotransformation Methods

Substrates are prepared as 5 mg/mL stock solutions in water and filter sterilized. The stock solution is added to BPM17statgal shake-flasks (each containing 25 mL of medium) to give a final concentration of 100 mg/L. Substrate compounds are added at the time of inoculation. Fermentations are conducted for 3 days.

Hydrolysis of Esters

Compounds of the invention, prepared by fermentation may be isolated as mixtures which include esters. Alternatively, and in particular, mixtures of esters wherein $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are independently H or —C(O)—Y—Z; Y is a single bond; and Z is straight or branched chain alkyl($C_1$-$C_{20}$) or straight or branched chain alkenyl($C_2$-$C_{20}$) may optionally be hydrolyzed following fermentation and preferably before isolation of antibiotics by adding suitable bases to the broth which include: aqueous sodium hydroxide and (3-[cyclo-hexylamino]-1-propanesulfonic acid) CAPS and the like and adjusting the pH with hydrochloric acid, acetic acid or (3-[N-morpholino)propanesulfonic acid) MOPS and the like to afford products where $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are H followed by recovery of the antibiotics.

Analytical HPLC Analysis of Glycopeptide Antibiotics

Cells are removed for fermentation broth by centrifugation. The clarified supernatant is applied to a wetted BAKERBOND™ spe carboxylic acid extraction column (catalog #7211-03). Columns are washed with 50% aqueous methanol and eluted with acetonitrile/water/trifluoroacetic acid (70/30/0.5). The solvent is evaporated, and the residue is reconstituted in 0.2-0.4 mL methanol/water (1/1). In some instances supernatants are analyzed directly. Samples are analyzed using a Hewlett Packard model 1090 liquid chromatograph with photodiode array detection. The compounds are resolved by reverse phase chromatography using a YMC ODS-A 4.6×150 mm HPLC column, with a mobile phase of 10% acetonitrile: 0.01% trifluoroacetic acid (solvent A) and 50% acetonitrile:0.01% trifluoroacetic acid (solvent B). A linear gradient from 0% B to 100% B in 22 min, with a flow rate of 1 mL/min, is used for elution. Novel metabolites are identified by the appearance of HPLC peaks which possess characteristic UV absorption spectra but displayed novel retention times. Relative retention times (RRT) are calculated by dividing the peak retention times of novel compounds of the invention by that of (Example 281a) Cyclo[glycyl-.β.-methylphenylalanyl-O-(4-O-hexopyranosylhexopyranosyl) tyrosyl-3-(2-iminoimidazolidin-4-yl)seryl-3-(3-hexopyranosyl-2-iminoimidazolidin-4-yl)serylseryl]. Subsequent LC/MS analysis is then performed on fermentation extracts to determine molecular weights.

LC/MS Analysis of Glycopeptide Antibiotics from Fermentations

The molecular weights of new glycopeptide antibiotics from fermentations are determined using a Hewlett-Packard API-electrospray LC/MS system with an HP 5989B Mass Spectrometer, HP 59987A API-Electrospray, HP 1090 series II HPLC and HP ChemStation data system with HP G1047A LC/MS software. Extracts are resolved by reverse phase HPLC as described above. UV detection is at 226 nm. The MS electrospray is performed in positive mode with a scan range of 400-1700 m/z.

General Procedure for the Isolation of Fermentation Products

Typical representative methods for the recovery and isolation of glycopeptide antibiotics of the invention from the fermentation broth include:

a) loading fermentation broth on polyacrylate resin, XAD-7, prewashed sequentially with methanol, acetone and water. Eluting the resin with 1:1 acetonitrile-water containing 0.1% trifluoroacetic acid, concentrating under reduced pressure to a small volume then extracting with 1:4 water-N,N-dimethylformamide and fractionating the residue of the evaporated extract by reverse phase HPLC on a C18 column by elution with a gradient of acetonitrile-water containing trifluoroacetic acid;

b) using method a) above and fractionating the residue by reverse phase HPLC on a C18 column by elution with a gradient of methanol-water containing trifluoroacetic acid;

c) loading fermentation broth on CG-61 resin, and eluting with 40%:60% acetonitrile-water containing 0.01% trifluoroacetic acid, concentrating product fractions under reduced pressure and adjusting the pH to 12.5 with sodium hydroxide for 45 min to 3 h or until esters are hydrolyzed. Adjusting the pH to 3.0 with hydrochloric acid and collecting the antibiotic from acetonitrile;

d) adding diatomaceous earth to the fermentation, filtering and adjusting the pH of the filtrate to pH 12.8 with sodium hydroxide and holding for up to 3 h, neutralizing with acetic acid and loading on SP207 resin. Washing the resin with water, methanol and eluting with 1:1 methanol-water-3% acetic acid and collecting product from concentrated fractions with isopropanol-acetonitrile.

e) adding an equal volume of 50 mM CAPS buffer (pH 13) to the fermentation broth until esters have been hydrolyzed, adding three volumes of 1M MOPS buffer (pH 7.0) to neutralized the mixture and loading on a CG-71C column, eluting with 1:1 acetonitrile-water-0.05% trifluoroacetic acid and purifying antibiotic product fractions by reverse phase HPLC on a C18 column using a gradient of methanol-water-0.05% trifluoroacetic acid; or f) adding an equal volume of 50 mM CAPS buffer (pH 13) to the fermentation broth until esters are hydrolyzed, adding three volumes of 1M MOPS buffer (pH 7.0) to neutralized the mixture and separating antibiotic product by reverse phase HPLC on a C18 column by elution with 10%-90% acetonitrile-water containing 0.01% trifluoroacetic acid.

Further preparation of compounds of this invention is described below and is illustrated in the following Schemes.

Compounds of this invention may be prepared as shown in Scheme I by nitrations and halogenations of glycopeptide antibiotics 1 to give glycopeptide antibiotics 2 which may be further modified by herein described subsequent transformations. Halogenation of glycopeptide antibiotics 1 to afford glycopeptide antibiotics 2 may be achieved by methods known to those skilled in the art, including treatment with bromine, iodine, sodium hypochlorite, N-bromosuccinimide, N-chlorosuccinimide, N-iodosuccinimide, iodine monochloride, benzyltrimethylammonium dichloroiodate, and the like, in a solvent which include a concentrated mineral acid, such as aqueous hydrochloric acid, sulfuric acid, and the like, or a concentrated carboxylic acid such as acetic acid or trifluoroacetic acid, and the like, at temperatures about 0° to about 30° C. Nitration of glycopeptide antibiotics 1 to afford glycopeptide antibiotics 2 may be achieved by methods known to those skilled in the art, by treatment with nitrating reagents, which include metal nitrate salts including potassium nitrate in a solvent such as a concentrated mineral acid or a concentrated carboxylic acid such as acetic acid or trifluoroacetic acid, at temperatures about −20° C. to about 30° C.

Scheme I

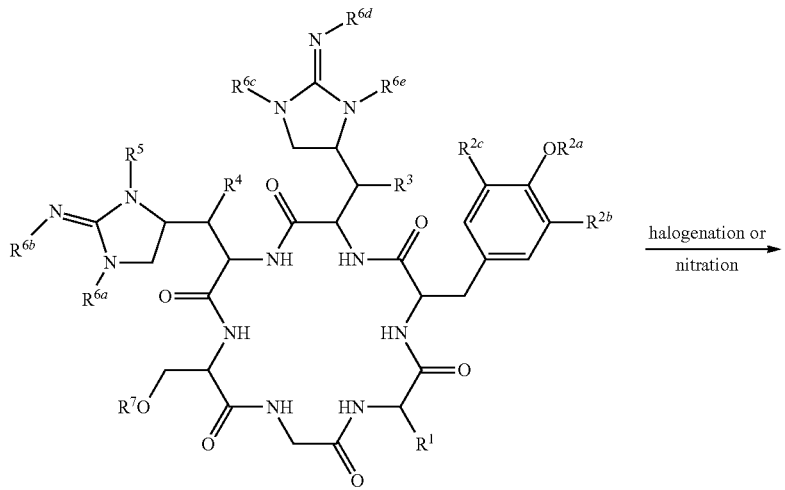

$R^{2b} = R^{2c} = H$

1

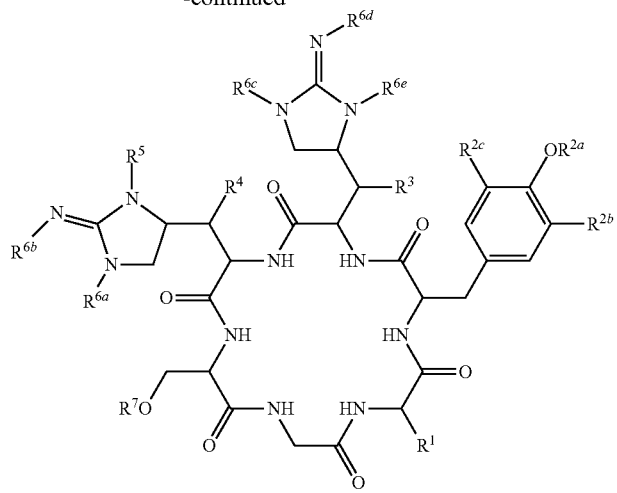

$R^{2b}$ = Cl, Br, I, or $NO_2$
$R^{2c}$ = Cl, Br, I or H
2

As further shown in Scheme II, compounds in which $R^{2b}$ and/or $R^{2c}$ of glycopeptide antibiotics 2 are bromine or iodine serve as precursors to compounds of formula 3 wherein $R^{2b}$ and/or $R^{2c}$ are alkyl($C_1$-$C_{20}$), cycloalkyl($C_3$-$C_{20}$), alkenyl ($C_2$-$C_{20}$), alkynyl($C_2$-$C_{20}$), aryl and heteroaryl, all of which may be prepared by transition metal mediated coupling reactions, which include the palladium(0) mediated couplings of aryl bromides or iodides with organostannanes which include $(R^{2b})_4Sn$, $(R^{2c})_4Sn$, $R^{2b}Sn(butyl)_3$ or $R^{2c}Sn(butyl)_3$, and the like (Stifle couplings; as described in Farina, V. and Roth, G. P. Advances in Metal-Organic Chemistry 1996, 5, 1-53 and references therein), with organoboron compounds which include $R^{2b}$-(9-borabicyclo[3.3.1]nonane) ($R^{2b}$-9-BBN), $R^{2c}$-(9-borabicyclo[3.3.1]nonane) ($R^{2c}$-9-BBN), $R^{2b}$—B$(OH)_2$, $R^{2c}$—B$(OH)_2$, $R^{2b}$—B(O-alkyl($C_1$-$C_{20}$))$_2$, $R^{2c}$—B(O-alkyl($C_1$-$C_{20}$))$_2$, $R^{2b}$—B(O-O-benzodioxole) or $R^{2c}$—B(O-O-benzodioxole)

(Suzuki couplings; as described in Miyaura, N. and Suzuki, A. Chem. Rev. 1995, 95, 2457-2483 and references therein), or with alkenes or terminal alkynes (Heck couplings; as described in de Meijere, A. and Meyer, F. E. Angew. Chem. Int. Ed. Eng. 1994, 33, 2379-2411 and references therein). In those instances wherein the transition metal mediated coupling reaction is a palladium(0) mediated coupling of a terminal alkyne with glycopeptide antibiotics 2, wherein $R^{2a}$ is H, the formation of products 3a containing a benzofuran moiety may also be produced.

Scheme II

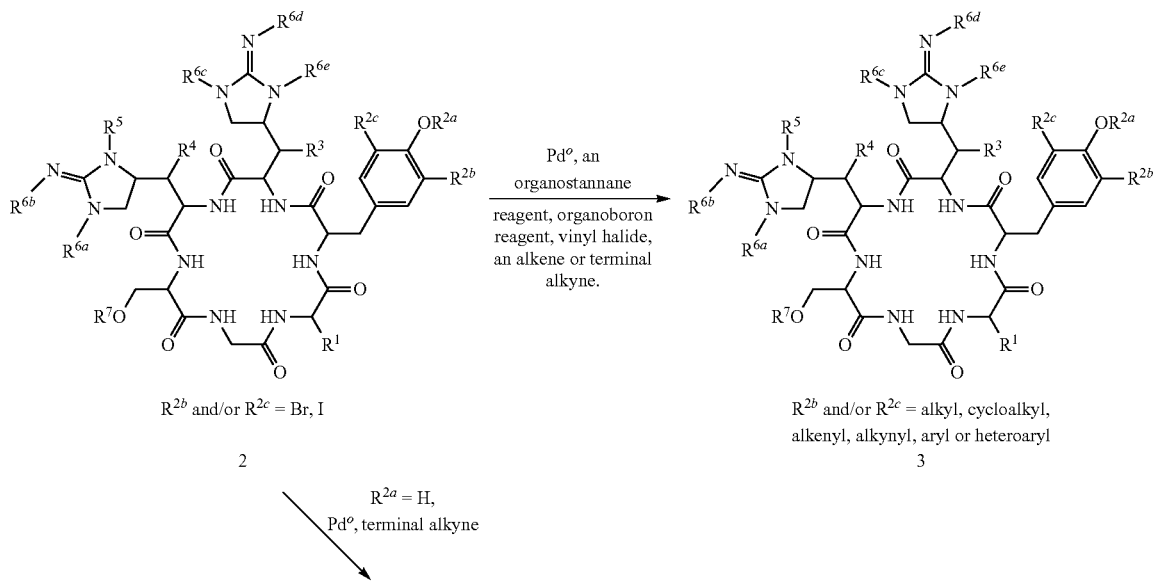

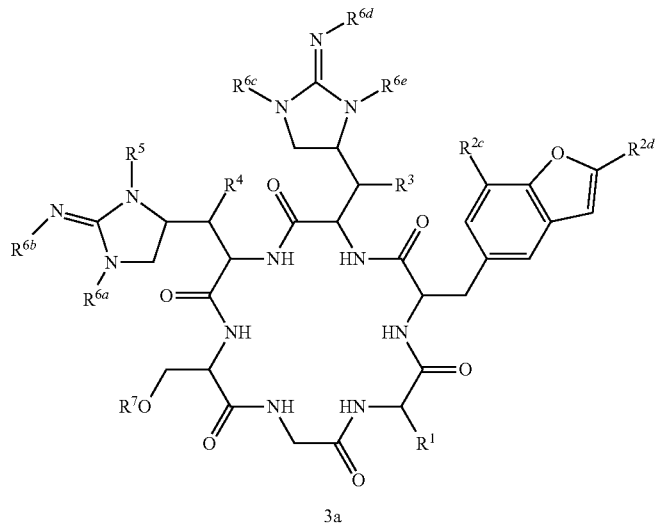

3a

Scheme III describes the synthesis of amine 4 in which $R^{2b}$ is —$NH_2$ which maybe prepared from the corresponding glycopeptide antibiotic 2 in which $R^{2b}$ is —$NO_2$, by reduction using standard methods known to those skilled in the art, including hydrogenation under an atmosphere of hydrdgen at pressures from about 1 to about 250 psi, over a suitable catalyst such as palladium or platinum, and the like, either alone or adsorbed onto a suitable support such as carbon, alumina or diatomaceous earth, in solvents such as water, methanol, ethanol, and the like, alone or in combination, in the presence or absence of a mineral or carboxylic acid, such as hydrochloric acid, sulfuric acid, or acetic acid, at temperatures from about 25° C. to the reflux temperature of the solvent. Alternatively, amine 4 may also be prepared by the reduction of glycopeptide antibiotic 2 over metals such as iron or zinc in solvents such as water, methanol, ethanol, and the like, alone or in combination, in the presence of a mineral or carboxylic acid, such as hydrochloric acid, sulfuric acid, or acetic acid, at temperatures from ambient temperature to the reflux temperature of the solvent.

Scheme III

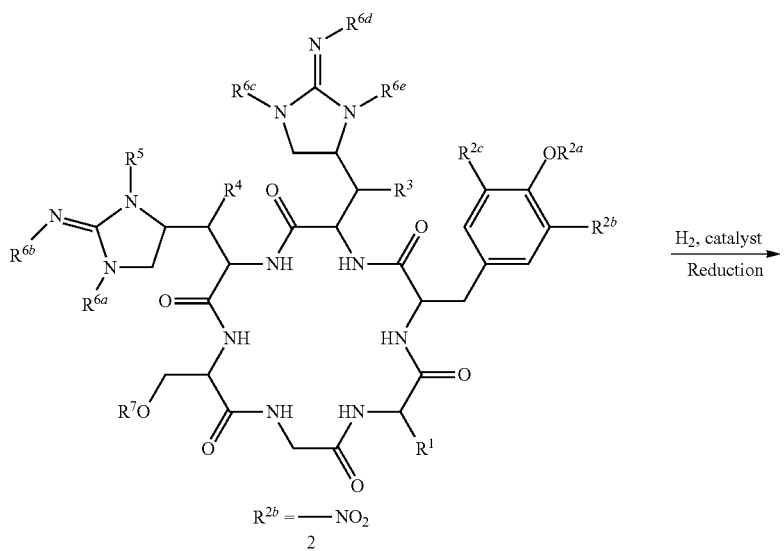

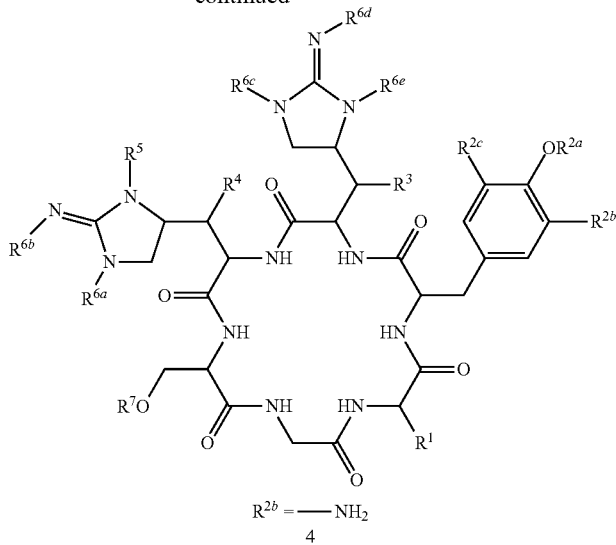

$R^{2b} = \text{---}NH_2$
4

As further described in Scheme IV, amine 5 in which $R^{2b}$ is —$NR^{2f}R^{28}$, wherein $R^{2f}$ is alkyl($C_1$-$C_{20}$), cycloalkyl($C_3$-$C_{20}$), alkenyl($C_3$-$C_{20}$) or alkynyl($C_3$-$C_{20}$) and $R^{2g}$ is H, may be prepared from amine 4 in which $R^{2b}$ is —$NH_2$, by methods known to those skilled in the art, such as by alkylation with an appropriate alkyl halide $R^{2f}X$, where X is Cl, Br, I, —O-tosylate, —O-mesylate, or —O-triflate, in the presence or absence of a suitable base. Amine 5 may be further alkylated in the case where $R^{2g}$ is H to give disubstituted amine 6 where $R^{2b}$ is —$NR^{2f}R^{2g}$, wherein $R^{2f}$ and $R^{2g}$ are independently alkyl($C_1$-$C_{20}$), cycloalkyl($C_3$-$C_{20}$), alkenyl($C_3$-$C_{20}$) or alkynyl($C_3$-$C_{20}$), by treatment with an appropriate alkyl halide $R^{2g}X$, where X is Cl, Br, I, —O-tosylate, —O-mesylate, or —O-triflate, in the presence or absence of a suitable base as above. Alternatively, amine 5 in which $R^{2b}$ is —$NR^{2f}R^{2g}$, wherein $R^{2f}$ is alkyl($C_1$-$C_{20}$), cycloalkyl($C_3$-$C_{20}$), alkenyl ($C_3$-$C_{20}$) or alkynyl($C_3$-$C_{20}$) may be prepared from amine 4 in which $R^{2b}$ is —$NH_2$, by methods known to those skilled in the art, such as by treatment with an aldehyde or keto form of the formula $R^{2f}(R^{2f}(O))$ and a reductant (reductive amination) which include but are not limited to sodium borohydride, sodium cyanoborohydride, and hydrogen and a catalyst selected from palladium and platinum, and the like. Amine 5 may undergo further reductive amination in the case where $R^{2g}$ is H to give disubstituted amine 6 where $R^{2b}$ is —$NR^{2f}R^{2g}$, wherein $R^{2f}$ and $R^{2g}$ are independently alkyl($C_1$-$C_{20}$), cycloalkyl($C_3$-$C_{20}$), alkenyl($C_3$-$C_{20}$) or alkynyl($C_3$-$C_{20}$), by treatment with an aldehyde or keto form of the formula $R^{2g}(R^{2g}(O))$ and a reductant as above. Alternatively, amine 5 in which $R^{2b}$ and/or $R^{2c}$ are —$NR^{21}R^{2g}$, wherein $R^{21}$ is alkyl($C_1$-$C_{20}$), cycloalkyl($C_3$-$C_{20}$), alkenyl($C_3$-$C_{20}$), alkynyl($C_3$-$C_{20}$), aryl, or heteroaryl and $R^{2g}$ is H, or amine 6, wherein $R^{2b}$ and/or $R^{2c}$ are —$NR^{2f}R^{2g}$, wherein $R^{2f}$ and $R^{2g}$ are independently alkyl($C_1$-$C_{20}$), cycloalkyl($C_3$-$C_{20}$), alkenyl($C_3$-$C_{20}$), alkynyl($C_3$-$C_{20}$), aryl, or heteroaryl, may be prepared from glycopeptide antibiotic 2 in which $R^{2b}$ and/or $R^{2c}$ are bromine or iodine, by methods known to those skilled in the art, such as by palladium(0) mediated amination with an appropriate amine $R^{21}NH_2$ or $R^{21}R^{2g}NH$, respectively (J. F. Hartwig, Angew. Chem. Int. Ed. 1998, 37, 2046-2067, and references therein).

Scheme IV

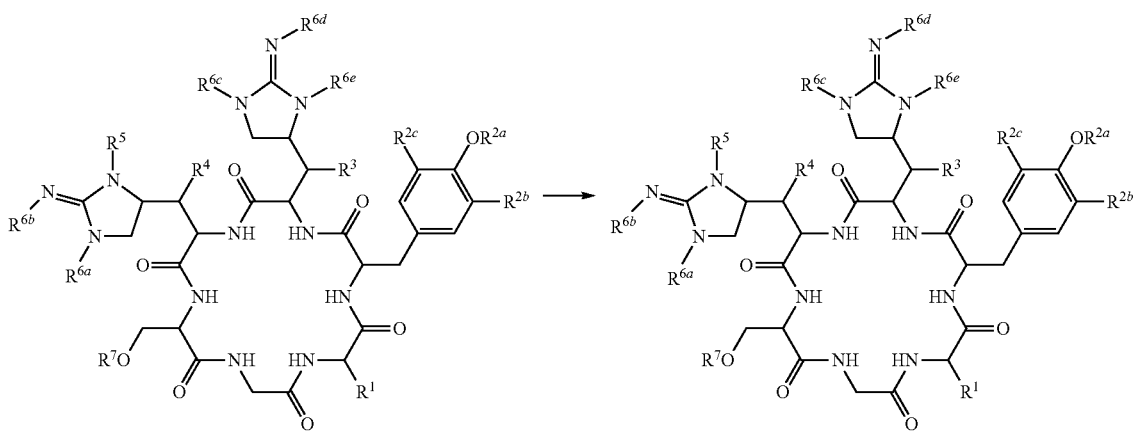

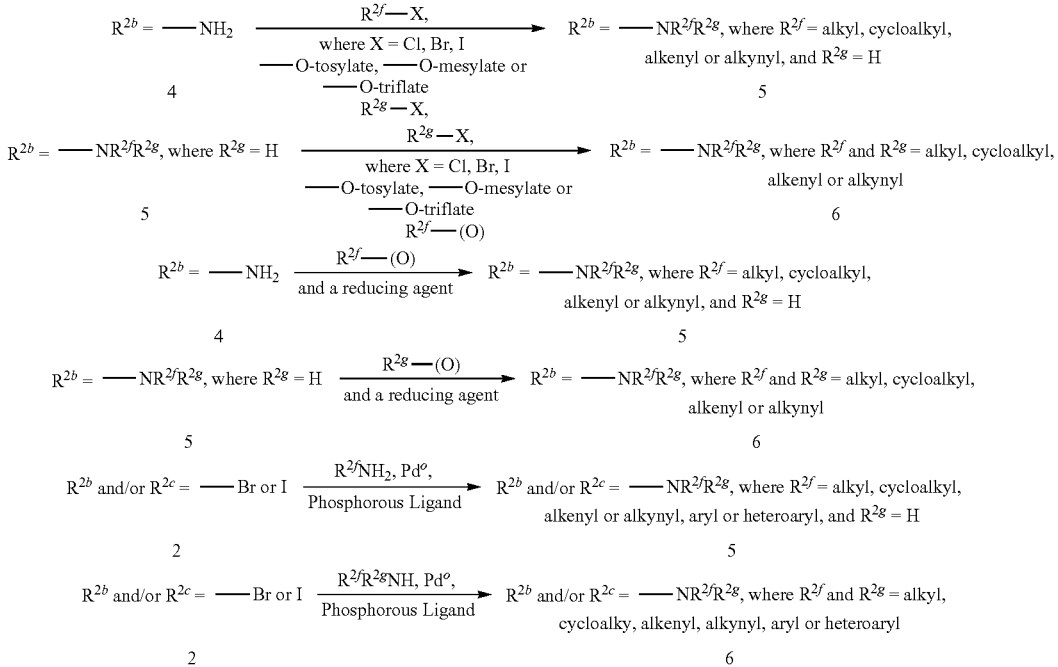

As shown in Scheme V, glycopeptide antibiotics 7 in which $R^{2b}$ is $-NR^{2f}R^{2g}$, wherein $R^{2g}$ is the group D-E-G, wherein D is $-C(O)-$, E is a single bond and G is H, alkyl($C_1$-$C_{20}$), cycloalkyl($C_3$-$C_{20}$), alkenyl($C_2$-$C_{20}$), alkynyl($C_2$-$C_{20}$), perfluoroalkyl($C_1$-$C_6$), aryl or heteroaryl, may be prepared from amine 4 or amine 5 in which $R^{2b}$ is $-NR^{2f}R^{2g}$, where $R^{2f}$ is hereinbefore defined and $R^{2g}$ is H, by methods known to those skilled in the art. Such methods include employing any of a variety of acylation reactions using a carboxylic acid halide G-C(O)—Cl, carboxylic acid anhydride (G-C(O))$_2$—O, or a carboxylic acid G-C(O)—OH in combination with an appropriate activating agent, such as 1,3-dicyclohexylcarbodiimide, 1-(3-dimethylaminopropyl)-3-ethylcarbodiimide hydrochloride, benzotriazol-1-yloxy-tris(dimethylamino) phosphonium hexafluorophosphate, O-benzotriazol-1-yl-N,N,N',N'-tetramethyluronium hexafluorophosphate, 1,1'-carbonyldiimidazole, and the like, in the presence or absence of a suitable base to give glycopeptide antibiotics 7.

Scheme V

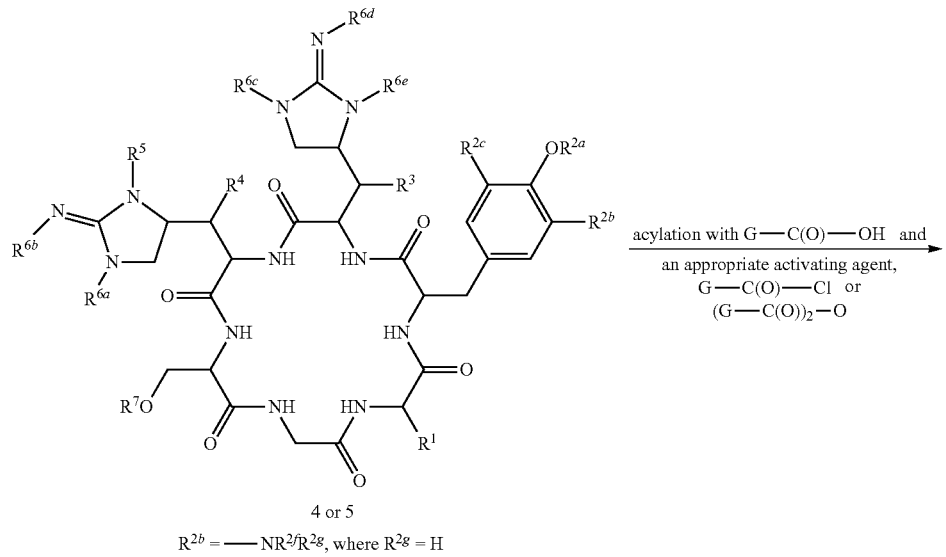

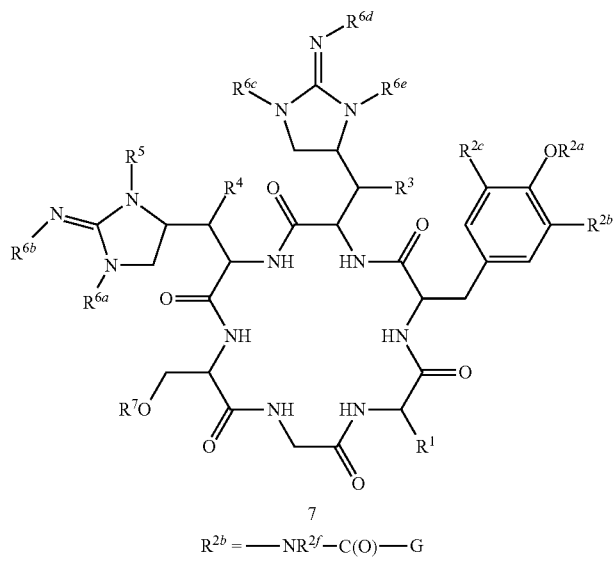

7

$R^{2b} = \text{—}NR^{2f}\text{—}C(O)\text{—}G$

As described in Scheme VI, glycopeptide antibiotics 8 in which $R^{2b}$ is —$NR^{2f}R^{2g}$, where $R^{2g}$ is the group D-E-G- as described above, wherein D is —C(S)—, E is a single bond and G is H, alkyl($C_1$-$C_{20}$), cycloalkyl($C_3$-$C_{20}$), alkenyl($C_2$-$C_{20}$), alkynyl($C_2$-$C_{20}$), perfluoroalkyl($C_1$-$C_6$), aryl or heteroaryl, may be prepared from glycopeptide antibiotics 7 in which D is —C(O)— by methods known to those skilled in the art such as by treatment with 2,4-bis(4-methoxyphenyl)-1,3-dithia-2,4-diphosphetane-2,4-disulfide.

Scheme VI

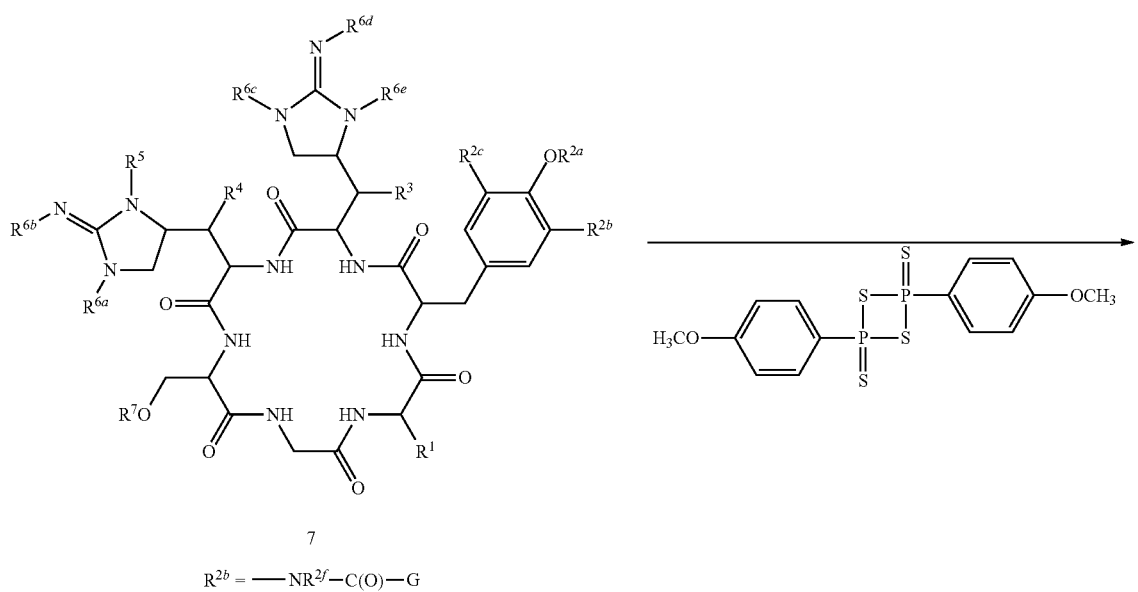

7

$R^{2b} = \text{—}NR^{2f}\text{—}C(O)\text{—}G$

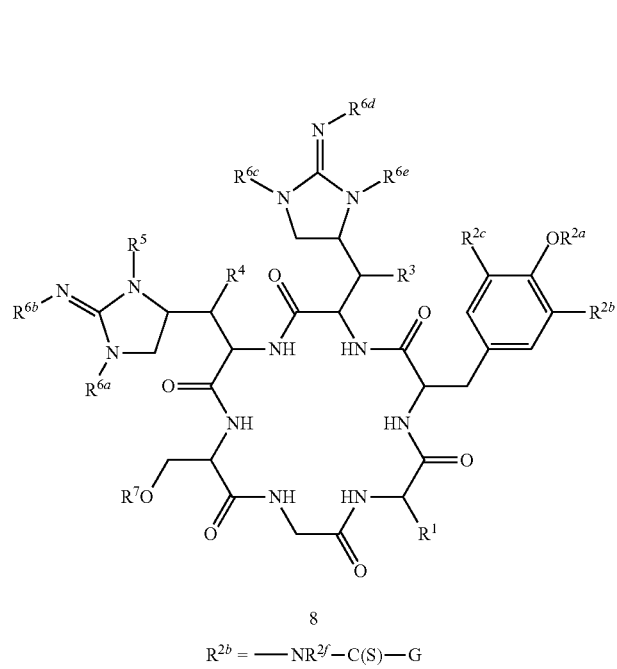

8

$R^{2b} = —NR^{2f}—C(S)—G$

As described in Scheme VII, glycopeptide antibiotics 9 in which $R^{2b}$ is $—NR^{2f}R^{2g}$, wherein $R^{2g}$ is the group D-E-G, D is $—S(O)_2—$, E is a single bond and G is alkyl($C_1$-$C_{20}$), cycloalkyl($C_3$-$C_{20}$), alkenyl($C_2$-$C_{20}$), alkynyl($C_2$-$C_{20}$), perfluoroalkyl($C_1$-$C_6$), aryl or heteroaryl, may be prepared from the corresponding primary amine 4 or secondary amine 5 in which $R^{2b}$ is $—NR^{2f}R^{2g}$, where $R^{ef}$ is hereinbefore defined and $R^{2g}$ is H, by methods known to those skilled in the art, such as by treatment with an appropriate sulfonic acid halide $G-S(O)_2—Cl$ or sulfonic acid anhydride $(G-S(O)_2)_2O$, in the presence or absence of a suitable base.

Scheme VII

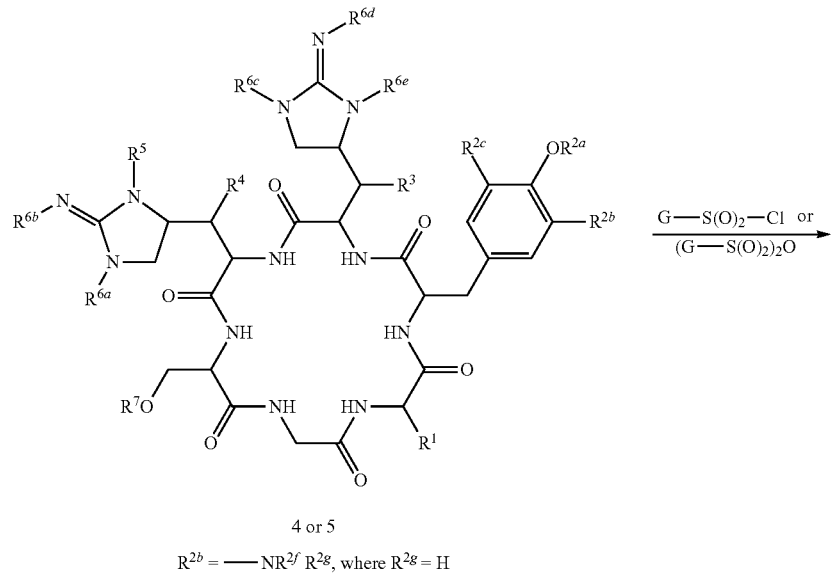

4 or 5

$R^{2b} = —NR^{2f} R^{2g}$, where $R^{2g} = H$

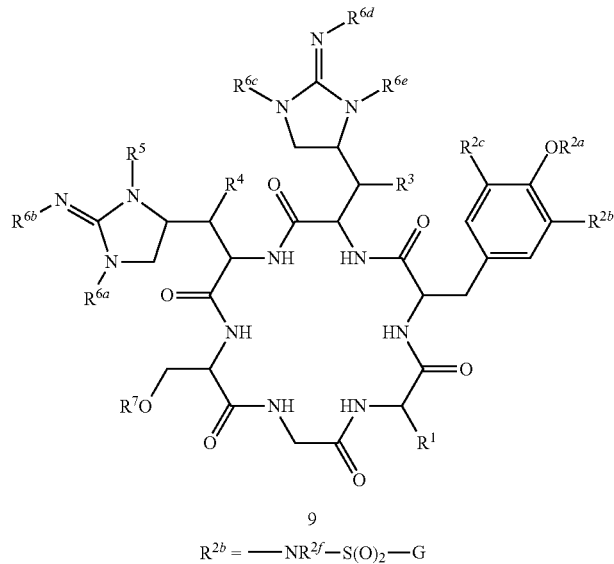

9

$R^{2b} = \text{—}NR^{2f}\text{—}S(O)_2\text{—}G$

Glycopeptide antibiotics 10, in which $R^{2b}$ is —$NR^{2f}R^{2g}$, wherein $R^{2g}$ is the group wherein D is —C(O)—, E is —O— and G is alkyl($C_1$-$C_{20}$), cycloalkyl($C_3$-$C_{20}$), alkenyl($C_3$-$C_{20}$), alkynyl($C_3$-$C_{20}$), perfluoroalkyl($C_1$-$C_6$), aryl or heteroaryl, may be prepared as shown in Scheme VIII from primary amine 4 or secondary amine 5 in which $R^{2b}$ is —$NR^{2f}R^{2g}$, where $R^{2f}$ is hereinbefore defined and $R^{2g}$ is H, by methods known to those skilled in the art. Methods include treatment with an appropriate chloroformate G-O—C(O)—Cl, N-hydroxysuccinimide carbonate G-O—C(O)—OSu or, alternatively, by sequential treatment with phosgene or a phosgene equivalent such as triphosgene, 1,1'-carbonyldiimidazole, 1,1'-carbonyl-bis(1,2,4)-triazole, or a chloronitrophenylformate, and the like, followed by treatment with an alcohol G-OH, in the presence or absence of a suitable base to give glycopeptide antibiotics 10.

Scheme VIII

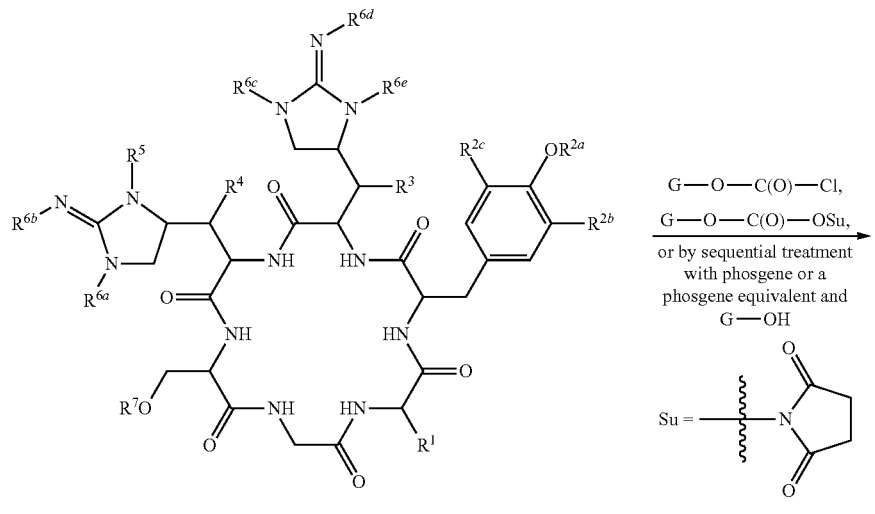

4 or 5

$R^{2b} = \text{———}NR^{2f}R^{2g}$, where $R^{2g}$ is H

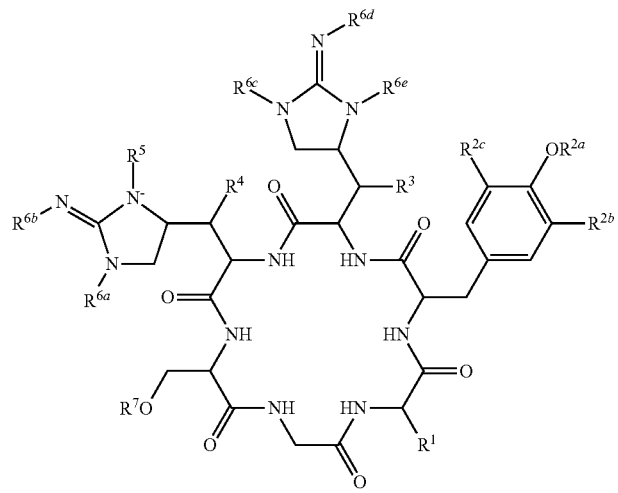

10

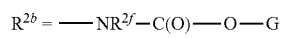

Glycopeptide antibiotics 11, in which $R^{2b}$ is —$NR^{2f}R^{2g}$, wherein $R^{2g}$ is the group D-E-G wherein D is —C(O)—, E is —$NR^{2h}$— and G is alkyl($C_1$-$C_{20}$), cycloalkyl($C_3$-$C_{20}$), alkenyl($C_3$-$C_{20}$), alkynyl($C_3$-$C_{20}$), perfluoroalkyl($C_1$-$C_6$), aryl or heteroaryl, may be prepared as shown in Scheme IX from primary amine 4 or secondary amine 5 where $R^{2b}$ is —$NR^{2f}R^{2g}$, where $R^{2f}$ is hereinbefore defined and $R^{2g}$ is H, by methods known to those skilled in the art. Methods include treatment with an appropriate isocyanate G-N=C=O or, alternatively, by sequential treatment with phosgene or a phosgene equivalent such as triphosgene, 1,1'-carbonyldiimidazole, 1,1'-carbonyl-bis(1,2,4)-triazole, or a chloronitrophenylformate, and the like, followed by treatment with a primary or secondary amine, G-$NHR^{2h}$ in the presence or absence of a suitable base to give glycopeptide antibiotics 11.

Scheme IX

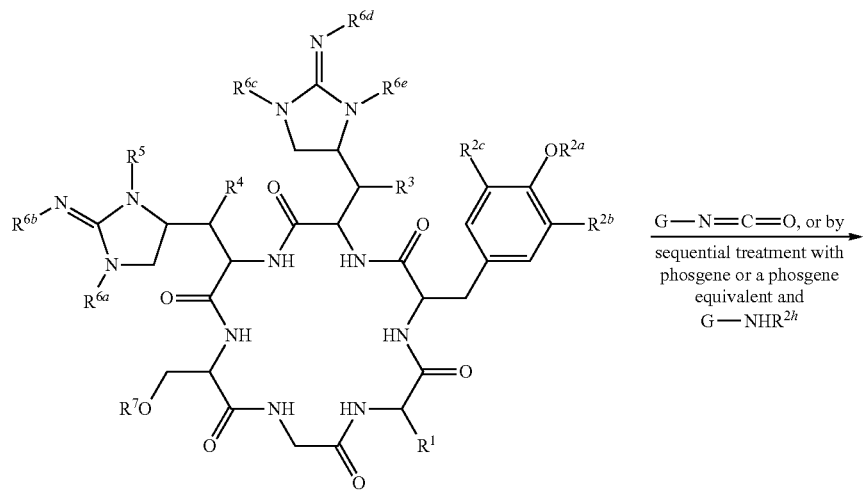

4 or 5

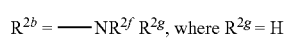

-continued

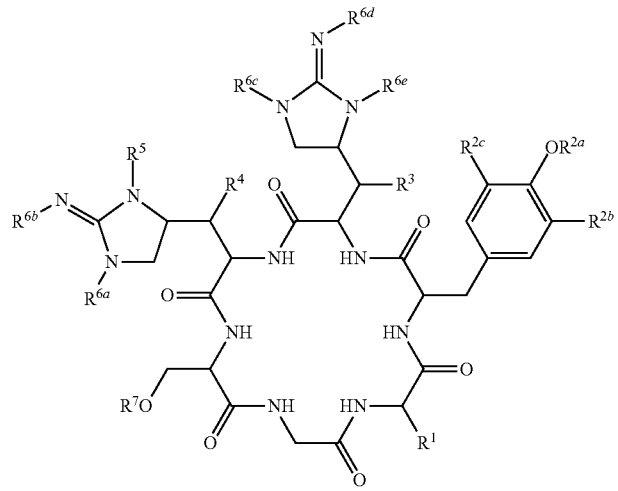

11

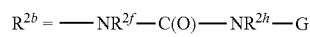

Glycopeptide antibiotics 12, in which $R^{2b}$ is $-NR^{2f}R^{2g}$, wherein $R^{2g}$ is the group D-E-G wherein D is $-C(S)-$, E is $-O-$ and G is alkyl($C_1$-$C_{20}$), cycloalkyl($C_3$-$C_{20}$), alkenyl ($C_3$-$C_{20}$), alkynyl($C_3$-$C_{20}$), perfluoroalkyl($C_1$-$C_6$), aryl or heteroaryl, may be prepared as shown in Scheme X from primary amine 4 or secondary amine 5 in which $R^{2b}$ is $-NR^{2f}R^{2g}$ where $R^{2f}$ is hereinbefore defined and $R^{2g}$ is H, by methods known to those skilled in the art. Methods include sequential treatment of primary amine 4 or secondary amine 5 with thiophosgene or a thiophosgene equivalent such as 1,1'-thiocarbonyldiimidazole or 1,1'-thiocarbonyl-bis(1,2,4)-triazole followed by treatment with an alcohol G-OH in the presence or absence of a suitable base to give glycopeptide antibiotics 12.

Scheme X

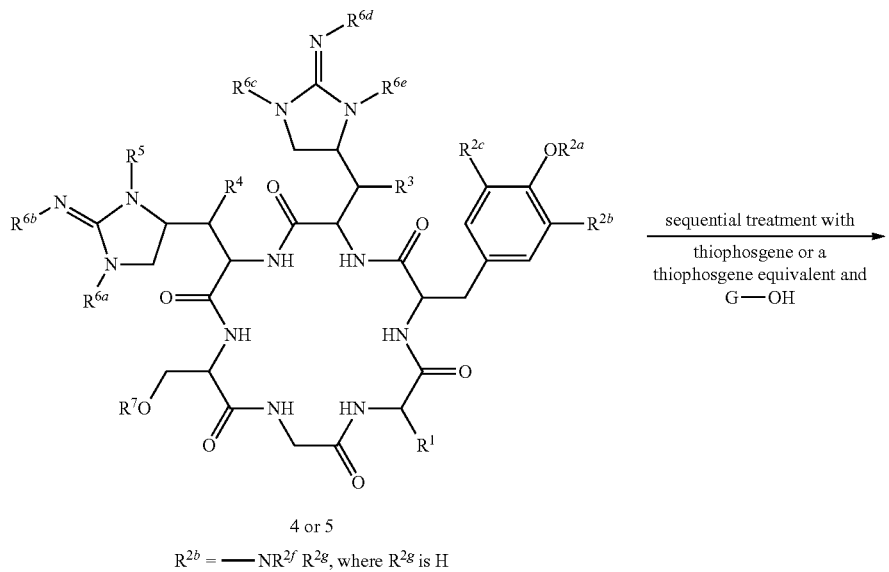

4 or 5

$R^{2b} = -NR^{2f} R^{2g}$, where $R^{2g}$ is H

-continued

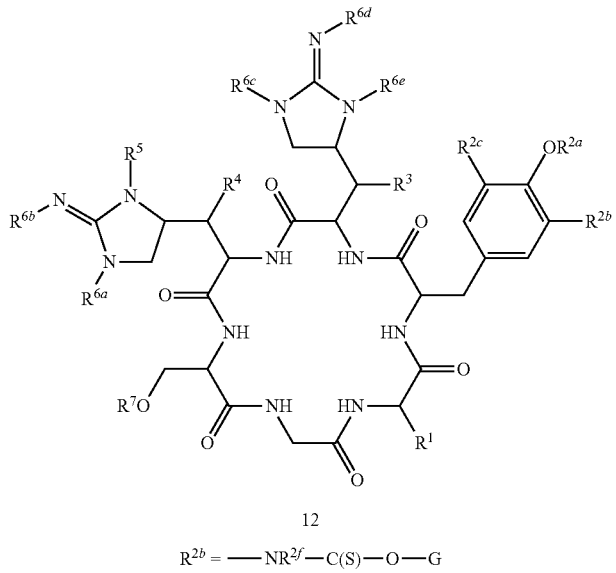

12

$R^{2b} = \text{---} NR^{2f}\text{---}C(S)\text{---}O\text{---}G$

Glycopeptide antibiotics 13, in which $R^{2b}$ is $-NR^{2f}R^{2g}$, wherein $R^{2g}$ is the group D-E-G, D is $-C(S)-$, E is $-NR^{2h}-$ and G is alkyl($C_1$-$C_{20}$), cycloalkyl($C_3$-$C_{20}$), alkenyl($C_3$-$C_{20}$), alkynyl($C_3$-$C_{20}$), perfluoroalkyl($C_1$-$C_6$), aryl or heteroaryl, may be prepared as shown in Scheme XI from primary amine 4 or secondary amine 5 in which $R^{2b}$ is $-NR^{2f}R^{2g}$, where $R^{2g}$ is H and $R^{2f}$ is hereinbefore defined by methods known to those skilled in the art. Methods include treatment of primary amine 4 or secondary amine 5 with an appropriate isothiocyanate G-N=C=S or, alternatively, by sequential treatment with thiophosgene or a thiophosgene equivalent such 1,1'-thiocarbonyldiimidazole or 1,1'-thiocarbonyl-bis(1,2,4)-triazole followed by treatment with a primary or secondary amine G-NHR$^{2h}$ in the presence or absence of a suitable base to give glycopeptide antibiotics 13.

Scheme XI

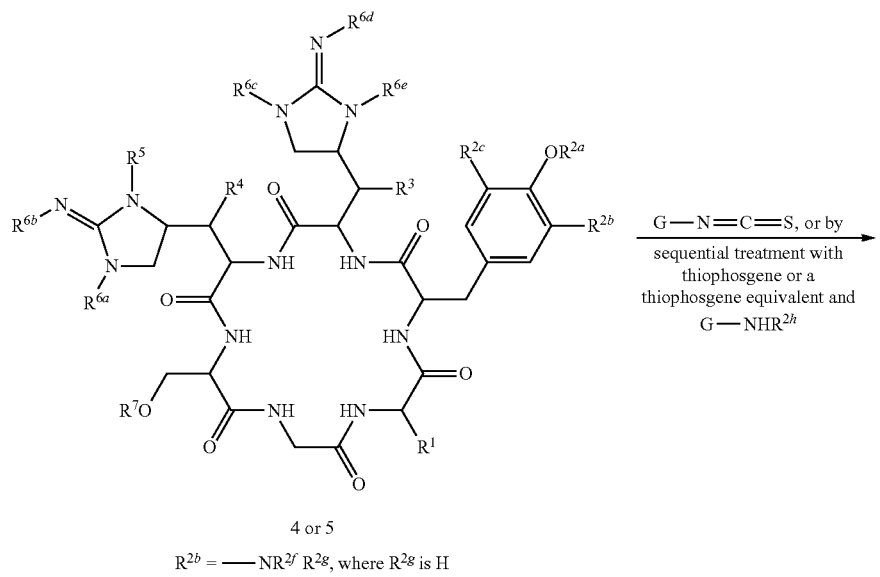

4 or 5

$R^{2b} = \text{---} NR^{2f} R^{2g}$, where $R^{2g}$ is H

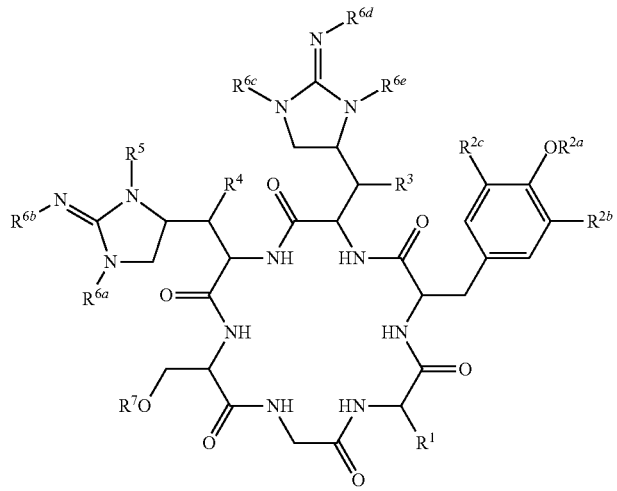

13

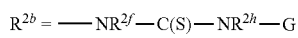

As shown in Scheme XII, glycopeptide antibiotics 14, wherein $R^{2d}$ is alkyl($C_1$-$C_{20}$), alkenyl($C_2$-$C_{20}$), alkynyl($C_2$-$C_{20}$), aryl or heteroaryl, may be prepared from amine 4 in which $R^{2b}$ is —$NH_2$ by methods known to those skilled in the art. Methods include treatment with an appropriate alkenyl-, alkynyl-, aryl- or heteroaryl-aldehyde $R^{2d}$—CHO or aldehyde dialkyl-acetal $R^{2d}$—CH(O-alkyl($C_1$-$C_{20}$))$_2$ and an excess of an oxidant, such as 2,3-dichloro-5,6-dicyano-1,4-benzoquinone or it's equivalent to give glycopeptide antibiotics 14.

Scheme XII

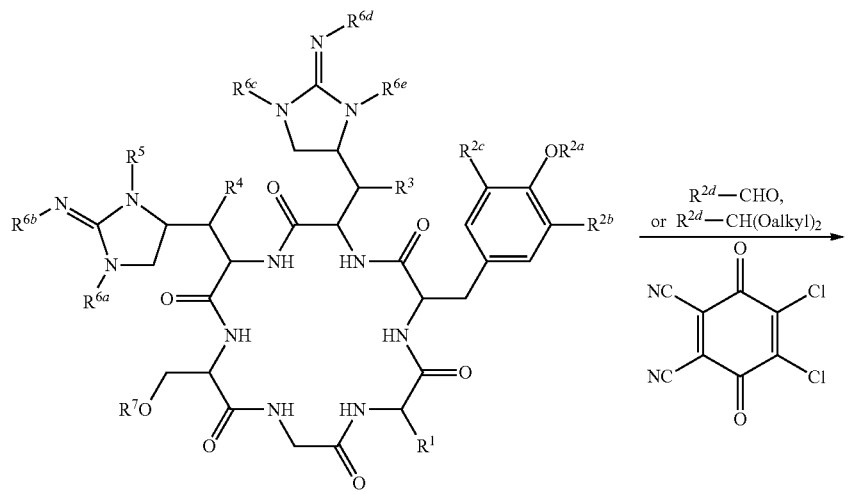

4

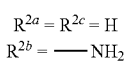

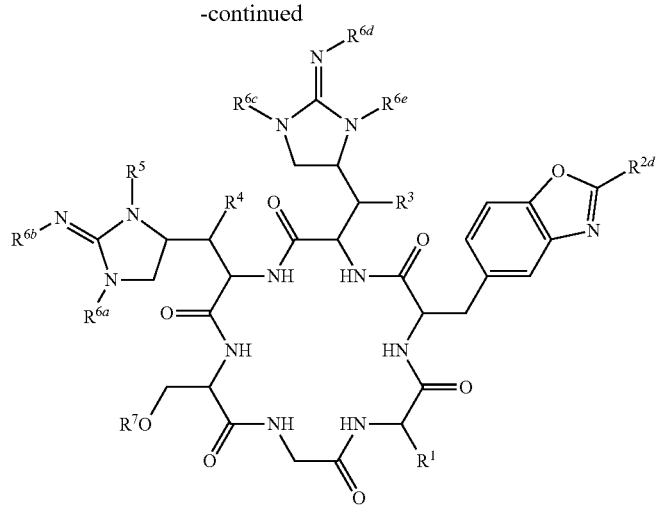

14

$R^{2d}$ = alkyl, alkenyl, alkynyl, aryl or heteroaryl

Glycopeptide antibiotics 15 wherein $R^{2e}$ is O, may be prepared as shown in Scheme XIII from an amine 4 by methods known to those skilled in the art. Methods include treatment of amine 4 with phosgene or a phosgene equivalent such as triphosgene, 1,1'-carbonyldiimidazole, 1,1'-carbonyl-bis(1,2,4)-triazole, or a chloronitrophenylformate, in the presence or absence of a suitable base to give glycopeptide antibiotics 15. Alternatively, glycopeptide antibiotics 15 may be prepared from glycopeptide antibiotics 10, by treatment with a suitable base.

Scheme XIII

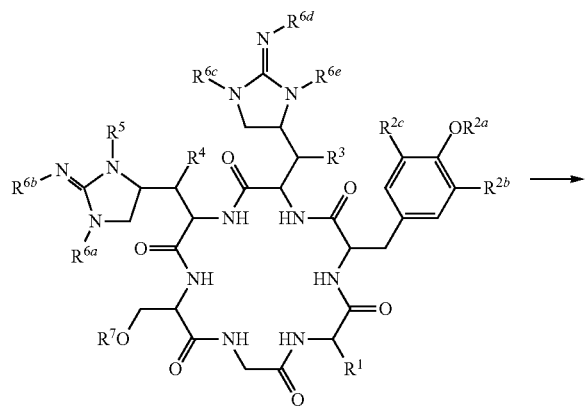

-continued

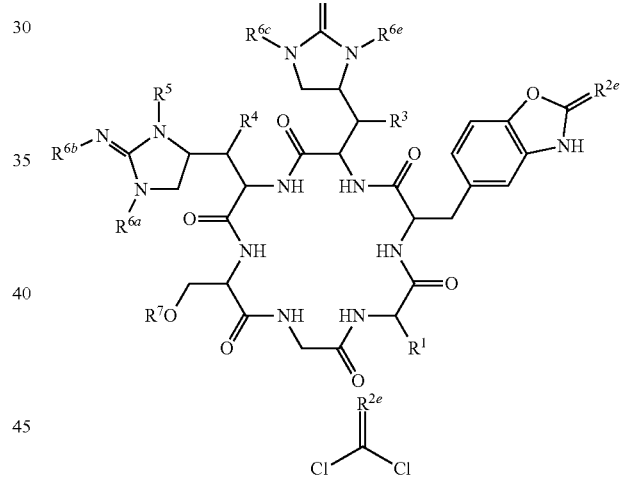

Glycopeptide antibiotics 16 wherein Rte is S, may be prepared as shown in Scheme XIV from amine 4, by methods known to those skilled in the art. Methods include treatment of amine 4 with thiophosgene or a thiophosgene equivalent such as 1,1'-thiocarbonyldiimidazole or 1,1'-thiocarbonyl-bis(1,2,4)-triazole, in the presence or absence of a suitable base to give glycopeptide antibiotics 16. Alternatively, glycopeptide antibiotics 16 may be prepared from glycopeptide antibiotics 12 in which G is aryl, by treatment with a suitable base.

Scheme XIV

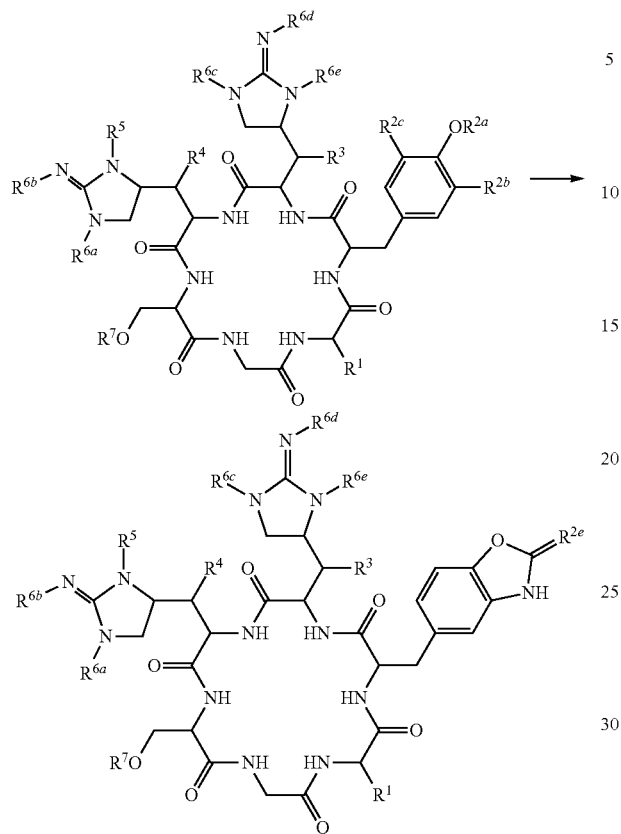

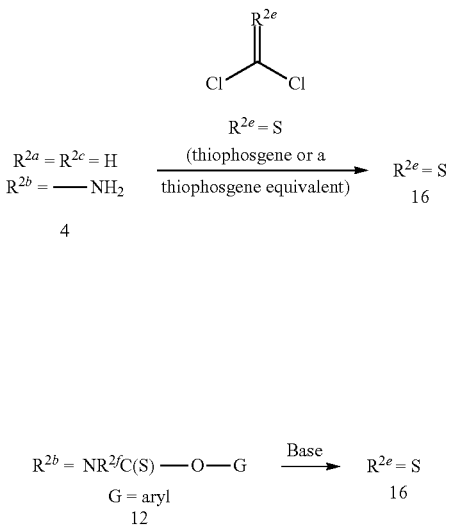

Glycopeptide antibiotics 17 in which $R^{2d}$ is the group L-M, where L is —S— or —SCH$_2$C(O)—, and M is as described above may be prepared as shown in Scheme XV from glycopeptide antibiotics 16 in which $R^{2e}$ is S, by methods known to those skilled in the art. Methods include treatment of glycopeptide antibiotics 16 with an appropriate alkylating agent M-X or M-C(O)—CH$_2$—X, where X is Cl, Br, or I, in the presence or absence of a suitable base to give glycopeptide antibiotics 12.

Scheme XV

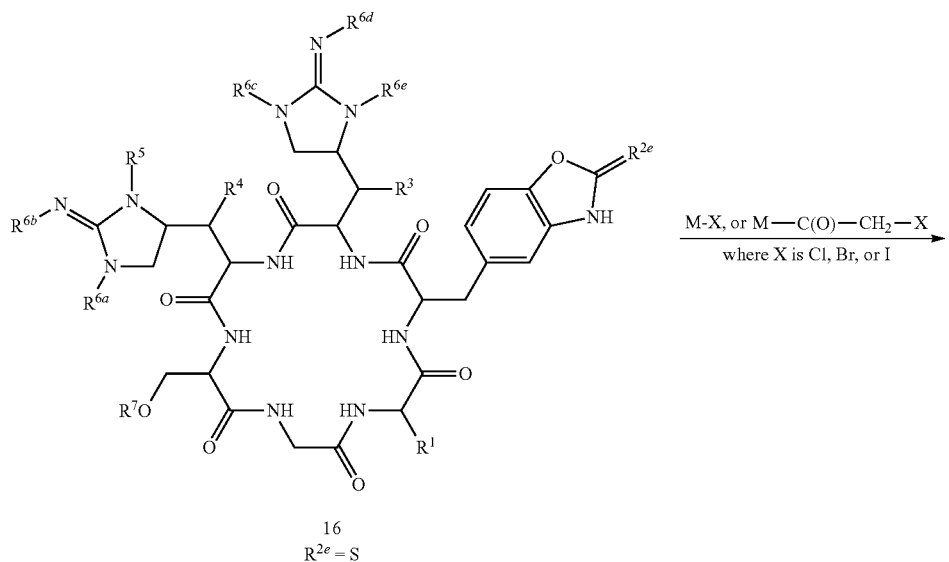

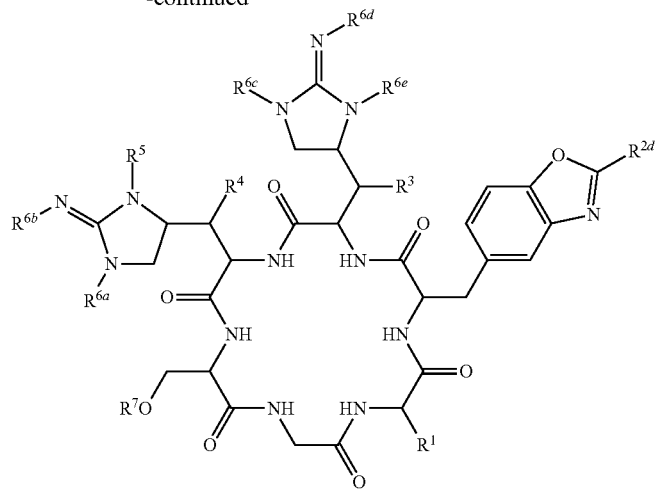

17

$R^{2d}$ = —S—M, —S—CH$_2$C(O)—M

As shown in Scheme XVI, glycopeptide antibiotics 18 in which $R^{2d}$ is the group L-M where L is —NH—, and M is as described above may be prepared from glycopeptide antibiotics 13 in which $R^{2b}$ is —NR$^{2f}$R$^{2g}$, wherein $R^{2f}$ is H and $R^{2g}$ is the group D-E-G where D is —C(S)—, E is —NR$^{2h}$— and G is alkyl(C$_1$-C$_{20}$), cycloalkyl(C$_3$-C$_{20}$), alkenyl(C$_3$-C$_{20}$), alkynyl(C$_3$-C$_{20}$), aryl or heteroaryl by methods known to those skilled in the art. Methods include treatment of glycopeptide antibiotics 13 with a suitable mercury (II) salt, such a mercuric chloride, in the presence or absence of a suitable base to give glycopeptide tibiotics 18.

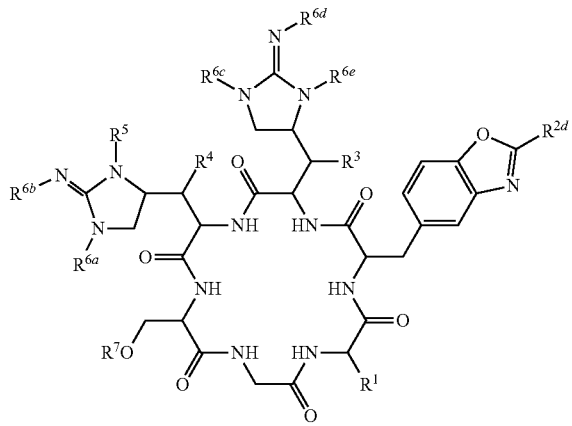

18

$R^{2d}$ = —NR$^{2h}$—M, where M = G

As shown in Scheme XVII, glycopeptide antibiotics 20, may be prepared from glycopeptide antibiotics 19, where $R^{1a}$ is H;

$R^{2a}$ is H or a moiety of the formulae:

Scheme XVI

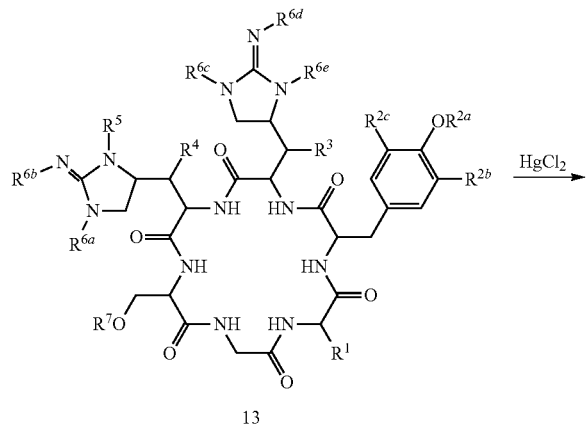

13

$R^{2a}$ = $R^{2c}$ = H
$R^{2b}$ = —NR$^{2f}$—C(S)—NR$^{2h}$—G

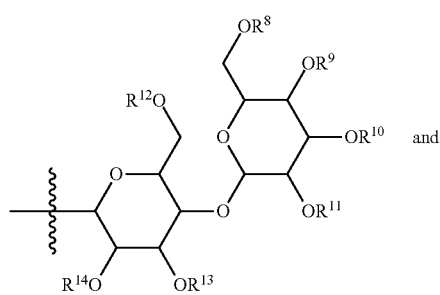

and

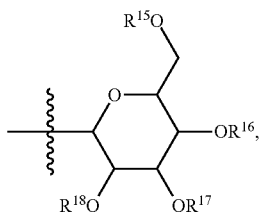

and $R^{2b}$ and $R^{2c}$ are H, by reduction under suitable reducing conditions which include hydrogenation under an atmosphere of hydrogen at pressures from about 1 to about 250 psi, over a suitable catalyst such as rhodium, either alone or adsorbed onto a suitable support such as carbon, alumina or diatomaceous earth in solvents such as water, methanol, ethanol, and the like, alone or in combination, in the presence or absence of a mineral or carboxylic acid, such as hydrochloric acid, sulfuric acid, or acetic acid, and the like, at temperatures from about 25° C. to the reflux temperature of the solvent to give glycopeptide antibiotics 20. The extent of the hydrogenation may be controlled by variations in the reaction temperature, hydrogen pressure, amount of catalyst, composition of the catalyst and support, amount of acid additive and the reaction time.

Scheme XVII

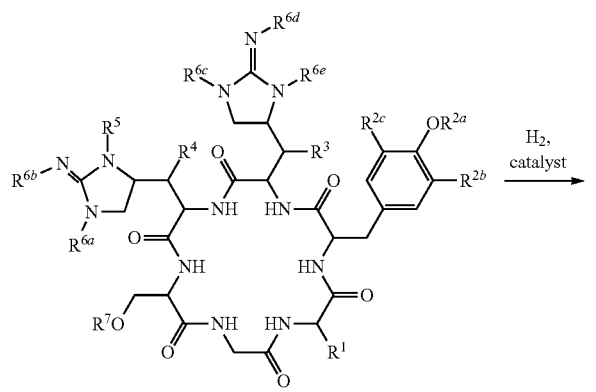

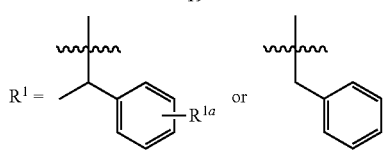

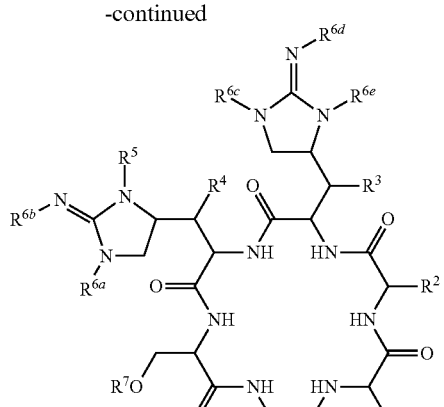

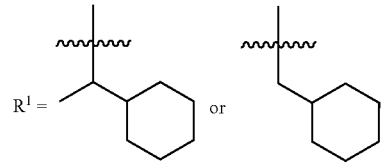

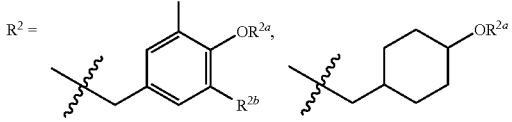

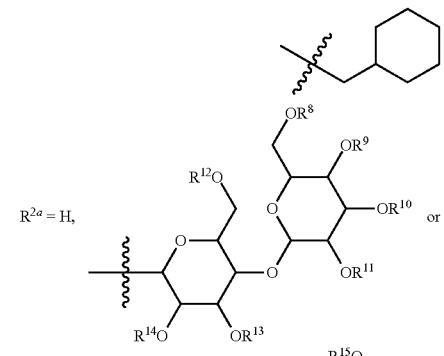

As described in Scheme XVIII, glycopeptide antibiotics 22, may be prepared from the corresponding glycopeptide antibiotics 21 as shown by methods known to those skilled in the art, such as by treatment with an aqueous mineral acid, such as hydrochloric acid, sulfuric acid, nitric acid, and the like, either alone or in a suitable solvent such as methanol, ethanol, water, N,N-dimethylformamide, dimethyl sulfoxide, and the like, at temperatures ranging from about 25° C. to about 90° C. Alternatively, and when $R^8$, $R^9$, $R^{10}$, $R^{11}$, $R^{12}$, $R^{13}$, $R^{14}$, $R^{15}$, $R^{16}$, $R^{17}$ and $R^{18}$ are H, such compounds may also be prepared by treatment with α-mannosidase enzymes, such as purified α-mannosidase derived from sources such as *Canavalia ensiformis* or *Prunus amygdalus* or crude α-mannosidase present in jack bean meal or almond meal, in buffered aqueous systems, preferably in 0.1M sodium acetate buffer at about pH 3.5 to about 6.5, in the presence or absence of added metal salts, such as zinc chloride, and in the presence or absence of added cosolvents.

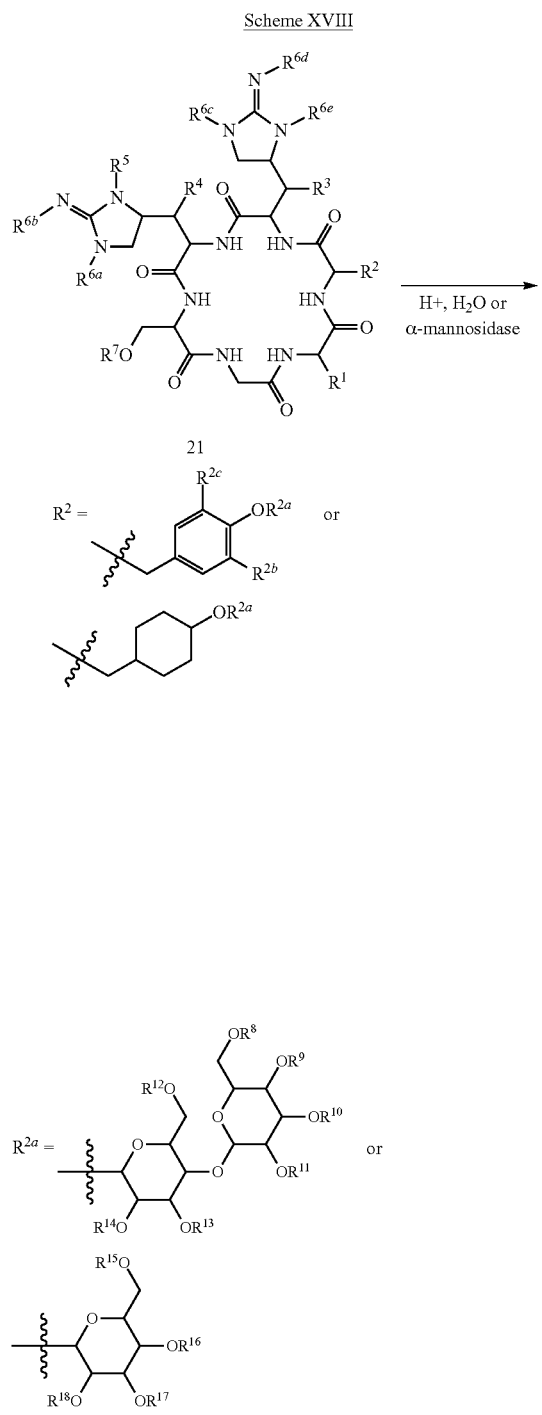

Scheme XVIII

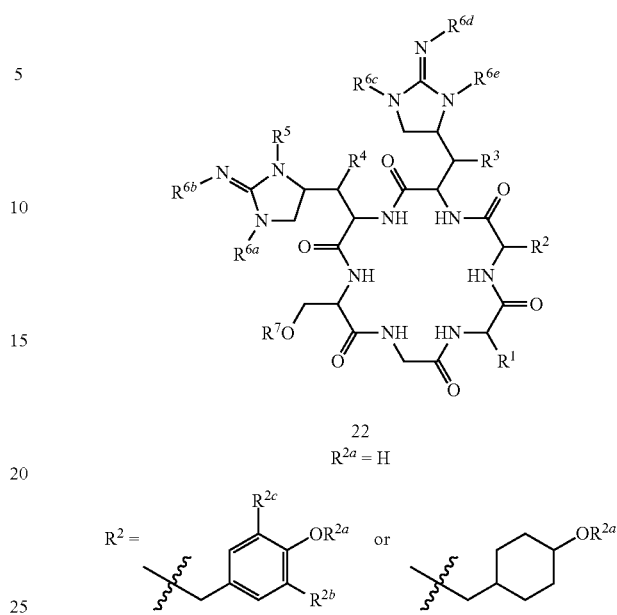

22
$R^{2a} = H$

As described in Scheme XIX glycopeptide antibiotics 24, may be prepared from the corresponding glycopeptide antibiotics 23 by treatment with α-mannosidase enzymes, such as purified α-Mannosidase readily derived from sources such as *Canavalia ensiformis* or *Prunus amygdalus* or crude α-mannosidase present in jack bean meal or almond meal, in buffered aqueous systems, preferably 0.1M sodium acetate buffer at pH about 3.5 to about 6.5, in the presence or absence of added metal salts such as zinc chloride, and in the presence or absence of added cosolvents.

Scheme XIX

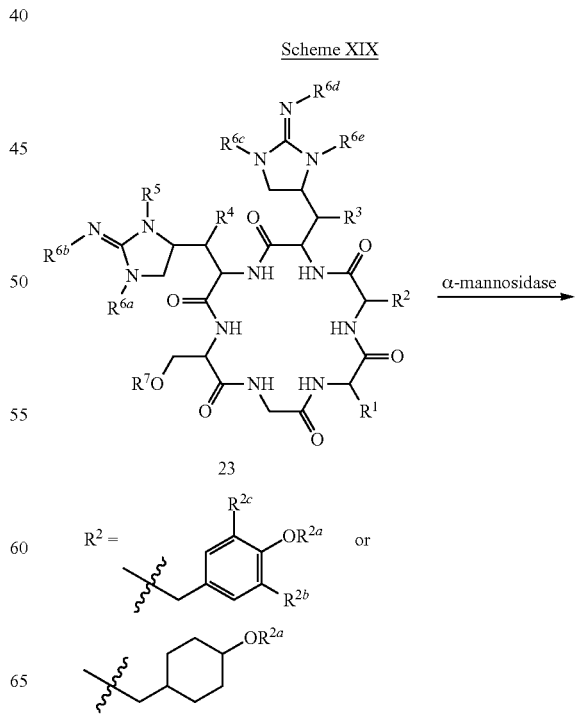

23

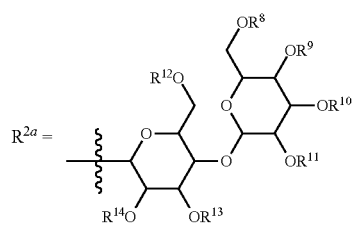

where $R^8$, $R^9$, $R^{10}$ and $R^{11}$ = H

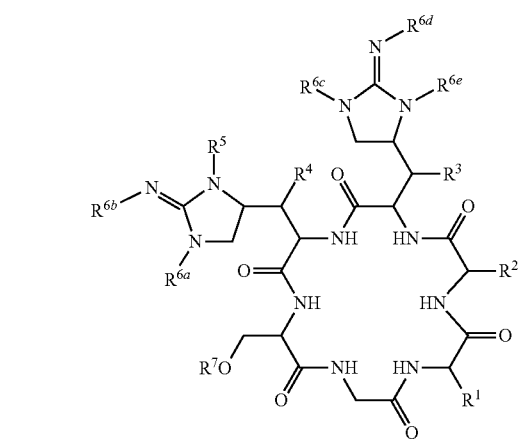

24

$R^{16}$ = H

Scheme XX

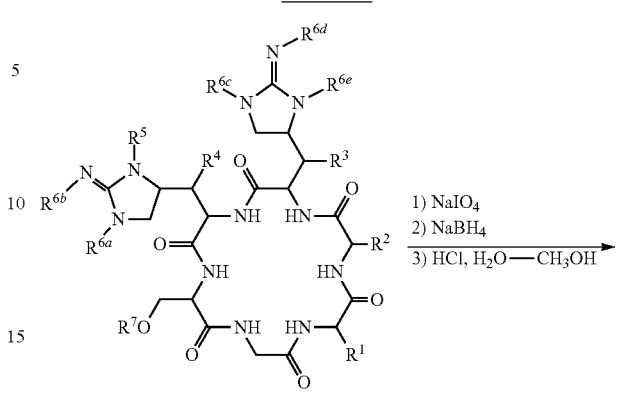

25

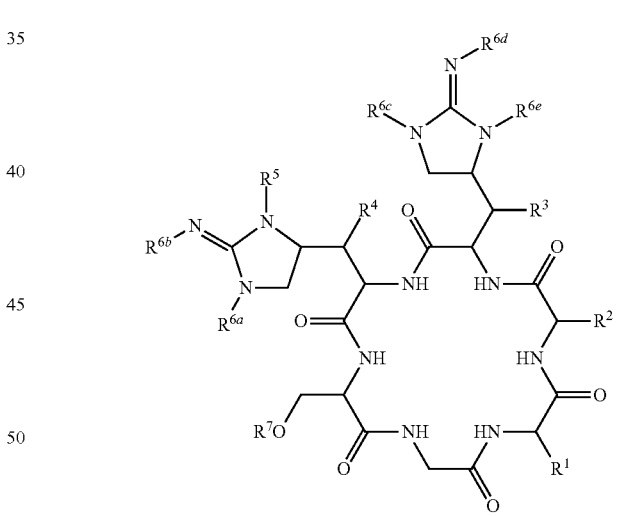

26
$R^5$ = H

Glycopeptide antibiotics 26 in which $R^5$ is H, may be prepared as described in Scheme XX from the corresponding glycopeptide antibiotics 25 as shown in which $R^{19}$, $R^{20}$, $R^{21}$ and $R^{22}$ are H, by methods known to those skilled in the art, such methods include sequential treatment with sodium periodate, followed by a reductant such as sodium borohydride, followed by an aqueous mineral acid, such as hydrochloric acid, sulfuric acid, nitric acid, and the like, either alone or in a suitable solvent at temperatures ranging from about 25° C. to about 90° C.

As shown in Scheme XXI, glycopeptide antibiotics 27 in which $R^5$ is alkyl($C_1$-$C_{20}$), cycloalkyl($C_3$-$C_{20}$), alkenyl($C_3$-$C_{20}$) or alkynyl($C_3$-$C_{20}$) may be prepared from the corresponding glycopeptide antibiotics 26 in which $R^5$ is H, by methods known to those skilled in the art, such as by alkylation with an appropriate alkylating agent $R^5$—X, where X is Cl, Br, I, —O-tosylate, —O-mesylate, or —O-triflate, in the presence or absence of a suitable base.

Scheme XXI

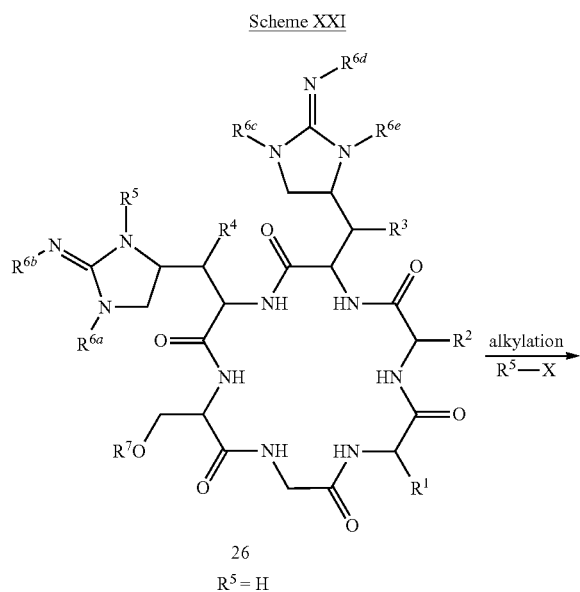

26
$R^5 = H$

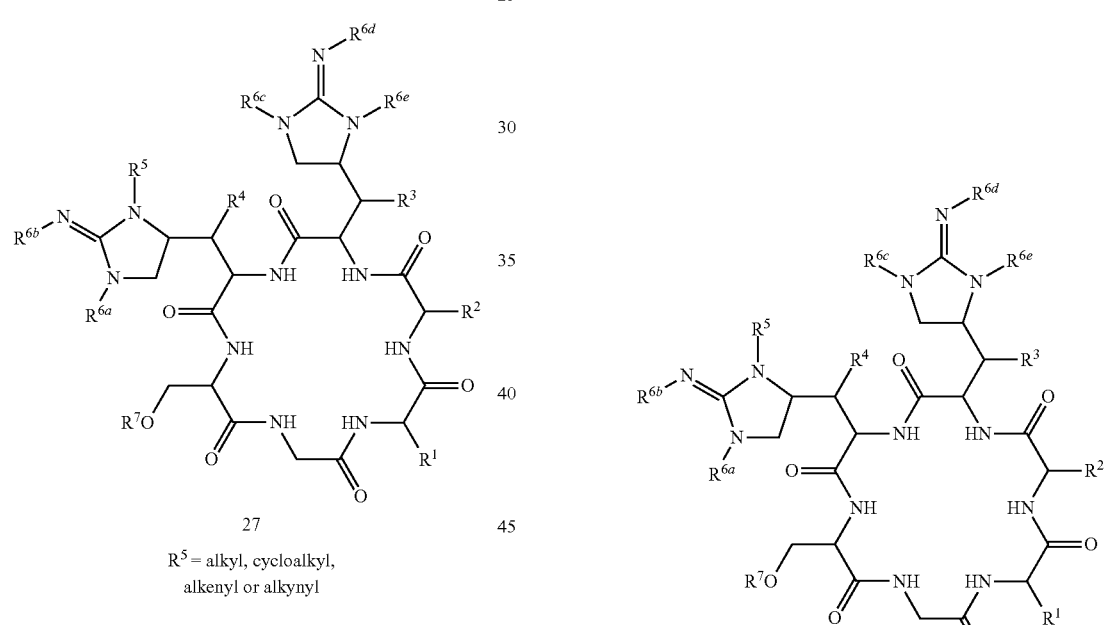

27
$R^5$ = alkyl, cycloalkyl, alkenyl or alkynyl

Scheme XXII

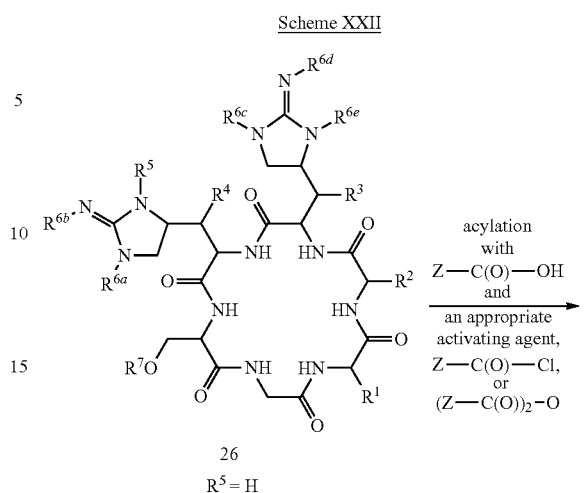

26
$R^5 = H$

28
$R^5 = $ —C(O)—Z

Glycopeptide antibiotics 28, in which $R^5$ is —C(O)—Y—Z, wherein Y is a single bond and Z is H, alkyl($C_1$-$C_{20}$), cycloalkyl ($C_3$-$C_{20}$), alkenyl($C_2$-$C_{20}$), alkynyl($C_2$-$C_{20}$), perfluoroalkyl($C_1$-$C_6$), aryl or heteroaryl, may be prepared as shown in Scheme XXII from the corresponding compounds 26 in which $R^5$ is H, by methods known to those skilled in the art, such as by employing any of a variety of acylation reactions using a carboxylic acid halide Z—C(O)—Cl, carboxylic acid anhydride (Z—C(O))$_2$—O, or a carboxylic acid Z—C(O)—OH in combination with an appropriate activating agent, such as 1,3-dicyclohexylcarbodiimide, 1-(3-dimethylaminopropyl)-3-ethylcarbodiimide hydrochloride, benzotriazol-1-yloxy-tris(dimethylamino)phosphonium hexafluorophosphate, O-benzotriazol-1-yl-N,N,N',N'-tetramethyluronium hexafluorophosphate, 1,1'-carbonyldiimidazole, and the like, in the presence or absence of a suitable base.

As described in Scheme XXIII glycopeptide antibiotics 29 in which $R^5$ is —C(O)—Y—Z, wherein Y is —O— and Z is alkyl($C_1$-$C_{20}$), cycloalkyl($C_3$-$C_{20}$), alkenyl($C_3$-$C_{20}$), alkynyl($C_3$-$C_{20}$), perfluoroalkyl($C_1$-$C_6$), aryl or heteroaryl, may be prepared from the corresponding glycopeptide antibiotics 26 in which $R^5$ is H, by methods known to those skilled in the art, such as by treatment with an appropriate chloroformate Z—O—C(O)—Cl or N-hydroxysuccinimide carbonate Z—O—C(O)—OSu, and the like, in the presence or absence of a suitable base.

Scheme XXIII

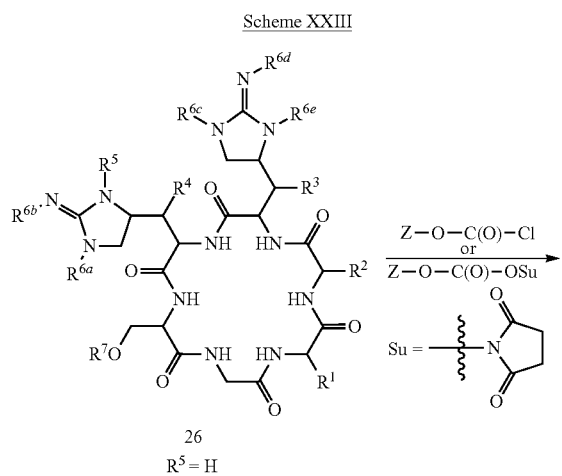

26
R⁵ = H

Scheme XXIV

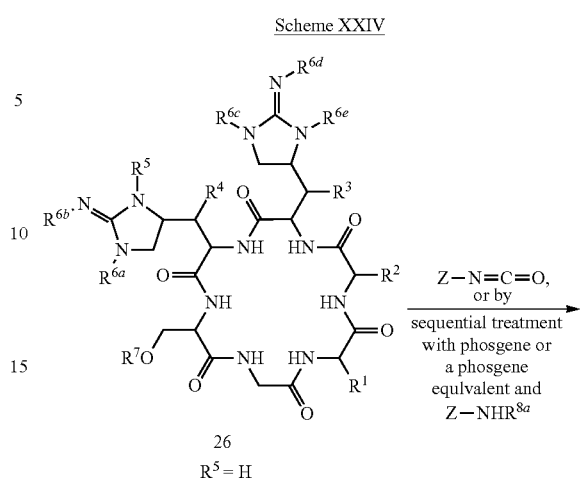

26
R⁵ = H

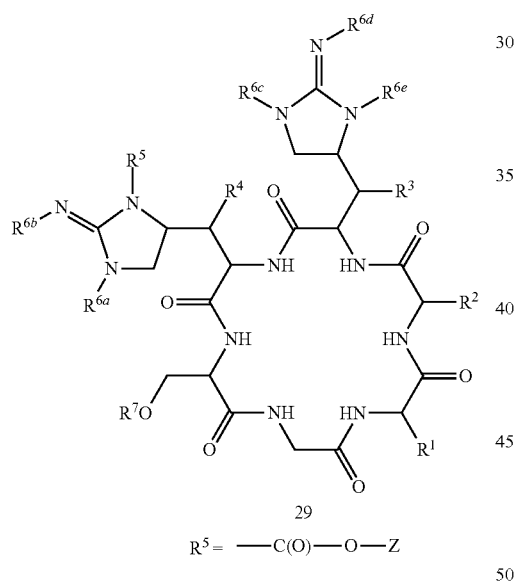

29
R⁵ = —C(O)—O—Z

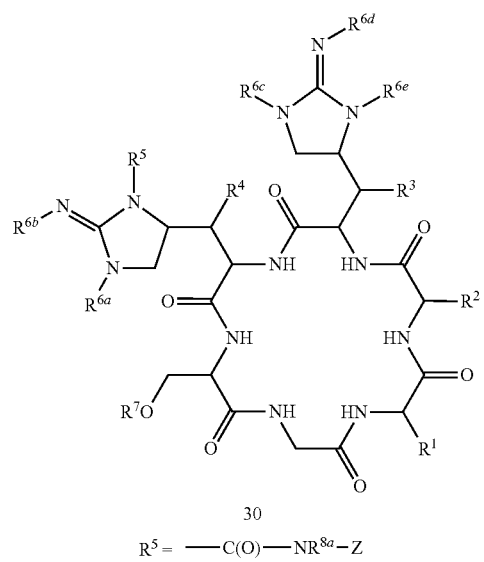

30
R⁵ = —C(O)—NR⁸ᵃ—Z

Glycopeptide antibiotics 30 in which R⁵ is —C(O)—Y—Z, wherein Y is —NR⁸ᵃ— and Z is alkyl($C_1$-$C_{20}$), cycloalkyl ($C_3$-$C_{20}$), alkenyl($C_3$-$C_{20}$), alkynyl($C_3$-$C_{20}$), perfluoroalkyl ($C_1$-$C_6$), aryl or heteroaryl, may be prepared as shown in Scheme XXIV from the corresponding glycopeptide antibiotics 26 in which R⁵ is H, by methods known to those skilled in the art, such as by treatment with appropriate isocyanate Z—N=C=O, or, alternatively, by sequential treatment with phosgene or a phosgene equivalent such as triphosgene, 1,1'-carbonyldiimidazole, 1,1'-carbonyl-bis(1,2,4)-triazole, or a chloronitrophenylformate, and the like, followed by treatment with a primary or secondary amine, Z—NHR⁸ᵃ in the presence or absence of a suitable base.

As shown in Scheme XXV, glycopeptide antibiotics 31 in which R⁵ is as shown may be prepared from the corresponding glycopeptide antibiotics 26 in which R⁵ is H, by methods known to those skilled in the art, such as by treatment with aryl halides, tosylates, and triflates, such as a 2-chloropyrimidine, a 2-chlorobenzoxazole, a 2-chlorobenzothiazole, a 4-chlorobenzopyrimidine, a 2-fluoronitrobenzene, a 4-fluoronitrobenzene, and the like, in the presence or absence of a suitable base.

Scheme XXV

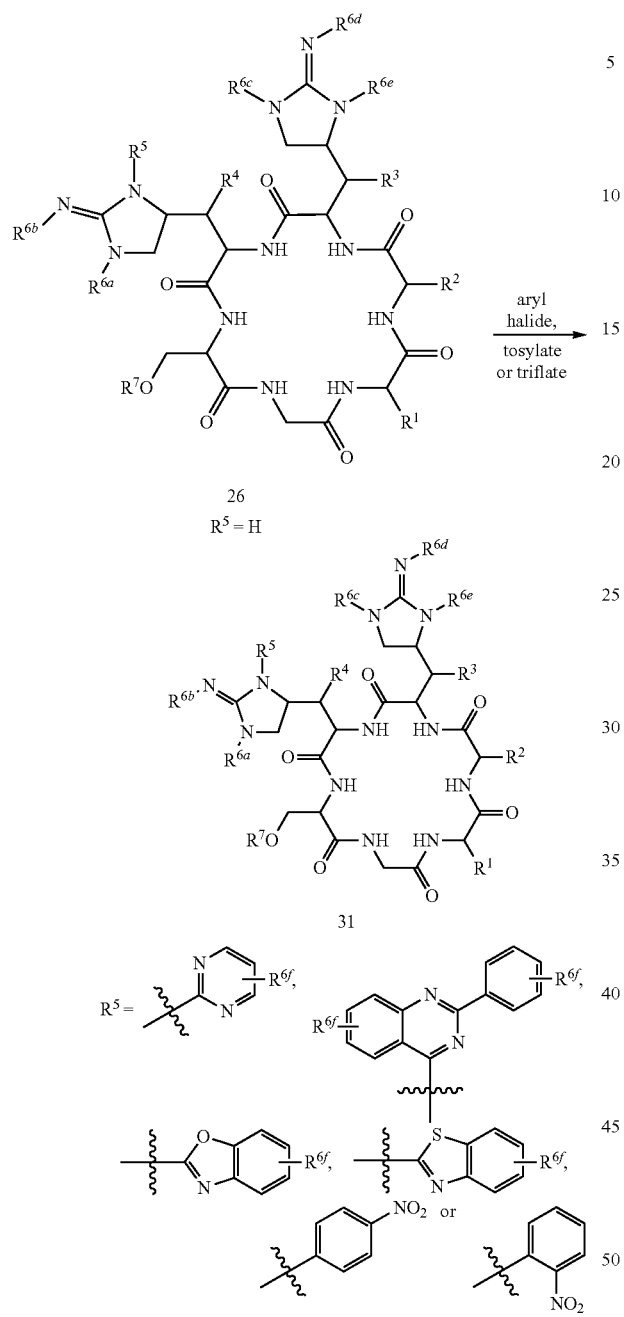

26
$R^5 = H$

31

Scheme XXVI

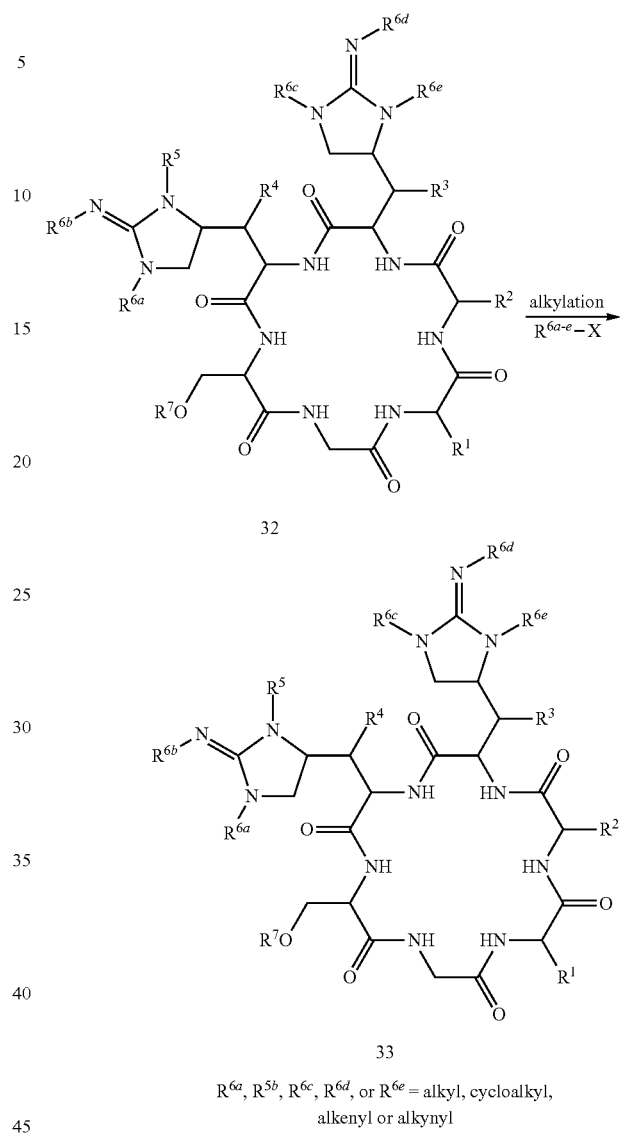

32

33

$R^{6a}$, $R^{5b}$, $R^{6c}$, $R^{6d}$, or $R^{6e}$ = alkyl, cycloalkyl, alkenyl or alkynyl As shown in Scheme XXVI, glycopeptide antibiotics 33 in which $R^{6a}$, $R^{6b}$, $R^{6c}$, $R^{6d}$ or $R^{6e}$ are independently alkyl($C_1$-$C_{20}$), cycloalkyl($C_3$-$C_{20}$), alkenyl($C_3$-$C_{20}$) or alkynyl($C_3$-$C_{20}$) may be prepared from the corresponding glycopeptide antibiotics 32 in which at least one of $R^{6a}$, $R^{6b}$, $R^{6c}$, $R^{6d}$ and $R^{6e}$ are H, by methods known to those skilled in the art, such as by alkylation with an appropriate alkylating agent $R^{6a}X$, $R^{6b}X$, $R^{6c}X$, $R^{6d}X$ or $R^{6e}X$ where X is Cl, Br, I, —O-tosylate, —O-mesylate, or —O-triflate, in the presence or absence of a suitable base. As recognized by those skilled in the art, the extent of alkylation may be controlled by the stoichiometry of the alkylating agent as well as variations in the reaction temperature, and reaction time.

As shown in Scheme XXVII, glycopeptide antibiotics 34 in which $R^{6a}$, $R^{6b}$, $R^{6c}$, $R^{6d}$ or $R^{6e}$ are independently —C(O)—Y—Z, wherein Y is a single bond and Z is H, alkyl($C_1$-$C_{20}$), cycloalkyl($C_3$-$C_{20}$), alkenyl($C_2$-$C_{20}$), alkynyl ($C_2$-$C_{20}$), perfluoroalkyl($C_1$-$C_6$), aryl or heteroaryl, may be prepared from the corresponding glycopeptide antibiotics 32 in which at least one of $R^{6a}$, $R^{6b}$, $R^{6c}$, $R^{6d}$ and $R^{6e}$ are H, by methods known to those skilled in the art, such as by employing any of a variety of acylation reactions using reagents such as a carboxylic acid halide Z—C(O)—Cl, carboxylic acid anhydride (Z—C(O))$_2$—O, or a carboxylic acid Z—C(O)—OH in combination with an appropriate activating agent, such as 1,5-dicyclohexylcarbodiimide, 1-(3-dimethylaminopropyl)-3-ethylcarbodiimide hydrochloride, benzotriazol-1-yloxy-tris(dimethylamino)phosphonium hexafluorophosphate, O-benzotriazol-1-yl-N,N,N',N'-tetramethyluronium hexafluorophosphate, 1,1'-carbonyldiimidazole, and the like, in the presence or absence of a suitable base. The extent of acylation may be controlled by variations in reagent stoichiometry, reaction temperature, and reaction time.

Scheme XXVII

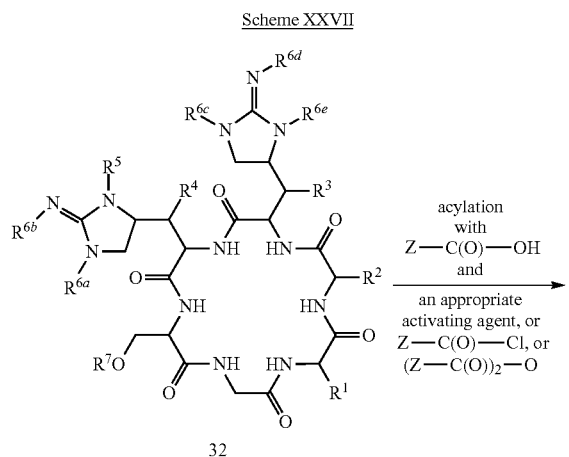

Scheme XXVIII

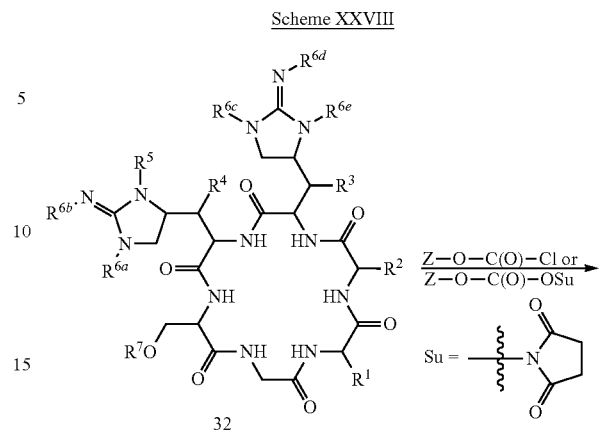

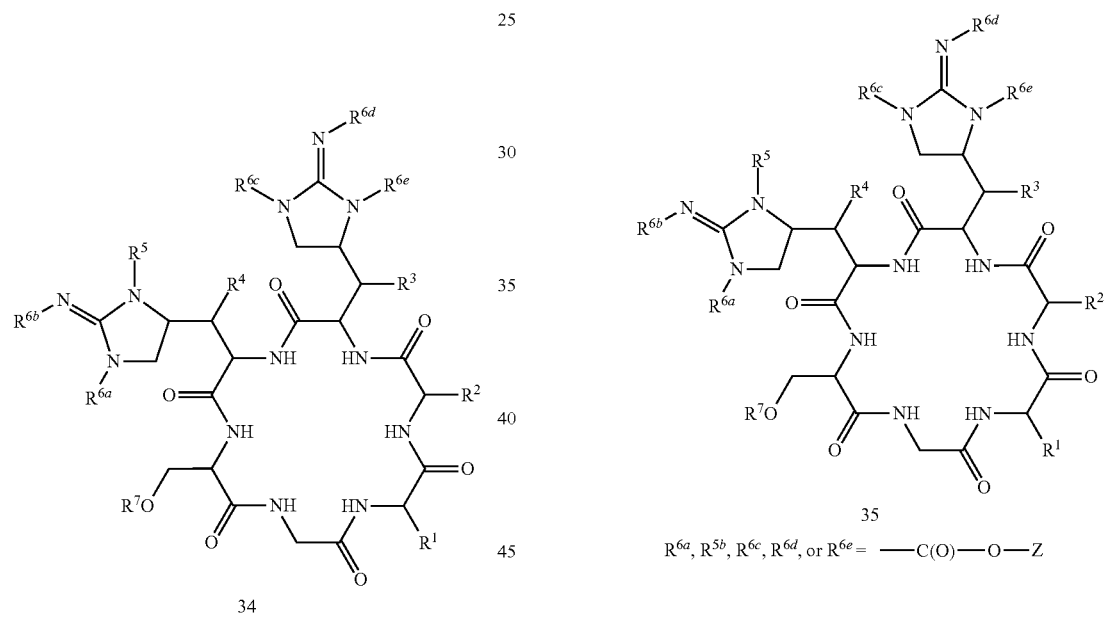

As shown in Scheme XXVIII glycopeptide antibiotics 35 in which $R^{6a}$, $R^{6b}$, $R^{6c}$, $R^{6d}$ or $R^{6e}$ are independently —C(O)—Y—Z, wherein Y is —O— and Z is alkyl($C_1$-$C_{20}$), cycloalkyl($C_3$-$C_{20}$), alkenyl($C_3$-$C_{20}$), alkynyl($C_3$-$C_{20}$), perfluoroalkyl($C_1$-$C_6$), aryl or heteroaryl, may be prepared from the corresponding glycopeptide antibiotics 32 in which at least one of $R^{6a}$, $R^{6b}$, $R^{6c}$, $R^{6d}$ and $R^{6e}$ are H, by methods known to those skilled in the art, such as by treatment with reagents which include an appropriate chloroformate Z—O—C(O)—Cl or N-hydroxysuccinimide carbonate Z—O—C(O)—OSu, and the like, in the presence or absence of a suitable base. The extent of acylation may be controlled by variations in reagent stoichiometry, reaction temperature, and reaction time.

Glycopeptide antibiotics 36 in which $R^{6a}$, $R^{6b}$, $R^{6c}$, $R^{6d}$ or $R^{6e}$ are independently —C(O)—Y—Z, wherein Y is —$NR^{8a}$— and Z is alkyl($C_1$-$C_{20}$), cycloalkyl($C_3$-$C_{20}$), alkenyl($C_3$-$C_{20}$), alkynyl($C_3$-$C_{20}$), aryl or heteroaryl, may be prepared as shown in Scheme XXIX from the corresponding glycopeptide antibiotics 32 in which at least one of $R^{6a}$, $R^{6b}$, $R^{6c}$, $R^{6d}$ and $R^{6e}$ are H, by methods known to those skilled in the art, such as by treatment with reagents Which include an appropriate isocyanate Z—N=C=O, or, alternatively, by sequential treatment with reagents which include phosgene or a phosgene equivalent such as triphosgene, 1,1'-carbonyldiimidazole, 1,1'-carbonyl-bis(1,2,4)-triazole, or a chloronitrophenyl formate, and the like, followed by treatment with a primary or secondary amine, Z—$NHR^{8a}$ in the presence or absence of a suitable base. The extent of acylation may be controlled by variations in reagent stoichiometry, reaction temperature, and reaction time.

Scheme XXIX

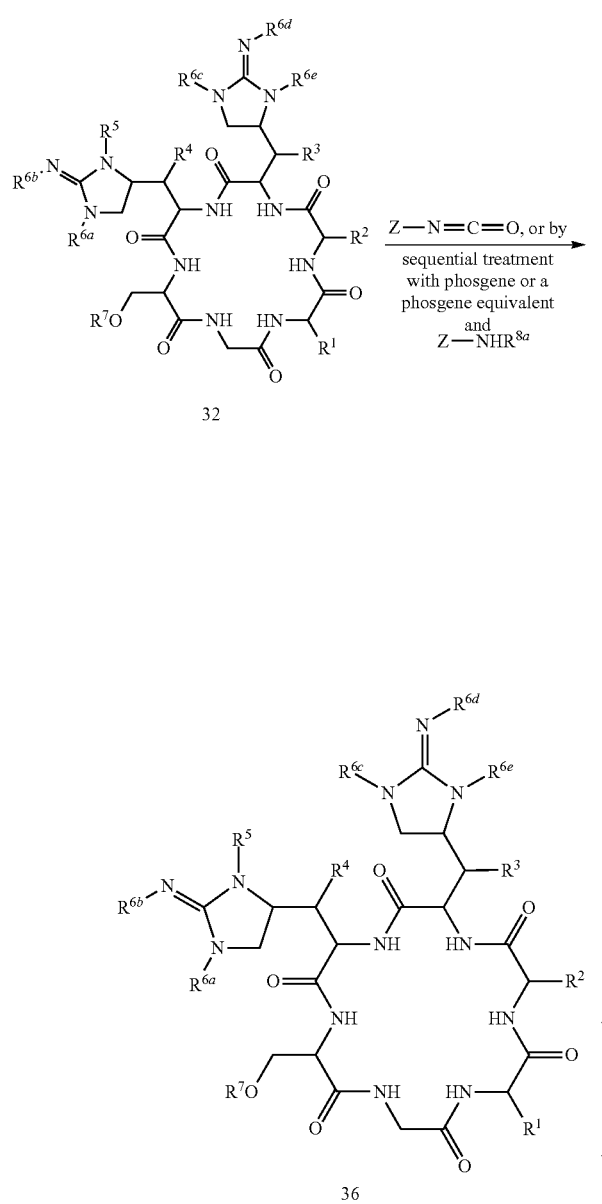

$R^{6a}$, $R^{6b}$, $R^{6c}$, $R^{6d}$, or $R^{6e}$ = —C(O)—$NR^{8a}$—Z

Scheme XXX

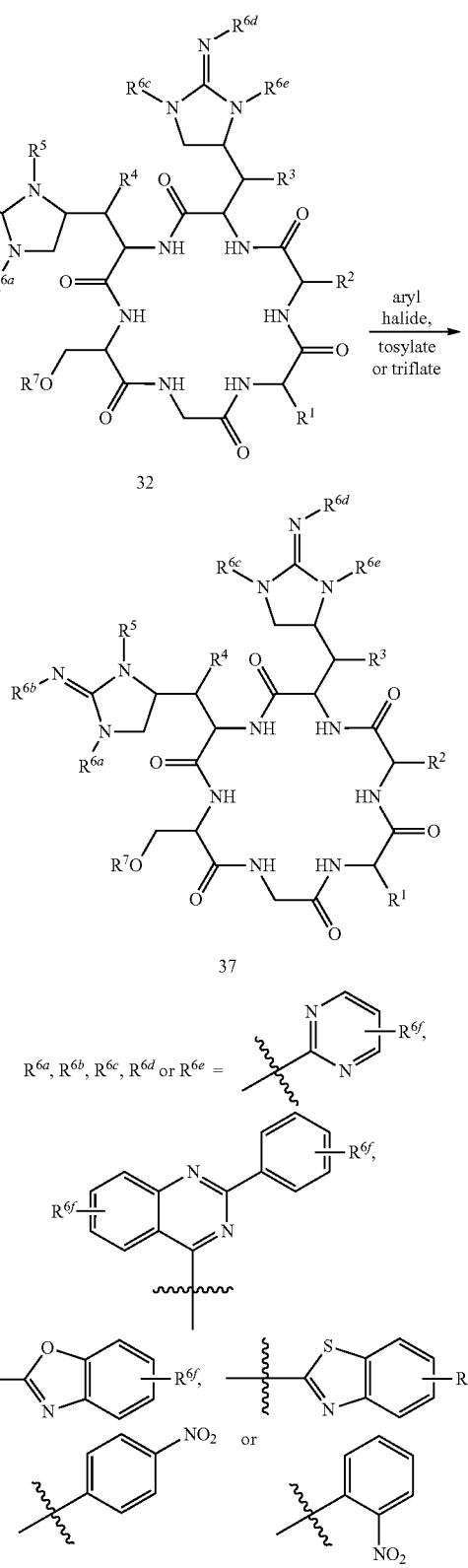

As shown in Scheme XXX, glycopeptide antibiotics 37 in which $R^{6a}$, $R^{6b}$, $R^{6c}$, $R^{6d}$ and $R^{6e}$ are independently as shown may be prepared from the corresponding glycopeptide antibiotics 32 in which at least one of $R^{6a}$, $R^{6b}$, $R^{6c}$, $R^{6d}$ and $R^{6e}$ are H, by methods known to those skilled in the art, such as by treatment with reagents which include appropriate aryl halides, tosylates, and triflates, such as a 2-chloropyrimidine, a 2-chlorobenzoxazole, a 2-chlorobenzothiazole, a 4-chlorobenzopyrimidine, a 2-fluoronitrobenzene, a 4-fluoronitrobenzene, and the like, in the presence or absence of a suitable base. The extent of alkylation may be controlled by variations in reagent stoichiometry, reaction temperature, and reaction time.

As shown in Scheme XXXI, glycopeptide antibiotics 39 in which $R^7$ is —C(O)—Y—Z, wherein Y is a single bond and Z is H, alkyl($C_1$-$C_{20}$), cycloalkyl($C_3$-$C_{20}$), alkenyl($C_2$-$C_{20}$), alkynyl($C_2$-$C_{20}$), perfluoroalkyl($C_1$-$C_6$), aryl or heteroaryl, may be prepared from the corresponding glycopeptide antibiotics 38 in which $R^7$ is H, by methods known to those skilled in the art, such as by employing any of a variety of acylation reactions using a carboxylic acid halide Z—C(O)—Cl, carboxylic acid anhydride (Z—C(O))$_2$—O, or a carboxylic acid Z—C(O)—OH in combination with an appropriate activating agent, such as 1,3-dicyclohexylcarbodiimide, 1-(3-dimethylaminopropyl)-3-ethylcarbodiimide hydrochloride, benzotriazol-1-yloxy-tris(dimethylamino)phosphonium hexafltiorophosphate, O-benzotriazol-1-yl-N,N,N',N'-tetramethyluronium hexafluorophosphate, 1,1'-carbonyldiimidazole, and the like, in the presence or absence of a suitable base.

or a chloronitrophenylformate, and the like, followed by treatment with an alcohol, Z—OH, in the presence or absence of a suitable base.

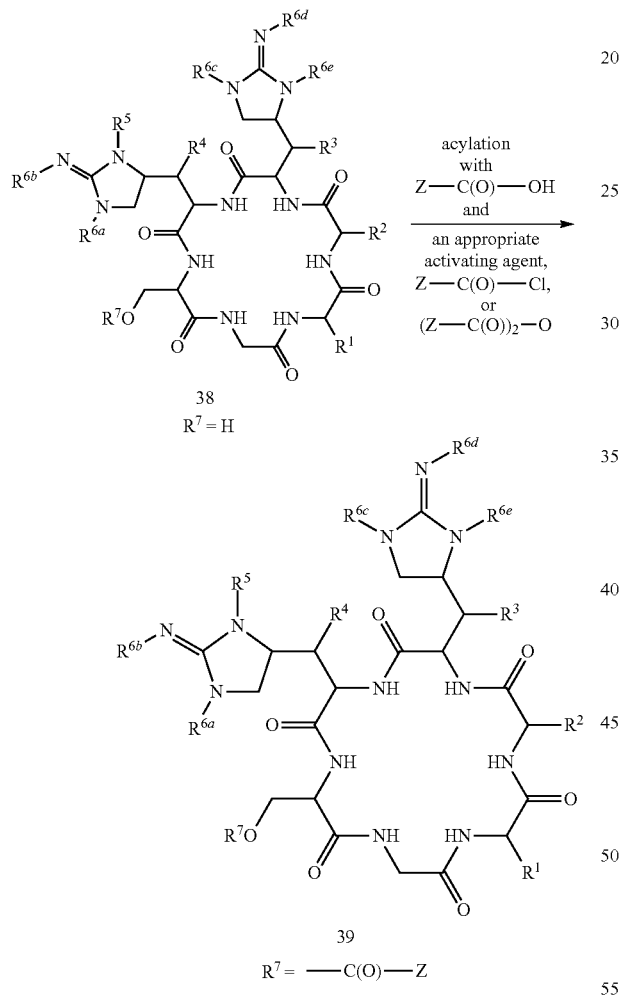

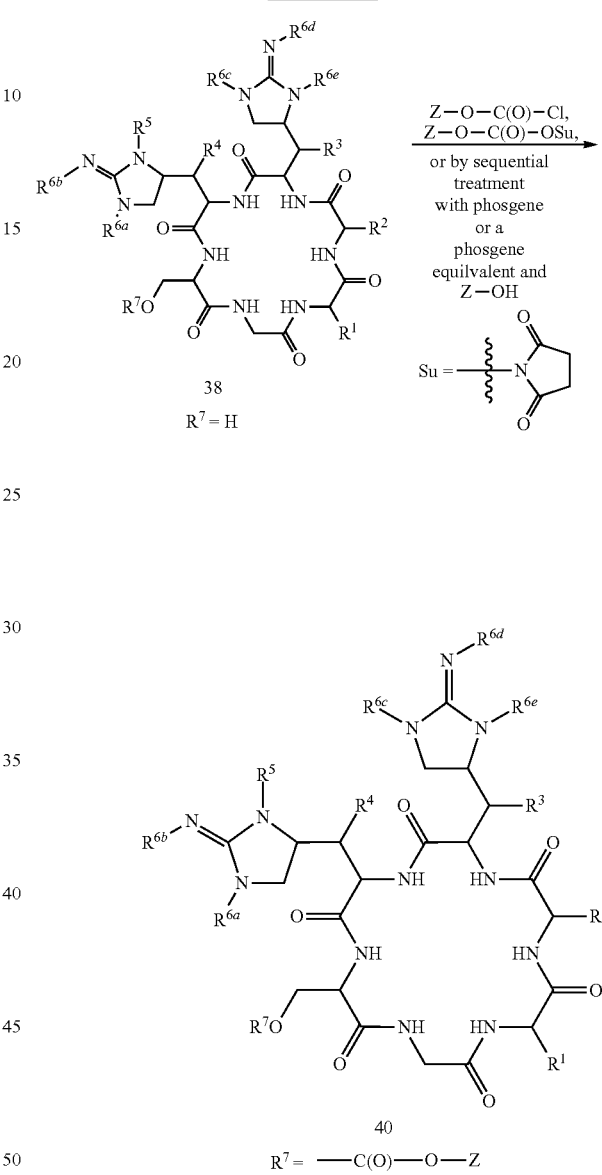

Glycopeptide antibiotics 40 in which $R^7$ is —C(O)—Y—Z, wherein Y is —O— and Z is alkyl($C_1$-$C_{20}$), cycloalkyl($C_3$-$C_{20}$), alkenyl($C_3$-$C_{20}$), alkynyl($C_3$-$C_{20}$), perfluoroalkyl($C_7$-$C_6$), aryl or heteroaryl, may be prepared as shown in Scheme XXXII from the corresponding glycopeptide antibiotics 38 in which $R^7$ is H, by methods known to those skilled in the art, such as by treatment with an appropriate chloroformate Z—O—C(O)—Cl or N-hydroxysuccinimide carbonate Z—O—C(O)—OSu or, alternatively, by sequential treatment with phosgene or a phosgene equivalent such as triphosgene, 1,1'-carbonyldiimidazole, 1,1'-carbonyl-bis(1,2,4)-triazole, As shown in Scheme XXXIII glycopeptide antibiotics 41 in which $R^7$ is —C(O)—Y—Z, wherein Y is —$NR^{8a}$— and Z is alkyl($C_1$-$C_{20}$), cycloalkyl($C_3$-$C_{20}$), alkenyl($C_3$-$C_{20}$), alkynyl($C_3$-$C_{20}$), perfluoroalkyl($C_1$-$C_6$), aryl or heteroaryl, may be prepared from the corresponding compounds 38 in which $R^7$ is H, by methods known to those skilled in the art, such as by treatment with appropriate isocyanate Z—N=C=O or, alternatively, by sequential treatment with phosgene or a phosgene equivalent such as triphosgene, 1,1'-carbonyldiimidazole, 1,1'-carbonyl-bis(1,2,4)-triazole, or a chloronitrophenylformate, and the like, followed by treatment with an amine Z-$NHR^{8a}$, in the presence or absence of a suitable base.

Scheme XXXIII

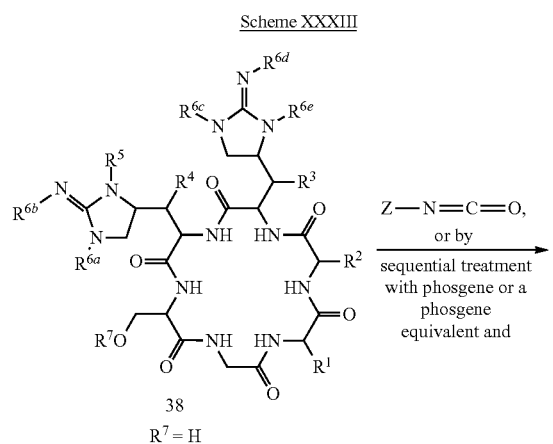

38
R⁷ = H

Scheme XXXIV

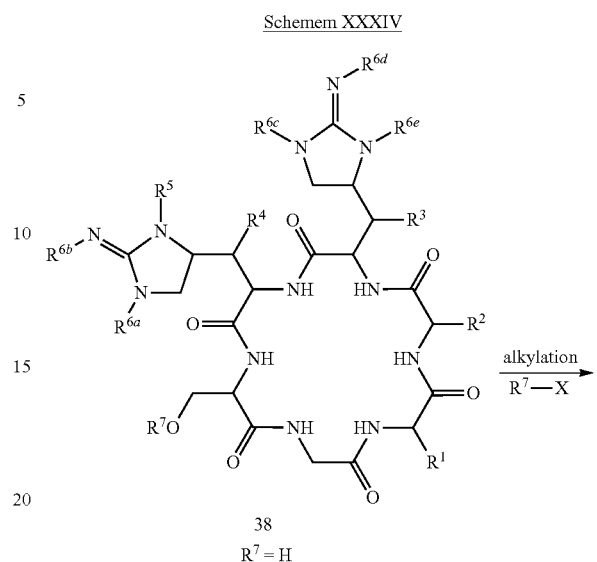

38
R⁷ = H

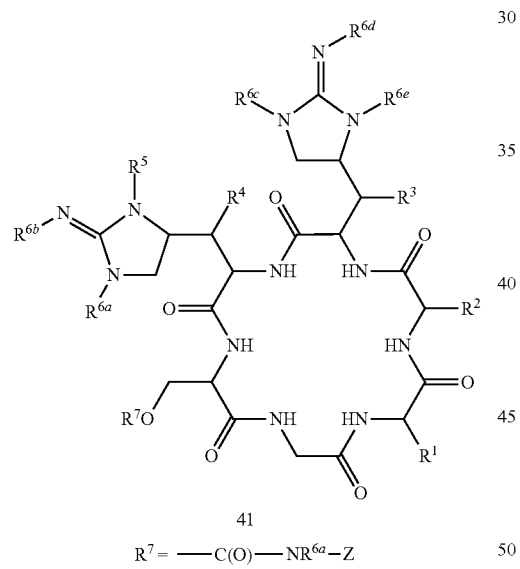

41
R⁷ = —C(O)—NR⁶ᵃ—Z

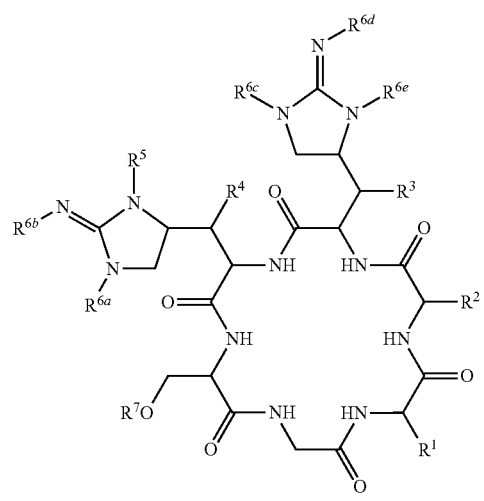

42
R⁷ = alkyl, cycloalkyl, alkenyl or alkynyl

As shown in Scheme XXXIV glycopeptide antibiotics 42 in which $R^7$ is alkyl($C_1$-$C_{10}$), cycloalkyl($C_3$-$C_{20}$), alkenyl ($C_3$-$C_{20}$) or alkynyl($C_3$-$C_{20}$), may be prepared from the corresponding glycopeptide antibiotics 38 in which $R^7$ is H, by methods known to those skilled in the art, such as by alkylation with an appropriate alkylating agent $R^7$—X, where X is Cl, Br, I, —O-tosylate, —O-mesylate, or —O-triflate, in the presence or absence of a suitable base.

Glycopeptide antibiotics 43 in which $R^7$ is trialkylsilyl may be prepared from the corresponding glycopeptide antibiotics 38 as shown in Scheme XXXV in which $R^7$ is H, by methods known to those skilled in the art, such as by treatment with an appropriate silylating agent, such as trimethylsilyl chloride, trimethylsilyl triflate, t-butyldimethylsilyl chloride, t-butyldimethylsilyl triflate, t-butyldiphenylsilyl triflate, and comparable silylating agents commonly used to protect alcohol functionality, in the presence or absence of a suitable base.

Scheme XXXV

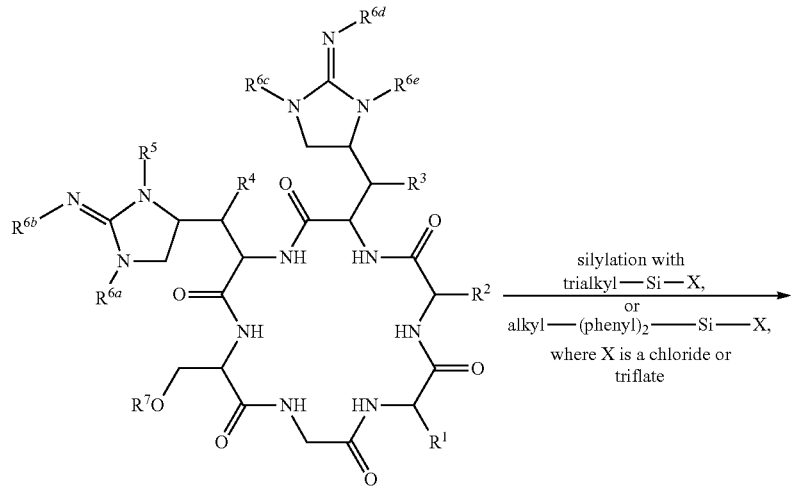

38
$R^7 = H$ silylation with
trialkyl—Si—X,
or
alkyl—(phenyl)$_2$—Si—X,
where X is a chloride or triflate

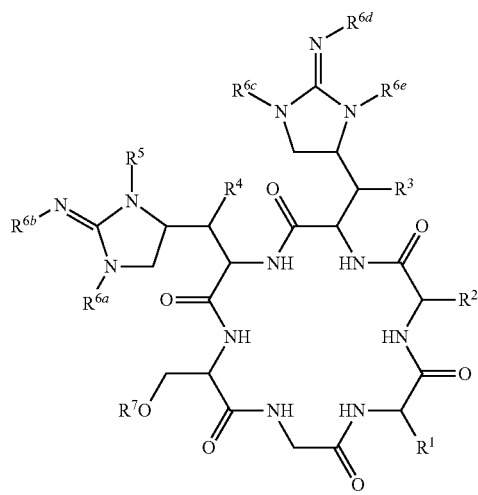

43
$R^7 = $ —Si—(alkyl)$_3$, —Si(alkyl)(phenyl)$_2$

As shown in Scheme XXXVI glycopeptide antibiotics 45 in which $R^{2a}$ is as shown and $R^8, R^9, R^{10}, R^{11}, R^{12}, R^{13}, R^{14}, R^{15}, R^{16}, R^{17}$ or $R^{18}$ are independently —C(O)—Y—Z, wherein Y is a single bond and Z is H, alkyl($C_1$-$C_{20}$), cycloalkyl($C_3$-$C_{20}$), alkenyl($C_2$-$C_{20}$), alkynyl($C_2$-$C_{20}$), perfluoroalkyl($C_1$-$C_6$), aryl or heteroaryl, may be prepared from the corresponding glycopeptide antibiotics 44 in which $R^{2a}$ is, as shown and at least one of $R^8, R^9, R^{10}, R^{11}, R^{12}, R^{13}, R^{14}, R^{15}, R^{16}, R^{17}$ and $R^{18}$ are H, by methods known to those skilled in the art, such as by employing any of a variety of acylation reactions using reagents such as a carboxylic acid halide Z—C(O)—Cl, carboxylic acid anhydride (Z—C(O))$_2$—O, or a carboxylic acid Z—C(O)—OH in combination with an appropriate activating agent, such as 1,3-dicyclohexylcarbodiimide, 1-(3-dimethylaminopropyl)-3-ethyl-carbodiimide hydrochloride, benzotriazol-1-yloxy-tris(dimethylamino)phosphonium hexafluorophosphate, O-benzotriazol-1-yl-N,N,N',N'-tetramethyluronium hexafluorophosphate, 1,1'-carbonyldiimidazole, and the like, in the presence or absence of a suitable base. The extent of acylation may be controlled by variations in reagent stoichiometry, reaction temperature, and reaction time.

Scheme XXXVI

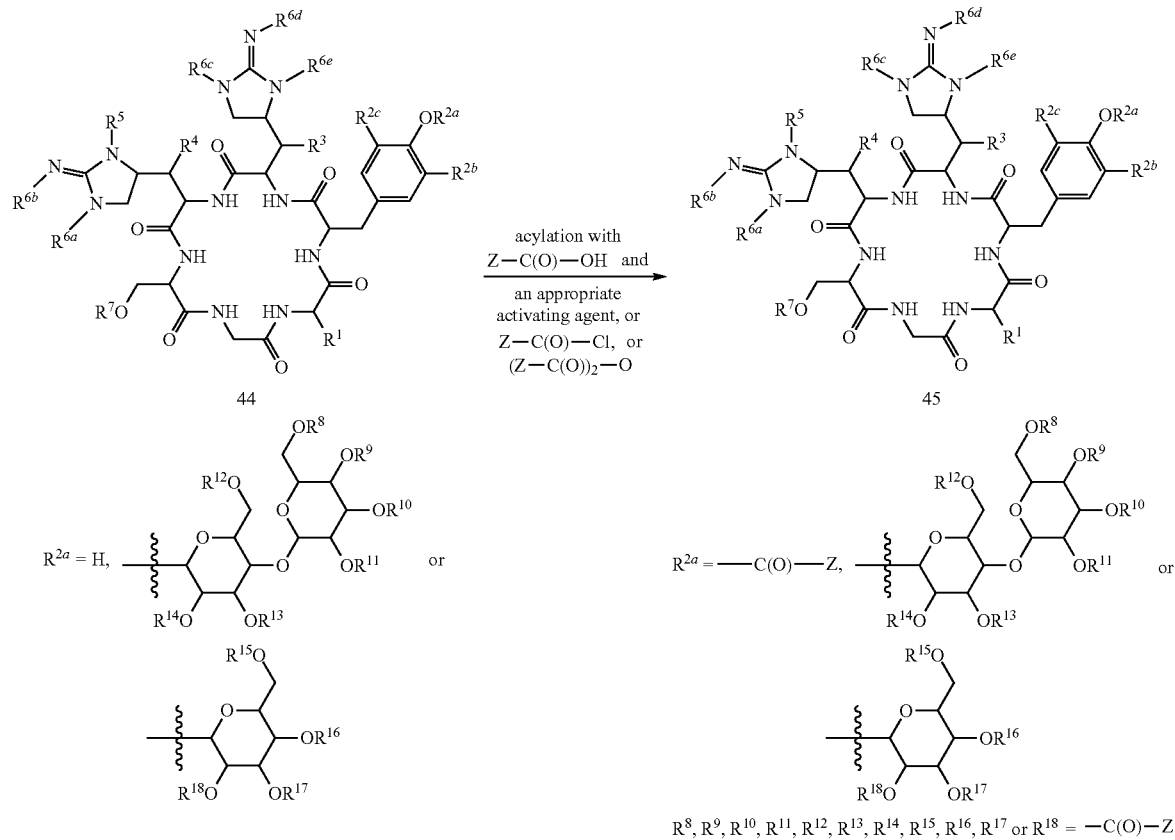

As shown in Scheme XXXVII glycopeptide antibiotics 46 in which $R^{2a}$ is as shown and $R^8$, $R^9$, $R^{10}$, $R^{11}$, $R^{12}$, $R^{13}$, $R^{14}$; $R^{15}$, $R^{16}$, $R^{17}$ or $R^{18}$ are independently —C(O)—Y—Z, wherein Y is —O— and Z is alkyl($C_1$-$C_{20}$), cycloalkyl($C_3$-$C_{20}$), alkenyl($C_3$-$C_{20}$), alkynyl($C_3$-$C_{20}$), perfluoroalkyl($C_1$-$C_6$), aryl or heteroaryl, may be prepared from the corresponding glycopeptide antibiotics 4-4 in which $R^{2a}$ is as shown and at least one of $R^8$, $R^9$, $R^{10}$, $R^{11}$, $R^{12}$, $R^{13}$, $R^{14}$; $R^{15}$, $R^{16}$, $R^{17}$ and $R^{18}$ are H, by methods known to those skilled in the art, such as by treatment with reagents which include an appropriate chloroformate Z—O—C(O)—Cl or N-hydroxysuccinimide carbonate Z—O—C(O)—OSu or, alternatively, by sequential treatment with reagents such as phosgene or a phosgene equivalent such as triphosgene, 1,1'-carbonyldiimidazole, 1,1'-carbonyl-bis(1,2,4)-triazole, or a chloronitrophenylformate, and the like, followed by treatment with an alcohol Z—OH, in the presence or absence of a suitable base. The extent of reaction may be controlled by variations in reagent stoichiometry, reaction temperature, and reaction time.

Scheme XXXVII

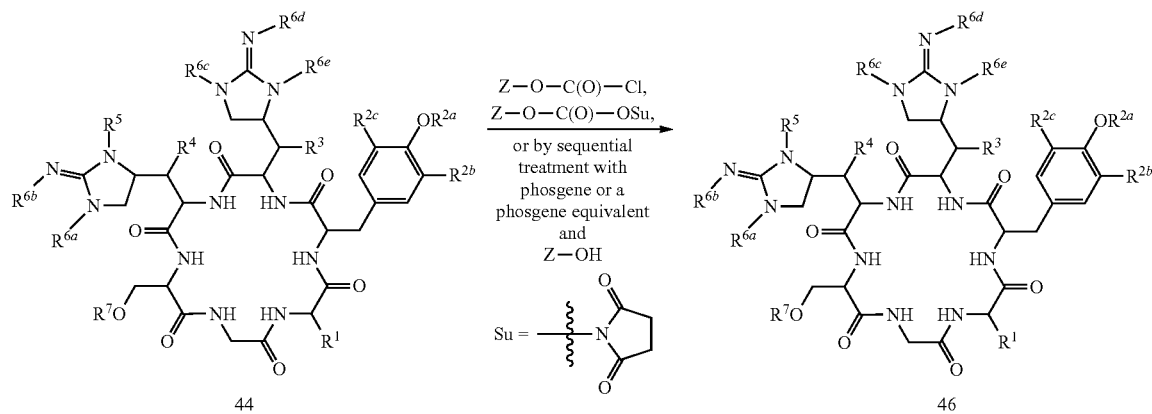

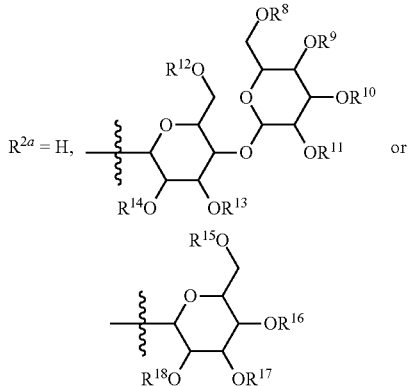

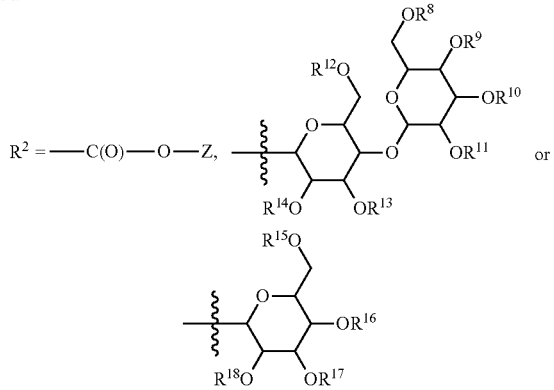

As shown in Scheme XXXVIII glycopeptide antibiotics 47 in which $R^{2a}$ is as shown and $R^5$, $R^9$, $R^{10}$, $R^{11}$, $R^{12}$, $R^{13}$, $R^{14}$, $R^{15}$, $R^{16}$, $R^{17}$ and $R^{18}$ are independently —C(O)—Y—Z, wherein Y is —$NR^{8a}$— and Z is alkyl ($C_1$-$C_{20}$), cycloalkyl ($C_3$-$C_{10}$), alkenyl($C_3$-$C_{20}$), alkynyl($C_3$-$C_{20}$), perfluoroalkyl ($C_1$-$C_6$), aryl or heteroaryl, may be prepared from the corresponding glycopeptide antibiotics 44 in which $R^{2a}$ is as shown and at least one of $R^8$, $R^9$, $R^{10}$, $R^{11}$, $R^{12}$, $R^{13}$, $R^{14}$, $R^{15}$, $R^{16}$, $R^{17}$ and $R^{18}$ are H, by methods known to those skilled in the art, such as by treatment with reagents which include an appropriate isocyanate Z—N=C=O or, alternatively, by sequential treatment with reagents which include phosgene or a phosgene equivalent such as triphosgene, 1,1'-carbonyldiimidazole, 1,1'-carbonyl-bis(1,2,4)-triazole, or a chloronitrophenylformate, and the like, followed by treatment with an amine Z—$NHR^{8a}$, in the presence or absence of a suitable base. The extent of reaction may be controlled by variations in reagent stoichiometry, reaction temperature, and reaction time.

Scheme XXXVIII

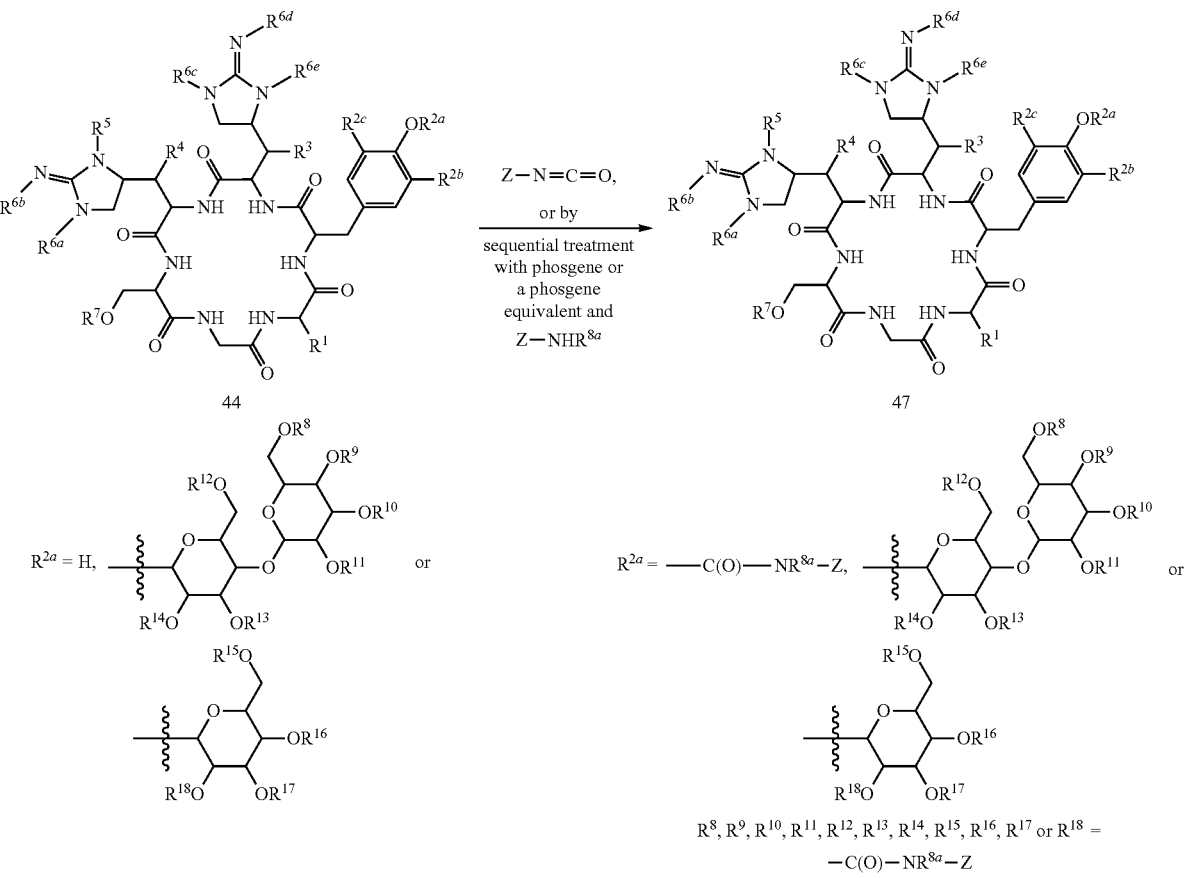

As shown in Scheme XXXIX glycopeptide antibiotics 49 in which $R^8$ and $R^9$, $R^9$ and $R^{10}$, $R^{10}$ and $R^{11}$, $R^{13}$ and $R^{14}$, $R^{15}$ and $R^{16}$, $R^{16}$ and $R^{17}$, or $R^{17}$ and $R^{18}$ are independently joined forming moieties of the formula:

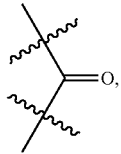

where n is an integer of from 1 to 3 may be prepared from the corresponding glycopeptide antibiotics 48 in which $R^8$, $R^9$, $R^{10}$, $R^{11}$, $R^{13}$, $R^{14}$, $R^{15}$, $R^{16}$, $R^{17}$ and $R^{18}$ are H, by methods known to those skilled in the art, such as by treatment with reagents which include phosgene or a phosgene equivalent reagent such as triphosgene, 1,1'-carbonyldiimidazole, 1,1'-carbonyl-bis(1,2,4)-triazole, or a chloronitrophenylformate, in the presence or absence of a suitable base. The extent of the reaction may be controlled by variations in reagent stoichiometry, reaction temperature, and reaction time.

Scheme XXXIX

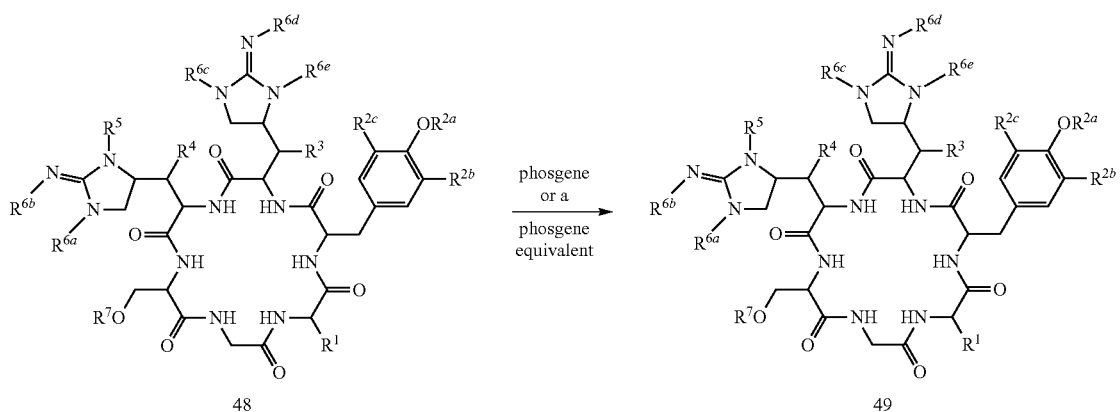

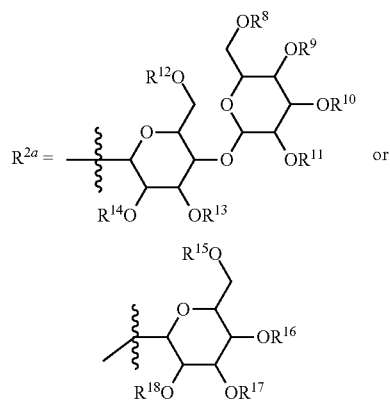

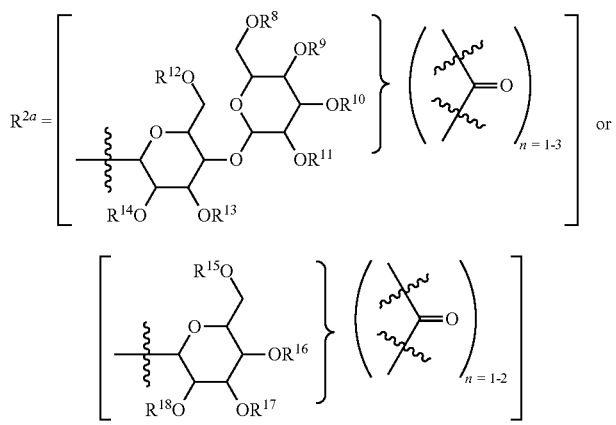

As shown in Scheme XL glycopeptide antibiotics 50 in which $R^8$ and $R^9$, $R^9$ and $R^{10}$, $R^{10}$ and $R^{11}$, $R^{13}$ and $R^{14}$, $R^{15}$ and $R^{16}$, $R^{16}$ and $R^{17}$, or $R^{17}$ and $R^{18}$ are independently joined forming moieties of the formula:

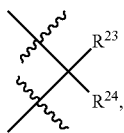

where n is an integer of from 1 to 3 may be prepared from the corresponding glycopeptide antibiotics 48 in which at least one pair of $R^8$ and $R^9$, $R^9$ and $R^{10}$, $R^{10}$ and $R^{11}$, $R^{13}$ and $R^{14}$, $R^{15}$ and $R^{16}$, $R^{16}$ and $R^{17}$, or $R^{17}$ and $R^{18}$ are H, by methods known to those skilled in the art, such as by treatment with reagents which include an appropriate dialkyl acetal or dialkyl ketal of the formula $R^{23}R^{24}$—$C(O\text{-alkyl}(C_1\text{-}C_{20}))_2$, such as a dimethyl acetal or dimethyl ketal, in the presence of a suitable acid catalyst, such as hydrochloric acid, p-toluene sulfonic acid mono-hydrate, camphor sulfonic acid, pyridinium p-toluene sulfonate, Amberlyst, or an equivalent mineral acid, carboxylic acid, or sulfonic acid commonly used by those skilled in the art. The extent of the reaction may be controlled by variations in reagent stoichiometry, reaction temperature, and reaction time.

Scheme XL

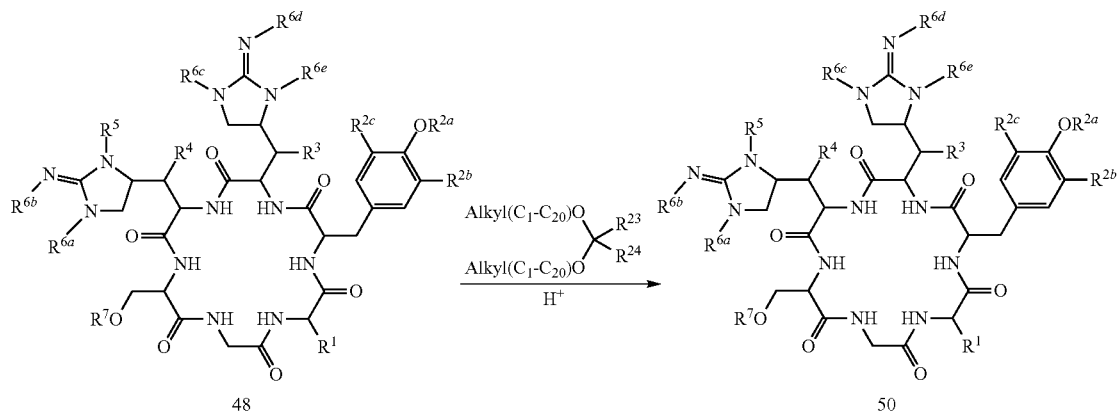

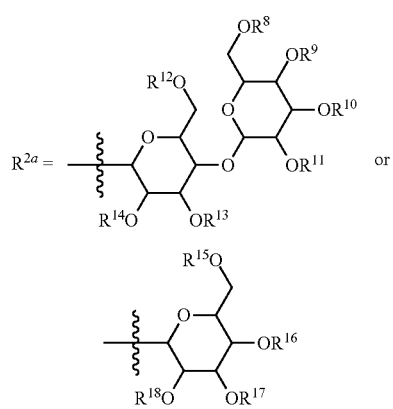

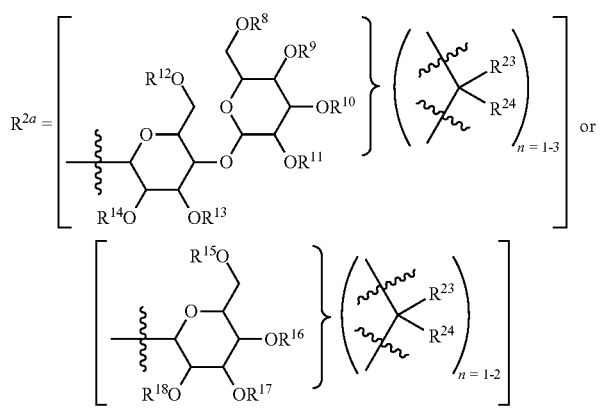

As shown in Scheme XLI, glycopeptide antibiotics 52 in which $R^8$, $R^9$, $R^{10}$, $R^{11}$, $R^{13}$, $R^{14}$, $R^{15}$, $R^{16}$, $R^{17}$ or $R^{18}$ are independently —$(CH_2)$-alkenyl$(C_2$-$C_{20})$, —$(CH_2)$-alkynyl $(C_2$-$C_{20})$, —$(CH_2)$-aryl or —$(CH_2)$-heteroaryl, may be prepared from the corresponding glycopeptide antibiotics 51 prepared using the conditions described in Scheme XL (by treatment with a compound of the formula $R^{23}R^{24}$—C(O-alkyl$(C_1$-$C_{20}))_2$ where $R^{23}$ is H and $R^{24}$ is alkenyl$(C_2$-$C_{20})$, alkynyl$(C_2$-$C_{20})$, aryl, or heteroaryl), in which at least one known to those skilled in the art, such as by treatment with a reductant and a protic acid or Lewis acid. Suitable combinations of reductants and acids include: sodium cyanoborohydride and trifluoroacetic acid, sodium cyanoborohydride and hydrochloride acid, triethylsilane-trifluoroacetic acid, borane-trimethylamine complex-aluminium chloride, borane-dimethylamine complex-boron trifluoride diethyl etherate, borane-dibutylboron triflate, or lithium aluminium hydride-aluminium chloride, and the like.

Scheme XLI

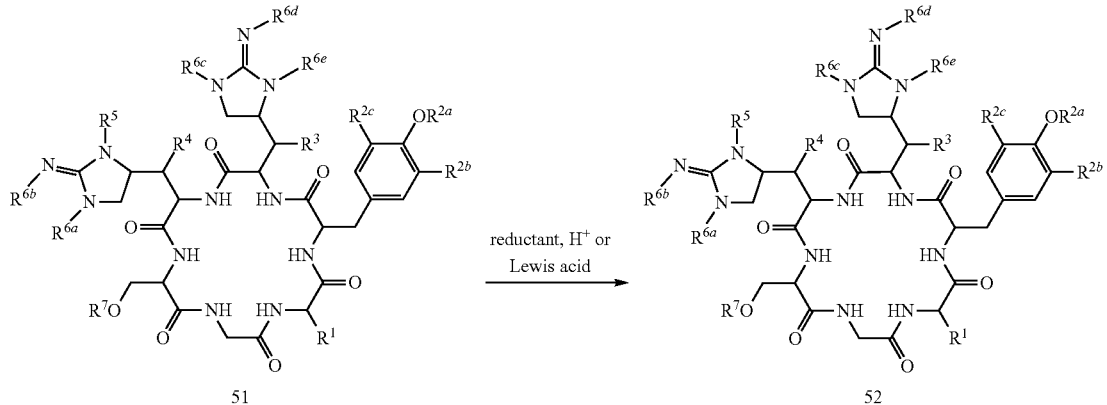

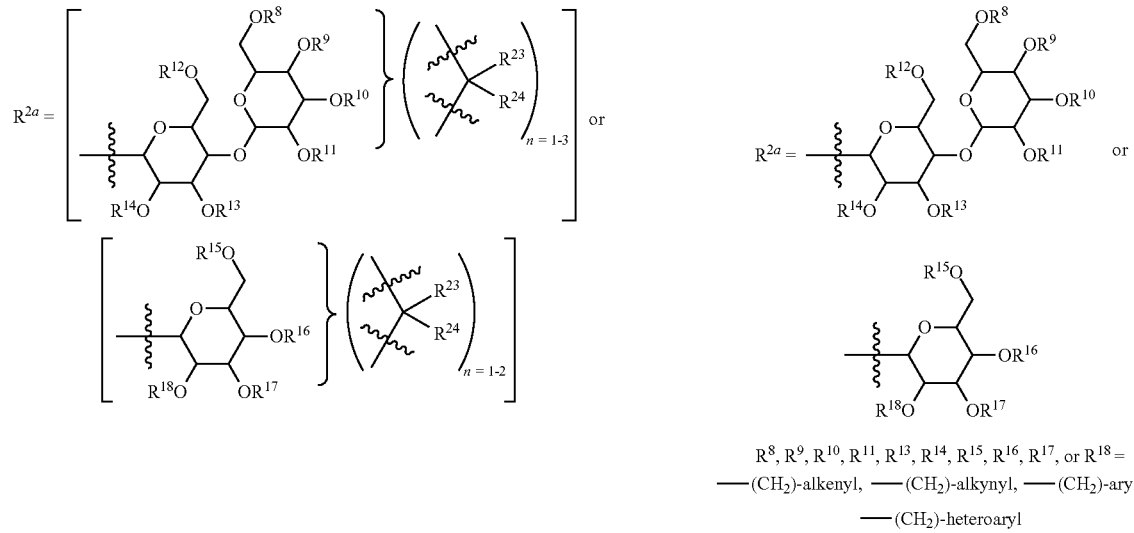

$R^8$, $R^9$, $R^{10}$, $R^{11}$, $R^{13}$, $R^{14}$, $R^{15}$, $R^{16}$, $R^{17}$, or $R^{18}$ =
—$(CH_2)$-alkenyl, —$(CH_2)$-alkynyl, —$(CH_2)$-aryl or
—$(CH_2)$-heteroaryl pair of $R^8$ and $R^9$, $R^9$ and $R^{10}$, $R^{10}$ and $R^{11}$, $R^{13}$ and $R^{14}$, $R^{15}$ and $R^{16}$, $R^{16}$ and $R^{17}$, and $R^{17}$ and $R^{18}$ are moieties of the formula:

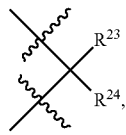

where $R^{23}$ is H and $R^{24}$ is alkenyl$(C_2$-$C_{20})$, alkynyl$(C_2$-$C_{20})$, aryl, or heteroaryl, and n is an integer of 1 to 3 by methods Alternatively, glycopeptide antibiotics 53 in which $R^{2a}$ is as shown and $R^8$, $R^9$, $R^{10}$, $R^{11}$, $R^{12}$, $R^{13}$, $R^{14}$, $R^{15}$, $R^{16}$, $R^{17}$ or $R^{18}$ are independently alkyl$(C_1$-$C_{20})$, cycloalkyl$(C_3$-$C_{20})$, alkenyl$(C_3$-$C_{20})$ or alkynyl$(C_3$-$C_{20})$ may be prepared as described in Scheme XLII from the corresponding glycopeptide antibiotics 44 in which $R^{2a}$ is as shown, and at least one of $R^8$, $R^9$, $R^{10}$, $R^{11}$, $R^{12}$, $R^{13}$, $R^{14}$, $R^{15}$, $R^{16}$, $R^{17}$ and $R^{18}$ are H, by methods known to those skilled in the art, such as by alkylation with an appropriate alkyling agent $R^8X$, $R^9X$, $R^{10}X$, $R^{11}X$, $R^{12}X$, $R^{13}X$, $R^{14}X$, $R^{15}X$, $R^{16}X$, $R^{17}X$ and $R^{18}X$, where X is Cl, Br, I, —O-tosylate, —O-mesylate, or —O-triflate, in the presence or absence of a suitable base.

Scheme XLII

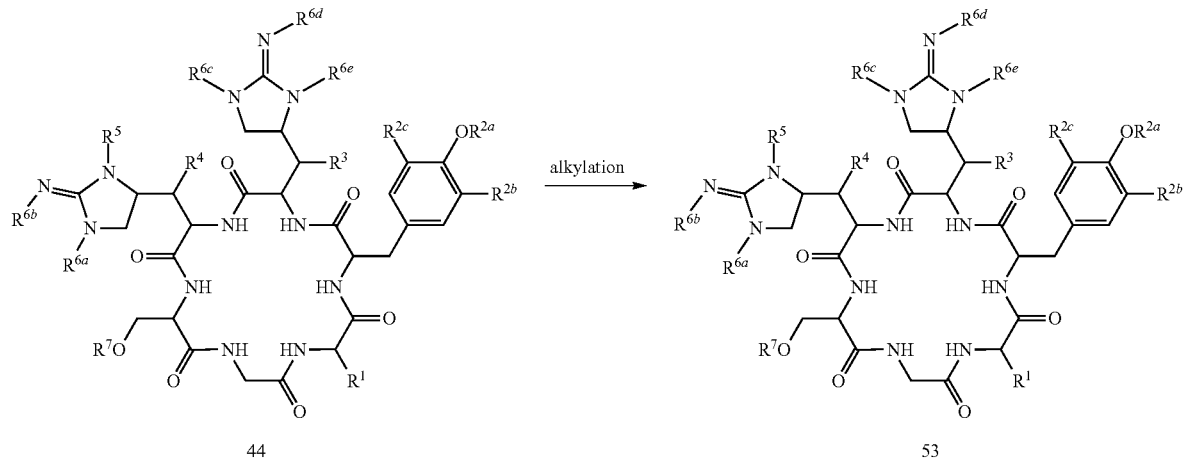

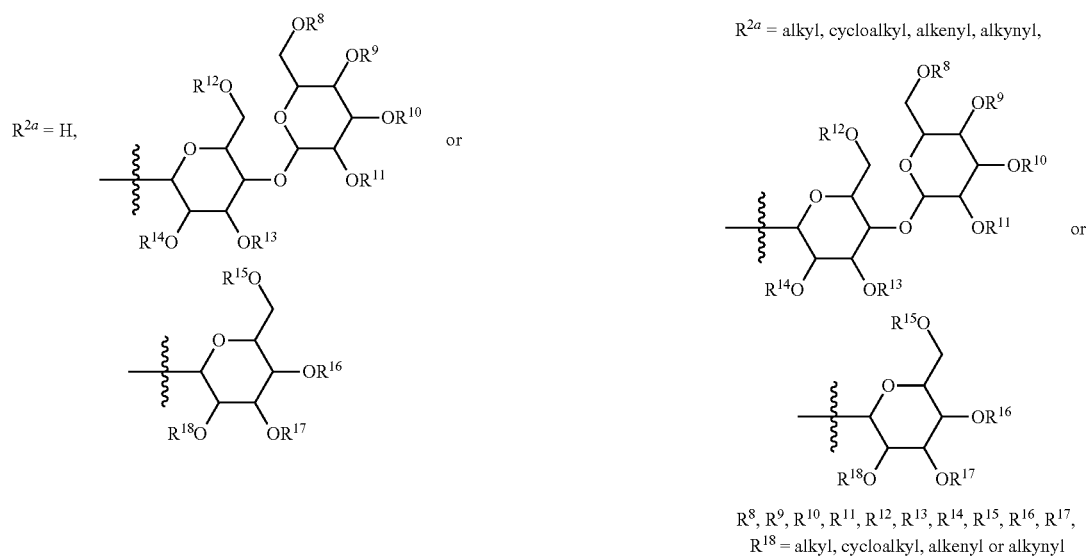

As shown in Scheme XLIII, glycopeptide antibiotics 55 in which $R^{19}$, $R^{20}$, $R^{21}$ or $R^{22}$ are independently —C(O)—Y—Z, wherein Y is a single bond and Z is H, alkyl($C_1$-$C_{20}$), cycloalkyl($C_3$-$C_{20}$), alkenyl($C_2$-$C_{20}$), alkynyl($C_2$-$C_{20}$), perfluoroalkyl($C_1$-$C_6$), aryl or heteroaryl, may be prepared from the corresponding glycopeptide antibiotics 54 in which at least one of $R^{19}$, $R^{20}$, $R^{21}$ and $R^{22}$ are H, by methods known to those skilled in the art, such as by employing any of a variety of acylation reactions using reagents such as a carboxylic acid halide Z—C(O)—Cl, carboxylic acid anhydride (Z—C(O))$_2$—O, or a carboxylic acid Z—C(O)—OH in combination with an appropriate activating agent, such as 1,3-dicyclohexylcarbodiimide, 1-(3-dimethylaminopropyl)-3-ethylcarbodiimide hydrochloride, benzotriazol-1-yloxy-tris (dimethylamino)phosphonium hexafluorophosphate, O-benzotriazol-1-yl-N,N,N',N'-tetramethyluronium hexafluorophosphate, 1,1'-carbonyldiimidazole, and the like, in the presence or absence of a suitable base. The extent of acylation may be controlled by variations in reagent stoichiometry, reaction temperature, and reaction time.

Scheme XLIII

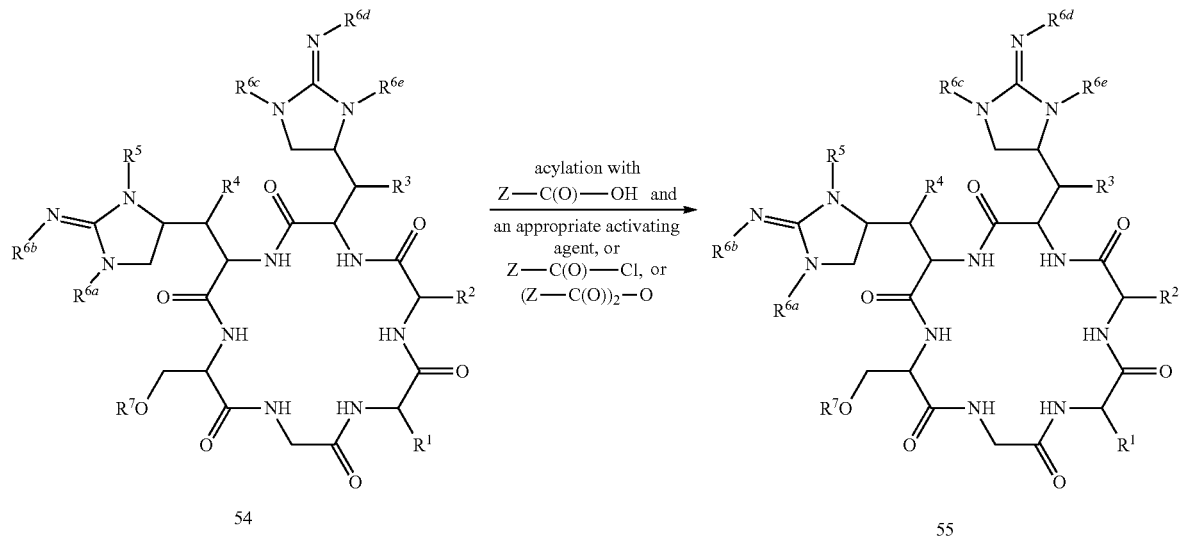

$R^{19}, R^{20}, R^{21}$ or $R^{22}$ = —C(O)—Z

As shown in Scheme XLIV glycopeptide antibiotics 56 in which $R^{19}$, $R^{20}$, $R^{21}$ or $R^{22}$ are independently —C(O)—Y—Z, wherein Y is —O— and Z is alkyl($C_1$-$C_{20}$), cycloalkyl($C_3$-$C_{20}$), alkenyl($C_3$-$C_{20}$), alkynyl($C_3$-$C_{20}$), perfluoroalkyl($C_1$-$C_6$), aryl or heteroaryl, may be prepared from the corresponding glycopeptide antibiotics 54 in which at least one of $R^{19}$, $R^{20}$, $R^{21}$ and $R^{22}$ are H, by methods known to those skilled in the art, such as by treatment with reagents which include an appropriate chloroformate Z—O—C(O)—Cl or N-hydroxysuccinimide carbonate Z—O—C(O)—OSu or, alternatively, by sequential treatment with reagents which include phosgene or a phosgene equivalent such as triphosgene, 1,1'-carbonyldiimidazole, 1,1'-carbonyl-bis(1,2,4)-triazole, or a chloronitrophenylformate, and the like, followed by treatment with an alcohol Z—OH, in the presence or absence of a suitable base. The extent of acylation may be controlled by variations in reagent stoichiometry, reaction temperature, and reaction time.

Scheme XLIV

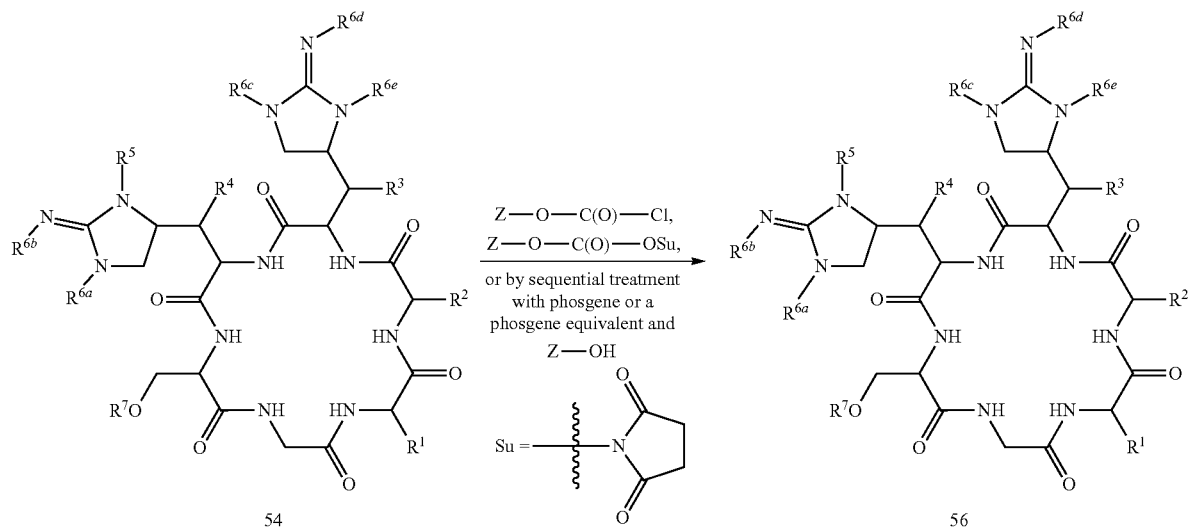

As described in Scheme XLV, glycopeptide antibiotics 57 in which $R^{19}$, $R^{20}$, $R^{21}$ and $R^{22}$ are independently —C(O)—Y—Z, wherein Y is —$NR^{8a}$— and Z is alkyl($C_1$-$C_{20}$), cycloalkyl($C_3$-$C_{20}$), alkenyl($C_3$-$C_{20}$), alkynyl($C_3$-$C_{20}$), perfluoroalkyl($C_1$-$C_6$), aryl or heteroaryl, may be prepared from the corresponding glycopeptide antibiotics 54 in which at least one of $R^{19}$, $R^{20}$, $R^{21}$ and $R^{22}$ are H, by methods known to those skilled in the art, such as by treatment with reagents which include an appropriate isocyanate Z—N=C=O or, alternatively, by sequential treatment with reagents such as phosgene or a phosgene equivalent such as triphosgene, 1,1'-carbonyldiimidazole, 1,1'-carbonyl-bis(1,2,4)-triazole, or a chloronitrophenylformate, and the like, followed by treatment with an amine. Z—$NHR^{8a}$ in the presence or absence of a suitable base. The extent of acylation may be controlled by variations in reagent stoichiometry, reaction temperature, and reaction time.

Scheme XLV

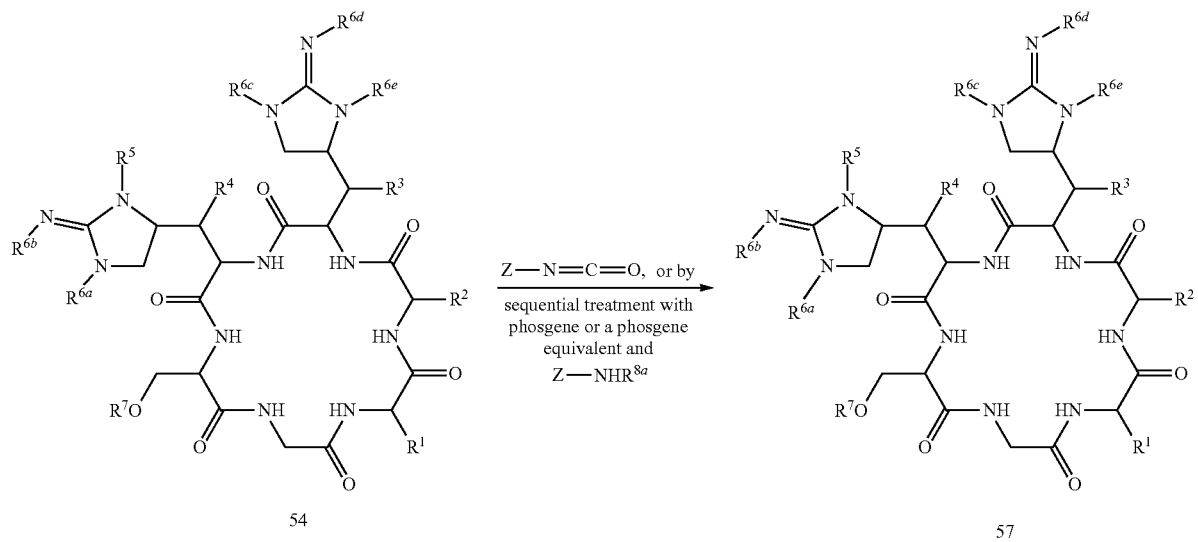

As shown in Scheme XLVI, glycopeptide antibiotics 58 in which $R^{19}$ and $R^{20}$, $R^{20}$ and $R^{21}$, or $R^{21}$ and $R^{22}$ are independently joined forming moieties of the formula:

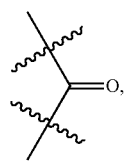

where n is an integer of 1 or 2 may be prepared from the corresponding glycopeptide antibiotics 54 in which at least one pair of $R^{19}$ and $R^{20}$, $R^{20}$ and $R^{21}$, and $R^{21}$ and $R^{22}$ are H, by methods known to those skilled in the art, such as by treatment with a reagent such as phosgene or a phosgene equivalent such as triphosgene, 1,1'-carbonyldiimidazole, 1,1'-carbonyl-bis(1,2,4)-triazole, or a chloronitrophenylformate, in the presence or absence of a suitable base. The extent of the reaction may be controlled by variations in reagent stoichiometry, reaction temperature, and reaction time.

Scheme XLVI

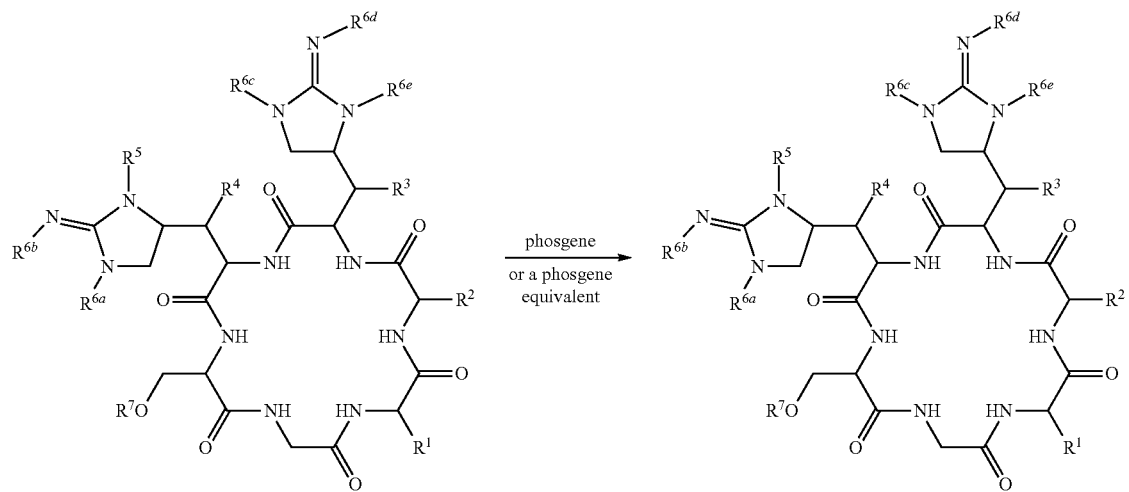

As shown in Scheme XLVII, glycopeptide antibiotics 59 in which $R^{19}$ and $R^{20}$, $R^{20}$ and $R^{21}$, or $R^{21}$ and $R^{22}$ are independently joined forming moieties of the formula:

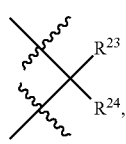

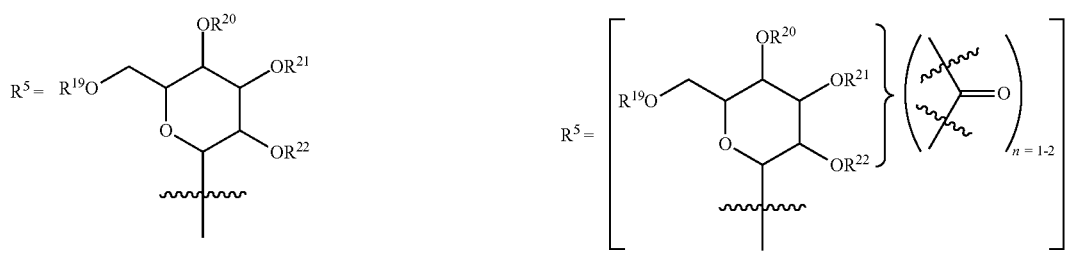

where n is an integer of 1 or 2, may be prepared from the corresponding glycopeptide antibiotics 54 in which at least one pair of $R^{19}$ and $R^{20}$, $R^{20}$ and $R^{21}$, and $R^{21}$ and $R^{22}$ are H, by methods known to those skilled in the art, such as by treatment with a dialkyl acetal or dialkyl ketal of the formula $R^{23}R^{24}$—C(O-alkyl($C_1$-$C_{20}$))$_2$, such as a dimethyl acetal or dimethyl ketal, in the presence of a suitable acid catalyst, such as hydrochloric acid, p-toluene sulfonic acid mono-hydrate, camphor sulfonic acid, pyridinium p-toluene sulfonate, Amberlyst, or any equivalent mineral acid, carboxylic acid, or sulfonic acid commonly used by those skilled in the art. The extent of the reaction may be controlled by variations in reagent stoichiometry, reaction temperature, and reaction time.

Scheme XLVII

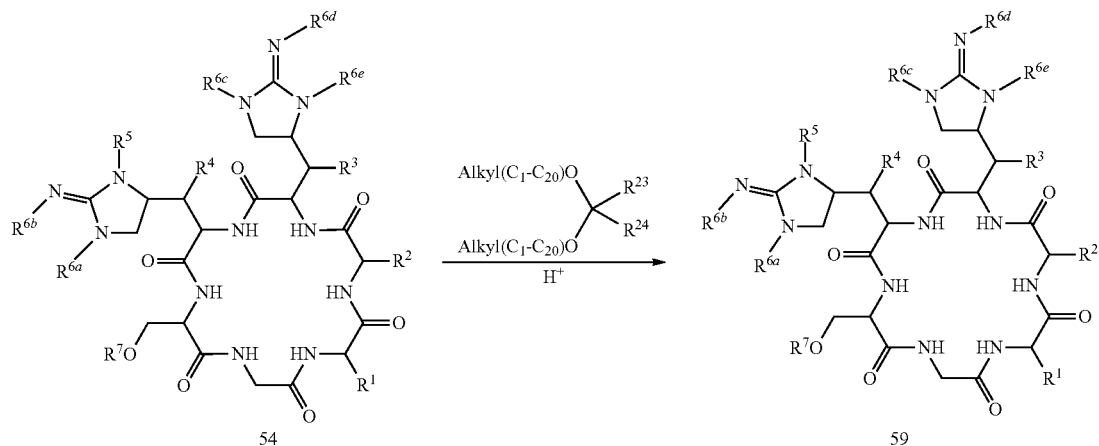

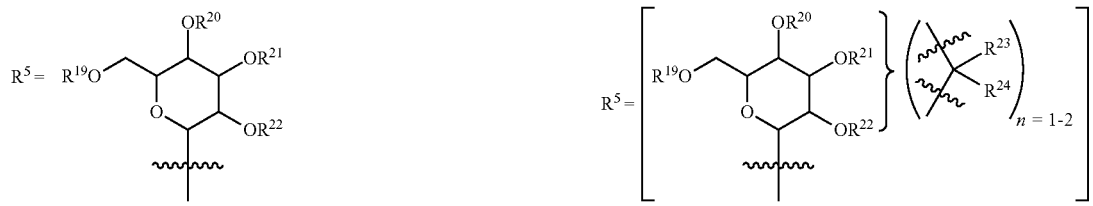

As described in Scheme XLVIII, glycopeptide antibiotics 61 in which $R^{19}$, $R^{20}$, $R^{20}$ and $R^{22}$ are independently —($CH_2$)-alkenyl($C_2$-$C_{20}$), —($CH_2$)-alkynyl($C_2$-$C_{20}$), —($CH_2$)-aryl or —($CH_2$)-heteroaryl, may be prepared from the corresponding glycopeptide antibiotics 60 prepared using the conditions described in Scheme XLVII (by treatment with a compound of the formula $R^{23}R^{24}$—C(O-alkyl($C_1$-$C_{20}$))$_2$ where $R^{23}$ is H and $R^{24}$ is alkenyl($C_2$-$C_{20}$), alkynyl($C_2$-$C_{20}$), aryl, or heteroaryl) in which at least one pair $R^{19}$ and $R^{20}$, $R^{20}$ and $R^{21}$, and $R^{21}$ and $R^{22}$ are moieties of the formula:

where $R^{23}$ is H and $R^{24}$ is alkenyl($C_2$-$C_{20}$), alkynyl($C_2$-$C_{20}$), aryl, or heteroaryl, where n is an integer of 1 or 2, by methods known to those skilled in the art, such as by treatment with a reductant and a protic acid or Lewis acid. Suitable combinations of reductants and acids include: sodium cyanoborohydride and trifluoroacetic acid, sodium cyanoborohydride and hydrochloride acid, triethylsilane-trifluoroatetic acid, borane-trimethylamine complex-aluminium chloride, borane-dimethylamine complex-boron trifluoride diethyl etherate, borane-dibutylboron triflate, or lithium aluminium hydride-aluminium chloride, and the like.

Scheme XLVIII

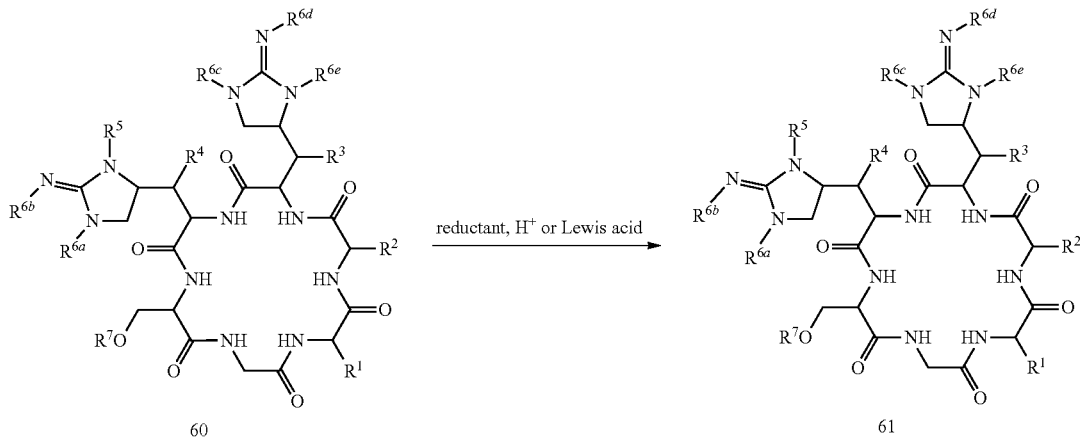

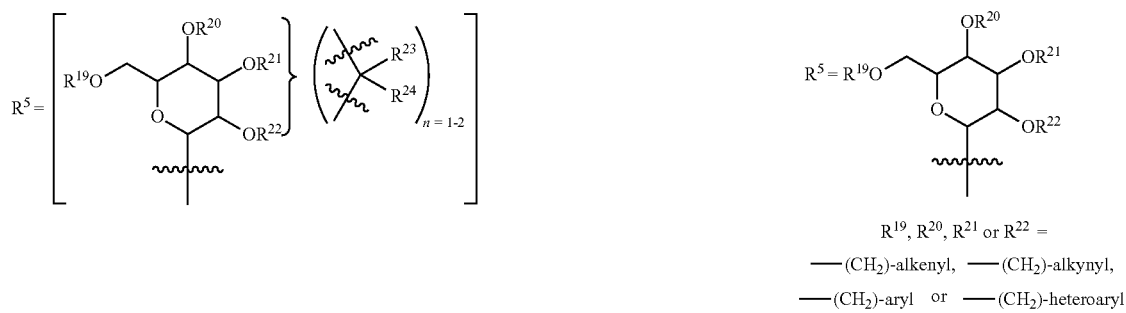

As described in Scheme XLIX, glycopeptide antibiotics 62 in which $R^{19}$, $R^{20}$, $R^{21}$ and $R^{22}$ are independently alkyl($C_1$-$C_{20}$), cycloalkyl($C_3$-$C_{70}$), alkenyl($C_3$-$C_{20}$) or alkynyl($C_3$-$C_{20}$) may be prepared from the corresponding compounds 54 in which at least one of $R^{19}$, $R^{20}$, $R^{21}$ and $R^{22}$ are H, by methods known to those skilled in the art, such as by alkylation with an appropriate alkylating agent $R^{19}X$, $R^{20}X$, $R^{21}X$ or $R^{22}X$, where X is Cl, Br, I, —O-tosylate, —O-mesylate, or —O-triflate, in the presence or absence of a suitable base. The extent of the reaction may be controlled by variations in the stoichiometry of the alkylating agent, reaction temperature, and reaction time.

Scheme XLIX

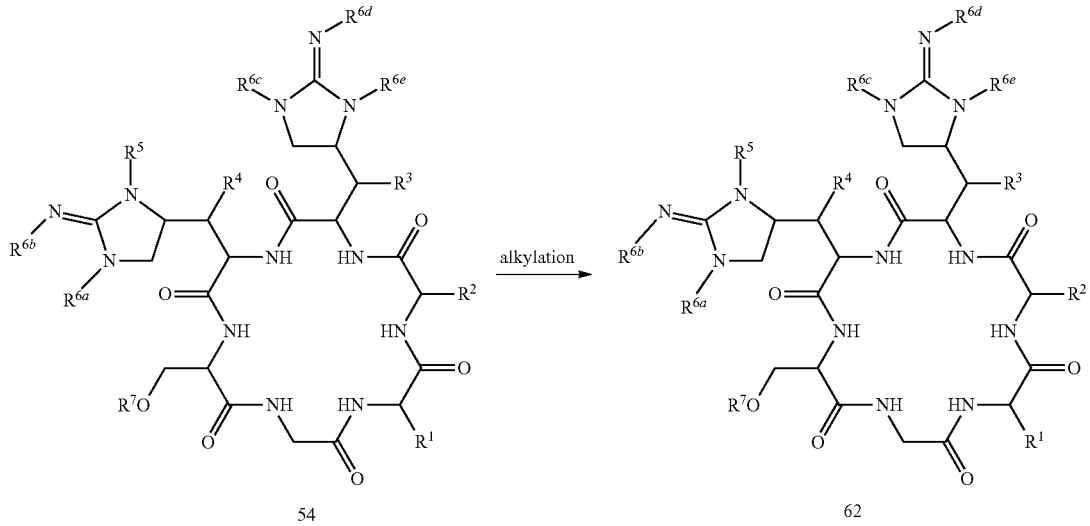

179
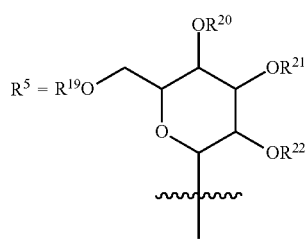
180
-continued
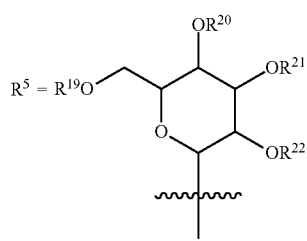
$R^{19}, R^{20}, R^{21}$ or $R^{22}$ = alkyl, cycloalkyl, alkenyl, or alkynyl
As described in Scheme XLX glycopeptide antibiotics 64 wherein $R^2$ and $R^{2a}$ are as shown may be prepared by fermentation of glycopeptide antibiotics 63 wherein $R^2$ and $R^{2a}$ are as shown in the presence of modified strains of *Streptomyces hygroscopicus* and in particular, strain LL4780.
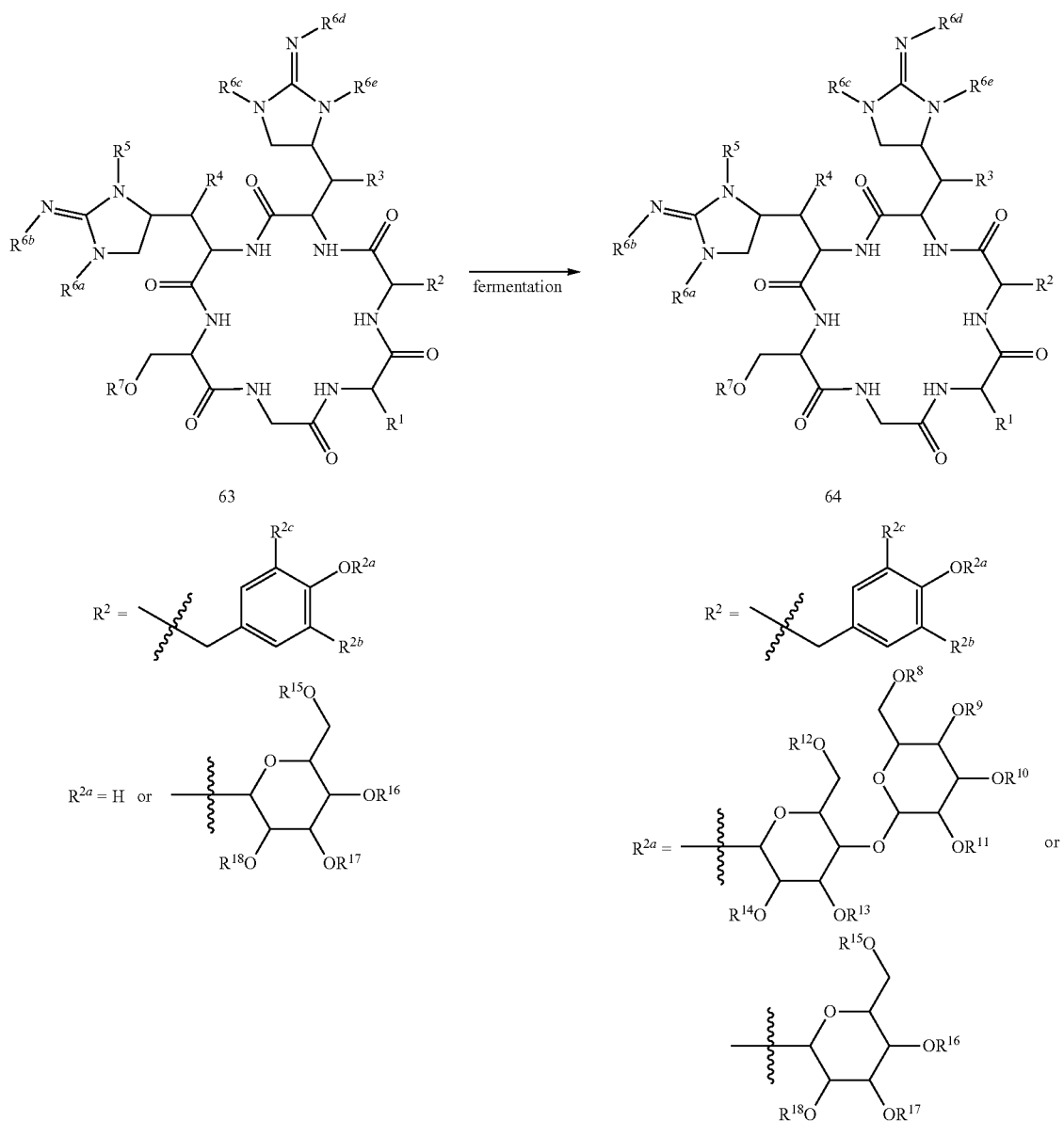
Scheme XLX Generally, reactions described herein may be conducted in a solvent or solvents which are compatible with the reaction conditions contemplated, as is known by those skilled in the art, which include but are not limited to water, N,N-dimethylformamide, N,N-dimethylacetamide, dimethylsulfoxide, N,N-dimethylpropyleneurea, N-methylpyrrolidinone, and the like, at temperatures ranging from −15° C. to the reflux temperature of the solvent.

Additionally, reactions are performed in a solvent appropriate to the reagents and materials employed and suitable for the transformation being effected. Various functionalities present on the molecule must be consistent with the chemical transformations proposed. This may necessitate judgement as to the order of synthetic steps and that substituents on the starting materials may be incompatible with some of the reaction conditions. Such restrictions to the substituents which are compatible with the reaction conditions will be apparent to one skilled in the art.

Suitable bases employed in the reactions as described in Schemes IV-XI, XIII-XVI, XXI-XXXIX, and XLII-XLVI include but are not limited to amine bases such as ammonia, triethylamine, NN-diisopropylethylamine, pyridine, 2,6-di-tert-butyl pyridine, 1,5-diazabicyclo[4.3.0]non-5-ene, 1,8-diazabicyclo[5.4.0]undec-7-ene, and the like, carbonate bases such as sodium carbonate, potassium carbonate, cesium carbonate, and the like, hydroxide bases such as sodium hydroxide, potassium hydroxide, lithium hydroxide, barium hydroxide, and the like, or hydride bases such as sodium hydride, potassium hydride, calcium hydride, and the like.

Reactions may be monitored by reverse-phase thin-layer chromatography, electrospray mass spectrometry, analytical high-pressure liquid chromatography (HPLC), liquid chromatography-mass spectrometry (LC-MS), and/or other analytical methods commonly employed by those skilled in the art.

Reaction products may be isolated by the removal of heterogeneous materials, if present, in the reaction vessel by filtration, followed by the removal of solvent by evaporation and/or by direct precipitation of the crude product upon addition of sufficient quantities of a co-solvent in which the product is minimally soluble, such as acetonitrile, acetone, methanol, ethanol, ethyl acetate, diethyl ether, and the like, followed by filtration or centrifugation.

Reaction products may be purified by reverse-phase preparative HPLC over commonly marketed reverse phase supports, such as the C18-coated silica ODS packing support marketed by the YMC corporation (currently a wholly-owned subsidiary of the Waters corporation), employing isocratic elution conditions, gradient elution conditions, or a combination of both isocratic and gradient elution conditions, using mixed solvent systems consisting of an organic solvent, such as methanol, acetonitrile, and the like, and water, and containing approximately 0.005-0.01% by volume of trifluoroacetic acid, or, alternatively, approximately 0.01-0.05% by volume of acetic acid. In those instances wherein the isolated product exhibits limited stability in the acidic media of the elution solvents, such as those cases in which the product(s) is a (are) ketal(s) or aryl-acetal(s), it is advantageous to employ 0.01% of acetic acid and to neutralize the product-containing fractions to pH 6 (pH paper) by the addition of sufficient quantities of aqueous ammonium hydroxide. Excess ammonium acetate thus produced is removed from the final desired product following concentration of the product-containing fractions in vacuo, by lyophilization, or by washing with a solvent in which the product is minimally soluble, such as ethanol, 2-propanol, and the like.

Typically dialkyl acetals or dialkyl ketals of the formula $R^{23}R^{24}$—C(O-alkyl($C_1$-$C_{20}$))$_2$, used in the hereinbefore described schemes include the dimethyl acetals of acetaldehyde, propionaldehyde, butyraldehyde, 3-methylbutyraldehyde, 3,3-dimethylbutyraldehyde, cyclopentanecarboxaldehyde, cyclohexanecarboxaldehyde, 2-ethyl-butyraldehyde, phenylacetaldehyde, 4-methoxyphenylacetaldehyde, 4-bromophenylacetaldehyde, 3-phenyl-propionaldehyde, 2-(N-benzyloxycarbonyl-4-piperidinyl)-acetaldehyde (prepared in two steps from 2-(4-piperidnyl)-ethanol by N-funtionalization and oxidation), 1-adamantylcarboxaldehyde, benzaldehyde, 3-(4-methylphenoxy)-benzaldehyde, 3-nitro-4-methoxy-benzaldehyde, 4-benzyloxybenzaldhyde, 3-benzyloxybenzaldhyde, 4-carboxymethylbenzaldehyde, 4-(2-propyl)benzaldehyde, 4-(1-propyl)benzaldehyde, 4-phenylbenzaldehyde, piperonal, 1-naphthaldehyde, 2-naphthaldehyde, 6-methoxy-2-naphthaldehyde, 4-methoxy-1-naphthaldehyde, and the like, and the dimethyl ketals of acetone, cyclopentanone, cyclohexanone, 2-methylcyclohexanone, 4-tert-butylcyclohexanone, 2,2-dimethylcyclohexanone, 2,5-dimethylcyclohexanone, 3,3,5,5-tetramethylcyclohexanone, 2-adamantanone, bicyclo[3.3.11nonan-9-one, tetrahydrothiopyran-4-one, acetophenone, 4-fluoroacetophenone, (R)-camphor, (S)-camphor, carvone, and the like.

In those instances where the parent aldehyde or ketone is not commercially available, the aldehyde or ketone is prepared from readily accessible compounds by methods known to those skilled in the art, such as by oxidation of the corresponding alcohols, by Kornblum-type oxidation of the corresponding alkyl- or benzyl-bromides, by oxidation of aryl methanes, by benzylic bromination of aryl methanes followed by Kornblum oxidation of the resultant benzyl bromide or hydrolysis of the resultant benzylic dibromides, by reduction of the corresponding esters, carboxylic acids, or nitriles, or, in the case of alkoxy-substituted benzaldehydes, by alkylation of commerically available phenolic benzaldehydes or an appropriate precursor thereof, or, in the case of aryl- or heteroaryl-substituted benzaldehydes, by palladium-mediated couplings of bromo- or iodo-substituted benzaldehydes or an appropriate precursor thereof with aromatic or heteroaromatic boronic acids, or, in the case of acyl-substituted benzaldehydes, by Friedel-Crafts acylation of a benzaldehyde or an appropriate precursor thereof.

Aldehydes or ketones used in these reactions are easily converted to their corresponding dialkyl-acetals, typically dimethylacetals, by methods known to those skilled in the art, such as by reaction of the aldehyde or ketone with trimethylorthoformate (to prepare dimethyl acetals) in the presence of an acid catalyst, such as hydrochloric acid, sulfuric acid, p-toluenesulfonic acid, camphorsulfonic acid, immobilized sulfonic acid resins (anionic exchange resins) and the like, or, by reaction of the aldehyde or ketone with an alcohol in the presence of an acid catalyst such as those listed above while employing the use of a dehydrating agent such as molecular sieves or by employing the use of a Dean-Stark apparatus, or employing any other conditions that permit the efficient removal of water from the reaction.

Biological Activity

Methods for In Vitro Antibacterial Evaluation(Table 1)

The minimum inhibitory concentration (MIC), the lowest concentration of the antibiotic which inhibits growth of the test organism, is determined by the broth dilution method using Muller-Hinton II agar (Baltimore Biological Laboratories) following the recommendations of the National Committee for Clinical Laboratory Standards [Methods for dilution antimicrobial susceptibility tests for bacteria that grow aerobically, approved standard M7-A2, National Committee for Clinical Laboratory Standards, Villanova, Pa].

An inoculum level of $5 \times 10^5$ CFU/mL, and a range of antibiotic concentrations (64-0.06 µg/mL) is used. The MIC is determined after the microtiter plates are incubated for 18 hours at 35° C. in an ambient air incubator. The test organisms include a spectrum of Gram-positive bacteria comprised of *Staphylococcus* sp., *Streptococcus* sp. and *Enterococcus* sp. These organisms include recent clinical isolates that are resistant to methicillin, penicillin and/or vancomycin. The results of representative examples of the invention are given in Table 2.

TABLE 2

| EXAMPLE NUMBER | Staphylococcus aureus-SMITH (GC 4543) | Staphylococcus haemolyticus (GC 4546) | Staphylococcus aureus (GC 1131) | Staphylococcus aureus (GC 3051) | Staphylococcus aureus (GC 3053) | Coagulase Negative Staphylococcus (GC 4537) | Coagulase Negative Staphylococcus (GC 4538) | Staphylococcus aureus (GC 4535) | Staphylococcus aureus (GC 4541) | Coagulase Negative Staphylococcus (GC 4547) | Coagulase Negative Staphylococcus (GC 4548) | Staphylococcus aureus (GC 4542) | Coagulase Negative Staphylococcus (GC 4549) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|---|---|---|---|---|---|---|---|
| Example 3 | >128 | >128 | >128 | | | | | | | | | | | | | | |
| Example 12 | >128 | >128 | >128 | | | >128 | | | >128 | >128 | >128 | >128 | 128 | >128 | >128 | >128 | |
| Example 13 | 64 | 64 | 64 | | | 64 | | | 64 | 64 | 64 | 64 | 32 | 64 | 64 | 64 | |
| Example 14 | >128 | >128 | >128 | | | >128 | | | >128 | >128 | >128 | >128 | >128 | >128 | >128 | >128 | |
| Example 15 | >128 | >128 | >128 | | | >128 | | | >128 | >128 | >128 | >128 | >128 | >128 | >128 | >128 | |
| Example 16 | 128 | 128 | 128 | | | 128 | | | 64 | >128 | >128 | 128 | 128 | 128 | 32 | 128 | |
| Example 17 | >64 | >64 | >64 | | | >64 | | | >64 | >128 | >128 | >64 | >64 | >64 | >64 | >64 | |
| Example 18 | >128 | >128 | >128 | | | >128 | | | >128 | >128 | >128 | >128 | >128 | >128 | >128 | >128 | |
| Example 19 | >128 | >128 | >128 | | | >128 | | | >128 | >128 | >128 | >128 | >128 | >128 | >128 | >128 | |
| Example 22 | >128 | >128 | >128 | | | >128 | | | >128 | >128 | >128 | >128 | >128 | >128 | >128 | >128 | |
| Example 24 | >64 | >64 | >64 | | | >64 | | | >64 | >64 | >64 | >64 | >64 | >64 | >64 | >64 | |
| Example 25 | >128 | >128 | >128 | | | >128 | | | >128 | >128 | >128 | >128 | >128 | >128 | >128 | >128 | |
| Example 26 | 16 | 16 | 16 | | | 16 | | | 32 | 32 | 64 | 16 | 16 | 16 | 32 | 32 | |
| Example 27 | 16 | 16 | 8 | | | 8 | | | 16 | 16 | 16 | 8 | 8 | 8 | 8 | 8 | |
| Example 28 | 8 | 4 | 4 | | | 4 | | | 8 | 8 | 8 | 8 | 8 | 4 | 4 | 8 | |
| Example 29 | 8 | 8 | 8 | | | 8 | | | 8 | 8 | 8 | 8 | 8 | 8 | 8 | 8 | |
| Example 30 | 16 | 16 | 16 | | | 16 | | | 16 | 16 | 16 | 8 | 8 | 8 | 8 | 16 | |
| Example 31 | 16 | 16 | 16 | | | 16 | | | 16 | 16 | 16 | 8 | 8 | 16 | 16 | 16 | |
| Example 32 | 2 | 2 | 2 | | | 4 | | | 2 | 2 | 2 | 2 | 2 | 2 | 2 | 4 | |
| Example 33 | 4 | 16 | 8 | | | 8 | | | 8 | 8 | 8 | 8 | 8 | 4 | 8 | 8 | |
| Example 34 | 32 | 16 | 32 | | | 32 | | | 32 | 32 | 32 | 32 | 32 | 16 | 32 | 32 | |
| Example 35 | 8 | 8 | 8 | | | 8 | | | 8 | 8 | 8 | 8 | 8 | 8 | 8 | 8 | |
| Example 36 | >128 | >128 | >128 | | | >128 | | | >128 | >128 | >128 | >128 | >128 | >128 | >128 | >128 | |
| Example 37 | 8 | 8 | 8 | | | 8 | | | 8 | 8 | 8 | 8 | 8 | 8 | 16 | 16 | |
| Example 38 | 32 | 64 | 64 | | | 64 | | | 64 | 64 | 64 | 64 | 64 | 32 | 32 | 64 | |
| Example 39 | 16 | 16 | 16 | | | 8 | | | 16 | 16 | 16 | 16 | 16 | 16 | 8 | 16 | |
| Example 40 | 64 | 64 | 64 | | | 64 | | | 64 | 64 | 64 | 64 | 64 | 32 | 32 | 64 | |
| Example 41 | >64 | >64 | >64 | | | >64 | | | >64 | >64 | >64 | >64 | >64 | >64 | >64 | >64 | |
| Example 42 | 2 | 8 | 2 | | | 4 | | | 2 | 2 | 2 | 2 | 2 | 2 | 2 | 4 | |
| Example 44 | 64 | 8 | 64 | | | 32 | | | 64 | 64 | 64 | 64 | 64 | 16 | 16 | 64 | |
| Example 45 | 8 | 8 | 8 | | | 8 | | | 16 | 16 | 16 | 8 | 8 | 8 | 8 | 8 | |
| Example 46 | 8 | 8 | 8 | | | 8 | | | 8 | 8 | 8 | 8 | 8 | 8 | 8 | 8 | |
| Example 47 | 32 | 32 | 16 | | | 16 | | | 16 | 16 | 16 | 16 | 16 | 16 | 16 | 16 | |
| Example 48 | 16 | 16 | 16 | | | 16 | | | 16 | 16 | 16 | 16 | 16 | 16 | 16 | 32 | |
| Example 49 | 4 | 4 | 4 | | | 4 | | | 4 | 4 | 4 | 4 | 4 | 2 | 2 | 8 | |
| Example 51 | >128 | 32 | >128 | | | 64 | | | 32 | 32 | >128 | >128 | 32 | 32 | 32 | 32 | |

| EXAMPLE NUMBER | Coagulase Negative Staphylococcus (GC 6257) | Coagulase Negative Staphylococcus (ID-3941) |
|---|---|---|
| Example 3 | | 128 |
| Example 12 | >128 | |
| Example 13 | 32 | |
| Example 14 | >128 | |
| Example 15 | >128 | |

TABLE 2-continued

| Example Number | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|---|
| Example 16 | 64 | 8 | | | 16 | 32 | 4 | 32 | | 8 |
| Example 17 | >64 | >64 | | | 64 | >64 | 32 | >64 | | 64 |
| Example 18 | >128 | 128 | | | 128 | 128 | 64 | >128 | | 128 |
| Example 19 | >128 | >128 | | | >128 | >128 | 128 | >128 | | >128 |
| Example 22 | >128 | >128 | | | >128 | >128 | 64 | >128 | | 128 |
| Example 24 | >64 | 64 | | | 64 | 64 | 64 | >64 | | 32 |
| Example 25 | >128 | >128 | | | >128 | >128 | >128 | >128 | | >128 |
| Example 26 | 16 | 4 | | | 8 | 16 | 4 | 16 | | 4 |
| Example 27 | 8 | 4 | | | 4 | 8 | 8 | 8 | | 4 |
| Example 28 | 8 | 4 | | | 4 | 4 | 4 | 8 | | 4 |
| Example 29 | 8 | 4 | | | 4 | 4 | 2 | 8 | | 4 |
| Example 30 | 8 | 4 | | | 4 | 4 | 16 | 16 | | 4 |
| Example 31 | 16 | 8 | | | 8 | 8 | 16 | 16 | | 2 |
| Example 32 | 2 | 2 | | | 2 | 1 | 2 | 4 | | 4 |
| Example 33 | 4 | 4 | | | 4 | 4 | 1 | 8 | | 4 |
| Example 34 | 16 | 8 | | | 16 | 16 | 4 | 32 | | 8 |
| Example 35 | 8 | 8 | | | 8 | 8 | 8 | 8 | | 2 |
| Example 36 | >128 | 64 | | | 64 | 128 | 64 | >128 | | 64 |
| Example 37 | 8 | 8 | | | 16 | 8 | 8 | 8 | | 4 |
| Example 38 | 64 | 16 | | | 32 | 32 | 64 | 64 | | 16 |
| Example 39 | 16 | 8 | | | 8 | 8 | 4 | 8 | | 4 |
| Example 40 | 64 | 64 | | | 64 | 32 | 16 | 32 | | 16 |
| Example 41 | >64 | 64 | | | >64 | >64 | 32 | 64 | | |
| Example 42 | 2 | 2 | | | 2 | 2 | 1 | 4 | | 1 |
| Example 44 | 32 | 64 | | | 64 | 64 | 2 | 16 | | 8 |
| Example 45 | 4 | 4 | | | 4 | 4 | 4 | 8 | | 4 |
| Example 46 | 4 | 8 | | | 4 | 8 | 2 | 4 | | 2 |
| Example 47 | 8 | 8 | | | 8 | 2 | 0.5 | 8 | | 4 |
| Example 48 | 16 | 8 | | | 4 | 8 | 4 | 16 | | 4 |
| Example 49 | 2 | 1 | | | 4 | 2 | 1 | 4 | | 1 |
| Example 51 | 32 | 32 | | | 16 | 16 | 4 | 64 | | 4 |
| Example 52 | 16 | 16 | 32 | | 16 | 8 | 16 | 8 | 16 | |
| Example 53 | 4 | 2 | 4 | | 4 | 2 | 4 | 2 | 2 | |
| Example 53a | >128 | >128 | >128 | | >128 | >128 | >128 | >128 | >128 | |
| Example 54 | >128 | >128 | >128 | | >128 | >128 | >128 | >128 | >128 | |
| Example 54a | >128 | >128 | >128 | | >128 | >128 | >128 | >128 | >128 | |
| Example 58 | 8 | 16 | 32 | | 16 | 16 | 16 | 8 | 16 | |
| Example 59 | >128 | >128 | >128 | | >128 | >128 | >128 | >128 | >128 | |
| Example 60 | >128 | >128 | >128 | | >128 | >128 | >128 | >128 | >128 | |
| Example 60a | >128 | >128 | >128 | | >128 | >128 | >128 | >128 | >128 | |
| Example 61 | >128 | >128 | >128 | | >128 | >128 | >128 | >128 | >128 | |
| Example 62 | >128 | >128 | >128 | | >128 | >128 | >128 | >128 | >128 | |
| Example 64 | >128 | >128 | 128 | | >128 | >128 | >128 | >128 | >128 | |
| Example 65 | 16 | 8 | 8 | | 8 | 8 | 8 | 4 | 8 | |
| Example 66 | >128 | >128 | >128 | | >128 | >128 | >128 | >128 | >128 | |
| Example 66a | >128 | >128 | >128 | | >128 | >128 | >128 | >128 | >128 | |
| Example 67 | >128 | >128 | >128 | | >128 | >128 | >128 | >128 | >128 | |
| Example 69 | >128 | >128 | >128 | | >128 | >128 | >128 | >128 | >128 | |

TABLE 2-continued

| EXAMPLE NUMBER | Staphylococcus aureus-SMITH (GC 4543) | Staphylococcus haemolyticus (GC 4546) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|
| Example 72 | >128 | >128 | >128 | | >128 | >128 | >128 | >128 | >128 | |
| Example 73 | >128 | >128 | >128 | | >128 | >128 | >128 | >128 | >128 | |
| Example 74 | >128 | >128 | >128 | | >128 | >128 | >128 | >128 | >128 | |
| Example 76 | 4-8 | 2-8 | 2-8 | | 2-4 | 2-8 | 2-8 | 4-8 | 2-8 | |
| Example 77 | 16 | 8-16 | 16 | | 4-8 | 4-8 | 8-16 | 16 | 8-16 | |
| Example 78 | 8 | 8 | 8 | | 4 | 4 | 8 | 8 | 8 | |
| Example 79 | 8 | 4 | 4 | | 4 | 4 | 4 | 4 | 4 | |
| Example 80 | 32 | 32 | 64 | | 32 | 32 | 32 | 32 | 32 | |
| Example 81 | >128 | >128 | >128 | | >128 | >128 | >128 | >128 | >128 | |
| Example 82 | 16 | 8 | 16 | | 8 | 8 | 16 | 16 | 8 | |
| Example 83 | 4 | 4 | 4 | | 2 | 2 | 4 | 4 | 2 | |
| Example 84 | 8 | 8 | 8 | | 4 | 4 | 8 | 8 | 8 | |
| Example 89 | 64 | 64 | 64 | | 64 | 64 | 64 | 64 | 64 | |
| Example 92 | >128 | >128 | >128 | | >128 | >128 | >128 | >128 | >128 | |
| Example 93 | >128 | >128 | >128 | | >128 | >128 | >128 | >128 | >128 | |
| Example 94 | >64 | >64 | >64 | | >64 | >64 | >64 | >64 | >64 | |
| Example 95 | >64 | | | >64 | | | | | >64 | >64 |
| Example 95a | 4 | | | 8 | | | | | 4 | 4 |
| Example 95b | 1 | | | 2 | | | | | 1 | 1 |
| Example 96c | 0.5 | 2-4 | | | | | | 0.5 | | |
| Example 96 | >128 | >128 | >128 | | >128 | >128 | >128 | >128 | >128 | |

| EXAMPLE NUMBER | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) |
|---|---|---|---|---|---|
| Example 52 | 8 | 8 | 4 | 8 | |
| Example 53 | 2 | 2 | 1 | 2 | |
| Example 53a | >128 | >128 | >128 | >128 | >128 |
| Example 54 | >128 | >128 | >128 | >128 | >128 |
| Example 54a | 128 | >128 | >128 | >128 | >128 |
| Example 58 | 4 | 4 | 4 | 8 | |
| Example 59 | >128 | >128 | >128 | >128 | >128 |
| Example 60 | >128 | >128 | >128 | >128 | >128 |
| Example 60a | 128 | >128 | 128 | >128 | >128 |
| Example 61 | >128 | >128 | >128 | >128 | >128 |
| Example 62 | >128 | >128 | >128 | >128 | >128 |
| Example 64 | >128 | >128 | >128 | >128 | >128 |
| Example 65 | >128 | >128 | >128 | >128 | >128 |
| Example 66 | 4 | 4 | 4 | 8 | 4 |
| Example 66a | 4 | 4 | 4 | | |
| Example 67 | >128 | >128 | >128 | >128 | >128 |
| Example 69 | >128 | >128 | >128 | >128 | >128 |
| Example 72 | >128 | >128 | >128 | >128 | >128 |
| Example 73 | >128 | >128 | >128 | >128 | >128 |
| Example 74 | >128 | >128 | >128 | >128 | >128 |
| Example 76 | 2-4 | 2-4 | 2-4 | 2-8 | 0.5-2 |
| Example 77 | 4 | 4 | 4-8 | 8 | 2 |
| Example 78 | 4 | 4 | 8 | 4 | 2 |
| Example 79 | 4 | 4 | 2 | 4 | 4 |
| Example 80 | 32 | 32 | 32 | 32 | 8 |
| Example 81 | >128 | >128 | >128 | >128 | >128 |

TABLE 2-continued

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|---|
| Example 82 | 8 | | | | 4 | | 4 | | | 8 |
| Example 83 | 2 | | | | 2 | | 2 | | | 2 |
| Example 84 | 4 | | | | 4 | | 4 | | | 4 |
| Example 89 | 64 | | | | 32 | | 64 | | | 64 |
| Example 92 | >128 | | | | >128 | | >128 | | | >128 |
| Example 93 | >128 | | | | >128 | | >128 | | | >128 |
| Example 94 | >64 | | | >64 | >64 | | >64 | | | >64 |
| Example 95 | | | 8 | 4 | 4 | | | | | |
| Example 95a | | | 2 | 1 | | | | | | |
| Example 95b | | | | | | | | | | |
| Example 96c | 0.5 | 0.5 | | | 1 | | 1 | | | 0.5 |
| Example 96 | >128 | >128 | | | >128 | 0.25 | >128 | | | 128 |
| Example 96a | >128 | | | | 128 | >128 | >128 | >128 | >128 | >64 |
| Example 96b | 2 | | | | 1 | 2 | 2 | 1 | 1 | 0.5 |
| Example 97 | >64 | | | >64 | | | | | >64 | 0.5 |
| Example 97a | 2 | | 1-2 | 2 | | | | | 1 | 0.5 |
| Example 97b | 1 | | 2 | 1 | | | | | 1 | 8 |
| Example 98b | 16 | | 0.5 | 16 | | | | | 16 | 2 |
| Example 98c | 2 | | 1-2 | 4 | | | | | 2 | |
| Example 99b | 4 | | 0.5-2 | | 4 | 4 | 4 | 4 | 4 | |
| Example 99c | 2 | | 2 | 2 | 2 | 1 | 2 | 1 | 1 | 2 |
| Example 100b | 2 | | 8 | 1 | | | | | 2 | 1 |
| Example 100c | 1 | | | | | | | | 1 | |
| Example 101 | 4 | | | | 4 | 8 | 8 | 4 | 4 | |
| Example 101a | 4 | | | | 2 | 4 | 4 | 4 | 2 | |
| Example 102 | 2 | 1 | | | 1-2 | 0.5-1 | 1-2 | 0.5-1 | 1-2 | |
| Example 103 | 2 | 1 | | | 2 | 2 | 2 | 1 | 2 | |
| Example 104 | 2 | 1 | | | 1 | 0.5 | 1 | 0.5-1 | 1 | |
| Example 104a | 0.5-64 | 0.5 | | | 0.5-32 | 0.5 | 0.5 | 0.5 | 0.5-64 | |
| Example 104b | 0.5 | 0.5 | | | 0.5 | 0.5 | 0.5 | 0.5 | 0.5 | |
| Example 105 | 0.25-1 | 0.5-2 | 1-2 | | <0.5-1 | 0.5-1 | 0.25-2 | <0.5-1 | <0.5-1 | |
| Example 106 | 0.5-2 | 2 | 0.5-2 | | 0.5-2 | 0.25-1 | 0.25-2 | 0.5-2 | 0.5-2 | |
| Example 106a | 2 | 8 | 2 | | 2 | 2 | 4 | 2 | 2 | |
| Example 106b | 8 | | 8 | | 16 | 8 | 16 | 8 | 8 | |
| Example 107 | 2 | 1 | | | 2 | 1 | 2 | 1 | 1 | |
| Example 108 | 1 | | | | 1 | 1 | 1 | 1 | 1 | |
| Example 109 | 1 | | | | 1 | 2 | 2 | 1 | 1 | |
| Example 110 | 1 | | | | 1 | 1 | 1 | 1 | 1 | |
| Example 111 | 0.5-1 | | 1 | | 0.5-1 | 0.5-2 | 0.5-2 | 1-2 | 0.5-64 | |
| Example 112 | 2 | | 1 | | 0.5 | 0.5 | 0.5 | 0.5 | 0.5 | |
| Example 113 | 2 | 1 | 1 | | 2 | 1 | 2 | 1 | 2 | |
| Example 114 | 2 | 2 | 1 | | 2 | 1 | 2 | 1 | 2 | |
| Example 115 | 1 | 1 | 2 | | 1 | 1 | 1 | 1 | 1 | |
| Example 116 | 1 | 1 | 1 | | 1 | 0.5 | 1 | 1 | 1 | |
| Example 117 | 2 | 1 | 1 | | 1 | 0.5 | 1 | 1 | 1 | |
| Example 118 | <0.5-1 | <0.5-1 | 2 | | <0.5-1 | <0.5-1 | <0.5-1 | <0.5-1 | <0.5-1 | |
| Example 119 | 1 | 1 | 1 | | 1 | 1 | 1 | 1 | 1 | |
| Example 120 | <0.5 | <0.5 | 1 | | <0.5 | <0.5 | <0.5 | <0.5 | <0.5 | |

TABLE 2-continued

| EXAMPLE NUMBER | Staphylococcus aureus-SMITH (GC 4543) | Staphylococcus haemolyticus (GC 4546) | Staphylococcus aureus (GC 3051) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|---|
| Example 121 | | 2 | | 1 | | 1 | 1 | 1 | 2 | | |
| Example 122 | | 2 | | 2 | | 2 | 2 | 2 | 1 | | |
| Example 96a | >128 | 128 | | | | 128 | >128 | 64 | 128 | | 64 |
| Example 96b | 2 | 1 | | | | 1 | 0.5 | 0.5 | 2 | | 0.5 |
| Example 97 | | | | >64 | >64 | >64 | | | | | |
| Example 97a | | | | 4 | 2 | 2 | | | | | |
| Example 97b | | | | 1 | 1 | 1 | | | | | |
| Example 98b | | | | 16 | 8 | 8 | | | | | |
| Example 98c | | | | 2 | 1 | 1 | | | | | |
| Example 99b | 4 | 4 | | | | 4 | 4 | 2 | 8 | | 2 |
| Example 99c | 1 | 1 | | | | 1 | 1 | 1 | 2 | | 1 |
| Example 100b | | | | 2 | 1 | 1 | | | | | |
| Example 100c | | | | 1 | 1 | 1 | | | | | |
| Example 101 | 4 | 4 | | | | 2 | 2 | 1 | 8 | | 1 |
| Example 101a | 8 | 1 | | | | 1 | 1 | 1 | 2 | | 1 |
| Example 102 | 0.5-1 | 0.5-1 | | | | 1 | 0.5-1 | 0.5-1 | 1-2 | 0.5 | |
| Example 103 | 1 | 1 | | | | 2 | 1 | 1 | 2 | 1 | |
| Example 104 | 0.5-1 | 0.5 | | | | 1 | 0.5-1 | 0.5 | 1 | 0.5 | |
| Example 104a | 0.5-64 | 32 | | | | 32 | 16-32 | 16-32 | 32 | 16 | |
| Example 104b | 0.5 | 0.5 | | | | 4 | 4 | 4 | 8 | 2 | |
| Example 105 | 0.25-1 | <0.5-1 | | | | 0.5-1 | <0.5-1 | 0.5-1 | <0.5-1 | 0.5-1 | |
| Example 106 | 0.25-1 | 0.5-1 | | | | 0.5-2 | 0.25-1 | <0.12-1 | 0.25-1 | 0.25 | |
| Example 106a | 2 | 2 | | | | 2 | 1 | 1 | 2 | | |
| Example 106b | 8 | 4 | | | | 8 | 4 | 4 | 8 | | |
| Example 107 | 1 | 1 | | | | 1 | <0.5 | 1 | 1 | | 1 |
| Example 108 | 1 | 1 | | | | 1 | <0.5 | 1 | 1 | | 1 |
| Example 109 | 1 | 1 | | | | 1 | 1 | 1 | 1 | | 1 |
| Example 110 | 1 | 1 | | | | 1 | 1 | 0.5 | 1 | | 1 |
| Example 111 | 0.5-1 | 1 | | | | 0.5 | 0.5-1 | 0.5-1 | 0.5-1 | 1 | 0.5 |
| Example 112 | 1 | 1 | | | | 0.5-1 | 0.5 | 1 | 1 | 0.5 | |
| Example 113 | 2 | 1 | | | | 2 | 1 | 2 | 2 | 1 | |
| Example 114 | 1 | 1 | | | | 1 | 1 | 1 | 1 | 0.5 | |
| Example 115 | 1 | 0.5 | | | | 1 | 0.5 | 1 | 1 | 0.5 | |
| Example 116 | 1 | 0.5 | | | | 1 | 1 | 1 | 1 | 0.5 | |
| Example 117 | 1 | 1 | | | | 1 | 1 | 1 | 2 | 0.5 | |
| Example 118 | <0.5-1 | <0.5-<0.5 | | | | <0.5-1 | 0.25-0.25 | <0.5-<0.5 | <0.5-1 | 0.25-0.25 | |
| Example 119 | 1 | 1 | | | | 1 | 1 | 1 | 1 | <0.5 | |
| Example 120 | <0.5 | <0.5 | | | | | <0.5 | <0.5 | <0.5 | <0.5 | |
| Example 121 | 1 | 1 | | | | 1 | 0.5 | 0.5 | 2 | 1 | |
| Example 122 | 2 | 2 | | | | 2 | 1 | 1 | 2 | 1 | |

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|---|
| Example 123 | 8 | 8 | 8 | 8 | 4 | 4 | 8 | 8 | 8 | 8 |
| Example 124 | 2 | 2 | 2 | 2 | 2 | 1 | 2 | 2 | 2 | 2 |

TABLE 2-continued

| EXAMPLE NUMBER | Staphylococcus aureus-SMITH (GC 4543) | Staphylococcus haemolyticus (GC 4546) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|
| Example 125 | 4 | 32 | 32 | 32 | 8 | 32 | 32 | 32 | 32 | 32 |
| Example 126 | 2 | 8 | 8 | 8 | 8 | 8 | 8 | 8 | 8 | 8 |
| Example 127 | 32 | 2 | 2 | 2 | 4 | 4 | 4 | 2 | 2 | 2 |
| Example 128 | 8 | 2 | 2 | 2 | 2 | 2 | 2 | 2 | 2 | 2 |
| Example 129 | 2 | 2 | 2 | 2 | 2 | 2 | 2 | 2 | 2 | 4 |
| Example 130 | 2 | 32 | 32 | 32 | 32 | 32 | 32 | 32 | 32 | 32 |
| Example 132 | 2 | 2 | 2 | 2 | 2 | 2 | 2 | 2 | 2 | 2 |
| Example 133 | 32 | 1 | 4 | 4 | 1 | 4 | 4 | 4 | 4 | 4 |
| Example 135 | 2 | 2 | 1 | 1 | 1 | 2 | 2 | 2 | 1 | 1 |
| Example 136 | 2 | 16 | 16 | 32 | 8 | 16 | 16 | 16 | 16 | 16 |
| Example 137 | 1 | 2 | 1-2 | 2-4 | 1-2 | 1-2 | 2 | 2 | 2-4 | 1-2 |
| Example 137a | 32 | 32 | 32 | 32 | 16 | 32 | 32 | 32 | 32 | 32 |
| Example 137b | 16 | 16 | 16 | 16 | 8 | 16 | 16 | 16 | 16 | 16 |
| Example 138 | 2 | 2 | 2 | 2 | 2 | 2 | 2 | 2 | 2 | 2 |
| Example 140 | 1 | 1 | 1 | <0.5 | 1 | 1 | 1 | <0.5 | <0.5 | 1 |
| Example 141 | >64 | >64 | >64 | >64 | >64 | >64 | >64 | >64 | >64 | >64 |
| Example 143 | 2-4 | 2-4 | 2-4 | 4-8 | 2-4 | 1-4 | 2-8 | 2-4 | 2-4 | 2-4 |
| Example 144 | 1 | 1 | 1 | 1 | 0.5 | 0.5 | 4 | 1 | 1 | 2 |
| Example 145 | <0.5 | <0.5 | 1 | 1 | <0.5 | <0.5 | 1 | <0.5 | <0.5 | 1 |
| Example 146 | 8 | 8 | 8 | 8 | 8 | 4 | 8 | 8 | 8 | 8 |
| Example 147 | <0.5-<0.5 | <0.5-<0.5 | 0.5 | 0.5 | <0.5-<0.5 | 0.5-1 | 0.5-1 | 0.5-1 | 0.5-1 | <0.5-<0.5 |
| Example 149 | 2 | 2 | 4 | 2 | 2 | 2 | 2 | 2 | 2 | 2 |
| Example 150 | 4 | 4 | 2 | 8 | 2 | 2 | 2 | 2 | 2 | 2 |
| Example 150a | 32 | 32 | 32 | 32 | 16 | 32 | 32 | 32 | 32 | 32 |
| Example 151 | 8 | 8 | 16 | 8 | 4 | 8 | 8 | 4 | 8 | 8 |
| Example 152 | 16 | 16 | 32 | 16 | 16 | 16 | 8 | 16 | 16 | 16 |
| Example 153 | 2 | 2 | 4 | 4 | 2 | 2 | 4 | 2 | 2 | 2 |
| Example 154 | 1 | 1 | 1 | 1 | 1 | 1 | 1 | 1 | 1 | 1 |
| Example 155 | <0.5-<0.5 | <0.5-<0.5 | 0.5 | 0.5 | <0.5-<0.5 | <0.5-<0.5 | <0.5-<0.5 | <0.5-<0.5 | <0.5-<0.5 | <0.5-<0.5 |
| Example 156 | 2 | 2 | 2 | 4 | 2 | 2 | 2 | 2 | 2 | 2 |
| Example 157 | 32 | 32 | 16 | 32 | 16 | 32 | 32 | 16 | 32 | 32 |
| Example 158 | 2 | 2 | 1 | 2 | 1 | 1 | 2 | 2 | 2 | 2 |
| Example 161 | 8 | 8 | 8 | 8 | 4 | 4 | 8 | 4 | 4 | 4 |
| Example 162 | 16 | 32 | 16 | 16 | 16 | 16 | 16 | 16 | 16 | 16 |
| Example 163 | 4 | 8 | 8 | 8 | 4 | 4 | 4 | 4 | 4 | 4 |
| Example 164 | 16 | 16 | 8 | 8 | 8 | 16 | 8 | 4 | 8 | 8 |

TABLE 2-continued

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|---|
| Example 136 | 16 | 16 | | | 8 | 8 | 8 | 8 | 8 | 4 |
| Example 137 | 1-2 | 1 | | | 1-2 | 0.5-2 | 8 | 8 | 8 | 1 |
| Example 137a | 16 | 16 | | | 16 | 16 | 16 | 16 | 16 | 8 |
| Example 137b | 8 | 8 | | | 8 | 4 | 2 | 1 | 1 | 4 |
| Example 138 | 1 | 2 | | | 4 | 1 | 32 | 32 | 32 | 2 |
| Example 140 | 1 | 1 | | | <0.5 | <0.5 | 2 | 4 | 4 | <0.5 |
| Example 141 | >64 | >64 | | | >64 | >64 | >64 | >64 | >64 | >64 |
| Example 143 | 2-4 | 0.5-2 | | | 1-2 | 1-2 | 2-4 | 2-4 | 2-4 | 1-2 |
| Example 144 | 1 | 1 | | | 1 | 0.25 | 0.5 | 0.5 | 0.5 | 0.25 |
| Example 145 | <0.5 | <0.5 | | | 1 | <0.5 | 1 | <0.5 | <0.5 | 0.5 |
| Example 146 | 8 | 8 | | | 8 | 4 | 8 | 8 | 8 | 4 |
| Example 147 | 0.5-1 | 1-2 | | | 1-2 | <0.5-1 | <0.5-1 | 1 | 1 | 2 | 1 |
| Example 149 | 2 | 1 | | | 1 | 1 | 1 | 1 | 1 | 1 |
| Example 150 | 2 | 2 | | | 2 | 2 | 2 | 2 | 2 | 8 |
| Example 150a | 16 | 16 | | | 16 | 8 | 8 | 32 | 32 | 2 |
| Example 151 | 8 | 2 | | | 4 | 4 | 2 | 8 | 4 | 8 |
| Example 152 | 8 | 8 | | | 8 | 8 | 8 | 16 | 4 | 8 |
| Example 153 | 1 | 1 | | | 1 | 0.5 | 0.25 | 2 | 2 | 0.5 |
| Example 154 | 1 | 1 | | | 2 | 0.5 | 0.5 | 2 | 4 | 1 |
| Example 155 | <0.5-<0.5 | <0.5-1 | | | <0.5-2 | <0.5-1 | <0.5-1 | <0.5-1 | <0.5-1 | 1 | <0.5 |
| Example 156 | 2 | 2 | | | 2 | 1 | 2 | 2 | 2 | 2 |
| Example 157 | 16 | 16 | | | 16 | 8 | 8 | 32 | 32 | 4 |
| Example 158 | 2 | 0.5 | | | 2 | 1 | 1 | 2 | 2 | 1 |
| Example 161 | 4 | 4 | | | 4 | 2 | 2 | 4 | 4 | 8 |
| Example 162 | 16 | 16 | | | 16 | 8 | 8 | 32 | 32 | 2 |
| Example 163 | 4 | 4 | | | 8 | 4 | 4 | 2 | 2 | 8 |
| Example 164 | 2 | 2 | | | 4 | 0.5 | 1 | 4 | 2 | 1 |
| Example 164a | 8 | 8 | 8 | | 8 | 16 | 8 | 8 | 8 | |
| Example 165 | 16 | 32 | 16 | | 16 | 16 | 16 | 16 | 16 | |
| Example 166 | 8 | | 8 | | 8 | | | | 8 | |
| Example 167 | 16 | 16 | 16 | | 8 | 16 | 16 | 16 | 16 | |
| Example 168 | 1 | 1 | 1 | | 1 | 1 | 2 | 1 | 1 | |
| Example 169 | 32 | 32 | >64 | | 32 | 32 | 32 | 32 | 32 | |
| Example 170 | 4 | 4 | 1 | | 2 | 4 | 2 | 4 | 4 | |
| Example 172 | 8 | 4 | 4 | | 4 | 2 | 8 | 2 | 4 | |
| Example 173 | 2 | 2 | 4 | | 0.5 | 0.5 | 2 | 2 | 4 | |
| Example 174 | 1 | 0.5 | 1 | | 2 | 2 | 2 | 1 | 2 | |
| Example 175 | 4 | 2 | 2 | | 4 | 2 | 2 | 2 | 4 | |
| Example 177 | 2 | 4 | 4 | | 4 | 2 | 2 | 2 | 2 | |
| Example 178 | 4 | 4 | 4 | | 8 | 2 | 8 | 4 | 4 | |
| Example 179 | 32 | 8 | 32 | | 32 | 8 | 32 | 32 | 16 | |
| Example 180 | 2 | 32 | 4 | | 2 | 32 | 2 | 2 | 32 | |
| Example 181 | 4 | 1 | 4 | | 4 | 2 | 4 | 4 | 4 | |
| Example 182 | >64 | >64 | >64 | | >64 | >64 | >64 | >64 | >64 | |
| Example 183 | 8 | 2 | 2 | | 8 | 4 | 4 | 4 | 4 | |
| Example 184 | 32 | 32 | 32 | | 32 | 32 | 32 | 32 | 32 | |
| Example 185 | >64 | >64 | >64 | | >64 | >64 | >64 | >64 | >64 | |
| Example 186 | 2 | 2 | 2 | | 2 | 1 | 2 | 2 | 2 | |

TABLE 2-continued

| EXAMPLE NUMBER | Staphylococcus aureus-SMITH (GC 4543) | Staphylococcus haemolyticus (GC 4546) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|
| Example 187 | 64 | 64 | 32 | | 64 | 64 | 64 | 64 | 64 | |
| Example 190 | 16 | 16 | 16 | | 8 | 8 | 16 | 16 | 16 | |
| Example 191 | 8 | 8 | 8 | | 4 | 4 | 8 | 4 | 4 | |
| Example 192 | 4 | 1 | 2 | | 2 | 2 | 2 | 2 | 1 | |
| Example 193 | 1 | 1 | 0.5 | | 0.5 | 0.25 | 0.5 | 1 | 0.5 | |
| Example 194 | 1 | 1 | 1 | | 0.5 | 0.5 | 1 | 1 | 1 | |
| Example 195 | 0.5 | 0.5 | 0.5 | | 0.5 | 0.5 | 0.5 | 0.5 | 0.5 | |
| Example 196 | >64 | >64 | >64 | | >64 | >64 | >64 | >64 | >64 | |
| Example 197 | 16 | 64 | 64 | | 16 | 64 | 32 | 32 | 32 | |
| Example 198 | 1 | 1 | 0.5 | | 0.5 | 0.25 | 0.5 | 1 | 0.5 | |
| Example 199 | 2 | 2 | 2 | | 2 | 1 | 1 | 2 | 2 | |
| Example 200 | 2 | 2 | 2 | | 1 | 1 | 2 | 4 | 1 | |
| Example 201 | 0.25 | 0.5 | 0.5 | | 0.5 | 0.25 | 0.25 | 0.25 | 0.25 | |
| Example 202 | 4 | 4 | 4 | | 4 | 4 | 4 | 4 | 4 | |
| Example 203 | 2 | 2 | 2 | | 1 | 1 | 1 | 1 | 1 | |
| Example 204 | 8 | 4 | 4 | | 4 | 4 | 4 | 4 | 4 | |
| Example 205 | 2 | 2 | 2 | | 2 | 2 | 2 | 2 | 2 | |
| Example 164a | 8 | 4 | | | 8 | 4 | 4 | 8 | 4 | |
| Example 165 | 16 | 16 | | | 16 | 8 | 8 | 16 | 8 | |
| Example 166 | 4 | | | | 4 | 4 | 4 | | 4 | |
| Example 167 | 16 | 16 | | | 8 | 8 | 8 | 16 | 8 | |
| Example 168 | 1 | 0.5 | | | 2 | 0.5 | 0.5 | 1 | | |
| Example 169 | 32 | 32 | | | 32 | 32 | 16 | >64 | 8 | |
| Example 170 | 4 | 8 | | | 4 | 1 | 2 | 1 | 1 | |
| Example 172 | 8 | 8 | | | 8 | 2 | 2 | 4 | 2 | |
| Example 173 | 0.5 | 1 | | | 2 | 0.5 | 0.25 | 0.5 | 0.5 | |
| Example 174 | 1 | 2 | | | 2 | 2 | 1 | 1 | 2 | |
| Example 175 | 4 | 4 | | | 8 | 2 | 2 | 4 | 2 | |
| Example 177 | 2 | 2 | | | 4 | 1 | 2 | 4 | 1 | |
| Example 178 | 4 | 8 | | | 32 | 2 | 2 | 4 | 2 | |
| Example 179 | 32 | 32 | | | 32 | 32 | 16 | 32 | 32 | |
| Example 180 | 2 | 2 | | | 2 | 1 | 1 | 1 | 0.5 | |
| Example 181 | 4 | 2 | | | 8 | 2 | 1 | 2 | 2 | |
| Example 182 | >64 | >64 | | | >64 | >64 | >64 | >64 | >64 | |
| Example 183 | 4 | 8 | | | 4 | 2 | 4 | 4 | 2 | |
| Example 184 | 32 | 32 | | | 32 | 16 | 32 | 32 | 16 | |
| Example 185 | >64 | >64 | | | >64 | >64 | >64 | >64 | >64 | |
| Example 186 | 2 | 1 | | | 2 | 1 | 1 | 2 | 2 | |
| Example 187 | 64 | 128 | | | 128 | 16 | 64 | 32 | 0.5 | |
| Example 190 | 4 | 8 | | | 8 | 8 | 8 | 16 | 32 | |
| Example 191 | 4 | 4 | | | 8 | 4 | 4 | 4 | 8 | |
| Example 192 | 2 | 1 | | | 2 | 1 | 1 | 4 | 4 | |
| Example 193 | 0.5 | 0.5 | | | 1 | 0.25 | 0.25 | 0.5 | 0.25 | |
| Example 194 | 0.5 | 0.5 | | | 1 | 0.5 | 0.5 | 1 | 0.5 | |
| Example 195 | 0.5 | 2 | | | 4 | 2 | 1 | 4 | 2 | |
| Example 196 | >64 | 32 | | | 32 | 64 | 64 | >64 | 64 | |
| Example 197 | 16 | 32 | | | 32 | 8 | 8 | 16 | 4 | |

TABLE 2-continued

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|---|
| Example 198 | | 0.5 | | | | <0.12 | 0.5 | | 0.5 | |
| Example 199 | | 1 | | | | 0.5 | 0.5 | 1 | | |
| Example 200 | | 1 | | | | 1 | 1 | 2 | | |
| Example 201 | | 0.25 | | | | 0.25 | 0.25 | 0.25 | | |
| Example 202 | | 2 | | | | 2 | 1 | 4 | | |
| Example 203 | | 2 | | | | 1 | 2 | 4 | | |
| Example 204 | | 4 | | | | 4 | 4 | 4 | 2 | |
| Example 205 | | 2 | | | | 1 | 2 | 2 | 1 | |
| Example 206 | 1 | 1 | 1 | | 1 | 1 | 1 | 1 | 1 | |
| Example 207 | 2 | 2 | 1 | | 1 | 1 | 1 | 1 | 1 | |
| Example 208 | 8 | 4 | 4 | | 8 | 4 | 8 | 4 | 4 | |
| Example 209 | 2 | 2 | | | 2 | | | | 4 | |
| Example 210 | 32 | 32 | 32 | | 32 | 32 | 32 | 32 | 32 | |
| Example 210a | 4 | 8 | 4 | | 4 | 8 | 8 | 4 | 4 | |
| Example 212 | 4 | 2 | 4 | | 2 | 2 | 4 | 2 | 2 | |
| Example 214 | 1 | 32 | 2 | | 2 | 1 | 1 | 1 | 2 | |
| Example 215 | 0.5 | 0.5 | 1 | | 0.5 | 0.5 | 0.5 | 1 | 0.5 | |
| Example 216 | 2 | 4 | 2 | | 1 | 1 | 2 | 1 | 2 | |
| Example 217 | 4 | 4 | 8 | | 4 | 4 | 8 | 4 | 4 | |
| Example 218 | 4 | 4 | 2 | | 2 | 4 | 4 | 4 | 4 | |
| Example 219 | 4 | 2 | 2 | | 2 | 4 | 8 | 2 | 4 | |
| Example 220 | 1 | 1 | 1 | | 1 | 0.5 | 1 | 0.5 | 0.5 | |
| Example 221 | 2 | 2 | 2 | | 2 | 2 | 2 | 2 | 1 | |
| Example 222 | >64 | >64 | >64 | | >64 | >64 | >64 | >64 | >64 | |
| Example 223 | >64 | 64 | >64 | | 64 | 64 | 64 | 64 | >64 | |
| Example 224 | 4 | 2 | 4 | | 1 | 4 | 4 | 2 | 2 | |
| Example 225 | 8 | 4 | 8 | | 4 | 8 | 8 | 4 | 4 | |
| Example 226 | 16 | 16 | 16 | | 8 | 16 | 16 | 16 | 16 | |
| Example 227 | 128 | 128 | >128 | | 128 | 128 | 128 | 128 | 128 | |
| Example 228 | 32 | 32 | 32 | | 32 | 32 | 32 | 32 | 32 | |
| Example 229 | >128 | >128 | >128 | | >128 | >128 | >128 | >128 | >128 | |
| Example 229a | >128 | >128 | >128 | | >128 | >128 | >128 | >128 | >128 | |
| Example 229b | >128 | >128 | >128 | | >128 | >128 | >128 | >128 | >128 | |
| Example 230 | 2 | 2 | 2 | | 1 | 2 | 2 | 1 | 2 | |
| Example 230a | 0.5-2 | 1-2 | 1-2 | | 0.5-2 | 0.25-2 | 1-2 | 0.5-1 | 1-2 | |
| Example 230b | 4 | 2 | 2 | | 2 | 1 | 4 | 2 | 2 | |
| Example 230c | 128 | 128 | 128 | | 64 | >128 | 128 | 128 | 128 | |
| Example 231 | 2-4 | 1-2 | 1-2 | | 1-2 | 2-4 | 2-4 | 1-4 | 1-4 | |
| Example 231a | 1-2 | 1 | 1-2 | | 1-2 | 0.5-1 | 2-4 | 1-2 | 1-2 | |
| Example 231b | 4-64 | 4-64 | 8-64 | | 4-32 | 4-32 | 4-64 | 4-32 | 4-64 | |
| Example 231c | 2 | 2 | 2 | | 2 | 2 | 2 | 2 | 1 | |
| Example 232 | 4 | 4 | 8 | | 4 | 4 | 4 | 4 | 4 | |
| Example 234 | 2 | 2 | 2 | | 2 | 2 | 2 | 2 | 2 | |
| Example 235 | 1-2 | 0.5-2 | 1-2 | | 0.5-1 | 0.5-2 | 1-2 | 0.5-1 | 0.5-1 | |
| Example 236 | 2 | 2 | 2 | | 2 | 4 | 2 | 2 | 2 | |
| Example 237 | 4 | 2 | 4 | | 2 | 8 | 4 | 2 | 4 | |

TABLE 2-continued

| EXAMPLE NUMBER | Staphylococcus aureus-SMITH (GC 4543) | Staphylococcus haemolyticus (GC 4546) | Staphylococcus aureus (GC 3051) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|---|
| Example 206 | 1 | 0.5 | | | | 1 | 0.5 | 0.5 | 1 | | |
| Example 207 | 1 | 1 | | | | 1 | 0.5 | 0.5 | 4 | | |
| Example 208 | 4 | 4 | | | | 4 | 4 | 4 | 4 | 4 | |
| Example 209 | 1 | | | | | 4 | 1 | 1 | | 2 | |
| Example 210 | 32 | 32 | | | | 32 | 32 | 8 | 32 | 32 | |
| Example 210a | 4 | 8 | | | | 4 | 4 | 2 | 4 | 4 | |
| Example 212 | 2 | 2 | | | | 2 | 2 | | 2 | 1 | |
| Example 214 | 0.5 | 1 | | | | 1 | 1 | 0.5 | 1 | | |
| Example 215 | <0.12 | 0.5 | | | | 0.5 | 0.5 | <0.12 | 0.5 | 1 | |
| Example 216 | 2 | 1 | | | | 2 | 1 | 1 | 2 | | |
| Example 217 | 2 | 2 | | | | 4 | 1 | 2 | 8 | | |
| Example 218 | 2 | 4 | | | | 4 | 4 | 4 | 8 | 4 | |
| Example 219 | 2 | 2 | | | | 2 | 2 | 2 | 4 | 1 | |
| Example 220 | 1 | 0.25 | | | | 0.5 | 0.25 | 0.25 | 0.5 | | |
| Example 221 | 2 | 2 | | | | 2 | 1 | 1 | 2 | | |
| Example 222 | >64 | >64 | | | | >64 | >64 | >64 | >64 | | |
| Example 223 | 64 | 64 | | | | 64 | 64 | 64 | 64 | | |
| Example 224 | 2 | 1 | | | | 2 | 1 | 1 | 2 | | |
| Example 225 | 4 | 4 | | | | 4 | 2 | 2 | 4 | | |
| Example 226 | 8 | 8 | | | | 8 | 8 | 16 | 8 | 2 | |
| Example 227 | 128 | 64 | | | | 32 | 4 | 32 | 8 | | |
| Example 228 | 32 | 16 | | | | 16 | 16 | 16 | 16 | | |
| Example 229 | >128 | >128 | | | | >128 | >128 | >128 | >128 | >128 | |
| Example 229a | >128 | >128 | | | | >128 | >128 | >128 | >128 | >128 | |
| Example 229b | >128 | >128 | | | | >128 | >128 | >128 | >128 | >128 | |
| Example 230 | 1 | 1 | | | | 1 | 0.5 | 1 | 2 | 0.5 | |
| Example 230a | 0.5-2 | 0.25-1 | | | | 0.5-2 | 0.12-0.5 | 0.12-0.5 | 0.25-1 | 0.25-0.5 | |
| Example 230b | 2 | 1 | | | | 2 | 1 | 1 | 2 | 1 | |
| Example 230c | 64 | 64 | | | | 64 | 64 | 64 | 64 | 32 | |
| Example 231 | 2 | 1-4 | | | | 1-2 | 0.5-1 | 0.25-0.5 | 0.5-1 | 0.5-1 | |
| Example 231a | 1 | 1 | | | | 1 | 0.12-0.25 | <0.12-0.25 | 0.5 | 0.5 | |
| Example 231b | 4-64 | 4-32 | | | | 4-32 | 2-32 | 2-16 | 8-32 | 1-32 | |
| Example 231c | 1 | 1 | | | | 2 | 0.5 | 0.5 | 1 | 0.5 | |
| Example 232 | 4 | 1 | | | | 2 | 2 | 1 | 4 | 0.5 | |
| Example 234 | 2 | 2 | | | | 1 | 1 | 0.5 | 2 | 1 | |
| Example 235 | 0.5-1 | 0.25-0.5 | | | | 0.5-1 | 0.25-0.5 | 0.25-0.5 | 0.5-1 | 0.25-0.5 | |
| Example 236 | 2 | 2 | | | | 2 | 0.5 | 0.5 | 2 | 1 | |
| Example 237 | 2 | | | | | 2 | 1 | 1 | 4 | 1 | |

| EXAMPLE NUMBER | Staphylococcus aureus (GC 1131) | Staphylococcus aureus (GC 3051) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|
| Example 238 | 4 | 8 | | 4 | 4 | 8 | 2 | 4 | |
| Example 239 | 2 | 2 | | 4 | 2 | 2 | 2 | 2 | |
| Example 239a | 4 | 4 | | 4 | 4 | 4 | 4 | 4 | |
| Example 240 | 4 | 4 | | 1 | 2 | 4 | 4 | 4 | |
| Example 241 | 2 | 2 | | 2 | 2 | 2 | 2 | 2 | |

TABLE 2-continued

| | Staphylococcus aureus-SMITH (GC 4543) | Staphylococcus haemolyticus (GC 4546) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|
| Example 241a | 2 | 2 | 2 | | 2 | 2 | 2 | 2 | 2 | |
| Example 242 | 8 | 8 | 8 | | 4 | 4 | 4 | 4 | 4 | |
| Example 243 | 64 | 64 | 64 | | 64 | 64 | 64 | 64 | 64 | |
| Example 243a | 32 | 32 | 32 | | 32 | 32 | 32 | 32 | 32 | |
| Example 244 | 8 | 8 | 16 | | 8 | 8 | 8 | 8 | 8 | |
| Example 245 | 4 | 4 | 4 | | 4 | 4 | 4 | 4 | 4 | |
| Example 245a | 2 | 2 | 2 | | 2 | 2 | 2 | 2 | 2 | |
| Example 245b | 16 | 16 | 16 | | 8 | 16 | 16 | 16 | 16 | |
| Example 245c | >128 | 128 | >128 | | 128 | 128 | 128 | 128 | 128 | |
| Example 246 | 8 | 4 | 4 | | 4 | 4 | 4 | 4 | 4 | |
| Example 246a | 4 | 1 | 2 | | 1 | 1 | 2 | 2 | 2 | |
| Example 246b | 128 | 64 | 128 | | 64 | 64 | 64 | 64 | 64 | |
| Example 246c | >128 | >128 | >128 | | >128 | >128 | >128 | >128 | >128 | |
| Example 248 | 32 | 64 | >128 | | 32 | 64 | 32 | 32 | 32 | |
| Example 249 | 128 | 128 | 64 | | 64 | 64 | 64 | 128 | 128 | |
| Example 251 | >64 | | 128 | | >64 | >64 | >64 | >64 | >64 | |
| Example 251a | >64 | | | | 64 | 64 | 64 | 64 | >64 | |
| Example 251b | 8 | | | | 8 | 8 | 8 | 8 | 16 | |
| Example 253 | >64 | >64 | >64 | | >64 | >64 | >64 | >64 | >64 | |
| Example 253a | 4 | 2 | 4 | | 4 | 4 | 4 | 2 | 4 | |
| Example 253b | 4 | 2 | 8 | | 2 | 2 | 2 | 2 | 4 | |
| Example 254 | 4 | | | | 4 | 4 | 4 | 2 | 4 | |
| Example 254b | 4 | | | | 4 | 8 | 8 | 8 | 8 | |
| Example 255 | >0.5 | 0.5 | 0.5 | | 0.5 | 0.5 | 0.5 | 0.5 | >0.5 | |
| Example 255a | >0.5 | 0.5 | 0.5 | | >0.5 | >0.5 | >0.5 | >0.5 | >0.5 | |
| Example 256 | >64 | | | | >64 | >64 | >64 | >64 | >64 | |
| Example 256a | >64 | | | | >64 | >64 | >64 | >64 | >64 | |
| Example 257 | 0.5 | 0.5 | 0.5 | | 0.5 | 0.5 | 0.5 | 0.5 | 0.5 | |
| Example 257a | 0.5 | 0.5 | 0.5 | | 0.5 | 0.5 | 0.5 | 0.5 | 0.5 | |
| Example 257b | 0.5 | 0.5 | 0.5 | | 0.5 | 0.5 | 0.5 | 0.5 | 0.5 | |
| Example 261a | >64 | >64 | | | >64 | >64 | >64 | >64 | >64 | |
| Example 261b | 16 | 16 | | | 16 | 16 | 8 | 16 | 8 | |
| Example 261c | 8 | 8 | | | 8 | 8 | 8 | 8 | 8 | |

| EXAMPLE NUMBER | Staphylococcus aureus-SMITH (GC 4543) | Staphylococcus haemolyticus (GC 4546) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) |
|---|---|---|---|---|---|---|---|
| Example 238 | 4 | 2 | 2 | 2 | 2 | 4 | 1 |
| Example 239 | 2 | 1 | 2 | 1 | 1 | 2 | 1 |
| Example 239a | 2 | 2 | 2 | 1 | 2 | 2 | 2 |
| Example 240 | 2 | 2 | 2 | 1 | 2 | 4 | 2 |
| Example 241 | 2 | 2 | 4 | 2 | 2 | 4 | 1 |
| Example 241a | 8 | 4 | 8 | 4 | 4 | 16 | 2 |
| Example 242 | 64 | 64 | 64 | 32 | 32 | 64 | 32 |
| Example 243 | 32 | 32 | 32 | 32 | 16 | 32 | 16 |
| Example 243a | 4 | 4 | 4 | 2 | 2 | 4 | 2 |
| Example 244 | 4 | 4 | 4 | 2 | 1 | 8 | 2 |
| Example 245 | 2 | 1 | 2 | 1 | 0.5 | 2 | 1 |
| Example 245a | 16 | 8 | 8 | 8 | 2 | 8 | 4 |
| Example 245b | 128 | 128 | 128 | 128 | 64 | 128 | 64 |
| Example 245c | | | | | | | |

TABLE 2-continued

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|---|
| Example 246 | 4 | | | | 4 | 4 | 4 | | 8 | |
| Example 246a | 1 | | | | 1 | 1 | 1 | | 2 | |
| Example 246b | 128 | | | | 64 | 64 | 32 | | 64 | |
| Example 246c | >128 | | | | >128 | >128 | >128 | | >128 | |
| Example 248 | 32 | | | | 16 | 32 | 32 | | 32 | |
| Example 249 | 128 | | | | 64 | 128 | 128 | | 64 | |
| Example 251 | >64 | | | | >64 | >64 | >64 | | >64 | |
| Example 251a | 64 | | | | 64 | 64 | 32 | | 64 | 64 |
| Example 251b | 32 | | | | 8 | 8 | 4 | | 16 | 16 |
| Example 253 | 4 | | | | 64 | 64 | 64 | | >64 | 4 |
| Example 253a | 2 | | | | 4 | 4 | 1 | | 8 | |
| Example 253b | 2 | | | | 2 | 2 | 2 | | 4 | |
| Example 254 | 4 | | | | 4 | 4 | 4 | | 4 | |
| Example 254b | 4 | | | | 8 | 2 | 4 | 32 | 4 | 2 |
| Example 255 | 0.5 | | | | 32 | 64 | 32 | | 64 | 2 |
| Example 255a | >0.5 | | | | 64 | >64 | 64 | | >64 | |
| Example 256 | >64 | | | | >64 | >64 | >64 | | >64 | >64 |
| Example 256a | >64 | | | | >64 | >64 | >64 | | >64 | 64 |
| Example 257 | 0.5 | | | | 2 | 2 | 2 | 1 | 8 | |
| Example 257a | 0.5 | | | | 8 | 8 | 8 | 4 | 32 | |
| Example 257b | 0.5 | | | | 2 | 2 | 2 | 1 | 4 | |
| Example 261a | >64 | | | | >64 | >64 | >64 | | >64 | |
| Example 261b | 8 | | | | 8 | 4 | 4 | | 8 | |
| Example 261c | 8 | | | | 4 | 4 | 4 | | 16 | |

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) |
|---|---|---|---|---|---|---|---|---|---|
| Example 262a | 128 | | | | 64 | >128 | 64 | 64 | 64 |
| Example 262b | 4 | | | | 2 | 2 | 2 | 2 | 4 |
| Example 263 | 64 | | | | 64 | 64 | >64 | 64 | 64 |
| Example 264a | 16 | | | | 16 | 16 | 8 | 8 | 16 |
| Example 264b | 8 | | | | 8 | 8 | 8 | 4 | 8 |
| Example 265a | 32 | | | | 16 | 16 | 8 | 16 | 16 |
| Example 265b | 32 | | | | 16 | 8 | 8 | 8 | 16 |
| Example 270a | 4 | | | | 4 | 4 | 4 | 4 | 4 |
| Example 270b | 8 | | | | 4 | 8 | 8 | 4 | 8 |
| Example 271a | 4 | | | | 4 | 8 | 8 | 4 | 4 |
| Example 277a | >128 | >128 | | | >128 | >128 | >128 | >128 | >128 |
| Example 277b | >64 | >64 | | | >64 | >64 | >64 | >64 | >64 |
| Example 278b | 8 | 4 | 8 | | 8 | 8 | 8 | 4 | 8 |
| Example 278c | 8 | 2 | 8 | | 4 | 4 | 4 | 4 | 4 |
| Example 279a | >64 | >64 | >64 | | >64 | >64 | >64 | >64 | >64 |
| Example 280a | >128 | >128 | >128 | | >128 | >128 | >128 | >128 | >128 |
| Example 280b | 128 | 128 | >128 | | 128 | 128 | 128 | 64 | 128 |
| Example 282 | >128 | >128 | >128 | | >128 | >128 | >128 | >128 | >128 |
| Example 283a | 64 | 64 | 128 | | 64 | 64 | 64 | 64 | 64 |
| Example 283b | 64 | 64 | 64 | | 128 | 64 | 128 | 128 | 128 |
| Example 283c | 32 | 32 | 64 | | 32 | 32 | 32 | 16 | 32 |
| Example 284b | >128 | >128 | >128 | | >128 | >128 | >128 | >128 | >128 |
| Example 287 | >64 | >64 | >64 | | >64 | >64 | >64 | >64 | >64 |
| Example 296 | >128 | >128 | >128 | | >128 | >128 | >128 | >128 | >128 |

TABLE 2-continued

| EXAMPLE NUMBER | Staphylococcus aureus-SMITH (GC 4543) | Staphylococcus haemolyticus (GC 4546) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|
| Example 262a | 64 | 64 | | | 64 | 64 | 16 | 128 | | |
| Example 262b | 1 | 2 | | | 2 | 1 | 1 | 2 | | |
| Example 263 | 32 | 32 | | | 64 | 32 | 16 | 64 | | |
| Example 264a | 8 | 8 | | | 8 | 4 | 4 | 16 | | |
| Example 264b | 8 | 4 | | | 4 | 4 | 4 | 8 | | |
| Example 265a | 8 | 8 | | | 8 | 8 | 4 | 8 | | |
| Example 265b | 4 | 2 | | | 2 | 4 | 4 | 4 | | |
| Example 270a | 4 | 4 | | | 4 | 4 | 4 | 4 | | |
| Example 270b | 4 | 4 | | | 4 | 4 | 4 | 4 | | |
| Example 271a | 8 | 4 | | | 4 | 2 | 4 | 4 | | |
| Example 277a | >128 | >128 | | | >128 | >128 | >128 | >128 | | |
| Example 277b | >64 | >64 | | | >64 | >64 | >64 | >64 | >64 | |
| Example 278a | 8 | 4 | | | 4 | 4 | 2 | 8 | 2 | |
| Example 278b | 4 | 2 | | | 4 | 2 | 2 | 8 | 2 | |
| Example 278c | 4 | 4 | | | 4 | 2 | 2 | 4 | | |
| Example 279a | >64 | 64 | | | 64 | >64 | 64 | >64 | 64 | |
| Example 280a | 128 | 128 | | | 128 | 128 | 128 | >128 | 128 | |
| Example 280b | 64 | 32 | | | 32 | 32 | 32 | 128 | 32 | |
| Example 282 | >128 | >128 | | | >128 | >128 | >128 | >128 | | |
| Example 283a | 64 | 64 | | | 64 | 64 | 32 | 64 | | |
| Example 283b | 64 | 64 | | | 64 | 64 | 64 | 64 | | |
| Example 283c | 16 | 16 | | | 16 | 8 | 16 | 32 | | |
| Example 284a | >128 | >128 | | | >128 | >128 | >128 | >128 | | |
| Example 284b | >64 | >64 | | | >64 | >64 | >64 | >64 | >64 | |
| Example 287 | >128 | >128 | | | >128 | >128 | >128 | >128 | | |
| Example 296 | | | | | | | | | | |

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) |
|---|---|---|---|---|---|---|---|---|---|
| Example 3 | >128 | | >128 | >128 | >128 | >128 | >128 | >128 | >128 |
| Example 12 | 128 | 128 | 128 | 128 | 128 | | >128 | >128 | >64 |
| Example 13 | 16 | 2 | 4 | 4 | 8 | | 64 | 64 | >128 |
| Example 14 | 128 | 128 | 64 | >128 | >128 | | >128 | >128 | >128 |
| Example 15 | 128 | 128 | 64 | 128 | >128 | | >128 | >128 | >128 |
| Example 16 | 64 | 64 | 128 | 128 | 16 | | >128 | >128 | >128 |
| Example 17 | >64 | 64 | >64 | >64 | >64 | | >64 | >64 | >64 |
| Example 18 | 128 | 64 | 128 | 128 | 128 | | >128 | >128 | >128 |
| Example 19 | >128 | 64 | 128 | 128 | >128 | | >128 | >128 | >128 |
| Example 22 | 32 | 8 | 8 | 8 | 32 | | >128 | >128 | >128 |
| Example 24 | >64 | 64 | >64 | >64 | 64 | | 64 | 64 | >64 |
| Example 25 | >128 | 128 | >128 | >128 | >128 | | >128 | >128 | >128 |
| Example 26 | 16 | 16 | 32 | 32 | 8 | | 64 | 32 | 64 |
| Example 27 | 32 | 32 | 16 | 16 | 8 | | 32 | 32 | 32 |
| Example 28 | 4 | 4 | 4 | 4 | 1 | | 4 | 4 | 8 |
| Example 29 | 32 | 32 | 32 | 32 | 16 | | 32 | 8 | 64 |
| Example 30 | 8 | 16 | 16 | 8 | 4 | | 32 | 32 | 64 |
| Example 31 | 32 | 32 | 64 | 16 | 8 | | 64 | 64 | 128 |

TABLE 2-continued

| EXAMPLE NUMBER | | | | | | | | |
|---|---|---|---|---|---|---|---|---|
| Example 32 | 16 | 16 | 16 | 16 | 8 | 4 | 8 | 8 |
| Example 33 | 32 | 32 | 64 | 32 | 16 | 16 | 16 | 32 |
| Example 34 | 32 | 16 | 32 | 32 | 8 | 32 | 32 | 64 |
| Example 35 | 8 | 8 | 16 | 8 | 2 | 16 | 16 | 32 |
| Example 36 | >128 | 128 | >128 | >128 | 128 | >128 | >128 | >128 |
| Example 37 | 16 | 16 | 16 | 32 | 4 | 16 | 16 | 16 |
| Example 38 | 32 | 32 | 64 | 32 | 32 | 128 | 128 | 128 |
| Example 39 | 16 | 8 | 16 | 8 | 4 | 16 | 16 | 16 |
| Example 40 | 64 | 32 | 128 | 64 | 32 | 128 | 128 | >128 |
| Example 41 | 64 | 64 | >64 | 64 | 32 | 64 | 64 | >64 |
| Example 42 | 8 | 16 | 16 | 8 | 4 | 8 | 16 | 16 |
| Example 44 | 16 | 16 | 32 | 16 | 4 | 16 | 16 | 32 |
| Example 45 | 16 | 16 | 32 | 32 | 4 | 16 | 32 | 32 |
| Example 46 | 8 | 8 | 8 | 8 | 1 | 8 | 16 | 32 |
| Example 47 | 2 | 2 | 8 | 4 | 1 | 4 | 32 | 64 |
| Example 48 | 16 | 8 | 32 | 16 | 8 | 64 | 64 | 64 |
| Example 49 | 4 | 4 | 8 | 8 | 2 | 16 | 16 | 32 |
| Example 51 | 16 | 64 | 64 | 8 | 8 | 64 | >64 | >64 |
| Example 52 | 8 | 8 | 16 | 8 | 8 | 32 | 32 | 32 |

| EXAMPLE NUMBER | Enterococcus faecalis (GC 4552) | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) |
|---|---|---|---|---|---|---|---|---|---|
| Example 3 | >128 | >128 | >128 | >128 | >128 | >128 | >128 | >128 | >128 |
| Example 12 | >128 | >128 | >128 | >128 | >128 | >128 | >128 | >128 | 128 |
| Example 13 | >64 | 64 | >64 | >64 | >64 | 64 | 64 | 64 | 64 |
| Example 14 | >128 | >128 | >128 | >128 | >128 | >128 | >128 | >128 | 128 |
| Example 15 | >128 | >128 | >128 | >128 | >128 | 128 | >128 | >128 | 128 |
| Example 16 | >128 | 64 | >64 | >64 | >64 | >64 | 64 | 16 | 128 |
| Example 17 | >64 | >64 | >64 | >64 | >64 | >128 | >128 | 128 | 128 |
| Example 18 | >128 | 128 | >128 | >128 | >128 | >128 | >128 | 64 | 128 |
| Example 19 | >128 | 128 | >128 | >128 | >128 | >128 | >128 | 128 | >128 |
| Example 22 | >128 | >128 | >128 | >128 | >128 | >128 | >128 | 32 | 64 |
| Example 24 | >64 | 32 | >64 | >64 | >64 | 64 | 64 | 64 | 128 |
| Example 25 | >128 | >128 | >128 | >128 | >128 | >128 | >128 | 128 | 32 |
| Example 26 | 64 | 32 | 64 | 32 | 32 | 32 | 64 | 32 | 16 |
| Example 27 | 64 | 16 | 32 | 32 | 32 | 32 | 64 | 16 | 4 |
| Example 28 | 8 | 4 | 8 | 8 | 8 | 8 | 8 | 4 | 16 |
| Example 29 | 64 | 16 | 32 | 32 | 32 | 16 | 64 | 8 | 16 |
| Example 30 | 64 | 16 | 64 | 32 | 64 | 32 | 64 | 8 | 8 |
| Example 31 | 128 | 16 | 128 | 64 | 64 | 32 | 128 | 8 | 4 |
| Example 32 | 8 | 8 | 4 | 4 | 8 | 4 | 4 | 2 | 8 |
| Example 33 | 16 | 16 | 16 | 16 | 32 | 8 | 64 | 8 | 4 |
| Example 34 | 32 | 32 | 32 | 32 | 64 | 32 | 64 | 4 | 16 |
| Example 35 | 32 | 8 | 32 | 32 | 16 | 8 | 32 | 4 | 8 |
| Example 36 | >128 | 128 | >128 | >128 | >128 | >128 | >128 | 128 | 128 |
| Example 37 | 16 | 4 | 16 | 16 | 16 | 8 | 16 | 4 | 4 |
| Example 38 | 128 | 64 | 128 | 128 | 128 | 128 | 128 | 32 | 64 |
| Example 39 | 16 | 8 | 32 | 16 | 16 | 8 | 32 | 8 | 8 |
| Example 40 | >128 | 64 | >128 | 128 | 128 | 64 | 128 | 16 | 64 |
| Example 41 | 64 | 64 | 64 | >64 | 128 | 64 | 32 | 64 | 64 |
| Example 42 | 8 | 8 | 8 | 8 | 8 | 4 | 16 | 2 | 4 |

TABLE 2-continued

| EXAMPLE NUMBER | Streptococcus agalactie (GC 4564) | Streptococcus pneumoniae (GC 1894) | Streptococcus pneumoniae (GC 4565) | Streptococcus pneumonia (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) |
|---|---|---|---|---|---|---|---|---|---|
| Example 44 | 16 | 8 | 32 | 16 | 16 | 8 | 32 | 8 | 8 |
| Example 45 | 16 | 16 | 16 | 16 | 32 | 16 | 32 | 4 | 8 |
| Example 46 | 8 | 4 | 16 | 16 | 8 | 4 | 16 | 8 | 4 |
| Example 47 | 16 | 4 | 64 | 32 | 8 | 4 | 8 | 4 | 2 |
| Example 48 | 64 | 16 | 64 | 64 | 64 | 16 | 64 | 64 | 8 |
| Example 49 | 2 | 4 | 16 | 16 | 16 | 8 | 8 | 2 | 4 |
| Example 51 | >64 | >64 | >64 | >64 | >64 | >64 | >64 | 16 | 64 |
| Example 52 | 32 | 16 | 64 | 32 | 64 | 16 | 32 | 8 | 32 |
| Example 53 | 1 | 1 | 4 | 1 | 1 | | 8 | 8 | 8 |
| Example 53a | 64 | 32 | 64 | 64 | 64 | | >128 | >128 | >128 |
| Example 54 | >128 | 128 | >128 | >128 | >128 | | >128 | >128 | >128 |
| Example 54a | >128 | 128 | >128 | >128 | >128 | | >128 | >128 | >128 |
| Example 58 | 16 | 8 | 16 | 8 | 8 | | 64 | 64 | 64 |
| Example 59 | >128 | 64 | 128 | 128 | >128 | | >128 | >128 | >128 |
| Example 60 | >128 | 64 | 128 | 128 | >128 | | >128 | >128 | >128 |
| Example 60a | >128 | 64 | 64 | 128 | >128 | | >128 | >128 | >128 |
| Example 61 | 128 | 64 | 64 | 128 | >128 | | 128 | 128 | 128 |
| Example 62 | >128 | 64 | 128 | 128 | >128 | | >128 | >128 | >128 |
| Example 64 | >128 | 128 | 128 | 128 | 128 | | >128 | >128 | >128 |
| Example 65 | >128 | 128 | 128 | 128 | 128 | | >128 | >128 | >128 |
| Example 66 | 32 | 32 | 64 | 32 | 16 | | 16 | 32 | 32 |
| Example 66a | >128 | >128 | >128 | >128 | >128 | | >128 | >128 | >128 |
| Example 67 | 128 | 64 | 128 | 128 | 128 | | 128 | 128 | 128 |
| Example 69 | >128 | 128 | >128 | >128 | >128 | | >128 | >128 | >128 |
| Example 72 | 128 | 16 | 64 | 64 | 64 | | >128 | >128 | >128 |
| Example 73 | >128 | 64 | 128 | 128 | >128 | | >128 | >128 | >128 |
| Example 74 | 128 | 128 | >128 | >128 | >128 | | >128 | >128 | >128 |
| Example 76 | 0.25-2 | <0.06-0.25 | 0.25-4 | <0.12-1 | 0.25-2 | | 4-16 | 4-16 | 4-32 |
| Example 77 | 1 | 0.25-0.5 | 2-4 | 2 | 1 | | 16 | 16 | 16 |
| Example 78 | 1 | 0.25 | 2 | 1 | 0.5 | | 16 | 16 | 16 |
| Example 79 | 4 | 8 | 8 | 4 | 4 | | 16 | 8 | 32 |
| Example 80 | 8 | 4 | 16 | 8 | 8 | | 32 | 64 | 64 |
| Example 81 | 128 | 128 | >128 | >128 | >128 | | >128 | >128 | >128 |
| Example 82 | 0.5 | 0.25 | 2 | 2 | 1 | | 16 | 16 | 16 |
| Example 83 | 0.25 | <0.12 | 0.25 | 0.5 | 0.25 | | 4 | 4 | 4 |
| Example 84 | 1 | 0.12 | 1 | 1 | 0.5 | | 8 | 8 | 8 |
| Example 89 | 32 | 4 | 8 | 16 | 32 | | 64 | 64 | 64 |
| Example 92 | >128 | 128 | 128 | 128 | >128 | | >128 | >128 | >128 |
| Example 93 | >128 | 128 | >128 | 128 | >128 | | >128 | >128 | >128 |
| Example 94 | >64 | >64 | >64 | >64 | >64 | | >64 | >64 | >64 |
| Example 95 | | | | | | | >64 | | |
| Example 95a | | | | | | | 16 | | |
| Example 95b | | | | | | | 8 | | |
| Example 96c | <0.06 | <0.06 | <0.06 | | | <0.06 | 1 | | |
| Example 96 | >128 | >128 | >128 | | | >128 | >128 | | |

TABLE 2-continued

| EXAMPLE NUMBER | Enterococcus faecalis (GC 4552) | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) |
|---|---|---|---|---|---|---|---|---|---|
| Example 53 | 8 | 4 | 16 | 4 | 8 | 2 | 8 | 2 | 4 |
| Example 53a | >128 | >128 | >128 | >128 | >128 | >128 | >128 | >128 | >128 |
| Example 54 | >128 | >128 | >128 | >128 | >128 | >128 | >128 | 128 | 128 |
| Example 54a | >128 | >128 | >128 | >128 | >128 | >128 | >128 | 128 | 128 |
| Example 58 | 64 | 32 | 64 | 64 | 64 | 32 | 64 | 8 | 32 |
| Example 59 | >128 | >128 | >128 | >128 | >128 | >128 | >128 | 128 | 128 |
| Example 60 | >128 | 128 | >128 | >128 | >128 | >128 | >128 | 128 | 128 |
| Example 60a | >128 | 128 | >128 | >128 | >128 | >128 | >128 | 128 | 128 |
| Example 61 | 128 | 128 | 128 | 128 | 128 | 128 | 128 | 128 | 64 |
| Example 62 | >128 | >128 | >128 | >128 | >128 | >128 | >128 | 64 | 128 |
| Example 64 | >128 | >128 | >128 | >128 | >128 | >128 | >128 | >128 | 128 |
| Example 65 | >128 | 128 | >128 | >128 | >128 | 128 | >128 | 128 | 128 |
| Example 66 | 32 | 8 | 64 | 32 | 16 | 8 | 32 | 4 | 4 |
| Example 66a | >128 | >128 | >128 | >128 | >128 | >128 | >128 | >128 | 128 |
| Example 67 | 128 | 128 | 128 | 128 | 128 | >128 | >128 | 128 | 64 |
| Example 69 | 32 | 4 | 16 | 8 | 8 | 8 | 32 | 2 | 128 |
| Example 72 | >128 | 64 | 64 | 64 | 64 | 32 | 64 | 16 | 64 |
| Example 73 | >128 | >128 | >128 | >128 | >128 | >128 | >128 | 128 | 128 |
| Example 74 | >128 | >128 | >128 | >128 | >128 | >128 | >128 | 128 | 128 |
| Example 76 | 4-16 | 4-8 | 4-32 | 4-16 | 4-16 | 2-8 | 4-16 | 1-2 | 2-8 |
| Example 77 | 16 | 8 | 16-32 | 16 | 16 | 8 | 16 | 1-2 | 4 |
| Example 78 | 8 | 8 | 16 | 16 | 8 | 8 | 16 | 2 | 4 |
| Example 79 | 32 | 4 | 16 | 8 | 8 | 8 | 32 | 4 | 4 |
| Example 80 | 64 | 32 | 64 | 64 | 64 | 32 | 64 | 16 | 32 |
| Example 81 | >128 | 128 | >128 | >128 | >128 | >128 | >128 | 128 | 128 |
| Example 82 | 16 | 8 | 32 | 16 | 16 | 8 | 16 | 2 | 4 |
| Example 83 | 4 | 2 | 4 | 4 | 4 | 2 | 8 | 1 | 4 |
| Example 84 | 8 | 8 | 16 | 8 | 8 | 4 | 8 | 1 | 8 |
| Example 89 | 64 | 64 | 64 | 64 | 64 | 64 | 64 | 32 | 32 |
| Example 92 | >128 | 128 | >128 | >128 | >128 | >128 | >128 | 128 | 128 |
| Example 93 | >128 | >128 | >128 | >128 | >128 | >128 | >128 | 128 | 128 |
| Example 94 | >64 | >64 | >64 | >64 | >64 | >64 | >64 | >64 | >64 |
| Example 95 | >64 | | | | 32 | | | | |
| Example 95a | 32 | | | | 4 | | | | |
| Example 95b | 8 | | | | | | | | |
| Example 96 | 2 | 2 | 2 | 2 | 2 | 2 | 2 | 1 | 2 |
| Example 96 | >128 | >128 | >128 | >128 | >128 | >128 | >128 | 128 | >128 |

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) |
|---|---|---|---|---|---|---|---|---|---|
| Example 96a | 32 | | 16 | | | 32 | >128 | | |
| Example 96b | 0.25 | | <0.12 | | | 0.25 | 4 | | |
| Example 97 | | | | | | | >64 | | |
| Example 97a | | | | | | | 4 | | |
| Example 97b | | | | | | | 2 | | |
| Example 98b | | | | | | | 64 | | |
| Example 98c | | | | | | | 8 | | |

TABLE 2-continued

| EXAMPLE NUMBER | Enterococcus faecalis (GC 4552) | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) |
|---|---|---|---|---|---|---|---|---|---|
| Example 99b | 2 | | <0.5 | | | | 16 | | |
| Example 99c | <0.5 | | <0.5 | | | | 4 | | |
| Example 100b | | | | | | | 8 | | |
| Example 100c | | | | | | | 2 | | |
| Example 101 | 2 | | <0.5 | | | | 16 | | |
| Example 101a | 1 | | <0.5 | | | | 8 | | |
| Example 102 | <0.12–0.25 | <0.06 | <0.12–<0.12 | | <0.12–0.25 | | 2–4 | 2–4 | 2–4 |
| Example 103 | 0.5 | 0.12 | 0.12 | | 0.25 | | 4 | 8 | 8 |
| Example 104 | <0.12–0.25 | <0.12 | 0.12 | | <0.12 | | 2 | 4 | 4 |
| Example 104b | 0.5 | 0.12–8 | 0.12–16 | | 0.12 | | >64 | >64 | >0.5 |
| Example 105 | 0.5 | 0.12 | 0.12 | | 0.12 | | 0.5 | 0.5 | 0.5 |
| Example 106 | <0.06–0.25 | <0.06 | <0.06 | | <0.06–0.12 | | 1–2 | 1–2 | 1–2 |
| Example 106a | <0.03 | <0.03 | <0.03 | | <0.03 | | 0.5–2 | 1–2 | 1–2 |
| Example 106b | 0.25 | <0.06 | <0.06 | | 0.25 | | 0.5–2 | 4 | 8 |
| Example 107 | 0.5 | 0.12 | 0.5 | | 0.5 | | 4 | 16 | 16 |
| Example 108 | 0.25 | | <0.12 | | | 0.25 | 4 | | |
| Example 109 | <0.5 | | <0.5 | | | <0.5 | 2 | | |
| Example 110 | <0.5 | | <0.5 | | | <0.5 | 2 | | |
| Example 111 | <0.5 | | 0.5 | | | 0.5 | 1 | | |
| Example 112 | 1 | | | | | 0.5 | 1–2 | 2 | 2 |
| Example 113 | <0.12 | <0.06 | <0.12 | | <0.12 | | 4 | 4 | 8 |
| Example 114 | 0.12 | <0.06 | <0.06 | | <0.06 | | 4 | 4 | 2 |
| Example 115 | 0.5 | <0.06 | 0.25 | | 0.5 | | 2 | 2 | 2 |
| Example 116 | 0.25 | <0.06 | 0.12 | | 0.25 | | 2 | 2 | 4 |
| Example 117 | 0.25 | <0.06 | <0.06 | | 0.25 | | 2 | 4 | 4 |
| Example 118 | 0.25 | <0.06 | 0.12 | | <0.06 | | <0.5–2 | 1–2 | 1–2 |
| Example 119 | <0.06 | <0.06 | 1 | | <0.5 | | 2 | 2 | >64 |
| Example 120 | <0.5 | <0.5 | <0.5 | | <0.5 | | 1 | 1 | 1 |
| Example 121 | <0.5 | <0.5 | <0.06 | | <0.5 | | 2 | 4 | |
| | 0.25 | <0.06 | <0.06 | | 0.25 | | | | |

| EXAMPLE NUMBER | Enterococcus faecalis (GC 4552) | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) |
|---|---|---|---|---|---|---|---|---|---|
| Example 96a | >128 | >128 | >128 | | >128 | 128 | >128 | | >128 |
| Example 96b | 8 | 8 | 8 | | 8 | 8 | 8 | | 4 |
| Example 97 | >64 | | | | >64 | | | | |
| Example 97a | 16 | | | | 8 | | | | |
| Example 97b | 4 | | | | 4 | | | | |
| Example 98b | 128 | | | | 64 | | | | |
| Example 98c | 16 | | | | 16 | | | | |
| Example 99b | 32 | 16 | 32 | | 16 | 16 | 16 | 4 | 16 |
| Example 99c | 4 | 4 | 4 | | 4 | 4 | 4 | 2 | 4 |
| Example 100b | 8 | | | | 8 | | | | |
| Example 100c | 4 | | | | 4 | | | | |
| Example 101 | 64 | 32 | 64 | | 32 | 32 | 32 | 2 | 32 |
| Example 101a | 16 | 16 | 16 | | 16 | 16 | 16 | 1–2 | 16 |
| Example 102 | 2–4 | 2–4 | 2–4 | 2–4 | 2–4 | 2–4 | 2–4 | 2 | 2–4 |
| Example 103 | 8 | 8 | 8 | 4 | 4 | 4 | 4 | 2 | 8 |
| Example 104 | 4 | 4 | 4 | 2 | 2–4 | 2 | 2–4 | 0.5 | 2–4 |
| Example 104a | >0.5 | >0.5 | >0.5 | >64 | >64 | >64 | >64 | 0.5 | >64 |
| Example 104b | 0.5 | 0.5 | 0.5 | 0.5 | 0.5 | 0.5 | 0.5 | 1–2 | 1 |
| Example 105 | 1–2 | 1–2 | 1–2 | 1–2 | 1–2 | 1–2 | 1–2 | | 1–2 |

TABLE 2-continued

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) |
|---|---|---|---|---|---|---|---|---|---|
| Example 106 | 1-2 | 1-2 | 1-2 | 1-2 | 0.5-2 | 0.5-2 | 0.5-2 | 0.5-2 | 1-2 |
| Example 106a | 4 | 4 | 8 | 4 | 8 | 4 | 8 | 2 | 4 |
| Example 106b | 8 | 8 | 16 | 8 | 8 | 4 | 4 | 4 | 4 |
| Example 107 | 4 | 4 | 4 | 4 | 4 | 2 | 4 | 1 | 8 |
| Example 108 | 2 | 2 | 2 | 2 | 2 | 2 | 2 | 2 | 2 |
| Example 109 | 2 | 2 | 2 | 2 | 2 | 1 | 2 | 1 | 4 |
| Example 110 | 4 | 4 | 2 | 2 | 4 | 4 | 4 | 1 | 2 |
| Example 111 | 2 | 2 | 2 | 2 | 2 | 1 | 2 | 2 | 2 |
| Example 112 | 2 | 2-4 | 2 | 2 | 2 | 1-2 | 0.5-2 | 0.5 | 2 |
| Example 113 | 2 | 2 | 2 | 2 | 2 | 2 | 2 | 2 | 4 |
| Example 114 | 4 | 8 | 4 | 4 | 4 | 2 | 4 | 2 | 64 |
| Example 115 | 2 | 2 | 2 | 2 | 2 | 2 | 2 | 2 | 16 |
| Example 116 | 2 | 2 | 2 | 2 | 2 | 2 | 2 | 2 | 8 |
| Example 117 | 2 | 4 | 2 | 2 | 2 | 2 | 4 | 2 | 2 |
| Example 118 | 1-2 | 1-2 | 1-2 | 1-2 | 1-2 | 1 | <0.5-1 | <0.5-2 | 1-2 |
| Example 119 | 2 | 4 | 4 | 2 | 2 | 4 | 2 | 1 | 4 |
| Example 120 | 1 | 1 | 1 | 1 | 1 | 1 | 1 | 1 | 1 |
| Example 121 | 2 | 4 | 2 | 2 | 2 | 2 | 2 | 2 | 4 |
| Example 122 | 0.12 | <0.06 | 0.12 | <0.06 | <0.06 | | 2 | 2 | 2 |
| Example 123 | 2 | 1 | 2 | 1 | 0.5 | | 8 | 16 | 16 |
| Example 124 | 1 | <0.06 | <0.06 | <0.06 | 0.12 | | 4 | 4 | 4 |
| Example 125 | 1 | 0.12 | 0.25 | 0.25 | 0.5 | | 32 | 32 | 32 |
| Example 126 | 1 | <0.06 | <0.06 | <0.06 | 0.12 | | 8 | 8 | 8 |
| Example 127 | <0.12 | <0.12 | <0.12 | <0.12 | 0.25 | | 4 | 4 | 4 |
| Example 128 | 0.25 | <0.06 | 0.12 | 0.25 | 0.5 | | 4 | 4 | 4 |
| Example 129 | <0.06 | <0.06 | <0.06 | <0.06 | <0.06 | | 2 | 2 | 2 |
| Example 130 | 8 | 1 | 4 | 8 | 16 | | 32 | 32 | 64 |
| Example 132 | 0.5 | 0.12 | 0.25 | 0.25 | 0.5 | | 8 | 8 | 16 |
| Example 133 | <0.5 | 0.5 | 4 | 0.5 | <0.5 | | 4 | 4 | 8 |
| Example 135 | 0.25 | <0.06 | <0.06 | <0.06 | 0.25 | | 2 | 2 | 2 |
| Example 136 | 8 | 1 | 4 | 2 | 8 | | 64 | >64 | >64 |
| Example 137 | 0.5 | <0.06 | 0.25 | 0.12 | 0.25 | | 4-8 | 4-8 | 4-8 |
| Example 137a | 16 | 4 | 16 | 8 | 16 | | >64 | >64 | >64 |
| Example 137b | 4 | 1 | 4 | 4 | 4 | | 32 | 32 | 64 |
| Example 138 | 0.12 | <0.06 | <0.06 | <0.06 | 0.25 | | 4 | 8 | 4 |
| Example 140 | <0.5 | 0.5 | 0.5 | 0.5 | <0.5 | | <1 | 1 | 1 |
| Example 141 | >64 | >64 | >64 | >64 | >64 | | >64 | >64 | >64 |
| Example 143 | 0.5-1 | 0.06-0.12 | 0.25-0.5 | 0.12-0.5 | 0.25-1 | 0.5 | 4-16 | 8 | 8-16 |
| Example 144 | <0.06 | <0.06 | <0.06 | <0.06 | <0.06 | | 2 | 2 | 4 |
| Example 145 | 0.5 | 0.5 | 0.5 | 0.5 | 1 | | <0.5 | 1 | 1 |
| Example 146 | 0.12 | <0.06 | <0.06 | <0.06 | <0.06 | | 8 | 8 | 16 |
| Example 147 | <0.12 | <0.06 | <0.5-<0.5 | <0.06 | >0.12 | | 0.5-1 | 0.5 | 0.5 |
| Example 149 | 1 | <0.5 | 2 | <0.5 | <0.5 | | 8 | 8 | 8 |
| Example 150 | 1 | 0.12 | 0.25 | 0.25 | 0.5 | | 4 | 4 | 8 |
| Example 150a | 32 | 8 | 16 | 8 | 16 | | >64 | >64 | >64 |
| Example 151 | 4 | 0.5 | 1 | 1 | 2 | | 16 | 32 | 32 |
| Example 152 | 8 | 0.5 | 2 | 2 | 4 | | 32 | 32 | 32 |
| Example 153 | 0.5 | <0.06 | <0.06 | 0.06 | 0.25 | | 4 | 8 | 8 |

TABLE 2-continued

| | | | | | | | | | | | | | | |
|---|---|---|---|---|---|---|---|---|---|---|---|---|---|---|
| Example 154 | <0.06 | <0.12 | 0.5 | 16 | 0.25 | 1 | 0.12 | | | | | 2 | 0.5-1 | 2 |
| Example 155 | <0.12 | <0.5-<0.5 | 0.12 | 4 | <0.06 | 0.5 | <0.06 | | | | | 0.5-1 | 16 | 0.5-1 |
| Example 156 | 0.5 | 0.12 | <0.06 | | | | | | | | | 4 | 4 | 8 |
| Example 157 | 16 | 4 | 4 | | | | | | | | | 64 | >64 | 64 |
| Example 158 | 0.25 | <0.06 | 0.12 | | | | | | | | | 4 | 4 | 4 |
| Example 161 | 1 | 0.12 | 0.5 | | | | | | | | | 16 | 16 | 16 |
| Example 162 | 0.12 | <0.06 | 0.12 | | <0.5 | | | | | | | 16 | 16 | 32 |

| EXAMPLE NUMBER | Enterococcus faecalis (GC 4552) | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) |
|---|---|---|---|---|---|---|---|---|---|
| Example 122 | 2 | 4 | 2 | 2 | 2 | 2 | 2 | 4 | 2 |
| Example 123 | 8 | 16 | 16 | 8 | 8 | 8 | 8 | 8 | 16 |
| Example 124 | 4 | 4 | 4 | 4 | 4 | 4 | 4 | 1 | 0.25 |
| Example 125 | 32 | 32 | 32 | 32 | 32 | 32 | 32 | 16 | 32 |
| Example 126 | 8 | 8 | 8 | 8 | 8 | 8 | 8 | 8 | 8 |
| Example 127 | 4 | 4 | 4 | 4 | 4 | 4 | 4 | 4 | 2 |
| Example 128 | 4 | 4 | 4 | 4 | 4 | 4 | 4 | 4 | 4 |
| Example 129 | 2 | 2 | 2 | 2 | 2 | 2 | 2 | 2 | 2 |
| Example 130 | 32 | 8 | 32 | 32 | 32 | 8 | 64 | 32 | 16 |
| Example 132 | 8 | 16 | 8 | 8 | 8 | 8 | 8 | 4 | 16 |
| Example 133 | 4 | 4 | 4 | 4 | 8 | 8 | 8 | 2 | 8 |
| Example 135 | 2 | 2 | 2 | 2 | 2 | 2 | 2 | 2 | 2 |
| Example 136 | >64 | >64 | >64 | 64 | >64 | >64 | 64 | 8 | 64 |
| Example 137 | 4-8 | 4-8 | 4-8 | 4 | 4-8 | 4-8 | 4-8 | 2-4 | 4-8 |
| Example 137a | >64 | >64 | >64 | >64 | >64 | >64 | >64 | 16 | 64 |
| Example 137b | 32 | 32 | 64 | 32 | 32 | 64 | 32 | 8 | 32 |
| Example 138 | 4 | 8 | 8 | 4 | 4 | 4 | 8 | 2 | 4 |
| Example 140 | 1 | 1 | 1 | 1 | <0.5 | 1 | 1 | 1 | 1 |
| Example 141 | >64 | >64 | >64 | >64 | >64 | >64 | >64 | 64 | >64 |
| Example 143 | 8-16 | 8-16 | 8-16 | 4-16 | 8-16 | 8-16 | 8-16 | 2-8 | 8-16 |
| Example 144 | 2 | 4 | 4 | 2 | 2 | 2 | 2 | 2 | 4 |
| Example 145 | 1 | 2 | 1 | 1 | 1 | 1 | 1 | 1 | 1 |
| Example 146 | 8 | 8 | 16 | 8 | 8 | 8 | 8 | 8 | 8 |
| Example 147 | 0.5-1 | 0.5-1 | 0.5-1 | 0.5 | 0.5-2 | 1-2 | 2 | 1-2 | 0.5-2 |
| Example 149 | 8 | 8 | 8 | 8 | 8 | 8 | 8 | 8 | 8 |
| Example 150 | 8 | 8 | 8 | 8 | 8 | 8 | 8 | 4 | 8 |
| Example 150a | >64 | >64 | >64 | >64 | >64 | >64 | >64 | 16 | 64 |
| Example 151 | 32 | 32 | 32 | 64 | 32 | 32 | 32 | 8 | 32 |
| Example 152 | 32 | 64 | 32 | 32 | 32 | 32 | 32 | 16 | 32 |
| Example 153 | 8 | 8 | 8 | 4 | 8 | 4 | 4 | 2 | 8 |
| Example 154 | 2 | 2 | 2 | 2 | 2 | 2 | 2 | 2 | 1 |
| Example 155 | <0.5-<0.5 | 0.5-<0.5 | 0.5-1 | 0.5 | 0.5-1 | <0.5-1 | 1-2 | 1-2 | 0.5-1 |
| Example 156 | 8 | 8 | 8 | 8 | 8 | 4 | 8 | 8 | 8 |
| Example 157 | >64 | >64 | >64 | >64 | >64 | 64 | >64 | 8 | 64 |
| Example 158 | 8 | 4 | 4 | 4 | 4 | 4 | 4 | 8 | 4 |
| Example 161 | 16 | 16 | 16 | 16 | 16 | 16 | 16 | 8 | 16 |
| Example 162 | 16 | 32 | 32 | 16 | 16 | 16 | 32 | 16 | 4 |

TABLE 2-continued

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) |
|---|---|---|---|---|---|---|---|---|---|
| Example 163 | <0.5 | <0.5 | | <0.5 | <0.5 | | 4 | 4 | 8 |
| Example 164 | 0.12 | <0.06 | <0.06 | <0.06 | 0.12 | | 4 | 4 | 8 |
| Example 164a | 1 | 0.25 | 1 | 1 | 0.5 | | 16 | 16 | 16 |
| Example 165 | 1 | <0.06 | 0.12 | 0.12 | 0.12 | | 16 | 16 | 16 |
| Example 166 | | 1 | 1 | 1 | | | 32 | | |
| Example 167 | 2 | 0.25 | 1 | 1 | 1 | | 32 | 32 | 32 |
| Example 168 | <0.12 | <0.12 | <0.12 | <0.06 | 0.5 | | 2 | 2 | 2 |
| Example 169 | 32 | 8 | 8 | 8 | 16 | | >64 | >64 | >64 |
| Example 170 | <0.06 | <0.06 | <0.06 | <0.06 | <0.06 | | 4 | 4 | 4 |
| Example 172 | <0.06 | <0.06 | <0.12 | <0.12 | 0.12 | | 4 | 4 | 8 |
| Example 173 | <0.12 | <0.12 | <0.12 | <0.12 | <0.12 | | 2 | 2 | 2 |
| Example 174 | <0.06 | <0.06 | <0.06 | <0.06 | <0.06 | | 2 | 2 | 2 |
| Example 175 | 0.12 | <0.06 | <0.06 | <0.06 | <0.06 | | 4 | 4 | 4 |
| Example 177 | <0.06 | <0.06 | <0.06 | <0.06 | <0.06 | | 2 | 2 | 2 |
| Example 178 | <0.06 | <0.06 | <0.06 | <0.06 | 0.12 | | 2 | 1 | 2 |
| Example 179 | 1 | 0.12 | 0.12 | 0.25 | 0.25 | | 32 | 32 | 16 |
| Example 180 | <0.06 | <0.06 | <0.06 | <0.06 | <0.06 | | 4 | 2 | 32 |
| Example 181 | <0.06 | <0.06 | <0.06 | <0.06 | 0.5 | | 2 | 2 | 2 |
| Example 182 | 32 | 8 | 8 | 4 | 64 | | >64 | >64 | 4 |
| Example 183 | <0.06 | <0.06 | <0.06 | <0.06 | <0.06 | | 8 | 2 | 4 |
| Example 184 | 0.12 | 0.12 | 0.25 | 0.25 | 0.25 | | 32 | 32 | 32 |
| Example 185 | 1 | 16 | 16 | 16 | 16 | | >64 | >64 | >64 |
| Example 186 | <0.06 | <0.06 | <0.06 | <0.06 | <0.06 | | 2 | 2 | 2 |
| Example 187 | <0.12 | <0.12 | <0.12 | <0.12 | 0.5 | | 64 | 16 | 128 |
| Example 190 | 4 | 8 | 8 | 8 | 16 | | 32 | 32 | 32 |
| Example 191 | 0.25 | 1 | 2 | 1 | 2 | | 8 | 8 | 8 |
| Example 192 | 0.5 | 0.5 | 0.25 | 0.5 | 0.5 | | 2 | 4 | 4 |
| Example 193 | <0.06 | <0.06 | <0.06 | <0.06 | <0.06 | | 4 | 2 | 4 |
| Example 194 | <0.06 | <0.06 | <0.06 | <0.06 | <0.06 | | 2 | 2 | 2 |
| Example 195 | 0.5 | 0.12 | 0.12 | 0.12 | 0.12 | | 2 | 2 | 1 |
| Example 196 | >64 | 64 | 64 | 64 | 32 | | >64 | >64 | 1 |
| Example 197 | 16 | 8 | 4 | 4 | 16 | | >64 | >64 | 0.5 |
| Example 198 | <0.12 | <0.12 | <0.12 | <0.12 | <0.12 | | 1 | 1 | >64 |
| Example 199 | <0.12 | <0.12 | <0.12 | <0.12 | <0.12 | | 2 | 4 | >64 |
| Example 200 | 0.12 | 0.12 | <0.06 | <0.06 | <0.06 | | 0.5 | 2 | 1 |
| Example 201 | <0.12 | <0.12 | <0.12 | <0.12 | <0.12 | | 1 | 1 | 4 |
| Example 202 | 2 | <0.5 | 8 | <0.5 | 1 | | 16 | 16 | 64 |

| EXAMPLE NUMBER | Enterococcus faecalis (GC 4552) | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) |
|---|---|---|---|---|---|---|---|---|---|
| Example 163 | 8 | 4 | 8 | 4 | 8 | 8 | 4 | 8 | 4 |
| Example 164 | 8 | 8 | 16 | 4 | 8 | 8 | 8 | 4 | 8 |
| Example 164a | 16 | 16 | 16 | 16 | 16 | 8 | 16 | 4 | 8 |
| Example 165 | 16 | 16 | 32 | 16 | 16 | 16 | 16 | 16 | 16 |
| Example 166 | | | | | | | | | |
| Example 167 | 32 | 32 | 32 | 32 | 32 | 32 | 32 | | 32 |
| Example 168 | 2 | 2 | 2 | 2 | 2 | 2 | 2 | 1 | 2 |

TABLE 2-continued

| | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) |
|---|---|---|---|---|---|---|---|---|---|
| Example 169 | >64 | >64 | >64 | >64 | >64 | >64 | >64 | 32 | >64 |
| Example 170 | 4 | 4 | 4 | 4 | 4 | 4 | 4 | 4 | 4 |
| Example 172 | 8 | 4 | 4 | 4 | 8 | 8 | 8 | 8 | 4 |
| Example 173 | 2 | 2 | 2 | 1 | 2 | 1 | 1 | 2 | 1 |
| Example 174 | 1 | 1 | 1 | 2 | 1 | 2 | 4 | 2 | 2 |
| Example 175 | 4 | 4 | 4 | 4 | 4 | 4 | 2 | 4 | 2 |
| Example 177 | 2 | 2 | 2 | 2 | 2 | 2 | 4 | 2 | 2 |
| Example 178 | 4 | 2 | 8 | 4 | 4 | 4 | 2 | 2 | 1 |
| Example 179 | 4 | 2 | 2 | 1 | 4 | 4 | 4 | 4 | 4 |
| Example 180 | 32 | 32 | 32 | 16 | 32 | 32 | 32 | 16 | 16 |
| Example 181 | 2 | 2 | 2 | 2 | 2 | 2 | 2 | 2 | 2 |
| Example 182 | 2 | 1 | 2 | 2 | 2 | 2 | 4 | 4 | 4 |
| Example 183 | >64 | >64 | >64 | >64 | >64 | >64 | >64 | >64 | >64 |
| Example 184 | 8 | 4 | 4 | 2 | 8 | 8 | 8 | 4 | 2 |
| Example 185 | 32 | 16 | 32 | 32 | 32 | 16 | 32 | 32 | 32 |
| Example 186 | >64 | 32 | >64 | >64 | >64 | 32 | >64 | >64 | 64 |
| Example 187 | 2 | 2 | 2 | 1 | 2 | 2 | 2 | 2 | 2 |
| Example 190 | 64 | 32 | 32 | 16 | 64 | 16 | 128 | 16 | 16 |
| Example 191 | 32 | 32 | 32 | 32 | 32 | 32 | 32 | 8 | 16 |
| Example 192 | 16 | 8 | 16 | 8 | 16 | 8 | 8 | 4 | 4 |
| Example 193 | 4 | 4 | 4 | 2 | 4 | 4 | 4 | 2 | 2 |
| Example 194 | 1 | 2 | 2 | 0.5 | 1 | 1 | 1 | 2 | 2 |
| Example 195 | 2 | 2 | 2 | 0.5 | 2 | 1 | 2 | 2 | 2 |
| Example 196 | 0.5 | 0.5 | 0.5 | 0.5 | 0.5 | 0.5 | 0.5 | 0.5 | 0.5 |
| Example 197 | >64 | >64 | >64 | >64 | >64 | 64 | >64 | 8 | 32 |
| Example 198 | >64 | >64 | >64 | 64 | >64 | 64 | >64 | 8 | 16 |
| Example 199 | 1 | 1 | 1 | 1 | 1 | 1 | 1 | 1 | 1 |
| Example 200 | 4 | 4 | 4 | 2 | 4 | 4 | 4 | 2 | 2 |
| Example 201 | 2 | 4 | 4 | 4 | 4 | 4 | 4 | 2 | 4 |
| Example 202 | 32 | 32 | 32 | 16 | 32 | 32 | 16 | 4 | 32 |

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) |
|---|---|---|---|---|---|---|---|---|---|
| Example 203 | 1 | 0.12 | 0.25 | 0.5 | 0.5 | | | | |
| Example 204 | 1 | 0.25 | 0.5 | 0.5 | 0.5 | | | | |
| Example 205 | <0.12 | <0.12 | <0.12 | <0.12 | <0.12 | | | | |
| Example 206 | 0.25 | <0.12 | <0.12 | <0.12 | 1 | | | | |
| Example 207 | <0.12 | <0.12 | <0.12 | <0.12 | <0.12 | | | | |
| Example 208 | 0.12 | <0.06 | <0.06 | <0.06 | 0.12 | | | | |
| Example 209 | | <0.06 | | <0.06 | | | | | |
| Example 210 | 0.25 | <0.06 | <0.06 | 0.25 | 2 | | | | |
| Example 210a | 2 | <0.06 | 0.25 | 0.5 | 1 | | | | |
| Example 212 | 1 | <0.06 | 0.25 | 0.5 | 2 | | | | |
| Example 214 | <0.12 | <0.12 | <0.12 | <0.12 | <0.12 | | | | |
| Example 215 | <0.12 | <0.12 | <0.12 | <0.12 | <0.12 | | | | |
| Example 216 | 0.5 | <0.06 | 0.25 | 0.25 | 0.5 | | | | |
| Example 217 | 2 | 0.25 | 0.5 | 1 | 1 | | | | |
| Example 218 | 0.25 | <0.06 | 0.12 | 0.12 | 0.5 | | | | |
| Example 219 | 2 | 1 | 2 | 0.5 | 2 | | | | |
| Example 220 | <0.06 | <0.06 | <0.06 | <0.06 | <0.06 | | | | |
| Example 221 | <0.12 | <0.12 | <0.12 | <0.12 | <0.12 | | | | |

TABLE 2-continued

| EXAMPLE NUMBER | Enterococcus faecalis (GC 4552) | Enterococcus faecalis (GC 4553) | Enterococcus faecalis (GC 4554) | Enterococcus faecalis (GC 6189) | Enterococcus faecalis (ATCC 29212) |
|---|---|---|---|---|---|
| Example 222 | >64 | 64 | 64 | 64 | 64 |
| Example 223 | >64 | >64 | >64 | >64 | >64 |
| Example 224 | <0.12 | 0.25 | 0.25 | 0.25 | 0.25 |
| Example 225 | 0.5 | 1 | 0.5 | 0.5 | 0.5 |
| Example 226 | 4 | 4 | 1 | 2 | 2 |
| Example 227 | 64 | 64 | 4 | 32 | 32 |
| Example 228 | 16 | 8 | 64 | 8 | 8 |
| Example 229 | >128 | >128 | >128 | >128 | >128 |
| Example 229a | >128 | >128 | >128 | >128 | >128 |
| Example 229b | 128 | 128 | 128 | 128 | >128 |
| Example 230 | 0.5 | <0.06 | 0.12 | 0.12 | 0.25 |
| Example 230a | <0.06–0.12 | <0.06 | <0.06 | <0.06 | <0.06–0.25 |
| Example 230b | 0.5 | <0.12 | 0.25 | 0.25 | 0.5 |
| Example 230c | 32 | 16 | 32 | 32 | 64 |
| Example 231 | <0.06 | <0.06 | <0.06 | <0.06 | <0.06 |
| Example 231a | <0.06 | <0.06 | <0.06 | <0.06 | <0.06 |
| Example 231b | 1–8 | 0.5–8 | 0.5–8 | 0.25–2 | 1–8 |
| Example 231c | <0.12 | <0.12 | <0.12 | <0.12 | <0.12 |
| Example 232 | 2 | 0.5 | 1 | 0.5 | 2 |

| EXAMPLE NUMBER | Enterococcus faecalis (GC 4552) | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) |
|---|---|---|---|---|---|---|---|---|---|
| Example 203 | 8 | 8 | 8 | 8 | 8 | 8 | 4 | 4 | 8 |
| Example 204 | 16 | 16 | 16 | 16 | 16 | 16 | 16 | 8 | 16 |
| Example 205 | 4 | 2 | 4 | 2 | 2 | 2 | 2 | 4 | 2 |
| Example 206 | 2 | 2 | 2 | 1 | 1 | 1 | 1 | 2 | 1 |
| Example 207 | 4 | 4 | 4 | 2 | 4 | 4 | 4 | 2 | 4 |
| Example 208 | 4 | 4 | 8 | 8 | 8 | 8 | 8 | 8 | 4 |
| Example 209 | 8 | 8 | 8 | 1 | 4 | 1 | 4 | 8 | 4 |
| Example 210 | 32 | 16 | 32 | 16 | 32 | 32 | 32 | 32 | 16 |
| Example 210a | 8 | 8 | 8 | 8 | 8 | 4 | 8 | 4 | 4 |
| Example 212 | 8 | 8 | 8 | 8 | 8 | 8 | 8 | 4 | 4 |
| Example 214 | 2 | 2 | 2 | 2 | 2 | 2 | 2 | 2 | 2 |
| Example 215 | 1 | 0.5 | 1 | 1 | 0.5 | 0.5 | 1 | 0.5 | 0.5 |
| Example 216 | 4 | 4 | 4 | 4 | 4 | 4 | 4 | 4 | 4 |
| Example 217 | 16 | 32 | 32 | 16 | 16 | 16 | 16 | 8 | 16 |
| Example 218 | 4 | 4 | 4 | 4 | 4 | 4 | 8 | 4 | 4 |
| Example 219 | 8 | 8 | 8 | 8 | 16 | 8 | 8 | 4 | 4 |
| Example 220 | 2 | 1 | 2 | 1 | 2 | 1 | 2 | 1 | 2 |
| Example 221 | 2 | 2 | 2 | 1 | 2 | 2 | 2 | 2 | 2 |
| Example 222 | >64 | >64 | >64 | >64 | >64 | >64 | >64 | 64 | 64 |
| Example 223 | >64 | 64 | >64 | >64 | >64 | >64 | >64 | 64 | 64 |
| Example 224 | 2 | 2 | 4 | 4 | 4 | 2 | 4 | 0.5 | 2 |
| Example 225 | 8 | 4 | 16 | 16 | 8 | 4 | 8 | 1 | 4 |
| Example 226 | 32 | 16 | 32 | 32 | 32 | 32 | 32 | 8 | 8 |
| Example 227 | 64 | 8 | 128 | 64 | 64 | 64 | 64 | 8 | 8 |
| Example 228 | 32 | 16 | 32 | 32 | 32 | 16 | 32 | 16 | 8 |
| Example 229 | >128 | >128 | >128 | >128 | >128 | >128 | >128 | >128 | 128 |
| Example 229a | >128 | >128 | >128 | >128 | >128 | >128 | >128 | >128 | 128 |
| Example 229b | >128 | 128 | >128 | >128 | >128 | >128 | 128 | 128 | 64 |
| Example 230 | 8 | 8 | 8 | 4 | 8 | 8 | 8 | 2 | 8 |

TABLE 2-continued

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) |
|---|---|---|---|---|---|---|---|---|---|
| Example 230a | 2-4 | 2-4 | 1-4 | 2-4 | 2-4 | | 2-4 | 1-2 | 2-4 |
| Example 230b | 8 | 8 | | 8 | 8 | | 8 | 0.5 | 2 |
| Example 230c | >128 | 128 | >128 | >128 | 128 | | >128 | 32 | 128 |
| Example 231 | 4 | 4 | 2-4 | 4 | 4 | | 4 | 1-2 | 2-4 |
| Example 231a | 8-128 | 8-128 | 8-64 | 8-128 | 8-128 | | 16-128 | 4-16 | 8-64 |
| Example 231b | 4 | 4 | | 4 | 4 | | 4 | | 4 |
| Example 231c | | | | | | | | 2 | |
| Example 232 | 32 | 32 | 64 | 32 | 16 | | 32 | 4 | 32 |
| Example 234 | 0.5 | 0.12 | 0.25 | 0.25 | 0.5 | | 4 | 4 | 8 |
| Example 235 | 0.25-0.5 | <0.06 | <0.06-0.12 | 0.12 | 0.25 | | 4 | 4 | 4-8 |
| Example 236 | 0.12 | <0.06 | <0.06 | <0.06 | <0.06 | | 4 | 2 | 2 |
| Example 237 | 2 | 0.25 | 0.5 | 0.5 | 1 | | 16 | 16 | 32 |
| Example 238 | 2 | 0.5 | 1 | 1 | 1 | | 16 | 16 | 32 |
| Example 239 | 0.25 | <0.06 | <0.06 | <0.06 | 0.25 | | 4 | 4 | 4 |
| Example 239a | 1 | <0.06 | 0.25 | 0.25 | 2 | | 8 | 8 | 8 |
| Example 240 | 0.5 | <0.12 | 0.25 | <0.12 | 0.5 | | 16 | 8 | 8 |
| Example 241 | <0.06 | <0.06 | <0.06 | <0.06 | <0.06 | | 4 | 4 | 2 |
| Example 241a | <0.06 | <0.06 | <0.06 | <0.06 | <0.06 | | 4 | 2 | 2 |
| Example 242 | 2 | 0.5 | 0.5 | 1 | 2 | | 16 | 16 | 16 |
| Example 243 | 32 | 8 | 16 | 32 | 32 | | 64 | >64 | >64 |
| Example 243a | 16 | 1 | 2 | 16 | 8 | | 32 | 32 | 32 |
| Example 244 | 4 | 0.5 | 1 | 1 | 2 | | 32 | 32 | 64 |
| Example 245 | 4 | 1 | 4 | 2 | 4 | | 16 | 16 | 16 |
| Example 245a | 1 | <0.12 | 1 | 0.5 | 1 | | 4 | 8 | 4 |
| Example 245b | 8 | 1 | 8 | 4 | 8 | | 32 | 64 | 64 |
| Example 245c | 128 | 32 | 64 | 64 | 128 | | >128 | >128 | >128 |
| Example 246 | 2 | 0.5 | 2 | 2 | 4 | | 16 | 32 | 32 |
| Example 246a | 0.5 | <0.12 | 0.25 | 0.25 | 0.5 | | 4 | 4 | 4 |
| Example 246b | 64 | 32 | 64 | 32 | 64 | 64 | 128 | 128 | 128 |
| Example 246c | >128 | 64 | 128 | 128 | >128 | 16 | >128 | >128 | >128 |
| Example 248 | 64 | 64 | 128 | 64 | 32 | 2 | 64 | 32 | 128 |
| Example 249 | 128 | 32 | 64 | 64 | 128 | | 32 | 128 | 128 |
| Example 251 | >64 | | 64 | | | | >64 | | |
| Example 251a | 32 | | 8 | | | 8 | >64 | | |
| Example 251b | | | 1 | | | <0.5 | 32 | | |
| Example 253 | 32 | 8 | 16 | 16 | 32 | | >64 | >64 | >64 |
| Example 253a | 1 | 0.25 | 0.5 | 0.5 | 1 | | 16 | 16 | 32 |
| Example 253b | 1 | <0.06 | 0.25 | 0.25 | 1 | | 8 | 8 | 16 |
| Example 254 | 4 | | 16 | | | | 8 | | |
| Example 254b | <0.5 | | <0.5 | | | | 8 | | |
| Example 255 | 32 | | 16 | | 16 | | >0.5 | | |
| Example 255a | 64 | | 32 | | 32 | | >0.5 | >0.5 | >0.5 |
| Example 256 | >64 | | >64 | | | 64 | >64 | | |
| Example 256a | >64 | | >64 | | | 64 | >64 | | |
| Example 257 | 2 | 0.25 | 1 | 0.25 | 0.12 | | 0.5 | 0.5 | 0.5 |

TABLE 2-continued

| EXAMPLE NUMBER | Enterococcus faecalis (GC 4552) | Streptococcus agalactiae (GC 4564) | Streptococcus pneumoniae (GC 1894) | Enterococcus faecalis (GC 4553) | Streptococcus pneumoniae (GC 4565) | Enterococcus faecalis (GC 4554) | Streptococcus pneumoniae (ATCC 6301) | Enterococcus faecalis (GC 6189) | Streptococcus pneumoniae (GC 4563) | Enterococcus faecalis (ATCC 29212) | Streptococcus pyogenes (GC 4563) | Enterococcus faecium (GC 2243) | Streptococcus pyogenes (ID-3187) | Enterococcus faecium (GC 4556) | Enterococcus faecium (GC 4557) | Enterococcus avium (GC 4558) |
|---|---|---|---|---|---|---|---|---|---|---|---|---|---|---|---|---|
| Example 234 | 8 | 8 | 1 | 8 | 4 | 8 | | 8 | | 8 | | 8 | | 8 | 2 | 8 |
| Example 235 | 4 | 1 | 0.25 | 4 | 0.5 | 4-8 | | 4 | | 4 | | 4 | | 4 | 0.5-2 | 4 |
| Example 236 | 4 | >64 | | 4 | | 4 | | 2 | | 4 | | 4 | | 4 | 4 | 2 |
| Example 237 | 16 | 8 | | 16 | | 32 | | 16 | | 16 | | 16 | | 16 | 4 | 16 |
| Example 238 | 32 | 4 | | 32 | | 32 | | 16 | | 16 | | 16 | | 32 | 4 | 16 |
| Example 239 | 4 | | | 4 | | 4 | | 4 | | 4 | | 4 | | 4 | 2 | 4 |
| Example 239a | 8 | | | 8 | | 16 | | 8 | | 8 | | 8 | | 8 | 4 | 8 |
| Example 240 | 16 | | | 16 | | 16 | | 8 | | 16 | | 16 | | 16 | 4 | 8 |
| Example 241 | 4 | | | 4 | | 4 | | 2 | | 4 | | 4 | | 4 | 2 | 4 |
| Example 241a | 4 | | | 4 | | 4 | | 2 | | 4 | | 2 | | 2 | 2 | 2 |
| Example 242 | 16 | | | 16 | | 16 | | 16 | | 16 | | 16 | | 16 | 8 | 16 |
| Example 243 | >64 | | | 64 | | >64 | | 64 | | >64 | | 64 | | >64 | 32 | 32 |
| Example 243a | 32 | | | 32 | | 32 | | 32 | | 32 | | 32 | | 32 | 16 | 16 |
| Example 244 | 32 | | | 32 | | 64 | | 32 | | 32 | | 32 | | 32 | 4 | 32 |
| Example 245 | 16 | | | 16 | | 32 | | 32 | | 32 | | 16 | | 16 | 4 | 16 |
| Example 245a | 8 | | | 4 | | 8 | | 8 | | 8 | | 4 | | 4 | 2 | 4 |
| Example 245b | 64 | | | 32 | | 64 | | 32 | | 64 | | 32 | | 64 | 8 | 32 |
| Example 245c | >128 | | | >128 | | >128 | | >128 | | >128 | | >128 | | >128 | 64 | >128 |
| Example 246 | 16 | | | 8 | | 32 | | 16 | | 16 | | 16 | | 16 | 4 | 8 |
| Example 246a | 4 | | | 2 | | 4 | | 4 | | 4 | | 4 | | 4 | 2 | 2 |
| Example 246b | 128 | | | 128 | | >128 | | 128 | | 128 | | 128 | | 128 | 32 | 64 |
| Example 246c | >128 | | | 128 | | >128 | | >128 | | >128 | | >128 | | >128 | 128 | 64 |
| Example 248 | 128 | | | 16 | | 64 | | 32 | | 64 | | 32 | | 32 | 16 | 8 |
| Example 249 | 64 | | | 64 | | 128 | | 64 | | 16 | | 64 | | 32 | 64 | 32 |
| Example 251 | >64 | | | >64 | | >64 | | >64 | | >64 | | >64 | | >64 | 64 | >64 |
| Example 251a | >64 | | | >64 | | >64 | | >64 | | >64 | | >64 | | >64 | 64 | >64 |
| Example 251b | >64 | | | >64 | | >64 | | >64 | | >64 | | >64 | | >64 | 64 | >64 |
| Example 253 | >64 | | | >64 | | >64 | | >64 | >64 | >64 | | >64 | | >64 | 32 | >64 |
| Example 253a | 32 | | | 16 | | 32 | | 16 | 8 | 16 | | 16 | | 16 | 4 | 16 |
| Example 253b | 8 | | | 8 | | 8 | | 8 | | 8 | | 8 | | 8 | 2 | 8 |
| Example 254 | 4 | | | 4 | | 4 | | 4 | | 4 | | 4 | | 8 | 2 | 4 |
| Example 254b | 8 | | | 8 | | 4 | | 8 | | 8 | | 4 | | 8 | 8 | 2 |
| Example 255 | >0.5 | >0.5 | >0.5 | >0.5 | >0.5 | >0.5 | | >0.5 | >0.5 | >0.5 | | >0.5 | >64 | >0.5 | 16 | >0.5 |
| Example 255a | >0.5 | >0.5 | >0.5 | >0.5 | >0.5 | >0.5 | | >0.5 | >0.5 | >0.5 | | >0.5 | 4 | >0.5 | 32 | >0.5 |
| Example 256 | >64 | >64 | >64 | >64 | >64 | >64 | | >64 | >64 | >64 | | >64 | 4 | >64 | 64 | >64 |
| Example 256a | >64 | >64 | | >64 | | >64 | | >64 | | >64 | | >64 | 32 | >64 | 32 | >64 |
| Example 257 | 0.5 | 1 | 0.5 | 0.5 | >0.5 | >0.5 | | 0.5 | | 0.5 | | 16 | 1 | 16 | 2 | 0.5 |

| EXAMPLE NUMBER | Enterococcus faecalis (GC 2242) | Enterococcus faecium (GC 2691) | Enterococcus faecalis (GC 3059) |
|---|---|---|---|
| Example 257a | >0.5 | 0.5 | >0.5 |
| Example 257b | 0.5 | 0.5 | 0.5 |
| Example 261a | >64 | | |
| Example 261b | 64 | | |
| Example 261c | 32 | | |
| Example 262a | >128 | | |
| Example 262b | 16 | | |

TABLE 2-continued

| EXAMPLE NUMBER | | |
|---|---|---|
| Example 263 | 32 | |
| Example 264a | 8 | |
| Example 264b | 4 | |
| Example 265a | 4 | |
| Example 265b | 8 | 4 |
| Example 270a | 1 | |
| Example 270b | 2 | |
| Example 271a | 4 | |
| Example 277a | >128 | >128 |
| Example 277b | >64 | 64 |
| Example 278b | 4 | 1 |
| Example 278c | 2 | 1 |
| Example 279a | >64 | 64 |
| Example 280a | >128 | >128 |
| Example 280b | 128 | 64 |
| Example 282 | >128 | 128 |
| Example 283a | 64 | 16 |
| Example 283b | 64 | 32 |
| Example 284b | 16 | 8 |
| Example 283c | >128 | >128 |
| Example 287 | >64 | 64 |
| Example 296 | >128 | >128 |

| | | | | | | | | |
|---|---|---|---|---|---|---|---|---|
| | | | | 32 | 4 | | | |
| | | | | 4 | 64 | | | |
| | | | | 4 | 32 | | | |
| 4 | | | | 64 | | | | |
| | | | | 1 | 4 | | | |
| | | | | 2 | 16 | | | |
| | | | | 2 | 16 | | | |
| >128 | | | | 16 | >128 | | | |
| 64 | >128 | | | >64 | >64 | | | |
| 2 | 1 | | | 32 | 32 | | | |
| 1 | 1 | | | 16 | 16 | | | |
| 64 | 64 | | | >64 | >64 | | | |
| >128 | >128 | | | >128 | >128 | | | |
| 32 | 64 | | | 128 | 128 | | | |
| 128 | 128 | | | >128 | >128 | | | |
| 16 | 64 | | | 128 | 128 | | | |
| 32 | 64 | | | 128 | 128 | | | |
| 8 | 16 | | | | | | | |
| >128 | >128 | | | >128 | >128 | | | |
| 64 | >128 | | | >64 | >64 | | | |
| >128 | >128 | | | >128 | >128 | | | |

| EXAMPLE NUMBER | Enterococcus faecalis (GC 4552) | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) |
|---|---|---|---|---|---|---|---|---|---|
| Example 257a | >0.5 | >0.5 | >0.5 | >0.5 | >0.5 | >32 | >32 | 8 | >0.5 |
| Example 257b | >0.5 | 0.5 | >0.5 | 0.5 | 0.5 | 16 | 16 | 2 | 0.5 |
| Example 261a | >64 | >64 | >64 | | >64 | >64 | >64 | >64 | >64 |
| Example 261b | 64 | 64 | 64 | | 64 | 64 | 64 | 16 | 64 |
| Example 261c | 64 | 64 | 64 | | 64 | 64 | 64 | 8 | 64 |
| Example 262a | >128 | >128 | >128 | | >128 | >128 | >128 | >128 | >128 |
| Example 262b | 32 | 32 | 32 | | 32 | 16 | 16 | 2 | 16 |
| Example 263 | >64 | >64 | >64 | | >64 | >64 | >64 | 32 | >64 |
| Example 264a | >64 | >64 | >64 | | >64 | >64 | >64 | 32 | >64 |
| Example 264b | >64 | >64 | >64 | | 64 | 64 | 64 | 8 | 64 |
| Example 265a | >64 | >64 | >64 | | >64 | >64 | >64 | 8 | 64 |
| Example 265b | 64 | 64 | 64 | | 32 | 32 | 16 | 8 | 16 |
| Example 270a | 16 | 16 | 32 | | 16 | 16 | 32 | 4 | 16 |
| Example 270b | 32 | 32 | 32 | | 32 | 32 | 64 | 8 | 32 |
| Example 271a | 32 | 32 | 32 | | 32 | 32 | 64 | 4 | 32 |
| Example 277a | >128 | >128 | >128 | >128 | >128 | >128 | >128 | 128 | 128 |
| Example 277b | >64 | >64 | >64 | >64 | >64 | >64 | >64 | >64 | >64 |
| Example 278b | 32 | 32 | 32 | 32 | 32 | 32 | 32 | 8 | 32 |
| Example 278c | 32 | 32 | 32 | 32 | 32 | 32 | 32 | 8 | 32 |
| Example 279a | >64 | >64 | >64 | >64 | >64 | >64 | >64 | 64 | >64 |
| Example 280a | >128 | >128 | >128 | >128 | >128 | >128 | >128 | >128 | >128 |
| Example 280b | >64 | >64 | >64 | | 128 | 128 | 128 | 64 | 128 |
| Example 282 | >128 | >128 | >128 | >128 | >128 | >128 | >128 | 128 | 128 |
| Example 283a | >128 | >128 | >128 | >128 | >128 | >128 | >128 | 64 | >128 |
| Example 283b | >128 | >128 | >128 | >128 | >128 | >128 | >128 | 64 | 128 |
| Example 283c | 128 | 128 | >128 | 128 | 128 | 128 | 128 | 16 | 128 |

TABLE 2-continued

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|---|
| Example 284b | >128 | >128 | | >128 | >128 | >128 | >128 | >128 | >128 | 128 |
| Example 287 | >64 | >64 | | >64 | >64 | >64 | >64 | >64 | >64 | 64 |
| Example 296 | >128 | >128 | | >128 | >128 | >128 | >128 | >128 | >128 | 128 |
| Example 3 | >128 | >128 | | | >128 | >128 | >128 | >128 | >128 | |
| Example 6 | >128 | >128 | | | >128 | >128 | >128 | >128 | >128 | |
| Example 8 | >128 | >128 | | | >128 | >128 | >128 | >128 | >128 | |
| Example 10 | >64 | >64 | >64 | | >64 | >64 | >64 | >64 | >64 | |
| Example 12 | >128 | >128 | >128 | | >128 | >128 | >128 | >128 | >128 | |
| Example 13 | 64 | 64 | 64 | | 64 | 64 | 64 | 64 | 64 | |
| Example 14 | >128 | >128 | >128 | | >128 | >128 | >128 | >128 | >128 | |
| Example 15 | >128 | >128 | >128 | | >128 | >128 | >128 | >128 | >128 | |
| Example 16 | 128 | 128 | 128 | | 64 | 128 | 128 | 32 | 128 | |
| Example 17 | >64 | >64 | >64 | | >64 | >64 | >64 | >64 | >64 | |
| Example 18 | >128 | >128 | >128 | | >128 | >128 | >128 | >128 | >128 | |
| Example 19 | >128 | >128 | >128 | | >128 | >128 | >128 | >128 | >128 | |
| Example 22 | >64 | >64 | >64 | | >64 | >64 | >64 | >64 | >64 | |
| Example 24 | >128 | >128 | >128 | | >128 | >128 | >128 | >128 | >128 | |
| Example 25 | >128 | >128 | >128 | | >128 | >128 | >128 | >128 | >128 | |
| Example 26 | 16 | 16 | 16 | | 32 | 16 | 16 | 32 | 32 | |
| Example 27 | 16 | 16 | 8 | | 16 | 8 | 8 | 8 | 8 | |
| Example 28 | 8 | 4 | 4 | | 8 | 8 | 8 | 4 | 8 | |
| Example 29 | 8 | 8 | 8 | | 8 | 8 | 8 | 8 | 8 | |
| Example 30 | 8 | 16 | 16 | | 16 | 8 | 8 | 8 | 8 | |
| Example 31 | 16 | 16 | 16 | | 16 | 8 | 16 | 16 | 16 | |
| Example 32 | 2 | 2 | 4 | | 2 | 2 | 2 | 2 | 4 | |
| Example 33 | 4 | 16 | 8 | | 8 | 8 | 4 | 8 | 8 | |
| Example 34 | 32 | 16 | 32 | | 32 | 32 | 16 | 32 | 32 | |
| Example 35 | 8 | 8 | 8 | | 8 | 8 | 8 | 8 | 8 | |
| Example 36 | >128 | >128 | >128 | | >128 | >128 | >128 | >128 | >128 | |
| Example 37 | 8 | 8 | 8 | | 8 | 8 | 8 | 16 | 16 | |
| Example 38 | 32 | 64 | 64 | | 64 | 64 | 64 | 32 | 64 | |
| Example 39 | 16 | 16 | 8 | | 16 | 16 | 16 | 16 | 16 | |
| Example 40 | 64 | 64 | 64 | | 64 | 64 | 32 | 32 | 64 | |
| Example 41 | >64 | >64 | >64 | | >64 | >64 | >64 | >64 | >64 | |
| Example 42 | 2 | 2 | 4 | | 2 | 2 | 2 | 2 | 4 | |
| Example 44 | 64 | 64 | 32 | | 64 | 64 | 16 | 16 | 64 | |
| Example 45 | 8 | 8 | 8 | | 16 | 8 | 8 | 8 | 8 | |
| Example 46 | 8 | 8 | 8 | | 8 | 8 | 8 | 8 | 8 | |
| Example 47 | 32 | 32 | 16 | | 16 | 16 | 16 | 16 | 16 | |
| Example 48 | 16 | 16 | 16 | | 16 | 16 | 16 | 16 | 32 | |
| Example 49 | 4 | 4 | 4 | | 4 | 4 | 4 | 2 | 8 | |
| Example 51 | 32 | 32 | 64 | | 32 | 32 | 32 | 32 | 32 | |
| Example 52 | 16 | 16 | 32 | | 16 | 16 | 16 | 16 | 16 | |
| Example 53 | 4 | 2 | 4 | | 4 | 2 | 4 | 2 | 2 | |
| Example 53a | >128 | >128 | >128 | | >128 | >128 | >128 | >128 | >128 | |
| Example 54 | >128 | >128 | >128 | | >128 | >128 | >128 | >128 | >128 | |

TABLE 2-continued

| EXAMPLE NUMBER | Staphylococcus aureus-SMITH (GC 4543) | Staphylococcus haemolyticus (GC 4546) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|
| Example 3 | >128 | >128 | | | >128 | >128 | 128 | >128 | | 128 |
| Example 6 | >128 | >128 | | | >128 | >128 | >128 | >128 | | >128 |
| Example 8 | >128 | >128 | | | >128 | >128 | >128 | >128 | | >128 |
| Example 10 | >64 | >64 | | | >64 | >64 | >64 | >64 | >64 | |
| Example 12 | >128 | >128 | | | >128 | >128 | >128 | >128 | >128 | |
| Example 13 | 64 | 64 | | | 64 | 64 | 32 | 64 | 32 | |
| Example 14 | >128 | >128 | | | >128 | >128 | >128 | >128 | >128 | |
| Example 15 | >128 | >128 | | | >128 | >128 | >128 | >128 | >128 | |
| Example 16 | 64 | 8 | | | 16 | 32 | 4 | 32 | 8 | |
| Example 17 | >64 | >64 | | | 64 | >64 | 32 | >64 | 64 | |
| Example 18 | >128 | 128 | | | 128 | 128 | 64 | >128 | 128 | |
| Example 19 | >128 | >128 | | | >128 | >128 | 128 | >128 | >128 | |
| Example 22 | >128 | >128 | | | >128 | 128 | 64 | >128 | 128 | |
| Example 24 | >64 | 64 | | | 64 | 64 | >64 | >64 | 32 | |
| Example 25 | >128 | >128 | | | >128 | >128 | >128 | >128 | >128 | |
| Example 26 | 16 | 4 | | | 8 | 16 | 4 | 16 | 4 | |
| Example 27 | 8 | 4 | | | 8 | 8 | 8 | 8 | 4 | |
| Example 28 | 4 | 4 | | | 8 | 4 | 4 | 4 | 2 | |
| Example 29 | 8 | 4 | | | 4 | 4 | 2 | 8 | 4 | |
| Example 30 | 8 | 4 | | | 8 | 4 | 16 | 8 | 4 | |
| Example 31 | 16 | 8 | | | 8 | 8 | 16 | 16 | 4 | |
| Example 32 | 2 | 2 | | | 2 | 1 | 2 | 4 | 2 | |
| Example 33 | 4 | 4 | | | 4 | 4 | 1 | 8 | 4 | |
| Example 34 | 16 | 8 | | | 16 | 16 | 4 | 32 | 8 | |
| Example 35 | 8 | 8 | | | 8 | 8 | 8 | 8 | 2 | |
| Example 36 | >128 | 64 | | | 64 | 128 | 64 | >128 | 64 | |
| Example 37 | 8 | 8 | | | 16 | 8 | 8 | 8 | 4 | |
| Example 38 | 64 | 16 | | | 32 | 32 | 64 | 64 | 16 | |
| Example 39 | 16 | 8 | | | 8 | 8 | 4 | 8 | 4 | |
| Example 40 | 64 | 16 | | | 16 | 32 | 16 | 32 | 16 | |
| Example 41 | >64 | 64 | | | 64 | >64 | 32 | 64 | | |
| Example 42 | 2 | 2 | | | 2 | 1 | 1 | 4 | 1 | |
| Example 44 | 32 | 64 | | | 64 | 16 | 2 | 16 | 8 | |
| Example 45 | 8 | 4 | | | 4 | 8 | 4 | 8 | 4 | |
| Example 46 | 4 | 8 | | | 4 | 8 | 2 | 4 | | |
| Example 47 | 8 | 8 | | | 16 | 2 | 2 | 8 | | |
| Example 48 | 16 | 8 | | | 4 | 4 | 0.5 | 16 | | |
| Example 49 | 8 | 1 | | | 4 | 8 | 4 | 4 | 1 | |
| Example 51 | 2 | 32 | | | 4 | 2 | 1 | 4 | 8 | |
| Example 52 | 32 | 32 | | | 16 | 16 | 4 | 64 | 4 | |
| Example 53 | 16 | 4 | | | 8 | 8 | 4 | 8 | | |
| Example 53a | 2 | 1 | | | 2 | 2 | 1 | 2 | | |
| Example 53 | >128 | >128 | | | >128 | >128 | >128 | >128 | | |
| Example 54 | >128 | >128 | | | >128 | >128 | >128 | >128 | | |

TABLE 2-continued

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) | Enterococcus faecalis (GC 4552) |
|---|---|---|---|---|---|---|---|---|---|---|
| Example 3 | >128 | | | | | >128 | >128 | | | >128 |
| Example 6 | >128 | | | | | >128 | >128 | | | >128 |
| Example 8 | >128 | | | | | >128 | >128 | | | >128 |
| Example 10 | >64 | >64 | >64 | >64 | | | >64 | >64 | >64 | >64 |
| Example 12 | 128 | 128 | 128 | >128 | >128 | | >128 | >128 | >128 | >128 |
| Example 13 | 16 | 2 | 4 | 4 | 8 | | 64 | >64 | >64 | >64 |
| Example 14 | 128 | 128 | 64 | >128 | >128 | | >128 | >128 | >128 | >128 |
| Example 15 | 128 | 128 | 64 | >128 | >128 | | >128 | >128 | >128 | >128 |
| Example 16 | 64 | 64 | 128 | 128 | 16 | | >128 | >128 | >128 | >128 |
| Example 17 | >64 | 64 | >64 | >64 | >64 | | >64 | >64 | >64 | >64 |
| Example 18 | 128 | 64 | 128 | 128 | 128 | | >128 | >128 | >128 | >128 |
| Example 19 | >128 | 64 | 128 | 128 | >128 | | >128 | >128 | >128 | >128 |
| Example 22 | 32 | 8 | 8 | 8 | 32 | | >128 | >128 | >128 | >128 |
| Example 24 | >64 | 64 | >64 | >64 | 64 | | 64 | >64 | >64 | >64 |
| Example 25 | >128 | 128 | >128 | >128 | >128 | | >128 | >128 | >128 | >128 |
| Example 26 | 16 | 16 | 32 | 32 | 8 | | 64 | 32 | 64 | 64 |
| Example 27 | 32 | 32 | 16 | 16 | 8 | | 32 | 32 | 32 | 64 |
| Example 28 | 4 | 4 | 4 | 4 | 1 | | 4 | 8 | 8 | 8 |
| Example 29 | 32 | 32 | 32 | 32 | 16 | | 32 | 32 | 64 | 64 |
| Example 30 | 8 | 16 | 16 | 8 | 4 | | 32 | 32 | 64 | 64 |
| Example 31 | 32 | 32 | 32 | 16 | 8 | | 64 | 64 | 128 | 128 |
| Example 32 | 16 | 16 | 16 | 16 | 8 | | 4 | 8 | 8 | 8 |
| Example 33 | 32 | 32 | 64 | 32 | 16 | | 16 | 16 | 32 | 16 |
| Example 34 | 32 | 16 | 32 | 32 | 8 | | 32 | 32 | 32 | 32 |
| Example 35 | 8 | 8 | 16 | 8 | 2 | | 16 | 16 | 16 | 16 |
| Example 36 | >128 | 128 | >128 | >128 | 128 | | >128 | >128 | >128 | >128 |
| Example 37 | 16 | 16 | 16 | 32 | 4 | | 16 | 16 | 16 | 16 |
| Example 38 | 32 | 32 | 64 | 32 | 32 | | 128 | 128 | >128 | 128 |
| Example 39 | 16 | 8 | 16 | 8 | 4 | | 16 | 16 | 16 | 16 |
| Example 40 | 64 | 32 | 128 | 64 | 32 | | 128 | 128 | >128 | >128 |
| Example 41 | 64 | 64 | >64 | 64 | 32 | | 64 | 64 | >64 | 64 |
| Example 42 | 8 | 16 | 16 | 16 | 4 | | 8 | 8 | 8 | 8 |
| Example 44 | 16 | 16 | 32 | 16 | 4 | | 16 | 16 | 16 | 16 |
| Example 45 | 16 | 16 | 32 | 32 | 4 | | 16 | 16 | 32 | 16 |
| Example 46 | 8 | 8 | 8 | 8 | 1 | | 8 | 16 | 16 | 16 |
| Example 47 | 2 | 2 | 8 | 4 | 1 | | 4 | 32 | 32 | 8 |
| Example 48 | 16 | 32 | 32 | 16 | 8 | | 64 | 64 | >64 | 64 |
| Example 49 | 4 | 8 | 8 | 8 | 2 | | 16 | 16 | 16 | 2 |
| Example 51 | 16 | 4 | 8 | 8 | 8 | | 64 | >64 | >64 | >64 |
| Example 52 | 8 | 8 | 16 | 8 | 1 | | 32 | 32 | 32 | 32 |
| Example 53 | 1 | 1 | 4 | 1 | 1 | | 8 | 8 | 8 | 8 |
| Example 53a | 64 | 32 | 64 | 64 | 64 | | >128 | >128 | >128 | >128 |
| Example 54 | >128 | 128 | >128 | >128 | >128 | | >128 | >128 | >128 | >128 |

TABLE 2-continued

| EXAMPLE NUMBER | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) | Escherichia coli (GC 4559) | Escherichia coli (GC 4560) | Escherichia coli (ATCC 25922) |
|---|---|---|---|---|---|---|---|---|---|---|---|
| Example 3 | >128 | >128 | | >128 | >128 | >128 | >128 | >128 | >128 | 64 | >128 |
| Example 6 | >128 | >128 | | >128 | >128 | >128 | >128 | >128 | >128 | >128 | >128 |
| Example 8 | >128 | >128 | >64 | >128 | >128 | >128 | >128 | >128 | >128 | >128 | >128 |
| Example 10 | >64 | >64 | >64 | >64 | >64 | >64 | >64 | >64 | >64 | >64 | >64 |
| Example 12 | >128 | >128 | >128 | >128 | >128 | >128 | >128 | 128 | >128 | 128 | >128 |
| Example 13 | 64 | >64 | >64 | >64 | 64 | 64 | 64 | 64 | >64 | 32 | >64 |
| Example 14 | >128 | >128 | >128 | >128 | 64 | >128 | >128 | 128 | >128 | 128 | >128 |
| Example 15 | >128 | >128 | >128 | >128 | >128 | >128 | >128 | 128 | >128 | 128 | >128 |
| Example 16 | 64 | >128 | >128 | >128 | 128 | >128 | 16 | 128 | 32 | 8 | 32 |
| Example 17 | >64 | >64 | >64 | >64 | >64 | 64 | 64 | 64 | 32 | 16 | 64 |
| Example 18 | 128 | >128 | >128 | >128 | >128 | >128 | 64 | 128 | 32 | 16 | 64 |
| Example 19 | >128 | >128 | >128 | >128 | >128 | >128 | 128 | 128 | 128 | 128 | 128 |
| Example 22 | >128 | >128 | >128 | >128 | >128 | >128 | 64 | >128 | >128 | >128 | >128 |
| Example 24 | 32 | >64 | >64 | 64 | 64 | 64 | 32 | 64 | >64 | 32 | >64 |
| Example 25 | >128 | >128 | >128 | >128 | >128 | >128 | 128 | 128 | >128 | >128 | >128 |
| Example 26 | 32 | 64 | 32 | 32 | 32 | 64 | 8 | 32 | 64 | 16 | 64 |
| Example 27 | 16 | 32 | 32 | 32 | 32 | 64 | 8 | 16 | 32 | 8 | 32 |
| Example 28 | 4 | 8 | 8 | 8 | 8 | 8 | 4 | 4 | 64 | 8 | 64 |
| Example 29 | 16 | 32 | 32 | 32 | 16 | 64 | 8 | 16 | 16 | 4 | 16 |
| Example 30 | 16 | 64 | 32 | 64 | 32 | 64 | 8 | 16 | 32 | 8 | 32 |
| Example 31 | 16 | 128 | 64 | 64 | 32 | 4 | 4 | 8 | >128 | 32 | >128 |
| Example 32 | 8 | 4 | 4 | 8 | 4 | 8 | 2 | 4 | 16 | 4 | 16 |
| Example 33 | 16 | 16 | 16 | 32 | 8 | 64 | 4 | 4 | 64 | 16 | 64 |
| Example 34 | 32 | 32 | 64 | 64 | 32 | 64 | 8 | 16 | 64 | 16 | 64 |
| Example 35 | 8 | 32 | 16 | 16 | 8 | 32 | 4 | 8 | 16 | 16 | 16 |
| Example 36 | 128 | >128 | >128 | >128 | >128 | >128 | 128 | 128 | >128 | 64 | >128 |
| Example 37 | 4 | 16 | 16 | 16 | 8 | 16 | 4 | 8 | 128 | 4 | >128 |
| Example 38 | 64 | 128 | 128 | 128 | 128 | 128 | 32 | 64 | >128 | 4 | 128 |
| Example 39 | 8 | 32 | 16 | 16 | 8 | 32 | 8 | 8 | 64 | 32 | 64 |
| Example 40 | 64 | >128 | 128 | 128 | 64 | 128 | 16 | 64 | 128 | 16 | 128 |
| Example 41 | 64 | 64 | >64 | 64 | 64 | 64 | 64 | 64 | 32 | 16 | 32 |
| Example 42 | 8 | 8 | 8 | 8 | 4 | 16 | 2 | 4 | >64 | 1 | >64 |
| Example 44 | 8 | 32 | 16 | 16 | 8 | 32 | 8 | 4 | >64 | 64 | >64 |
| Example 45 | 16 | 16 | 16 | 32 | 16 | 32 | 4 | 8 | 16 | 4 | 16 |
| Example 46 | 4 | 16 | 16 | 8 | 4 | 16 | 4 | 4 | 64 | 16 | 64 |
| Example 47 | 4 | 64 | 32 | 8 | 4 | 16 | 4 | 2 | >64 | 32 | >64 |
| Example 48 | 16 | 64 | 64 | 64 | 16 | 64 | 16 | 8 | 32 | 4 | 32 |
| Example 49 | 4 | 16 | 16 | 16 | 8 | 32 | 4 | 4 | 8 | 4 | 16 |
| Example 51 | >64 | >64 | >64 | >64 | >64 | >64 | 2 | 64 | 64 | 8 | >64 |
| Example 52 | 16 | 64 | 32 | 64 | 16 | 32 | 16 | 32 | 64 | 16 | 64 |
| Example 53 | 4 | 16 | 4 | 8 | 2 | 8 | 2 | 4 | 128 | 4 | 128 |
| Example 53a | >128 | >128 | >128 | >128 | >128 | >128 | >128 | >128 | >128 | >128 | >128 |
| Example 54 | >128 | >128 | >128 | >128 | >128 | >128 | 128 | 128 | >128 | >128 | >128 |

TABLE 2-continued

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus SMITH (GC 4536) |
|---|---|---|---|---|---|---|---|---|---|---|
| Example 54a | >128 | >128 | >128 | | >128 | >128 | >128 | >128 | >128 | |
| Example 58 | 8 | 16 | 32 | | 16 | 16 | 16 | 8 | 16 | |
| Example 59 | >128 | >128 | >128 | | >128 | >128 | >128 | >128 | >128 | |
| Example 60 | >128 | >128 | >128 | | >128 | >128 | >128 | >128 | >128 | |
| Example 60a | >128 | >128 | >128 | | >128 | >128 | >128 | >128 | >128 | |
| Example 61 | >128 | >128 | 128 | | >128 | >128 | >128 | >128 | >128 | |
| Example 62 | >128 | >128 | >128 | | >128 | >128 | >128 | >128 | >128 | |
| Example 64 | >128 | >128 | >128 | | >128 | >128 | >128 | >128 | >128 | |
| Example 65 | >128 | >128 | >128 | | >128 | >128 | >128 | >128 | >128 | |
| Example 66 | 16 | 8 | 8 | | 8 | 8 | 8 | 4 | 8 | |
| Example 66a | >128 | >128 | >128 | | >128 | >128 | >128 | >128 | >128 | |
| Example 67 | >128 | >128 | >128 | | >128 | >128 | >128 | >128 | >128 | |
| Example 69 | >128 | >128 | >128 | | >128 | >128 | >128 | >128 | >128 | |
| Example 71 | >128 | >128 | >128 | | >128 | >128 | >128 | >128 | >128 | |
| Example 72 | >128 | >128 | >128 | | >128 | >128 | >128 | >128 | >128 | |
| Example 73 | >128 | >128 | >128 | | >128 | >128 | >128 | >128 | >128 | |
| Example 74 | >128 | >128 | >128 | | >128 | >128 | >128 | >128 | >128 | |
| Example 76 | 4-8 | 2-8 | 2-8 | | 2-4 | 2-8 | 4-8 | 2-8 | 2-8 | |
| Example 77 | 16 | 8-16 | 16 | | 4-8 | 8-16 | 16 | 8 | 8-16 | |
| Example 78 | 8 | 8 | 8 | | 8 | 8 | 8 | 8 | 8 | |
| Example 79 | 8 | 4 | 4 | | 4 | 4 | 4 | 4 | 4 | |
| Example 80 | 32 | 32 | 64 | | 32 | 32 | 32 | 32 | 32 | |
| Example 81 | >128 | >128 | >128 | | >128 | >128 | >128 | >128 | >128 | |
| Example 82 | 16 | 8 | 16 | | 8 | 16 | 16 | 8 | 8 | |
| Example 83 | 4 | 4 | 4 | | 2 | 4 | 4 | 2 | 2 | |
| Example 84 | 8 | 8 | 8 | | 4 | 8 | 8 | 8 | 8 | |
| Example 89 | 64 | 64 | 64 | | 64 | 64 | 64 | 64 | 64 | |
| Example 92 | >128 | >128 | >128 | | >128 | >128 | >128 | >128 | >128 | |
| Example 93 | >128 | >128 | >128 | | >128 | >128 | >128 | >128 | >128 | |
| Example 94 | >64 | >64 | >64 | >64 | >64 | >64 | >64 | >64 | >64 | >64 |
| Example 95 | 4 | | | 8 | | | | | 4 | 4 |
| Example 95a | 4 | | | 2 | | | | | | 1 |
| Example 95b | 1 | | | | | | | | | |
| Example 96c | 0.5 | | | | 0.5 | 1 | 1 | 0.5 | 1 | |
| Example 96 | >128 | | | >64 | >128 | >128 | >128 | >128 | >128 | |
| Example 96a | >128 | | | 2 | 128 | >128 | >128 | >128 | >128 | |
| Example 96b | 2 | | | 1 | 1 | 2 | 2 | 1 | 1 | |
| Example 97 | >64 | | | 16 | | | | | >64 | >64 |
| Example 97a | 2 | | | 4 | | | | | 1 | 0.5 |
| Example 97b | 1 | | | | | | | | 1 | 0.5 |
| Example 98b | 16 | | | | | | | | 16 | 8 |
| Example 98c | 2 | | | | | | | | 2 | 2 |
| Example 99b | 4 | | | | 4 | 4 | 4 | 4 | 4 | |

TABLE 2-continued

| EXAMPLE NUMBER | Staphylococcus aureus SMITH (GC 4543) | Staphylococcus haemolyticus (GC 4546) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|
| Example 54a | >128 | 128 | | | 128 | >128 | >128 | >128 | >128 | |
| Example 58 | 4 | 4 | | | 4 | 4 | 4 | 8 | | |
| Example 59 | >128 | >128 | | | >128 | >128 | >128 | >128 | >128 | |
| Example 60 | >128 | >128 | | | >128 | >128 | >128 | >128 | >128 | |
| Example 60a | >128 | >128 | | | >128 | >128 | >128 | >128 | >128 | |
| Example 61 | >128 | >128 | | | >128 | >128 | >128 | >128 | >128 | |
| Example 62 | >128 | >128 | | | >128 | 128 | 128 | >128 | >128 | |
| Example 64 | >128 | >128 | | | >128 | >128 | >128 | >128 | >128 | |
| Example 65 | 8 | 4 | | | 4 | 8 | 4 | 8 | 4 | |
| Example 66 | >128 | >128 | | | >128 | >128 | >128 | >128 | >128 | |
| Example 66a | >128 | 128 | | | 128 | >128 | >128 | >128 | >128 | |
| Example 67 | >128 | >128 | | | >128 | >128 | >128 | >128 | >128 | |
| Example 69 | >128 | >128 | | | >128 | >128 | >128 | >128 | >128 | |
| Example 71 | >128 | >128 | | | >128 | >128 | >128 | >128 | >128 | |
| Example 72 | >128 | >128 | | | >128 | >128 | >128 | >128 | >128 | |
| Example 73 | >128 | >128 | | | >128 | >128 | >128 | >128 | >128 | |
| Example 74 | >128 | >128 | | | >128 | >128 | >128 | >128 | >128 | |
| Example 76 | 1-4 | 2-4 | | | 2-4 | 2-4 | 2-4 | 2-8 | 0.5-2 | |
| Example 77 | 8 | 4-8 | | | 4 | 4 | 4-8 | 8 | 2 | |
| Example 78 | 4 | 4 | | | 4 | 4 | 8 | 8 | 2 | |
| Example 79 | 4 | 4 | | | 4 | 4 | 2 | 4 | 4 | |
| Example 80 | 32 | 32 | | | 32 | 32 | 32 | 32 | 8 | |
| Example 81 | >128 | >128 | | | >128 | >128 | >128 | >128 | >128 | |
| Example 82 | 8 | 4 | | | 4 | 4 | 4 | 8 | | |
| Example 83 | 2 | 2 | | | 2 | 1 | 2 | 2 | | |
| Example 84 | 4 | 4 | | | 4 | 4 | 4 | 4 | | |
| Example 89 | 64 | 32 | | | 32 | 64 | 64 | 64 | 2 | |
| Example 92 | >128 | >128 | | | >128 | >128 | >128 | >128 | 32 | |
| Example 93 | >128 | >128 | | | >128 | >128 | >128 | >128 | | |
| Example 94 | >64 | >64 | | | >64 | >64 | >64 | >64 | | |
| Example 95 | | | >64 | >64 | 4 | | | | | |
| Example 95a | | | 8 | 4 | | | | | | |
| Example 95b | | | 2 | 1 | 1 | 0.25 | 1 | 1 | | 0.5 |
| Example 96c | 0.5 | 0.5 | | | >128 | >128 | >128 | >128 | | 128 |
| Example 96 | >128 | >128 | | | 128 | >128 | 64 | 128 | | 64 |
| Example 96a | >128 | 128 | | | 128 | >128 | 64 | 128 | | 64 |
| Example 96b | 2 | 1 | | | 1 | 0.5 | 0.5 | 2 | | 0.5 |
| Example 97 | | | >64 | >64 | >64 | | | | | |
| Example 97a | | | 4 | 2 | 2 | | | | | |
| Example 97b | | | 1 | 1 | 1 | | | | | |
| Example 98b | | | 16 | 8 | 8 | | | | | |
| Example 98c | | | 2 | 1 | 1 | | | | | |
| Example 99b | 4 | 4 | | | 4 | 4 | 2 | 8 | 2 | 2 |

TABLE 2-continued

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) | Enterococcus faecalis (GC 4552) |
|---|---|---|---|---|---|---|---|---|---|---|
| Example 54a | >128 | 128 | >128 | >128 | >128 | | >128 | >128 | >128 | >128 |
| Example 58 | 16 | 8 | 16 | 8 | 8 | | 64 | 64 | 64 | 64 |
| Example 59 | >128 | 64 | 128 | 128 | >128 | | >128 | >128 | >128 | >128 |
| Example 60 | >128 | 64 | 128 | 128 | >128 | | >128 | >128 | >128 | >128 |
| Example 60a | >128 | 64 | 128 | >128 | >128 | | >128 | >128 | >128 | >128 |
| Example 61 | 128 | 64 | 64 | 128 | 128 | | 128 | 128 | 128 | 128 |
| Example 62 | >128 | 64 | >128 | >128 | >128 | | >128 | >128 | >128 | >128 |
| Example 64 | >128 | 128 | >128 | >128 | >128 | | >128 | >128 | >128 | >128 |
| Example 65 | >128 | 128 | >128 | 128 | 128 | | >128 | >128 | >128 | >128 |
| Example 66 | 32 | 32 | 64 | 32 | 16 | | 16 | 32 | 32 | 32 |
| Example 66a | >128 | >128 | >128 | >128 | >128 | | >128 | >128 | >128 | >128 |
| Example 67 | 128 | 64 | 128 | 128 | 128 | | 128 | 128 | 128 | 128 |
| Example 69 | 128 | 128 | 128 | 128 | >128 | | >128 | >128 | >128 | >128 |
| Example 71 | >128 | >128 | >128 | >128 | >128 | | >128 | >128 | >128 | >128 |
| Example 72 | 128 | 16 | 64 | 64 | 64 | | 32 | 64 | 64 | 64 |
| Example 73 | >128 | 64 | 128 | 128 | >128 | | >128 | >128 | >128 | >128 |
| Example 74 | 128 | 128 | >128 | >128 | >128 | | >128 | >128 | >128 | >128 |
| Example 76 | 0.25-2 | <0.06-0.25 | 0.25-4 | <0.12-1 | 0.25-2 | | 4-16 | 4-16 | 4-32 | 4-16 |
| Example 77 | 1 | 0.25-0.5 | 2-4 | 2 | 1 | | 16 | 16 | 16 | 16 |
| Example 78 | 1 | 0.25 | 2 | 1 | 0.5 | | 16 | 16 | 16 | 8 |
| Example 79 | 4 | 8 | 8 | 4 | 4 | | 16 | 8 | 32 | 32 |
| Example 80 | 8 | 4 | 16 | 8 | 8 | | 32 | 64 | 64 | 64 |
| Example 81 | 128 | 128 | >128 | >128 | >128 | | >128 | >128 | >128 | >128 |
| Example 82 | 0.5 | 0.25 | 2 | 2 | 1 | | 16 | 16 | 16 | 16 |
| Example 83 | 0.25 | <0.12 | 0.25 | 0.5 | 0.25 | | 4 | 4 | 4 | 4 |
| Example 84 | 1 | 0.12 | 1 | 1 | 0.5 | | 8 | 8 | 8 | 8 |
| Example 89 | 32 | 4 | 8 | 16 | 32 | | 64 | 64 | 64 | 64 |
| Example 92 | >128 | 128 | 128 | 128 | >128 | | >128 | >128 | >128 | >128 |
| Example 93 | >128 | 128 | >128 | >128 | >128 | | >128 | >128 | >128 | >128 |
| Example 94 | >64 | >64 | >64 | >64 | >64 | | >64 | >64 | >64 | >64 |
| Example 95 | | | | | | | >64 | | | >64 |
| Example 95a | | | | | | | 16 | | | 32 |
| Example 95b | | | | | | | 8 | | | 8 |
| Example 96c | <0.06 | <0.06 | | | | <0.06 | 1 | | | 2 |
| Example 96 | >128 | >128 | >128 | | | >128 | >128 | | | >128 |
| Example 96a | 32 | 16 | 16 | | | 32 | >128 | | | >128 |
| Example 96b | 0.25 | 0.25 | <0.12 | | | 0.25 | 4 | | | 8 |
| Example 97 | | | | | | | >64 | | | >64 |
| Example 97a | | | | | | | 4 | | | 16 |
| Example 97b | | | | | | | 2 | | | 4 |
| Example 98b | | | | | | | 64 | | | 128 |
| Example 98c | | | | | <0.5 | | 8 | | | 16 |
| Example 99b | 2 | | | | | 1 | 16 | | | 32 |

TABLE 2-continued

| EXAMPLE NUMBER | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) | Escherichia coli (GC 4559) | Escherichia coli (GC 4560) | Escherichia coli (ATCC 25922) |
|---|---|---|---|---|---|---|---|---|---|---|---|
| Example 54a | >128 | >128 | >128 | >128 | >128 | >128 | 128 | 128 | >128 | >128 | >128 |
| Example 58 | 32 | 64 | 64 | 64 | 32 | 64 | 8 | 32 | 8 | 16 | 16 |
| Example 59 | >128 | >128 | >128 | >128 | >128 | >128 | 128 | 128 | >128 | >128 | >128 |
| Example 60 | 128 | >128 | >128 | >128 | >128 | >128 | 128 | 128 | >128 | 16 | >128 |
| Example 60a | 128 | >128 | >128 | 128 | >128 | 128 | 128 | 128 | 128 | 16 | 128 |
| Example 61 | 128 | 128 | 128 | 128 | >128 | 128 | 128 | 64 | 128 | 8 | 128 |
| Example 62 | >128 | >128 | >128 | >128 | >128 | >128 | 64 | 128 | >128 | 4 | >128 |
| Example 64 | >128 | >128 | >128 | >128 | >128 | >128 | >128 | 128 | >128 | >128 | >128 |
| Example 65 | >128 | >128 | >128 | >128 | >128 | >128 | >128 | 128 | >128 | 32 | >128 |
| Example 66 | 8 | 64 | 32 | 16 | 8 | 32 | 4 | 4 | >128 | 4 | >128 |
| Example 66a | >128 | >128 | >128 | >128 | >128 | >128 | >128 | >128 | >128 | 8 | >128 |
| Example 67 | >128 | >128 | 128 | 128 | >128 | >128 | 128 | 64 | >128 | 32 | >128 |
| Example 69 | >128 | >128 | >128 | >128 | >128 | >128 | >128 | >128 | >128 | >128 | >128 |
| Example 71 | >128 | >128 | >128 | >128 | >128 | >128 | >128 | >128 | >128 | 128 | >128 |
| Example 72 | 64 | >128 | >128 | >128 | >128 | >128 | >128 | 64 | >128 | 32 | >128 |
| Example 73 | >128 | >128 | >128 | >128 | >128 | >128 | >128 | 128 | >128 | 16 | >128 |
| Example 74 | >128 | >128 | >128 | >128 | >128 | >128 | >128 | >128 | >128 | >128 | >128 |
| Example 76 | 4-8 | 4-32 | 4-16 | 4-16 | 2-8 | 4-16 | 1-2 | 2-8 | 64->64 | 2-4 | 64->64 |
| Example 77 | 8 | 16-32 | 16 | 16 | 8 | 16 | 1-2 | 4 | >128 | 4 | >128 |
| Example 78 | 8 | 16 | 16 | 8 | 8 | 16 | 2 | 4 | 128 | 4 | 128 |
| Example 79 | 4 | 16 | 8 | 8 | 8 | 32 | 4 | 2 | >128 | 2 | >128 |
| Example 80 | 32 | 64 | 64 | 64 | 32 | 64 | 16 | 32 | >64 | 8 | >64 |
| Example 81 | 128 | >128 | >128 | >128 | >128 | >128 | 128 | 128 | >128 | 128 | >128 |
| Example 82 | 8 | 32 | 16 | 16 | 8 | 16 | 2 | 4 | >128 | 2 | >128 |
| Example 83 | 2 | 4 | 4 | 4 | 2 | 4 | 1 | 2 | 32 | 4 | 64 |
| Example 84 | 8 | 16 | 8 | 8 | 4 | 8 | 1 | 8 | 64 | 2 | >64 |
| Example 89 | 64 | 64 | 64 | 64 | 64 | 64 | 32 | 32 | >64 | 32 | >64 |
| Example 92 | 128 | >128 | >128 | >128 | >128 | >128 | 128 | 128 | >128 | >128 | >128 |
| Example 93 | >128 | >128 | >128 | >128 | >128 | >128 | 128 | 128 | >128 | >128 | >128 |
| Example 94 | >64 | >64 | >64 | >64 | >64 | >64 | >64 | >64 | >64 | >64 | >64 |
| Example 95 |  |  |  | >64 |  |  |  |  | >64 | 64 |  |
| Example 95a |  |  |  | 32 |  |  |  |  | >64 | 8 |  |
| Example 95b |  |  |  | 4 |  |  |  |  | 64 | 2 |  |
| Example 96c | 2 | 2 |  | 2 | 2 | 2 | 1 | 2 |  | <0.5 | 64 |
| Example 96 | >128 | >128 |  | >128 | >128 | >128 | 128 | >128 |  |  | >128 |
| Example 96a | >128 | >128 |  | >128 | 128 | >128 | 32 | >128 |  |  | >128 |
| Example 96b | 8 | 8 |  | 8 | 8 | 8 | 1 | 4 |  |  | >128 |
| Example 97 |  |  |  | >64 |  |  |  |  | >64 | 2 |  |
| Example 97a |  |  |  | 8 |  |  |  |  | >64 | 1 |  |
| Example 97b |  |  |  | 4 |  |  |  |  | 32 | 1 |  |
| Example 98b |  |  |  | 64 |  |  |  |  | >128 | 2 |  |
| Example 98c |  |  |  | 16 |  |  |  |  | 64 | 0.5 |  |
| Example 99b | 16 | 32 |  | 16 | 16 | 16 | 4 | 16 |  |  | >64 |

TABLE 2-continued

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|---|
| Example 99c | 2 | | | | 2 | 1 | 2 | 1 | 1 | |
| Example 100b | 2 | | | 2 | | | | | 1 | 2 |
| Example 100c | 1 | | | 1 | | | | | 1 | 1 |
| Example 101 | 4 | | | | | | | | 4 | |
| Example 101a | 4 | | | | | | 8 | 4 | 2 | |
| Example 102 | 2 | 1 | 1-2 | | 4 | 8 | 8 | 4 | 4 | |
| Example 103 | 2 | 1 | 2 | | 2 | 4 | 4 | 4 | 2 | |
| Example 104 | 1 | 1 | 1 | | 1 | 0.5-1 | 1-2 | 0.5-1 | 1-2 | |
| Example 104a | 0.5-64 | 0.5 | 0.5 | | 0.5-32 | 2 | 2 | 1 | 2 | |
| Example 104b | 0.5 | 0.5 | 0.5 | | 0.5 | 0.5 | 0.5 | 0.5 | 0.5-64 | |
| Example 105 | 0.25-1 | 0.5-1 | 1-2 | | <0.5-1 | 0.5 | 0.5 | <0.5-1 | 0.5 | |
| Example 106 | 0.5-2 | 0.5-2 | 0.5-2 | | 0.5-2 | 0.5-1 | 0.25-2 | 0.5-2 | <0.5-1 | |
| Example 106a | 2 | 2 | 2 | | 2 | 2 | 4 | 2 | 0.5-2 | |
| Example 106b | 8 | 8 | 8 | | 16 | 8 | 16 | 8 | 2 | |
| Example 107 | 2 | 2 | | | 2 | 1 | 2 | 1 | 8 | |
| Example 108 | 1 | 1 | | | 1 | 1 | 1 | 1 | 1 | |
| Example 109 | 1 | 1 | | | 1 | 1 | 2 | 1 | 1 | |
| Example 110 | 1 | 1 | | | 1 | 1 | 1 | 1 | 1 | |
| Example 111 | 1 | <0.5 | | | 1 | 1 | 0.5-2 | 1-2 | 1 | |
| Example 112 | 0.5-1 | 1 | 1 | | 2 | 1 | 2 | 2 | 1 | |
| Example 113 | 2 | 2 | 2 | | 2 | 2 | 2 | 2 | 2 | |
| Example 114 | 1 | 1 | 1 | | 1 | 4 | 1 | 0.5 | 1 | |
| Example 115 | 8 | 8 | 8 | | 4 | 0.5 | 8 | 8 | 8 | |
| Example 116 | 2 | 2 | 2 | | 2 | 0.5 | 2 | 2 | 2 | |
| Example 117 | 1 | 1 | 1 | | 1 | 1 | 1 | 1 | 1 | |
| Example 118 | <0.5-1 | <0.5-1 | 2 | | 2 | 2 | 2 | 2 | <0.5-1 | |
| Example 119 | 1 | 1 | 1 | | <0.5-1 | <0.5-1 | <0.5-1 | <0.5-1 | 1 | |
| Example 120 | <0.5 | <0.5 | 1 | | <0.5 | <0.5 | <0.5 | <0.5 | <0.5 | |
| Example 121 | 2 | 1 | 1 | | 1 | 1 | 2 | 2 | 1 | |
| Example 122 | 2 | 2 | 2 | | 2 | 2 | 2 | 2 | 2 | |
| Example 123 | 8 | 8 | 8 | | 4 | 4 | 8 | 8 | 8 | |
| Example 124 | 2 | 2 | 2 | | 2 | 1 | 2 | 2 | 2 | |
| Example 125 | 32 | 32 | 32 | | 8 | 32 | 32 | 32 | 32 | |
| Example 126 | 8 | 8 | 8 | | 8 | 8 | 8 | 8 | 8 | |
| Example 127 | 4 | 2 | 2 | | 4 | 2 | 4 | 2 | 2 | |
| Example 128 | 4 | 2 | 2 | | 2 | 2 | 4 | 2 | 2 | |
| Example 129 | 2 | 2 | 2 | | 2 | 2 | 2 | 2 | 4 | |
| Example 130 | 32 | 32 | 32 | | 32 | 32 | 32 | 32 | 32 | |
| Example 132 | 2 | 2 | 4 | | 2 | 2 | 4 | 2 | 4 | |
| Example 133 | 2 | 1 | 2 | | 1 | 2 | 2 | 1 | 2 | |
| Example 135 | 1 | 1 | 1 | | 1 | 1 | 2 | 1 | 1 | |
| Example 136 | 16 | 16 | 32 | | 8 | 16 | 16 | 16 | 16 | |
| Example 137 | 2 | 1-2 | 2-4 | | 1-2 | 1-2 | 2 | <2-4 | 1-2 | |

TABLE 2-continued

| EXAMPLE NUMBER | Staphylococcus aureus-SMITH (GC 4543) | Staphylococcus haemolyticus (GC 4546) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|
| Example 99c | 1 | 1 | | | 1 | 1 | 1 | 2 | | 1 |
| Example 100b | | | 2 | 1 | 1 | | | | | |
| Example 100c | | | 1 | 1 | 1 | | | | | |
| Example 101 | 4 | 4 | | | 2 | 2 | 1 | 8 | 0.5 | 1 |
| Example 101a | 8 | 1 | | | 1 | 1 | 1 | 2 | 1 | 1 |
| Example 102 | 0.5-1 | 0.5-1 | | | 1 | 0.5-1 | 0.5-1 | 1-2 | 0.5 | |
| Example 103 | 1 | 1 | | | 2 | 1 | 1 | 2 | 1 | |
| Example 104 | 0.5-1 | 0.5 | | | 1 | 0.5-1 | 0.5 | 1 | 0.5 | |
| Example 104a | 0.5-64 | 32 | | | 32 | 16-32 | 16-32 | 32 | 16 | |
| Example 104b | 0.5 | 0.5 | | | 4 | 4 | 4 | 8 | 2 | |
| Example 105 | 0.25-1 | <0.5-1 | | | 0.5-1 | <0.5-1 | 0.5-1 | <0.5-1 | 0.5-1 | |
| Example 106 | 0.25-1 | 0.5-1 | | | 0.5-2 | 0.25-1 | <0.12-1 | 0.25-1 | 0.25 | |
| Example 106a | 2 | 2 | | | 2 | 4 | 4 | 2 | | |
| Example 106b | 8 | 4 | | | 8 | 4 | 4 | 8 | | |
| Example 107 | 1 | 1 | | | 1 | 1 | 1 | 1 | | 1 |
| Example 108 | 1 | 1 | | | 1 | <0.5 | 1 | 1 | | 1 |
| Example 109 | 1 | 1 | | | 1 | <0.5 | 1 | 1 | | 1 |
| Example 110 | 1 | 1 | | | 1 | 1 | 0.5 | 1 | | 1 |
| Example 111 | 0.5-1 | 1 | | | 0.5 | 1 | 0.5-1 | 0.5-1 | | 0.5 |
| Example 112 | 1 | 1 | | | 0.5-1 | 0.5-1 | 1 | 1 | 1 | |
| Example 113 | 1 | 1 | | | 1 | 0.5 | 1 | 2 | 0.5 | |
| Example 114 | 2 | 1 | | | 2 | 1 | 2 | 2 | 1 | |
| Example 115 | 1 | 0.5 | | | 1 | 0.5 | 1 | 8 | 0.5 | |
| Example 116 | 1 | 0.5 | | | 1 | 1 | 1 | 2 | 0.5 | |
| Example 117 | 1 | 1 | | | 1 | 1 | 1 | 2 | 0.5 | |
| Example 118 | <0.5-1 | <0.5-<0.5 | | | <0.5-1 | 0.25-0.25 | <0.5-<0.5 | <0.5-1 | 0.25-0.25 | |
| Example 119 | 1 | 1 | | | 1 | 1 | 1 | 1 | <0.5 | |
| Example 120 | <0.5 | <0.5 | | | 1 | <0.5 | <0.5 | <0.5 | 0.5 | |
| Example 121 | 1 | 1 | | | 1 | 0.5 | 0.5 | 2 | 1 | |
| Example 122 | 2 | 1 | | | 2 | 1 | 1 | 2 | 1 | |
| Example 123 | 4 | 8 | | | 8 | 4 | 4 | 8 | 4 | |
| Example 124 | 2 | 2 | | | 2 | 1 | 1 | 2 | 1 | |
| Example 125 | 32 | 32 | | | 32 | 32 | 32 | 32 | 32 | |
| Example 126 | 8 | 8 | | | 8 | 8 | 8 | 8 | 8 | |
| Example 127 | 2 | 2 | | | 4 | 2 | 1 | 2 | 2 | |
| Example 128 | 2 | 2 | | | 2 | 2 | 2 | 4 | 1 | |
| Example 129 | 2 | 2 | | | 32 | 1 | 4 | 4 | 2 | |
| Example 130 | 32 | 32 | | | 32 | 32 | 16 | 32 | 32 | |
| Example 132 | 2 | 1 | | | 2 | 1 | 1 | 2 | 1 | |
| Example 133 | 1 | 1 | | | 1 | <0.5 | 1 | 1 | 1 | |
| Example 135 | 1 | 0.5 | | | 1 | 0.5 | 0.5 | 1 | 0.5 | |
| Example 136 | 16 | 16 | | | 8 | 8 | 4 | 32 | 4 | |
| Example 137 | 1-2 | 1 | | | 1-2 | 0.5-2 | 0.5-1 | 1-2 | 1 | |

TABLE 2-continued

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) | Enterococcus faecalis (GC 4552) |
|---|---|---|---|---|---|---|---|---|---|---|
| Example 99c | <0.5 | | | | | <0.5 | | | | 4 |
| Example 100b | | | | | | | | | | 8 |
| Example 100c | | | | | | | | | | 4 |
| Example 101 | 2 | | | | | 2 | | | | 64 |
| Example 101a | 1 | | <0.5 | | | 1 | | | | 16 |
| Example 102 | <0.12-0.25 | <0.06 | <0.5 | <0.06 | <0.12-0.25 | | 4 | 2-4 | 2-4 | 2-4 |
| Example 103 | 0.5 | 0.12 | 0.12-<0.1 | 0.12 | 0.25 | | 8 | 8 | 8 | 8 |
| Example 104 | <0.12-0.25 | <0.12 | 0.12 | <0.12 | <0.12 | | 2 | 4 | 4 | 4 |
| Example 104a | 0.5 | 0.12-8 | 0.12 | 0.12-16 | 0.12 | | 16 | >0.5 | >0.5 | 64 |
| Example 104b | 0.5 | 0.12 | 0.12 | 0.12 | 0.12 | | 8 | 0.5 | 0.5 | 16 |
| Example 105 | <0.06-0.25 | <0.06 | <0.06 | <0.06 | <0.06-0.12 | | 0.5-2 | 1-2 | 1-2 | 2-4 |
| Example 106 | <0.03 | <0.03 | <0.03 | <0.03 | <0.03 | | 0.5-2 | 1-2 | 1-2 | >0.5 |
| Example 106a | 0.25 | <0.06 | <0.06 | 0.12 | <0.06 | | 4 | 4 | 8 | 0.5 |
| Example 106b | 0.5 | <0.12 | 0.5 | 0.5 | 0.25 | | 8 | 16 | 16 | 4 |
| Example 107 | 0.25 | | <0.5 | | 0.5 | 0.25 | 4 | | | 8 |
| Example 108 | <0.5 | | <0.5 | | <0.12 | <0.5 | 2 | | | 4 |
| Example 109 | <0.5 | | <0.5 | | <0.5 | <0.5 | 2 | | | 2 |
| Example 110 | <0.5 | | 0.5 | | <0.5 | <0.5 | 2 | | | 2 |
| Example 111 | 1 | | 0.5 | 1 | 0.5 | 0.5 | 1 | | | 4 |
| Example 112 | <0.12 | <0.06 | <0.12 | <0.06 | <0.12 | | 1-2 | 2 | 2 | 2 |
| Example 113 | 0.12 | 0.06 | 0.06 | 0.12 | 0.06 | | 4 | 4 | 2 | 2 |
| Example 114 | 0.5 | 0.06 | 0.25 | <0.06 | 0.5 | | 4 | 4 | 8 | 4 |
| Example 115 | 0.25 | 0.06 | 0.12 | <0.06 | 0.25 | | 2 | 4 | 2 | 2 |
| Example 116 | 0.25 | <0.06 | <0.06 | <0.06 | 0.25 | | 2 | 2 | 2 | 2 |
| Example 117 | 0.25 | <0.06 | 0.12 | <0.06 | <0.06 | | 2 | 4 | 4 | 4 |
| Example 118 | <0.06 | <0.06 | <0.06 | <0.06 | <0.5 | | <0.5-2 | 1-2 | 1-2 | 1-2 |
| Example 119 | <0.5 | 0.5 | 1 | 0.5 | 0.5 | | 2 | 2 | >64 | 2 |
| Example 120 | <0.5 | <0.5 | <0.5 | <0.5 | <0.5 | | 1 | 1 | 1 | 1 |
| Example 121 | 0.25 | <0.06 | <0.06 | <0.06 | 0.25 | | 2 | 4 | 2 | 2 |
| Example 122 | 0.12 | <0.06 | 0.12 | <0.06 | <0.06 | | 1 | 2 | 2 | 2 |
| Example 123 | 2 | 1 | 2 | 1 | 0.5 | | 8 | 16 | 16 | 8 |
| Example 124 | 1 | <0.06 | <0.06 | <0.06 | 0.12 | | 4 | 4 | 4 | 4 |
| Example 125 | 1 | 0.12 | 0.25 | 0.25 | 0.5 | | 32 | 32 | 32 | 32 |
| Example 126 | 1 | <0.06 | <0.06 | <0.06 | 0.12 | | 8 | 8 | 8 | 8 |
| Example 127 | <0.12 | <0.12 | 0.12 | <0.12 | 0.12 | | 4 | 4 | 2 | 4 |
| Example 128 | 0.25 | <0.06 | 0.12 | 0.25 | 0.5 | | 4 | 4 | 4 | 4 |
| Example 129 | <0.06 | <0.06 | <0.06 | <0.06 | <0.06 | | 2 | 2 | 2 | 2 |
| Example 130 | 8 | 1 | 4 | 8 | 16 | | 32 | 32 | 64 | 32 |
| Example 132 | 0.5 | 0.12 | 0.25 | 0.25 | 0.5 | | 8 | 8 | 16 | 8 |
| Example 133 | <0.5 | <0.5 | 4 | <0.5 | <0.5 | | 4 | 4 | 8 | 4 |
| Example 135 | 0.25 | <0.06 | <0.06 | <0.06 | 0.25 | | 2 | 2 | 2 | 2 |
| Example 136 | 8 | 1 | 4 | 2 | 8 | | 64 | >64 | >64 | >64 |
| Example 137 | 0.5 | <0.06 | 0.25 | 0.12 | 0.25 | | 4-8 | 4-8 | 4-8 | 4-8 |

TABLE 2-continued

| EXAMPLE NUMBER | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) | Escherichia coli (GC 4559) | Escherichia coli (GC 4560) | Escherichia coli (ATCC 25922) |
|---|---|---|---|---|---|---|---|---|---|---|---|
| Example 99c | 4 | 4 | | 4 | 4 | 4 | 2 | 4 | | | 64 |
| Example 100b | | | | 8 | | | | | >128 | 0.5 | >64 |
| Example 100c | | | | 4 | | | | | 32 | 0.5 | 64 |
| Example 101 | 32 | 64 | | 32 | 32 | 32 | | 32 | | | 16-64 |
| Example 101a | 16 | 16 | | 16 | 16 | 16 | | 16 | | | 64 |
| Example 102 | 2-4 | 2-4 | 2-4 | 2-4 | 2-4 | 2-4 | 1-2 | 2-4 | 16-32 | 0.5-1 | 16-64 |
| Example 103 | 8 | 8 | 4 | 4 | 4 | 4 | 2 | 8 | 64 | 1 | 64 |
| Example 104 | 4 | 4 | 2 | 2-4 | 2 | 2-4 | 2 | 2-4 | 16-32 | 0.5-1 | 32-64 |
| Example 104a | >0.5 | >0.5 | >64 | >64 | >64 | >64 | 0.5 | >64 | >64 | 0.5-16 | >64 |
| Example 104b | 0.5 | 0.5 | 0.5 | 0.5 | 0.5 | 0.5 | 0.5 | 0.5 | >0.5 | 0.5 | >0.5 |
| Example 105 | 1-2 | 1-2 | 1-2 | 1-2 | 1-2 | 0.5-2 | 1-2 | 1-2 | 32 | 0.5-2 | 16-32 |
| Example 106 | 1-2 | 1-2 | 1-2 | 0.5-2 | 0.5-2 | 0.5-2 | 0.5-2 | 1-2 | 32-64 | 0.5-2 | 32-64 |
| Example 106a | 4 | 8 | 4 | 8 | 4 | 8 | 2 | 4 | 32 | 2 | 32 |
| Example 106b | 8 | 16 | 8 | 8 | 8 | 8 | 4 | 8 | 32 | 8 | 64 |
| Example 107 | 2 | 4 | | 4 | 8 | 4 | 2 | 2 | | | 64 |
| Example 108 | 2 | 2 | | 2 | 2 | 2 | 1 | 2 | | | 32 |
| Example 109 | 4 | 4 | | 4 | 2 | 4 | 1 | 4 | | | 16 |
| Example 110 | 2 | 2 | | 2 | 1 | 2 | 2 | 2 | | | 64 |
| Example 111 | 2 | 2 | | 2 | 4 | 2 | 0.5 | 2 | | | 32 |
| Example 112 | 2-4 | 2 | 2 | 2 | 1-2 | 2 | 0.5-2 | 2 | >16 | 1 | 32 |
| Example 113 | 2 | 2 | 2 | 2 | 2 | 2 | 2 | 2 | 32 | 1 | 32 |
| Example 114 | 8 | 4 | 4 | 4 | 4 | 4 | 2 | 8 | 64 | 1 | 64 |
| Example 115 | 4 | 2 | 2 | 2 | 2 | 2 | 2 | 2 | 64 | 1 | 32 |
| Example 116 | 2 | 2 | 2 | 2 | 2 | 2 | 2 | 2 | 64 | 1 | 32 |
| Example 117 | 4 | 4 | 2 | 2 | 2 | 2 | 2 | 4 | 32 | 1 | 64 |
| Example 118 | 1-2 | 1-2 | 1-2 | 1-2 | 1 | <0.5-1 | <0.5-2 | 1-2 | 16 | 1 | 16-32 |
| Example 119 | 2 | 2 | 2 | 2 | 2 | 2 | 1 | 4 | 32 | 1 | 32 |
| Example 120 | 1 | 1 | 1 | 1 | 4 | 1 | 1 | 1 | 16 | <0.5 | 16 |
| Example 121 | 2 | 2 | 2 | 2 | 2 | 1 | 2 | 4 | 32 | 1 | 32 |
| Example 122 | 4 | 2 | 2 | 2 | 2 | 2 | 2 | 4 | 32 | 2 | 32 |
| Example 123 | 4 | 16 | 8 | 8 | 8 | 8 | 4 | 8 | >64 | 8 | >64 |
| Example 124 | 2 | 4 | 4 | 4 | 4 | 4 | 1 | 0.25 | 32 | 1 | 32 |
| Example 125 | 32 | 32 | 32 | 32 | 32 | 32 | 16 | 32 | >64 | 32 | >64 |
| Example 126 | 8 | 8 | 8 | 8 | 8 | 8 | 8 | 8 | 64 | 8 | 64 |
| Example 127 | 4 | 4 | 4 | 4 | 4 | 4 | 4 | 16 | 32 | 4 | 64 |
| Example 128 | 4 | 4 | 4 | 8 | 8 | 8 | 4 | 4 | >64 | 4 | 32 |
| Example 129 | 2 | 2 | 2 | 2 | 2 | 2 | 2 | 2 | 32 | 2 | 32 |
| Example 130 | 8 | 32 | 32 | 32 | 32 | 64 | 32 | 16 | >64 | 64 | >64 |
| Example 132 | 16 | 8 | 8 | 8 | 8 | 8 | 4 | 16 | 32 | 1 | 64 |
| Example 133 | 8 | 8 | 4 | 8 | 8 | 8 | 2 | 8 | 32 | 8 | 64 |
| Example 135 | 2 | 2 | 2 | 2 | 2 | 2 | 2 | 2 | 32 | <0.5 | 32 |
| Example 136 | >64 | >64 | 64 | >64 | >64 | 64 | 8 | 64 | >64 | 0.5 | >64 |
| Example 137 | 4-8 | 4-8 | 4 | 4-8 | 4-8 | 4-8 | 2-4 | 4-8 | 32-64 | 1 | 64 |

TABLE 2-continued

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|---|
| Example 137a | 32 | 32 | 32 | | 16 | 32 | 32 | 32 | 32 | |
| Example 137b | 16 | 16 | 16 | | 8 | 16 | 16 | 16 | 16 | |
| Example 138 | 2 | 2 | 2 | | 2 | 2 | 2 | 2 | 2 | |
| Example 140 | 1 | 1 | <0.5 | | 1 | 1 | 1 | <0.5 | 1 | |
| Example 141 | >64 | >64 | >64 | | >64 | >64 | >64 | >64 | >64 | |
| Example 143 | 2-4 | 2-4 | 4-8 | | 2-4 | 1-4 | 2-8 | 2-4 | 2-4 | |
| Example 144 | 1 | 1 | 1 | | 0.5 | 0.5 | 4 | 1 | 2 | |
| Example 145 | <0.5 | 1 | 1 | | <0.5 | <0.5 | 1 | 1 | 2 | |
| Example 146 | 8 | 8 | 8 | | 8 | 4 | 8 | 8 | 8 | |
| Example 147 | <0.5-<0.5 | 0.5 | 0.5 | | <0.5-<0.5 | 0.5-1 | 0.5-1 | 0.5-1 | <0.5-<0.5 | |
| Example 149 | 2 | 2 | 4 | | 2 | 2 | 2 | 2 | 2 | |
| Example 150 | 4 | 2 | 8 | | 2 | 2 | 2 | 2 | 2 | |
| Example 150a | 32 | 32 | 32 | | 16 | 32 | 32 | 16 | 32 | |
| Example 151 | 8 | 8 | 16 | | 4 | 8 | 8 | 4 | 8 | |
| Example 152 | 16 | 16 | 32 | | 16 | 16 | 16 | 8 | 16 | |
| Example 153 | 2 | 2 | 4 | | 2 | 2 | 2 | 2 | 2 | |
| Example 154 | 1 | 1 | 2 | | 1 | 1 | 2 | 1 | 1 | |
| Example 155 | <0.5-<0.5 | 0.5 | 0.5 | | <0.5-<0.5 | <0.5-<0.5 | <0.5-<0.5 | 0.5-1 | <0.5-<0.5 | |
| Example 156 | 2 | 2 | 4 | | 2 | 2 | 2 | 2 | 2 | |
| Example 157 | 32 | 16 | 32 | | 16 | 32 | 32 | 16 | 32 | |
| Example 158 | 2 | 1 | 2 | | 1 | 1 | 2 | 2 | 2 | |
| Example 161 | 8 | 8 | 8 | | 4 | 4 | 8 | 4 | 4 | |
| Example 162 | 16 | 32 | 16 | | 16 | 16 | 16 | 16 | 16 | |
| Example 163 | 4 | 8 | 8 | | 4 | 4 | 8 | 8 | 4 | |
| Example 164 | 4 | 16 | 8 | | 8 | 16 | 8 | 8 | 8 | |
| Example 164a | 8 | 8 | 8 | | 8 | 16 | 8 | 8 | 8 | |
| Example 165 | 16 | 32 | 16 | | 16 | 16 | 16 | 16 | 16 | |
| Example 166 | 8 | | | | 8 | | | | 8 | |
| Example 167 | 16 | 16 | 16 | | 8 | 16 | 16 | 16 | 16 | |
| Example 168 | 1 | 1 | 1 | | 1 | 1 | 2 | 1 | 1 | |
| Example 169 | 32 | 32 | >64 | | 32 | 32 | 32 | 32 | 32 | |
| Example 170 | 2 | 4 | 1 | | 2 | 4 | 2 | 4 | 4 | |
| Example 172 | 8 | 4 | 4 | | 4 | 2 | 8 | 2 | 4 | |
| Example 173 | 2 | 0.5 | 1 | | 0.5 | 0.5 | 2 | 1 | 1 | |
| Example 174 | 1 | 2 | 2 | | 2 | 2 | 2 | 2 | 2 | |
| Example 175 | 4 | 4 | 4 | | 4 | 4 | 4 | 4 | 4 | |
| Example 177 | 2 | 4 | 4 | | 4 | 4 | 4 | 4 | 4 | |
| Example 178 | 4 | 8 | 4 | | 8 | 8 | 8 | 4 | 16 | |
| Example 179 | 32 | 32 | 32 | | 32 | 32 | 32 | 32 | 32 | |
| Example 180 | 2 | 1 | 2 | | 2 | 2 | 2 | 2 | 2 | |
| Example 181 | 4 | 4 | 4 | | 4 | 4 | 4 | 4 | 4 | |
| Example 182 | >64 | >64 | >64 | | >64 | >64 | >64 | >64 | >64 | |
| Example 183 | 8 | 2 | 2 | | 8 | 4 | 4 | 4 | 4 | |

TABLE 2-continued

| EXAMPLE NUMBER | Staphylococcus aureus-SMITH (GC 4543) | Staphylococcus haemolyticus (GC 4546) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|
| Example 137a | 16 | 16 | | | 16 | 8 | 8 | 16 | 8 | |
| Example 137b | 8 | 8 | | | 8 | 4 | 8 | 8 | 4 | |
| Example 138 | 1 | 2 | | | 4 | 1 | 1 | 2 | 2 | |
| Example 140 | 1 | 1 | | | <0.5 | <0.5 | <0.5 | <0.5 | <0.5 | |
| Example 141 | >64 | >64 | | | >64 | >64 | >64 | >64 | >64 | |
| Example 143 | 2-4 | 0.5-2 | | | 1-2 | 1-2 | 1 | 2-4 | 1-2 | |
| Example 144 | 1 | 1 | | | 1 | 0.25 | 0.12 | 0.5 | 0.25 | |
| Example 145 | <0.5 | <0.5 | | | 1 | <0.5 | 1 | <0.5 | 0.5 | |
| Example 146 | 8 | 8 | | | 8 | 4 | 4 | 8 | 4 | |
| Example 147 | 0.5-1 | 1-2 | | | 1-2 | <0.5-1 | <0.5-1 | 1 | 2 | 1 |
| Example 149 | 2 | 1 | | | 1 | 1 | 1 | 1 | 1 | |
| Example 150 | 2 | 1 | | | 2 | 1 | 1 | 2 | 1 | |
| Example 150a | 16 | 16 | | | 16 | 8 | 8 | 32 | 8 | |
| Example 151 | 8 | 2 | | | 4 | 4 | 2 | 8 | 2 | |
| Example 152 | 8 | 8 | | | 8 | 8 | 8 | 16 | 8 | |
| Example 153 | 1 | 1 | | | 1 | 0.5 | 0.5 | 2 | 0.5 | |
| Example 154 | 2 | 2 | | | 2 | 0.5 | 0.25 | 2 | 1 | |
| Example 155 | <0.5-<0.5 | <0.5-1 | | | <0.5-2 | <0.5-1 | <0.5-1 | <0.5-1 | 1 | <0.5 |
| Example 156 | 2 | 2 | | | 2 | 1 | 1 | 2 | 1 | |
| Example 157 | 16 | 16 | | | 16 | 8 | 8 | 32 | 4 | |
| Example 158 | 2 | 0.5 | | | 2 | 1 | 1 | 2 | 1 | |
| Example 161 | 4 | 4 | | | 4 | 2 | 2 | 8 | 2 | |
| Example 162 | 16 | 16 | | | 16 | 8 | 8 | 8 | 8 | |
| Example 163 | 1 | 4 | | | 8 | 1 | 4 | 2 | 2 | |
| Example 164 | 4 | 4 | | | 4 | 0.5 | 0.5 | 4 | 1 | |
| Example 164a | 8 | 4 | | | 8 | 4 | 4 | 8 | 4 | |
| Example 165 | 16 | 16 | | | 16 | 8 | 8 | 16 | 8 | |
| Example 166 | 4 | | | | 4 | 8 | 4 | | 4 | |
| Example 167 | 16 | 16 | | | 8 | 8 | 8 | 16 | 8 | |
| Example 168 | 1 | 0.5 | | | 2 | 0.5 | 0.5 | 1 | | |
| Example 169 | 32 | 32 | | | 32 | 32 | 16 | >64 | | |
| Example 170 | 4 | 8 | | | 4 | 1 | 2 | 1 | 8 | |
| Example 172 | 8 | 8 | | | 8 | 2 | 2 | 4 | 1 | |
| Example 173 | 0.5 | 1 | | | 2 | 2 | 2 | 0.5 | 2 | |
| Example 174 | 1 | 2 | | | 2 | 0.5 | 0.25 | 1 | 0.5 | |
| Example 175 | 4 | 4 | | | 8 | 0.5 | 1 | 4 | 0.5 | |
| Example 177 | 2 | 4 | | | 4 | 2 | 2 | 4 | 2 | |
| Example 178 | 4 | 2 | | | 32 | 1 | 2 | 4 | 1 | |
| Example 179 | 32 | 32 | | | 32 | 0.5 | 2 | 32 | 2 | |
| Example 180 | 2 | 2 | | | 2 | 32 | 16 | 1 | 32 | |
| Example 181 | 4 | 8 | | | 8 | 1 | 1 | 2 | 0.5 | |
| Example 182 | >64 | >64 | | | >64 | >64 | >64 | >64 | >64 | |
| Example 183 | 4 | 8 | | | 4 | 2 | 4 | 4 | 2 | |

TABLE 2-continued

| EXAMPLE NUMBER | Streptococcus agalactiae (GC 4564) | Streptococcus pneumoniae (GC 1894) | Streptococcus pneumoniae (GC 4565) | Streptococcus pneumoniae (AITCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) | Enterococcus faecalis (GC 4552) |
|---|---|---|---|---|---|---|---|---|---|---|
| Example 137a | 16 | 4 | 16 | 8 | 16 | | >64 | >64 | >64 | >64 |
| Example 137b | 4 | 1 | 2 | 2 | 4 | | 32 | 32 | 64 | 32 |
| Example 138 | 0.12 | <0.06 | <0.06 | <0.06 | 0.25 | | 4 | 8 | 4 | 4 |
| Example 140 | <0.5 | <0.5 | <0.5 | <0.5 | <0.5 | | <1 | 1 | 1 | 1 |
| Example 141 | >64 | >64 | >64 | >64 | >64 | | >64 | >64 | >64 | >64 |
| Example 143 | 0.5-1 | <0.06-0.12 | 0.25-0.5 | 0.12-0.5 | 0.25-1 | | 4-16 | 8 | 8-16 | 8-16 |
| Example 144 | <0.06 | <0.06 | <0.06 | <0.06 | <0.06 | | 2 | 2 | 4 | 2 |
| Example 145 | <0.5 | <0.5 | <0.5 | <0.5 | 1 | | <0.5 | 1 | 1 | 1 |
| Example 146 | 0.12 | <0.06 | <0.06 | <0.06 | <0.06 | | 8 | 8 | 8 | 8 |
| Example 147 | <0.12 | | <0.5-<0.5 | | >0.12 | <0.5 | 0.5-1 | 0.5 | 16 | 0.5-1 |
| Example 149 | 1 | <0.5 | 2 | <0.5 | <0.5 | | 8 | 8 | 0.5 | 8 |
| Example 150 | 1 | 0.12 | 0.25 | 0.25 | 0.5 | | 4 | 4 | 8 | 8 |
| Example 150a | 32 | 8 | 16 | 8 | 16 | | >64 | >64 | >64 | >64 |
| Example 151 | 4 | 0.5 | 1 | 1 | 2 | | 16 | 32 | 32 | 32 |
| Example 152 | 8 | 0.5 | 2 | 2 | 4 | | 32 | 32 | 32 | 32 |
| Example 153 | 0.5 | <0.06 | <0.06 | <0.06 | 0.25 | | 4 | 8 | 8 | 8 |
| Example 154 | <0.06 | <0.06 | <0.06 | <0.06 | <0.06 | | 2 | 2 | 2 | 2 |
| Example 155 | <0.12 | 0.12 | <0.5-<0.5 | 0.12 | >0.12 | <0.5 | 0.5-1 | 0.5 | 0.5 | <0.5-<0.5 |
| Example 156 | 0.5 | <0.06 | 0.12 | 0.12 | 0.25 | | 4 | 8 | 8 | 8 |
| Example 157 | 16 | 4 | 4 | 4 | 8 | | 64 | >64 | >64 | >64 |
| Example 158 | 0.25 | <0.06 | <0.06 | 0.12 | 0.25 | | 4 | 4 | 4 | 8 |
| Example 161 | 1 | 0.12 | 0.5 | 0.5 | 1 | | 16 | 16 | 16 | 16 |
| Example 162 | <0.12 | <0.06 | <0.06 | 0.12 | 0.12 | | 16 | 16 | 32 | 16 |
| Example 163 | <0.5 | <0.5 | 1 | <0.5 | <0.5 | | 4 | 4 | 8 | 8 |
| Example 164 | 0.12 | <0.06 | <0.06 | <0.06 | 0.12 | | 4 | 8 | 8 | 8 |
| Example 164a | 1 | 0.25 | 1 | 1 | 0.5 | | 16 | 16 | 16 | 16 |
| Example 165 | 1 | <0.06 | 0.12 | 0.12 | 0.12 | | 16 | 16 | 16 | 16 |
| Example 166 | | | | | | | 32 | | | |
| Example 167 | 2 | 0.25 | 1 | 1 | 1 | | 32 | 32 | 32 | 32 |
| Example 168 | <0.12 | <0.12 | <0.12 | <0.12 | 0.5 | | 2 | 2 | 2 | 2 |
| Example 169 | 32 | 8 | 8 | 8 | 16 | | >64 | >64 | >64 | >64 |
| Example 170 | <0.06 | <0.06 | <0.06 | <0.06 | <0.06 | | 4 | 4 | 4 | 4 |
| Example 172 | <0.06 | <0.06 | <0.06 | <0.06 | 0.12 | | 2 | 2 | 8 | 8 |
| Example 173 | <0.12 | <0.12 | <0.06 | <0.12 | <0.12 | | 2 | 2 | 2 | 2 |
| Example 174 | <0.06 | <0.06 | <0.06 | <0.06 | <0.06 | | 4 | 4 | 2 | 1 |
| Example 175 | 0.12 | <0.06 | <0.06 | <0.06 | <0.06 | | 2 | 4 | 4 | 4 |
| Example 177 | <0.06 | <0.06 | <0.06 | <0.06 | <0.06 | | 4 | 4 | 4 | 4 |
| Example 178 | <0.06 | <0.06 | <0.06 | <0.06 | 0.12 | | 2 | 2 | 2 | 4 |
| Example 179 | 1 | 0.12 | 0.12 | 0.25 | 0.25 | | 32 | 1 | 16 | 4 |
| Example 180 | <0.06 | <0.06 | <0.06 | <0.06 | <0.06 | | 4 | 32 | 32 | 32 |
| Example 181 | <0.06 | <0.06 | <0.06 | <0.06 | 0.5 | | 2 | 4 | 2 | 2 |
| Example 182 | 32 | 8 | 8 | 4 | 64 | | >64 | >64 | >64 | >64 |
| Example 183 | <0.06 | <0.06 | <0.06 | <0.06 | <0.06 | | 8 | 2 | 4 | 8 |

TABLE 2-continued

| EXAMPLE NUMBER | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) | Escherichia coli (GC 4559) | Escherichi coli (GC 4560) | Escherichia coli (ATCC 25922) |
|---|---|---|---|---|---|---|---|---|---|---|---|
| Example 137a | >64 | >64 | >64 | >64 | >64 | >64 | 16 | 64 | >64 | 8 | >64 |
| Example 137b | 32 | 64 | 32 | 32 | 64 | 32 | 8 | 32 | >64 | 4 | >64 |
| Example 138 | 8 | 8 | 4 | 4 | 4 | 8 | 2 | 4 | 64 | 0.5 | 64 |
| Example 140 | 1 | 1 | 1 | <0.5 | 1 | 1 | 1 | 1 | 64 | 1 | 64 |
| Example 141 | >64 | >64 | >64 | >64 | >64 | >64 | 64 | >64 | >64 | >64 | >64 |
| Example 143 | 8-16 | 8-16 | 4-16 | 8-16 | 8-16 | 8-16 | 2-8 | 8-16 | 64 | 1-2 | 64 |
| Example 144 | 4 | 4 | 2 | 2 | 2 | 2 | 2 | 4 | 32 | | 32 |
| Example 145 | 2 | 2 | 1 | 1 | 1 | 1 | 1 | 1 | 32 | <0.5 | 64 |
| Example 146 | 8 | 16 | 8 | 8 | 8 | 8 | 8 | 8 | 64 | | 64 |
| Example 147 | 0.5-1 | 0.5-1 | 0.5 | 0.5-2 | 1-2 | 2 | 1-2 | 0.5-2 | 64 | 0.5-2 | 64-64 |
| Example 149 | 8 | 8 | 8 | 8 | 8 | 8 | 2 | 8 | 64 | <0.5 | >64 |
| Example 150 | 8 | 8 | 8 | 8 | 8 | 8 | 4 | 8 | 32 | 1 | >64 |
| Example 150a | >64 | >64 | >64 | >64 | >64 | >64 | 16 | 64 | >64 | 16 | >64 |
| Example 151 | 32 | 32 | 64 | 32 | 32 | 32 | 8 | 32 | 64 | 2 | 64 |
| Example 152 | 64 | 32 | 32 | 32 | 32 | 32 | 16 | 32 | 64 | 8 | 64 |
| Example 153 | 8 | 8 | 4 | 8 | 4 | 4 | 2 | 8 | 64 | | 64 |
| Example 154 | 2 | 2 | 2 | 2 | 2 | 2 | 2 | 1 | 32 | 2 | 32 |
| Example 155 | <0.5-0.5 | 0.5-1 | 0.5 | 0.5-1 | <0.5-1 | 1-2 | 1-2 | 0.5-1 | >64 | 0.5-2 | >64 |
| Example 156 | 8 | 8 | 8 | 8 | 8 | 8 | 2 | 8 | 32 | 0.5 | 64 |
| Example 157 | >64 | >64 | >64 | >64 | 64 | >64 | 8 | 64 | >64 | | >64 |
| Example 158 | 4 | 4 | 4 | 4 | 4 | 8 | 8 | 4 | 64 | 1 | 64 |
| Example 161 | 16 | 16 | 16 | 16 | 16 | 16 | 2 | 16 | >64 | 2 | >64 |
| Example 162 | 32 | 32 | 16 | 16 | 16 | 32 | 8 | 4 | >64 | 16 | >64 |
| Example 163 | 4 | 4 | 4 | 4 | 4 | 4 | 16 | 4 | >64 | 8 | >64 |
| Example 164 | 8 | 16 | 16 | 8 | 8 | 8 | 8 | 8 | 64 | 4 | 32 |
| Example 164a | 16 | 16 | 16 | 16 | 16 | 16 | 4 | 8 | 32 | 8 | >64 |
| Example 165 | 16 | 32 | 16 | 16 | 16 | 16 | 16 | 16 | >64 | 16 | >64 |
| Example 166 | | | 32 | 32 | 32 | 32 | | 32 | >64 | 2 | >64 |
| Example 167 | 32 | 32 | 32 | 32 | 32 | 32 | 8 | 32 | >128 | 8 | >128 |
| Example 168 | 2 | 2 | 2 | 2 | 2 | 2 | 1 | 2 | 16 | 0.5 | 64 |
| Example 169 | >64 | >64 | >64 | >64 | >64 | >64 | 32 | >64 | >64 | 8 | 64 |
| Example 170 | 4 | 4 | 4 | 4 | 4 | 4 | 4 | 4 | >64 | 4 | >64 |
| Example 172 | 4 | 4 | 2 | 8 | 8 | 8 | 8 | 4 | >64 | 2 | >64 |
| Example 173 | 2 | 2 | 1 | 1 | 1 | 1 | 2 | 1 | 16 | 0.5 | 32 |
| Example 174 | 1 | 1 | 1 | 1 | 1 | 1 | 2 | 2 | 16 | 4 | >64 |
| Example 175 | 4 | 8 | 8 | 4 | 4 | 4 | 4 | 2 | 64 | 4 | >64 |
| Example 177 | 2 | 2 | 1 | 4 | 4 | 4 | 2 | 1 | 64 | 4 | 64 |
| Example 178 | 2 | 2 | 0.5 | 4 | 4 | 4 | 8 | 4 | >64 | 16 | >64 |
| Example 179 | 32 | 32 | 16 | 32 | 32 | 32 | 16 | 16 | 64 | 32 | >64 |
| Example 180 | 2 | 2 | 2 | 4 | 2 | 2 | 2 | 2 | 64 | 2 | >64 |
| Example 181 | 1 | 2 | 2 | 2 | 2 | 4 | 4 | 4 | >64 | 16 | >64 |
| Example 182 | >64 | >64 | >64 | >64 | >64 | >64 | >64 | >64 | >64 | >64 | >64 |
| Example 183 | 4 | 4 | 2 | 8 | 2 | 8 | 4 | 2 | >64 | 4 | >64 |

TABLE 2-continued

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus -SMITH (GC 4536) |
|---|---|---|---|---|---|---|---|---|---|---|
| Example 184 | 32 | 32 | 32 | | 32 | 32 | 32 | 32 | 32 | |
| Example 185 | >64 | >64 | >64 | | >64 | >64 | >64 | >64 | >64 | |
| Example 186 | 2 | 2 | 2 | | 2 | 1 | 2 | 2 | 2 | |
| Example 187 | 64 | 64 | 32 | | 64 | 64 | 64 | 64 | 64 | |
| Example 190 | 16 | 16 | 16 | | 8 | 4 | 16 | 16 | 16 | |
| Example 191 | 8 | 8 | 8 | | 4 | 4 | 8 | 4 | 4 | |
| Example 192 | 4 | 4 | 2 | | 2 | 4 | 2 | 2 | 4 | |
| Example 193 | 1 | 1 | 0.5 | | 0.5 | 0.25 | 1 | 0.5 | 0.5 | |
| Example 194 | 1 | 1 | 1 | | 0.5 | 0.5 | 2 | 1 | 0.5 | |
| Example 195 | 0.5 | 0.5 | 0.5 | | 0.5 | 0.5 | 0.5 | 0.5 | 0.5 | |
| Example 196 | >64 | >64 | >64 | | 64 | >64 | >64 | 64 | >64 | |
| Example 197 | 16 | 64 | 64 | | 16 | 64 | 32 | 32 | 32 | |
| Example 198 | 1 | 0.5 | 0.5 | | 0.5 | 0.25 | 0.5 | 0.5 | 0.5 | |
| Example 199 | 2 | 1 | 2 | | 2 | 1 | 2 | 1 | 2 | |
| Example 200 | 2 | 1 | 2 | | 1 | 1 | 2 | 1 | 1 | |
| Example 201 | 0.25 | 0.5 | 0.5 | | 0.5 | 0.25 | 0.25 | 0.25 | 0.25 | |
| Example 202 | 4 | 4 | 8 | | 4 | 4 | 4 | 4 | 4 | |
| Example 203 | 2 | 2 | 4 | | 1 | 1 | 2 | 1 | 1 | |
| Example 204 | 8 | 4 | 8 | | 4 | 4 | 8 | 4 | 4 | |
| Example 205 | 2 | 2 | 2 | | 2 | 4 | 2 | 4 | 4 | |
| Example 206 | 1 | 1 | 1 | | 1 | 1 | 2 | 1 | 1 | |
| Example 207 | 2 | 2 | 2 | | 1 | 1 | 1 | 1 | 1 | |
| Example 208 | 8 | 2 | 4 | | 8 | 4 | 8 | 4 | 4 | |
| Example 209 | 2 | 4 | 2 | | 2 | 2 | 2 | 2 | 4 | |
| Example 210 | 32 | 32 | 32 | | 32 | 32 | 32 | 32 | 32 | |
| Example 210a | 4 | 8 | 4 | | 4 | 8 | 8 | 4 | 4 | |
| Example 212 | 4 | 4 | 4 | | 2 | 2 | 4 | 2 | 2 | |
| Example 214 | 1 | 32 | 2 | | 2 | 1 | 1 | 2 | 2 | |
| Example 215 | 0.5 | 0.5 | 1 | | 0.5 | 0.5 | 0.5 | 1 | 0.5 | |
| Example 216 | 2 | 2 | 2 | | 1 | 1 | 2 | 1 | 2 | |
| Example 217 | 4 | 4 | 8 | | 4 | 4 | 8 | 4 | 4 | |
| Example 218 | 4 | 4 | 4 | | 4 | 4 | 4 | 4 | 4 | |
| Example 219 | 4 | 4 | 2 | | 4 | 4 | 4 | 4 | 4 | |
| Example 220 | 1 | 1 | 1 | | 1 | 1 | 8 | 2 | 2 | |
| Example 221 | 2 | 2 | 1 | | 2 | 2 | 0.5 | 0.5 | 0.5 | |
| Example 222 | >64 | >64 | >64 | | >64 | >64 | >64 | >64 | >64 | |
| Example 223 | >64 | 64 | >64 | | 64 | 64 | 64 | 64 | >64 | |
| Example 224 | 4 | 2 | 4 | | 1 | 4 | 4 | 2 | 2 | |
| Example 225 | 8 | 4 | 8 | | 4 | 8 | 8 | 4 | 4 | |
| Example 226 | 16 | 16 | 16 | | 8 | 16 | 16 | 16 | 16 | |
| Example 227 | 128 | 128 | >128 | | 128 | 128 | 128 | 128 | 128 | |
| Example 228 | 32 | 32 | 32 | | 32 | 32 | 32 | 32 | 32 | |
| Example 229 | >128 | >128 | >128 | | >128 | >128 | >128 | >128 | >128 | |

TABLE 2-continued

| EXAMPLE NUMBER | Staphylococcus aureus-SMITH (GC 4543) | Staphylococcus haemolyticus (GC 4546) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|
| Example 184 | 32 | 32 | | | 32 | 16 | 32 | 32 | 16 | |
| Example 185 | >64 | >64 | | | >64 | >64 | >64 | >64 | >64 | |
| Example 186 | 2 | 1 | | | 2 | 1 | 1 | 2 | 0.5 | |
| Example 187 | 64 | 128 | | | 128 | 16 | 64 | 32 | 32 | |
| Example 190 | 4 | 8 | | | 8 | 8 | 4 | 16 | 8 | |
| Example 191 | 4 | 4 | | | 8 | 4 | 4 | 4 | 4 | |
| Example 192 | 2 | 1 | | | 2 | 1 | 1 | 4 | 2 | |
| Example 193 | 0.5 | 0.5 | | | 1 | 0.25 | 0.25 | 0.5 | 0.25 | |
| Example 194 | 0.5 | 0.5 | | | 0.5 | 0.5 | 0.5 | 1 | 0.5 | |
| Example 195 | 0.5 | 2 | | | 4 | 2 | 1 | 4 | 2 | |
| Example 196 | >64 | 32 | | | 32 | 64 | 64 | >64 | 64 | |
| Example 197 | 16 | 32 | | | 32 | 8 | 8 | 16 | 4 | |
| Example 198 | 0.5 | 0.5 | | | 1 | >0.12 | 0.5 | 0.5 | | |
| Example 199 | 1 | 1 | | | 2 | 0.5 | 0.5 | 1 | | |
| Example 200 | 1 | 1 | | | 2 | 1 | 1 | 2 | | |
| Example 201 | 0.5 | 0.25 | | | 0.25 | 0.25 | 0.25 | 0.25 | | |
| Example 202 | 4 | 2 | | | 2 | 2 | 4 | 4 | 2 | |
| Example 203 | 2 | 1 | | | 2 | 1 | 1 | 2 | 1 | |
| Example 204 | 4 | 2 | | | 4 | 4 | 2 | 4 | | |
| Example 205 | 2 | 2 | | | 2 | 2 | 1 | 2 | | |
| Example 206 | 1 | 0.5 | | | 1 | 0.5 | 0.5 | 1 | | |
| Example 207 | 1 | 1 | | | 1 | 0.5 | 0.5 | 4 | | |
| Example 208 | 4 | 4 | | | 4 | 4 | 4 | 4 | 4 | |
| Example 209 | 1 | | | | 4 | 1 | 1 | 1 | 2 | |
| Example 210 | 32 | 32 | | | 32 | 32 | 8 | 32 | 32 | |
| Example 210a | 8 | 8 | | | 4 | 4 | 2 | 4 | 4 | |
| Example 212 | 2 | 2 | | | 2 | 2 | 2 | 2 | 1 | |
| Example 214 | 0.5 | 1 | | | 1 | 1 | 0.5 | 1 | | |
| Example 215 | <0.12 | 0.5 | | | 0.5 | 0.5 | <0.12 | 0.5 | 1 | |
| Example 216 | 2 | 2 | | | 2 | 1 | 1 | 2 | | |
| Example 217 | 2 | 1 | | | 4 | 2 | 2 | 8 | | |
| Example 218 | 4 | 4 | | | 4 | 4 | 4 | 8 | 4 | |
| Example 219 | 2 | 2 | | | 2 | 2 | 2 | 4 | 1 | |
| Example 220 | 1 | 0.25 | | | 0.5 | 0.25 | 0.25 | 0.5 | | |
| Example 221 | 2 | 2 | | | 2 | 1 | 1 | 2 | | |
| Example 222 | >64 | >64 | | | >64 | >64 | >64 | >64 | | |
| Example 223 | 64 | 64 | | | 64 | 64 | 64 | 64 | | |
| Example 224 | 2 | 1 | | | 2 | 1 | 1 | 2 | | |
| Example 225 | 4 | 4 | | | 4 | 2 | 2 | 4 | | |
| Example 226 | 8 | 8 | | | 8 | 8 | 16 | 8 | 2 | |
| Example 227 | 128 | 64 | | | 32 | 4 | 32 | 8 | | |
| Example 228 | 32 | 16 | | | 16 | 16 | 16 | 16 | | |
| Example 229 | >128 | >128 | | | >128 | >128 | >128 | >128 | >128 | |

TABLE 2-continued

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) | Enterococcus faecalis (GC 4552) |
|---|---|---|---|---|---|---|---|---|---|---|
| Example 184 | 0.12 | <0.06 | <0.06 | <0.06 | 0.25 | | 32 | 32 | 32 | 32 |
| Example 185 | 1 | <0.06 | <0.06 | 0.12 | 16 | | >64 | >64 | >64 | >64 |
| Example 186 | <0.06 | <0.06 | <0.06 | <0.06 | 0.25 | | 2 | 2 | 2 | 2 |
| Example 187 | <0.12 | <0.12 | <0.12 | <0.12 | 0.5 | | 64 | 16 | 128 | 64 |
| Example 190 | 16 | 4 | 8 | 8 | 16 | | 32 | 32 | 32 | 32 |
| Example 191 | 2 | 0.25 | 2 | 1 | 2 | | 8 | 8 | 8 | 16 |
| Example 192 | 0.5 | <0.06 | 0.5 | 0.25 | 0.5 | | 2 | 4 | 4 | 4 |
| Example 193 | <0.06 | <0.06 | <0.06 | 0.12 | <0.06 | | 1 | 2 | 1 | 1 |
| Example 194 | <0.06 | 0.12 | <0.06 | 0.25 | <0.06 | | 1 | 2 | 1 | 1 |
| Example 195 | 0.5 | 0.12 | 0.12 | 0.12 | 0.12 | | 0.5 | 0.5 | 0.5 | 0.5 |
| Example 196 | >64 | 64 | 64 | 64 | 32 | | >64 | >64 | >64 | >64 |
| Example 197 | 16 | 8 | 8 | 4 | 16 | | >64 | >64 | >64 | >64 |
| Example 198 | <0.12 | <0.12 | <0.12 | <0.12 | <0.12 | | 1 | 1 | 1 | 1 |
| Example 199 | <0.12 | <0.12 | <0.12 | <0.12 | <0.12 | | 2 | 4 | 4 | 4 |
| Example 200 | 0.12 | <0.12 | <0.06 | <0.06 | <0.06 | | 0.5 | 4 | 2 | 2 |
| Example 201 | <0.12 | <0.12 | <0.12 | <0.12 | <0.12 | | 1 | 1 | 1 | 1 |
| Example 202 | 2 | <0.5 | 8 | <0.5 | 1 | | 16 | 16 | 64 | 32 |
| Example 203 | 1 | 0.12 | 0.25 | 0.5 | 0.5 | | 4 | 8 | 8 | 8 |
| Example 204 | 1 | 0.25 | 0.5 | 0.5 | 0.5 | | 16 | 16 | 16 | 16 |
| Example 205 | <0.12 | <0.12 | <0.12 | <0.12 | <0.12 | | 4 | 4 | 2 | 4 |
| Example 206 | 0.25 | <0.12 | <0.12 | <0.12 | 1 | | 2 | 2 | 1 | 2 |
| Example 207 | <0.12 | <0.12 | <0.12 | <0.12 | <0.12 | | 4 | 4 | 2 | 4 |
| Example 208 | 0.12 | 0.12 | <0.06 | <0.06 | 0.12 | | 8 | 8 | 8 | 8 |
| Example 209 | | <0.06 | | <0.06 | | | 4 | | | |
| Example 210 | 0.25 | <0.06 | <0.06 | 0.25 | 2 | | 16 | 8 | 32 | 32 |
| Example 210a | 2 | <0.06 | 0.25 | 0.5 | 1 | | 8 | 8 | 8 | 8 |
| Example 212 | 1 | <0.06 | 0.25 | 0.5 | 1 | | 8 | 8 | 8 | 8 |
| Example 214 | <0.12 | <0.12 | <0.12 | <0.12 | <0.12 | | 2 | 2 | 2 | 2 |
| Example 215 | <0.12 | <0.12 | <0.12 | <0.12 | <0.12 | | 1 | 1 | 1 | 1 |
| Example 216 | 0.5 | <0.06 | 0.25 | 0.25 | 0.5 | | 4 | 4 | 4 | 4 |
| Example 217 | 2 | 0.25 | 0.5 | 1 | 1 | | 16 | 16 | 32 | 16 |
| Example 218 | 0.25 | <0.06 | 0.12 | 0.12 | 0.5 | | 4 | 4 | 4 | 4 |
| Example 219 | 2 | 1 | 2 | 0.5 | 2 | | 8 | 8 | 16 | 8 |
| Example 220 | <0.06 | <0.06 | <0.06 | <0.06 | <0.06 | | 1 | 2 | 2 | 2 |
| Example 221 | <0.12 | <0.12 | <0.12 | <0.12 | <0.12 | | 2 | 2 | 1 | 2 |
| Example 222 | >64 | 32 | 64 | 64 | 64 | | >64 | >64 | >64 | >64 |
| Example 223 | >64 | 32 | >64 | 64 | 64 | | >64 | >64 | >64 | >64 |
| Example 224 | <0.12 | <0.12 | 0.25 | 0.25 | 0.25 | | 4 | 4 | 4 | 4 |
| Example 225 | 0.5 | <0.12 | 1 | 0.5 | 0.5 | | 8 | 16 | 16 | 8 |
| Example 226 | 4 | 0.5 | 4 | 4 | 2 | | 16 | 32 | 32 | 32 |
| Example 227 | 64 | 32 | 64 | 32 | 32 | | 64 | 64 | 128 | 64 |
| Example 228 | 16 | 8 | 8 | 8 | 8 | | 32 | 32 | 32 | 32 |
| Example 229 | >128 | >128 | >128 | >128 | >128 | | >128 | >128 | >128 | >128 |

TABLE 2-continued

| EXAMPLE NUMBER | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) | Escherichia coli (GC 4559) | Escherichia coli (GC 4560) | Escherichia coli (ATCC 25922) |
|---|---|---|---|---|---|---|---|---|---|---|---|
| Example 184 | 16 | 32 | 32 | 32 | 16 | 32 | 32 | 32 | >64 | 32 | >64 |
| Example 185 | 32 | >64 | >64 | >64 | 32 | >64 | >64 | 64 | >64 | >64 | >64 |
| Example 186 | 2 | 2 | 1 | 2 | 2 | 2 | 2 | 2 | 64 | 4 | 64 |
| Example 187 | 32 | 64 | 16 | 64 | 16 | 128 | 16 | 16 | >128 | 128 | >128 |
| Example 190 | 32 | 32 | 32 | 32 | 32 | 32 | 8 | 16 | >64 | 16 | >64 |
| Example 191 | 8 | 16 | 8 | 16 | 8 | 8 | 8 | 4 | 64 | 8 | 64 |
| Example 192 | 4 | 4 | 2 | 4 | 2 | 4 | 2 | 2 | 32 | 4 | 32 |
| Example 193 | 2 | 2 | 0.5 | 1 | 1 | 1 | 2 | 2 | 32 | 2 | |
| Example 194 | 2 | 2 | 0.5 | 2 | 1 | 1 | 2 | 2 | 32 | 2 | |
| Example 195 | 0.5 | 1 | 0.5 | 0.5 | 0.5 | 0.5 | 0.5 | 0.5 | >0.5 | 0.5 | >0.5 |
| Example 196 | 64 | >64 | >64 | >64 | 64 | >64 | 8 | 32 | 64 | 8 | 64 |
| Example 197 | 64 | 64 | 64 | 64 | 64 | >64 | 8 | 16 | 64 | 16 | 32 |
| Example 198 | 1 | 1 | 1 | 1 | 1 | 1 | 1 | 1 | 32 | 1 | 32 |
| Example 199 | 4 | 4 | 2 | 4 | 4 | 4 | 2 | 2 | 32 | 1 | 64 |
| Example 200 | 4 | 4 | 2 | 4 | 4 | 4 | 2 | 4 | 32 | 1 | 32 |
| Example 201 | 1 | 1 | 1 | 1 | 1 | 1 | 0.5 | 1 | 16 | 0.25 | 16 |
| Example 202 | 32 | 32 | 16 | 32 | 32 | 16 | 4 | 32 | 16 | 2 | 32 |
| Example 203 | 8 | 8 | 8 | 8 | 8 | 4 | 4 | 8 | 32 | 2 | 64 |
| Example 204 | 16 | 16 | 16 | 16 | 16 | 16 | 8 | 16 | 128 | 4 | 128 |
| Example 205 | 2 | 4 | 2 | 2 | 2 | 2 | 4 | 4 | 128 | 1 | 64 |
| Example 206 | 2 | 2 | 1 | 1 | 2 | 1 | 2 | 4 | 32 | 2 | 32 |
| Example 207 | 4 | 4 | 2 | 4 | 4 | 4 | 2 | 4 | 64 | 2 | 32 |
| Example 208 | 8 | 8 | 8 | 8 | 8 | 8 | 8 | 4 | >64 | 8 | 64 |
| Example 209 | | | 1 | 4 | 1 | 4 | 1 | 4 | >64 | 4 | 64 |
| Example 210 | 16 | 32 | 16 | 32 | 32 | 32 | 32 | 16 | >64 | 64 | >64 |
| Example 210a | 8 | 8 | 8 | 8 | 8 | 8 | 4 | 4 | >64 | 16 | >64 |
| Example 212 | 8 | 8 | 8 | 8 | 8 | 8 | 4 | 4 | 32 | 2 | 32 |
| Example 214 | 2 | 2 | 2 | 2 | 1 | 2 | 2 | 2 | 64 | 2 | 64 |
| Example 215 | 0.5 | 1 | 1 | 0.5 | 0.5 | 1 | 0.5 | 0.5 | 32 | 1 | 32 |
| Example 216 | 4 | 4 | 4 | 4 | 4 | 4 | 8 | 4 | 16 | 2 | 32 |
| Example 217 | 32 | 32 | 16 | 16 | 16 | 16 | 8 | 16 | 32 | 2 | 64 |
| Example 218 | 4 | 4 | 4 | 4 | 4 | 4 | 4 | 4 | >64 | 8 | 64 |
| Example 219 | 8 | 8 | 8 | 16 | 8 | 8 | 4 | 4 | 64 | 4 | 64 |
| Example 220 | 1 | 2 | 1 | 2 | 1 | 1 | 1 | 2 | 16 | 0.5 | 32 |
| Example 221 | 2 | 2 | 2 | 2 | 2 | 2 | 1 | 2 | 32 | 2 | 64 |
| Example 222 | >64 | >64 | >64 | >64 | >64 | >64 | 64 | 64 | >64 | 64 | >64 |
| Example 223 | 64 | >64 | >64 | >64 | >64 | >64 | 64 | 64 | >64 | 32 | >64 |
| Example 224 | 2 | 4 | 4 | 4 | 2 | 4 | 0.5 | 4 | 64 | 2 | 128 |
| Example 225 | 4 | 16 | 16 | 8 | 4 | 8 | 1 | 8 | 128 | 4 | 128 |
| Example 226 | 16 | 32 | 32 | 32 | 16 | 32 | 2 | 8 | 128 | 4 | >128 |
| Example 227 | 8 | 128 | 64 | 64 | 32 | 64 | 8 | 8 | >128 | 8 | >128 |
| Example 228 | 16 | 32 | 32 | 32 | 16 | 32 | 16 | 8 | >64 | 16 | >64 |
| Example 229 | >128 | >128 | >128 | >128 | >128 | >128 | >128 | 128 | >128 | >128 | >128 |

TABLE 2-continued

| EXAMPLE NUMBER | Staphylococcus aureus (GC 1131) | Staphylococcus aureus (GC 3051) | Staphylococcus aureus (GC 3053) | Staphylococcus aureus (GC 4535) | Staphylococcus aureus (GC 4541) | Staphylococcus aureus (GC 4542) | Staphylococcus aureus (GC 4544) | Staphylococcus aureus (GC 4545) | Staphylococcus aureus (ATCC 29213) | Staphylococcus aureus-SMITH (GC 4536) |
|---|---|---|---|---|---|---|---|---|---|---|
| Example 229a | >128 | >128 | >128 | | >128 | >128 | >128 | >128 | >128 | |
| Example 229b | >128 | >128 | >128 | | >128 | >128 | >128 | >128 | >128 | |
| Example 230 | 2 | 2 | 2 | | 1 | 2 | 2 | 2 | 2 | |
| Example 230a | 0.5-2 | 1-2 | 1-2 | | 0.5-2 | 0.25-2 | 1-2 | 0.5-1 | 1-2 | |
| Example 230b | 4 | 2 | 2 | | 2 | 1 | 4 | 2 | 2 | |
| Example 230c | 128 | 128 | 128 | | 64 | >128 | 128 | 128 | 128 | |
| Example 231 | 2-4 | 1-2 | 1-2 | | 1-4 | 2-4 | 2-4 | 1-4 | 1-4 | |
| Example 231a | 1-2 | 1 | 1-2 | | 1-2 | 0.5-1 | 1-2 | 1-2 | 1-2 | |
| Example 231b | 4-64 | 4-64 | 8-64 | | 4-32 | 4-32 | 4-64 | 4-32 | 4-64 | |
| Example 231c | 2 | 2 | 2 | | 2 | 2 | 2 | 2 | 1 | |
| Example 232 | 4 | 4 | 8 | | 4 | 4 | 4 | 4 | 4 | |
| Example 234 | 2 | 2 | 2 | | 2 | 2 | 2 | 2 | 2 | |
| Example 235 | 1-2 | 0.5-2 | 1-2 | | 0.5-1 | 0.5-2 | 1-2 | 1-2 | 0.5-1 | |
| Example 236 | 2 | 2 | 2 | | 2 | 4 | 4 | 2 | 2 | |
| Example 237 | 4 | 4 | 4 | | 2 | 4 | 2 | 2 | 4 | |
| Example 238 | 4 | 4 | 8 | | 2 | 8 | 8 | 2 | 4 | |
| Example 239 | 2 | 2 | 2 | | 2 | 2 | 2 | 2 | 2 | |
| Example 239a | 4 | 1 | 4 | | 4 | 4 | 4 | 4 | 4 | |
| Example 240 | 4 | 0.5 | 4 | | 1 | 2 | 4 | 4 | 4 | |
| Example 241 | 2 | 2 | 2 | | 2 | 2 | 2 | 2 | 2 | |
| Example 241a | 2 | 2 | 2 | | 2 | 2 | 4 | 2 | 2 | |
| Example 242 | 8 | 8 | 8 | | 4 | 4 | 4 | 4 | 8 | |
| Example 243 | 64 | 64 | 64 | | 64 | 64 | 64 | 64 | 64 | |
| Example 243a | 32 | 32 | 32 | | 32 | 32 | 32 | 32 | 32 | |
| Example 244 | 8 | 8 | 16 | | 8 | 1 | 8 | 8 | 8 | |
| Example 245 | 8 | 4 | 4 | | 4 | 4 | 8 | 4 | 4 | |
| Example 245a | 4 | 2 | 2 | | 2 | 4 | 2 | 2 | 2 | |
| Example 245b | 16 | 16 | 16 | | 8 | 16 | 16 | 8 | 16 | |
| Example 245c | >128 | 128 | >128 | | 128 | 128 | 128 | 128 | 128 | |
| Example 246 | 8 | 4 | 4 | | 4 | 4 | 8 | 4 | 4 | |
| Example 246a | 4 | 1 | 2 | | 1 | 1 | 2 | 2 | 2 | |
| Example 246b | 128 | 64 | 128 | | 64 | 64 | 64 | 64 | 64 | |
| Example 246c | >128 | >128 | >128 | | >128 | >128 | >128 | >128 | >128 | |
| Example 247 | >64 | >64 | >64 | >64 | >64 | >64 | >64 | >64 | >64 | |
| Example 248 | 32 | 64 | 64 | | 32 | 64 | 32 | 32 | 32 | |
| Example 249 | 128 | 128 | 128 | | 128 | 64 | 64 | 128 | 128 | |
| Example 251 | >64 | >64 | | | >64 | >64 | >64 | >64 | >64 | |
| Example 251a | >64 | >64 | | | >64 | >64 | >64 | >64 | >64 | |
| Example 251b | 8 | | | | 8 | 8 | 16 | 8 | 16 | |
| Example 252 | >64 | >64 | >64 | | >64 | >64 | >64 | >64 | >64 | |
| Example 253 | >64 | >64 | >64 | | 64 | >64 | >64 | >64 | >64 | |
| Example 253a | 4 | 2 | 4 | | 4 | 4 | 4 | 2 | 4 | |
| Example 253b | 4 | 2 | 8 | | 2 | 4 | 4 | 4 | 4 | |
| Example 254 | 4 | | | | 4 | 4 | 4 | 8 | 4 | |
| Example 254b | 4 | | | | 4 | 8 | 8 | 8 | 8 | |
| Example 255 | >0.5 | 0.5 | 0.5 | | 0.5 | 0.5 | 0.5 | 0.5 | >0.5 | |

TABLE 2-continued

| EXAMPLE NUMBER | Staphylococcus aureus-SMITH (GC 4543) | Staphylococcus haemolyticus (GC 4546) | Coagulase Negative Staphylococcus (GC 4537) | Coagulase Negative Staphylococcus (GC 4538) | Coagulase Negative Staphylococcus (GC 4547) | Coagulase Negative Staphylococcus (GC 4548) | Coagulase Negative Staphylococcus (GC 4549) | Coagulase Negative Staphylococcus (GC 4551) | Coagulase Negative Staphylococcus (GC 6257) | Coagulase Negative Staphylococcus (ID-3941) |
|---|---|---|---|---|---|---|---|---|---|---|
| Example 229a | >128 | >128 | | | >128 | >128 | >128 | >128 | >128 | |
| Example 229b | >128 | >128 | | | >128 | >128 | >128 | >128 | >128 | |
| Example 230 | 1 | 1 | | | 1 | 0.5 | 1 | 2 | 0.5 | |
| Example 230a | 0.5-2 | 0.25-1 | | | 0.5-2 | 0.12-0.5 | 0.12-0.5 | 0.25-1 | 0.25-0.5 | |
| Example 230b | 2 | 1 | | | 2 | 1 | 1 | 2 | 1 | |
| Example 230c | 64 | 64 | | | 64 | 64 | 64 | 64 | 32 | |
| Example 231 | 2 | 1-4 | | | 1-2 | 0.5-1 | 0.25-0.5 | 1 | 0.5-1 | |
| Example 231a | 1 | 1 | | | 1 | 1 | <0.12-0.25 | 0.5 | 0.5 | |
| Example 231b | 4-64 | 4-32 | | | 4-32 | 2-32 | 2-16 | 8-32 | 12-32 | |
| Example 231c | 1 | 1 | | | 2 | 0.5 | 0.5 | 1 | 0.5 | |
| Example 232 | 4 | 2 | | | 2 | 2 | 1 | 4 | 2 | |
| Example 234 | 2 | 1 | | | 2 | 1 | 0.5 | 2 | 1 | |
| Example 235 | 0.5-1 | 0.25-0.5 | | | 0.5-1 | 0.25-0.5 | 0.25-0.5 | 0.5-1 | 0.25-0.5 | |
| Example 236 | 2 | 2 | | | 2 | 0.5 | 0.5 | 2 | 1 | |
| Example 237 | 2 | 1 | | | 2 | 1 | 1 | 4 | 1 | |
| Example 238 | 4 | 2 | | | 2 | 1 | 1 | 2 | 1 | |
| Example 239 | 2 | 2 | | | 2 | 2 | 2 | 2 | 2 | |
| Example 239a | 2 | 1 | | | 2 | 2 | 2 | 2 | 2 | |
| Example 240 | 2 | 2 | | | 4 | 2 | 2 | 2 | 2 | |
| Example 241 | 2 | 2 | | | 2 | 1 | 1 | 4 | 2 | |
| Example 241a | 2 | 2 | | | 4 | 2 | 2 | 4 | 1 | |
| Example 242 | 8 | 4 | | | 8 | 4 | 4 | 4 | 2 | |
| Example 243 | 64 | 64 | | | 64 | 32 | 32 | 16 | 32 | |
| Example 243a | 32 | 32 | | | 32 | 32 | 16 | 64 | 16 | |
| Example 244 | 4 | 4 | | | 4 | 2 | 2 | 32 | 2 | |
| Example 245 | 4 | 4 | | | 4 | 2 | 1 | 8 | 2 | |
| Example 245a | 2 | 1 | | | 2 | 1 | 0.5 | 2 | 1 | |
| Example 245b | 16 | 8 | | | 8 | 8 | 2 | 8 | 4 | |
| Example 245c | 128 | 128 | | | 128 | 128 | 64 | 128 | 64 | |
| Example 246 | 4 | 4 | | | 4 | 4 | 4 | 8 | 2 | |
| Example 246a | 1 | 1 | | | 1 | 1 | 1 | 2 | 2 | |
| Example 246b | >64 | 128 | | | 64 | 64 | 32 | 64 | 64 | |
| Example 246c | >128 | >128 | | | >128 | >128 | >128 | >128 | >128 | |
| Example 247 | >64 | >64 | | | >64 | >64 | >64 | >64 | >64 | |
| Example 248 | 32 | 16 | | | 16 | 32 | 32 | 32 | 16 | |
| Example 249 | 128 | 128 | | | 64 | 128 | 128 | 64 | 128 | |
| Example 251 | >64 | >64 | | | >64 | >64 | >64 | >64 | | 64 |
| Example 251a | 64 | 64 | | | 64 | 64 | 64 | >64 | | 16 |
| Example 251b | 8 | 8 | | | 8 | 8 | 32 | 16 | | 4 |
| Example 252 | >64 | >64 | | | >64 | >64 | >64 | >64 | | >64 |
| Example 253 | 64 | 64 | | | 64 | 64 | 64 | 8 | 32 | |
| Example 253a | 2 | 4 | | | 4 | 4 | 1 | 4 | 1 | |
| Example 253b | 2 | 2 | | | 4 | 2 | 2 | 4 | 2 | |
| Example 254 | 4 | 4 | | | 4 | 4 | 4 | 4 | | 2 |
| Example 254b | 4 | 8 | | | 8 | 2 | 2 | 4 | | 2 |
| Example 255 | 0.5 | 32 | | | 32 | 64 | 32 | 64 | 32 | |

TABLE 2-continued

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | Enterococcus faecalis (GC 2242) | Enterococcus faecalis (GC 2691) | Enterococcus faecalis (GC 3059) | Enterococcus faecalis (GC 4552) |
|---|---|---|---|---|---|---|---|---|---|---|
| Example 229a | >128 | 128 | >128 | >128 | >128 | | >128 | >128 | >128 | >128 |
| Example 229b | >128 | 128 | 128 | 128 | >128 | | 128 | >128 | >128 | >128 |
| Example 230 | 0.5 | <0.06 | 0.12 | 0.12 | 0.25 | | 8 | 4 | 4 | 8 |
| Example 230a | <0.06-0.12 | <0.06 | <0.06 | <0.06 | <0.06-0.25 | | 2-4 | 2-4 | 2-4 | 2-4 |
| Example 230b | 0.5 | <0.12 | 0.25 | 0.25 | 0.5 | | 8 | 8 | 8 | 8 |
| Example 230c | 32 | 16 | 32 | 32 | 64 | | >128 | >128 | >128 | >128 |
| Example 231 | <0.06 | <0.06 | <0.06 | <0.06 | <0.06 | | 4 | 2-4 | 2-4 | 4 |
| Example 231a | <0.06 | <0.06 | <0.06 | <0.06 | <0.06 | | 2-4 | 2 | 1-2 | 4 |
| Example 231b | 1-8 | <0.06-2 | 0.5-8 | 0.25-2 | 1-8 | | 8-64 | 16-64 | 16-128 | 8-128 |
| Example 231c | <0.12 | <0.12 | <0.12 | <0.12 | <0.12 | | 4 | 8 | 4 | 4 |
| Example 232 | 2 | 0.5 | 1 | 0.5 | 2 | | 16 | 32 | 32 | 32 |
| Example 234 | 0.5 | 0.12 | 0.25 | 0.25 | 0.5 | | 4 | 8 | 8 | 8 |
| Example 235 | 0.25-0.5 | <0.06 | <0.06-0.12 | 0.12 | 0.25 | | 4 | 4 | 4-8 | 4 |
| Example 236 | 0.12 | <0.06 | <0.06 | <0.06 | <0.06 | | 4 | 2 | 2 | 4 |
| Example 237 | 2 | 0.25 | 0.5 | 0.5 | 1 | | 16 | 16 | 32 | 16 |
| Example 238 | 2 | 0.5 | 1 | 1 | 1 | | 16 | 16 | 32 | 32 |
| Example 239 | 0.25 | <0.06 | <0.06 | <0.06 | 0.25 | | 4 | 4 | 4 | 4 |
| Example 239a | 0.5 | <0.06 | 0.25 | 0.25 | 2 | | 8 | 8 | 8 | 8 |
| Example 240 | 0.5 | <0.12 | 0.25 | <0.12 | 0.5 | | 16 | 8 | 8 | 16 |
| Example 241 | <0.06 | <0.06 | <0.06 | <0.06 | <0.06 | | 4 | 4 | 2 | 4 |
| Example 241a | <0.06 | <0.06 | <0.06 | <0.06 | <0.06 | | 4 | 4 | 2 | 4 |
| Example 242 | 2 | 0.5 | 0.5 | 1 | 2 | | 16 | 16 | 16 | 16 |
| Example 243 | 32 | 8 | 16 | 32 | 32 | | 64 | >64 | >64 | >64 |
| Example 243a | 16 | 1 | 2 | 16 | 8 | | 32 | 32 | 32 | 32 |
| Example 244 | 4 | 0.5 | 2 | 1 | 2 | | 32 | 32 | 64 | 32 |
| Example 245 | 4 | 1 | 4 | 2 | 4 | | 16 | 16 | 16 | 16 |
| Example 245a | 1 | <0.12 | 1 | 0.5 | 1 | | 4 | 8 | 4 | 8 |
| Example 245b | 8 | 1 | 8 | 4 | 8 | | 32 | 64 | 64 | 64 |
| Example 245c | 128 | 32 | 64 | 64 | 128 | | >128 | >128 | >128 | >128 |
| Example 246 | 2 | 0.5 | 2 | 2 | 4 | | 16 | 32 | 32 | 16 |
| Example 246a | 0.5 | <0.12 | 0.25 | 0.25 | 0.5 | | 4 | 8 | 4 | 4 |
| Example 246b | 64 | 32 | 64 | 32 | 64 | | 128 | 128 | 128 | 128 |
| Example 246c | >128 | 64 | 128 | 128 | >128 | | >128 | >128 | >128 | >128 |
| Example 247 | >64 | >64 | >64 | >64 | >64 | | >64 | >64 | >64 | >64 |
| Example 248 | 64 | 64 | 128 | 64 | 32 | | 64 | 32 | 64 | 128 |
| Example 249 | 128 | 64 | 64 | 64 | 128 | | 32 | 128 | 128 | 128 |
| Example 251 | >64 | 32 | 64 | 64 | | 64 | >64 | >64 | >64 | >64 |
| Example 251a | 32 | 0.5 | 8 | 2 | | 16 | >64 | 32 | 32 | >64 |
| Example 251b | 4 | <0.12 | 1 | 2 | | 2 | 32 | 4 | 4 | 4 |
| Example 252 | >64 | 32 | >64 | 32 | | >64 | >64 | >64 | 128 | >64 |
| Example 253 | 32 | 8 | 16 | 16 | 32 | | >64 | >64 | >64 | >64 |
| Example 253a | 1 | 0.25 | 0.5 | 0.5 | 1 | | 16 | 16 | 32 | 32 |
| Example 253b | 1 | <0.06 | 0.25 | 0.25 | 1 | | 8 | 8 | 16 | 8 |
| Example 254 | 4 | | 16 | 16 | | 8 | 8 | 8 | | 8 |
| Example 254b | <0.5 | | <0.5 | <0.5 | | <0.5 | 8 | 8 | | 8 |
| Example 255 | 32 | | 16 | 16 | 16 | | >0.5 | >0.5 | >0.5 | >0.5 |

TABLE 2-continued

| EXAMPLE NUMBER | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) | Escherichia coli (GC 4559) | Escherichia coli (GC 4560) | Escherichia coli (ATCC 25922) |
|---|---|---|---|---|---|---|---|---|---|---|---|
| Example 229a | >128 | >128 | >128 | >128 | >128 | >128 | >128 | 128 | >128 | >128 | >128 |
| Example 229b | 128 | >128 | >128 | >128 | >128 | >128 | 128 | 64 | >128 | 32 | >128 |
| Example 230 | 8 | 8 | 4 | 8 | 8 | 8 | 2 | 8 | >64 | 1 | 64 |
| Example 230a | 2-4 | 2-4 | 1-4 | 2-4 | 2-4 | 2-4 | 1-2 | 2-4 | 32 | 0.25-1 | 32 |
| Example 230b | 8 | 8 | 4 | 8 | 8 | 8 | 0.5 | 2 | 128 | 1 | 128 |
| Example 230c | 128 | >128 | >128 | >128 | 128 | >128 | 32 | 128 | >128 | 32 | >128 |
| Example 231 | 4 | 4 | 2-4 | 4 | 4 | 4 | 1-2 | 2-4 | >128 | 0.5-2 | >128 |
| Example 231a | 4 | 4 | 1-2 | 2 | 2 | 4 | 2 | 2 | 32 | 0.5-2 | 32-64 |
| Example 231b | 8-128 | 16-128 | 8-64 | 8-128 | 8-128 | 16-128 | 4-16 | 8-64 | >128 | 0.25-4 | >128 |
| Example 231c | 4 | 4 | 4 | 4 | 4 | 4 | 4 | 4 | >128 | 2 | >128 |
| Example 232 | 32 | 32 | 64 | 32 | 16 | 32 | 4 | 32 | 64 | 2 | >64 |
| Example 234 | 8 | 8 | 8 | 8 | 8 | 8 | 2 | 8 | 64 | 1 | 64 |
| Example 235 | 4 | 4-8 | 4 | 4 | 4 | 4 | 0.5-2 | 4 | 32->64 | 0.5-1 | 32->64 |
| Example 236 | 4 | 4 | 2 | 4 | 4 | 4 | 2 | 2 | >64 | 1 | >64 |
| Example 237 | 16 | 32 | 16 | 16 | 16 | 16 | 2 | 16 | 64 | 1 | >64 |
| Example 238 | 32 | 32 | 16 | 16 | 16 | 32 | 4 | 16 | >64 | 2 | >64 |
| Example 239 | 4 | 4 | 4 | 4 | 4 | 4 | 4 | 4 | >64 | 1 | >64 |
| Example 239a | 8 | 16 | 8 | 8 | 8 | 8 | 4 | 8 | 32 | 2 | >64 |
| Example 240 | 16 | 16 | 8 | 16 | 16 | 16 | 2 | 4 | >128 | 2 | 128 |
| Example 241 | 4 | 4 | 2 | 4 | 4 | 4 | 2 | 4 | >64 | 2 | >64 |
| Example 241a | 4 | 4 | 4 | 4 | 2 | 2 | 4 | 2 | >64 | 2 | >64 |
| Example 242 | 16 | 16 | 16 | 16 | 16 | 16 | 8 | 16 | >64 | 2 | >64 |
| Example 243 | 64 | 64 | 64 | >64 | 64 | >64 | 32 | 32 | >64 | 64 | >64 |
| Example 243a | 32 | 32 | 32 | 32 | 32 | 32 | 16 | 16 | >64 | 32 | >64 |
| Example 244 | 32 | 64 | 32 | 32 | 32 | 32 | 4 | 32 | 32 | 2 | 64 |
| Example 245 | 16 | 32 | 32 | 32 | 16 | 16 | 2 | 16 | 32 | 4 | 32 |
| Example 245a | 4 | 8 | 8 | 8 | 4 | 4 | 4 | 4 | 64 | 2 | 64 |
| Example 245b | 32 | 64 | 32 | 64 | 32 | 64 | 2 | 32 | 64 | 8 | 128 |
| Example 245c | >128 | >128 | >128 | >128 | >128 | >128 | 64 | >128 | >128 | 32 | >128 |
| Example 246 | 8 | 32 | 16 | 16 | 16 | 16 | 4 | 8 | 64 | 4 | 128 |
| Example 246a | 2 | 4 | 4 | 4 | 4 | 4 | 2 | 2 | 16 | 2 | 16 |
| Example 246b | 128 | >128 | 128 | 128 | 128 | 128 | 32 | 64 | >128 | 32 | >128 |
| Example 246c | 128 | >128 | >128 | >128 | >128 | >128 | 128 | 64 | >128 | 32 | >128 |
| Example 247 | >64 | >64 | >64 | >64 | >64 | >64 | >64 | >64 | >64 | >64 | >64 |
| Example 248 | 16 | 64 | 32 | 64 | 32 | 32 | 16 | 8 | 32 | 8 | 64 |
| Example 249 | 64 | 128 | 64 | 16 | 64 | 32 | 64 | 32 | 128 | 128 | 128 |
| Example 251 | >64 | >64 | | >64 | >64 | >64 | 16 | >64 | 64 | 4 | >64 |
| Example 251a | >64 | >64 | | >64 | >64 | >64 | 16 | 8 | >128 | 8 | >64 |
| Example 251b | >64 | >64 | | >64 | >64 | >64 | 4 | 8 | >128 | 2 | >64 |
| Example 252 | >64 | >64 | >64 | >64 | >64 | >64 | >64 | >64 | >64 | >64 | >64 |
| Example 253 | >64 | >64 | >64 | >64 | >64 | >64 | 32 | >64 | >64 | 2 | >64 |
| Example 253a | 16 | 32 | 16 | 16 | 16 | 16 | 4 | 16 | >64 | 2 | >64 |
| Example 253b | 8 | 8 | 8 | 8 | 8 | 8 | 2 | 8 | 8 | 8 | 64 |
| Example 254 | 4 | 8 | | 8 | 4 | 8 | 2 | 4 | 64 | 4 | 64 |
| Example 254b | 4 | 4 | | 8 | 4 | 8 | 8 | 4 | 64 | 16 | 64 |
| Example 255 | >0.5 | >0.5 | >0.5 | >0.5 | >64 | >64 | 16 | >0.5 | >0.5 | 0.5 | >0.5 |

TABLE 2-continued

| EXAMPLE NUMBER | Staphylococcus aureus (GC 1131) | Staphylococcus haemolyticus (GC 4546) | Staphylococcus aureus-SMITH (GC 4543) | Coagulase Negative Staphylococcus (GC 4537) | Staphylococcus aureus (GC 3053) | Staphylococcus aureus (GC 4535) | Staphylococcus aureus (GC 4541) | Coagulase Negative Staphylococcus (GC 4547) | Coagulase Negative Staphylococcus (GC 4548) | Staphylococcus aureus (GC 4542) | Staphylococcus aureus (GC 4544) | Coagulase Negative Staphylococcus (GC 4549) | Staphylococcus aureus (GC 4545) | Staphylococcus aureus (ATCC 29213) | Staphylococcus aureus-SMITH (GC 4536) |
|---|---|---|---|---|---|---|---|---|---|---|---|---|---|---|---|
| Example 255a | >0.5 | | >0.5 | | | | >0.5 | | | >0.5 | >0.5 | | >0.5 | >0.5 | |
| Example 256 | >64 | 64 | >64 | | | | >64 | 64 | >64 | >64 | >64 | 64 | >64 | >64 | |
| Example 256a | >64 | >64 | >64 | | | | >64 | >64 | >64 | >64 | >64 | >64 | >64 | >64 | |
| Example 257 | 0.5 | 2 | 0.5 | | | | 0.5 | 2 | 2 | 0.5 | 0.5 | 2 | 0.5 | 0.5 | |
| Example 257a | 0.5 | 8 | 0.5 | | | | 0.5 | 8 | 8 | 0.5 | 0.5 | 8 | 0.5 | 0.5 | |
| Example 257b | 0.5 | 2 | 0.5 | | | | 0.5 | 2 | 2 | 0.5 | 0.5 | 2 | 0.5 | 0.5 | |
| Example 261a | >64 | >64 | >64 | | | | >64 | >64 | >64 | >64 | >64 | >64 | >64 | >64 | |
| Example 261b | 16 | | 8 | | | | 16 | | | 16 | 8 | | 16 | 8 | |
| Example 261c | 8 | | 8 | | | | 8 | | | 8 | 8 | | 8 | 8 | |
| Example 262a | 128 | | | | | | 64 | | | >128 | 64 | | 64 | 64 | |
| Example 262b | 4 | | | | | | 2 | | | 2 | 4 | | 2 | 4 | |
| Example 263 | 64 | | | | | | 64 | | | 64 | >64 | | 64 | 64 | |
| Example 264a | 16 | | | | | | 16 | | | 16 | 8 | | 8 | 16 | |
| Example 264b | 8 | | | | | | 8 | | | 8 | 8 | | 4 | 8 | |
| Example 265a | 32 | | | | | | 16 | | | 16 | 8 | | 16 | 16 | |
| Example 265b | 32 | | | | | | 8 | | | 8 | 8 | | 8 | 16 | |
| Example 270a | 4 | | | | | | 4 | | | 4 | 4 | | 4 | 4 | |
| Example 270b | 8 | | | | | | 8 | | | 8 | 8 | | 4 | 8 | |
| Example 271a | 4 | | | | | | 4 | | | 8 | 8 | | 4 | 4 | |
| Example 277a | >128 | >128 | >128 | | | | >128 | >128 | >128 | >128 | >128 | >128 | >128 | >128 | |
| Example 277b | >64 | >64 | >64 | | | | >64 | >64 | >64 | >64 | >64 | >64 | >64 | >64 | |
| Example 277c | >64 | >64 | >64 | | | | >64 | >64 | >64 | >64 | >64 | >64 | >64 | >64 | |
| Example 278b | 8 | 4 | 8 | | | | 8 | 8 | 8 | 8 | 8 | 8 | 8 | 8 | |
| Example 278c | 8 | 2 | 8 | | | | 4 | 2 | 4 | 4 | 4 | 4 | 4 | 4 | |
| Example 279a | >64 | >64 | >64 | | | | >64 | >64 | >64 | >64 | >64 | >64 | >64 | >64 | |
| Example 280a | >128 | >128 | >128 | | | | >128 | >128 | >128 | >128 | >128 | >128 | >128 | >128 | |
| Example 280b | 128 | 128 | 128 | | | | 128 | 128 | 128 | 128 | 128 | 128 | 128 | 128 | |
| Example 282 | >128 | >128 | >128 | | | | >128 | >128 | >128 | >128 | >128 | >128 | >128 | >128 | |
| Example 283a | 64 | 64 | 64 | | | | 64 | 64 | 64 | 64 | 64 | 64 | 64 | 64 | |
| Example 283b | 64 | 64 | 64 | | | | 128 | 128 | 128 | 128 | 128 | 128 | 64 | 128 | |
| Example 283c | 32 | 32 | 32 | | | | 32 | 32 | 32 | 32 | 32 | 32 | 16 | 32 | |
| Example 284b | >128 | >128 | >128 | | | | >128 | >128 | >128 | >128 | >128 | >128 | >128 | >128 | |
| Example 287 | >64 | >64 | >64 | | | | >64 | >64 | >64 | >64 | >64 | >64 | >64 | >64 | |
| Example 296 | >128 | >128 | >128 | | | | >128 | >128 | >128 | >128 | >128 | >128 | >128 | >128 | |

| EXAMPLE NUMBER | Coagulase Negative Staphylococcus (GC 4551) | Coagulase Negative Staphylococcus (GC 6257) | Coagulase Negative Staphylococcus (ID-3941) |
|---|---|---|---|
| Example 255a | >64 | 64 | |
| Example 256 | >64 | | >64 |
| Example 256a | >64 | | 64 |
| Example 257 | 8 | 1 | |
| Example 257a | 32 | 4 | |
| Example 257b | 4 | 1 | |
| Example 261a | >64 | | |
| Example 261b | 8 | | |
| Example 261c | 16 | | |

TABLE 2-continued

| EXAMPLE NUMBER | Streptococcus agalactiae (GC 4564) | Streptococcus pneumoniae (GC 1894) | Streptococcus pneumoniae (GC 4565) | Streptococcus pneumoniae (ATCC 6301) | Streptococcus pyogenes (GC 4563) | Streptococcus pyogenes (ID-3187) | | |
|---|---|---|---|---|---|---|---|---|
| Example 262a | 64 | 64 | | | | | 64 | 16 |
| Example 262b | 1 | 2 | | | | | 1 | 1 |
| Example 263 | 32 | 32 | | | | | 32 | 16 |
| Example 264a | 8 | 8 | | | | | 4 | 4 |
| Example 264b | 8 | 4 | | | | | 8 | 8 |
| Example 265a | 8 | 8 | | | | | 8 | 4 |
| Example 265b | 4 | 2 | | | | | 2 | 4 |
| Example 270a | 4 | 4 | | | | | 4 | 4 |
| Example 270b | 4 | 4 | | | | | 2 | 2 |
| Example 271a | 8 | 4 | | | | | 4 | 4 |
| Example 277a | >128 | >128 | | | | | >128 | >128 |
| Example 277b | >64 | >64 | | | | | >64 | >64 |
| Example 277c | >64 | >64 | | | | | >64 | >64 |
| Example 278b | 8 | 4 | | | | | 4 | 8 |
| Example 278c | 4 | 2 | | | | | 2 | 2 |
| Example 279a | >64 | 64 | | | | | >64 | >64 |
| Example 280a | 128 | 128 | | | | | 128 | >128 |
| Example 280b | 64 | 32 | | | | | 128 | 128 |
| Example 282 | >128 | >128 | | | | | >128 | 32 |
| Example 283a | 64 | 64 | | | | | 64 | 64 |
| Example 283c | 64 | 64 | | | | | 64 | 64 |
| Example 284b | 16 | 16 | | | | | 8 | 16 |
| Example 287 | >64 | >64 | | | | | >64 | >64 |
| Example 296 | >128 | >128 | | | | | >128 | >128 |

| EXAMPLE NUMBER | | | | | | | Enterococcus faecalis (GC 2242) | Enterococcus faecalis (GC 2691) | Enterococcus faecalis (GC 3059) | Enterococcus faecalis (GC 4552) |
|---|---|---|---|---|---|---|---|---|---|---|
| Example 255a | | | | | | | >0.5 | >0.5 | >0.5 | >0.5 |
| Example 256 | | | | | | | >64 | | | >64 |
| Example 256a | | | | | | | >64 | | | >64 |
| Example 257 | | | | | | | 0.5 | 0.5 | 0.5 | >0.5 |
| Example 257a | | | | | | | >0.5 | 0.5 | >0.5 | >0.5 |
| Example 257b | | | | | | | 0.5 | 0.5 | 0.5 | >0.5 |
| Example 261a | | | | | | | >64 | | | >64 |
| Example 261b | | | | | | | 64 | | | 64 |
| Example 261c | | | | | | | 32 | | | 64 |
| Example 262a | | | | | | | >128 | | | >128 |
| Example 262b | | | | | | | >64 | | | 32 |
| Example 263 | | | | | | | >64 | | | >64 |
| Example 264a | | | | | | | 64 | | | >64 |
| Example 264b | | | | | | | 32 | | | 64 |
| Example 265a | | | | | | | 64 | | | 64 |
| Example 265b | | | | | | | 16 | | | 16 |
| Example 270a | | | | | | | 16 | | | 32 |
| Example 270b | | | | | | | 16 | | | 32 |
| Example 271a | | | | | | | >128 | >128 | >128 | >128 |
| Example 277a | | | | | | | >64 | >64 | >64 | >64 |
| Example 277b | | | | | | | >64 | >64 | >64 | >64 |
| Example 277c | | | | | | | 32 | 32 | 64 | 32 |
| Example 278b | | | | | | | | | | |

TABLE 2-continued

| EXAMPLE NUMBER | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) | Escherichia coli (GC 4559) | Escherichia coli (GC 4560) | Escherichia coli (ATCC 25922) |
|---|---|---|---|---|---|---|---|---|---|---|---|
| Example 278c | 2 | 0.5 | | 1 | 1 | | | 16 | | 32 | 32 |
| Example 279a | >64 | 64 | | >64 | 64 | | | >64 | | >64 | >64 |
| Example 280a | >64 | 128 | | >128 | >128 | | | >128 | | >128 | >128 |
| Example 280b | 128 | 64 | | 128 | 32 | | | 64 | | >128 | >128 |
| Example 282 | >128 | 128 | | >128 | 128 | | | >128 | | >128 | >128 |
| Example 283a | 64 | 16 | | 16 | 16 | | | 128 | | >128 | >128 |
| Example 283b | 64 | 16 | | 32 | 32 | | | >128 | | >128 | 128 |
| Example 283c | 16 | 4 | | 8 | 8 | | | 16 | | >128 | 128 |
| Example 284b | >128 | 128 | | >128 | >128 | | | >128 | | >128 | >128 |
| Example 287 | >64 | 64 | | 64 | >64 | | | >64 | | >64 | >64 |
| Example 296 | >128 | 128 | | >128 | >128 | | | >128 | | >128 | >128 |

| EXAMPLE NUMBER | Enterococcus faecalis (GC 4553) | Enterococcus faecalis (GC 4554) | Enterococcus faecalis (GC 6189) | Enterococcus faecalis (ATCC 29212) | Enterococcus faecium (GC 2243) | Enterococcus faecium (GC 4556) | Enterococcus faecium (GC 4557) | Enterococcus avium (GC 4558) | Escherichia coli (GC 4559) | Escherichia coli (GC 4560) | Escherichia coli (ATCC 25922) |
|---|---|---|---|---|---|---|---|---|---|---|---|
| Example 255a | >0.5 | >0.5 | >0.5 | >0.5 | >64 | >64 | 32 | >0.5 | >0.5 | 0.5 | >0.5 |
| Example 256 | >64 | >64 | | >64 | >64 | >64 | 64 | >64 | >64 | 32 | >64 |
| Example 256a | >64 | >64 | | >64 | >64 | >64 | 32 | >64 | >64 | 8 | >64 |
| Example 257 | 0.5 | >0.5 | 0.5 | 0.5 | 16 | 16 | 2 | 0.5 | >0.5 | 0.5 | >0.5 |
| Example 257a | >0.5 | >0.5 | >0.5 | >0.5 | >32 | >32 | 8 | >0.5 | >0.5 | 0.5 | >0.5 |
| Example 257b | 0.5 | >0.5 | 0.5 | 0.5 | 16 | 16 | 2 | 0.5 | >0.5 | 0.5 | >0.5 |
| Example 261a | >64 | >64 | | >64 | >64 | >64 | >64 | >64 | >64 | >64 | >64 |
| Example 261b | 64 | >64 | | >64 | 64 | 64 | 16 | 64 | >64 | 4 | >64 |
| Example 261c | 64 | 64 | | 64 | 64 | 64 | 8 | 64 | >64 | 4 | >64 |
| Example 262a | >128 | >128 | | >128 | >128 | >128 | >128 | >128 | >128 | 16 | >128 |
| Example 262b | 32 | 32 | | 32 | 16 | 16 | 2 | 16 | >64 | 1 | >64 |
| Example 263 | >64 | >64 | | >64 | >64 | >64 | 32 | >64 | >64 | 16 | >64 |
| Example 264a | >64 | >64 | | 64 | >64 | >64 | 32 | >64 | >64 | 4 | 64 |
| Example 264b | 64 | 64 | | 64 | 64 | 64 | 8 | 64 | >64 | 4 | 64 |
| Example 265a | >64 | >64 | | 64 | >64 | >64 | 8 | >64 | >64 | 4 | 64 |
| Example 265b | 64 | >64 | | 64 | >64 | >64 | 8 | 64 | 64 | 4 | 64 |
| Example 270a | 16 | 32 | | 16 | 16 | 16 | 4 | 16 | 64 | 2 | 64 |
| Example 270b | 32 | 32 | | 32 | 32 | 32 | 8 | 32 | >64 | 4 | >64 |
| Example 271a | 32 | 32 | | 32 | 32 | 64 | 4 | 32 | >64 | 2 | 64 |
| Example 277a | >128 | >128 | | >128 | >128 | >128 | 128 | 128 | >128 | >128 | >128 |
| Example 277b | >64 | >64 | | >64 | 128 | >64 | 64 | >64 | >64 | 32 | >64 |
| Example 277c | >64 | >64 | | >64 | >64 | >64 | >64 | >64 | >64 | >64 | >64 |
| Example 278a | 32 | 32 | | 32 | 32 | 32 | 8 | 32 | >64 | 4 | 64 |
| Example 278b | 32 | 32 | | 32 | 32 | 32 | 8 | 32 | >64 | 2 | 64 |
| Example 278c | >64 | >64 | | >64 | >64 | >64 | 64 | >64 | >64 | 32 | >64 |
| Example 279a | >128 | >128 | | >128 | >128 | >128 | >128 | >128 | >128 | 64 | 128 |
| Example 280a | >128 | >128 | | >128 | 128 | >128 | 64 | 128 | 64 | 32 | 32 |
| Example 280b | >128 | >128 | | >128 | >128 | >128 | 64 | 128 | 16 | 128 | >128 |
| Example 282 | >128 | >128 | | >128 | >128 | >128 | 64 | 128 | >128 | 128 | >128 |
| Example 283a | >128 | >128 | | >128 | 128 | >128 | 64 | 128 | >128 | 32 | >128 |
| Example 283b | >128 | >128 | | >128 | >128 | >128 | 16 | 128 | >128 | 32 | 128 |
| Example 283c | 128 | >128 | | 128 | 128 | 128 | 128 | 128 | >128 | 8 | 128 |
| Example 284b | >128 | >128 | | >128 | >128 | >128 | >128 | >128 | >128 | >128 | >128 |
| Example 287 | >64 | >64 | | >64 | >64 | >64 | 64 | 64 | >64 | >64 | >64 |
| Example 296 | >128 | >128 | | >128 | >128 | >128 | 128 | 128 | >128 | >128 | >128 |

Zone of Inhibition

Protocol for Assay Plate *Staphylococcus aureus*

Inoculate 10 mL of Tryptic Soy Broth with a loopful of slant culture, *Staphylococcus aureus*, and place in a stationary rack at 37° C. After 16-18 hour incubation, the Optical Density (OD) of the culture is read @ $A_{600}$ nm, using a 1:10 dilution. OD should be between 0.1-0.3, and if not adjust with Tryptic Soy Broth. A 40 mL sample of Nutrient Agar, pH 6.8 is inoculated with 90 µl of *S. aureus* culture and poured into a sterile petri dish. When the agar has solidified, wells (5 mm) are plated using an automated welling device. Wells are inoculated with 25 µl of extract and incubated overnight at 37° C. Zones of inhibition are measured and recorded the following morning. The results of representative examples of the invention are given in Table 3.

TABLE 3

| Example No. | Zone of Inhibition vs. S. aureus (mm) |
|---|---|
| 270c | 11 |
| 271c | 12 |
| 272b | 8 |
|  | 8 |
| 273b | 8 |
|  | 9 |
| 274a | 9 |
| 274b | 10 |

Methods for In Vivo Antibacterial Evaluation

The therapeutic effects of glycopeptide antibiotics of Formula I are determined against acute lethal infections with *S. aureus* (strain Smith), a penicillin resistant strain of *S. pneumoniae* (strain GC 1894), and a vancomycin resistant strain of *E. fecalis* (strain GC 6189 and GC 2246). Female mice, CD-1 (Charles River Laboratories), 20 +1-2 gm, are challenged by intraperitoneal injection of sufficient bacteria (suspended in Trypticase Soy Broth or hog gastric mucin) to kill non-treated controls within 24-48 hr. Antibacterial agents, contained in 0.2 mL of saline or 5% dextrose solution, are administered intravenously 30 min. after infection. Five mice are treated at each dose level. The 7 day survival ratios from 3 separate tests are pooled for calculation of median effective dose (ED50). The results of representative examples of the invention are given in Table 4.

TABLE 4

In Vivo Antibacterial Activity of Glycopeptide Antibiotics in Acute Lethal Infections in Mice

| EXAMPLE | Enterococcus faecalis (GC 2246) | Enterococcus faecalis (GC 6189) | Staphylococcus aureus- SMITH (GC 4543) | Streptococcus pneumoniae (GC 1894) |
|---|---|---|---|---|
| 28 |  |  | 8 |  |
| 52 |  |  | >4 |  |
| 55 |  |  | >8 |  |
| 59 |  |  | >8 |  |
| 60 |  |  | >8 |  |
| 61 |  |  | >8 |  |
| 62 |  |  | >8 |  |
| 64 |  |  | >8 |  |
| 65 |  |  | >8 |  |
| 66 |  |  | >8 |  |
| 66a |  |  | >4 |  |
| 67 |  |  | >8 |  |
| 69 |  |  | >8 |  |
| 71 |  |  | >8 |  |
| 72 |  |  | >8 |  |
| 73 |  |  | >8 |  |
| 74 |  |  | >8 |  |
| 77 |  |  | 4 |  |
| 78 |  |  | 2 |  |
| 80 |  |  | >8 |  |
| 81 |  |  | >8 |  |
| 89 |  |  | >8 |  |
| 95b |  |  | 4 |  |
| 96c | 5.2 |  | 0.29 |  |
| 97b |  |  | 8 |  |
| 99c | 4.3 |  | 0.52 |  |
| 102 |  | 1.04 | 0.23-0.43 |  |
| 103 |  |  | 0.28 |  |
| 104 |  | 0.39-0.63 | 0.19 | 0.22 |
| 105 |  | 1.8-1.96 | 0.04-0.08 | 0.04 |
| 106 |  |  |  | 0.07 |
| 111 |  | 0.28 | 0.14 | 0.03 |
| 112 |  | 0.19-0.28 | 0.07-0.08 | 0.02 |
| 113 |  | 1.04 | 0.26 |  |
| 115 |  | 0.36 | 0.23 |  |
| 116 |  | 0.46 | 0.08-0.19 |  |
| 117 |  | 0.38 | 0.26-0.5 |  |
| 119 |  | 0.41 | 0.19 |  |
| 120 |  |  | 0.06 |  |
| 121 |  | 0.5 | 0.32 |  |
| 135 |  | 0.26 | 0.07 |  |
| 137 |  |  | 0.24 |  |
| 141 |  |  | >8 |  |
| 143 |  |  | 0.28 |  |
| 154 |  |  | 0.1 |  |
| 158 |  |  | 0.14 |  |
| 174 |  |  | 0.08 |  |
| 177 |  |  | 0.1 |  |
| 180 |  |  | 0.05 |  |
| 219 |  |  | 0.5 |  |
| 220 |  |  | 0.19 |  |
| 221 |  |  | 0.03 |  |
| 230 |  |  | 0.12 |  |
| 230a |  |  | 0.06 |  |
| 231 |  |  | 0.25 |  |
| 231a |  |  | 0.06 |  |
| 235 |  |  | 0.59 |  |
| 245 |  |  | 4 |  |
| 245a |  |  | 1 |  |
| 262b |  |  | 1.22 |  |
| 263 |  |  | >8 |  |
| 277a |  |  | >8 |  |
| 277b |  |  | >8 |  |
| 277c |  |  | >8 |  |
| 280a |  |  | >8 |  |
| 280b |  |  | >8 |  |

Table 5

In Vivo Antibacterial Activity of Glycopeptide Antibiotics in Non-Lethal Thigh Infections in Mice The therapeutic effects of glycopeptide antibiotics of the invention are also determined against a non-lethal thigh infection model in mice infected with *S. aureus* (strain Smith and PT 5679), a penicillin resistant strain of *S. pneumoniae* (strain GC 1894), a penicillin sensitive strain of *S. pneumoniae* (GC 6242), and a vancomycin resistant strain of *E. fecalis* (strain GC 6189). Female mice, CD-1 (Charles River Laboratories), 20+/−2 gm, are challenged by intramuscular injection of sufficient bacteria (suspended in Trypticase Soy Broth or hog gastric mucin) to cause biohazard class 1-2 (Biosafety in Microbiological and Medical Laboratories, HHS Publication NO(NIH) 88-8395, 3rd edition, 1993) infection in mice. Broth cultures of freshly plated bacteria are grown into log phase overnight to an optical density of 0.3 at 580 nm. After a 1:10 dilution into fresh broth, 0.1 mL (approximately 106 CFU) is injected intramuscularly into the thigh of each mouse. Antibacterial agents, contained in 0.2 mL of saline or 5% dextrose solution, are administered intravenously beginning 2 hr after infection. Two-fold serial dilutions of each antibiotic are administered at selected time intervals for up to 22 hr post-infection to achieve a range of drug concentrations in serum for a complete dose-response relationship from no effect to maximal effect. After 24 hr. animals are sacrificed, thighs are removed and homogenized in 10 mL of 0.85% iced saline. Duplicate aliquots are plated for serial dilutions to determine the bacterial population. Efficacy is calculated by subtracting the $\log_{10}$CFU per thigh of untreated control mice just before therapy and at the end of therapy (24 hr) from the treated groups. The results of representative examples of the invention are given in Table 5.

TABLE 5

In Vivo Antibacterial Activity of Glycopeptide Antibiotics in Mouse Thigh Infection

| EXAMPLE NO. | Enterococcus faecalis (GC 6189) | Staphylococcus aureus (PT 5679) | Staphylococcus aureus-SMITH (GC 4543) | Streptococus pneumoniae (GC 1894) | Streptococcus pneumoniae (GC 6242) |
|---|---|---|---|---|---|
| 76 | | | 10.63 | | |
| 102 | 0.5 | | 2.03 | | |
| 104 | 1.22-1.8 | | 1.42 | | |
| 105 | 1 | 2.46 | 1.02-1.84 | | 0.53 |
| 106 | | | 0.59 | | |
| 111 | 0.48 | | 1.73-2 | | |
| 112 | 0.33-0.65 | | 1.57-1.95 | 0.13 | |
| 113 | | | 1.25 | | |
| 115 | 0.56-1.37 | | 1.22 | | |
| 116 | 1.21-1.65 | | 1.1-1.9 | | |
| 117 | 0.67 | | 2.53 | | |
| 119 | 1.39 | | 1.15 | | |
| 135 | 1.02 | | 1.27 | | |
| 137 | 1.19 | | 0.87 | | |

Clinical Pathology:

20-day-old CD-1 mice were divided into a vehicle control group (5 mice) and a treatment group (5 mice). Samples of glycopeptide antibiotics were administered at 20 mg/kg intravenously daily for 9 days. Animals were necropsied on day 10 Sera were analyzed for BUN (blood urea nitrogen), creatinine, AST (aspartic aminotransferase), and ALT (alanine aminotransferase) by routine, standard, automated methods using an Hitachi 747 chemistry analyzer. Results of representative examples of the invention are given in Table 6.

Anatomic Pathology:

Samples of tissues from necropsied mice were formalin-fixed, paraffin-embedded, sectioned, stained with hematoxylin and eosin, and examined microscopically. Histopathologic findings were recorded. These findings were subjectively graded on a scale corresponding to slight, mild, moderate, marked and severe as compared to untreated controls. Results of representative examples of the invention are given in Table 6.

TABLE 6

Clinical Chemistry and Anatomical Pathology Comparison in Mice Results based on 20 mg/kg Intravenous Dose

| | Clinical Chemistry (Day 10) % of Control | | | | Anatomical Pathology (Day 10) | |
|---|---|---|---|---|---|---|
| Ex. No. | AST | ALT | BUN | Creatinine | Heart[b] | Kidney |
| 28 | No samples | | | | 0 | 0 |
| 52 | NS | NS | 211% | NS | 0 | +++ |
| 59 | NS | NS | NS | NS | 0 | 0 |
| 60 | NS | NS | NS | NS | 0 | 0 |
| 61 | NS | NS | +157% | +122% | 0 | +++ |
| 62 | NT* | | | | NT* | NT* |
| 64 | NS | NS | NS | NS | 0 | 0 |
| 65 | +182% | +196% | +161% | NS | 0 | +++ |
| 66 | 147% | 182% | NS | NS | 0 | 0 |
| 66a | NS | NS | NS | NS | 0 | ++ |
| 67 | NS | NS | NS | NS | 0 | 0 |
| 69 | NS | NS | NS | NS | 0 | 0 |
| 71 | NS | NS | NS | NS | 0 | 0 |
| 72 | NS | NS | +122% | NS | 0 | ++ |
| 73 | NT* | | | | NT* | NT* |
| 74 | NS | NS | NS | NS | 0 | 0 |
| 76 | NS | NS | NS | NS | 0 | ++ |

TABLE 6-continued

Clinical Chemistry and Anatomical Pathology Comparison in Mice Results based on 20 mg/kg Intravenous Dose

| | Clinical Chemistry (Day 10) % of Control | | | | Anatomical Pathology (Day 10) | |
|---|---|---|---|---|---|---|
| Ex. No. | AST | ALT | BUN | Creatinine | Heart[b] | Kidney |
| 77 | NS | NS | NS | NS | 0 | 0 |
| 78 | NS | NS | NS | NS | 0 | ++ |
| 80 | NT* | | | | NT* | NT* |
| 81 | NS | NS | NS | NS | 0 | 0 |
| 102 | +340% | +672% | +249% | +100% | +++ | +++ |
| 104 | +87% | NS | +203% | +65% | +++ | +++ |
| 105 | +205% | +480% | +35% | NS | +++ | +++ |
| 106 | NS | NS | NS | NS | 0 | +/− |
| 141 | NS | NS | +308% | +113% | 0 | +++ |
| 219 | NS | NS | NS | NS | 0 | +++ |
| 220 | NS | NS | 149% | 121% | 0 | +++ |
| 221 | NS | NS | NS | NS | 0 | 0 |
| 230 | NS | NS | +179% | +124% | 0 | +++ |

TABLE 6-continued

Clinical Chemistry and Anatomical Pathology Comparison in Mice
Results based on 20 mg/kg Intravenous Dose

| Ex. No. | Clinical Chemistry (Day 10) % of Control | | | | Anatomical Pathology (Day 10) | |
|---|---|---|---|---|---|---|
| | AST | ALT | BUN | Creatinine | Heart[b] | Kidney |
| 230a | NS | NS | NS | NS | 0 | + |
| 245 | NS | NS | +160% | +138% | 0 | +++ |
| 245a | NS | NS | +212% | +133% | + | +++ |
| 263 | NS | NS | NS | +116% | + | ++ |
| 277a | NS | NS | +110% | NS | 0 | ++ |
| 277b | +138% | +164% | +113% | NS | 0 | + |
| 277c | +253% | NS | NS | NS | 0 | + |
| 280a | NS | NS | NS | NS | 0 | ++ |
| 280b | NT* | | | | NT* | NT* |

[a]Clinical chemisitry- Liver function tests included AST and ALT measurements.
Renal function tests includes BUN and Creatinine measurements
Degree of elevation reported as a % above untreated control animals.
[b]Anatomical Pathology- Heart and kidneys were examined for microscopic histopathology
Degree of severity and number of animals affected were scored by 0, +, ++, or +++ as compared to untreated control animals.
NS—not significant change from controls.
NT* - animals did not survive treatment regimin.

In therapeutic use, the compounds of this invention may be administered in the form of conventional pharmaceutical composition appropriate for the intended use as antibacterials. Such compositions may be formulated so as to be suitable for oral, parenteral or topical administration. The active ingredient may be combined in admixture with nontoxic pharmaceutical carrier may take a variety of forms, depending on the form of preparation desired for administration, i.e. oral, parenteral, or topical.

When the compounds are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 0.001 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional nontoxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition of the host undergoing therapy.

Additionally, the antibacterially effective amount of the glycopeptide antibiotics of the invention may be administered at a dosage and frequency without inducing side effects commonly experienced with conventional antibiotic therapy which could include hypersensitivity, neuromuscular blockade, vertigo, photosensitivity, discoloration of teeth, hematologic changes, gastrointestinal disturbances, ototoxicity, and renal, hepatic, or cardiac impairment. Further the frequency and duration of dosage may be monitored to substantially limit harmful effects to normal tissues caused by administration at or above the antibacterially effective amount of the glycopeptide antibiotics of the invention.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA. These active compounds may also be administered parenterally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion, medium containing, for example, water, ethanol, polyol (e.g., glycerol, propylene glycol and liquid polyethylene glycol), suitable mixtures thereof, and vegetable oil.

The invention accordingly provides a pharmaceutical composition which comprises a compound of this invention in combination or association with a pharmaceutically acceptable carrier. In particular, the present invention provides a pharmaceutical composition which comprises an antibacterially effective amount of a compound of this invention and a pharmaceutically acceptable carrier.

The present invention further provides a method of treating bacterial infections in warm-blooded animals including man, which comprises administering to the afflicted warm-blooded animals an antibacterially effective amount of a compound or a pharmaceutical composition of a compound of the invention. The invention will be more fully described in conjunction with the following specific examples which are not to be construed as limiting the scope of the invention.

The following examples illustrate the preparation of the compounds of the invention by fermentation and synthetic procedures and as such are not to be considered as limiting the invention set forth in the claims appended hereto.

EXAMPLE 1

(Cyclo[glycyl-β-methylphenylalanyl-3-bromo-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

A stirred solution of the bis-trifluoroacetate salt of cyclo [glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (152 mg) in trifluoroacetic acid (4 mL) is treated with N-bromosuccinimide (23 mg) and the reaction mixture is then stirred at room temperature for 2 h. Volatiles are then removed in vacuo and the resulting residue is triturated with ether, the solid collected and washed with ethyl acetate and then diethyl ether to give the crude monobromo-derivative of cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]. The product is then purified by reverse phase HPLC. MS (+ES), m/z: 687 $(M+2H)^{2+}$.

EXAMPLE 2

(Cyclo[glycyl-β-methylphenylalanyl-3-bromotyrosyl-3-(2-iminoimidazolidin-4-yl)seryl-3-(3-hexopyranosyl-2-iminoimidazolidin-4-yl)serylseryl])

A stirred solution the bis-hydrochloride salt of cyclo[glycyl-β-methylphenylalanyltyrosyl-3-(2-iminoimidazolidin-4-yl)seryl-3-(3-hexopyranosyl-2-iminoimidazolidin-4-yl)serylseryl] (21 mg) in trifluoroacetic acid (0.5 mL) is treated with 3 mg of bromine in 0.3 mL of acetic acid and the reaction is stirred at room temperature for 45 min, then poured into diethyl ether (8 mL). The resulting solid is collected by filtration and washed with diethyl ether to give 18 mg of the crude monobromo-derivative of cyclo[glycyl-β-methylphenylalanyltyrosyl-3-(2-iminoimidazolidin-4-yl)seryl-3-(3-hexopyranosyl-2-iminoimidazolidin-4-yl)serylseryl]. The product is then purified by reverse phase HPLC. MS (+ES), m/z: 525.1 $(M+2H)^{2+}$.

EXAMPLE 3

(Cyclo[glycyl-β-methylphenylalanyl-3,5-dibromotyrosyl-3-(2-iminoimidazolidin-4-yl)seryl-3-(3-hexopyranosyl-2-iminoimidazolidin-4-yl)serylseryl])

A stirred solution of the bis-hydrochloride salt of cyclo[glycyl-β-methylphenylalanyltyrosyl-3-(2-iminoimidazolidin-4-yl)seryl-3-(3-hexopyranosyl-2-iminoimidazolidin-4-yl)serylseryl] (31 mg) in trifluoroacetic acid (1 mL) is treated with N-bromosuccinimide (10 mg) and the reaction mixture is then stirred at room temperature for 2 h. Volatiles are then removed in vacuo and the resulting residue is triturated with ether, the solid collected and washed with ethyl acetate and then diethyl ether to give the crude dibromo-derivative of cyclo[glycyl-βmethylphenylalanyltyrosyl-3-(2-iminoimidazolidin-4-yl)seryl-3-(3-hexopyranosyl-2-iminoimidazolidin-4-yl)serylseryl). The product is then purified by reverse phase HPLC. MS (+ES), m/z: 565 $(M+2H)^{2+}$.

EXAMPLE 4

(Cyclo[glycyl-β-methylphenylalanyl-3,5-dibromotyrosyl-3-(2-iminoimidazolidin-4-yl)seryl-3-(2-iminoimidazolidin-4-yl)serylseryl])

The title compound is prepared from cyclo[glycyl-11:methylphenylalanyltyrosyl-3-(2-iminoimidazolidin-4-yl)seryl-3-(2-iminoimidazolidin-4-yl)serylseryl] by the fi procedure described for example 3. MS (+ES), m/z: 484 $(M+2H)^{2+}$.

EXAMPLE 5

(Cyclo[glycyl-β-methylphenylalanyl-3-iodotyrosyl-3-(2-iminoimidazolidin-4-yl)seryl-3-(3-hexopyranosyl-2-iminoimidazolidin-4-yl)serylseryl])

A stirred solution of the bis-hydrochloride salt of cyclo[glycyl-β-methylphenylalanyltyrosyl-3-(2-iminoimidazolidin-4-yl)seryl-3-(3-hexopyranosyl-2-iminoimidazolidin-4-yl)serylseryl] (31 mg) in trifluoroacetic acid (1 mL) is treated with N-iodosuccinimide (12 mg) and the reaction mixture is then stirred at 4-8° C. for 2 h. Volatiles are then removed in vacuo and the resulting residue is triturated with ether, the solid is collected by filtration and washed with ethyl acetate and then diethyl ether to give the crude monoiodo-derivative of cyclo[glycyl-β-methylphenylalanyltyrosyl-3-(2-iminoimidazolidin-4-yl)seryl-3-(3-hexopyranosyl-2-iminoimidazolidin-4-yl)serylseryl]. The product is then purified by reverse phase HPLC. MS (+ES), m/z: 549 $(M+2H)^{2+}$.

EXAMPLE 6

(Cyclo[glycyl-β-methylphenylalanyl-O-(4-O-hexopyranosyl)hexopyranosyl)-3-iodo-tyrosyl-3-(2-iminoimidazolidin-4-yl)seryl-3-(3-hexopyranosyl-2-iminoimidazolidin-4-yl)serylseryl])

The title compound is prepared by the procedure described for example 5 using the bis-trifluoroacetate salt of cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]. MS (+ES), m/z: 711.3 $(M+2H)^{2+}$.

EXAMPLE 7

(Cyclo[glycyl-β-methylphenylalanyl-O-(4-O-hexopyranosylhexopyranosyl)-3;5-diiodo-tyrosyl-3-(2-iminoimidazolidin-4-yl)seryl-3-(3-hexopyranosyl-2-iminoimidazolidin-4-yl)serylseryl])

A stirred solution of the bis-trifluoroacetate salt of cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (304 mg) in trifluoroacetic acid (10 mL) is treated with N-iodosuccinimide (99 mg) and the reaction mixture is then stirred at 4-8° C. for 2 h. Volatiles are then removed in vacuo and the resulting residue is triturated with ether, the solid collected and washed with ethyl acetate and then diethyl ether to give the crude diiodo-derivative of cyclo[glycyl-β-methylphenylalanyl-O-(4-O-hexopyranosylhexopyranosyl)tyrosyl-3-(2-iminoimidazolidin-4-yl)seryl-3-β-hexopyranosyl-2-iminoimidazolidin-4-yl)serylseryl]. The product is then purified by reverse phase HPLC. MS (+ES), m/z: 774 $(M+2H)^{2+}$.

EXAMPLE 8

(Cyclo[glycyl-β-methylphenylalanyl-3-nitrotyrosyl-3-(2-iminoimidazolidin-4-yl)seryl-3-(3-hexopyranosyl-2-iminoimidazolidin-4-yl)serylseryl])

A stirred solution of the bis-hydrochloride salt of cyclo[glycyl-β-methylphenylalanyltyrosyl-3-(2-iminoimidazolidin-4-yl)seryl-3-(3-hexopyranosyl-2-iminoimidazolidin-4-yl)serylseryl] (4.62 g) in trifluoroacetic acid (10 mL) at 3° C. is treated with potassium nitrate (492 mg) and the reaction mixture is then stirred with cooling in an ice bath for 45 min. Volatiles are then removed in vacuo and the resulting residue is triturated with ethanol to provide an amber solid, which is then collected by filtration and washed with ethanol and then diethyl ether to give the crude mono-nitro derivative of cyclo [glycyl-β-methylphenylalanyltyrosyl-3-(2-iminoimidazolidin-4-yl)seryl-3-(3-hexopyranosyl-2-iminoimidazolidin-4-yl)serylseryl]. The product is then purified by reverse phase HPLC. MS (+ES), m/z: 508 (M+2H)$^{2+}$.

EXAMPLE 9

(Cyclo[glycyl-β-methylphenylalanyl-3-nitrotyrosyl-3-(2-iminoimidazolidin-4-yl)seryl-3-(2-iminoimidazolidin-4-yl)serylseryl])

The title compound is prepared from cyclo[glycyl-β-methylphenylalanyltyrosyl-3-(2-iminoimidazolidin-4-yl)seryl-3-(2-iminoimidazolidin-4-yl)serylseryl] by the procedure described for example 8. MS (+ES), m/z: 427.8 (M+2H)$^{2+}$.

EXAMPLE 10

(Cyclo[3-(2-iminoimidazolidin-4-yl)alanyl-3-(3-hexopyranosyl-2-iminoimidazolidin-4-yl)-alanylserylglycyl-β-methylphenylalanyl-3-nitrotyrosyl])

The title compound is prepared from cyclo[3-(2-iminoimidazolidin-4-yl)alanyl-3-(3-hexopyranosyl-2-iminoimidazolidin-4-yl)-alanylserylglycyl-β-methylphenylalanyltyrosyl] by the procedure described for example 8. MS (+ES), m/z: 492.9 (M+2H)$^{2+}$.

EXAMPLE 11

(Cyclo[glycyl-β-methylphenylalanyl-3-aminotyrosyl-3-(2-iminoimidazolidin-4-yl)seryl-3-(3-hexopyranosyl-2-iminoimidazolidin-4-yl)serylseryl])

A stirred solution of the crude bis-trifluoroacetate salt of cyclo[glycyl-β-methylphenylalanyl-3-nitrotyrosyl-3-(2-iminoimidazolidin-4-yl)seryl-3-(3-hexopyranosyl-2-iminoimidazolidin-4-yl)serylseryl] (16 g) in 15% aqueous acetic acid (160 mL) and ethanol (10 mL) is hydrogenated under balloon pressure at room temperature over 10% palladium on carbon (1.2 g) for 3.5 h. The catalyst is then removed by filtration through diatomaceous earth, the filtrate is concentrated to a volume of ~70 mL, then added to acetonitrile (450 mL) and the precipitated product is collected by filtration. The precipitate is then washed with acetonitrile and diethyl ether and air dried to give the desired product. MS (+ES), m/z: 493.9 (M+2H)$^{2+}$.

EXAMPLE 12

(Cyclo[glycyl-β-methylphenylalanyl-3-(dimethylamino)tyrosyl-3-(2-iminoimidazolidin-4-yl)-seryl-3-(3-hexopyranosyl-2-iminoimidazolidin-4-yl)serylseryl])

A stirred solution of the bis-trifluoroacetate salt of cyclo [glycyl-β-methylphenylalanyl-3-aminotyrosyl-3-(2-iminoimidazolidin-4-yl)seryl-3-(3-hexopyranosyl-2-iminoimidazolidin-4-yl)serylseryl] (100 mg) in ethanol (10 mL) is treated with glacial acetic acid (1.5 mL) and aqueous formaldehyde (37%, 1 mL), and is then hydrogenated under balloon pressure at room temperature over 10% palladium on carbon for 1 hour. The catalyst is removed by filtration through diatomaceous earth, and the filtrate is concentrated to a volume of ~4 mL. The concentrated filtrate is then added to acetonitrile (15 mL) and diethyl ether (30 mL) and the precipitated product is collected by filtration. The precipitate is then washed with acetonitrile and diethyl ether and air dried to give the desired product. MS (+ES), m/z: 507.8 (M+2H)$^{2+}$.

EXAMPLE 13

(Cyclo[glycyl-β-methylphenylalanyl-3-acetamidotyrosyl-3-(2-iminoimidazolidin-4-yl)seryl-3-(3-hexopyranosyl-2-iminoimidazolidin-4-yl)serylseryl])

A stirred solution of the bis-trifluoroacetate salt of cyclo [glycyl-β-methylphenylalanyl-3-aminotyrosyl-3-(2-iminoimidazolidin-4-yl)seryl-3-(3-hexopyranosyl-2-iminoimidazolidin-4-yl)serylseryl] (100 mg) in neat acetic anhydride (0.2 mL) is stirred at room temperature for 45 min. Acetic anhydride is removed under a stream of nitrogen and the residue is triturated with diethyl ether. The resulting precipitate is collected by filtration, washed, and air dried. The product is then purified by reverse phase HPLC. MS (+ES), m/z: 515 (M+2H)$^{2+}$.

EXAMPLE 14

(Cyclo[glycyl-β-methylphenylalanyl-3-(propanamido)tyrosyl-3-(2-iminoimidazolidin-4-yl)seryl-3-(3-hexopyranosyl-2-iminoimidazolidin-4-yl)serylseryl])

A stirred solution of the bis-trifluoroacetate salt of cyclo [glycyl-β-methylphenylalanyl-3-aminotyrosyl-3-(2-iminoimidazoliclin-4-yl)seryl-3-(3-hexopyranosyl-2-iminoimidazolidin-4-yl)serylseryl] (100 mg) in tetrahydrofuran (0.2 mL) is treated with propionic anhydride (2 mL) and the reaction mixture is stirred at room temperature for 75 min. The reaction mixture is then triturated with acetonitrile and diethyl ether, and the resulting precipitate is collected by filtration, washed with diethyl ether and air dried. MS (+ES), m/z: 522.2 (M+2H)$^{2+}$.

EXAMPLE 15

(Cyclo[glycyl-β-methylphenylalanyl-3-(2-methylpropanamido)tyrosyl-3-(2-iminoimidazolidin-4-yl)seryl-3-(3-hexopyranosyl-2-iminoimidazolidin-4-yl)serylseryl])

The title compound is prepared by the procedure described for example 14 using isobutyric anhydride to give the corresponding isobutyryl amide derivative. MS (+ES), m/z: 528.9 (M+2H)$^{2+}$.

EXAMPLE 16

(Cyclo[glycyl-β-methylphenylalanyl-3-(heptanamido)tyrosyl-3-(2-iminoimidazolidin-4-yl)seryl-3-(3-hexopyranosyl-2-iminoimidazolidin-4-yl)serylseryl])

The title compound is prepared by the procedure described for example 14 using heptanoic anhydride to give the corresponding heptyl amide derivative. MS (+ES), m/z: 550.2 (M+2H)$^{2+}$.

299

EXAMPLE 17

(Cyclo[glycyl-β-methylphenylalanyl-3-(benzamido)tyrosyl-3-(2-iminoimidazolidin-4-yl)seryl-3-(3-hexopyranosyl-2-iminoimidazolidin-4-yl)serylseryl])

A stirred solution of the bis-trifluoroacetate salt of cyclo[glycyl-β-methylphenylalanyl-3-aminotyrosyl-3-(2-iminoimidazolidin-4-yl)seryl-3-(3-hexopyranosyl-2-iminoimidazolidin-4-yl)serylseryl] (250 mg) in tetrahydrofuran (3 mL) is treated with benzoyl chloride (0.3 mL) and the reaction mixture is then stirred at room temperature for 45 min. Solvent is removed under a stream of nitrogen and the residue is triturated with diethyl ether. The resulting precipitate is collected by filtration, washed with diethyl ether and air dried. The product is then purified by reverse phase HPLC. MS (+ES), m/z: 545.9 $(M+2H)^{2+}$.

EXAMPLE 18

(Cyclo[glycyl-β-methylphenylalanyl-3-formamidotyrosyl-3-(2-iminoimidazolidin-4-yl)seryl-3-(3-hexopyranosyl-2-iminoimidazolidin-4-yl)serylseryl])

A stirred suspension of the bis-trifluoroacetate salt of cyclo[glycyl-β-methylphenylalanyl-3-aminotyrosyl-3-(2-iminoimidazolidin-4-yl)seryl-3-(3-hexopyranosyl-2-iminoimidazolidin-4-yl)serylseryl] (180 mg) in 88% formic acid (2.5 mL) at 0° C. is treated with acetic anhydride (0.25 mL) and the reaction mixture is then stirred for 45 min. The reaction mixture is then diluted with diethyl ether and the resulting precipitate is collected by filtration, washed with diethyl ether and air dried. The product is then purified by reverse phase HPLC. MS (+ES), m/z: 508.5 $(M+2H)^{2+}$.

EXAMPLE 19

(Cyclo[glycyl-β-methylphenylalanyl-3-[[(4-methylphenoxy)carbonyl]amino]tyrosyl-3-(2-iminoimidazolidin-4-yl)seryl-3-(3-hexopyranosyl-2-iminoimidazolidin-4-yl)serylseryl])

A stirred suspension of the bis-trifluoroacetate salt of cyclo[glycyl-β-methylphenylalanyl-3-aminotyrosyl-3-(2-iminoimidazolidin-4-yl)seryl-3-(3-hexopyranosyl-2-iminoimidazolidin-4-yl)serylseryl] (61 mg) in glacial acetic acid (5 mL) is treated dropwise with a solution of p-tolyl chloroformate (8.5 mg) in glacial acetic acid (0.5 mL) and the reaction mixture is then stirred at 70° C. for 2 h. The reaction mixture is then diluted with diethyl ether and acetonitrile and the resulting precipitate is collected by filtration, washed with diethyl ether and air dried. The product is then purified by reverse phase HPLC. MS (+ES), m/z: 561 $(M+2H)^{2+}$.

EXAMPLE 20

(Cyclo[glycyl-β-methylphenylalanyl-3-[(methoxycarbonylamino)tyrosyl-3-(2-iminoimidazolidin-4-yl)seryl-3-(3-hexopyranosyl-2-iminoimidazolidin-4-yl)serylseryl])

The title compound is prepared by the procedure described for example 19 using methyl chloroformate to form the corresponding urethane derivative. MS (+ES), m/z: 523.5 $(M+2H)^{2+}$.

300

EXAMPLE 21

(Cyclo[glycyl-β-methylphenylalanyl-3-[(phenylmethoxycarbonyl)amino]tyrosyl-3-(2-iminoimidazolidin-4-yl)seryl-3-(3-hexopyranosyl-2-iminoimidazolidin-4-yl)serylseryl])

The title compound is prepared by the procedure described for example 19 using benzyl chloroformate to form the corresponding urethane derivative. MS (+ES), m/z: 561 $(M+2H)^{2+}$.

EXAMPLE 22

(Cyclo[3-(2,3-dihydro-2-oxo-1,3-benzoxazol-5-yl)alanyl-3-(2-iminoimidazolidin-4-yl)seryl-3-(3-hexopyranosyl-2-iminoimidazolidin-4-yl)serylserylglycyl-β-methylphenylalanyl])

A stirred suspension of the bis-trifluoroacetate salt of cyclo[glycyl-β-methylphenylalanyl-3-aminotyrosyl-3-(2-iminoimidazolidin-4-yl)seryl-3-(3-hexopyranosyl-2-iminoimidazolidin-4-yl)serylseryl] (106 mg) in glacial acetic acid (9.5 mL) is treated dropwise with a solution of 4-chlorophenyl chloroformate (17 mg) in glacial acetic acid (0.5 mL) and the reaction mixture is then stirred at 70° C. for 3 h. The reaction mixture is then diluted with diethyl ether and the resulting precipitate is collected by filtration, washed with diethyl ether and air dried. The resulting solid (71 mg) is dissolved in 0.1N NaOH (2 mL) and stirred at room temperature for 1 h. The solution is then diluted with acetonitrile and the resulting precipitate is collected by filtration, washed with acetonitrile then diethyl ether and air dried. The product is then purified by reverse phase HPLC. MS (+ES), m/z: 507 $(M+2H)^{2+}$.

EXAMPLE 23

(Cyclo[3-(2,3-dihydro-2-thio-1,3-benzoxazol-5-yl)alanyl-3-(2-iminoimidazolidin-4-yl)seryl-3-(3-hexopyranosyl-2-iminoimidazolidin-4-yl)serylserylglycyl-β-methylphenylalanyl])

A stirred solution of cyclo[glycyl-β-methylphenylalanyl-3-aminotyrosyl-3-(2-iminoimidazolidin-4-yl)seryl-3-(3-hexopyranosyl-2-iminoimidazolidin-4-yl)serylseryl](177 mg) in N,N-dimethylformamide (3 mL) is treated with 1,1'-thiocarbonyldiimidazole (32 mg) and the mixture is stirred at room temperature for 1 h. The reaction mixture is then diluted with diethyl ether and the resulting precipitate is collected by filtration, washed with diethyl ether and air dried. The product is then purified by reverse phase HPLC. MS (+ES), m/z: 515 $(M+2H)^{2+}$.

EXAMPLE 24

(Cyclo[glycyl-β-methylphenylalanyl-3-[[[3,5-bis(trifluoromethyl)phenyl]carbamothioyl]amino]-tyrosyl-3-(2-iminoimidazolidin-4-yl)seryl-3-(3-hexopyranosyl-2-iminoimidazolidin-4-yl)-serylseryl])

A stirred suspension of the bis-trifluoroacetate salt of cyclo[glycyl-β-methylphenylalanyl-3-aminotyrosyl-3-(2-iminoimidazolidin-4-yl)seryl-3-(3-hexopyranosyl-2-iminoimidazolidin-4-yl)serylseryl] (135 mg) in THF (0.5 mL) is treated with 3,5-ditrifluoromethylphenyl isothiocyanate (0.6 mL) and the mixture is stirred at room temperature for 3 days. The reaction mixture is then diluted with diethyl ether and the resulting precipitate is collected by filtration, washed with diethyl ether and air dried. The product is then purified by reverse phase HPLC. MS (+ES), m/z: 629.2 (M+2H)$^{2+}$.

EXAMPLE 25

(Cyclo[3-[2-(4-carboxyphenyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl])

A stirred suspension of the bis-trifluoroacetate salt of cyclo[glycyl-β-methylphenylalanyl-3-aminotyrosyl-3-(2-iminoimidazolidin-4-yl)seryl-3-(3-hexopyranosyl-2-iminoimidazolidin-4-yl)serylseryl] (121 mg) in N,N-dimethylformamide (5 mL) at room temperature is treated with 4-carboxybenzaldehyde (75 mg) and 2,3-dichloro-5,6-dicyano-1,4-benzoquinone (57 mg), and the reaction mixture is stirred for 2 h. The reaction mixture is then poured into a mixture of diethyl ether and acetonitrile, and the resulting solid is collected by filtration, washed with diethyl ether and air dried. The product is then purified by reverse phase HPLC. MS (+ES), m/z: 558.7 (M+2H)$^{2+}$.

EXAMPLE 26

(Cyclo[3-[2-(3-nitrophenyl)-1,3-benzoxazol-5-yl)alanyl-3-(2-iminoimidazolidin-4-yl)seryl-3-(3-hexopyranosyl-2-iminoimidazolidin-4-yl)serylserylglycyl-β-methylphenylalanyl])

The title compound is prepared by the procedure described for example 25 using the appropriate aldehyde to form the corresponding benzoxazole derivative. MS (+ES), m/z: 559.5 (M+2H)$^{2+}$.

EXAMPLE 27

(Cyclo[3-[2-(4-bromaphenyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl])

The title compound is prepared by the procedure described for example 25 using the appropriate aldehyde to form the corresponding benzoxazole derivative. MS (+ES), m/z: 576.6 (M+2H)$^{2+}$.

EXAMPLE 28

(Cyclo[3-[2-β-(4-methylphenoxy)phenyl]-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenyl-alanyl])

The title compound is prepared by the procedure described for example 25 using the appropriate aldehyde to form the corresponding benzoxazole derivative. MS (+ES), m/z: 590.2 (M+2H)$^{2+}$.

EXAMPLE 29

(Cyclo[3-[2-[4-(dimethylamino)phenyl]-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenyl-alanyl])

The title compound is prepared by the procedure described for example 25 using the appropriate aldehyde to form the corresponding benzoxazole derivative. MS (+ES), m/z: 558.6 (M+2H)$^{2+}$.

EXAMPLE 30

(Cyclo[3-[2-(3-fluorophenyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl])

The title compound is prepared by the procedure described for example 25 using the appropriate aldehyde to form the corresponding benzoxazole derivative. MS (+ES), m/z: 545.8 (M+2H)$^{2+}$.

EXAMPLE 31

(Cyclo[3-[2-[4-(phenylmethoxy)phenyl]-1,3-benzoxazol-5-yl]alanyl-3-(2-iminoimidazolidin-4-yl)seryl-3-(3-hexopyranosyl-2-iminoimidazolidin-4-yl)serylserylglycyl-β-methyl-phenylalanyl])

The title compound is prepared by the procedure described for example 25 using the appropriate aldehyde to form the corresponding benzoxazole derivative. MS (+ES), m/z: 589.9 (M+2H)$^{2+}$.

EXAMPLE 32

(Cyclo[3-[2-(4-tert-butylphenyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl])

The title compound is prepared by the procedure described for example 25 using the appropriate aldehyde to form the corresponding benzoxazole derivative. MS (+ES), m/z: 565 (M+2H)$^{2+}$.

EXAMPLE 33

(Cyclo[3-[2-([1,1-biphenyl]-4-yl)-1,3-benzoxazol-5-yl]alanyl-3-(2-iminoimidazolidin-4-yl)-seryl-3-(3-hexopyranosyl-2-iminoimidazolidin-4-yl)serylserylglycyl-β-methylphenylalanyl])

The title compound is prepared by the procedure described for example 25 using the appropriate aldehyde to form the corresponding benzoxazole derivative. MS (+ES), m/z: 574.9 (M+2H)$^{2+}$.

EXAMPLE 34

(Cyclo[3-[2-(3,4,5-trimethoxyphenyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenyl-alanyl])

The title compound is prepared by the procedure described for example 25 using the appropriate aldehyde to form the corresponding benzoxazole derivative. MS (+ES), m/z: 581.9 $(M+2H)^{2+}$.

EXAMPLE 35

(Cyclo[3-[2-β-(4-methoxyphenoxy)phenyl]-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenyl-alanyl])

The title compound is prepared by the procedure described for example 25 using the appropriate aldehyde to form the corresponding benzoxazole derivative. MS (+ES), m/z: 597.9 $(M+2H)^{2+}$.

EXAMPLE 36

(Cyclo[3-[2-(hexopyranosyloxy)phenyl]-1,3-benzoxazol-5-yl]alanyl-3-(2-iminoimidazolidin-4-yl)seryl-3-(3-hexopyranosyl-2-iminoimidazolidin-4-yl)serylserylglycyl-β-methyl-phenylalanyl])

The title compound is prepared by the procedure described for example 25 using the appropriate aldehyde to form the corresponding benzoxazole derivative. MS (+ES), m/z: 625.6 $(M+2H)^{2+}$.

EXAMPLE 37

(Cyclo[3-[2-(9H-fluoren-2-yl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl])

The title compound is prepared by the procedure described for example 25 using the appropriate aldehyde to form the corresponding benzoxazole derivative. MS (+ES), m/z: 581.6 $(M+2H)^{2+}$.

EXAMPLE 38

(Cyclo[3-[2-(3-furyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl])

The title compound is prepared by the procedure described for example 25 using the appropriate aldehyde to form the corresponding benzoxazole derivative. MS (+ES), m/z: 531.9 $(M+2H)^{2+}$.

EXAMPLE 39

(Cyclo[3-[2-(2,2-diphenylethenyl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl])

The title compound is prepared by the procedure described for example 25 using the appropriate aldehyde to form the corresponding benzoxazole derivative. MS (+ES), m/z: 588.1 $(M+2H)^{2+}$.

EXAMPLE 40

(Cyclo[3-[2-(2-methylprop-1-en-1-yl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenyl-alanyl])

The title compound is prepared by the procedure described for example 25 using the appropriate aldehyde to form the corresponding benzoxazole derivative. MS (+ES), m/z: 526.1 $(M+2H)^{2+}$.

EXAMPLE 41

(Cyclo[3-[2-[4-(3-methylphenoxy)phenyl]benzoxazol-5-yl]alanyl-3-(2-iminoimidazolidin-4-yl)-seryl-3-(2-iminoimidazolidin-4-yl)serylserylglycyl-β-methylphenylalanyl])

The title compound is prepared from cyclo[glycyl-β-methylphenylalanyltyrosyl-3-(2-iminoimidazolidin-4-yl)seryl-3-(2-iminoimidazolidin-4-yl)serylseryl] by the procedure described for example 25 using the appropriate aldehyde to form the corresponding benzoxazole derivative. MS (+ES), m/z: 508.7 $(M+2H)^{2+}$.

EXAMPLE 42

(Cyclo[3-[2-(9H-fluoren-2-yl)-1,3-benzoxazol-5-yl]alanyl-3-(2-iminoimidazolidin-4-yl)alanyl-3-(3-hexopyranosyl-2-iminoimidazolidin-4-yl)alanylserylglycyl-β-methylphenylalanyl])

The title compound is prepared from cyclo[3-(2-iminoimidazolidin-4-yl)alanyl-3-(3-hexopyranosyl-2-iminoimidazolidin-4-yl)-alanylserylglycyl-β-methylphenylalanyltyrosyl] by the procedure described for example 25 using the appropriate aldehyde to form the corresponding benzoxazole derivative. MS (+ES), m/z: 564.9 $(M+2H)^{2+}$.

EXAMPLE 43

(Cyclo[3-[2-(6-methoxynaphth-2-yl)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl])

The title compound is prepared from cyclo[3-(2-iminoimidazolidin-4-yl)alanyl-3-(3-hexopyranosyl-2-iminoimidazolidin-4-yl)-alanylserylglycyl-β-methylphenylalanyltyrosyl] by the procedure described for example 25 using the appropriate aldehyde to form the corresponding benzoxazole derivative. MS (+ES), m/z: 577.2 $(M+2H)^{2+}$.

EXAMPLE 44

(Cyclo[3-[[2-(2,3,4,6-tetra-O-benzoylhexopyranosyl)amino]-1,3-benzoxazol-5-yl]alanyl-3-(2-iminoimidazolidin-4-yl)seryl-3-(3-hexopyranosyl-2-iminoimidazolidin-4-yl)seryl-serylglycyl-β-methylphenylalanyl])

A suspension of the bis-trifluoroacetate salt of cyclo[glycyl-β-methylphenylalanyl-3-aminotyrosyl-3-(2-iminoimidazolidin-4-yl)seryl-3-(3-hexopyranosyl-2-iminoimidazoliclin-4-yl)serylseryl](300 mg) in THF (5 mL) is treated with 2,3,4,6-tetra-O-benzoyl-β-D-glucopyranosyl isothiocyanate (300 mg) and the mixture is stirred at room temperature for 11 days. The reaction mixture is then diluted with diethyl ether and the resulting precipitate is collected by filtration, washed with diethyl ether and air dried. The resulting solid is then dissolved in methanol (5 mL) and treated with mercuric chloride (350 mg) and the reaction mixture is stirred at room temperature for 18 h. Methanol is then evaporated under a gentle stream of nitrogen and the title compound is then isolated by reverse phase HPLC. MS (+ES), m/z: 795.9 $(M+214)^{2+}$.

EXAMPLE 45

(Cyclo[3-[2-(benzylthio)-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl])

A stirred solution of the bis-trifluoroacetate salt of cyclo[3-(2,3-dihydro-2-thio-1,3-benzoxazol-5-yl)alanyl-3-(2-iminoimidazolidin-4-yl)seryl-3-(3-hexopyranosyl-2-iminoimidazolidin-4-yl)serylserylglycyl-β-methylphenylalanyl] (100 mg) in N,N-dimethylformamide (0.6 mL) is treated with benzyl bromide (40 mg) and N,N-diisopropylethylamine (40 uL), and the mixture is stirred at room temperature for 30 min. The reaction mixture is then diluted with diethyl ether and the resulting precipitate is collected by filtration, washed with diethyl ether and air dried. The product is then purified by reverse phase HPLC. MS (+ES), m/z: 560 $(M+2H)^{2+}$.

EXAMPLE 46

(Cyclo[3-[2-[(naphthylmethyl)thio]-1,3-benzoxazol-5-yl]alanyl-3-(2-iminoimidazolidin-4-yl)-seryl-3-(3-hexopyranosyl-2-iminoimidazolidin-4-yl)serylserylglycyl-β-methylphenylalanyl])

The title compound is prepared by the procedure described for example 45 using 2-(bromomethyl)naphthalene to form the corresponding 2-thiobenzoxazole derivative. MS (+ES), m/z: 584.8 $(M+2H)^{2+}$.

EXAMPLE 47

(Cyclo[3-[[2-[(4-phenylbenzyl)thio]-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl])

The title compound is prepared by the procedure described for example 45 using 4-phenylbenzyl chloride to form the corresponding 2-thiobenzoxazole derivative. MS (+ES), m/z: 598 $(M+2H)^{2+}$.

EXAMPLE 48

(Cyclo[3-[2-[(2-oxo-2-phenylethyl)thiol-1,3-benzoxazol-5-yl]alanyl-3-(2-iminoimidazolidin-4-yl)-seryl-3-(3-hexopyranosyl-2-iminoimidazolidin-4-yl)serylserylglycyl-β-methylphenyl-alanyl])

A stirred solution of the bis-trifluoroacetate salt of cyclo[3-(2,3-dihydro-2-thio-1,3-benzoxazol-5-yl)alanyl-3-(2-iminoimidazolidin-4-yl)seryl-3-(3-hexopyranosyl-2-iminoimidazolidin-4-yl)serylserylglycyl-β-methylphenylalanyl] (100 mg) in N,N-dimethylformamide (3 mL) is treated with 2-bromo-acetophenone (200 mg), and the mixture is stirred at room temperature for 2 h. The reaction mixture is then diluted with diethyl ether and the resulting precipitate is collected by filtration, washed with diethyl ether and air dried. The product is then purified by reverse phase HPLC. MS (+ES), m/z: 573.7 $(M1-2H)^{2+}$.

EXAMPLE 49

(Cyclo[3-[2-[[2-(4-chlorophenyl)-2-oxoethyl]thiol-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl])

The title compound is prepared by the procedure described for example 48 using 2-bromo-4'-chloroacetophenone to form the corresponding 2-thiobenzoxazole derivative. MS (+ES), m/z: 590.7 $(M+2H)^{2+}$.

EXAMPLE 50

(Cyclo[3-cyclohexylalanyl-O-(4-O-hexopyranosyl-hexopyranosyl)tyrosyl-3-(2-iminoimidazolidin-4-yl)seryl-3-(3-hexopyranosyl-2-iminoimidazolidin-4-yl)serylserylglycyl])

A stirred solution of the bis-hydrochloride salt of cyclo[glycylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (10 g) in 10% aqueous acetic acid (300 mL) containing n-butanol (10 mL) is hydrogenated under balloon pressure over 3% rhodium on carbon (20 g) and monitored periodically by electrospray mass spectrometry until the majority of the starting material is consumed. Catalyst is removed by filtration through diatomaceous earth and the filtrate is concentrated in vacuo to provide a gum. This material is then triturated with 1:1 acetonitrile-diethyl ether (300 mL) and the resulting precipitate is filtered, washed with acetonitrile and diethyl ether, and air dried. MS (+ES), m/z: 644.3 $(M+2H)^{2+}$.

EXAMPLE 51

(Cyclo[3-cyclohexyl-2-aminobutyl-O-(4-O-hexopyranosylhexopyranosyl)tyrosyl-3-(2-iminoimidazolidin-4-yl)seryl-3-(3-hexopyranosyl-2-iminoimidazolidin-4-yl)-serylserylglycyl])

The title compound is prepared from cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] by the procedure described for example 50. The product is then purified by reverse phase HPLC. MS (+ES), m/z: 651.1 $(M+2H)^{2+}$.

EXAMPLE 52

(Cyclo[3-cyclohexylalanyl-3-cyclohexylalanyl-3-(2-iminoimidazolidin-4-yl)seryl-3-(3-hexopyranosyl-2-iminoimidazolidin-4-yl)serylserylglycyl])

EXAMPLE 52a (Cyclo[3-cyclohexylalanyl-3-[4-[(4-O-hexopyranosylhexopyranosyl)oxy]cyclohexyl]alanyl-3-(2-iminoimidazolidin-4-yl)seryl-3-(3-hexopyranosyl-2-iminoimidazolidin-4-yl)serylserylglycyl])

EXAMPLE 52b (Cyclo[3-cyclohexylalanyl-3-[4-[(4-O-hexopyranosylhexopyranosyl)oxy]cyclohexyl]alanyl-3-(2-iminoimidazolidin-4-yl)seryl-3-(3-hexopyranosyl-2-iminoimidazolidin-4-yl)serylserylglycyl])

A solution of the bis-hydrochloride salt of cyclo[glycylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (350 mg) in 10% aqueous acetic acid (10 mL) containing n-butanol (1 mL) is hydrogenated over 3% Rh/C (250 mg) in a Parr apparatus at an initial pressure of 50 psi and monitored periodically by electrospray mass spectrometry until the starting material has been completely converted to products of the desired molecular weight. Catalyst is removed by filtration through diatomaceous earth and the filtrate is concentrated in vacuo to provide a gum. This material is then subjected to reverse phase HPLC separation to provide the three title compounds. Cyclo[3-cyclohexylalanyl-3-cyclohexylalanyl-3-(2-iminoimidazolidin-4-yl)seryl-3-(3-hexopyranosyl-2-iminoimidazolidin-4-yl)serylserylglycyl]: MS (+ES), m/z: 477.1 $(M+2H)^{2+}$; Cyclo[3-cyclohexylalanyl-3-[4-[(4-O-hexopyranosylhexopyranosyl)oxy]cyclohexyl]alanyl-3-(2-iminoimidazolidin-4-yl)seryl-3-(3-hexopyranosyl-2-iminoimidazolidin-4-yl)serylserylglycyl]: MS (+ES), m/z: 647.1 $(M+2H)^{2+}$; Cyclo[3-cyclohexylalanyl-3-[4[(4-O-hexopyranosylhexopyranosyl)oxy]cyclohexyl]alanyl-3-(2-iminoimidazolidin-4-yl)seryl-3-(3-hexopyranosyl-2-iminoimidazolidin-4-yl)serylserylglycyl]: MS (+ES), m/z: 647.2 $(M+2H)^{2+}$.

EXAMPLE 53

(Cyclo[3-cyclohexylalanyl-3-(2-iminoimidazolidin-4-yl)seryl-3-(3-hexopyranosyl-2-iminoimidazolidin-4-yl)serylserylglycyl-3-cyclohexyl-2-aminobutanoyl])

EXAMPLE 53a (Cyclo[3-[4-[(4-O-hexopyranosylhexopyranosyl)oxy]cyclohexyl]alanyl-3-(2-iminoimidazolidin-4-yl)seryl-3-(3-hexopyranosyl-2-iminoimidazolidin-4-yl)serylserylglycyl-3-cyclohexyl-2-aminobutanoyl])

The title compounds are prepared from cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] by the procedure described for example 52. Cyclo[3-cyclohexylalanyl-3-(2-iminoimidazolidin-4-yl)seryl-3-(3-hexopyranosyl-2-iminoimidazolidin-4-yl)serylserylglycyl-3-cyclohexyl-2-aminobutanoyl]: MS (+ES), m/z: 484 $(M+2H)^{2+}$; Cyclo[3-[4-[(4-O-hexopyranosylhexopyranosyl)oxy]cyclohexyl]alanyl-3-(2-iminoimidazoliclin-4-yl)seryl-3-(3-hexopyranosyl-2-iminoimidazolidin-4-yl)serylserylglycyl-3-cyclohexyl-2-aminobutanoyl]: MS (+ES), m/z: 654.1 $(M+2H)^{2+}$.

EXAMPLE 54

(Cyclo[3-(syn-4-hydroxycyclohexyl)alanyl-3-(2-iminoimidazolidin-4-yl)seryl-3-(3-hexopyranosyl-2-iminoimidazolidin-4-yl)serylserylglycyl-3-cyclohexyl-2-aminobutanoyl])

EXAMPLE 54a (Cyclo[3-(anti-4-hydroxycyclohexyl)alanyl-3-(2-iminoimidazolidin-4-yl)seryl-3-(3-hexopyranosyl-2-iminoimidazolidin-4-yl)serylserylglycyl-3-cyclohexyl-2-aminobutanoyl])

The title compounds are prepared from cyclo[glycyl-β-methylphenylalanyltyrosyl-3-(2-iminoimidazolidin-4-yl)seryl-3-(3-hexopyranosyl-2-iminoimidazolidin-4-yl)serylseryl] by the procedure described for example 52. Cyclo[3-cyclohexylalanyl-3-(2-iminoimidazolidin-4-yl)seryl-3-(3-hexopyranosyl-2-iminoimidazolidin-4-yl)serylserylglycyl-3-cyclohexyl-2-aminobutanoyl]: MS (+ES), m/z: 484 $(M+2H)^{2+}$; Cyclo[3-(syn-4-hydroxycyclohexyl)alanyl-3-(2-iminoimidazolidin-4-yl)seryl-3-(3-hexopyranosyl-2-iminoimidazolidin-4-yl)serylserylglycyl-3-cyclohexyl-2-aminobutanoyl]: MS (+ES), m/z: 492.5 $(M+2H)^{2+}$; Cyclo[3-(anti-4-hydroxycyclohexyl)alanyl-3-(2-iminoimidazolidin-4-yl)seryl-3-(3-hexopyranosyl-2-iminoimidazolidin-4-yl)serylserylglycyl-3-cyclohexyl-2-aminobutanoyl]: MS (+ES), m/z: 492.3 $(M+2H)^{2+}$.

EXAMPLE 55

(Cyclo[glycyl-β-methylphenylalanyltyrosyl-3-(2-iminoimidazolidin-4-yl)seryl-3-(3-hexopyranosyl-2-iminoimidazolidin-4-yl)serylseryl])

A stirred solution of the bis-hydrochloride salt of cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (10 g) in dimethyl sulfoxide (80 mL) is treated with concentrated hydrochloric acid (37%, 5 mL) and the mixture is heated at 60° C. for 20 hrs. The solution is then filtered to remove insoluble material and the filtrate is treated dropwise at 60° C. with acetonitrile (180 mL) to precipitate the product. The mixture is cooled to room temperature and the precipitate is removed by filtration, the filter cake is washed with acetonitrile and diethyl ether and air dried to provide the product as a tan powder. MS (+ES), m/z: 486.4 $(M+2H)^{2+}$.

EXAMPLE 56

(Cyclo[glycylphenylalanyltyrosyl-3-(2-iminoimidazolidin-4-yl)seryl-3-(3-hexopyranosyl-2-iminoimidazolidin-4-yl)serylseryl])

The title compound is prepared from cyclo[glycylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]by the procedure described for example 55. MS (+ES), m/z: 479.5 (M+2H)$^{2+}$.

EXAMPLE 57

(Cyclo[glycyl-β-methylphenylalanyltyrosyl-3-(2-iminoimidazolidin-4-yl)seryl-3-(2-iminoimidazolidin-4-yl)serylseryl])

To a suspension of the bis-hydrochloride salt of cyclo[glycyl-β-methylphenylalanyltyrosyl-3-(2-iminoimidazolidin-4-yl)seryl-3-(3-hexopyranosyl-2-iminoimidazolidin-4-yl)serylseryl] (1.5 g) in water (60 mL) is added sodium periodate (616 mg) and the mixture is stirred for 5 h. at room temperature. Methanol (45 mL) is added, followed by sodium borohydride (326 mg) and the mixture is stirred for 16 h. The volume of the solution is adjusted to 150 mL by the addition of methanol, and then concentrated hydrochloric acid (37%, 9 mL) is added and the solution is stirred at 60° C. for 16 h. The solution is cooled and concentrated in vacuo to provide a gum, which is subjected to flash chromatography over a reverse phase support (MCI CHP20P) to provided the desired product. MS (+ES), m/z: 405.4 (M+2H)$^{2+}$.

EXAMPLE 58

(Cyclo[3-cyclohexylalanyl-3-cyclohexylalanyl-3-(2-iminoimidazolidin-4-yl)seryl-3-(2-iminoimidazolidin-4-yl)-serylserylglycyl])

The title compound is prepared from cyclo[3-cyclohexylalanyl-3-cyclohexylalanyl-3-(2-iminoimidazolidin-4-yl)seryl-3-(3-hexopyranosyl-2-iminoimidazolidin-4-yl)serylserylglycyl] by the procedure described for example 57. MS (+ES), m/z: 396.4 (M+2H)$^{2+}$.

EXAMPLE 59

(Cyclo[glycyl-β-methylphenylalanyl-O-(4-O-hexopyranosylhexopyranosyl)tyrosyl-(2-iminoimidazolidin-4-yl)seryl-3-[1-benzyl-3-hexopyranosyl-2-iminoimidazolidin-4-yl]serylseryl])

A stirred solution of the bis-hydrochloride salt of cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (1.0 g) in dimethyl sulfoxide (25 mL) and water (4 mL) is treated with benzyl bromide (2.0 mL) and potassium carbonate (2.0 g) and the mixture is stirred for 2 h at room temperature. The reaction mixture is filtered and the filtrate is treated with acetonitrile (100 mL) to precipitate the crude product. The precipitate is filtered, washed with acetonitrile, and air-dried. The desired product is purified by reverse phase HPLC. MS (+ES), m/z: 693.3 (M+2H)$^{2+}$.

EXAMPLE 60

(Cyclo[glycyl-β-methylphenylalanyl-O-(4-O-hexopyranosylhexopyranosyl)tyrosyl-(2-iminoimidazolidin-4-yl)seryl-3-[1-(4-tert-butylbenzyl)-3-hexopyranosyl-2-iminoimidazolidin-4-yl]-serylseryl])

EXAMPLE 60a (Di-N-(4-tert-butylbenzyl)-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

A stirred solution of the bis-hydrochloride salt of cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (0.5 g) in dimethyl sulfoxide (10 mL) and water (1 mL) is treated with 4-t-butylbenzyl bromide (0.8 g) and potassium carbonate (0.8 g) and the mixture is stirred for 3 h at room temperature. The reaction mixture is filtered and the filtrate is treated with acetonitrile (100 mL) to precipitate the crude products. The precipitate is filtered, washed with acetonitrile, and air-dried. The desired products are purified by reverse phase HPLC. Cyclo[glycyl-β-methylphenylalanyl-O-(4-O-hexopyranosylhexopyranosyl)tyrosyl-(2-iminoimidazolidin-4-yl)seryl-3-[1-(4-tert-butylbenzyl)-3-hexopyranosyl-2-iminoimidazolidin-4-yl]-serylseryl]: MS (+ES), m/z: 721.4 (M+2H)$^{2+}$; Di-N-(4-tert-butylbenzyl)-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES), m/z: 794.5 (M+2H)$^{2+}$.

EXAMPLE 61

(Cyclo[glycyl-β-methylphenylalanyl-O-(4-O-hexopyranosylhexopyranosyl)tyrosyl-3-(2-iminoimidazolidin-4-yl)seryl-3-β-hexopyranosyl-1-(12-hydroxydodecyl)-2-iminoimidazolidin-4-yl]-serylseryl])

A stirred solution of the bis-hydrochloride salt of cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl](1.0 g) in dimethyl sulfoxide (20 mL) and water (4 mL) is treated with 12-bromo-1-dodecanol (0.66 g) and potassium carbonate (0.8 g) and the mixture is stirred for 2 h at room temperature. The reaction mixture is filtered and the filtrate is treated with acetonitrile (100 mL) to precipitate the crude product. The precipitate is filtered, washed with acetonitrile, and air-dried. The desired product is purified by reverse phase HPLC. MS (+ES), m/z: 740.4 (M+2H)$^{2+}$.

EXAMPLE 62

(Cyclo[glycyl-β-methylphenylalanyl-O-(4-O-hexopyranosylhexopyranosyl)tyrosyl-3-[1,3-dibenzyl-2-(benzylimino)imidazolidin-4-yl]seryl-3-[1-benzyl-2-(benzylimino)-3-hexopyranosylimidazolidin-4-yl]serylseryl])

A stirred solution of the bis-hydrochloride salt of cyclo[glycyl-β-methylphenylalanyl-0-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (1.0 g) in dimethyl sulfoxide (25 mL) and water (4 mL) is treated with benzyl bromide (2.0 mL) and potassium carbonate (2.0 g) and the mixture is stirred for 16 h at room temperature. Additional benzyl bromide (1.0 mL), potassium carbonate (0.6 g) and water (5 mL) is then added and the mixture is stirred for 20 h. The reaction mixture is filtered and the filtrate is treated with acetonitrile (180 mL) to precipitate the crude product. The precipitate is filtered, washed with acetonitrile, and air-dried. The desired product is purified by reverse phase HPLC. MS (+ES), m/z: 873.4 (M+2H)$^{2+}$.

EXAMPLE 63

(Cyclo[glycyl-β-methylphenylalanyl-O-(4-O-hexopyranosylhexopyranosyl)tyros yl-3-(2-iminoimidazolidin-4-yl)seryl-3-[1-butyl-3-hexopyranosyl-2-iminoimidazolidin-4-yl]serylseryl])

A stirred solution of the bis-hydrochloride salt of cyclo[glycyl-β-methylphenylalanyl-0-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (1.0 g) in dimethyl sulfoxide (20 mL) and water (2.0 mL) is treated with 1-bromobutane (0.24 mL) and potassium carbonate (0.6 g) and the mixture is stirred for 24 h at room temperature. The reaction mixture is filtered and the filtrate is treated with acetonitrile to precipitate the crude product. The precipitate is filtered, washed with acetonitrile, and air-dried. The desired product is purified by reverse phase HPLC. MS (+ES), m/z: 676.4 $(M+2H)^{2+}$.

EXAMPLE 64

(Cyclo[glycyl-β-methylphenylalanyl-O-(4-O-hexopyranosylhexopyranosyl)tyrosyl-3-(1,3-dimethyl-2-(methylimino)imidazolidin-4-yl)seryl-3-[3-hexopyranosyl-1-methyl-2-(methylimino)imidazolidin-4-yl]-serylseryl])

A stirred solution of the bis-hydrochloride salt of cyclo [glycyl-β-methylphenylalanyl-0-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (0.8 g) in dimethyl sulfoxide (15 mL) and water (1.5 mL) is treated with methyl iodide (0.35 mL) and potassium carbonate (1.0 g) and the mixture is stirred for 16 h at room temperature. Additional benzyl bromide (1.0 mL), potassium carbonate (0.6 g) and water (5 mL) is then added and the mixture is stirred for 20 h. The reaction mixture is filtered and the filtrate is treated with acetonitrile (180 mL) to precipitate the crude product. The precipitate is filtered, washed with acetonitrile, and air-dried. The desired product is purified by reverse phase HPLC. MS (+ES), m/z: 697.6 $(M)^{2+}$.

EXAMPLE 65

(Cyclo[glycyl-β-methylphenylalanyl-O-(4-O-hexopyranoslhexopyranosyl)tyrosyl-3-(2-iminoimidazolidin-4-yl)seryl-3-β-hexopyranosyl-2-imino-1-(2-phenylbenzyl)-imidazolidin-4-yl]-serylseryl])

The title compound is prepared by the procedure described for example 59 using the appropriate arylmethyl halide. MS (+ES), m/z: 731.6 $(M+2H)^{2+}$.

EXAMPLE 66

(Cyclo[glycyl-β-methylphenylalanyl-O-(4-O-hexopyranosylhexopyranosyl)tyrosyl-3-β-(4-phenylbenzyl)-2-[(4-phenylbenzyl)imino]imidazolidin-4-yl] seryl-3-β-hexopyranosyl-2-imino-1-(4-phenylbenzyl)-imidazolidin-4-yl]serylseryl])

EXAMPLE 66a (Cyclo[glycyl-β-methylphenylalanyl-O-(4-O-hexopyranosylhexopyranosyl)tyrosyl-3-(2-iminoimidazolidin-4-yl)seryl]-3-β-hexopyranosyl-2-imino-1-(4-phenylbenzyl)-imidazolidin-4-yl]-serylseryl])

The title compound is prepared by the procedure described for example 60 using the appropriate arylmethyl halide. Cyclo[glycyl-β-methylphenylalanyl-O-(4-O-hexopyranosylhexopyranosyl)tyrosyl-3-β-(4-phenylbenzyl)-2-[(4-phenylbenzyl)imino]imidazolidin-4-yl]seryl-3,3-hexopyranosyl-2-imino-1-(4-phenylbenzyl)-imidazolidin-4-yl] serylseryl]: MS (+ES), m/z: 897.6$(M+2H)^{2+}$; Cyclo[glycyl-β-methylphenylalanyl-O-(4-O-hexopyranosylhexopyranosyl)tyrosyl-3-(2-iminoimidazolidin-4-yl)seryl]-3-β-hexopyranosyl-2-imino-1-(4-phenylbenzyl)-imidazolidin-4-yl]-serylseryl]: MS (+ES), m/z: 731.6$(M+2H)^{2+}$.

EXAMPLE 67

(Cyclo[glycyl-β-methylphenylalanyl-O-(4-O-hexopyranosylhexopyranosyl)tyrosyl-3-(2-iminoimidazolidin-4-yl)seryl-3-β-hexopyranosyl-2-imino-1-(2-naphthylmethyl)-imidazolidin-4-yl]-serylseryl])

The title compound is prepared by the procedure described for example 59 using the appropriate arylmethyl halide. MS (+ES), m/z: 718.7$(M+2H)^{2+}$.

EXAMPLE 68

(Cyclo[glycyl-β-methylphenylalanyl-O-(4-O-hexopyranosylhexopyranosyl)tyrosyl-3-(2-iminoimidazolidin-4-yl)seryl]-3-β-hexopyranosyl-2-imino-1-(4-trifluoromethylbenzyl)-imidazolidin-4-yl]-serylseryl])

The title compound is prepared by the procedure described for example 59 using the appropriate arylmethyl halide. MS (+ES), m/z: 727.5$(M+2H)^{2+}$.

EXAMPLE 69

(Cyclo[glycyl-β-methylphenylalanyl-O-(4-O-hexopyranosylhexopyranosyl)tyrosyl-3-(2-iminoimidazolidin-4-yl)seryl-3-[1-(4-carboxybenzyl)-2-imino-3-hexopyranosylimidazolidin-4-yl]-serylseryl])

EXAMPLE 69a (Di-N-(4-carboxybenzyl)-cyclo[glycyl-β-methylphenylalanyl-O-(4-O-hexopyranosylhexopyranosyl) tyrosyl-3-(2-iminoimidazolidin-4-yl)seryl-3-(3-hexopyranosyl-2-iminoimidazolidin-4-yl)serylseryl])

EXAMPLE 69b (Tri-N-(4-carboxybenzyl)-Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

The title compounds are prepared by the procedure described for example 60 using the appropriate arylmethyl halide. Cyclo[glycyl-β-methylphenylalanyl-O-(4-O-hexopyranosylhexopyranosyl)tyrosyl-3-(2-iminoimidazolidin-4-yl)seryl-3,1-(4-carboxybenzyl)-2-imino-3-hexopyranosylimidazolidin-4-yl]-serylseryl]: MS (+ES), m/z: 715.4$(M+2H)^{2+}$; Di-N-(4-carboxybenzyl)-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES), m/z: 782.4 $(M+2H)^{2+}$; Tri-N-(4-carboxybenzyl)-cCyclo[glycyl-β-methylphenylalanyl-O-(4-O-hexopyranosylhexopyranosyl) tyrosyl-3-(2-iminoimidazolidin-4-yl)seryl-3-(3-hexopyranosyl-2-iminoimidazolidin-4-yl)serylseryl]: MS (+ES), m/z: 849.2$(M+211)^{2+}$.

EXAMPLE 70

(Cyclo[glycyl-β-methylphenylalanyl-O-(4-O-hex-opyranosylhexopyranosyl)tyrosyl-3-(2-iminoimidazolidin-4-yl)seryl-3-β-hexopyranosyl-2-imino-1-(3-methyl-but-2-enyl)imidazolidin-4-yl]serylseryl])

The title compound is prepared by the procedure described for example 59 using the appropriate allylic halide. MS (+ES), m/z: 682.5(M+2H)$^{2+}$.

EXAMPLE 71

(Cyclo[glycyl-β-methylphenylalanyl-O-(4-O-hex-opyranosylhexopyranosyl]tyrosyl-3-(2-iminoimidazolidin-4-yl)seryl-3-[1-heptyl-3-hexopyranosyl-2-iminoimidazolidin-4-yl]serylseryl])

The title compound is prepared by the procedure described for example 63 using the appropriate alkyl halide. MS (+ES), m/z: 697.4(M+2H)$^{2+}$.

EXAMPLE 72

(Cyclo[glycyl-β-methylphenylalanyl-O-(4-O-hex-opyranosylhexopyranosyl)tyrosyl-3-(2-iminoimidazolidin-4-yl)seryl-3-[1-(10-carboxydecyl)-3-hexopyranosyl-2-iminoimidazolidin-4-yl]serylseryl])

EXAMPLE 72a (Di-N-(10-carboxydecyl)-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

The title compounds are prepared by the procedure described for example 61 using the appropriate alkyl halide. Cyclo[glycyl-β-methylphenylalanyl-O-(4-O-hexopyranosylhexopyranosyl)tyrosyl-3-(2-iminoimidazolidin-4-yl)seryl-3,1-(10-carboxydecyl)-3-hexopyranosyl-2-iminoimidazolidin-4-yl]serylseryl]: MS (+ES), m/z: 740.7(M+2H)$^{2+}$; Di-N-(10-carboxydecyl)-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES), m/z: 832.9(M+2H)$^{2+}$.

EXAMPLE 73

Cyclo[3-[1,3-benzyl-2-(benzylimino)imidazolidin-4-yl]alanyl-3-[1-benzyl-2-(benzylimino)-3-hexopyranosylimidazolidin-4-yl]alanylserylglycyl-β-methylphenylalanyl-O-(4-O-hexopyranosylhexopyranosyl)tyrosyl])

The title compound is prepared from cyclo[3-(2-iminoimidazolidin-4-yl)alanyl-3-(3-hexopyranosyl-2-iminoimidazolidin-4-yl)-alanylserylglycyl-β-methylphenylalanyl-O-(4-O-hexopyranosylhexopyranosyl)tyrosyl] by the procedure described for example 62 using the appropriate alkyl halide. MS (+ES), m/z: 857.9 (M+21-1)$^{2+}$.

EXAMPLE 74

(Cyclo[3-[1,3-dimethyl-2-(methylimino)imidazolidin-4-yl]alanyl-3-β-hexopyranosyl-1-methyl-2-(methylimino)imidazolidin-4-yl]alanylserylglycyl-β-methylphenylalanyl-O-(4-O-hexopyranosylhexopyranosyl)tyrosyl])

The title compound is prepared from cyclo[3-(2-iminoimidazolidin-4-yDalanyl-3-(3-hexopyranosyl-2-iminoimidazolidin-4-yl)-alanylserylglycyl-β-methylphenylalanyl-O-(4-O-hexopyranosylhexopyranosyl)tyrosyl] by the procedure described for example 64. MS (+ES), m/z: 681.7(M)$^{2+}$.

EXAMPLE 75

(Cyclo[glycyl-β-methylphenylalanyl-O-(methyl)tyrosyl-3-(1,3-dimethyl-2-(methylimino)imidazolidin-4-yl)seryl-3-β-hexopyranosyl-1-methyl-2-(methylimino)imidazolidin-4-yl]-serylseryl])

The title compound is prepared from cyclo[glycyl-β-methylphenylalanyltyrosyl-3-(2-iminoimidazolidin-4-yl)seryl-3-(3-hexopyranosyl-2-iminoimidazolidin-4-yl)serylseryl] by the procedure described for example 64. MS (+ES), m/z: 542.6(M)$^{2+}$.

EXAMPLE 76

(Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-[2-(benzylimino)-3-hexopyranosylimidazolidin-4-yl]serylseryl])

The title compound is prepared from cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)serylseryl] by the procedure described for example 59. MS (+ES) m/z: 759.4 (M+2H)$^{2+}$.

EXAMPLE 77

(Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-[2-[1-(4-tert-butylbenzyl)-3-hexopyranosyl-2-imidazolidin-4-yl]serylseryl]

The title compound is prepared from cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)serylseryl] by the procedure described for example 59 using the appropriate arylmethyl halide. MS (+ES) m/z: 787.7 (M+2H)$^{2+}$.

EXAMPLE 78

(Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-β-hexonyranosyl-2-imino-1-(2-naphthylmethyl)-imidazolidin-4-yl]serylseryl]

The title compound is prepared from cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)serylseryl] by the procedure described for example 59 using the appropriate arylmethyl halide. MS (+ES) m/z: 784.6 (M+2H)$^{2+}$.

EXAMPLE 79

(Cyclo[glycyl-β-methylphenylalanyl-O-[4-O-[4,6-O-(2-adamantylidene)hexopyranosyl]hexopyranosyl] tyrosyl-3-[1,3-dibenzyl-2-(benzylimino)imidazolidin-4-yl]seryl-3-[1-benzyl-2-(benz ylimino)-3-hexopyranosylimidazolidin-4-yl]serylseryl])

The title compound is prepared from cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)serylseryl] by the procedure described for example 62 using the appropriate arylmethyl halide. MS (+ES) m/z: 939.9 (M+2H)$^{2+}$.

EXAMPLE 80

(Cyclo[3-(2-iminoimidazolidin-4-yl)alanyl-3-(1-benzyl-3-hexopyranosyl-2-iminoimidazolidin-4-yl) alanylserylglycyl-β-methylphenylalanyl-O-[4-O-[4, 6-O-(2-adamantylidene)hexopyranosyl] hexopyranosyl]tyrosyl])

The title compound is prepared from cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[4,6-O-(2-adamantylidene)hexopyranosyl]-hexopyranosyl]tyrosyl] by the procedure described for example 59. MS (+ES) m/z: 743.6 (M+2H)$^{2+}$.

EXAMPLE 81

(Cyclo[glycyl-β-methylphenylalanyl-O-[4-O-[4,6-O-(2-adamantylidene)hexopyranosyl]hexopyranosyl] tyrosyl-3-[1,3-dimethyl-2-(methylimino)imidazolidin-4-yl]seryl-3-β-hexopyranosyl-1-methyl-2-(methylimino)imidazolidin-4-yl]serylseryl])

The title compound is prepared from cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)serylseryl] by the procedure described for example 64. MS (+ES) m/z: 763.6 (M)$^{2+}$.

EXAMPLE 82

(Cyclo[glycyl-β-methylphenylalanyl-O-[4-O-[4,6-O-(2-adamantylidene)hexopyranosyl]hexopyranosyl] tyrosyl-3-(2-iminoimidazolidin-4-yl)seryl-3-[1-[(3,7-dimethylocta-2,6-dien-1-yl)-imino]-3-hexopyranosylimidazolidin-4-yl]serylseryl])

The title compound is prepared from cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)serylseryl] by the procedure described for example 59. MS (+ES) m/z: 782.5 (M+2H)$^{2+}$.

EXAMPLE 83

(Cyclo[glycyl-β-methylphenylalanyl-O-[4-O-[4,6-O-(2-adamantylidene)hexopyranosyl]hexopyranosyl] tyrosyl-3-(2-iminoimidazolidin-4-yl)seryl-3-[1-heptyl-3-hexopyranosyl-2-iminoimidazolidin-4-yl] serylseryl]

The title compound is prepared from cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)serylseryl] by the procedure described for example 63 using the appropriate alkyl halide. MS (+ES) m/z: 763.5 (M+2H)$^{2+}$.

EXAMPLE 84

(Cyclo[glycyl-β-methylphenylalanyl-O-[4-O-[4,6-O-(2-adamantylidene)hexopyranosyl]-hexopyranosyl] tyrosyl-3-(2-iminoimidazolidin-4-yl)seryl-3-β-hexopyranosyl-2-(hexylimino)imidazolidin-4-yl] serylseryl])

The title compound is prepared from cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)serylseryl]by the procedure described for example 63 using the appropriate alkyl halide. MS (+ES) m/z: 756.5 (M+2H)$^{2+}$.

EXAMPLE 85

(Cyclo[3-[2-[2-(hexopyranosyloxy)phenyl]-1,3-benzoxazol-5-yl]alanyl-3-(2-iminoimidazolidin-4-yl) seryl-3-(1-benzyl-3-hexopyranosyl-2-iminoimidazolidin-4-yl)serylserylglycyl-β-methyl-phenylalanyl])

The title compound is prepared from cyclo[3-[2-[2-(hexopyranosyloxy)phenyl]-1,3-benzoxazol-5-yl]alanyl-3-(2-iminoimidazolidin-4-yl)seryl-3-(3-hexopyranosyl-2-iminoimidazolidin-4-yl)serylserylglycyl-β-methylphenylalanyl] by the procedure described for example 59. MS (+ES) m/z: 671.0 (M+2H)$^{2+}$.

EXAMPLE 86

(Cyclo[glycyl-β-methylphenylalanyl-O-[4-O-hexopyranosylhexopyranosyl)tyrosyl-3-[2-iminoimidazolidin-4-yl)seryl-3-(2-decanoylimino-3-hexopyranosylimidazolidin-4-yl)serylseryl])

A stirred solution of the bis-hydrochloride salt of cyclo [glycyl-β-methylphenylalanyl-0-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (0.1 g) in N,N-dimethylformamide (1.5 mL) and 2,4,6-collidine (1.2 mL) is treated with decanoic anhydride (0.07 mL) and the mixture is stirred for 30 h at room temperature. The reaction mixture is then concentrated in vacuo to provide a gum, which is triturated with ethyl acetate to precipitate the crude product. The precipitate is filtered, washed with ethyl acetate, and air-dried. The desired product is purified by reverse phase HPLC. MS (+ES), m/z: 725.2 (M+2H)$^{2+}$.

EXAMPLE 87

(Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-(3-methylbutyrylimino)-imidazolidin-4-yl)serylseryl])

The title compound is prepared by the procedure described for example 86 using the appropriate carboxylic acid anhydride. MS (+ES), m/z: 690.2 (M+2H)$^{2+}$.

EXAMPLE 88

(Cyclo[glycyl-β-methylphenylalanyl-O-[4-O-hexopyranosylhexopyranosyl)tyrosyl-3-(2-iminoimidazolidin-4-yl)seryl-3-[2-(2-ethyl-butyrylimino)-3-hexopyranosylimidazolidin-4-yl)serylseryl])

The title compound is prepared by the procedure described for example 86 using the appropriate carboxylic acid anhydride. MS (+ES), m/z: 697.2 (M+2H)$^{2+}$.

EXAMPLE 89

(Tri-N-[(phenylmethoxy)carbonyl]-cyclo[glycyl-β-methylphenylalanyltyrosyl-3-(2-iminoimidazolidin-4-yl)seryl-3-(3-hexopyranosyl-2-iminoimidazolidin-4-yl)serylseryl])

A stirred solution of the bis-acetate salt of cyclo[glycyl-β-methylphenylalanytyrosyl-3-(2-iminoimidazolidin-4-yl)seryl-3-(3-hexopyranosyl-2-iminoimidazolidin-4-yl)serylseryl] (0.2 g) in dimethyl sulfoxide (1.5 mL) is treated with N,N-diisopropylethylamine (0.105 mL) and a solution of N-(benzyloxycarbonyloxy)-succinimide (160 mg) in dimethyl sulfoxide (0.3 mL) and the mixture is stirred for 16 h at room temperature. Acetonitrile (8 mL) is then added to precipitate the crude product. The precipitate is filtered, washed with acetonitrile and diethyl ether, and air-dried. The desired product is purified by reverse phase HPLC. MS (+ES), m/z: 687.3 (M+2H)$^{24}$.

EXAMPLE 90

(N-[(Phenylmethoxy)carbonyl]-cyclo[glycyl-β-methylphenylalanyl-O-(4-O-hexopyranosylhexopyranosyl)tyrosyl-3-[2-iminoimidazolidin-4-yl)seryl-3-(3-hexopyranosyl-2-iminoimidazolidin-4-yl)serylseryl])

A stirred solution of the bis-hydrochloride salt of cyclo[glycyl-β-methylphenylalanyl-0-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (50 mg) in N,N-dimethylformamide (0.8 mL) is treated with N,N-diisopropylethylamine (0.013 mL) and N-(benzyloxycarbonyloxy)-succinimide (13 mg) and the mixture is stirred for 16 h at room temperature. Acetonitrile is then added to precipitate the crude product. The precipitate is filtered, washed with ethyl acetate, and air-dried. The desired product is purified by reverse phase HPLC. MS (+ES), m/z: 715.8 (M+2H)$^{2+}$.

EXAMPLE 91

(Tri-N-[(phenylmethoxy)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

The title compound is prepared from cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] by the procedure described for example 89. MS (+ES), m/z: 849.7 (M+2H)$^{2+}$.

EXAMPLE 92

(Cyclo[glycyl-β-methylphenylalanyl-O-(4-O-hexopyranosylhexopyranosyl)tyrosyl-3-[2-(pyrimidin-2-ylimino)imidazolidin-4-yl]seryl-3-β-hexopyranosyl-2-imino-1-(pyrimidin-2-yl)imidazolidin-4-yl]serylseryl])

A stirred solution of the bis-hydrochloride salt of cyclo[glycyl-β-methylphenylalanyl-0-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (0.908 g) in dimethyl sulfoxide (20 mL) is treated with potassium carbonate (0.912 g) and 2-chloropyrimidine (0.756 g) and the mixture is stirred for 20 h at 50° C. The mixture is cooled to room temperature, decanted into acetonitrile (64 mL) and the resultant precipitate collected by centrifugation. The precipitate is resuspended in acetonitrile (64 mL) and recentrifuged. The resulting pale brown solid is purified by reverse phase HPLC. MS (+ES), m/z: 726.4 (M+2H)$^{2+}$.

EXAMPLE 93

(Cyclo[glycyl-β-methylphenylalanyl-O-(4-O-hexopyranosylhexopyranosyl)tyrosyl-3-[2-(1,3-benzoxazol-2-ylimino)imidazolidin-4-yl]seryl-3-[1-(1,3-benzoxaxol-2-yl)-3-hexopyranosyl-2-iminoimidazolidin-4-yl]serylseryl])

A stirred solution of the bis-hydrochloride salt of cyclo[glycyl-β-methylphenylalanyl-0-(4-O-hexopyranosylhexopyranosyl)tyrosyl-3-(2-iminoimidazolidin-4-yl)seryl-3-(3-hexopyranosyl-2-iminoimidazolidin-4-yl)serylseryl](0.908 g) in dimethyl sulfoxide (20 mL) is treated with potassium carbonate (0.912 g) and 2-chlorobenzoxazole (0.674 g) and the mixture is stirred for 4 h at room temperature. The reaction mixture is decanted into acetonitrile (64 mL) and the resultant precipitate collected by centrifugation. The precipitate is resuspended in acetonitrile (64 mL) and recentrifuged. The resulting pale brown solid is purified by reverse phase HPLC. MS (+ES), m/z: 765.3 (M+2H)$^{2+}$.

EXAMPLE 94

(Cyclo[glycyl-β-methylphenylalanyl-O-(4-O-hexopyranosylhexopyranosyl)tyrosyl-3-[2-(1,3-benzothiazol-2-ylimino)imidazolidin-4-yl]seryl-3-[1-(1,3-benzo-thiazol-2-yl)-2-imino-3-hexonyranosylimidazolidin-4-yl]serylseryl])

A stirred solution of the bis-hydrochloride salt of cyclo[glycyl-β-methylphenylalanyl-0-(4-O-hexopyranosylhexopyranosyl)tyrosyl-3-(2-iminoimidazolidin-4-yl)seryl-3-(3-hexopyranosyl-2-iminoimidazolidin-4-yl)serylseryl) (0.24 g) in dimethyl sulfoxide (5 mL) is treated with potassium carbonate (0.24 g) and 2-chlorobenzothiazole (0.297 g) and the mixture is stirred for 5 days at 35° C. The mixture is cooled to room temperature, decanted into acetonitrile (64 mL) and the resultant precipitate collected by centrifugation. The precipitate is resuspended in acetonitrile (64 mL) and recentrifuged. The resulting pale brown solid is purified by reverse phase HPLC. MS (+ES), m/z: 781.2 (M+2H)$^{2+}$.

EXAMPLE 95

(Cyclo[glycyl-β-methylphenylalanyl-O-(4-O-hexopyranosylhexopyranosyl)tyrosyl-3-(2-iminoimidazolidin-4-yl)seryl-3-β-(6-O-hexanoylhexopyranosyl)-2-iminoimidazolidin-4-yl]serylseryl])

EXAMPLE 95a (Cyclo[glycyl-β-methylphenylalanyl-O-(6-O-hexanoyl-4-O-hexopyranosylhexopyranosyl)-tyrosyl-3-(2-iminoimidazolidin-4-yl)seryl-3-(3-hexopyranosyl-2-iminoimidazolidin-4-yl)-serylseryl])

EXAMPLE 95b (Cyclo[glycyl-β-methylphenylalanyl-O-[4-O-(6-O-hexanoylhexopyranosyl)hexopyranosyl]-tyrosyl-3-[2-iminoimidazolidin-4-yl]seryl-3-(3-hexopyranosyl-2-iminoimidazolidin-4-yl)-serylseryl])

A stirred solution of the bis-trifluoroacetate salt of cyclo [glycyl-β-methylphenylalanyl-O-(4-O-hexopyranosylhexopyranosyl)tyrosyl-3-(2-iminoimidazoliclin-4-yl)seryl-3-(3-hexopyranosyl-2-iminoimidazolidin-4-yl)serylseryl] (0.38 g) in N,N-dimethylformamide (50 mL) and pyridine (0.4 mL) is treated dropwise with a solution of hexanoic anhydride (0.25 g) in N,N-dimethylformamide (2 mL) and the reaction mixture is stirred for 16 h at room temperature. The reaction is then quenched by the addition of methanol (100 mL), stirred for 30 min, and the volatiles are removed in vacuo. The resulting residue is purified by reverse phase HPLC to provide the title compounds. Cyclo[glycyl-β-methylphenylalanyl-O-(4-O-hexopyranosylhexopyranosyl)tyrosyl-3-(2-iminoimidazolidin-4-yl)seryl-3-β-(6-O-hexanoylhexopyranosyl)-2-iminoimidazolidin-4-yl]serylseryl]: MS (+ES), m/z: 697.4 (M+2H)$^{2+}$; Cyclo[glycyl-β-methylphenylalanyl-O-(6-O-hexanoyl-4-O-hexopyranosylhexopyranosyl)-tyrosyl-3-(2-iminoimidazolidin-4-yl)seryl-3-(3-hexopyranosyl-2-iminoimidazolidin-4-yl)-serylseryl]: MS (+ES), m/z: 697.4 (M+2H)$^{2+}$; Cyclo(glycyl-β-methylphenylalanyl-O-[4-O-(6-O-hexanoylhexopyranosyl)hexopyranosyl]-tyrosyl-3-(2-iminoimidazolidin-4-yl)seryl-3-(3-hexopyranosyl-2-iminoimidazolidin-4-yl)-serylseryl]: MS (+ES), m/z: 697.4 (M+2H)$^{2+}$.

EXAMPLE 96

(Cyclo[glycyl-β-methylphenylalanyl-O-(4-O-hexopyranosylhexopyranosyl)tyrosyl-3-(2-iminoimidazolidin-4-yl)seryl-3-β-[6-O-(diphenylacetyl)hexopyranosyl]-2-iminoimidazolidin-4-yl]-serylseryl])

EXAMPLE 96a (Cyclo[glycyl-β-methylphenylalanyl-O-[4-O-hexopyranosylhexopyranosyl)tyrosyl-3-(2-iminoimidazolidin-4-yl)seryl-3-(3-hexopyranosyl-2-iminoimidazolidin-4-yl)seryl-O-(diphenylacetyl)-seryl])

EXAMPLE 96b (Cyclo[glycyl-β-methylphenylalanyl-O-[6-O-(diphenylacetyl)-4-O-hexopyranosylhexopyranosyl]tyrosyl-3-(2-iminoimidazolidin-4-yl)seryl-3-(3-hexopyranosyl-2-iminoimidazolidin-4-yl)serylseryl])

EXAMPLE 96c (Cyclo[glycyl-β-methylphenylalanyl-O-[4-O-[6-O-(diphenylacetyl)hexopyranosyl)hexopyranosyl]tyrosyl-3-(2-iminoimidazolidin-4-yl)seryl-3-(3-hexopyranosyl-2-iminoimidazolidin-4-yl)serylseryl])

A stirred solution of the bis-trifluoroacetate salt of cyclo [glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (1.0 g) in N,N-dimethylformamide (100 mL) and pyridine (1.0 mL) is treated dropwise with a solution of diphenylacetyl chloride (0.8 g) in N,N-dimethylformamide (2 mL) at −5° C. The resulting mixture is warmed to room temperature and stirred for 1 h. The reaction is then quenched by the addition of methanol (100 mL), stirred for 30 min, and the volatiles are removed in vacuo. The resulting residue is purified by reverse phase HPLC to provide the title compounds. Cyclo[glycyl-β-methylphenylalanyl-O-(4-O-hexopyranosylhexopyranosyl)tyrosyl-3-(2-iminoimidazolidin-4-yl)seryl-3-β-[6-O-(diphenylacetyphexopyranosyl)-2-iminoimidazolidin-4-yl]-serylseryl]: MS (+ES), m/z: 745.2 (M+2H)$^{2+}$; Cyclo[glycyl-iminoimidazolidin-4-yl)seryl-3-(3-hexopyranosyl-2-iminoimidazolidin-4-yl)seryl-O-(diphenylacetyl)-seryl]: MS (+ES), m/z: 745.4 (M+2H)$^{2+}$; Cyclo[glycyl-β-methylphenylalanyl-O-[6-O-(diphenylacetyl)-4-O-hexopyranosylhexopyranosyl]tyrosyl-3-(2-iminoimidazolidin-4-yl)seryl-3-(3-hexopyranosyl-2-iminoimidazolidin-4-yl)serylseryl]: MS (+ES), m/z: 745.3 (M+2H)$^{2+}$; Cyclo[glycyl-β-methylphenylalanyl-O-[4-O-[6-O-(diphenylacetyl)hexopyranosyl]hexopyranosyl]tyrosyl-3-(2-iminoimidazolidin-4-yl)seryl-3-(3-hexopyranosyl-2-iminoimidazolidin-4-yl)serylseryl]: MS (+ES), m/z: 745.4 (M+2H)$^{2+}$.

EXAMPLE 97

(Cyclo[glycyl-β-methylphenylalanyl-O-(4-O-hexopyranosylhexopyranosyl)tyrosyl-3-(2-iminoimidazolidin-4-yl)seryl-3-β-(6-O-heptanoylhexopyranosyl)-2-iminoimidazolidin-4-yl]seryl-seryl])

EXAMPLE 97a (Cyclo[glycyl-β-methylphenylalanyl-O-(6-O-heptanoyl-4-O-hexopyranosylhexopyranosyl)-tyrosyl-3-(2-iminoimidazolidin-4-yl)seryl-3-(3-hexopyranosyl-2-iminoimidazolidin-4-yl)-serylseryl])

EXAMPLE 97b

Cyclo[glycyl-β-methylphenylalanyl-O-[4-O-(6-O-heptanoylhexopyranosyl)hexopyranosyl]-tyrosyl-3-(2-iminoimidazolidin-4-yl)seryl-3-(3-hexopyranosyl-2-iminoimidazolidin-4-yl)-serylseryl])

The title compounds are prepared by the procedure described for example 95 using the appropriate carboxylic acid anhydride. Cyclo[glycyl-β-methylphenylalanyl-O-(4-O-hexopyranosylhexopyranosyl)tyrosyl-3-(2-iminoimidazolidin-4-yl)seryl-3-β-(6-O-heptanoylhexopyranosyl)-2-iminoimidazolidin-4-yl]seryl-seryl]: MS (+ES) m/z: 704.4 $(M+2H)^{2+}$; Cyclo[glycyl-β-methylphenylalanyl-O-(6-O-heptanoyl-4-O-hexopyranosylhexopyranosyl)-tyrosyl-3-(2-iminoimidazolidin-4-yl)seryl-3-(3-hexopyranosyl-2-iminoimidazolidin-4-yl)-serylseryl]: MS (+ES) m/z: 704.4 $(M+2H)^{2+}$; Cyclo[glycyl-β-methylphenylalanyl-O-[4-O-(6-O-heptanoylhexopyranosyl)hexopyranosyl]-tyrosyl-3-(2-iminoimidazolidin-4-yl)seryl-3-(3-hexopyranosyl-2-iminoimidazolidin-4-yl)-serylseryl]: MS (+ES) m/z: 704.4 $(M+2H)^{2+}$.

EXAMPLE 98

(Cyclo[glycyl-β-methylphenylalanyl-O-[4-O-hexopyranosylhexopyranosyl)tyrosyl-3-(2-iminoimidazolidin-4-yl)seryl-3-β-(6-O-(phenylacetyl)hexopyranosyl-2-iminoimidazolidin-4-yl-serylseryl])

EXAMPLE 98a (Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazoliclin-4-yl-seryl-O-(phenylacetyl)seryl]

EXAMPLE 98b (Cyclo[glycyl-β-methylphenylalanyl-O-[4-O-hexopyranosyl-6-O-(phenylacetyl)hexopyranosyl]-tyrosyl-3-(2-iminoimidazolidin-4-yl)seryl-3-(3-hexopyranosyl-2-iminoimidazolidin-4-yl-serylseryl])

EXAMPLE 98c (Cyclo[glycyl-β-methylphenylalanyl-O-[4-O-[6-O-(phenylacetyl)hexopyranosyl]hexopyranosyl]-tyrosyl-3-(2-iminoimidazolidin-4-yl)seryl-3-(3-hexopyranosyl-2-iminoimidazolidin-4-yl)-serylseryl])

The title compounds are prepared by the procedure described for example 96 using the appropriate carboxylic acid chloride. Cyclo[glycyl-β-methylphenylalanyl-O-(4-O-hexopyranosylhexopyranosyl)tyrosyl-3-(2-iminoimidazolidin-4-yl)seryl-3-(3-(6-O-(phenylacetyl)hexopyranosyl-2-iminoimidazolidin-4-yl-serylseryl]: MS (+ES) m/z: 707.4 $(M+2H)^{2+}$; Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazoliclin-4-yl-seryl-O-(phenylacetyl)seryl): MS (+ES) m/z: 707.4 $(M+2H)^{2+}$; Cyclo[glycyl-β-methylphenylalanyl-O-[4-O-hexopyranosyl-6-O-(phenylacetyl)hexopyranosyl]-tyrosyl-3-(2-iminoimidazolidin-4-yl)seryl-3-(3-hexopyranosyl-2-iminoimidazolidin-4-yl-serylseryl]: MS (+ES) m/z: 707.4 $(M+2H)^{2+}$; Cyclo[glycyl-β-methylphenylalanyl-O-[4-O-[6-O-(phenylacetyl)hexopyranosyl]hexopyranosyl]-tyrosyl-3-(2-iminoimidazolidin-4-yl)seryl-3-(3-hexopyranosyl-2-iminoimidazolidin-4-yl)-serylseryl]: MS (+ES) m/z: 707.2 $(M+2H)^{2+}$.

EXAMPLE 99

(Cyclo[glycyl-β-methylphenylalanyl-O-[4-O-[6-O-(2-propylpentanoyl)hexopyranosyl]-hexopyranosyl] tyrosyl-3-(2-iminoimidazolidin-4-yl)seryl-3-β-(6-O-(2-propylpentanoyl)-hexopyranosyl)-2-iminoimidazolidin-4-yl]serylseryl])

EXAMPLE 99a (Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)seryl-0-(2-propylpentanoyl)-seryl])

EXAMPLE 99b (Cyclo[glycyl-β-methylphenylalanyl-O-(4-O-hexopyranosyl-6-O-(2-propylpentanoyl)hexopyranosyl] tyrosyl-3-(2-iminoimidazolidin-4-yl)seryl-3-(3-hexopyranosyl-2-iminoimidazolidin-4-yl)serylseryl])

EXAMPLE 99c (Cyclo[glycyl-β-methylphenylalanyl-O-[4-O-[6-O-(2-propylpentanoyl)hexopyranosyl]-hexopyranosyl] tyrosyl-3-(2-iminoimidazolidin-4-yl)seryl-3-(3-hexopyranosyl-2-iminoimidazolidin-4-yl)serylseryl])

The title compounds are prepared by the procedure described for example 96 using the appropriate carboxylic acid chloride. Cyclo[glycyl-β-methylphenylalanyl-O-[4-O-6-O-(2-propylpentanoyl)hexopyranosyl]-hexopyranosyl]tyrosyl-3-(2-iminoimidazolidin-4-yl)seryl-3-β-(6-O-(2-propylpentanoyl)-hexopyranosyl)-2-iminoimidazolidin-4-yl] serylseryl]: MS (+ES) m/z: 711.2 $(M+2H)^{2+}$; Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)seryl-O-(2-propylpentanoyl)-seryl]: MS (+ES) m/z: 711.2 $(M+2H)^{2+}$; Cyclo[glycyl-β-methylphenylalanyl-O-[4-O-hexopyranosyl-6-O-(2-propylpentanoyl)hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 711.3 $(M+2H)^{2+}$; Cyclo[glycyl-β-methylphenylalanyl-O-[4-O-[6-O-(2-propylpentanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 711.3 $(M+2H)^{2+}$.

EXAMPLE 100

(Cyclo[glycyl-β-methylphenylalanyl-O-(4-O-hexopyranosylhexopyranosyl)tyrosyl-3-(2-iminoimidazolidin-4-yl)seryl-3-β-(6-O-(3-cyclopentylpropanoyl)-hexopyranosyl)-2-iminoimidazolidin-4-yl]serylseryl])

EXAMPLE 100a (Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)seryl-O-(3-cyclopentylpropanoyl)seryl])

EXAMPLE 100b (Cyclo[glycyl-β-methylphenylalanyl-O-[6-O-(3-cyclopentylpropanoyl)-4-O-hexopyranosyl-hexopyranosyl]tyrosyl-3-(2-iminoimidazolidin-4-yl)seryl-3-(3-hexopyranosyl-2-iminoimidazolidin-4-yl)serylseryl])

EXAMPLE 100c (Cyclo[glycyl-β-methylphenylalanyl-O-[4-O-[6-O-(3-cyclopentylpropanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compounds are prepared by the procedure described for example 96 using the appropriate carboxylic acid chloride. Cyclo[glycyl-β-methylphenylalanyl-O-(4-O-hexopyranosylhexopyranosyl)tyrosyl-3-(2-iminoimidazolidin-4-yl)seryl-3-β-(6-O-(3-cyclopentylpropanoyl)-hexopyranosyl)-2-iminoimidazoliclin-4-yl]serylseryl]: MS (+ES) m/z: 710.3 $(M+2H)^{2+}$; Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)seryl-O-(3-cyclopentylpropanoyl)seryl]: MS (+ES) m/z: 710.3 $(M+2H)^{2+}$; Cyclo[glycyl-β-methylphenylalanyl-O -[6-O-(3-cyclopentylpropanoyl)-4-O-hexopyranosyl-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 710.4 $(M+2H)^{2+}$; Cyclo[glycyl-β-methylphenylalanyl-O-[4-O-[6-O-(3-cyclopentylpropanoyl)hexopyranosyl]-hexopyranosyl]tyrosyl-3-(2-iminoimidazoliclin-4-yl)seryl-3-(3-hexopyranosyl-2-iminoimidazolidin-4-yl)serylseryl]: MS (+ES) m/z: 710.4 $(M+2H)^{2+}$.

EXAMPLE 101

(Cyclo[glycyl-β-methylphenylalanyl-O-[4-O-hexopyranosyl-6-O-[(phenylmethoxy)carbonyl]-hexopyranosyl]tyrosyl-3-(2-iminoimidazolidin-4-yl)seryl-3-(3-hexopyranosyl-2-iminoimidazolidin-4-1/1)serylseryl])

EXAMPLE 101a (Cyclo[glycyl-β-methylphenylalanyl-O-[4-O-[6-O-[(phenylmethoxy)carbonyl]hexopyranosyl]-hexopyranosyl]tyrosyl-3-(2-iminoimidazolidin-4-yl)seryl-3-(3-hexopyranosyl-2-iminoimidazolidin-4-yl)serylseryl])

A stirred solution of the bis-trifluoroacetate salt of cyclo [glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (80 mg) in pyridine (3 mL) is treated with benzyl chloroformate (15 µl). After stirring at room temperature for 20 hr, additional 10 IA of benzyl chloroformate is added. The mixture is stirred for 3 days at room temperature and the volatiles are then removed in vacuo. The residue is triturated with ethyl acetate (3 mL), and the resulting precipitate is collected by filtration, washed with ethyl acetate, dried under vacuum to give a brown solid. The solid is then purified by reverse phase HPLC to provide the title compounds; Cyclo[glycyl-β-methylphenylalanyl-O-[4-O-hexopyranosyl-6-O-[(phenylmethoxy)carbonyl]-hexopyranosyl]tyrosyl-3-(2-iminoimidazolidin-4-yl)seryl-3-(3-hexopyranosyl-2-iminoimidazolidin-4-yl)serylseryl]: MS (+ES), m/z: 715.3 $(M+2H)^{2+}$; Cyclo[glycyl-β-methylphenylalanyl-O-[4-O-[6-O-[(phenylmethoxy)carbonyl]hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES), m/z: 715.3 $(M+2H)^{2+}$.

EXAMPLE 102

(Cyclo[glycyl-β-methylphenylalanyl-O-[4-O-(4,6-O-phenethylidenehexopyranosyl)-hexopyranosyl]tyrosyl-3-(2-iminoimidazoliclin-4-yl)seryl-3-(3-hexopyranosyl-2-iminoimidazolidin-4-yl)serylseryl])

A stirred solution of the bis-trifluoroacetate salt of cyclo [glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (0.5 g) in N,N-dimethylformamide (35 mL) is treated with phenylacetaldehyde dimethyl acetal (0.165 g) and p-toluene sulfonic acid mono-hydrate (0.15 g) and the mixture is stirred at 60-65° C. for 12 h. The reaction mixture is then directly separated by reverse phase HPLC to provide the title compound. MS (+ES), m/z: 699.3 $(M+2H)^{2+}$.

EXAMPLE 103

(Cyclo[glycyl-β-methylphenylalanyl-O-[4-O-14,6-O-(4-methoxyphenethylidene)hexopyranosyl]-hexopyranosylltvrosyl-3-(2-iminoimidazolidin-4-yl)seryl-3-(3-hexopyranosyl-2-iminoimidazolidin-4-vDserylseryl]) A stirred solution of the bis-hydrochloride salt of cyclo[glycyl-β-methylphenylalanyl-0-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (0.5 g) in N,N-dimethylformamide (5 mL) and dimethyl sulfoxide (5 mL) is treated with 4-methoxyphenylacetaldehyde dimethyl acetal (0.215 g) and p-toluene sulfonic acid mono-hydrate (0.15 g) and the mixture is stirred at 60-65° C. for 12 h. The reaction mixture is then directly separated by reverse phase HPLC to provide the title compound. MS (+ES), m/z: 714.4 $(M+2H)^{2+}$.

EXAMPLE 104

(Cyclo[glycyl-β-methylphenylalanyl-O-[4-O-(4,6-O-benzylidenehexopyranosyl)hexopyranosyl]-tyrosyl-3-(2-iminoimidazolidin-4-yl)seryl-3-(3-hexopyranosyl-2-iminoimidazolidin-4-yl)-serylseryl])

EXAMPLE 104a (Cyclo[glycyl-β-methylphenylalanyl-O-[4-O-(2,3-O-benzylidenehexopyranosyl)hexopyranosyl]-tyrosyl-3-(2-iminoimidazolidin-4-yl)seryl-3-(3-hexopyranosyl-2-iminoimidazolidin-4-yl)-serylseryl])

EXAMPLE 104b (Cyclo[glycyl-β-methylphenylalanyl-O-[4-O-(2,3-O-benzylidenehexopyranosyl)hexopyranosyl]-tyrosyl-3 (2-iminoimidazolidin-4-yl)seryl-3-(3-hexopyranosyl-2-iminoimidazolidin-4-yl)-serylseryl])

A stirred solution of the bis-hydrochloride salt of cyclo [glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (20.9 g, 15.2 mmol) in dimethylsufloxide (100 mL) is treated with benzaldehyde dimethyl acetal (3.7 mL) and hydrogen chloride (1 mL of 4.0M solution in 1,4-dioxane) and the mixture is heated at 50° C. for 24 h. The reaction mixture is cooled to room temperature and acetonitrile (300 mL) is added to precipitate the crude products. The precipitate is collected by filtration, washed with acetonitrile (3×100 mL), and dried. The products are then purified by reverse phase HPLC. Cyclo [glycyl-β-methylphenylalanyl-O-[4-O-(4,6-O-benzylidenehexopyranosyl)hexopyranosyl]-tyrosyl-3-(2-iminoimidazolidin-4-yl)seryl-3-(3-hexopyranosyl-2-iminoimidazolidin-4-yl)-serylseryl]: MS (+ES), m/z: 692.4 (M+2H)$^{2+}$; Cyclo [glycyl-β-methylphenylalanyl-O-[4-O-(2,3-O-benzylidenehexopyranosyl)hexopyranosyl]-tyrosyl-3-(2-iminoimidazolidin-4-yl)seryl-3-(3-hexopyranosyl-2-iminoimidazolidin-4-yl)-serylseryl]: MS (+ES), m/z: 692.4 (M+2H)$^{2+}$; Cyclo[glycyl-β-methylphenylalanyl-O-[4-O-(2,3-O-benzylidenehexopyranosyl)hexopyranosyl]-tyrosyl-3-(2-iminoimidazolidin-4-yl)seryl-3-(3-hexopyranosyl-2-iminoimidazolidin-4-yl)-serylseryl]: MS (+ES), m/z: 692.4 (M+2H)$^{2+}$.

EXAMPLE 105

(Cyclo[glycyl-β-methylphenylalanyl-O-[4-O-[4,6-O-(2-adamantylidene)hexopyranosyl]hexopyranosyl] tyrosyl-3-(2-iminoimidazolidin-4-yl)seryl-3-(3-hexopyranosyl-2-iminoimidazoliclin-4-yl)serylseryl])

A stirred solution of the bis-hydrochloride salt of cyclo [glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (30.5 g, 22.3 mmol) in dimethyl sulfoxide (110 mL) is treated with adamantanone dimethyl ketal (8.0 g) and hydrogen chloride (1.6 mL of 4.0 M in 1,4-dioxane). The mixture is heated at 50° C. for 1 h before 10 mL of DMSO is removed in vacuo. The resulting solution is directly subjected to purification by reverse phase HPLC. MS (+ES), m/z: 714.4 (M+2H)$^{2+}$.

EXAMPLE 106

(Cyclo[3-cyclohexylalanyl-O-[4-O-[4,6-O-(2-adamantylidene)hexopyranosyl]hexopyranosyl]-tyrosyl-3-(2-iminoimidazolidin-4-yl)seryl-3-(3-hexopyranosyl-2-iminoimidazolidin-4-yl)-serylserylglycyl])

EXAMPLE 106a (Cyclo[3-cyclohexylalanyl-O-[4-O-[2,3-O-(2-adamantylidene)hexopyranosyl]hexopyranosyl]-tyrosyl-3-(2-iminoimidazolidin-4-yl)seryl-3-(3-hexopyranosyl-2-iminoimidazolidin-4-yl)-serylserylglycyl])

EXAMPLE 106b (Cyclo[3-cyclohexylalanyl-O-[4-O-12,3:4,6-di-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)-serylserylglycyl])

A stirred solution of the bis-acetate salt of cyclo[3-cyclohexylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylserylglycyl] (8.2 g) in dimethyl sulfoxide (110 mL) is treated with adamantanone dimethyl ketal (3.0 g) and hydrogen chloride (5 mL of 4.0 M in 1,4-dioxane). The mixture is heated at 50° C. for 2 h and then cooled and neutralized (pH paper) by the addition of N,N-diisopropylethylamine (1 mL). Acetonitrile (400 mL) is added to precipitate the crude products, which are collected by filtration and washed with acetonitrile, diethyl ether, and air dried. The resulting solids are subjected to purification by reverse phase HPLC. Cyclo[3-cyclohexylalanyl-O-[4-O-[4,6-O-(2-adamantylidene)hexopyranosyl]hexopyranosyl]-tyrosyl-3-(2-iminoimidazolidin-4-yl)seryl-3-(3-hexopyranosyl-2-iminoimidazolidin-4-yl)-serylserylglycyl]: MS (+ES), m/z: 710.6 (M+2H)$^{2+}$; Cyclo[3-cyclohexylalanyl-O-[4-O-[2,3-O-(2-adamantylidene)hexopyranosyl]hexopyranosyl)-tyrosyl-3-(2-iminoimidazolidin-4-yl)seryl-3-(3-hexopyranosyl-2-iminoimidazolidin-4-yl)-serylserylglycyl]: MS (+ES), m/z: 710.6 (M+2H)$^{2+}$; Cyclo[3-cyclohexylalanyl-O-[4-O-[2,3:4,6-di-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)-serylserylglycyl]: MS (+ES), m/z: 776.5 (M+2H)$^{2+}$.

EXAMPLE 107

(Cyclo[glycyl-β-methylphenylalanyl-O-[4-O-[4,6-O-(3-methylbutylidene)hexopyranosyl]-hexopyranosyl] tyrosyl-3-(2-iminoimidazolidin-4-yl)seryl-3-(3-hexopyranosyl-2-iminoimidazolidin-4-yl)serylseryl])

The title compound is prepared by the procedure described for example 102 using the appropriate dimethyl acetal. MS (+ES) m/z: 682.2 (M+2H)$^{2+}$.

EXAMPLE 108

(Cyclo[glycyl-β-methylphenylalanyl-O-[4-O-(4,6-O-hexylidenehexonyranosyl)hexopyranosyl]-tyrosyl-3-(2-iminoimidazolidin-4-yl)seryl-3-(3-hexopyranosyl-2-iminoimidazolidin-4-yl)-serylseryl])

The title compound is prepared by the procedure described for example 102 using the appropriate dimethyl acetal. MS (+ES) m/z: 689.4 (M+2H)$^{2+}$.

EXAMPLE 109

(Cyclo[glycyl-β-methylphenylalanyl-O-[4-O-(4,6-O-octylidenehexopyranosyl)hexopyranosyl]-tyrosyl-3-(2-iminoimidazoliclin-4-yl)seryl-3-(3-hexopyranosyl-2-iminoimidazolidin-4-yl)-serylseryl])

The title compound is prepared by the procedure described for example 102 using the appropriate dimethyl acetal. MS (+ES) m/z: 703.3 (M+2H)$^{2+}$.

EXAMPLE 110

(Cyclo[glycyl-β-methylphenylalanyl-O-[4-O-[4,6-O-[3,3-dimethylbutylidene)hexopyranosyl]-hexopyranosyl]tyrosyl-3-[2-iminoimidazolidin-4-yl)seryl-3-β-hexopyranosyl-2-iminoimidazolidin-4-yl)serylseryl])

The title compound is prepared by the procedure described for example 102 using the appropriate dimethyl acetal. MS (+ES) m/z: 689.1 (M+2H)$^{2+}$.

EXAMPLE 111

(Cyclo[glycyl-β-methylphenylalanyl-O-[4-O-[4,6-O-(2-methylpentylidene)hexopyranosyl]-hexopyranosyl]tyrosyl-3-[2-iminoimidazoliclin-4-yl)seryl-3-β-hexopyranosyl-2-iminoimidazolidin-4-yl)serylseryl])

The title compound is prepared by the procedure described for example 102 using the appropriate dimethyl acetal. MS (+ES) m/z: 689.3 (M+2H)$^{2+}$.

EXAMPLE 112

(Cyclo[glycyl-β-methylphenylalanyl-O-[4-O-[4,6-O-(cyclohexylmethylene)hexopyranosyl]-hexopyranosyl]tyrosyl-3-(2-iminoimidazolidin-4-yl)seryl-3-β-hexopyranosyl-2-iminoimidazolidin-4-yl)serylseryl])

The title compound is prepared by the procedure described for example 102 using the appropriate dimethyl acetal. MS (+ES) m/z: 695.3 (M+2H)$^{2+}$.

EXAMPLE 113

(Cyclo[glycyl-β-methylphenylalanyl-O-[4-O-[4,6-O-[2-[1-[(phenylmethoxy)carbonyl]piperidin-4-yl]ethylidene]hexopyranosyl]hexopyranosyl]tyrosyl-3-[2-iminoimidazolidin-4-yl)seryl-3-β-hexopyranosyl-2-iminoimidazolidin-4-yl)serylseryl])
The title compound is prepared by the procedure described for example 102 using the appropriate dimethyl acetal. MS (+ES) m/z: 769.8 (M+2H)$^{2+}$.

EXAMPLE 114

(Cyclo[glycyl-β-methylphenylalanyl-O-[4-O-[4,6-O-(4-butoxy-4-oxobutylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 102 using the appropriate di-n-butyl acetal. MS (+ES) m/z: 718.4 (M+2H)$^{2+}$.

EXAMPLE 115

(Cyclo[glycyl-β-methylphenylalanyl-O-[4-O-[4,6-O-(cyclohex-3-en-1-ylmethylene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 102 using the appropriate dimethyl acetal. MS (+ES) m/z: 694.4 (M+2H)$^{2+}$.

EXAMPLE 116

(Cyclo[glycyl-β-methylphenylalanyl-O-[4-O-[4,6-O-(2-ethylbutylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 102 using the appropriate dimethyl acetal. MS (+ES) m/z: 689.4 (M+2H)$^{2+}$.

EXAMPLE 117

(Cyclo[glycyl-β-methylphenylalanyl-O-[4-O-[4,6-O-(cyclopentylethylene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 102 using the appropriate dimethyl acetal. MS (+ES) m/z: 688.3 (M+2H)$^{2+}$.

EXAMPLE 118

(Cyclo[glycyl-β-methylphenylalanyl-O-[4-O-[4,6-O-(4-bromophenethylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 103 using the appropriate dimethyl acetal. MS (+ES) m/z: 738.8 (M+2H)$^{2+}$.

EXAMPLE 119

(Cyclo[glycyl-β-methylphenylalanyl-O-[4-O-[4,6-O-(4-methylphenethylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 103 using the appropriate dimethyl acetal. MS (+ES) m/z: 706.3 (M+2H)$^{2+}$.

EXAMPLE 120

(Cyclo[glycyl-β-methylphenylalanyl-O-[4-O-[4,6-O-(4-chlorophenethylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 103 using the appropriate dimethyl acetal. MS (+ES) m/z: 716.4 $(M+2H)^{2+}$.

EXAMPLE 121

(Cyclo[glycyl-β-methylphenylalanyl-O-[4-O-[4,6-O-(4-fluorophenethylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 103 using the appropriate dimethyl acetal. MS (+ES) m/z: 708.3 $(M+2H)^{2+}$.

EXAMPLE 122

(Cyclo[glycyl-β-methylphenylalanyl-O-[4-O-[4,6-O-[2-cyclohexylethylidene)hexopyranosyl]-hexopyranosyl]tyrosyl-3-[2-iminoimidazolidin-4-yl)seryl-3-β-hexopyranosyl-2-iminoimidazolidin-4-yl)serylseryl])

The title compound is prepared by the procedure described for example 104 using the appropriate dimethyl acetal. MS (+ES) m/z: 702 $(M+2H)^{2+}$.

EXAMPLE 123

(Cyclo[glycyl-β-methylphenylalanyl-O-[4-O-[4,6-O-[5-methylhex-4-en-1-ylidene)hexopyranosyl]hexopyranosyl]tyrosyl-3-[2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 695.3 $(M+2H)^{2+}$.

EXAMPLE 124

(Cyclo[glycyl-β-methylphenylalanyl-O-[4-O-[4,6-O-β-phenylpropylidene)hexopyranosyl]-hexopyranos]tyrosyl-3-(2-iminoimidazolidin-4-yl)seryl-3-β-hexopyranosyl-2-iminoimidazolidin-4-yl)serylseryl])

The title compound is prepared by the procedure described for example 104 using the appropriate dimethyl acetal. MS (+ES) m/z: 706.3 $(M+21:1)^{2+}$.

EXAMPLE 125

(Cyclo[glycyl-β-methylphenylalanyl-O-[4-O-[4,6-O-[2,6-dimethylhept-5-en-1-yidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 709 $(M+2H)^{2+}$.

EXAMPLE 126

(Cyclo[glycyl-β-methylphenylalanyl-O-[4-O-[4,6-O-[3,7-dimethyloct-6-en-1-ylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 716.1 $(M+2H)^{2+}$.

EXAMPLE 127

(Cyclo[glycyl-β-methylphenylalanyl-O-[4-O-[4,6-O-(1-adamantylmethylene)hexopyranosyl]-hexopyranosyl]tyrosyl-3-(2-iminoimidazolidin-4-yl)seryl-3-β-hexopyranosyl-2-iminoimidazolidin-4-yl)serylseryl])

The title compound is prepared by the procedure described for example 104 using the appropriate dimethyl acetal. MS (+ES) m/z: 721.4 $(M+2H)^{2+}$.

EXAMPLE 128

(Cyclo[glycyl-β-methylphenylalanyl-O-[4-O-[2,3-O-[2-(1-adamantyl)ethylidene]hexopyranosyl]hexopyranosyl]tyrosyl-3-(2-iminoimidazolidin-4-yl)seryl-3-β-hexopyranosyl-2-iminoimidazolidin-4-yl)serylseryl])

The title compound is prepared by the procedure described for example 104 using the appropriate dimethyl acetal. MS (+ES) m/z: 728.4 $(M+2H)^{2+}$.

EXAMPLE 129

(Cyclo[glycyl-β-methylphenylalanyl-O-[4-O-[4,6-O-[2-(1-adamantyl)ethylidene]hexopyranosyl]hexopyranosyl]tyrosyl-3-(2-iminoimidazolidin-4-yl)seryl-3-β-hexopyranosyl-2-iminoimidazolidin-4-yl)serylseryl])

The title compound is prepared by the procedure described for example 104 using the appropriate dimethyl acetal. MS (+ES) m/z: 728.8 $(M+2H)^{2+}$.

EXAMPLE 130

(Cyclo[glycyl-β-methylphenylalanyl-O-[4-O-[4,6-O-(3-methoxycholan-24-ylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 826.4 $(M+2H)^{2+}$.

EXAMPLE 131

(Cyclo[glycyl-β-methylphenylalanyl-O-[4-O-[4,6-O-[4-phenylbenzylidene)-hexopyranosyl)hexopyranosyl]-tyrosyl-3-[2-iminoimidazolidin-4-yl)seryl-3-(3-hexopyranosyl-2-iminoimidazolidin-4-yl)-serylseryl])

The title compound is prepared by the procedure described for example 104 using the appropriate dimethyl acetal. MS (+ES) m/z: 690.2 (M+2H)$^{2+}$.

EXAMPLE 132

(Cyclo[glycyl-β-methylphenylalanyl-O-[4-O-[4,6-O-(2-thienylmethylene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 696 (M+2H)$^{2+}$.

EXAMPLE 133

(Cyclo[glycyl-β-methylphenylalanyl-O-[4-O-[4,6-O-(3-thienylmethylene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 695 (M+2H)$^{2+}$.

EXAMPLE 134

(Cyclo[glycyl-β-methylphenylalanyl-O-[4-O-[4,6-O-(4-methylbenzylidene)hexopyranosyl]-hexopyranosyl]-tyrosyl-3-(2-iminoimidazolidin-4-yl)seryl-3-(3-hexopyranosyl-2-iminoimidazolidin-4-yl)-serylseryl])

The title compound is prepared by the procedure described for example 104 using the appropriate dimethyl acetal. MS (+ES) m/z: 699.2 (M+2H)$^{2+}$.

EXAMPLE 135

(Cyclo[glycyl-β-methylphenylalanyl-O-[4-O-[4,6-O-(3-methylbenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 699 (M+2H)$^{2+}$.

EXAMPLE 136

(Cyclo[glycyl-β-methylphenylalanyl-O-[4-O-[4,6-O-(3-hydroxybenzylidene)hexopyranosyl]-hexopyranosyl]tyrosyl-3-(2-iminoimidazolidin-4-yl)seryl-3-(3-hexopyranosyl-2-iminoimidazoliclin-4-yl)serylseryl])

The title compound is prepared by the procedure described for example 104 using the appropriate dimethyl acetal. MS (+ES) m/z: 700 (M+2H)$^{2+}$.

EXAMPLE 137

(Cyclo[glycyl-β-methylphenylalanyl-O-[4-O-[4,6-O-(3-methoxybenzylidene)hexopyranosyl]-hexopyranosyl]-tyrosyl-3-(2-iminoimidazolidin-4-yl)seryl-3-(3-hexopyranosyl-2-iminoimidazolidin-4-yl)serylseryl])

EXAMPLE 137a (Cyclo[glycyl-β-methylphenylalanyl-O-[4-O-[2,3-O-(3-methoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

EXAMPLE 137b (Cyclo[glycyl-β-methylphenylalanyl-O-[4-O-[2,3-O-(3-methoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compounds are prepared by the procedure described for example 104 using the appropriate dimethyl acetal. Cyclo[glycyl-β-methylphenylalanyl-O-[4-O-[4,6-O-(3-methoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 707.3 (M+2H)$^{2+}$; Cyclo[glycyl-β-methylphenylalanyl-O-[4-O-[2,3-O-(3-methoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 707.3 (M+2H)$^{2+}$; Cyclo[glycyl-β-methylphenylalanyl-O-[4-O-[2,3-O-(3-methoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 707.3 (M+2H)$^{2+}$.

EXAMPLE 138

(Cyclo[glycyl-β-methylphenylalanyl-O-[4-O-[4,6-O-(3-chlorobenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 709.2 (M+2H)$^{2+}$.

EXAMPLE 139

(Cyclo[glycyl-β-methylphenylalanyl-O-[4-O-[4,6-O-(4-isopropylbenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 713.4 (M+2H)$^{2+}$.

EXAMPLE 140

(Cyclo[glycyl-β-methylphenylalanyl-O-[4-O-[4,6-O-(4-propylbenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 713.3 $(M+2H)^{2+}$.

EXAMPLE 141

(Cyclo[glycyl-β-methylphenylalanyl-O-[4-O-[4,6-O-(4-carboxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 714.6 $(M+2H)^{2+}$.

EXAMPLE 142

(Cyclo[glycyl-β-methylphenylalanyl-O-[4-O-[4,6-O-(4-ethoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 714.3 $(M+2H)^{2+}$.

EXAMPLE 143

(Cyclo[glycyl-β-methylphenylalanyl-O-[4-O-[4,6-O-(1,3-benzodioxol-5-ylmethylene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 714.3 $(M+2H)^{2+}$.

EXAMPLE 144

(Cyclo[glycyl-β-methylphenylalanyl-O-[4-O-[4 (methylthio)benzylidene)hexopyranosyl]hexopyranosyl]tyrosyl-3-(2-iminoimidazolidin-4-yl)seryl-3-(3-hexonyranosyl-2-iminoimidazolidin-4-yl)serylseryl])

The title compound is prepared by the procedure described for example 104 using the appropriate dimethyl acetal. MS (+ES) m/z: 715 $(M+2H)^{2+}$.

EXAMPLE 145

(Cyclo[glycyl-β-methylphenylalanyl-O-[4-O-[4,6-O-(2-naphthylmethylene)hexopyranosyl]-hexopyranosyl]tyrosyl-3-(2-iminoimidazolidin-4-yl)seryl-3(3-hexopyranosyl-2-iminoimidazolidin-4-yl)serylseryl])

The title compound is prepared by the procedure described for example 104 using the appropriate dimethyl acetal. MS (+ES) m/z: 717.3 $(M+2H)^{2+}$.

EXAMPLE 146

(Cyclo[glycyl-β-methylphenylalanyl-O-[4-O-[4,6-O-β-(2-methylprop-1-en-1-yl)benzylidene]-hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 719.2 $(M+2H)^{2+}$.

EXAMPLE 147

(Cyclo[glycyl-β-methylphenylalanyl-O-[4-O-[4,6-O-(4-tert-butylbenzylidene)hexonyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 720.4 $(M+2H)^{2+}$.

EXAMPLE 148

(Cyclo[glycyl-β-methylphenylalanyl-O-[4-O-[4,6-O-(4-promloxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 721.3 $(M+2H)^{2+}$.

EXAMPLE 149

(Cyclo[glycyl-β-methylphenylalanyl-O-[4-O-[4,6-O-[(2,3-dihydro-1,4-benzodioxan-6-yl)-methylene]hexopyranosyl 1 hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 721 $(M+2H)^{2+}$.

EXAMPLE 150

(Cyclo[glycyl-β-methylphenylalanyl-O-[4-O-[4,6-O-(3,5-dimethoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

EXAMPLE 150a (Cyclo[glycyl-β-methylphenylalanyl-O-[4-O-[2,3-O-(3,5-dimethoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compounds are prepared by the procedure described for example 104 using the appropriate dimethyl acetal. Cyclo[glycyl-β-methylphenylalanyl-O-[4-O-[4,6-O-

(3,5-dimethoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 722.3 (M+2H)$^{2+}$; Cyclo[glycyl-β-methylphenylalanyl-O-[4-O-[2,3-O-(3,5-dimethoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 722.3 (M+2H)$^{2+}$.

EXAMPLE 151

(Cyclo[glycyl-β-methylphenylalanyl-O-[4-O-[4,6-O-(3-methyl-4-nitrobenzylidene)hexonyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 722.5 (M+2H)$^{2+}$.

EXAMPLE 152

(Cyclo[glycyl-β-methylphenylalanyl-O-[4-O-[4,6-O-(3-ethoxy-4-methoxybenzylidene)hexopyranosyl)hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 729.2 (M+2H)$^{2+}$.

EXAMPLE 153

(Cyclo[glycyl-β-methylphenylalanyl-O-[4-O-[4,6-O-(3-methoxy-4-nitrobenzylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 729.5 (M+2H)$^{2+}$.

EXAMPLE 154

(Cyclo[glycyl-β-methylphenylalanyl-O-[4-O-[4,6-O-(3-phenylbenzylidene)hexopyranosyl)-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 730.2 (M+2H)$^{2+}$.

EXAMPLE 155

(Cyclo[glycyl-β-methylphenylalanyl-O-(4-O-hexopyranosylhexopyranosyl)tyrosyl-3-[2-[(2,2-dimethylpropanoyl)imino]imidazolidin-4-yl]seryl-3-(3-hexopyranosyl-2-iminoimidazolidin-4-yl)serylseryl])

The title compound is prepared by the procedure described for example 104 using the appropriate dimethyl acetal. MS (+ES) m/z: 730.3 (M+2H)$^{2+}$.

EXAMPLE 156

(Cyclo[glycyl-β-methylphenylalanyl-O-[4-O-[4,6-O-β-(3-pyridyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 730.8 (M+2H)$^{2+}$.

EXAMPLE 157

(Cyclo[glycyl-β-methylphenylalanyl-O-[4-O-[4,6-O-(4-(methylsulfonyl)benzylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES)m/z: 731(M+2H)$^{2+}$.

EXAMPLE 158

(Cyclo[glycyl-β-methylphenylalanyl-O-[4-O-[4,6-O-[(6-chloro-1,3-benzodioxol-5-yl)-methylene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 731.2 (M+2H)$^{2+}$.

EXAMPLE 159

(Cyclo[glycyl-β-methylphenylalanyl-O-[4-O-[4,6-O-[(6-methoxy-2-naphthyl)-methylene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 732.3 (M+2H)$^{2+}$.

EXAMPLE 160

(Cyclo[glycyl-β-methylphenylalanyl-O-[4-O-[2,3-O-[(6-methoxy-2-naphthyl)-methylene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 732.5 (M+2H)$^{2+}$.

EXAMPLE 161

(Cyclo[glycyl-β-methylphenylalanyl-O-[4-O-[4,6-O-[1-(acetylindol-3-yl)methylene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 732.8 $(M+2H)^{2+}$.

EXAMPLE 162

(Cyclo[glycyl-β-methylphenylalanyl-O-[4-O-[4,6-O-β-(3-thienyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 733.3 $(M+2H)^{2+}$.

EXAMPLE 163

(Cyclo[glycyl-β-methylphenylalanyl-O-[4-O-[4,6-O-[4-(2-thienyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 733.3 $(M+2H)^{2+}$.

EXAMPLE 164

(Cyclo[glycyl-β-methylphenylalanyl-O-[4-O-[4,6-O-[4-(3-thienyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl])

EXAMPLE 164a (Cyclo[glycyl-β-methylphenylalanyl-O-[4-O-[2,3-O-[4-(3-thienyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compounds are prepared by the procedure described for example 104 using the appropriate dimethyl acetal. Cyclo[glycyl-β-methylphenylalanyl-O-[4-O-[4,6-O-[4-(3-thienyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 733.3 $(M+2H)^{2+}$; Cyclo[glycyl-β-methylphenylalanyl-O-[4-O-[2,3-O-[4-(3-thienyl)benzylidene]hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 733.3 $(M+2H)^{2+}$.

EXAMPLE 165

(Cyclo[glycyl-β-methylphenylalanyl-O-[4-O-[4,6-O-β-[(3-methylbut-2-en-1-yl)oxy]-benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 734 $(M+2H)^{2+}$.

EXAMPLE 166

(Cyclo[glycyl-β-methylphenylalanyl-O-[4-O-[4,6-O-β-(carboxymethoxy)benzylidene]hexopyranosyl]hexonyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 736.2 $(M+2H)^{2+}$.

EXAMPLE 167

(Cyclo[glycyl-β-methylphenylalanyl-O-[4-O-[4,6-O-(3-ethoxy-4-nitrobenzylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 736.8 $(M+2H)^{2+}$.

EXAMPLE 168

(Cyclo[glycyl-β-methylphenylalanyl-O-[4-O-[4,6-O-[4-(methylthio)-3-nitrobenzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 737.73 $(M+2H)^{2+}$.

EXAMPLE 169

(Cyclo[glycyl-β-methylphenylalanyl-O-[4-O-[4,6-O-(4-hydroxy-3-methoxy-4-nitro-benzylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 737.5 $(M+2H)^{2+}$.

EXAMPLE 170

(Cyclo[glycyl-β-methylphenylalanyl-O-[4-O-[4,6-O-(3-phenoxybenzylidene)hexopyranosyl]-hexopyranosyl]tyrosyl-3-(2-iminoimidazoliclin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 738 (M+2H)$^{2+}$.

EXAMPLE 171

(Cyclo[glycyl-β-methylphenylalanyl-O-[4-O-4,6-O-(4-phenoxybenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 738.3 (M+2H)$^{2+}$.

EXAMPLE 172

(Cyclo[glycyl-β-methylphenylalanyl-O-[4-O-4,6-O-[4-(2-phenylethenyl)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 743.4 (M+2H)$^{2+}$.

EXAMPLE 173

(Cyclo[glycyl-β-methylphenylalanyl-O-[4-O-[4,6-O-[4-benzoylbenzylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 744.2 (M+2H)$^{2+}$.

EXAMPLE 174

(Cyclo[glycyl-β-methylphenylalanyl-O-[4-O-[4,6-O-[4-(4-methylphenoxy)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 745 (M+2H)$^{2+}$.

EXAMPLE 175

(Cyclo[glycyl-β-methylphenylalanyl-O-[4-O-[4,6-O-β-(phenylmethoxy)benzylidene]hexopyranosyl]hexopyranosyl]tyrosyl-3-(2-iminoimidazolidin-4-yl)seryl-3-β-hexopyranosyl-2-iminoimidazolidin-4-yl)serylseryl])

The title compound is prepared by the procedure described for example 104 using the appropriate dimethyl acetal. MS (+ES) m/z: 745 (M+2H)$^{2+}$.

EXAMPLE 176

(Cyclo[glycyl-β-methylphenylalanyl-O-[4-O-4,6-O-[4-(phenylmethoxy)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 745.3 (M+2H)$^{2+}$.

EXAMPLE 177

(Cyclo[glycyl-β-methylphenylalanyl-O-[4-O-4,6-O-β-(4-chlorophenyl)benzylidene]hexopyranosyl 1 hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 747.3 (M+2H)$^{2+}$.

EXAMPLE 178

(Cyclo[glycyl-β-methylphenylalanyl-O-4-O-[4,6-O-[4-(4-chlorophenyl)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 747.3 (M+2H)$^{2+}$.

EXAMPLE 179

(Cyclo[glycyl-β-methylphenylalanyl-O-[4-O-[4,6-O-β-(1,1,2,2-tetrafluoroethoxy)benzylidene]-hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 750 (M+2H)$^{2+}$.

EXAMPLE 180

(Cyclo[glycyl-β-methylphenylalanyl-O-[4-O-[4,6-O-β-(4-methoxyphenoxy)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 753 (M+2H)$^{2+}$.

EXAMPLE 181

(Cyclo[glycyl-β-methylphenylalanyl-O-[4-O-[4,6-O-[4-(4-tert-butylphenoxy)benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 766 $(M+2H)^{2+}$.

EXAMPLE 182

(Cyclo[glycyl-β-methylphenylalanyl-O-[4-O-[4,6-O-(3-[[(4-nitrophenyl)methoxy]benzylidene]hexopyranosyl]hexopyranosyl]tyrosyl-3-(2-iminoimidazolidin-4-yl)seryl-3-β-hexopyranosyl-2-iminoimidazolidin-4-yl)serylseryl])

The title compound is prepared by the procedure described for example 104 using the appropriate dimethyl acetal. MS (+ES) m/z: 768.1 $(M+2H)^{2+}$.

EXAMPLE 183

(Cyclo[glycyl-β-methylphenylalanyl-O-[4-O-[4,6-O-[4-[(3,7-dimethylocta-2,6-dien-1-yl)oxy]-benzylidene]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 768 $(M+2H)^{2+}$.

EXAMPLE 184

(Cyclo[glycyl-β-methylphenylalanyl-O-[4-O-[4,6-O-β-β-(trifluoromethyl)phenoxy]-benzylidene]hexopyranosyl]hexopyranosyl]tyrosyl-3-(2-iminoimidazolidin-4-yl)seryl-3-β-hexopyranosyl-2-iminoimidazolidin-4-yl)serylseryl])

The title compound is prepared by the procedure described for example 104 using the appropriate dimethyl acetal. MS (+ES) m/z: 772 $(M+2H)^{2+}$.

EXAMPLE 185

(Cyclo[glycyl-β-methylphenylalanyl-O-[4-O-[4,6-O-[[3-(3,7,11-trimethyldodeca-2,6,10-trien-1-yl)oxy]benzylidene]hexopyranosyl]hexopyranosyl]tyrosyl-3-(2-iminoimidazolidin-4-yl)-seryl-3-β-hexopyranosyl-2-iminoimidazolidin-4-yl)serylseryl])

The title compound is prepared by the procedure described for example 104 using the appropriate dimethyl acetal. MS (+ES) m/z: 802 $(M+2H)^{2+}$.

EXAMPLE 186

(Cyclo[glycyl-β-methylphenylalanyl-O-[4-O-(4,6-O-[4-(4-iodobenzoyl)benzylidene]hexopyranosyl]hexopyranosyl]tyrosyl-3-(2-iminoimidazolidin-4-yl]seryl-3-β-hexopyranosyl-2-iminoimidazolidin-4-yl)serylseryl])

The title compound is prepared by the procedure described for example 104 using the appropriate dimethyl acetal. MS (+ES) m/z: 807.2 $(M+2H)^{2+}$.

EXAMPLE 187

(Cyclo[glycyl-6-methylphenylalanyl-O-[4-O-[4,6-O-[4-(3,4,5-triiodobenzoyl)benzylidene]-hexopyranosyl]hexopyranosyl]tyrosyl-3-(2-iminoimidazolidin-4-yl)seryl-3-β-hexopyranosyl-2-iminoimidazolidin-4-yl]serylseryl])

The title compound is prepared by the procedure described for example 104 using the appropriate dimethyl acetal. MS (+ES) m/z: 933.4 $(M+2H)^{2+}$.

EXAMPLE 188

(Cyclo[glycyl-β-methylphenylalanyl-O-[4-O-[4,6-[3,3-diphenylprop-2-enylidene)hexonyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 743.2 $(M+2H)^{2+}$.

EXAMPLE 189

(Cyclo[glycyl-β-methylphenylalanyl-O-[4-O-[4,6-O-(prop-2-enylidene)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl acetal. MS (+ES) m/z: 667.4 $(M+2H)^{2+}$.

EXAMPLE 190

(Cyclo[3-[2-iminoimidazolidin-4-yl)alanyl-3-(3-hexopyranosyl-2-iminoimidazolidin-4-yl)-alanylserylglycyl-β-methylphenylalanyl-O-[4-O-[4,6-O-[6-methoxy-2-naphthyl)-methylene]hexopyranosyl]hexopyranosyl]tyrosyl])

The title compound is prepared from cyclo[3-(2-iminoimidazolidin-4-yl)alanyl-3-(3-hexopyranosyl-2-iminoimidazoliclin-4-yl)-alanylserylglycyl-β-methylphenylalanyl-O-(4-O-hexopyranosylhexopyranosyl)tyrosyl] by the procedure described for example 104 using the appropriate dimethyl acetal. MS (+ES) m/z: 716.3 $(M+2H)^{2+}$.

EXAMPLE 191

(Cyclo[3-(2-iminoimidazolidin-4-yl)alanyl-3-β-hexopyranosyl-2-iminoimidazolidin-4-yl)-alanylserylglycyl-β-methylphenylalanyl-O-[4-O-[4,6-O-[4-phenylmethoxy)benzylidene]-hexopyranosyl] hexopyranosyl]tyrosyl])

The title compound is prepared from cyclo[3-(2-iminoimidazolidin-4-yl)alanyl-3-(3-hexopyranosyl-2-iminoimidazolidin-4-yl)-alanylserylglycyl-β-methylphenylalanyl-O-(4-O-hexopyranosylhexopyranosyl)tyrosyl] by the procedure described for example 104 using the appropriate dimethyl acetal. MS (+ES) m/z: 729.6 (M+2H)$^{2+}$.

EXAMPLE 192

(Cyclo[3-(2-iminoimidazolidin-4-yl)alanyl-3-(3-hexopyranosyl-2-iminoimidazolidin-4-yl)-alanylserylglycyl-β-methylphenylalanyl-O-4-O-[4,6-O-β-(4-methoxyphenoxy)benzylidene]-hexopyranosyl] hexopyranosyl]tyrosyl])

The title compound is prepared from cyclo[3-(2-iminoimidazolidin-4-yl)alanyl-3-(3-hexopyranosyl-2-iminoimidazolidin-4-yl)-alanylserylglycyl-β-methylphenylalanyl-0-(4-O-hexopyranosylhexopyranosyl)tyrosyl] by the procedure described for example 104 using the appropriate dimethyl acetal. MS (+ES) m/z: 737.4 (M+2H)$^{2+}$.

EXAMPLE 193

(Cyclo[glycyl-4-chloro-β-methylphenylalanyl-O-[4-O-[4,6-O-(cyclohexylmethylene)hexopyranosyl] hexopyranosyl]tyrosyl-3-(2-iminoimidazoliclin-4-yl) seryl-3-β-hexopyranosyl-2-iminoimidazolidin-4-yl) serylseryl])

The title compound is prepared from cyclo[glycyl-4-chloro-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]by the procedure described for example 104 using the appropriate dimethyl acetal. MS (+ES) m/z: 712.3 (M+2H)$^{2+}$.

EXAMPLE 194

(Cyclo[glycyl-4-chloro-β-methylphenylalanyl-O-[4-O-[4,6-O-(2-methylpentylidene)hexopyranosyl]hexopyranosyl]tyrosyl-3-(2-iminoimidazolidin-4-yl) seryl-3-(3-hexopyranosyl-2-iminoimidazolidin-4-yl) serylseryl])

The title compound is prepared from cyclo[glycyl-4-chloro-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] by the procedure described for example 104 using the appropriate dimethyl acetal. MS (+ES) m/z: 706.2 (M+2H)$^{2+}$.

EXAMPLE 195

(Cyclo[glycyl-4-chloro-β-methylphenylalanyl-O-[4-O-(4,6-O-benzylidenehexopyranosyl)-hexopyranosyl]tyrosyl-3-(2-iminoimidazolidin-4-yl)seryl-3-(3-hexopyranosyl-2-iminoimidazolidin-4-yl)serylseryl])

The title compound is prepared from cyclo[glycyl-4-chloro-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] by the procedure described for example 104 using the appropriate dimethyl acetal. MS (+ES) m/z: 709.5 (M+2H)$^{2+}$.

EXAMPLE 196

(Cyclo[glycyl-β-methylphenylalanyl-O-[4-O-(4,6-O-benzylidenehexopyranosyl)hexopyranosyl]-3-iodotyrosyl-3-(2-iminoimidazolidin-4-yl)seryl-3-(3-hexopyranosyl-2-iminoimidazolidin-4-yl)-serylseryl])

The title compound is prepared from cyclo(glycyl-β-methylphenylalanyl-O-(4-O-hexopyranosylhexopyranosyl)-3-iodo-tyrosyl-3-(2-iminoimidazolidin-4-yl)seryl-3-(3-hexopyranosyl-2-iminoimidazolidin-4-yl)serylseryl]by the procedure described for example 104 using the appropriate dimethyl acetal. MS (+ES) m/z: 755 (M+2H)$^{2+}$.

EXAMPLE 197

(Cyclo[glycyl-β-methylphenylalanyl-O-[4-O-[4,6-O-β-(4-methylphenoxy)benzylidene]hexopyranosyl] hexopyranosyl]tyrosyl-3-(2-iminoimidazolidin-4-yl) seryl-3-(3-hexopyranosyl-2-iminoimidazolidin-4-yl) serylseryl])

The title compound is prepared from cyclo[glycyl-β-methylphenylalanyl-O-(4-O-hexopyranosylhexopyranosyl)-3-iodo-tyrosyl-3-(2-iminoimidazolidin-4-yl)seryl-3-(3-hexopyranosyl-2-iminoimidazolidin-4-yl)serylseryl] by the procedure described for example 104 using the appropriate dimethyl acetal. MS (+ES) m/z: 808 (M+2H)$^{2+}$.

EXAMPLE 198

(Cyclo[3-cyclohexylalanyl-O-[4-O-[4,6-O-(3-phenylpropylidene)hexopyranosyl]hexopyranosyl]tyrosyl-3-(2-iminoimidazolidin-4-yl)seryl-3-(3-hexopyranosyl-2-iminoimidazolidin-4-yl) serylserylglycyl])

The title compound is prepared from cyclo[3-cyclohexylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylserylglycyl] by the procedure described for example 104 using the appropriate dimethyl acetal. MS (+ES) m/z: 702.3 (M+2H)$^{2+}$.

EXAMPLE 199

(Cyclo[3-cyclohexylalanyl-O-[4-O-(4,6-O-benzylidenehexopyranosyl)hexopyranosyl]tyrosyl-3-(2-iminoimidazolidin-4-yl)seryl-3-(3-hexopyranosyl-2-iminoimidazolidin-4-yl)-seryl-serylglycyl])

The title compound is prepared from cyclo[3-cyclohexylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylserylglycyl] by the procedure described for example 104 using the appropriate dimethyl acetal. MS (+ES) m/z: 688.1 (M4.2H)$^{2+}$.

EXAMPLE 200

(Cyclo[3-cyclohexylalanyl-O-[4-O-[4,6-O-phenethylidene-hexopyranosyl]hexopyranosyl]tyrosyl-3-(2-iminoimidazolidin-4-yl)seryl-3-(3-hexopyranosyl-2-iminoimidazolidin-4-yl)serylserylglycyl])

The title compound is prepared from cyclo[3-cyclohexylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylserylglycyl] by the procedure described for example 104 using the appropriate dimethyl acetal. MS (+ES) m/z: 695.2 $(M+2H)^{2+}$.

EXAMPLE 201

(Cyclo[3-cyclohexyl-2-aminobutanoyl-O-[4-O-[4,6-O-benzylidenehexonyranosyl]hexopyranosyl]tyrosyl-3-(2-iminoimidazolidin-4-yl)seryl-3-(3-hexopyranosyl-2-iminoimidazolidin-4-yl)serylserylglycyl])

The title compound is prepared from cyclo[3-cyclohexyl-2-aminobutanoyl-O-(4-O-hexopyranosylhexopyranosyl)tyrosyl-3-(2-iminoimidazolidin-4-yl)seryl-3-(3-hexopyranosyl-2-iminoimidazolidin-4-yl)-serylserylglycyl) by the procedure described for example 104 using the appropriate dimethyl acetal. MS (+ES) m/z: 695.1 $(M+2H)^{2+}$.

EXAMPLE 202

(Cyclo[glycyl-4-chloro-β-methylphenylalanyl-O-[4-O-(4,6-O-cyclopentylidenehexopyranosyl)-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 681.2 $(M+2H)^{2+}$.

EXAMPLE 203

(Cyclo[glycyl-β-methylphenylalanyl-O-[4-O-(4,6-O-cyclohexylidene-4-O-hexopyranosyl)hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 688.2 $(M+2H)^{2+}$.

EXAMPLE 204

(Cyclo[glycyl-β-methylphenylalanyl-O-[4-O-[4,6-O-(2-methylcyclohexylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 695.3 $(M+2H)^{2+}$.

EXAMPLE 205

(Cyclo[glycyl-β-methylphenylalanyl-O-[4-O-[4,6-O-(2,2-dimethylcyclohexylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 702.3 $(M+2H)^{2+}$.

EXAMPLE 206

(Cyclo[glycyl-β-methylphenylalanyl-O-[4-O-[4,6-O-(2,6-dimethylcyclohexylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 702.4 $(M+2H)^{2+}$.

EXAMPLE 207

(Cyclo[glycyl-β-methylphenylalanyl-O-[4-O-[4,6-O-(3,3,5,5-tetramethylcyclohexylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 716.3 $(M+2H)^{2+}$.

EXAMPLE 208

(Cyclo[glycyl-β-methylphenylalanyl-O-[4-O-[4,6-O-(4-tert, butylcyclohexylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 716 $(M+2H)^{2+}$.

EXAMPLE 209

(Cyclo[glycyl-β-methylphenylalanyl-O-[4-O-(4,6-O-cyclododecylidenehexopyranosyl)-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 730.4 $(M+2H)^{2+}$.

EXAMPLE 210

(Cyclo[glycyl-β-methylphenylalanyl-O-[4-O-(4,6-O-cyclotridecylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 737.2 $(M+2H)^{2+}$.

EXAMPLE 210a (Cyclo[glycyl-β-methylphenylalanyl-O-[4-O-(2,3-O-cyclotridecylidenehexopyranosyl)hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 737.2 $(M+2H)^{2+}$.

EXAMPLE 211

(Cyclo[glycyl-β-methylphenylalanyl-O-[4-O-[4,6-O-(bicylo-[3.2.1]oct-2-ylidene)-hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 701.1 $(M+2H)^{2+}$.

EXAMPLE 212

(Cyclo[glycyl-β-methylphenylalanyl-O-[4-O-(4,6-O-bicyclo[3.3.1]non-9-ylidenehexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 708.7 $(M+2H)^{2+}$.

EXAMPLE 213

(Cyclo[glycyl-β-methylphenylalanyl-O-4-O-(4,6-O-tricyclo[5.2.1.0(2,6)]decan-2-ylidenehexopyranosyl)hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z 714.3 $(M+2H)^{2+}$.

EXAMPLE 214

(Cyclo[glycyl-β-methylphenylalanyl-O-[4-O-[4,6-O-(1,7,7-trimethylbicyclo[2.2.1]hept-2-ylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 715.2 $(M+2H)^{2+}$.

EXAMPLE 215

(Cyclo[glycyl-β-methylphenylalanyl-O-[4-O-[4,6-O-(1,7,7-trimethylbicyclo[2.2.1]hept-2-ylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 715.3 $(M+2H)^{2+}$.

EXAMPLE 216

(Cyclo[glycyl-β-methylphenylalanyl-O-[4-O-[4,6-O-(4-fluoro-α-methylbenzylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 708.4 $(M+2H)^{2+}$.

EXAMPLE 217

(Cyclo[glycyl-β-methylphenylalanyl-O-[4-O-[4,6-O-(tetrahydrothiopyran-4-ylidene)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 104 using the appropriate dimethyl ketal. MS (+ES) m/z: 697.4 $(M+2H)^{2+}$.

EXAMPLE 218

(Cyclo[glycyl-β-methylphenylalanyl-O-[4-O-[4,6-O-(2-adamantylidene)-3-O-(3-methyl-butanoyl)-hexopyranosyl]hexopyranosyl]tyrosyl-3-(2-iminoimidazolidin-4-yl)-seryl-3-(3-hexopyranosyl-2-iminoimidazolidin-4-yl)serylseryl])

The title compound is prepared from cyclo[glycyl-β-methylphenylalanyl-O-[4-O-β-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl] by the procedure described for example 104 using the appropriate dimethyl ketal. MS (+ES) m/z: 756.4 $(M+2H)^{2+}$.

EXAMPLE 219

(Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-4,6-O-(2-adamantylidene)hexopyranosyl]-hexopyranosyl]tyrosyl])

The title compound is prepared from cyclo[3-(2-iminoimidazolidin-4-yl)alanyl-3-(3-hexopyranosyl-2-iminoimidazolidin-4-yl)-alanylserylglycyl-β-methylphenylalanyl-O-(4-O-hexopyranosylhexopyranosyl)tyrosyl] by the procedure described for example 104 using the appropriate dimethyl ketal. MS (+ES) m/z: 698.9 $(M+2H)^{2+}$.

EXAMPLE 220

(Cyclo[glycylphenylalanyl-O-[4-O-[4,6-O-(2-adamantylidene)hexopyranosyl]hexopyranosyl]-tyrosyl-3-(2-iminoimidazolidin-4-yl)seryl-3-(3-hexopyranosyl-2-iminoimidazolidin-4-yl]-serylseryl])

The title compound is prepared from cyclo[glycylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] by the procedure described for example 104 using the appropriate dimethyl ketal. MS (+ES) m/z: 707.4 (M+2H)$^{2+}$.

EXAMPLE 221

(Cyclo[3-cyclohexyl-2-aminobutanoyl-O-[4-O-[4,6-O-(2-adamantylidene)hexopyranosyl]hexopyranosyl]tyrosyl-3-(2-iminoimidazolidin-4-yl)seryl-3-(3-hexopyranosyl-2-iminoimidazolidin-4-yl)serylserylglycyl])

The title compound is prepared from cyclo[3-cyclohexyl-2-aminobutanoyl-O-(4-O-hexopyranosylhexopyranosyl)tyrosyl-3-(2-iminoimidazolidin-4-yl)seryl-3-(3-hexopyranosyl-2-iminoimidazolidin-4-yl)-serylserylglycyl] by the procedure described for example 104 using the appropriate dimethyl ketal. MS (+ES) m/z: 717.2 (M+2H)$^{2+}$.

EXAMPLE 222

(Cyclo[3-cyclohexylalanyl-3-[4-[4-O-[4,6-O-(2-adamantylidene)hexopyranosyl]hexopyranosyl]oxy]cyclohexyl]alanyl-3-(2-iminoimidazolidin-4-yl)seryl-3-(3-hexopyranosyl-2-iminoimidazolidin-4-yl)serylserylglycyl])

The title compound is prepared from cyclo[3-cyclohexylalanyl-3-[4-[(4-O-hexopyranosylhexopyranosyl)oxy]cyclohexyl]alanyl-3-(2-iminoimidazolidin-4-yl)seryl-3-(3-hexopyranosyl-2-iminoimidazolidin-4-yl)serylserylglycyl] by the procedure described for example 104 using the appropriate dimethyl ketal. MS (+ES) m/z: 713.3 (M+2H)$^{2+}$.

EXAMPLE 223

(Cyclo[3-cyclohexylalanyl-3-[4-[[4-O-4,6-O-(2-adamantylidene)hexopyranosyl]hexopyranosyl]oxy]cyclohexyl]alanyl-3-(2-iminoimidazolidin-4-yl)seryl-3-(3-hexopyranosyl-2-iminoimidazolidin-4-yl)serylserylglycyl])

The title compound is prepared from cyclo[3-cyclohexylalanyl-3-[4-[(4-O-hexopyranosylhexopyranosyl)oxy]cyclohexyl]alanyl-3-(2-iminoimidazolidin-4-yl)seryl-3-(3-hexopyranosyl-2-iminoimidazolidin-4-yl)serylserylglycyl] by the procedure described for example 104 using the appropriate dimethyl ketal. MS (+ES) m/z: 713.2 (M+2H)$^{2+}$.

EXAMPLE 224

(Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-(1-butyl-3-hexopyranosyl-2-iminoimidazolidin-4-yl)serylseryl])

The title compound is prepared from cyclo[glycyl-β-methylphenylalanyl-O-(4-O-hexopyranosylhexopyranosyl)tyrosyl-3-(2-iminoimidazolidin-4-yl)seryl-3-[1-butyl-3-hexopyranosyl-2-iminoimidazolidin-4-yl]serylseryl] by the procedure described for example 104 using the appropriate dimethyl ketal. MS (+ES) m/z: 742.6 (M+2H)$^{2+}$.

EXAMPLE 225

(Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3,3-hexopyranosyl-2-imino-1-(3-methylbut-2-en-1-iminoimidazolidin-4-yl]serylseryl])

The title compound is prepared from cyclo[glycyl-β-methylphenylalanyl-O-(4-O-hexopyranosylhexopyranosyl)tyrosyl-3-(2-iminoimidazolidin-4-yl)seryl-3,3-hexopyranosyl-2-imino-1-(3-methyl-but-2-iminoimidazolidin-4-yl]serylseryl]by the procedure described for example 104 using the appropriate dimethyl ketal. MS (+ES) m/z; 748.5 (M+2H)$^{2+}$.

EXAMPLE 226

(Cyclo[glycyl-β-methylphenylalanyl-O-[4-O-[4,6-O-(2-adamantylidene)hexopyranosyl]hexopyranosyl]tyrosyl-3-(2-iminoimidazolidin-4-yl)seryl-3-β-hexopyranosyl-2-imino-1-[4-(trifluoromethyl)-benzyl]imidazolidin-4-yl]serylseryl]

The title compound is prepared from cyclo[glycyl-β-methylphenylalanyl-O-(4-O-hexopyranosylhexopyranosyl)tyrosyl-3-(2-iminoimidazolidin-4-yl)seryl]-3-[3-hexopyranosyl-2-imino-1-(4-trifluoromethylbenzyl)-imidazolidin-4-yl]-serylseryl] by the procedure described for example 104 using the appropriate dimethyl ketal. MS (+ES) m/z: 793.5 (M+2H)$^{2+}$.

EXAMPLE 227

Di-N-(2-(1,3-benzoxazolyl)-cyclo[glycyl-β-methylphenylalanyl-O-[4-O-[4,6-O-(2-adamantylidene)hexopyranosyl]hexopyranosyl]tyrosyl-3-[2-iminoimidazolidin-4-yl]seryl-3-β-hexopyranosyl-2-iminoimidazolidin-4-yl]serylseryl]

The title compound is prepared from cyclo[glycyl-β-methylphenylalanyl-O-(4-O-hexopyranosylhexopyranosyl)tyrosyl-3-[2-(pyrimidin-2-ylimino)imidazolidin-4-yl]seryl-3,3-hexopyranosyl-2-imino-1-(pyrimidin-2-yl)imidazolidin-4-yl]serylseryl] by the procedure described for example 104 using the appropriate dimethyl ketal. MS (+ES) m/z 831.1 (M+2H)$^{2+}$.

EXAMPLE 228

Di-N-(2-(pyrimidinyl)-cyclo[glycyl-β-methylphenylalanyl-O-[4-O-[4,6-O-(2-adamantylidene)hexopyranosyl]hexopyranosyl]tyrosyl-3-[2-iminoimidazolidin-4-yl]seryl-3-β-hexopyranosyl-2-iminoimidazolidin-4-yl]serylseryl]

The title compound is prepared from cyclo[glycyl-β-methylphenylalanyl-O-(4-O-hexopyranosylhexopyranosyl)tyrosyl-3-[2-(1,3-benzoxazol-2-ylimino)imidazolidin-4-yl]seryl-3-[1-(1,3-benzoxaxol-2-yl)-3-hexopyranosyl-2-iminoimidazolidin-4-yl]serylseryl] by the procedure described for example 104 using the appropriate dimethyl ketal. MS (+ES) m/z: 792.2 (M+2H)$^{2+}$.

EXAMPLE 229

(Cyclo[glycyl-β-methylphenylalanyl-O-(2,3-O-isopropylidene-4-O-hexopyranosylhexopyranosyl)tyrosyl-3-(2-iminoimidazolidin-4-yl)seryl-3-[2-imino-(2,3-O-isopropylidene-hexopyranosyl)imidazolidin-4-yl]serylseryl])

EXAMPLE 229a (Cyclo[glycyl-β-methylphenylalanyl-O-[2,3-O-isopropylidene-4-O-(2,3-isopropylidenehexopyranosyl)hexopyranosyl]tyrosyl-3-(2-iminoimidazolidin-4-yl)seryl-3-[2-imino-3-(2,3-O-isopropylidenehexopyranosyl)imidazolidin-4-yl]serylseryl])

EXAMPLE 229b (Cyclo[glycyl-β-methylphenylalanyl-O-[2,3-O-isopropylidene-4-O-(2,3:4,6-di-O-isopropylidene-hexopyranosyl)hexopyranosyl]tyrosyl-3-(2-iminoimidazolidin-4-yl)seryl-3-[2-imino-(2,3-O-isopropylidenehexopyranosyl)imidazolidin-4-yl]serylseryl])

A stirred solution of the bis-hydrochloride salt of cyclo [glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (0.908 g) in N,N-dimethylformamide (16 mL) is treated with 2,2-dimethoxypropane (5 mL) and hydrogen chloride (0.15 mL of a 4.0 M solution in 1,4-dioxane) and the mixture is stirred for 3 days at room temperature. The resultant solution is concentrated in vacuo to approximately one-third of the original volume, added to acetonitrile (32 mL) and the resultant precipitate collected by centrifugation. The precipitate is resuspended in acetonitrile (32 mL) and recentrifuged. The products are then purified by reverse phase HPLC. Cyclo [glycyl-β-methylphenylalanyl-O-(2,3-O-isopropylidene-4-O-hexopyranosylhexopyranosyl)tyrosyl-3-(2-iminoimidazolidin-4-yl)seryl-3-[2-imino-(2,3-O-isopropylidene-hexopyranosyl)imidazolidin-4-yl]serylseryl]: MS (+ES) m/z: 688.6 (M+2H)$^{2+}$; Cyclo[glycyl-β-methylphenylalanyl-O-[2,3-O-isopropylidene-4-O-(2,3-isopropylidenehexopyranosyl)hexopyranosyl]tyrosyl-3-(2-iminoimidazolidin-4-yl)seryl-3-[2-imino-3-(2,3-O-isopropylidenehexopyranosyl)imidazolidin-4-yl]serylseryl]: MS (+ES) m/z: 708.5 (M+2H)$^{2+}$; Cyclo[glycyl-β-methylphenylalanyl-(2,3-O-isopropylidene-4-O-(2,3:4,6-di-O-isopropylidene-hexopyranosyl)hexopyranosyl]tyrosyl-3-(2-iminoimidazolidin-4-yl)seryl-3-[2-imino-(2,3-O-isopropylidenehexopyranosyl)imidazolidin-4-yl]serylseryl]: MS (+ES) m/z: 728.6 (M+2H)$^{2+}$.

EXAMPLE 230

(Cyclo[glycyl-β-methylphenylalanyl-O-[4-O-[6-O-[(6-methoxy-2-naphthyl)methyl]hexopyranosyl]hexopyranosyl]tyrosyl-3-(2-iminoimidazolidin-4-yl)seryl-3-(3-hexopyranosyl-2-iminoimidazolidin-4-yl)serylseryl])

EXAMPLE 230a (Cyclo[glycyl-β-methylphenylalanyl-O-[4-O-[4-O-[(6-methoxy-2-naphthyl)methyl]hexopyranosyl]hexopyranosyl]tyrosyl-3-(2-iminoimidazolidin-4-yl)seryl-3-(3-hexopyranosyl-2-iminoimidazolidin-4-yl)serylseryl])

EXAMPLE 230b (Cyclo[glycyl-β-methylphenylalanyl-O-[4-O-β-O-[(6-methoxy-2-naphthyl)methyl]hexopyranosyl]hexopyranosyl]tyrosyl-3-(2-iminoimidazolidin-4-yl)seryl-3-(3-hexopyranosyl-2-iminoimidazolidin-4-yl)serylseryl])

EXAMPLE 230c (Cyclo[glycyl-β-methylphenylalanyl-O-[4-O-[2-O-[(6-methoxy-2-naphthyl)methyl]hexopyranosyl]hexopyranosyl]tyrosyl-3-(2-iminoimidazolidin-4-yl)seryl-3-(3-hexopyranosyl-2-iminoimidazolidin-4-yl)serylseryl])

A stirred solution of the bis-hydrochloride salt of cyclo [glycyl-β-methylphenylalanyl-0-(4-O-hexopyranosylhexopyranosyl)tyrosyl-3-(2-iminoimidazolidin-4-yl)seryl-3-(3-hexopyranosyl-2-iminoimidazolidin-4-yl)serylseryl](5.46 g) in dimethyl sulfoxide (25 mL) is treated with 6-methoxy-2-naphthaldehyde dimethyl acetal (1.856 g) and hydrogen chloride (1 mL of 1.0M solution in diethyl ether), and the mixture is heated at 50° C. for 1 h. The reaction mixture is then cooled to room temperature and poured into water (100 mL) containing dilute sodium hydroxide solution. The pH of the solution is then adjusted to pH 10, and the resulting precipitates are filtered and washed with a mixture of acetonitrile and diethyl ether (1:1). The crude acetal thus obtained is air dried and used in the next step without further purification. An ice cold solution of trifluoroacetic acid (3.192 g) in N,N-dimethylformamide (5 mL) is added dropwise to a cooled (0° C.) mixture containing the above acetal derivative (2.04 g) and sodium cyanoborohydride (0.879 g) in N,N-dimethylformamide (20 mL). The mixture is then stirred for 24 h and gradually warmed to room temperature, and is then poured into water (50 mL). A dilute solution of sodium hydroxide is added to adjust to pH 10, the resulting solid is filtered, washed several times with water, then acetonitrile and dried. This solid is then purified by reverse phase HPLC to provide the title compounds. Cyclo(glycyl-β-methylphenylalanyl-O-[4-O-[6-O-[(6-methoxy-2-naphthypmethyl]hexopyranosyl]hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 733.2 (M+2H)$^{2+}$; Cyclo[glycyl-β-methylphenylalanyl-O-[4-O-[4-O-[(6-methoxy-2-naphthypmethyl]hexopyranosyl]hexopyranosyl]tyrosyl-3-(2-iminoimidazolidin-4-yl)seryl-3-(3-hexopyranosyl-2-iminoimidazoliclin-4-yl)serylseryl]: MS (+ES) m/z: 733.4 (M+2H)$^{2+}$; Cyclo[glycyl-β-methylphenylalanyl-O-[4-O-β-O-[(6-methoxy-2-naphthypmethyl]hexopyranosyl]hexopyranosyl]tyrosyl-3-

(2-iminoimidazolidin-4-yl)seryl-3-(3-hexopyranosyl-2-iminoimidazolidin-4-yl)serylseryl]: MS (4-ES) m/z: 733.3 (M+2H)$^{2+}$; Cyclo[glycyl-β-methylphenylalanyl-O-[4-O-[2-O-[(6-methoxy-2-naphthyl)methyl]hexopyranosyl]hexopyranosyl]tyrosyl-3-(2-iminoimidazolidin-4-yl)seryl-3-(3-hexopyranosyl-2-iminoimidazolidin-4-yl)serylseryl]: MS (ES) m/z: 733.2 (M+2H)$^{2+}$.

EXAMPLE 231

(Cyclo[glycyl-β-methylphenylalanyl-O-[4-O-[6-O-[4-(phenylmethoxy)benzyl]hexopyranosyl]-hexopyranosyl]tyrosyl-3-(2-iminoimidazolidin-4-yl)seryl-3-(3-hexopyranosyl-2-iminoimidazolidin-4-yl)serylseryl])

EXAMPLE 231a (Cyclo[glycyl-β-methylphenylalanyl-O-[4-O-[4-O-[4-(phenylmethoxy)benzyl]hexopyranosyl]-hexopyranosyl]tyrosyl-3-(2-iminoimidazolidin-4-yl)seryl-3-(3-hexopyranosyl-2-iminoimidazolidin-4-yl)serylseryl])

EXAMPLE 231b (Cyclo[glycyl-β-methylphenylalanyl-O-[4-O-[2-O-[4-(phenylmethoxy)benzyl]hexopyranosyl]-hexopyranosyl]tyrosyl-3-(2-iminoimidazolidin-4-yl)seryl-3-(3-hexopyranosyl-2-iminoimidazolidin-4-yl)serylseryl])

EXAMPLE 231c (Cyclo[glycyl-β-methylphenylalanyl-O-4-O-β-O-[4-(phenylmethoxy)benzyl]hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compounds are prepared by the procedure described for example 230 using the appropriate dimethyl acetal. Cyclo[glycyl-β-methylphenylalanyl-O-[4-O-[6-O-[4-(phenylmethoxy)benzyl]hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 746.4 (M+2H)$^{2+}$; Cyclo[glycyl-β-methylphenylalanyl-O-[4-O-[4-O-[4-(phenylmethoxy)benzyl]hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 746.3 (M+2H)$^{2+}$; Cyclo[glycyl-β-methylphenylalanyl-O-4-O-[2-O-[4-(phenylmethoxy)benzyl]hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 746.7 (M+2H)$^{2+}$: Cyclo[glycyl-β-methylphenylalanyl-O-[4-O-β-O-[4-(phenylmethoxy)benzyl]hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 746.7 (M+2H)$^{2+}$.

EXAMPLE 232

(Cyclo[glycyl-β-methylphenylalanyl-O-[4-O-[6-O-(4-methoxybenzyl)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 230 using the appropriate dimethyl acetal. MS (+ES) m/z: 708.3 (M+2H)$^{2+}$.

EXAMPLE 233

(Cyclo[glycyl-β-methylphenylalanyl-O-[4-O-[6-O-(4-ethoxybenzyl)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 230 using the appropriate dimethyl acetal. MS (+ES) m/z: 715.4 (M+2H)$^{2+}$.

EXAMPLE 234

(Cyclo[glycyl-β-methylphenylalanyl-O-[4-O-6-O-(4-methylbenzyl)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 230 using the appropriate dimethyl acetal. MS (+ES) m/z: 700.2 (M+2H)$^{2+}$.

EXAMPLE 235

(Cyclo[glycyl-β-methylphenylalanyl-O-[4-O-[6-O-(4-propoxybenzyl)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 230 using the appropriate dimethyl acetal. MS (+ES) m/z: 722.3 (M+2H)$^{2+}$.

EXAMPLE 236

(Cyclo[glycyl-β-methylphenylalanyl-O-[4-O-[6-O-(4-phenoxybenzyl)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 230 using the appropriate dimethyl acetal. MS (+ES) m/z: 739.2 (M+2H)$^{2+}$.

EXAMPLE 237

(Cyclo[glycyl-β-methylphenylalanyl-O-[4-O-[6-O-(3-fluoro-4-methoxybenzyl)hexopyranosyl]-hexopyranosyl]tyrosyl-3-(2-iminoimidazolidin-4-yl)seryl-3-β-hexopyranosyl-2-iminoimidazolidin-4-yl)serylseryl])

The title compound is prepared by the procedure described for example 230 using the appropriate dimethyl acetal. MS (+ES) m/z: 717.3 (M+2H)$^{2+}$.

EXAMPLE 238

(Cyclo[glycyl-β-methylphenylalanyl-O-4-O-[6-O-(3-ethoxy-4-methoxybenzyl)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 230 using the appropriate dimethyl acetal. MS (+ES) m/z: 7303 $(M+2H)^{2+}$.

EXAMPLE 239

(Cyclo[glycyl-β-methylphenylalanyl-O-[4-O-[6-O-[4-methoxy-3-Phenylmethoxy)benzyl]-hexopyranosyl]hexopyranosyl]tyrosyl-3-(2-iminoimidazolidin-4-yl)seryl-3-(3-hexopyranosyl-2-iminoimidazolidin-4-yl)serylseryl])

EXAMPLE 239a (Cyclo[glycyl-β-methylphenylalanyl-O-[4-O-[4-O-[4-methoxy-3-(phenylmethoxy)benzyl]-hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compounds are prepared by the procedure described for example 230 using the appropriate dimethyl acetal. Cyclo[glycyl-β-methylphenylalanyl-O-[4-O-[6-O-(4-methoxy-3-(phenylmethoxy)benzyl]-hexopyranosyl]hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 761.3 $(M+2H)^{2+}$; Cyclo[glycyl-β-methylphenylalanyl-O-[4-O-[4-O-[4-methoxy-3-(phenylmethoxy)benzyl]-hexopyranosyl]hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 761.8 $(M+2H)^{2+}$.

EXAMPLE 240

(Cyclo[glycyl-β-methylphenylalanyl-O-[4-O-[6-O-[(4-methoxy-1-naphthyl)methyl]hexo-pyranosyl]hexopyranosyl]tyrosyl-3-(2-iminoimidazolidin-4-yl)seryl-3-(3-hexopyranosyl-2-iminoimidazolidin-4-yl)serylseryl])

EXAMPLE 240a (Cyclo[glycyl-β-methylphenylalanyl-O-[4-O-[4-O-[(4-methoxy-1-naphthyl)methyl]hexo-pyranosyl]hexopyranosyl]tyrosyl-3-(2-iminoimidazolidin-4-yl)seryl-3-β-hexopyranosyl-2-iminoimidazolidin-4-yl)serylseryl])

EXAMPLE 240b (Cyclo[glycyl-β-methylphenylalanyl-O-[4-O-[2-O-[(4-methoxy-1-naphthyl)methyl]hexo-pyranosyl]hexopyranosyl]tyrosyl-3-(2-iminoimidazolidin-4-yl)seryl-3-(3-hexopyranosyl-2-iminoimidazolidin-4-yl)serylseryl])

The title compounds are prepared by the procedure described for example 230 using the appropriate dimethyl acetal. Cyclo[glycyl-β-methylphenylalanyl-O-[4-O-[6-O-[(4-methoxy-1-naphthyl)methyl]hexo-pyranosyl]hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 7316 $(M+2H)^{2+}$; Cyclo[glycyl-β-methylphenylalanyl-O-[4-O-[4-O-[(4-methoxy-1-naphthyl)methyl]hexo-pyranosy]lhexopyranosyl]tyrosyl-3-(2-iminoimidazolidin-4-yl)seryl-3-(3-hexopyranosyl-2-iminoimidazolidin-4-yl)serylseryl]: MS (+ES) m/z: 733.5 $(M+2H)^{2+}$; Cyclo[glycyl-β-methylphenylalanyl-O-4-O-[2-O-[(4-methoxy-1-naphthyl)methyl]hexo-pyranosy]lhexopyranosyl]tyrosyl-3-(2-iminoimidazolidin-4-yl)seryl-3-(3-hexopyranosyl-2-iminoimidazolidin-4-yl)serylseryl]: MS (+ES) m/z: 733.4 $(M+2H)^{2+}$.

EXAMPLE 241

(Cyclo[glycyl-β-methylphenylalanyl-O-[4-O-[6-O-[3,3-diphenylprop-2-en-1-yl)hexopyranosyl]-hexopyranosyl]tyrosyl-3-(2-iminoimidazolidin-4-yl)seryl-3-(3-hexopyranosyl-2-iminoimidazolidin-4-yl)serylseryl])

EXAMPLE 241a (Cyclo[glycyl-β-methylphenylalanyl-O-[4-O-[4-O-(3,3-diphenylprop-2-en-1-yl)hexopyranosyl]-hexopyranosyl]tyrosyl-3-(2-iminoimidazolidin-4-yl)seryl-3-[3-hexopyranosyl-2-iminoimidazolidin-4-yl)serylseryl])

The title compounds are prepared by the procedure described for example 230 using the appropriate dimethyl acetal. Cyclo[glycyl-β-methylphenylalanyl-O-[4-O-[6-O-(3,3-diphenylprop-2-en-1-yl)hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 744.4 $(M+2H)^{2+}$; Cyclo[glycyl-β-methylphenylalanyl-O-[4-O-[4-O-(3,3-diphenylprop-2-en-1-yl)hexopyranosyl]-hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 744.7 $(M+2H)^{2+}$.

EXAMPLE 242

(Cyclo[glycyl-β-methylphenylalanyl-O-[4-O-[6-O-(3-phenylprop-2-en-1-yl)hexopyranosyl]-hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 230 using the appropriate dimethyl acetal. MS (+ES) m/z: 706.3 $(M+21-1)^{2+}$.

EXAMPLE 243

(Cyclo[glycyl-β-methylphenylalanyl-O-[4-O-[6-O-β-[4-(dimethylamino)phenyl]prop-2-en-1-yl]hexopyranosyl]hexopyranosyl]tyrosyl-3-(2-iminoimidazolidin-4-yl)seryl-3-(3-hexopyranosyl-2-iminoimidazolidin-4-yl)serylseryl])

EXAMPLE 243a (Cyclo[glycyl-β-methylphenylalanyl-O-[4-O-[4-O-β-[4-(dimethylamino)phenyl]prop-2-en-1-yl]hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compounds are prepared by the procedure described for example 230 using the appropriate dimethyl acetal. Cyclo[glycyl-β-methylphenylalanyl-O-[4-O-[6-O-β-[4-(dimethylamino)phenyl]prop-2-en-1-yl]hexopyranosyl]hexopyranosyl]tyrosyl-3-(2-iminoimidazolidin-4-yl)seryl-3-(3-hexopyranosyl-2-iminoimidazolidin-4-yl)serylseryl]: MS (+ES) m/z: 728.0 (M+2H)$^{2+}$; Cyclo[glycyl-β-methylphenylalanyl-O-[4-O-[4-O-β-[4-(dimethylamino)phenyl]prop-2-en-1-yl]hexopyranosyl]hexopranosyl]tyrosyl-3-(2-iminoimidazolidin-4-yl)seryl-3-(3-hexopyranosyl-2-iminoimidazolidin-4-yl)serylseryl]: MS (+ES) m/z: 728.0 (M+2H)$^{2+}$.

EXAMPLE 244

(Cyclo[glycyl-β-methylphenylalanyl-O-[4-O-[6-O-(2-thienylmethyl)hexopyranosyl]hexopyranosyl]tyrosyl-3-(2-iminoimidazolidin-4-yl)seryl-3-(3-hexopyranosyl-2-iminoimidazolidin-4-yl)serylseryl])

The title compound is prepared by the procedure described for example 230 using the appropriate dimethyl acetal. MS (+ES) m/z: 696.3 (M+2H)$^{2+}$.

EXAMPLE 245

(Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[6-O-[(6-methoxy-2-naphthyl)methyl]-hexopyranosyl)hexopyranosyl]tyrosyl])

EXAMPLE 245a (Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[4-O-[(6-methoxy-2-naphthyl)methyl]-hexopyranosyl]hexopyranosyl]tyrosyl])

EXAMPLE 245b (Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-β-O-[(6-methoxy-2-naphthyl)methyl]-hexopyranosyl]hexopyranosyl]tyrosyl])

EXAMPLE 245c (Cyclo[3-(2-iminoimidazolidin-4-yl)alanyl-3-(3-hexopyranosyl-2-iminoimidazolidin-4-yl)-alanylserylglycyl-62-methylphenylalanyl-O-[4-O-[2-O-[(6-methoxy-2-naphthyl)methyl]-hexopyranosyl]hexopyranosyl]tyrosyl])

The title compounds are prepared from cyclo[3-(2-iminoimidazolidin-4-yl)alanyl-3-(3-hexopyranosyl-2-iminoimidazolidin-4-yl)-alanylserylglycyl-β-methylphenylalanyl-0-(4-O-hexopyranosylhexopyranosyl)tyrosyl] by the procedure described for example 230 using the appropriate dimethyl acetal. Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[6-O-[(6-methoxy-2-naphthyl)methyl]-hexopyranosyl]hexopyranosyl]tyrosyl]: MS (+ES) m/z: 717.6 (M+2H)$^{2+}$; Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[4-O-[(6-methoxy-2-naphthyl)methyl]-hexopyranosyl]hexopyranosyl]tyrosyl]: MS (+ES) m/z: 717.7 (M+2H)$^{2+}$; Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-β-O-[(6-methoxy-2-naphthypmethyl]-hexopyranosyl]hexopyranosyl]tyrosyl]: MS (+ES) m/z: 717.7 (M+2H)$^{2+}$: Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-(2-O-[(6-methoxy-2-naphthyl)methyl]-hexopyranosyl]hexopyranosyl]tyrosyl]: MS (+ES) m/z: 717.7 (M+2H)$^{2+}$.

EXAMPLE 246

(Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[6-O-[4-(phenylmethoxy)benzyl]hexopyranosyl]hexopyranosyl]tyrosyl])

EXAMPLE 246a (Cyclo[3-(2-iminoimidazolidin-4-yl)alanyl-3-β-hexopyranosyl-2-iminoimidazolidin-4-yl)-alanylserylglycyl-β-methylphenylalanyl-O-[4-O-[4-O-[4-(phenylmethoxy)benzyl]hexopyranosyl]hexopyranosyl]tyrosyl])

EXAMPLE 246b (Cyclo[3-(2-iminoimidazolidin-4-yl)alanyl-3-β-hexopyranosyl-2-iminoimidazolidin-4-yl)-alanylserylglycyl-β-methylphenylalanyl-O-[4-O-β-O-[4-phenylmethoxy)benzyl]hexopyranosyl]hexopyranosyl]tyrosyl])

EXAMPLE 246c (Cyclo[3-(2-iminoimidazolidin-4-yl)alanyl-3-β-hexopyranosyl-2-iminoimidazolidin-4-yl)-alanylserylglycyl-β-methylphenylalanyl-O-[4-O-[2-O-[4-(phenylmethoxy)benzyl]hexopyranosyl]hexopyranosyl]tyrosyl])

The title compounds are prepared from cyclo[3-(2-iminoimidazolidin-4-yl)alanyl-3-(3-hexopyranosyl-2-iminoimidazolidin-4-yl)-alanylserylglycyl-β-methylphenylalanyl-O-(4-O-hexopyranosylhexopyranosyl)tyrosyl] by the procedure described for example 230 using the appropriate dimethyl acetal. Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[6-O-[4-(phenylmethoxy)benzyl]hexopyranosyl]hexopyranosyl]tyrosyl]: MS (+ES) m/z: 717.6 (M+2H)$^{2+}$; Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[4-O-[4-(phenylmethoxy)benzyl]hexopyranosyl]hexopyranosyl]tyrosyl]: MS (+ES) m/z: 717.7 (M+2H)$^{2+}$; Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-β-O-[4-(phenylmethoxy)benzyl]hexopyranosyl]hexopyranosyl]tyrosyl]: MS (+ES) m/z: 717.7 (M+2H)$^{2+}$: Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[2-O-[4-(phenylmethoxy)benzyl]hexopyranosyl]hexopyranosyl]tyrosyl]: MS (+ES) m/z: 717.7 (M+2H)$^{2+}$.

EXAMPLE 247

(Cyclo[glycyl-β-methylphenylalanyltyrosyl-3-(2-iminoimidazolidin-4-yl)seryl-3-(2,3:4,6-diisopropylidenehexopyranosyl)-2-iminoimidazolidin-4-ylserylseryl])

A stirred solution of the bis-hydrochloride salt of cyclo [glycyl-β-methylphenylalanyltyrosyl-3-(2-iminoimidazolidin-4-yl)seryl-3-(3-hexopyranosyl-2-iminoimidazolidin-4-yl)serylseryl] (2.85 g) in N,N-dimethylformamide (20 mL) is treated with 2,2-dimethoxypropane (5.8 mL) and p-toluenesulfonic acid mono-hydrate (35 mg) and the mixture is stirred for 16 h at room temperature. Water (1 mL) is then added, the mixture is stirred for 30 min at room temperature, and then acetonitrile (100 mL) is added dropwise to precipitate the product. After stirring for 45 min at 0° C., the product is collected by filtration, and is then washed with acetonitrile, diethyl ether, and air dried. MS (+ES) m/z: 526.6 (M+2H)$^{2+}$.

EXAMPLE 248

(Cyclo[glycyl-β-methylphenylalanyltyrosyl-3-(2-iminoimidazolidin-4-yl)seryl-343-(2,3:4,6-di-O-isonronylidenehexopyranosyl)-2-iminoimidazolidin-4-yl]seryl-O-(tert-butyldimethylsilyl)seryl])

A stirred solution of the bis-hydrochloride salt of cyclo [glycyl-β-methylphenylalanyltyrosyl-3-(2-iminoimidazolidin-4-yl)seryl-3-(2,3:4,6-diisopropylidenehexopyranosyl)-2-iminoimidazolidin-4-ylserylseryl] (2.25 g) in N,N-dimethylformamide (15 mL) containing 2,6-lutidine (4 mL) is treated dropwise at −45° C. with a solution of t-buytyldimethylsilyl triflate in N,N-dimethylformamide (2 M, 5 mL) and the mixture is stirred for 2 h at −45° C. Methanol (1.5 mL) is added, and then diethyl ether (200 mL) is added to the reaction mixture. Stirring is stopped and the resulting oil is permitted to settle. The solvents are decanted and an additional portion of diethyl ether (200 mL) is added. After stirring briefly, and then allowing the oil to settle, the solvents are again decanted. Acetonitrile (175 mL) is added to precipitate the product, which is collected by filtration and then washed with acetonitrile, diethyl ether, and air dried. MS (+ES) m/z: 583.6 (M+2H)$^{2+}$.

EXAMPLE 249

(Tri-N-[(phenylmethoxy)carbonyl]-cyclo[glycyl-β-methylphenylalanyltyrosyl-3-(2-iminoimidazolidin-4-yl)seryl-3-β-(2,3:4,6-di-O-isopropylidenehexopyranosyl)-2-iminoimidazolidin-4-yl]seryl-O-(tert-butyldimethylsilyl)seryl])

A stirred solution of cyclo(glycyl-β-methylphenylalanyltyrosyl-3-(2-iminoimidazolidin-4-yl)seryl-3-β-(2,3:4,6-di-O-isopropylidenehexopyranosyl)-2-iminoimidazolidin-4-yl]seryl-O-(tert-butyldimethylsilyl)seryl] (1.97 g) in N,N-dimethylformamide (15 mL) containing N,N-diisopropylethylamine (1 mL) is treated with N-(benzyloxycarbonyloxy)-succinimide (1.48 g) and the mixture is stirred for 16 h at room temperature. The mixture is then diluted with ethyl acetate and washed twice with saturated aqueous sodium bicarbonate, twice with water, and then with saturated aqueous sodium chloride. The organic phase is then dried over anhydrous sodium sulfate, filtered and concentrated to provide an oil. This oil is dissolved in a minimal amount of dichloromethane and treated with hexanes to precipitate the product. The product is then collected by filtration, washed with hexanes, and dried. MS (+ES) m/z: 784.6 (M+2H)$^{24}$.

EXAMPLE 250

(Tetra-N-[(phenylmethoxy)carbonyl]-cyclo[glycyl-β-methylphenylalanyltyrosyl-3-(2-iminoimidazolidin-4-yl)seryl-3-(2-iminoimidazolidin-4-yl)seryl-O-(tert-butyldimethylsilyl)seryl])

A stirred solution of the bis-hydrochloride salt of cyclo [glycyl-β-methylphenylalanyltyrosyl-3-(2-iminoimidazolidin-4-yl)seryl-3-(2-iminoimidazolidin-4-yl)serylseryl] (590 mg) in N,N-dimethylformamide (6 mL) containing 2,6-lutidine (0.5 mL) is treated dropwise at −45° C. with t-buytyldimethylsilyl triflate (0.62 mL) and the mixture is stirred for 16 h and then gradually warmed to room temperature. Methanol (0.25 mL) is added, the mixture is stirred for 10 min, and then N,N-diisopropylethylamine (0.66 mL) and N-(benzyloxycarbonyloxy)-succinimide (0.84 g) are sequentially added. The mixture is stirred for 2 h, and then additional N,N-diisopropylethylamine (0.33 mL) and N-(benzyloxycarbonyloxy)-succinimide (0.33 g) are added. After 2 more hs, the mixture is diluted with ethyl acetate and washed twice with saturated aqueous sodium bicarbonate, twice with water, and then with saturated aqueous sodium chloride. The organic phase is then dried over anhydrous sodium sulfate, filtered and concentrated to provide an oil. This oil is chromatographed over silica gel to provide the title compound. MS (+ES) m/z: 730.9 (M+2H)$^{2+}$.

EXAMPLE 251

(α-O-[(Pentylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

EXAMPLE 251a (β-O-[(Pentylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

EXAMPLE 251b (γ-O-[(Pentylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

A solution of the bis-trifluoroacetate salt of cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (250 mg) in N,N-dimethylformamide (1.6 mL) at 0° C. is treated dropwise with a 1M solution of N,N'-carbonyldiimidazole in N,N-dimethylformamide (0.25 mL) and the reaction is stirred for 2 h at 0° C. Isoamyl amine (0.16 mL) is added and the reaction is stirred overnight at approximately 4° C. Acetonitrile (~2 mL) is then added to precipitate the products. Solids are collected by filtration, washed with acetonitrile and ether, air dried, and then purified by reverse phase HPLC. α-O-[(Pentylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]:MS (+ES) m/z: 704.8 $(M+2H)^{2+}$; β-O-[(Pentylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 704.8 $(M+2H)^{2+}$; γ-O-[(Pentylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 704.6 $(M+2H)^{2+}$.

EXAMPLE 252

(α-O-[(Butylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

EXAMPLE 252a (β-O-[(Butylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

The title compounds are prepared by the procedure described for example 251 using the appropriate alkyl amine. α-O-[(Butylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl): MS (+ES) m/z: 697.8 $(M+2H)^{2+}$; β-O-[(Butylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 697.9 $(M+2H)^{2+}$.

EXAMPLE 253

(α-O-[(Heptylamino)carbonyl]-cyclo(glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

EXAMPLE 253a (β-O-[(Heptylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

EXAMPLE 253b (γ-O-[(Heptylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

The title compounds are prepared by the procedure described for example 251 using the appropriate alkyl amine. α-O-[(Heptylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (4-ES) m/z: 718.8 $(M+2H)^{2+}$; β-O-[(Heptylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 718.9 $(M+2H)^{2+}$; γ-O-[(Heptylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 718.9 $(M+2H)^{2+}$.

EXAMPLE 254

(α-O-[(Dodecylanaino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazoliclin-4-yl)serylseryl])

EXAMPLE 254a (β-O-[(Dodecylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

EXAMPLE 254b (γ-O-[(Dodecylamino)carbonyl]-cyclo[glycyl-β-methylphenylalanyl-O-(4-O-hexopyranosylhexopyranosyl]tyrosyl-3-(2-iminoimidazolidin-4-yl)seryl-3-(3-hexopyranosyl-2-iminoimidazolidin-4-yl)serylseryl])

The title compounds are prepared by the procedure described for example 251 using the appropriate alkyl amine.

α-O-[(Doclecylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 753.8 (M+21-1)$^{2+}$; 13-O-[(Dodecylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 754.0 (M+2H)$^{2+}$; γ-O-[(Dodecylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 753.9 (M+2H)$^{2+}$.

EXAMPLE 255

(α-O-[(N-Methyl-2-methylpropylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

EXAMPLE 255a (β-O-[(N-Methyl-2-methylpropylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

The title compounds are prepared by the procedure described for example 251 using the appropriate alkyl amine. α-O-[(N-Methyl-2-methylpropylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 705.0 (M+2H)$^{2+}$; β-O-[(N-Methyl-2-methylpropylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 704.8 (M+2H)$^{2+}$.

EXAMPLE 256

(α-O-[(Cyclohexylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

EXAMPLE 256a (β-O-[(Cyclohexylamino)carbonyl]-cyclo[glycyl-β-methylphenylalanyl-O-(4-O-hexonyranosylhexopyranosyl)tyrosyl-3-(2-iminoimidazolidin-4-yl)seryl-3-(3-hexopyranosyl-2-iminoimidazolidin-4-yl)serylseryl])

The title compounds are prepared by the procedure described for example 251 using the appropriate alkyl amine. α-O-[(Cyclohexylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 710.7 (M+2H)$^{2+}$; β-O-[(Cyclohexylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 710.9 (M+2H)$^{2+}$.

EXAMPLE 257

(α-O-[(Benzylamino)carbonyl]-cyclo[glycyl-β-methylphenylalanyl-O-(4-O-hexopyranosylhexopyranosyl)tyrosyl-3(2-iminoimidazolidin-4-yl)seryl-3-(3-hexopyranosyl-2-iminoimidazolidin-4-yl)serylseryl])

EXAMPLE 257a

α-O-[(Benzylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

EXAMPLE 257b (γ-O-[(Benzylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl])

The title compounds are prepared by the procedure described for example 251 using the appropriate alkyl amine. α-O-[(Benzylamino)carbonyl)-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 714.8 (M+2H)$^{2+}$; β-O-[(Benzylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 714.8 (M+2H)$^{2+}$; γ-O-[(Benzylamino)carbonyl]-cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]: MS (+ES) m/z: 714.8 (M+2H)$^{2+}$.

EXAMPLE 258

Seed Preparation

A seed medium of the following formulation is prepared:

| | |
|---|---|
| Bacto tryptic soy broth[1] (dehydrated) | 3% |
| Dextrose | 2% |
| Distilled water | |

[1](Soybean-casein digest medium, Difco Laboratories, Detroit MI)

The seed medium is prepared by adding a filter-sterilized dextrose solution to the tryptic soy broth after autoclaving. Fifty mL of seed medium in a 250 mL Erlenmeyer flask is inoculated with cells from a mutant strain (see table below) cultured on ATCC agar medium #172 (ATCC Media Handbook, 1$^{st}$ edition, 1984). Sufficient inoculum from the agar culture is used to provide a turbid seed after 24-36 h. of growth. The seed is incubated at 30° C., 200 rpm using a gyro-rotary shaker with a 2 inch throw, for 24-36 h. To prepare inoculum for fermentors, 1 liter of the above seed medium in a 2.8 liter Fernbach flask is inoculated with 5 mL of cryo-preserved seed culture and is incubated as above.

EXAMPLE 259

Directed Biosynthesis of Glycopeptide Antibiotics

A fermentation medium of the following formulation is prepared:

| | |
|---|---|
| Pharmamedia[2] | 2% |
| Calcium carbonate | 0.5% |
| Dextrose | 4% |
| Distilled water | |

[2](Cottonseed flour, Traders Oil Mill Co., Fort Worth, TX Trader's Guide to Fermentation Media Formulation, 1980)

This medium is prepared by adding a filter-sterilized dextrose solution to autoclaved Pharmamedia™/calcium carbonate broth. A production medium volume of 50 mL in a 250 mL Erlenmeyer flask is supplemented to a final concentration, of 2 mM of a selected amino acid or 16 mM of a selected fatty acid. This flask is then inoculated with 1 mL of seed culture prepared as described in Example 258. Production fermentations are incubated at 30° C., 250 rpm, 2 in. throw for up to 7 days. For large-scale production of glycopeptide antibiotics of the invention, 15 L glass jar fermentors are prepared with 10 L of the above production medium supplemented with the selected amino acid or fatty acid. Fermentors are inoculated with 200 mL of seed culture and are incubated at 30° C., 800 rpm with an air flow rate of 10 L per minute.

EXAMPLE 260a

Isolation and Identification of Glycopeptide Antibiotics

The supernatant of a fermentation broth, obtained by centrifugation at 3000×g, is loaded on a column containing prewashed polyarylate absorbant resin XAD-7 at approximately a 1:10 resin/supernatant ratio (v/v) for a typical extraction. The column is then sequentially washed with water, methanol, and water (each with ~2 column volumes). The crude glycopeptide antibiotics are eluted by 1:1 acetonitrile in water containing 0.05-0.1% trifluoroacetic acid (2-3 column volumes). Upon evaporation under reduced pressure, the residue is redissolved in water or water/methanol mixture and subjected to reverse phase high performance liquid chromatography (HPLC) to afford the pure antibiotics. Typically the HPLC is performed with C18 reverse phase columns (YMC ODS-A, 120A pore size) using mixtures of acetonitrile or methanol in water containing small amounts of trifluoroacetic acid to control the acidity in the range of pH 3.5 and 5.5

The purified antibiotics are then subjected to structural determination by spectroscopic analysis. The molecular weights are usually determined by electrospray ionization mass spectrometry (ESI MS) measured with a Finnigan LCQ instrument in positive mode. The structures are determined by interpretation of 1-D and 2-D nuclear magnetic resonance (NMR) spectral data in 1:1 $D_2O/CD_3OD$, including $^1H$-$^1H$ COSY, TOCSY and $^1H$-$^{13}C$ HMBC, and HMQC data. New antibiotics discerned by the above described conditions are shown in the Examples 261a, 261b, 261c, 262a, 262b, 263, 264a, 264b, 265a, 265b, 270a, 270b, 271a, 275, 277a, 277b, 277c, 278a, 278b, 278c, 278d, 279a, 279b, 280a, 280b, 282, 283a, 283b, 283c, 284b and 296.

EXAMPLE 260b

Detection of Glycopeptide Antibiotics by HPLC and LC/MS

Fermentation broth is centrifuged (3000×g), and the supernatant is applied to a wetted BAKERBOND™ spe carboxylic acid extraction column (catalog #7211-03). Columns are washed with 50% aqueous methanol and are eluted with acetonitrile/water/trifluoroacetic acid (70/30/0.5). The solvent is evaporated, and the residue is reconstituted in 0.2 mL methanol/water (2/8). Samples are analyzed by HPLC, and the production of new glycopeptide antibiotics of the invention is monitored. Reverse phase HPLC is performed using a Hewlett Packard model 1090M liquid chromatograph with photodiode array detection, a YMC ODS-A 4.6×150 mm HPLC column, and a mobile phase of 0.02% trifluoroacetic acid in water (solvent A) and acetonitrile (solvent B). A linear gradient from 5% B to 34% B in 15 min, with a flow rate of 1 ml/min is used for elution. Relative retention times (RRT) are calculated by dividing the peak retention times of the new glycopeptide antibiotics prepared herein by that of cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]. The incorporation of amino acids or fatty acids into the glycopeptide antibiotics is indicated by liquid chromatography/mass spectrometry (LC/MS) analysis of fermentation extracts and a comparison of the molecular weights of new peaks with the predicted molecular weight of glycopeptide antibiotics containing the amino acid or fatty acid analogs.

The molecular weights of new glycopeptide antibiotics of the invention are determined using a Hewlett-Packard APCI-electrospray LC/MS system with an HP 5989B Mass Spectrometer, HP 59987A APCI-Electrospray, HP 1090 series II HPLC and HP ChemStation data system with HP G1047A LC/MS software. Extracts are resolved by reverse phase HPLC as described above. UV detection is at 226 nm. The ESI MS is performed in positive mode. New glycopeptide antibiotics discerned by the above described conditions are shown in the Examples 262c, 264c, 265c, 266a, 266b, 266c, 267a, 267b, 267c, 268, 269a, 269b, 269c, 270c, 271b, 271c, 272a, 272b, 273a, 273b, 274a, 274b, 276a and 276b.

EXAMPLES 261a, 261b and 261c

Glycopeptide Antibiotic Incorporating p-Fluoro-DL-Phenylalanine

EXAMPLE 261a

Cyclo[glycyl-4-fluoro-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]

EXAMPLE 261b

Cyclo[glycyl-4-fluoro-β-methylphenylalanyl-O-[4-O-[2-O-(3-methylbutanoyl)hexopyranosyl]-hexopyranosyl]tyrosyl-3-(2-iminoimidazolidin-4-yl)seryl-3-(3-hexopyranosyl-2-imino-imidazolidin-4-yl) serylseryl]

EXAMPLE 261c

Cyclo[glycyl-4-fluoro-β-methylphenylalanyl-O-[4-O-β-O-(3-methylbutanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl]

Approximately 10 L of supernatant of a 7-day fermentation of strain LL4690 supplemented with p-fluoro-DL-phenylalanine, conducted as described in Examples 258 and 259, is loaded on a column containing polyacrylate resin XAD-7 (1 L). The XAD-7 resin is washed sequentially with methanol (2 L), acetone (2 L), and water (4 L) before packing in the column. After loading, the column is sequentially washed with water (2 L), methanol (2 L), and water (2 L) followed by elution with 1:1 acetonitrile in water containing 0.1% trifluoroacetic acid (3 L). The acidic acetonitrile/water fraction is concentrated under reduced pressure to a small volume, and the residue after extraction with 1:4 water/dimethylformamide is fractionated by reverse phase high performance liquid chromatography (HPLC) on a C18 column (YMC ODS-A, 10 micron particle size, 70×500 mm). The mobile phase consists of a gradient from 14 to 50% by volume of acetonitrile in water with 0.02% trifluoroacetic acid over 55 min at a flow rate of 100 mL per min, and the effluent is monitored by UV absorbance at 226 nm. Peak fractions with retention times of approximately 26 min, 33 min, and 36 min are collected to afford Examples 261a, 261b, and 261c, respectively, upon e

EXAMPLE (261a)

a) Molecular Weight: MS(ESI) $[M+2H]^{2+}$=M/Z 657.2 (m.w.=1312)

b) The structure is consistent with the Proton Magnetic Resonance Spectral data (300 MHz, $CD_3OD/D_2O$ 1:1)

EXAMPLE (261b)

a) Molecular Weight: MS(ESI) $[M+2H]^{2+}$=M/Z 699.2 (m.w.=1396)

b) The structure is consistent with the Proton Magnetic Resonance Spectral data (300 MHz, $CD_3OD/D_2O$ 1:1)

EXAMPLE (261c)

a) Molecular Weight: MS(ESI) $[M+2H]^{2+}$=M/Z 699.3 (m.w.=1396)

b) The structure is consistent with the Proton Magnetic Resonance Spectral data (300 MHz, $CD_3OD/D_2O$ 1:1)

EXAMPLES 262a, and 262b

Glycopeptide Antibiotics Incorporating p-Chloro-DL-Phenylalanine

EXAMPLE 262a

Cyclo[glycyl-4-chloro-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]

EXAMPLE 262b

Cyclo[glycyl-4-chloro-β-methylphenylalanyl-O-[4-O-β-O-(3-methylbutanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl]

Approximately 3 L of supernatant from a 7-day fermentation of strain LL4614 supplemented with p-chloro-DL-phenylalanine, conducted as described in Examples 258 and 259, is processed using XAD-7 column chromatography and HPLC as described in Examples 261a, 261b, and 261c. Peak fractions A and B with respective HPLC retention times at approximately 26 and 36 min are concentrated under reduced pressure and the concentrates are further purified by reverse phase HPLC on a C18 column (YMC ODS-A, 8 micron particle size, 20×250 mm). Further HPLC chromatography of fraction A, using a mobile phase consisting of a gradient from 30 to 60% by volume of methanol in water with 0.02% trifluoroacetic acid over 20 min at a flow rate of 20 mL per min, afforded 262a at approximately 16 min, while chromatography of fraction B, using a gradient solvent system from 45 to 60% of methanol in water with 0.02% trifluoroacetic acid over 20 min, afforded 262b at approximately 18 min upon evaporation.

EXAMPLE (262a)

a) Molecular Weight: MS(ESI) $[M+2H]^{2+}$=M/Z 665.2 (m.w.=1328)

b) The structure is consistent with the Proton Magnetic Resonance Spectral data (300 MHz, $CD_3OD/D_2O$ 1:1)

EXAMPLE (262b)

a) Molecular Weight: MS(ESI) [M+2H]=M/Z 707 (m.w.=1412)

b) The structure is consistent with the Proton Magnetic Resonance Spectral data (300 MHz, $CD_3OD/D_2O$ 1:1)

EXAMPLE 262c

Glycopeptide Antibiotic Incorporating p-Chloro-DL-Phenylalanine

Cyclo[glycyl-4-chloro-β-methylphenylalanyl-O-[4-O-[2-O-(3-methylbutanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl]

A 50 mL fermentation of strain LL4690 supplemented with p-chloro-DL-phenylalanine is performed as described in Examples 258 and 259. A sample is removed and centrifuged to remove the cells. The supernatant is analyzed by analytical HPLC and LC/MS as described in Example 260b. A new HPLC peak containing glycopeptide antibiotic 262c with a molecular weight that is predicted if p-chloro-DL-phenylalanine is incorporated in place of phenylalanine is identified.

EXAMPLE (262c)

Molecular Weight: MS(ESI) $[M+2H]^{2+}$=M/Z 707 (m.w.=1412)

EXAMPLE 263

Glycopeptide Antibiotics Incorporating (S)-(−)-Alpha-Aminocyclohexane-Propionic Acid or Produced in the Presence of (S)-(−)-Alpha-Aminocyclohexane-Propionic Acid Cyclo[3-cyclohexylalanyl-O-(4-O-hexopyranosyl-hexopyranosyl)tyrosyl-3-(2-iminoimidazolidin-4-yl)seryl-3-(3-hexopyranosyl-2-iminoimidazolidin-4-yl)serylserylglycyl]

Approximately 10 L of supernatant of a 7-day fermentation of strain LL4728 supplemented with (S)-(−)-alpha-aminocyclohexane-propionic acid, conducted as described in Examples 258 and 259, is loaded onto an XAD-7 column (1.2 L). The column is sequentially washed with water (4 L), methanol (3 L), and water (3 L) followed by elution with 1:1 acetonitrile in water containing 0.15% trifluoroacetic acid (4 L). The acidic acetonitrile/water fraction is concentrated under reduced pressure to a small volume and lyophilized to dryness affording a brown powder. The brown powder is then extracted with 1:4 water/dimethylformamide, and the extract is fractionated by reverse phase HPLC on a C18 column (YMC ODS-A, 10 micron particle size, 70×500 mm). The mobile phase consists of a gradient from 12 to 40% by volume of acetonitrile in water with 0.02% trifluoroacetic acid over 40 min at a flow rate of 100 mL per min. The peak fraction with a retention time of approximately 29 min is concentrated and re-purified by reverse phase HPLC on another C18 column (MetaChem ODS3, 5 micron particle size, 20×250 mm). The mobile phase is a gradient solvent system from 20 to 50% by volume of acetonitrile in water with 0.02% trifluoroacetic acid over 41 min at a flow rate of 7 mL per min. The peak fraction at approximately 41 min affords Example 263 upon evaporation.

EXAMPLE (263)

a) Molecular Weight: MS(ESI) $[M+2H]^{2+}$=M/Z 644.4 (m.w.=1286)

b) The structure is consistent with the Proton Magnetic Resonance Spectral data (300 MHz, $CD_3OD/D_2O$ 1:1)

EXAMPLES 264a and 264b

Glycopeptide Antibiotics Incorporating m-Fluoro-DL-Phenylalanine

EXAMPLE 264a

Cyclo[glycyl-3-fluoro-β-methylphenylalanyl-O-[4-O-[2-O-β-methylbutanoyl)hexopyranosyl]-hexopyranosyl]tyrosyl-3-(2-iminoimidazolidin-4-yl)seryl-3-β-hexopyranosyl-2-iminoimidazolidin-4-yl)serylseryl]

EXAMPLE 264b

Cyclo[glycyl-3-fluoro-β-methylphenylalanyl-O-[4-O-β-O-β-methylbutanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl]

Approximately 10 L of supernatant from a 7-day fermentation of strain LL4690 supplemented with m-fluoro-DL-phenylalanine, conducted as described in Examples 258 and 259, is processed using an XAD-7 column, and the fraction concentrate that contained the glycopeptide antibiotics is extracted with 1:4 water/dimethylformamide, as described in Example 261. The extract is fractionated by reverse phase HPLC on a C18 column (YMC ODS-A, 10 micron particle size, 70×500). The mobile phase is a gradient solvent system from 20 to 35% acetonitrile in water with 0.02% trifluoroacetic acid over 55 min at flow rate of 100 mL per min. The peak fractions with retention times at approximately 38 and 46 min afford Examples 264a and 264b, respectively, upon evaporation of volatiles.

EXAMPLE (264a)

a) Molecular Weight: MS(ESI) $[M+2H]^{2+}$=M/Z 699.4 (m.w.=1396)

b) The structure is consistent with the Proton Magnetic Resonance Spectral data (300 MHz, $CD_3OD/D_2O$ 1:1)

EXAMPLE (264b)

a) Molecular Weight: MS(ESI) $[M+2H]^{2+}$=M/Z 699.4 (m.w.=1396)

b) The structure is consistent with the Proton Magnetic Resonance Spectral data (300 MHz, $CD_3OD/D_2O$ 1:1)

EXAMPLE 264c

Glycopeptide Antibiotics Incorporating m-Fluoro-DL-Phenylalanine

Cyclo[glycyl-3-fluoro-β-methylphenylalanyl-O-(4-O-hexopyranosylhexopyranosyl]tyrosyl-3-(2-iminoimidazolidin-4-yl)seryl-3-(3-hexopyranosyl-2-iminoimidazolidin-4-yl)serylseryl]

A 50 mL fermentation of strain LL4690 supplemented with m-fluoro-DL-phenylalanine is performed as described in Examples 258 and 259. A sample is removed and centrifuged to remove the cells. The supernatant is analyzed by analytical HPLC and LC/MS as described in Example 260b. A new HPLC peak containing glycopeptide antibiotic 264c with a molecular weight that is predicted if m-fluoro-DL-phenylalanine is incorporated in place of phenylalanine is identified.

EXAMPLE (264c)

Molecular Weight: MS(ESI) $[M+2H]^{2+}$=M/Z 657 (m.w.=1312)

EXAMPLES 265a and 265b

Glycopeptide Antibiotics Incorporating 3-(2-Thienyl)-DL-Alanine

Cyclo[3-(2-thienyl)-2-aminobutanoyl-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylserylglycyl]

EXAMPLE 265b

Cyclo[3-(2-thienyl)-2-aminobutanoyl-O-[4-O-β-O-(3-methylbutanoyl)hexopyranosyl]hexopyranosyl]tyrosyl-3-(2-iminoimidazolidin-4-yl)seryl-3(3-hexopyranosyl-2-iminoimidazolidin-4-yl)serylserylglycyl]

Approximately 10 L of supernatant from a 7-day fermentation of strain LL4690 supplemented with 3-(2-thienyl)-DL-alanine, conducted as described in Examples 258 and 259, is processed using an XAD-7 column. The fraction concentrate containing the glycopeptide antibiotics is extracted with 1:4 water/dimethylformamide, as described in Example 261. The extract is fractionated by reverse phase HPLC on a C18 column (YMC ODS-A, 10 micron particle size, 70×500). The mobile phase is a gradient solvent system from 20 to 35% acetonitrile in water with 0.02% trifluoroacetic acid over 55 min at flow rate of 100 mL per min. The peak fractions with retention times at approximately 27 and 33 min afford Examples 265a and 265b, respectively, upon evaporation of volatiles.

EXAMPLE (265a)

a) Molecular Weight: MS(ESI) $[M+2H]^{2+}$=M/Z 693.4 (m.w.=1384)

b) The structure is consistent with the Proton Magnetic Resonance Spectral data (300 MHz, $CD_3OD/D_2O$ 1:1)

EXAMPLE (265b)

a) Molecular Weight: MS(ESI) $[M+2H]^{2+}$=M/Z 693.4 (m.w.=1384)

b) The structure is consistent with the Proton Magnetic Resonance Spectral data (300 MHz, $CD_3OD/D_2O$ 1:1)

EXAMPLE 265c

Glycopeptide Antibiotics Incorporating 3-(2-Thienyl)-DL-Alanine

Cyclo[3-(2-thienyl)-2-aminobutanoyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylserylglycyl]

A 50 mL fermentation of strain LL4690 supplemented with 3-(2-thienyl)-DL-alanine is performed as described in Examples 258 and 259. A sample is centrifuged to remove the cells. The supernatant is analyzed by analytical HPLC and LC/MS as described in Example 260b. A new HPLC peak containing glycopeptide antibiotic 265c with a molecular weight that is predicted if 3-(2-thienyl)-DL-alanine is incorporated in place of phenylalanine is identified.

EXAMPLE (265c)

Molecular Weight: MS(ESI) $[M+2H]^{2+}$=M/Z 651 (m.w.=1300)

EXAMPLE 266a, 266b and 266c

Glycopeptide Antibiotics Incorporating m-Fluoro-DL-Tyrosine

EXAMPLE 266a

Cyclo[glycyl-β-methylphenylalanyl-3-fluoro-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]

EXAMPLE 266b

Cyclo[glycyl-β-methylphenylalanyl-3-fluoro-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

EXAMPLE 266c

Cyclo[glycyl-β-methylphenylalanyl-3-fluoro-O-[4-O-β-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl]serylseryl]

A 50 mL fermentation of strain LL4690 supplemented with m-fluoro-DL-tyrosine is performed as described in Examples 258 and 259. A sample is centrifuged to remove the cells. The supernatant is analyzed by analytical HPLC and LC/MS as described in Example 260b. New HPLC peaks containing glycopeptide antibiotics 266a, 266b, and 266c with molecular weights predicted if m-fluoro-DL-tyrosine is incorporated in place of tyrosine are identified.

EXAMPLE (266a)

Molecular Weight: MS(ESI) $[M+2H]^{2+}$=M/Z 657 (m.w.=1312)

EXAMPLE (266b)

Molecular Weight: MS(ESI) $[M+2H]^{2+}$=M/Z 699 (m.w.=1396)

EXAMPLE (266c)

Molecular Weight: MS(ESI) $[M+2H]^{2+}$=M/Z 699 (m.w.=1396)

EXAMPLE 267a, 267b and 267c

Glycopeptide Antibiotics Incorporating 3-Amino-L-Tyrosine

EXAMPLE 267a

Cyclo[glycyl-β-methylphenylalanyl-3-amino-O-(4-O-hexopyranosylhexopyranosyl)tyrosyl-3-(2-iminoimidazoliclin-4-yl)seryl-3-(3-hexopyranosyl-2-iminoimidazolidin-4-yl)serylseryl]

EXAMPLE 267b

Cyclo[glycyl-β-methylphenylalanyl-3-amino-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

EXAMPLE 267c

Cyclo[glycyl-β-methylphenylalanyl-3-amino-O-[4-O-β-O-β-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

A 50 mL fermentation of strain LL4728 supplemented with 3-amino-L-tyrosine is performed as described in Examples 258 and 259. A sample is centrifuged to remove the cells. The supernatant is analyzed by analytical HPLC and LC/MS as described in

EXAMPLE 260b

New HPLC peaks containing glycopeptide antibiotics 267a, 267b, and 267c with molecular weights predicted if 3-amino-L-tyrosine is incorporated in place of tyrosine are identified.

EXAMPLE (267a)

Molecular Weight: MS(ESI) $[M+2H]^{2+}$=M/Z 655.5 (m.w.=1309)

EXAMPLE (267b)

Molecular Weight: MS(ESI) $[M+2H]^{2+}$=M/Z 697.5 (m.w.=1393)

EXAMPLE (267c)

Molecular Weight: MS(ESI) $[M+2H]^{2+}$=M/Z 697.5 (m.w.=1393)

EXAMPLE 268

Glycopeptide Antibiotics Incorporating S-(+)-Phenylglycine

Cyclo[glycyl-phenylglycyl-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

A 50 mL fermentation of strain LL4728 supplemented with S-(+)-phenylglycine is performed as described in Examples 258 and 259. A sample is centrifuged to remove the cells. The supernatant is analyzed by analytical HPLC and LC/MS as described in Example 260b. A new HPLC peak containing glycopeptide antibiotic 268 with a molecular weight predicted if S-(+)-phenylglycine is incorporated in place of phenylalanine is identified.

EXAMPLE (268)

Molecular Weight: MS(ESI) $[M+2H]^{2+}$=M/Z 676 (m.w.=1350)

EXAMPLE 269a, 269b and 269c

Glycopeptide Antibiotics Incorporating O-Chloro-Phenylalanine

EXAMPLE 269a

Cyclo[glycyl-2-chloro-β-methylphenylalanyl-O-(4-O-hexopyranosylhexopyranosyl]tyrosyl-3-(2-iminoimidazolidin-4-yl)seryl-3-(3-hexopyranosyl-2-iminoimidazolidin-4-yl)serylseryl]

EXAMPLE 269b

Cyclo[glycyl-2-chloro-β-methylphenylalanyl-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

EXAMPLE 269c

Cyclo[glycyl-2-chloro-β-methylphenylalanyl-O-[4-O-β-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

A 50 mL fermentation of strain LL4728 supplemented with o-chloro-phenylalanine is performed as described in Examples 258 and 259. A sample is centrifuged to remove the cells. The supernatant is analyzed by analytical HPLC and LC/MS as described in Example 260b. New HPLC peaks containing glycopeptide antibiotics 269a, 269b, and 269c with molecular weights predicted if o-chloro-phenylalanine is incorporated in place of phenylalanine are identified.

EXAMPLE (269a)

Molecular Weight: MS(ESI) $[M+2H]^{2+}$=M/Z 665 (m.w.=1328)

EXAMPLE (269b)

Molecular Weight: MS(ESI) $[M+2H]^{2+}$=M/Z 707 (m.w.=1412)

EXAMPLE (269c)

Molecular Weight: MS(ESI) $[M+2H]^{2+}$=M/Z 707 (m.w.=1412)

EXAMPLES 270a and 270b

Glycopeptide Antibiotics Incorporating
4-Methyl-Valeric Acid

EXAMPLE 270a

Cyclo[glycyl-β-methylphenylalanyl-O-[4-O-[2-O-(4-methylpentanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl]

EXAMPLE 270b

Cyclo[glycyl-β-methylphenylalanyl-O-[4-O-[6-O-acetyl-3-O-(4-methylpentanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

Approximately 45 L of supernatant from a 7-day fermentation of strain LL-4690 supplemented with 4-methyl-valeric acid, conducted as described in Examples 258 and 259, is processed using an XAD-7 column. The fraction concentrate containing glycopeptide antibiotics is extracted with 1:4 water/dimethylformamide, as described in example 261. The extract is fractionated by reverse phase HPLC on a C18 column (YMC ODS-A, 10 micron particle size, 70×500). The mobile phase consists of a gradient solvent system from 10 to 40% acetonitrile in water with 0.02% trifluoroacetic acid over 62 min at flow rate of 100 mL per min. The broad fraction with a retention time of approximately 58 min is concentrated, and the residue is re-purified on a C18 column (MetaChem ODS3, 5 micron particle size, 20×250 mm). The mobile phase is a stepwise solvent system of 21% acetonitrile in water over the first 45 min and 23% acetonitrile in water over the next 25 min, both with 0.02% trifluoroacetic acid and at a flow rate of 7 mL per min. The peak fractions at approximately 19 and 63 min afford 270a and 270b upon evaporation of volatiles.

EXAMPLE (270a)

a) Molecular Weight: MS(ESI) [M+2H]$^{2+}$=M/Z 697.5 (m.w.=1392)
b) The structure is consistent with the Proton Magnetic Resonance Spectral data (300 MHz, CD$_3$OD/D$_2$O 1:1)

EXAMPLE (270b)

a) Molecular Weight: MS(ESI) [M+2H]$^{2+}$=M/Z 718.5 (m.w.=1434)
b) The structure is consistent with the Proton Magnetic Resonance Spectral data (300 MHz, CD$_3$OD/D$_2$O 1:1)

EXAMPLE 270c

Glycopeptide Antibiotics Incorporating
4-Methyl-Valeric Acid

Cyclo[glycyl-β-methylphenylalanyl-O-[4-O-[4-O-(4-methylpentanoyl)hexopyranosyl]-hexopyranosyl]tyrosyl-3-(2-iminoimidazolidin-4-yl)seryl-3-(3-hexopyranosyl-2-iminoimidazolidin-4-yl)seryl seryl]

A 50 mL fermentation of strain LL4666 supplemented with 4-methyl-valeric is performed as described in Examples 258 and 259. A sample is centrifuged to remove the cells. The supernatant is analyzed by analytical HPLC and LC/MS as described in Example 260b. A new HPLC peak containing glycopeptide antibiotic 270c with a molecular weight predicted if 4-methyl-valeric acid is incorporated in place of isovaleric acid is identified.

EXAMPLE (270c)

Molecular Weight: MS(ESI) [M+2H]$^{2+}$=M/Z 697 (m.w.=1392)

EXAMPLE 271a

Glycopeptide Antibiotics Incorporating
3-Methyl-Valeric Acid

Cyclo[glycyl-β-methylphenylalanyl-O-[4-O-β-O-(3-methylpentanoyl)hexopyranosyl]hexopyranosyl]tyrosyl-3-(2-iminoimidazolidin-4-yl)seryl-3-(3-hexopyranosyl-2-iminoimidazolidin-4-yl)seryl seryl]

Approximately 10 L of supernatant from a 7-day fermentation of strain LL-4690 supplemented with 3-methyl-valeric acid, conducted as described in Examples 258 and 259, is processed using an XAD-7 column. The fraction concentrate that contained glycopeptide antibiotics is extracted with 1:4 water/dimethylformamide, as described in example 261. The extract is fractionated by reverse phase HPLC on a C18 column (YMC ODS-A, 10 micron particle size, 70×500). The mobile phase consisted of a gradient solvent system from 20 to 40% acetonitrile in water with 0.02% trifluoroacetic acid over 55 min at flow rate of 100 mL per min. The peak fraction at approximately 43 min affords Example 271a upon evaporation.

EXAMPLE (271a)

a) Molecular Weight: MS(ESI) [M+2H]$^{2+}$=M/Z 697 (m.w.=1392)
b) The structure is consistent with the Proton Magnetic Resonance Spectral data (300 MHz, CD$_3$OD/D$_2$O 1:1)

EXAMPLE 271b and 271c

Glycopeptide Antibiotics Incorporating
3-Methyl-Valeric Acid

EXAMPLE 271b

Cyclo[glycyl-β-methylphenylalanyl-O-[4-O-[6-O-acetyl-3-O-(3-methylpentanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

EXAMPLE 271c

Cyclo[glycyl-β-methylphenylalanyl-O-[4-O-[4-O-(3-methylpentanoyl)hexopyranosyl]-hexopyranosyl]tyrosyl-3-(2-iminoimidazolidin-4-yl)seryl-3-(3-hexopyranosyl-2-iminoimidazolidin-4-yl)serylseryl]

Fermentations in 50 mL volumes of strains LL4690 or LL4666 supplemented with 3-methyl-valeric acid are performed as described in Examples 258 and 259. A sample is centrifuged to remove the cells. The supernatant is analyzed by analytical HPLC and LC/MS as described in Example 260b. New HPLC peaks containing glycopeptide antibiotics 271b and 271c with molecular weights predicted if 3-methyl-valeric acid is incorporated in place of isovaleric acid are identified.

EXAMPLE (271b)

Molecular Weight: MS(ESI) [M+2H]$^{2+}$=M/Z 718.5 (m.w.=1434)

EXAMPLE (271c)

Molecular Weight: MS(ESI) [M+2H]$^{2+}$=M/Z 697 (m.w.=1392)

EXAMPLE 272a and 272b

Glycopeptide Antibiotics Containing Butyrate Instead of Isovalerate

EXAMPLE 272a

Cyclo[glycyl-β-methylphenylalanyl-O-[4-O-(2-O-butanoyl-hexopyranosyl)-hexopyranosyl]tyrosyl-3-(2-iminoimidazolidin-4-yl)seryl-3-(3-hexopyranosyl-2-iminoimidazolidin-4-yl)serylseryl]

EXAMPLE 272b

Cyclo[glycyl-β-methylphenylalanyl-O-[4-O-(3-O-butanoyl-hexopyranosyl)-hexopyranosyl]tyrosyl-3-(2-iminoimidazolidin-4-yl)seryl-3-(3-hexopyranosyl-2-iminoimidazolidin-4-yl)serylseryl]

A 50 mL fermentation of strain LL-4690 supplemented with 3-phenyl-butyric acid is performed as described in Examples 258 and 259. A sample is centrifuged to remove the cells. The supernatant is analyzed by analytical HPLC and LC/MS as described in Example 260b. New HPLC peaks containing glycopeptide antibiotics 272a and 272b with molecular weights predicted if butyric acid is incorporated in place of isovaleric acid are identified.

EXAMPLE (272a)

Molecular Weight: MS(ESI) [M+2H]$^{2+}$=M/Z 683 (m.w.=1364)

EXAMPLE (272b)

Molecular Weight: MS(ESI) [M+2H]$^{2+}$=M/Z 683 (m.w.=1364)

EXAMPLE 273a and 273b

Glycopeptide Antibiotics Containing Hexanoic Acid Instead Of Isovaleric Acid

EXAMPLE 273a

Cyclo[glycyl-β-methylphenylalanyl-O-[4-O-(2-O-hexanoyl-hexopyranosyl)-hexopyranosyl]tyrosyl-3-(2-iminoimidazolidin-4-yl)seryl-3-(3-hexopyranosyl-2-iminoimidazoliclin-4-yl)serylseryl]

EXAMPLE 273b

Cyclo[glycyl-β-methylphenylalanyl-O-[4-O-β-O-hexanoyl-hexopyranosyl)-hexopyranosyl]tyrosyl-3-(2-iminoimidazolidin-4-yl)seryl-3-(3-hexopyranosyl-2-iminoimidazolidin-4-yl)serylseryl]

A 50 mL fermentation of strain LL-4690 supplemented with 2-methyl-hexanoic acid is performed as described in Examples 258 and 259. A sample is centrifuged to remove the cells. The supernatant is analyzed by analytical HPLC and LC/MS as described in Example 260b. New HPLC peaks containing glycopeptide antibiotics 273a and 273b with molecular weights predicted if hexanoic acid is incorporated in place of isovaleric acid are identified.

EXAMPLE (273a)

Molecular Weight: MS(ESI) [M+2H]$^{2+}$=M/Z 697 (m.w.=1392)

EXAMPLE (273b)

Molecular Weight: MS(ESI) [M+2H]$^{2+}$=M/Z 697 (m.w.=1392)

EXAMPLE 274a and 274b

Glycopeptide Antibiotics Incorporating n-Heptanoic Acid

EXAMPLE 274a

Cyclo[glycyl-β-methylphenylalanyl-O-[4-O-(2-O-heptanoyl-hexopyranosyl)-hexopyranosyl]tyrosyl-3-(2-iminoimidazolidin-4-yl)seryl-3-(3-hexopyranosyl-2-iminoimidazolidin-4-yl)serylseryl]

EXAMPLE 274b

Cyclo[glycyl-β-methylphenylalanyl-O-[4-O-(3-O-heptanoyl-hexopyranosyl)-hexopyranosyl]tyrosyl-3-(2-iminoimidazolidin-4-yl)seryl-3-(3-hexopyranosyl-2-iminoimidazolidin-4-yl)serylseryl]

A 50 mL fermentation of strain LL-4690 supplemented with n-heptanoic acid is performed as described in Examples 258 and 259. A sample is removed and centrifuged to remove the cells. The supernatant is analyzed by analytical HPLC and LC/MS as described in Example 260b. New HPLC peaks containing glycopeptide antibiotics 274a and 274b with molecular weights predicted if n-heptanoic acid is incorporated in place of isovaleric acid are identified.

EXAMPLE (274a)

Molecular Weight: MS(ESI) [M+2H]$^{2+}$=M/Z 704 (m.w.=1406)

EXAMPLE (274b)

Molecular Weight: MS(ESI) [M+2H]$^{2+}$=M/Z 704 (m.w.=1406)

EXAMPLE 275

Cyclo[glycyl-β-methylphenylalanyl-O-[4-O-[6-O-acetyl-3-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

Strain LL4614 is fermented for 4 days in medium BPM17. The supernatant from 7 L of fermentation broth is applied to a column containing XAD-7 resin. The column is sequentially washed with water (2 L), methanol (2 L) and water (2 L) followed by elution with 1:1 acetonitrile in water containing 0.1% trifluoroacetic acid (3L). The acetonitrile/water fraction is concentrated under reduced pressure to a small volume and the residue is applied to a reverse phase HPLC column (ODS-A, 10 micron particle size, 70×500 mm). The column is developed with a gradient of from 14 to 50% acetonitrile in water with 0.02% trifluoroacetic acid over 55 min at a flow rate of 100 mL per minute. The fraction with a retention time of approximately 37 min is collected and evaporated to afford (Example 275) MS (+ES) m/z: 711.4 $(M+2H)^{2+}$.

EXAMPLE 276a

Cyclo[glycyl-β-methylphenylalanyl-O-[4-O-[6-O-acetyl-hexopyranosyl]hexopyranosyl]tyrosyl-3-(2-iminoimidazolidin-4-yl)seryl-3-(3-hexopyranosyl-2-iminoimidazolidin-4-yl)serylseryl]

EXAMPLE 276b

Cyclo[glycyl-β-methylphenylalanyl-O-[4-O-[6-O-acetyl-2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

Strain LL4614 is fermented for 5 days in BPM17. Analysis of fermentation extracts prepared with carboxylic acid extraction columns by LC/MS showed the expected presence of an HPLC peak at RRT 1.79 with an associated molecular weight of 1420 which is cyclo[glycyl-β-methylphenylalanyl-O-[4-O-[6-O-acetyl-3-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl] (example 275) MS (+ES) m/z: 711.4 $(M+2H)^{2+}$. The analysis also indicates the presence of compounds with masses of 1337 and 1420 with relative retention times of 1.17 and 1.73. The compound eluting at RRT1.17 is the first title compound (Example 276a) MS (+ES) m/z: 669 $(M+2H)^{2+}$. The compound eluting at RRT 1.73 is the second title compound (Example 276b) MS (+ES) m/z: 711 $(M+2H)^{2+}$.

EXAMPLE 277a

Cyclo[3-(2-iminoimidazolidin-4-yl)alanyl-3-(3-hexopyranosyl-2-iminoimidazolidin-4-yl)-alanylserylglycyl-β-methylphenylalanyl-O-(4-O-hexopyranosyl-hexopyranosyl]tyrosyl]

EXAMPLE 277b

Cyclo[3-(2-iminoimidazolidin-4-yl)alanyl-3-(3-hexopyranosyl-2-iminoimidazolidin-4-yl)-alanylserylglycyl-β-methylphenylalanyl-O-[4-O-[2-O-β-methylbutanoyl)hexopyranosyl]-hexopyranosyl]tyrosyl]

EXAMPLE 277c

Cyclo[3-(2-iminoimidazolidin-4-yl)alanyl-3-(3-hexopyranosyl-2-iminoimidazolidin-4-yl)-alanylserylglycyl-β-methylphenylalanyl-O-(4-O-β-O-(3-methylbutanoyl)hexopyranosyl]-hexopyranosyl]tyrosyl]

Strain LL4641 is fermented for 5 days in medium BPM17. Three peaks are observed at RRT 1.04, 1.47 and 1.55. To afford isolation of these compounds, clarified fermentation broth (8.5 L) is applied to a column containing XAD7 resin. The column is sequentially washed with water (2 L), methanol (2 L) and water (2 L). The column is then eluted with acetonitrile-water (50:50) containing 0.5% TFA. The acetonitrile/water solution is evaporated to a small volume under reduced pressure, and the residue is fractionated by reverse phase HPLC on a C18 column (ODS-A, 10 micron particle size, 70×500 mm). The mobile phase employed is a gradient from 14 to 50% acetonitrile in water with 0.02% trifluoroacetic acid over 55 min at a flow rate of 100 mL per min. Fractions eluting at approximately 25 min, 31 min, and 34 min are collected and after evaporation of solvents, afford (Example 277a) MS (+ES) m/z: 632.2 $(M+2H)^{2+}$, (Example 277b) MS (+ES) m/z: 674.2 $(M+2H)^{2+}$, and (Example 277c) MS (+ES) m/z: 674.1 $(M+2H)^{2+}$.

Alternatively, five-day shake-flask fermentations of strain LL4783 are performed in medium BPM17statgal. LC/MS analysis of fermentation extracts prepared via carboxylic acid extraction columns shows the presence of compounds with RRTs of 1.04, 1.47 and 1.55 with associated molecular weights of 1262, 1346 and 1346. The data indicates that mutant LL4783 is accumulating (Example 277a) MS (+ES) m/z: 632.2 $(M+2H)^{2+}$, (Example 277b) MS (+ES) m/z: 674.2 $(M+2H)^{2+}$, and (Example 277c) MS (+ES) m/z: 674.1 $(M+2H)^{2+}$.

EXAMPLE 278a

Cyclo[glycyl-β-methylphenylalanyl-O-hexopyranosyltyrosyl-3-(2-iminoimidazolidin-4-yl)-seryl-3-(2-iminoimidazolidin-4-yl)serylseryl]

EXAMPLE 278b

Cyclo[glycyl-β-methylphenylalanyl-O-[4-O-[4-O-(2-methylbut-2-enoyl)hexopyranosyl]-hexopyranosyl]tyrosyl-3-(2-iminoimidazolidin-4-yl)seryl-3-(3-hexopyranosyl-2-imino-imidazolidin-4-yl)serylseryl]

EXAMPLE 278c

Cyclo[glycyl-β-methylphenylalanyl-O-[4-O-[4-O-(2-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

EXAMPLE 278d

Cyclo[glycyl-β-methylphenylalanyl-O-[4-O-β-O-(4-methylpentanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

EXAMPLE 278e

Cyclo[glycyl-β-methylphenylalanyl-O-[4-O-[4-O-β-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

Preliminary shake-flask fermentations of strain LL4666 are conducted in medium BPM17. HPLC and LC/MS analysis are then conducted on concentrates of fermentation broth prepared with carboxylic acid concentration columns. A metabolite with RRT 1.82 and molecular weight of 1378 is observed and identified as cyclo[glycyl-(3-methylphenylalanyl-O-[4-O-[4-O-β-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl] (Example 278e) MS (+ES) m/z: 690 $(M+2H)^{2+}$.

Five other separable metabolites, four with RRTs of >1.85, and one with RRT ~1.20, are observed which display molecular weights of 1392, 1392, 1376, 1378 and 970.

Larger volume fermentations are then conducted to afford the isolation of these five compounds.

Multiple shake-flask fermentations of mutant LL4666 are carried out for 5 days in medium BPM17. The multiple shake-flasks are then pooled to yield 17 L of fermentation broth. The pooled broth is centrifuged and the supernatant is loaded onto a pretreated XAD-7 column (1 L). The column is sequentially washed with water (2 L), methanol (2 L) and water (2 L) to remove media components and pigments. The compounds are then eluted with 1:1 acetonitrile in water containing 0.1% trifluoroacetic acid (3 L). The acidic acetonitrile/water solution is evaporated to a small volume under reduced pressure, and the residue is fractionated by reverse phase HPLC on a C18 column (ODS-A, 10 micron particle size, 70×500 mm). The mobile phase consists of a gradient from 14 to 50% acetonitrile in water with 0.02% trifluoroacetic acid over 55 min at a flow rate of 100 mL per min.

The small peak eluting at approximately 27 min and the broad peak at approximately 38 min are both collected and concentrated under reduced pressure. The residue from the former peak is subjected to further separation by HPLC on a C18 column (ODS-A, 8 micron particle size, 20×250 mm). The mobile phase consists of a gradient from 10 to 60% acetonitrile in water with 0.02% trifluoroacetic acid over 60 min at a flow rate of 20 mL per minute. The fraction eluting at approximately 25 min affords (Example 278a) MS (+ES) m/z: 486.2 $(M+2H)^{2+}$.

The residue of the latter peak is found to be a rather complicated mixture by HPLC analysis and a part of it (~1/5) is subjected to further separation by HPLC on a C18 column (YMC ODS-basic, 5 micron particle size, 10×250 mm). The mobile phase consists of a gradient from 26.5 to 28.8% acetonitrile in water with 0.02% trifluoroacetic acid over 15 min at a flow rate of 4 mL per minute. One fraction eluting at approximately 13.0 min was found to be identical to cyclo[glycyl-O-methylphenylalanyl-O-[4-O-β-O-(3-methylpentanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl] (Example 271a) MS (+ES) m/z: 697 $(M+2H)^{2+}$.

The fractions eluting at approximately 8.6, 9.7, 10.2 and 11.5 min are collected to afford (Example 278b) MS (+ES) m/z: 689.4 $(M+2H)^{2+}$, (Example 278c) MS (+ES) m/z: 690.1 $(M+2H)^{2+}$ and (Example 278d) MS (+ES) m/z: 697.4 $(M+2H)^{2+}$.

EXAMPLE 279a

Cyclo[glycylphenylalanyltyrosyl-3-(2-iminoimidazolidin-4-yl)seryl-3-(3-hexopyranosyl-2-iminoimidazolidin-4-yl)serylseryl]

EXAMPLE 279b

Cyclo[glycyl-β-methylphenylalanyltyrosyl-3-(2-iminoimidazolidin-4-yl]seryl-3-(3-hexopyranosyl-2-iminoimidazolidin-4-yl)serylseryl]

Shake-flask fermentations of strain LL4779 are conducted in medium BPM17statgal for 5 days. HPLC and LC/MS analysis of the fermentation supernatants and concentrates prepared using carboxylic acid extraction columns indicate the presence of an HPLC peak at RRT 1.29 with an associated molecular weight of 970 which is cyclo[glycyl-β-methylphenylalanyltyrosyl-3-(2-iminoimidazolidin-4-yl)seryl-3-(3-hexopyranosyl-2-iminoimidazolidin-4-yl)serylseryl](Example 279b) MS (+ES) m/z: 486 $(M+2H)^{2+}$.

A second peak is observed at RRT 1.19 displaying a molecular weight, of 956. To afford isolation of the RRT 1.19 compound, LL4779 is fermented at the 300 L scale in medium BPM17statgal. Clarified broth is loaded onto a column containing XAD-7 resin, which is then washed with two column volumes of methanol-water (50:50) and eluted with 8 column volumes of methanol-water-trifluoroacetic acid (50:50:0.2). Finally, the resin is washed with 4 column volumes of water. Fractions and washes are analyzed and the active fractions and washes are pooled, neutralized to pH 4-6 and concentrated to 3-4 L. A portion of the crude concentrated extract (0.5 L) is centrifuged and the supernatant is added into 1.5 L acetonitrile to afford a precipitate. The precipitate is collected by centrifugation, re-dissolved in water and loaded onto a C18 reversed-phase silica gel flash column (200 g). The column is eluted sequentially with water (1 L), 10% acetonitrile/90% water with 0.1% hydrochloric acid (0.5 L) and 15% acetonitrile/85% water with 0.1% hydrochloric acid. The 10% acetonitrile eluate is collected and evaporated to 200 mL to enrich for the RRT 1.19 component. The concentrated solution is loaded onto a C18 reversed-phase silica gel flash column (100 g) and eluted with water (0.5 L), 9% acetonitrile/91% water with 0.1% hydrochloric acid (1 L), 10% acetonitrile/90% water with 0.1% hydrochloric acid (2 L) sequentially, and the eluates are collected at 200 mL per fraction. Fraction-2 and fraction-3 are collected and combined, and after solvent evaporation, afford (Example 279a) MS (+ES) m/z: 479 $(M+2H)^{2+}$.

EXAMPLE 280a

Cyclo[glycylphenylalanyltyrosyl-3-(2-iminoimidazolidin-4-yl)seryl-3-(2-iminoimidazolidin-4-yl)serylseryl]

EXAMPLE 280b

Cyclo[glycyl-β-methylphenylalanyltyrosyl-3-(2-iminoimidazolidin-4-yl)seryl-3-(2-iminoimidazolidin-4-yl)serylseryl]

Strain LL4744 is fermented in medium BPM17statgal for 5 days. HPLC and LC/MS analysis of fermentation supernatants and concentrates prepared using carboxylic acid extraction columns show the presence of two peaks displaying relative retention times of 1.17 and 1.30 with molecular weights of 794 and 808. To isolate these compounds, clarified broth (300 L) is loaded onto a column containing XAD7 resin. The resin is washed with two column volumes of methanol-water (50:50), eluted with 8 column volumes of methanol-water-trifluoroacetic acid (50:50:0.2) and finally washed with 4 column volumes of water. The active fractions and washes are pooled, the pH adjusted to 4-6 with sodium hydroxide and concentrated to 3-4 L.

A portion of the resulting crude oil (1.4 L) is centrifuged. The supernatant is collected, and after adjusting the pH to 7.0, loaded onto a pre-treated BAKERBOND carboxylic acid silica gel flash column (250 g). The column is eluted with water (2.5 L), 40% acetonitrile/60% water with 0.1% hydrochloric acid (1 L), and 70% acetonitrile/30% water with 0.5% trifluoroacetic acid (1.5 L), sequentially.

The aqueous acetonitrile eluates are combined and evaporated to obtain a crude mixture of the RRT 1.17 and 1.30 compounds. This mixture is dissolved in water and loaded onto a reversed-phase C18 silica gel flash column (210 g) for further separation. The column is washed with water (0.5 L), 10% acetonitrile/90% water containing 0.1% trifluoroacetic acid (1 L), and 15% acetonitrile/85% water containing 0.1% trifluoroacetic acid (2 L). All eluates are collected at 100 mL per fraction. Fractions 9 to 12 are combined and solvents are evaporated under reduced pressure to afford (Example 280a) MS (+ES) m/z: 398 (M+2H)$^{2+}$. Fractions 15 to 20 are combined and solvents are evaporated under reduced pressure to afford (Example 280b) MS (+ES) m/z: 405 (M+2H)$^{2+}$.

Alternatively, the title compounds are prepared by fermentation of mutants LL4742 or LL4902 in media BPM17, BPM17stat or BPM17statgal. HPLC and LC/MS analysis of fermentation supernatants and concentrates prepared using carboxylic acid extraction columns show that strains LL4742 and LL4902 are both producing two compounds which display relative retention times of 1.17 and 1.30 with molecular weights of 794 and 808 which are (Example 280a) MS (+ES) m/z: 398 (M+2H)$^{2+}$ and (Example 280b) MS (+ES) m/z: 405 (M+2H)$^{2+}$.

Alternatively, strain BD2 is fermented for 5 days in medium BPM17statgal. HPLC and LC/MS analysis of fermentation supernatants and concentrates prepared using carboxylic acid extraction columns show the presence of a single peak at RRT 1.17 with an associated molecular weight of 794, indicating the production of (Example 280a) MS (+ES) m/z: 398 (M+2H)$^{2+}$.

Alternatively, strains BD20 or BD70 are fermented for 5 days in medium BPM27-man. HPLC and LC/MS analysis of fermentation supernatants and concentrates prepared using carboxylic acid extraction columns show the presence of a single peak at RRT 1.17 with an associated molecular weight of 794, indicating the production of (Example 280a) MS (+ES) m/z: 398 (M+2H)$^{2+}$.

EXAMPLE 281a

Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]

EXAMPLE 281b

Cyclo[glycyl-β-methylphenylalanyl-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

EXAMPLE 281c

Cyclo[glycyl-β-methylphenylalanyl-O-[4-O-β-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl].

Shake-flask fermentations of strains LL4742 and LL4902 are conducted in medium BPM17statman. Supernatants and concentrates are prepared from 5 day fermentation broth and analyzed by HPLC and LC/MS. Strains LL4742 and LL4902 fermented in BPM17statman accumulate metabolites with RRTs of 1.00, 1.43 and 1.64, displaying molecular weights of 1294, 1378 and 1378. The data indicate that mannose supplementation of strains LL4742 and LL4902 restores their ability to produce cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl (Example 281a) MS (+ES) m/z: 648 (M+2H)$^2$1, cyclo[glycyl-β-methylphenylalanyl-O-[4-O-[2-O-(3-methyl butanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl] (Example 281b) MS (+ES) m/z: 690 (M+2H)$^{2+}$, and cyclo[glycyl-(3-methylphenylalanyl-O-[4-O-β-O-(3-methylbutanoyl)hexopyranos yl]hexopyranosyl]tyrosyl-3-(2-iminoimidazolidin-4-yl)seryl-3-(3-hexopyranosyl-2-iminoimidazolidin-4-yl)serylseryl] (Example 281c) MS (+ES) m/z: 690 (M-2H)$^{2+}$.

EXAMPLE 282

Cyclo[glycylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]

Strain BD2 is fermented in BPM17statman for 5 days. HPLC and LC/MS analysis of fermentation supernatants and carboxylic acid concentrates indicate the accumulation of three peaks with novel retention times. The major component shows an RRT of 0.86 and a molecular weight of 1280. To afford isolation of the major component at RRT 0.86, cell free supernatant (7 L) is applied to a column containing CG-61 resin (600 mL). The column is washed with water (1 L) and eluted with 40% acetonitrile/60% water/0.01% TFA (2.5 L). Fractions containing the title compound are collected and pooled. After evaporation of the solvents, the pH of the resulting concentrate is adjusted to 12.5 with NaOH and held for 45 min to hydrolyze esters. The pH of the concentrate is then adjusted to 3.0 with HCl and acetonitrile (5 volumes) is added. The resulting precipitated material is collected, washed with acetonitrile and dried to afford the title compound, (Example 282) MS (+ES) m/z: 641 (M+2H)$^{2+}$.

Alternatively, strains BD20 or BD70 are fermented for 5 days in medium BPM27. HPLC and LC/MS analysis of fermentation supernatants and concentrates prepared using carboxylic acid extraction columns show the presence of a major metabolite at RRT 0.86 with an associated molecular weight of 1280, indicating the production of (Example 282) MS (+ES) m/z: 641 (M+2H)$^{2+}$.

Alternatively, strain BD70 is fermented for 5 days in medium BPM27 at the 300 L scale. Diatomaceous earth (4 kg) is added and the broth is filtered. The filtrate is then cooled to 4° C., adjusted to pH 12.8 with sodium hydroxide and held for 3 hours. The filtrate is then neutralized with acetic acid and loaded onto a 30 L column of SP207 resin. The resin is washed with 4 bed volumes of water, 4 bed volumes of methanol and eluted with 6 bed volumes of 50/50 methanol/water with 3% acetic acid. The eluate is concentrated to about 4 L by evaporation under vacuum. The concentrate is then precipitated by the addition of 3 volumes of isopropyl alcohol and one volume of acetonitrile. The resulting precipitate is filtered, washed with methanol and dried under vacuum to afford the title compound, (Example 282) MS (+ES) m/z: 641 (M+2H)$^{2+}$.

EXAMPLE 283a

Isolation of Cyclo[glycylphenylalanyl-O-[4-O-[6-O-(2-methylpropanoyl)-hexopyranosyl]hexopyranosyl-tyrosyl-3-(2-iminoimidazolidin-4-yl)seryl-3-(3-hexonyranosyl-2-iminoimidazolidin-4-yl)serylseryl]

EXAMPLE 283b

Cyclo[glycylphenylalanyl-O-[4-O-β-O-(2-methylpropanoyl)-hexopyranosyl]hexopyranosyl]tyrosyl-3-(2-iminoimidazolidin-4-yl)seryl-3-(3-hexopyranosyl-2-iminoimidazolidin-4-yl)serylseryl]

EXAMPLE 283c

Cyclo[glycylphenylalanyl-O-[4-O-[6-O-(3-methylbutanoyl)-hexopyranosyl]hexopyranosyl]tyrosyl-3-(2-iminoimidazolidin-4-yl)seryl-3-(3-hexopyranosyl-2-iminoimidazolidin-4-yl)serylseryl]

Strain BD20 is fermented in medium BPM27 for 5 days. HPLC and LC/MS analysis of fermentation supernatants indicates that a series of peaks are produced in addition to the expected major component, cyclo[glycylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (Example 282) MS (+ES) m/z: 641 (M+2H)$^{2+}$.

The compounds were observed to elute in two clusters with central RRTs of approximately 1.35 and 1.55. The three most prominent peaks observed show RRTs of 1.34, 1.38 and 1.52, with apparent molecular weights of 1350.6, 1350.6 and 1364.6.

To afford isolation of the compounds, strain BD20 is fermented in medium BPM27 for 5 days at the 300 L scale. The clarified broth from the fermentation is applied to XAD7 resin, eluted and fractions containing the compounds of interest are identified and concentrated as in example 279. A portion of the resulting crude oil (0.3 L) is centrifuged and the supernatant loaded onto a pre-treated C18 reverse phase silica gel flash column (250 g). The column is washed sequentially with water (1 L), 10% acetonitrile/90% water with 0.1% trifluoroacetic acid (3 L), 12.5% acetonitrile/87.5% water with 0.1% trifluoroacetic acid (6 L), and 15% acetonitrile/85% water with 0.1% trifluoroacetic acid (6 L). Column eluates are then collected at 400 mL/fraction.

Fractions 13 to 17 are combined to produce a crude mixture which is further fractionated by preparative HPLC on a YMC ODS-A column using a gradient of 12% to 30% acetonitrile in water with 0.01% trifluoroacetic acid over 60 min at a flow rate of 20 mL per minute. The appropriate fractions are collected and solvents are evaporated to afford (Example 283a) MS (+ES) m/z: 676.5 (M+2H)$^{2+}$ and (Example 283b) MS (+ES) m/z: 676.5 (M+2H)$^{2+}$.

Fractions 30 to 33 from the C18 reverse phase silica gel flash column elution are combined and evaporated to dryness. The resulting crude material is further purified on a C18 reverse phase flash column (100 g) via elution with 12.5% acetonitrile/87.5% water containing 0.01% TFA to afford (Example 283c) MS (+ES) m/z: 683.3 (M+2H)$^{2+}$.

EXAMPLE 284a

Cyclo[3-(2-iminoimidazolidin-4-yl)alanyl-3-(3-hexopyranosyl-2-iminoimidazolidin-4-yl)-serylserylglycyl-β-methylphenylalanyl-O-(4-O-hexopyranosyl-hexopyranosyl)tyrosyl]

EXAMPLE 284b

Cyclo[3-(3-hexopyranosyl-2-iminoimidazolidin-4-yl)-alanylserylglycyl-β-methylphenylalanyl-O-(4-O-hexopyranosylhexopyranosyl)tyrosyl-3-(2-iminoimidazolidin-4-yl)seryl]

EXAMPLE 284c

Cyclo[3-(2-iminoimidazolidin-4-yl)alanyl-3-β-hexopyranosyl-2-iminoimidazolidin-4-yl)-alanylserylglycylphenylalanyl-O-(4-O-hexopyranosylhexopyranosyl)tyrosyl]

Strain BD20 is fermented in medium BPM27 for 5 days. An equal volume of 50 mM CAPS buffer (pH 13) is mixed with broth to hydrolyze ester components. After 5 min incubation at room temperature, three volumes of 1M MOPS buffer (pH 7.0) is added to neutralize the mixture, which is then filtered and analyzed by modified HPLC and LC/MS procedures. The modified chromatographic system employs a YMC ODS-AQ 4.6×250 mm HPLC column. The chromatography is performed in the isocratic mode at 1.5 mL/min at 40° C. for 60 min employing a mobile phase of 10% acetonitrile:90% water:0.01% trifluoroacetic acid. Relative retention times (RRT) for metabolites showing characteristic UV absorption spectra are calculated by dividing the peak retention times of compounds by that of cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (Example 281a). LC/MS analysis is performed using an analogous chromatographic system.

The analysis of the saponified broth reveals the presence of a major component at RRT 0.62 with an associated molecular weight of 1280, which is cyclo[glycylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (Example 282) MS (+ES) m/z: 641 (M+2H)$^{2+}$.

Three additional components are also detected. Two of the additional compounds show RRTs of 0.66 and 0.73 with associated molecular weights of 1264 and 1248 and are, respectively, (Example 284a) MS (+ES) m/z: 633 (M+2H)$^{2+}$ and (Example 284c) MS (+ES) m/z: 625 (M+2H)$^2$.

The third compound displays an RRT of 0.71 with an associated molecular weight of 1264. To afford isolation of the RRT 0.71 compound, strain BD20 is fermented in shake-flasks at 30° C. for 5 days in a modified BPM27 fermentation medium. The modified formulation employs the reported BPM27 recipe with the following changes: the addition of 20 g/L galactose and 60 mg/L FeSO$_4$.7H$_2$O. Pharmamedia is batched at 60 g/L rather than the normal 20 g/L.

The resulting fermentation broth (3.8 L) is centrifuged and the supernatant loaded onto a pretreated CG-71C column (0.4 L) which is sequentially washed with water (0.4 L), 0.1% sodium chloride (0.8 L) and then eluted with 50% acetonitriole/50% water containing 0.05% trifluoroacetic acid (1 L). The acidic aqueous acetonitrile eluate is collected and concentrated to a small volume (0.1 L). This concentrated solution is loaded onto a C18 reverse phase silica gel flash column (140 g), washed with water (0.5 L), and then eluted with a gradient of aqueous methanol (18% methanol/82% water to 25% methanol/75% water containing 0.05% trifluoroacetic acid, total 4 L). All eluates are collected at 250 mL per fraction. Fractions 8 to 16 are combined and the solvent evaporated under reduced pressure. The resulting crude material is further purified by preparative HPLC on a YMC ODS-A column using a gradient of from 10.8% to 14.0% acetonitrile/water containing 0.01% TFA at a flow rate of 18 mL per minute to afford (Example 284b) MS (+ES) m/z: 633.4 (M+2H)$^{2+}$.

EXAMPLE 285a

Cyclo[glycylphenylalanyl-O-[4-O-β-O-(3-methylbutanoyl)-hexopyranosyl]hexopyranosyl]tyrosyl-3-(2-iminoimidazolidin-4-yl)seryl-3-(3-hexopyranosyl-2-iminoimidazolidin-4-yl)serylseryl]

EXAMPLE 285b

Cyclo[glycylphenylalanyl-O-[4-O-β-O-(3-methylbutanoyl)-hexopyranosyl]hexopyranosyl]tyrosyl-3-(2-iminoimidazolidin-4-yl)seryl-3-(3-hexopyranosyl-2-iminoimidazolidin-4-yl)serylseryl LL4780 mediated biotransformations are performed as described in the experimental biotransformation methods section. LL4780 processes the exogenously added metabolites cyclo[glycyl-β-methylphenylalanyltyrosyl-3-(2-iminoimidazolidin-4-yl)seryl-3-(2-hexopyranosyl-2-iminoimidazolidin-4-yl)serylseryl) (Example 279b) or cyclo(glycyl-β-methylphenylalanyltyrosyl-3-(2-iminoimidazolidin-4-yl)seryl-3-(2-iminoimidazolidin-4-yl)serylseryl] (Example 280b) to a mixture of metabolites exhibiting RRTS of 1.00, 1.43 and 1.64 with associated molecular weights of 1294, 1378 and 1378 which are cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (Example 281a) MS (+ES) m/z: 648(M+2H)$^{2+}$], cyclo[glycyl-β-methylphenylalanyl-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl] (Example 281b) MS (+ES) m/z: 690 (M+2H)$^{2+}$, and cyclo[glycyl-β-methylphenylalanyl-O-[4-O-β-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl] (Example 281c) MS (+ES) m/z: 690 (M+2H)$^{2+}$.

The addition of cyclo[glycylphenylalanyltyrosyl-3-(2-iminoimidazolidin-4-yl)seryl-3-(2-iminoimidazolidin-4-yl)serylseryl] (Example 280a) to fermentations of mutant LL4780 resulted in the formation of biotransformation products at RRT 0.86, 1.33 and 1.55 with associated molecular weights of 1280, 1364 and 1364. The RRT 0.86 product is cyclo[glycylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (Example 282) MS (+ES) m/z: 641 (M+2H)$^{2+}$. The two compounds observed at RRT 1.33 and 1.55 are (Example 285a) MS (+ES) m/z: 683 (M+2H)$^{2+}$ and (Example 285b) MS (+ES) m/z: 683 (M+2H)$^{2+}$.

EXAMPLE 286

Cyclo[glycyl-β-methylphenylalanyl-O-hexopyranosyl-2-(nitro)tyrosyl-3-(2-iminoimidazolidin-4-yl)]seryl-3-(3-hexopyranosyl-2-iminoimidazolidin-4-yl)serylseryl]

(Cyclo[glycyl-β-methylphenylalanyl-3-nitrotyrosyl-3-(2-iminoimidazolidin-4-yl)seryl-3-(3-hexopyranosyl-2-iminoimidazolidin-4-yl)serylseryl] (Example 8) is added to multiple shake-flask fermentations of strain LL4780 as described in the biotransformation methods section. Three-day fermentation broth is collected and pooled, yielding 4.0 L. Concentrates of a small sample of the pooled fermentation broth are analyzed by LC/MS which indicates the appearance of a peak at RRT 1.17 with an associated molecular weight of 1178.

For purification, 4 L of broth is centrifuged and the supernatant loaded onto a pretreated CG-71C column (0.2 L). The column is sequentially washed with water (0.2 L), 0.1% aqueous sodium chloride solution (0.5 L), 50% acetonitriole/50% water with 0.1% hydrochloric acid (0.7 L), and methanol (0.5 L). The acidic aqueous acetonitrile eluates are combined and evaporated to a small volume (0.05 L). The residue is added into acetonitrile/methanol (150:50) to afford a crude precipitate (120 mg) which is then dissolved in 50 mL water and loaded on a C18 reversed-phase silica gel flash column (150 g) for further purification. The flash column is eluted with water (0.5 L), and a gradient of aqueous acetonitrile (10% acetonitrile/water to 15% acetonitrile/water with 0.1% hydrochloric acid). Eluates are collected at 400 mL per fraction. Fractions 15 to 24 are combined and the solvents are evaporated under reduced pressure to afford (Example 286) MS (+ES) m/z: 590 (M+2H)$^{2+}$.

EXAMPLE 287

Cyclo[glycyl-β-methylphenylalanyl-2-amino-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]

(Cyclo[glycyl-β-methylphenylalanyl-3-aminotyrosyl-3-(2-iminoimidazolidin-4-yl)seryl-3-(3-hexopyranosyl-2-iminoimidazolidin-4-yl)serylseryl] (Example 11) is added to multiple shake-flask fermentations of strain LL4780 as described in the biotransformation methods section. Three-day fermentation broth is collected and pooled, yielding 4.25 L. Concentrates of a small sample of the pooled fermentation broth are prepared using carboxylic acid extraction columns which are then analyzed by LC/MS. The analysis indicates the appearance of a peak at RRT 0.94 with an associated molecular weight of 1310.

For isolation, 4 L of broth is centrifuged and the supernatant is loaded onto a pretreated BAKERBOND carboxylic acid silica gel column (200 g). The column is sequentially washed with water (0.8 L) and 70% acetonitrile/30% water with 0.5% trifluoroacetic acid (0.8 L). The acidic acetonitrile eluates are evaporated to 50 mL and added into acetonitrile/methanol (150:50) to obtain a crude precipitate which is then dissolved in water. This crude material is then purified by reverse phase HPLC employing a mobile phase gradient from 5% to 26% of acetonitrile in water with 0.01% trifluoroacetic acid applied over 35 min at a flow rate of 8 mL per minute. An HPLC peak with a retention time of approximately 10.3 min is collected. Evaporation of solvents under reduced pressure affords (Example 287) MS (+ES) m/z: 656 $(M+2H)^{2+}$.

EXAMPLE 288

EXAMPLE 281a

Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl]

EXAMPLE 281b

Cyclo[glycyl-β-methylphenylalanyl-O-[4-O-[2-O-β-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl]

EXAMPLE 281c

Cyclo[glycyl-β-methylphenylalanyl-O-[4-O-β-O-(3-methylbutanoyl)hexopyranosyl]hexopyranosyl]tyrosol-3-(2-iminoimidazolidin-4-yl)seryl-3-(3-hexopyranosyl-2-iminoimidazolidin-4-yl)serylseryl]

Strain LL4773 is fermented in medium BPM17statgal for 5 days. Supernatant samples prepared from the final fermentation broth are analyzed by HPLC and LC/MS. Three prominent HPLC peaks are observed at RRT 1.00, RRT 1.43 and RRT 1.64 with associated molecular weights of 1294, 1378 and 1378. The compounds produced are identical to cyclo[glycyl-β-methylphenylalanyl-O-(4-O-hexopyranosylhexopyranosyl) tyrosyl-3-(2-iminoimidazolidin-4-yl)seryl-3-(3-hexopyranosyl-2-iminoimidazolidin-4-yl)serylseryl] (Example 281a) MS (+ES) m/z: 648 $(M+2H)^{2+}$, cyclo[glycyl-β-methylphenylalanyl-O-[4-O-[2-O-(3-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl] (Example 281b) MS (+ES) m/z: 690 $(M+2H)^{2+}$ and cyclo[glycyl-O-methylphenylalanyl-O-[4-O-β-O-β-methylbutanoyl)hexopyranosyl]hexopyranosyl]tyrosyl-3-(2-iminoimidazolidin-4-yl)seryl-3-(3-hexopyranosyl-2-iminoimidazolidin-4-yl)serylseryl] (Example 281c) MS (+ES) m/z: 690 $(M+2H)^{2+}$.

To afford isolation of cyclo[glycyl-β-methylphenylalanyl-O-(4-O-hexopyranosyl hexopyranosyl]tyrosyl-3-(2-iminoimidazolidin-4-yl)seryl-3-(3-hexopyranosyl-2-iminoimidazolidin-4-yl)serylseryl] (Example 281a), strain LL4773 is fermented at the 300 L scale in medium BPM17statgal for 5 days. Diatomaceous earth (4 kg) is added and the broth is filtered. The filtrate is then loaded onto a 60 L column of XAD7 resin. The column is then washed with one bed volume of water and eluted with 6 bed volumes of 50/50 methanol/water with 0.1% TFA. The eluate is then concentrated to about 4 L by evaporation under vacuum. The resulting crude material is mixed with 4 L methanol and the pH is adjusted to 12.8 with sodium hydroxide. After one hour, the pH is adjusted to 1.8 with HCl, 500 g of Diatomaceous earth is added and the mixture is filtered. Acetone (12 L) is then added to the filtrate, the mixture is stirred briefly then allowed to settle overnight to form a precipitate, which is then filtered, washed with methanol (2 L) and dried in a vacuum oven at 30° C. to afford cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (Example 281a) MS (+ES) m/z: 648 $(M+2H)^{2+}$.

EXAMPLE 289

Jack bean α-mannosidase catalyzed conversion of Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl](Example 281a), To Cyclo [glycyl-.β.-methylphenylalanyltyrosyl-3-(2-iminoimidazolidin-4-yl)seryl-3-(3-hexopyranosyl-2-iminoimidazolidin-4-yl)serylseryl](Example 279b)

Jack bean α-mannosidase is added to a solution of Example (281a) Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (0.60 g) in 0.1M pH 5 sodium acetate buffer (200 mL, 0.02M in $ZnCl_2$) and the solution stirred at room temperature for 18 h. The mixture is adjusted to pH 7 then centrifuged. The supernatant is passed through an XAD-7 column (eluting with a solvent system of 1:1:0.001 water:acetonitrile: trifluoroacetic acid) and the fractions collected. The solid is dissolved in 5% aq. acetic acid solution and the pH adjusted to 7. This solution is filtered and the filtrate passed through an XAD-7 column (eluting with a solvent system of 1:1:0.001 water:acetonitrile: trifluoroacetic acid). The product fractions are combined with those above and further purified by elution through a C18 reverse phase preparative column (eluting with a solvent gradient of 6:1:0.0014 to 1:1:0.0014 water:acetonitrile: trifluoroacetic acid) to give the bis(trifluoroacetate) (316 mg) product of the Example as an off-white solid.

EXAMPLE 290

Jack bean α-mannosidase catalyzed conversion of Cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl](Example 281a), To Cyclo [glycyl-β-methylphenylalanyltyrosyl-3-(2-iminoimidazolidin-4-yl)seryl-3-(3-hexopyranosyl-2-iminoimidazolidin-4-yl)serylseryl]

(Example 279B)

Jack bean meal (0.60 g)) is added to a solution of Cyclo [glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl)bis (trifluoroacetate) (0.60 g) in 0.1M pH 5 sodium acetate buffer (200 mL, 0.02M in $ZnCl_2$) and the solution stirred at room temperature for 18 h. The mixture is filtered through diametaceous earth then purified by chromatography through XAD-7 (eluting with a solvent system of 1:1:0.001 water:acetonitrile: trifluoroacetic acid) then C18 reverse phase (eluting with a solvent gradient of 6:1:0.0014 to 1:1:0.0014 water:acetonitrile: trifluoroacetic acid) columns to give the product of the Example (312 mg) as an off-white solid [MS (+ES), m/z 486 $(M)^2$1.

EXAMPLE 291

Almond Meal Fraction Mediated Preparation of Cyclo[glycyl-β-methylphenylalanyl-O-hexopyranosyltyrosyl-3-(2-iminoimidazolidin-4-yl)-seryl-3-(3-hexopyranosyl-2-iminoimidazolidin-4-yl)serylseryl]

Almond meal (2.5 g) is suspended in 0.1M pH 5 sodium acetate buffer (200 mL) and the suspension stirred for ca. 1 h and centrifuged. The supernatant is adjusted to pH 5 by the addition of acetic acid then recentrifuged. Cyclo[glycyl-β-methylphenylalanyl-0-(4-O-hexopyranosylhexopyranosyl) tyrosyl-3-(2-iminoimidazolidin-4-yl)seryl-3-(3-hexopyranosyl-2-iminoimidazolidin-4-yl)serylseryl]bis (trifluoroacetate)bis(trifluoroacetate) (2 g) is added to 133 mL of the supernatant and the resultant solution stirred at room temperature for 18 h. The mixture is evaporated to dryness, resuspended in N,N-dimethylformamide, filtered and the filtrate purified by chromatography on a C18 reverse phase preparative column (eluting with a solvent gradient of 6:1:0.0014 to 7:3:0.002 water:acetonitrile: trifluoroacetic acid) to give the product of the Example as the bis(trifluoroacetate)salt (48 mg) as an off-white solid [MS (+ES), m/z 567 $(M)^2$ The following compounds are hydrolyzed using the procedure of Example 289 with jack bean α-mannosidase and the substrate as listed:

EXAMPLE 292

Cyclo[3-cyclohexylalanyltyrosyl-3-(2-iminoimidazolidin-4-yl)seryl-3-(3-hexopyranosyl-2-iminoimidazolidin-4-yl)serylserylglycyl]

Substrate (Example 50): Cyclo[3-cyclohexylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylserylglycyl]

EXAMPLE 292

| Molecular Formula | $C_{41}H_{62}N_{12}O_{15}$ |
|---|---|
| MS(ESI) $[M + 2H]^{2+}$ | 482.2 |
| MW | 962 |

EXAMPLE 293

Cyclo[3-(2-iminoimidazolidin-4-yl)alanyl-3-(3-hexopyranosyl-2-iminoimidazolidin-4-yl)-alanylserylglycyl-.β.-methylphenylalanyltyrosyl]

Substrate (Example 277a): Cyclo[3-(2-iminoimidazolidin-4-yl)alanyl-3-(3-hexopyranosyl-2-iminoimidazolidin-4-yl)-alanylserylglycyl-β-methylphenylalanyl-0-(4-O-hexopyranosylhexopyranosyl)tyrosyl]

EXAMPLE 293

| Molecular Formula | $C_{42}H_{58}N_{12}O_{13}$ |
|---|---|
| MS(ESI) $[M + 2H]^{2+}$ | 470.4 |
| MW | 938 |

EXAMPLE 294

Cyclo[3-cyclohexyl-2-aminobutanoyl-tyrosyl-3-(2-iminoimidazolidin-4-yl)seryl-3-(3-hexopyranosyl-2-iminoimidazolidin-4-yl)-serylserylglycyl]

Substrate (Example 51): Cyclo[3-cyclohexyl-2-aminobutanoyl-O-(4-O-hexopyranosylhexopyranosyl)tyrosyl-3-(2-iminoimidazolidin-4-yl)seryl-3-(3-hexopyranosyl-2-iminoimidazolidin-4-yl)-serylserylglycyl]

EXAMPLE 294

| Molecular Formula | $C_{42}H_{64}N_{12}O_{15}$ |
|---|---|
| MS(ESI) $[M + 2H]^{2+}$ | 489.3 |
| MW | 976 |

EXAMPLE 295

Cyclo[glycyl-β-methylphenylalanyl-O-(2,3-O-isopronylidene-hexopyranosyl)tyrosyl-3-(2-iminoimidazolidin-4-yl)seryl-3-[2-imino-(2,3-O-isopronylidene-hexopyranosyl)imidazolidin-4-yl]serylseryl]

Substrate (Example 229):Cyclo[glycyl-β-methylphenylalanyl-O-(2,3-O-isopropylidene-4-O-hexopyranosylhexopyranosyl)tyrosyl-3-(2-iminoimidazolidin-4-yl)seryl-3,2-imino-(2,3-O-isopropylidene-hexopyranosyl)imidazolidin-4-yl]serylseryl]

EXAMPLE 295

| Molecular Formula | $C_{54}H_{76}N_{12}O_{20}$ |
|---|---|
| MS(ESI) $[M + 2H]^{2+}$ | 607.5 |
| MW | 1212 |

EXAMPLE 296

Cyclo[glycylphenylalanyl-O-(4-O-hexopyranosyl-hexopyranosyl)tyrosyl-3-(2-iminoimidazolidin-4-yl)seryl-3-(2-iminoimidazolidin-4-yl)serylseryl]

Strain BD20 is fermented at the 300 L scale for 5 days in medium BPM27. A clarified broth from the fermentation is then applied to a XAD7 resin column, eluted and fractions collected. The active fractions are pooled and concentrated by evaporation and then saponified, precipitated and dried as in Example 282. Analysis by HPLC and LC/MS, as described in Example 284, shows the expected presence of a peak at RRT 0.62 with an associated molecular weight of 1280 which is cyclo[glycylphenylalanyl-O-(4-O-hexopyranosylhexopyranosyl)tyrosyl-3-(2-iminoimidazoliclin-4-yl)seryl-3-(3-hexopyranosyl-2-iminoimidazolidin-4-yl)serylseryl] (Example 282) MS (+ES) m/z: 641 $(M+2H)^{2+}$.

Analysis also reveals the presence of a related component at RRT 0.59, with a molecular mass of 1118.5. To afford isolation of the RRT 0.59 compound, 2 grams of dried precipitate is dissolved in 50 mL of water and applied to a pre-treated Sephadex LH-20 column. The column is eluted with water and 50 mL fractions are collected. Fractions 6 and 7 are combined and lyophilized to produce a crude mixture which is further fractionated by preparative HPLC on a YMC ODS-A column, employing a shallow gradient of acetonitrile/water (98% water/2% acetonitrile/0.01% TFA to 92% water/8% acetonitrile/0.01% TFA in 60 min) to yield (Example 296) MS (+ES) m/z: 560.5 $(M+2H)^{2+}$.

EXAMPLE 297

Cyclo[glycyl-β-methylphenylalanyl-O-(4-O-hexopyranosylhexopyranosyl)tyrosyl-3-(2-iminoimidazolidin-4-yl)seryl-3-(2-iminoimidazolidin-4-yl)serylseryl]

Strain LL4773 is fermented in medium BPM27 for 2 days. A supernatant from the resulting fermentation broth is saponified, neutralized and analyzed by HPLC and LC/MS as in example 284. The analysis indicates a major component displaying a RRT of 1.0 and an associated molecular weight of 1294 which represents the expected production of cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] (Example 281a) MS (+ES) m/z: 648 $(M+2H)^{2+}$.

Additionally, a component is noted at RRT 0.97 with an associated molecular weight of 1132. The observed chromatographic and spectral properties, and molecular weight for the RRT 0.97 compound, indicate it to be (Example 297) MS (+ES) m/z: 567 $(M+2H)^{2+}$.

As described in Table 7 for Examples of the Invention, Analytical HPLC is performed over a 5 um, 120A, 4.6×150 mm YMC ODS-A column, with UV detection (215 and 254 nm) employing gradient elution of increasing concentrations of water in acetonitrile, each containing 0.02% trifluoroacetic acid, at a flow rate of 1 mL/min. Retention times are reported relative to the retention time for cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl](Example 281a) and retention times for this standard are shown in parentheses after each of the elution methods shown below:

TABLE 7

Analytical HPLC retention times reported relative to the retention time for cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] for representative Examples of the Invention

| EXAMPLE | MOLECULAR FORMULA | RELATIVE RETENTION TIME | ELUTION METHOD |
|---|---|---|---|
| Example 1 | $C_{54}H_{77}BrN_{12}O_{25}$ | 1.16 | e |
| Example 2 | $C_{42}H_{57}BrN_{12}O_{15}$ | | |
| Example 3 | $C_{42}H_{56}Br_2N_{12}O_{15}$ | 1.57 | e |
| Example 4 | $C_{36}H_{46}Br_2N_{12}O_{10}$ | | |
| Example 5 | $C_{42}H_{57}IN_{12}O_{15}$ | 1.49 | e |
| Example 6 | $C_{54}H_{77}IN_{12}O_{25}$ | 1.18 | e |
| Example 7 | $C_{54}H_{76}I_2N_{12}O_{25}$ | | |
| Example 8 | $C_{42}H_{57}N_{13}O_{17}$ | 1.47 | e |
| Example 9 | $C_{36}H_{47}N_{13}O_{12}$ | | |
| Example 10 | $C_{42}H_{57}N_{13}O_{15}$ | | |
| Example 11 | $C_{42}H_{59}N_{13}O_{15}$ | | |
| Example 12 | $C_{44}H_{63}N_{13}O_{15}$ | 0.88 | e |
| Example 13 | $C_{44}H_{61}N_{13}O_{16}$ | 1.49 | e |
| Example 14 | $C_{45}H_{63}N_{13}O_{16}$ | 1.23 | e |
| Example 15 | $C_{46}H_{65}N_{13}O_{16}$ | 1.38 | e |
| Example 16 | $C_{49}H_{71}N_{13}O_{16}$ | 1.78 | e |
| Example 17 | $C_{49}H_{63}N_{13}O_{16}$ | 1.64 | e |
| Example 18 | $C_{43}H_{59}N_{13}O_{16}$ | 1.24 | g |
| Example 19 | $C_{50}H_{65}N_{13}O_{17}$ | 1.71 | e |
| Example 20 | $C_{44}H_{61}N_{13}O_{17}$ | 1.36 | e |
| Example 21 | $C_{50}H_{65}N_{13}O_{17}$ | 1.33 | e |
| Example 22 | $C_{43}H_{57}N_{13}O_{16}$ | 1.26 | e |
| Example 23 | $C_{42}H_{57}N_{13}O_{15}S$ | | |
| Example 24 | $C_{51}H_{62}F_6N_{14}O_{15}S$ | 2.02 | e |
| Example 25 | $C_{50}H_{61}N_{13}O_{17}$ | 2.09 | e |
| Example 26 | $C_{49}H_{60}N_{14}O_{17}$ | | |
| Example 27 | $C_{49}H_{60}BrN_{13}O_{15}$ | 2.00 | e |
| Example 28 | $C_{56}H_{67}N_{13}O_{16}$ | 2.01 | e |
| Example 29 | $C_{51}H_{66}N_{14}O_{15}$ | 2.03 | e |
| Example 30 | $C_{49}H_{60}FN_{13}O_{15}$ | 1.63 | e |
| Example 31 | $C_{56}H_{67}N_{13}O_{16}$ | 2.57 | e |
| Example 32 | $C_{53}H_{69}N_{13}O_{15}$ | 2.76 | e |
| Example 33 | $C_{55}H_{65}N_{13}O_{15}$ | 1.63 | e |
| Example 34 | $C_{52}H_{67}N_{13}O_{18}$ | 1.76 | e |
| Example 35 | $C_{56}H_{67}N_{13}O_{17}$ | 1.85 | g |
| Example 36 | $C_{55}H_{71}N_{13}O_{21}$ | 2.08 | e |
| Example 37 | $C_{56}H_{65}N_{13}O_{15}$ | 1.24 | g |
| Example 38 | $C_{47}H_{59}N_{13}O_{16}$ | 1.63 | g |
| Example 39 | $C_{57}H_{67}N_{13}O_{15}$ | 1.83 | e |
| Example 40 | $C_{47}H_{63}N_{13}O_{15}$ | 2.49 | e |
| Example 41 | $C_{50}H_{57}N_{13}O_{11}$ | 2.62 | e |
| Example 42 | $C_{56}H_{65}N_{13}O_{13}$ | 1.46 | e |
| Example 43 | $C_{54}H_{65}N_{13}O_{16}$ | 1.51 | e |
| Example 44 | $C_{77}H_{84}N_{14}O_{24}$ | 2.41 | e |
| Example 45 | $C_{50}H_{63}N_{13}O_{15}S$ | 1.83 | e |
| Example 46 | $C_{54}H_{65}N_{13}O_{15}S$ | 1.68 | h |
| Example 47 | $C_{56}H_{67}N_{13}O_{15}S$ | 4.64 | a |
| Example 48 | $C_{51}H_{63}N_{13}O_{16}S$ | 2.03 | d |
| Example 49 | $C_{51}H_{62}ClN_{13}O_{16}S$ | 2.10 | e |
| Example 50 | $C_{53}H_{82}N_{12}O_{25}$ | 1.05 | f |
| Example 51 | $C_{54}H_{84}N_{12}O_{25}$ | 1.16 | f |
| Example 52 | $C_{41}H_{68}N_{12}O_{14}$ | 1.97 | f |
| Example 52a | $C_{53}H_{88}N_{12}O_{25}$ | 1.04 | f |
| Example 52b | $C_{53}H_{88}N_{12}O_{25}$ | 0.83 | f |
| Example 53 | $C_{42}H_{70}N_{12}O_{14}$ | 1.97 | e |
| Example 53a | $C_{54}H_{90}N_{12}O_{25}$ | 1.29 | e |
| Example 54 | $C_{41}H_{68}N_{12}O_{14}$ | 1.46 | e |
| Example 54a | $C_{41}H_{68}N_{12}O_{14}$ | 1.59 | e |
| Example 55 | $C_{42}H_{58}N_{12}O_{15}$ | 1.15 | e |
| Example 56 | $C_{41}H_{56}N_{12}O_{15}$ | | |
| Example 57 | $C_{36}H_{48}N_{12}O_{10}$ | | |
| Example 58 | $C_{35}H_{58}N_{12}O_{9}$ | 1.68 | e |
| Example 59 | $C_{61}H_{84}N_{12}O_{25}$ | 1.05 | e |
| Example 60 | $C_{65}H_{92}N_{12}O_{25}$ | 1.37 | e |
| Example 60a | $C_{76}H_{106}N_{12}O_{25}$ | 1.74 | e |
| Example 61 | $C_{66}H_{102}N_{12}O_{26}$ | 1.46 | e |
| Example 62 | $C_{89}H_{108}N_{12}O_{25}$ | 1.82 | e |
| Example 63 | $C_{58}H_{86}N_{12}O_{25}$ | 0.89 | e |
| Example 64 | $C_{59}H_{88}N_{12}O_{25}$—$_2CH_3I$ | 0.99 | f |
| Example 65 | $C_{67}H_{88}N_{12}O_{25}$ | 1.05 | e |

TABLE 7-continued

Analytical HPLC retention times reported relative to the retention time for cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] for representative Examples of the Invention

| EXAMPLE | MOLECULAR FORMULA | RELATIVE RETENTION TIME | ELUTION METHOD |
|---|---|---|---|
| Example 66 | $C_{93}H_{108}N_{12}O_{25}$ | 1.88 | e |
| Example 66a | $C_{67}H_{88}N_{12}O_{25}$ | 1.18 | e |
| Example 67 | $C_{65}H_{86}N_{12}O_{25}$ | 1.25 | e |
| Example 68 | $C_{62}H_{83}F_3N_{12}O_{25}$ | 1.00 | e |
| Example 69 | $C_{62}H_{84}N_{12}O_{27}$ | 0.85 | e |
| Example 69a | $C_{70}H_{90}N_{12}O_{29}$ | 1.17 | e |
| Example 69b | $C_{78}H_{96}N_{12}O_{31}$ | 1.56 | e |
| Example 70 | $C_{59}H_{86}N_{12}O_{25}$ | 0.92 | f |
| Example 71 | $C_{61}H_{92}N_{12}O_{25}$ | 1.40 | e |
| Example 72 | $C_{65}H_{98}N_{12}O_{27}$ | 1.34 | e |
| Example 72a | $C_{76}H_{118}N_{12}O_{29}$ | 2.31 | e |
| Example 73 | $C_{89}H_{108}N_{12}O_{23}$ | 1.83 | e |
| Example 74 | $C_{59}H_{88}N_{12}O_{23}$—2$CH_3I$ | 1.02 | f |
| Example 75 | $C_{48}H_{70}N_{12}O_{15}$—2$CH_3I$ | 1.43 | e |
| Example 76 | $C_{71}H_{96}N_{12}O_{25}$ | 1.82 | e |
| Example 77 | $C_{75}H_{104}N_{12}O_{25}$ | 1.71 | e |
| Example 78 | $C_{75}H_{98}N_{12}O_{25}$ | 1.81 | e |
| Example 79 | $C_{99}H_{120}N_{12}O_{25}$ | 2.35 | e |
| Example 80 | $C_{71}H_{96}N_{12}O_{23}$ | 1.56 | e |
| Example 81 | $C_{69}H_{100}N_{12}O_{25}$—2$CH_3I$ | 1.70 | e |
| Example 82 | $C_{74}H_{106}N_{12}O_{25}$ | 1.86 | e |
| Example 83 | $C_{71}H_{104}N_{12}O_{25}$ | 1.86 | e |
| Example 84 | $C_{70}H_{102}N_{12}O_{25}$ | 1.90 | e |
| Example 85 | $C_{62}H_{77}N_{13}O_{21}$ | 1.54 | e |
| Example 86 | $C_{64}H_{96}N_{12}O_{26}$ | 2.22 | e |
| Example 87 | $C_{59}H_{86}N_{12}O_{26}$ | 1.30 | e |
| Example 88 | $C_{60}H_{88}N_{12}O_{26}$ | 2.08 | e |
| Example 89 | $C_{66}H_{76}N_{12}O_{21}$ | 2.28 | e |
| Example 90 | $C_{62}H_{84}N_{12}O_{27}$ | 1.14 | e |
| Example 91 | $C_{78}H_{96}N_{12}O_{31}$ | 1.83 | e |
| Example 92 | $C_{62}H_{82}N_{16}O_{25}$ | 1.09 | i |
| Example 93 | $C_{68}H_{84}N_{14}O_{27}$ | 1.45 | f |
| Example 94 | $C_{68}H_{84}N_{14}O_{25}S_2$ | 1.40 | i |
| Example 95 | $C_{60}H_{88}N_{12}O_{26}$ | | |
| Example 95a | $C_{60}H_{88}N_{12}O_{26}$ | | |
| Example 95b | $C_{60}H_{88}N_{12}O_{26}$ | | |
| Example 96c | $C_{68}H_{88}N_{12}O_{26}$ | | |
| Example 96 | $C_{68}H_{88}N_{12}O_{26}$ | | |
| Example 96a | $C_{68}H_{88}N_{12}O_{26}$ | | |
| Example 96b | $C_{68}H_{88}N_{12}O_{26}$ | | |
| Example 97 | $C_{61}H_{90}N_{12}O_{26}$ | | |
| Example 97a | $C_{61}H_{90}N_{12}O_{26}$ | | |
| Example 97b | $C_{61}H_{90}N_{12}O_{26}$ | | |
| Example 98 | $C_{62}H_{84}N_{12}O_{26}$ | | |
| Example 98a | $C_{62}H_{84}N_{12}O_{26}$ | | |
| Example 98b | $C_{62}H_{84}N_{12}O_{26}$ | | |
| Example 98c | $C_{62}H_{84}N_{12}O_{26}$ | | |
| Example 99 | $C_{62}H_{92}N_{12}O_{26}$ | | |
| Example 99a | $C_{62}H_{92}N_{12}O_{26}$ | | |
| Example 99b | $C_{62}H_{92}N_{12}O_{26}$ | | |
| Example 99c | $C_{62}H_{92}N_{12}O_{26}$ | | |
| Example 100 | $C_{62}H_{90}N_{12}O_{26}$ | | |
| Example 100a | $C_{62}H_{90}N_{12}O_{26}$ | | |
| Example 100b | $C_{62}H_{90}N_{12}O_{26}$ | | |
| Example 100c | $C_{62}H_{90}N_{12}O_{26}$ | | |
| Example 101 | $C_{62}H_{84}N_{12}O_{27}$ | 1.40 | e |
| Example 101a | $C_{62}H_{84}N_{12}O_{27}$ | 1.44 | e |
| Example 102 | $C_{62}H_{84}N_{12}O_{25}$ | 1.92 | g |
| Example 103 | $C_{63}H_{86}N_{12}O_{26}$ | 1.94 | g |
| Example 104 | $C_{61}H_{82}N_{12}O_{25}$ | 1.55 | e |
| Example 104a | $C_{61}H_{82}N_{12}O_{25}$ | 1.50 | e |
| Example 104b | $C_{61}H_{82}N_{12}O_{25}$ | 1.53 | e |
| Example 105 | $C_{64}H_{90}N_{12}O_{25}$ | 1.77 | e |
| Example 106 | $C_{63}H_{94}N_{12}O_{25}$ | 1.78 | e |
| Example 106a | $C_{63}H_{94}N_{12}O_{25}$ | | |
| Example 106b | $C_{73}H_{106}N_{12}O_{25}$ | 1.95 | e |
| Example 107 | $C_{59}H_{86}N_{12}O_{25}$ | 1.81 | g |
| Example 108 | $C_{60}H_{88}N_{12}O_{25}$ | 2.05 | g |
| Example 109 | $C_{62}H_{92}N_{12}O_{25}$ | 2.43 | g |
| Example 110 | $C_{60}H_{88}N_{12}O_{25}$ | 1.97 | g |
| Example 111 | $C_{60}H_{88}N_{12}O_{25}$ | 2.05 | g |
| Example 112 | $C_{61}H_{88}N_{12}O_{25}$ | 2.05 | g |
| Example 113 | $C_{69}H_{95}N_{13}O_{27}$ | 2.25 | g |
| Example 114 | $C_{62}H_{90}N_{12}O_{27}$ | 1.98 | G |
| Example 115 | $C_{61}H_{86}N_{12}O_{25}$ | 1.95 | G |
| Example 116 | $C_{60}H_{88}N_{12}O_{25}$ | 2.02 | G |
| Example 117 | $C_{60}H_{88}N_{12}O_{25}$ | 1.86 | G |
| Example 118 | $C_{62}H_{83}BrN_{12}O_{25}$ | 2.16 | G |
| Example 119 | $C_{63}H_{86}N_{12}O_{25}$ | 2.11 | G |
| Example 120 | $C_{62}H_{83}ClN_{12}O_{25}$ | 2.16 | G |
| Example 121 | $C_{62}H_{83}FN_{12}O_{25}$ | 2.00 | G |
| Example 122 | $C_{62}H_{90}N_{12}O_{25}$ | 1.93 | E |
| Example 123 | $C_{61}H_{88}N_{12}O_{25}$ | 1.53 | E |
| Example 124 | $C_{63}H_{86}N_{12}O_{25}$ | 1.53 | E |
| Example 125 | $C_{63}H_{92}N_{12}O_{25}$ | 1.80 | E |
| Example 126 | $C_{64}H_{94}N_{12}O_{25}$ | 1.88 | e |
| Example 127 | $C_{65}H_{92}N_{12}O_{25}$ | 1.98 | e |
| Example 128 | $C_{66}H_{94}N_{12}O_{25}$ | 2.05 | e |
| Example 129 | $C_{66}H_{94}N_{12}O_{25}$ | 2.09 | e |
| Example 130 | $C_{79}H_{118}N_{12}O_{26}$ | 2.93 | e |
| Example 131 | $C_{59}H_{86}N_{12}O_{26}$ | 1.68 | e |
| Example 132 | $C_{59}H_{80}N_{12}O_{25}S$ | 1.78 | e |
| Example 133 | $C_{59}H_{80}N_{12}O_{25}S$ | 1.41 | e |
| Example 134 | $C_{62}H_{84}N_{12}O_{25}$ | | |
| Example 135 | $C_{62}H_{84}N_{12}O_{25}$ | 1.51 | e |
| Example 136 | $C_{61}H_{82}N_{12}O_{26}$ | 1.26 | e |
| Example 137 | $C_{62}H_{84}N_{12}O_{26}$ | 1.45 | e |
| Example 137a | $C_{62}H_{84}N_{12}O_{26}$ | 1.42 | e |
| Example 137b | $C_{62}H_{84}N_{12}O_{26}$ | 1.43 | e |
| Example 138 | $C_{61}H_{81}ClN_{12}O_{25}$ | 1.55 | e |
| Example 139 | $C_{64}H_{88}N_{12}O_{25}$ | | |
| Example 140 | $C_{64}H_{88}N_{12}O_{25}$ | 1.96 | e |
| Example 141 | $C_{62}H_{82}N_{12}O_{27}$ | 1.14 | e |
| Example 142 | $C_{63}H_{86}N_{12}O_{26}$ | | |
| Example 143 | $C_{62}H_{82}N_{12}O_{27}$ | 1.43 | e |
| Example 144 | $C_{62}H_{84}N_{12}O_{25}S$ | 1.67 | e |
| Example 145 | $C_{65}H_{84}N_{12}O_{25}$ | 1.81 | e |
| Example 146 | $C_{65}H_{88}N_{12}O_{25}$ | 2.78 | e |
| Example 147 | $C_{65}H_{90}N_{12}O_{25}$ | 1.99 | e |
| Example 148 | $C_{64}H_{88}N_{12}O_{26}$ | | |
| Example 149 | $C_{63}H_{84}N_{12}O_{27}$ | 1.41 | e |
| Example 150 | $C_{63}H_{86}N_{12}O_{27}$ | 1.49 | e |
| Example 150a | $C_{63}H_{86}N_{12}O_{27}$ | 1.48 | e |
| Example 151 | $C_{61}H_{81}N_{13}O_{28}$ | 1.40 | e |
| Example 152 | $C_{64}H_{88}N_{12}O_{27}$ | 1.56 | e |
| Example 153 | $C_{62}H_{83}N_{13}O_{28}$ | 1.59 | e |
| Example 154 | $C_{67}H_{86}N_{12}O_{25}$ | 1.95 | e |
| Example 155 | $C_{67}H_{86}N_{12}O_{25}$ | 1.95 | e |
| Example 156 | $C_{66}H_{85}N_{13}O_{25}$ | 1.14 | e |
| Example 157 | $C_{62}H_{84}N_{12}O_{27}S$ | 1.21 | e |
| Example 158 | $C_{62}H_{81}ClN_{12}O_{27}$ | 1.50 | e |
| Example 159 | $C_{66}H_{86}N_{12}O_{26}$ | | |
| Example 160 | $C_{66}H_{86}N_{12}O_{26}$ | | |
| Example 161 | $C_{65}H_{85}N_{13}O_{26}$ | 1.55 | e |
| Example 162 | $C_{65}H_{84}N_{12}O_{25}S$ | 1.71 | e |
| Example 163 | $C_{65}H_{84}N_{12}O_{25}S$ | 1.93 | e |
| Example 164 | $C_{65}H_{84}N_{12}O_{25}S$ | 1.76 | e |
| Example 164a | $C_{65}H_{84}N_{12}O_{25}S$ | 1.66 | e |
| Example 165 | $C_{66}H_{90}N_{12}O_{26}$ | 1.77 | e |
| Example 166 | $C_{64}H_{86}N_{12}O_{28}$ | 1.57 | e |
| Example 167 | $C_{63}H_{85}N_{13}O_{28}$ | 1.64 | e |
| Example 168 | $C_{62}H_{83}N_{13}O_{27}S$ | 1.73 | e |
| Example 169 | $C_{62}H_{83}N_{13}O_{29}$ | 1.44 | e |
| Example 170 | $C_{67}H_{86}N_{12}O_{26}$ | 1.78 | e |
| Example 171 | $C_{67}H_{86}N_{12}O_{26}$ | | |
| Example 172 | $C_{69}H_{88}N_{12}O_{25}$ | 2.11 | e |
| Example 173 | $C_{68}H_{86}N_{12}O_{26}$ | 1.83 | e |
| Example 174 | $C_{68}H_{88}N_{12}O_{26}$ | 2.16 | e |
| Example 175 | $C_{68}H_{88}N_{12}O_{26}$ | 1.78 | e |
| Example 176 | $C_{68}H_{88}N_{12}O_{26}$ | | |

TABLE 7-continued

Analytical HPLC retention times reported relative to the retention time for cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] for representative Examples of the Invention

| EXAMPLE | MOLECULAR FORMULA | RELATIVE RETENTION TIME | ELUTION METHOD |
|---|---|---|---|
| Example 177 | $C_{67}H_{85}ClN_{12}O_{25}$ | 2.09 | e |
| Example 178 | $C_{67}H_{85}ClN_{12}O_{25}$ | 2.12 | e |
| Example 179 | $C_{63}H_{82}F_4N_{12}O_{26}$ | 1.66 | e |
| Example 180 | $C_{68}H_{88}N_{12}O_{27}$ | 1.87 | e |
| Example 181 | $C_{71}H_{94}N_{12}O_{26}$ | 2.11 | e |
| Example 182 | $C_{68}H_{87}N_{13}O_{28}$ | 1.91 | e |
| Example 183 | $C_{71}H_{98}N_{12}O_{26}$ | 2.12 | e |
| Example 184 | $C_{68}H_{85}F_3N_{12}O_{26}$ | 1.94 | e |
| Example 185 | $C_{76}H_{106}N_{12}O_{26}$ | 2.65 | e |
| Example 186 | $C_{68}H_{85}IN_{12}O_{26}$ | 2.05 | e |
| Example 187 | $C_{68}H_{83}I_3N_{12}O_{26}$ | 2.35 | e |
| Example 188 | $C_{69}H_{88}N_{12}O_{25}$ | | |
| Example 189 | $C_{57}H_{80}N_{12}O_{25}$ | 1.35 | e |
| Example 190 | $C_{66}H_{86}N_{12}O_{24}$ | | |
| Example 191 | $C_{68}H_{88}N_{12}O_{24}$ | | |
| Example 192 | $C_{68}H_{88}N_{12}O_{25}$ | 1.84 | e |
| Example 193 | $C_{61}H_{87}ClN_{12}O_{25}$ | 2.24 | g |
| Example 194 | $C_{60}H_{87}ClN_{12}O_{25}$ | 2.21 | g |
| Example 195 | $C_{61}H_{81}ClN_{12}O_{25}$ | 1.71 | e |
| Example 196 | $C_{61}H_{81}IN_{12}O_{25}$ | 1.59 | e |
| Example 197 | $C_{68}H_{87}IN_{12}O_{26}$ | 1.94 | e |
| Example 198 | $C_{62}H_{90}N_{12}O_{25}$ | 1.67 | e |
| Example 199 | $C_{60}H_{86}N_{12}O_{25}$ | 1.53 | e |
| Example 200 | $C_{61}H_{88}N_{12}O_{25}$ | | |
| Example 201 | $C_{61}H_{88}N_{12}O_{25}$ | 1.61 | e |
| Example 202 | $C_{59}H_{84}N_{12}O_{25}$ | 1.33 | e |
| Example 203 | $C_{60}H_{86}N_{12}O_{25}$ | 1.42 | e |
| Example 204 | $C_{61}H_{88}N_{12}O_{25}$ | 1.51 | e |
| Example 205 | $C_{62}H_{90}N_{12}O_{25}$ | 1.72 | e |
| Example 206 | $C_{62}H_{90}N_{12}O_{25}$ | 1.76 | e |
| Example 207 | $C_{64}H_{94}N_{12}O_{25}$ | 1.86 | e |
| Example 208 | $C_{64}H_{94}N_{12}O_{25}$ | 2.06 | e |
| Example 209 | $C_{66}H_{98}N_{12}O_{25}$ | 2.15 | e |
| Example 210 | $C_{67}H_{100}N_{12}O_{25}$ | 2.24 | e |
| Example 210a | $C_{67}H_{100}N_{12}O_{25}$ | 2.20 | e |
| Example 211 | $C_{62}H_{88}N_{12}O_{25}$ | | |
| Example 212 | $C_{63}H_{90}N_{12}O_{25}$ | | |
| Example 213 | $C_{64}H_{90}N_{12}O_{25}$ | | |
| Example 214 | $C_{64}H_{92}N_{12}O_{25}$ | 1.85 | e |
| Example 215 | $C_{64}H_{92}N_{12}O_{25}$ | 1.85 | e |
| Example 216 | $C_{62}H_{83}FN_{12}O_{25}$ | 1.51 | e |
| Example 217 | $C_{59}H_{84}N_{12}O_{25}S$ | | |
| Example 218 | $C_{69}H_{98}N_{12}O_{26}$ | 2.35 | e |
| Example 219 | $C_{64}H_{90}N_{12}O_{23}$ | 1.74 | e |
| Example 220 | $C_{63}H_{88}N_{12}O_{25}$ | 1.79 | e |
| Example 221 | $C_{64}H_{96}N_{12}O_{25}$ | 1.84 | e |
| Example 222 | $C_{63}H_{100}N_{12}O_{25}$ | 1.70 | e |
| Example 223 | $C_{63}H_{100}N_{12}O_{25}$ | 1.53 | e |
| Example 224 | $C_{68}H_{98}N_{12}O_{25}$ | 1.69 | e |
| Example 225 | $C_{69}H_{98}N_{12}O_{25}$ | 1.68 | e |
| Example 226 | $C_{72}H_{95}F_3N_{12}O_{25}$ | 1.87 | e |
| Example 227 | $C_{78}H_{96}N_{14}O_{27}$ | 1.87 | e |
| Example 228 | $C_{72}H_{94}N_{16}O_{25}$ | 1.63 | e |
| Example 229 | $C_{60}H_{86}N_{12}O_{25}$ | 1.18 | e |
| Example 229a | $C_{63}H_{90}N_{12}O_{25}$ | 1.51 | e |
| Example 229b | $C_{66}H_{94}N_{12}O_{25}$ | 1.67 | e |
| Example 230 | $C_{66}H_{88}N_{12}O_{26}$ | 1.64 | e |
| Example 230a | $C_{66}H_{88}N_{12}O_{26}$ | 1.70 | e |
| Example 230b | $C_{66}H_{88}N_{12}O_{26}$ | 1.61 | e |
| Example 230c | $C_{66}H_{88}N_{12}O_{26}$ | 1.53 | e |
| Example 231 | $C_{68}H_{90}N_{12}O_{26}$ | 1.85 | e |
| Example 231a | $C_{68}H_{90}N_{12}O_{26}$ | 1.93 | e |
| Example 231b | $C_{68}H_{90}N_{12}O_{26}$ | 1.78 | e |
| Example 231c | $C_{68}H_{90}N_{12}O_{26}$ | 1.72 | e |
| Example 232 | $C_{62}H_{86}N_{12}O_{25}$ | 1.45 | e |
| Example 233 | $C_{63}H_{88}N_{12}O_{25}$ | | |
| Example 234 | $C_{62}H_{86}N_{12}O_{25}$ | 1.56 | e |
| Example 235 | $C_{64}H_{90}N_{12}O_{25}$ | 1.71 | e |
| Example 236 | $C_{67}H_{88}N_{12}O_{26}$ | 1.83 | e |
| Example 237 | $C_{62}H_{85}FN_{12}O_{26}$ | 1.47 | e |
| Example 238 | $C_{64}H_{90}N_{12}O_{27}$ | 1.55 | e |
| Example 239 | $C_{69}H_{92}N_{12}O_{27}$ | 1.71 | e |
| Example 239a | $C_{69}H_{92}N_{12}O_{27}$ | 1.77 | e |
| Example 240 | $C_{66}H_{88}N_{12}O_{26}$ | 1.77 | d |
| Example 240a | $C_{66}H_{88}N_{12}O_{26}$ | 2.26 | b |
| Example 240b | $C_{66}H_{88}N_{12}O_{26}$ | 1.95 | b |
| Example 241 | $C_{69}H_{90}N_{12}O_{25}$ | | |
| Example 241a | $C_{69}H_{90}N_{12}O_{25}$ | | |
| Example 242 | $C_{63}H_{86}N_{12}O_{25}$ | 1.62 | e |
| Example 243 | $C_{65}H_{91}N_{13}O_{25}$ | 1.20 | e |
| Example 243a | $C_{65}H_{91}N_{13}O_{25}$ | 1.23 | e |
| Example 244 | $C_{59}H_{82}N_{12}O_{25}S$ | 1.38 | e |
| Example 245 | $C_{66}H_{88}N_{12}O_{24}$ | 1.60 | e |
| Example 245a | $C_{66}H_{88}N_{12}O_{24}$ | 1.67 | e |
| Example 245b | $C_{66}H_{88}N_{12}O_{24}$ | 1.58 | e |
| Example 245c | $C_{66}H_{88}N_{12}O_{24}$ | 1.54 | e |
| Example 246 | $C_{68}H_{90}N_{12}O_{24}$ | 1.73 | e |
| Example 246a | $C_{68}H_{90}N_{12}O_{24}$ | 1.80 | e |
| Example 246b | $C_{68}H_{90}N_{12}O_{24}$ | 1.67 | e |
| Example 246c | $C_{68}H_{90}N_{12}O_{24}$ | 1.60 | e |
| Example 247 | $C_{48}H_{66}N_{12}O_{15}$ | | |
| Example 248 | $C_{54}H_{80}N_{12}O_{15}Si$ | 1.84 | e |
| Example 249 | $C_{78}H_{98}N_{12}O_{21}Si$ | | |
| Example 250 | $C_{74}H_{86}N_{12}O_{18}Si$ | 2.62 | c |
| Example 251 | $C_{59}H_{87}N_{13}O_{26}$ | 1.35 | e |
| Example 251a | $C_{69}H_{87}N_{13}O_{26}$ | 1.43 | e |
| Example 251b | $C_{59}H_{87}N_{13}O_{26}$ | 1.49 | e |
| Example 252 | $C_{59}H_{87}N_{13}O_{26}$ | 1.27 | e |
| Example 252a | $C_{59}H_{87}N_{13}O_{26}$ | 1.39 | e |
| Example 253 | $C_{62}H_{93}N_{13}O_{26}$ | 1.60 | e |
| Example 253a | $C_{62}H_{93}N_{13}O_{26}$ | 1.63 | e |
| Example 253b | $C_{62}H_{93}N_{13}O_{26}$ | 1.68 | e |
| Example 254 | $C_{67}H_{103}N_{13}O_{26}$ | 2.26 | e |
| Example 254a | $C_{67}H_{103}N_{13}O_{26}$ | 2.32 | e |
| Example 254b | $C_{67}H_{103}N_{13}O_{26}$ | 2.51 | e |
| Example 255 | $C_{60}H_{89}N_{13}O_{26}$ | 1.60 | e |
| Example 255a | $C_{60}H_{89}N_{13}O_{26}$ | 1.63 | e |
| Example 256 | $C_{67}H_{103}N_{13}O_{26}$ | 1.26 | e |
| Example 256a | $C_{67}H_{103}N_{13}O_{26}$ | 1.39 | e |
| Example 257 | $C_{62}H_{85}N_{13}O_{26}$ | 1.42 | e |
| Example 257a | $C_{62}H_{85}N_{13}O_{26}$ | 1.45 | e |
| Example 257b | $C_{62}H_{85}N_{13}O_{26}$ | 1.49 | e |
| Example 261a | $C_{54}H_{77}FN_{12}O_{25}$ | 1.08 | k |
| Example 261b | $C_{59}H_{85}FN_{12}O_{26}$ | 1.51 | k |
| Example 261c | $C_{59}H_{85}FN_{12}O_{26}$ | 1.73 | k |
| Example 262a | $C_{54}H_{77}ClN_{12}O_{25}$ | 1.26 | k |
| Example 262b | $C_{59}H_{85}N_{12}O_{26}$ | 1.86 | k |
| Example 262c | $C_{59}H_{85}ClN_{12}O_{26}$ | 1.61 | k |
| Example 263 | $C_{53}H_{82}N_{12}O_{25}$ | 1.21 | k |
| Example 264a | $C_{59}H_{85}FN_{12}O_{26}$ | 1.57 | k |
| Example 264b | $C_{59}H_{85}FN_{12}O_{26}$ | 1.77 | k |
| Example 264c | $C_{54}H_{77}FN_{12}O_{25}$ | 1.11 | k |
| Example 265a | $C_{57}H_{84}N_{12}O_{26}S$ | 1.37 | k |
| Example 265b | $C_{57}H_{84}N_{12}O_{26}S$ | 1.60 | k |
| Example 265c | $C_{52}H_{76}N_{12}O_{25}S$ | 0.91 | k |
| Example 266a | $C_{54}H_{77}FN_{12}O_{25}$ | 1.06 | k |
| Example 266b | $C_{59}H_{85}FN_{12}O_{26}$ | 1.56 | k |
| Example 266c | $C_{59}H_{85}FN_{12}O_{26}$ | 1.77 | k |
| Example 267a | $C_{54}H_{79}N_{13}O_{25}$ | 0.84 | k |
| Example 267b | $C_{59}H_{87}N_{13}O_{26}$ | 1.22 | k |
| Example 267c | $C_{59}H_{87}N_{13}O_{26}$ | 1.46 | k |
| Example 268 | $C_{57}H_{82}N_{12}O_{26}$ | 1.35 | k |
| Example 269a | $C_{54}H_{77}ClN_{12}O_{25}$ | 1.20 | k |
| Example 269b | $C_{59}H_{85}ClN_{12}O_{26}$ | 1.67 | k |
| Example 269c | $C_{59}H_{85}ClN_{12}O_{26}$ | 1.83 | k |
| Example 270a | $C_{60}H_{88}N_{12}O_{26}$ | 1.66 | k |
| Example 270a | $C_{62}H_{90}N_{12}O_{27}$ | 1.90 | k |
| Example 270a | $C_{60}H_{88}N_{12}O_{26}$ | 2.02 | k |
| Example 271a | $C_{60}H_{88}N_{12}O_{26}$ | >1.85 | g |
| Example 271b | $C_{62}H_{90}N_{12}O_{77}$ | 2.00 | k |

TABLE 7-continued

Analytical HPLC retention times reported relative to the retention time for cyclo[glycyl-β-methylphenylalanyl-O-(4-O-hexopyranosylhexopyranosyl)tyrosyl-3-(2-iminoimidazolidin-4-yl)seryl-3-(3-hexopyranosyl-2-iminoimidazolidin-4-yl)serylseryl] for representative Examples of the Invention

| EXAMPLE | MOLECULAR FORMULA | RELATIVE RETENTION TIME | ELUTION METHOD |
|---|---|---|---|
| Example 271c | $C_{60}H_{88}N_{12}O_{26}$ | 2.06 | k |
| Example 272a | $C_{58}H_{84}N_{12}O_{26}$ | 1.38 | k |
| Example 272b | $C_{58}H_{84}N_{12}O_{26}$ | 1.61 | k |
| Example 273a | $C_{60}H_{88}N_{12}O_{26}$ | 1.64 | k |
| Example 273b | $C_{60}H_{88}N_{12}O_{26}$ | 1.89 | k |
| Example 274a | $C_6H_{90}N_{12}O_{26}$ | 1.93 | k |
| Example 274b | $C_{61}H_{90}N_{12}O_{26}$ | 2.13 | k |
| Example 275 | $C_{61}H_{88}N_{12}O_{27}$ | 1.79 | g |
| Example 276a | $C_{56}H_{80}N_{12}O_{26}$ | 1.17 | g |
| Example 276b | $C_{61}H_{88}N_{12}O_{27}$ | 1.73 | g |
| Example 277a | $C_{54}H_{78}N_{12}O_{23}$ | 1.04 | g |
| Example 277b | $C_{59}H_{86}N_{12}O_{24}$ | 1.47 | g |
| Example 277c | $C_{59}H_{86}N_{12}O_{24}$ | 1.55 | g |
| Example 278a | $C_{42}H_{58}N_{12}O_{15}$ | 1.20 | g |
| Example 278b | $C_{59}H_{84}N_{12}O_{26}$ | >1.85 | g |
| Example 278c | $C_{59}H_{86}N_{12}O_{26}$ | >1.85 | g |
| Example 278d | $C_{60}H_{88}N_{12}O_{26}$ | >1.85 | g |
| Example 278e | $C_{59}H_{86}N_{12}O_{26}$ | 1.82 | g |
| Example 279a | $C_{41}H_{56}N_{12}O_{15}$ | 1.19 | g |
| Example 279b | $C_{42}H_{58}N_{12}O_{15}$ | 1.29 | g |
| Example 280a | $C_{35}H_{46}N_{12}O_{10}$ | 1.17 | g |
| Example 280b | $C_{36}H_{48}N_{12}O_{10}$ | 1.30 | g |
| Example 281a | $C_{54}H_{78}N_{12}O_{25}$ | 1.00 | g |
| Example 281b | $C_{59}H_{86}N_{12}O_{26}$ | 1.43 | g |
| Example 281c | $C_{59}H_{86}N_{12}O_{26}$ | 1.64 | g |
| Example 282 | $C_{53}H_{76}N_{12}O_{25}$ | 0.86 | g |
| Example 283a | $C_{57}H_{82}N_{12}O_{26}$ | 1.34 | g |
| Example 283b | $C_{57}H_{82}N_{12}O_{26}$ | 1.38 | g |
| Example 283c | $C_{58}H_{84}N_{12}O_{26}$ | 1.52 | g |
| Example 284a | $C_{53}H_{76}N_{12}O_{24}$ | 0.66 | j* |
| Example 284b | $C_{53}H_{76}N_{12}O_{24}$ | 0.71 | j* |
| Example 284c | $C_{53}H_{76}N_{12}O_{23}$ | 0.73 | j* |
| Example 285a | $C_{58}H_{84}N_{12}O_{26}$ | 1.33 | g |
| Example 285b | $C_{58}H_{84}N_{12}O_{26}$ | 1.55 | g |
| Example 286 | $C_{48}H_{67}N_{13}O_{22}$ | 1.17 | g |
| Example 287 | $C_{54}H_{79}N_{13}O_{25}$ | 0.94 | g |
| Example 296 | $C_{47}H_{66}N_{12}O_{20}$ | 0.59 | j* |
| Example 297 | $C_{48}H_{68}N_{12}O_{20}$ | 0.97 | j* |

Analytical HPLC is performed over a 5 um, 120A, 4.6 × 150 mm YMC ODS-A column, with UV detection (215 and 254 nm) employing gradient elution of increasing concentrations of water in acetonitrile, each containing 0.02% trifluoroacetic acid, at a flow rate of 1 mL/min. Retention times are reported relative to the retention time for cyclo[glycyl-.beta.-methylphenylalanyl-O-(4-O-hexopyranosylhexopyranosyl)tyrosyl-3-(2-iminoimidazolidin-4-yl) seryl-3-(3- hexopyranosyl-2-iminoimidazolidin-4-yl)serylseryl], and retention times for this standard are shown in parentheses after each of the elution methods shown below:

a Gradient elution of 20-80% acetonitrile in water over 20 minutes (2.14 min)
b Gradient elution of 15-55% acetonitrile in water over 15 minutes (3.81 min)
c Gradient elution of 10-90% acetonitrile in water over 15 minutes (4.60 min)
d Gradient elution of 10-90% acetonitrile in water over 20 minutes (5.02 min)
e Gradient elution of 10-60% acetonitrile in water over 15 minutes (5.31 min)
f Gradient elution of 10-40% acetonitrile in water over 15 minutes (6.30 min)
g Gradient elution of 10-50% acetonitrile in water over 22 minutes (6.30 min)
h Gradient elution of 0-50% acetonitrile in water over 15 minutes (8.44 min)
i Gradient elution of 10-20% acetonitrile in water over 15 minutes (9.45 min)
j* Isocratic elution as described in example 284

We claim:

1. A biologically pure microorganism of *Streptomyces hygroscopicus* capable of producing one or more glycopeptides selected from the formulae

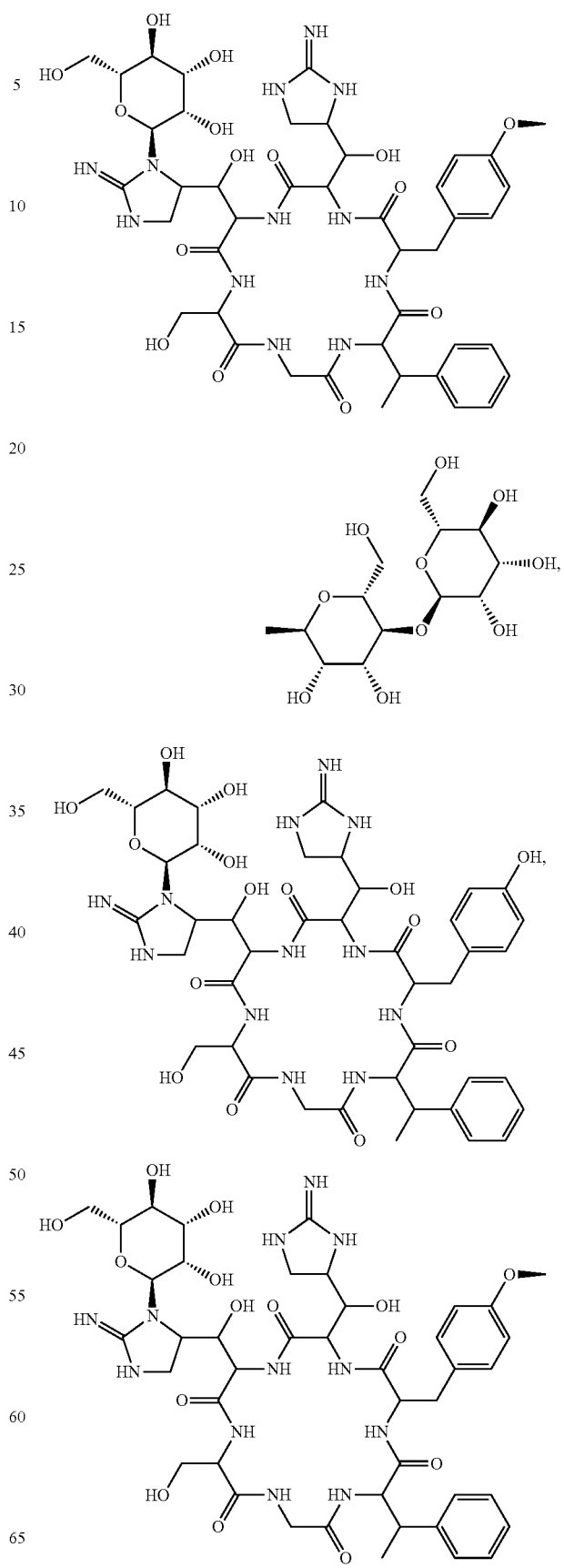

401
-continued

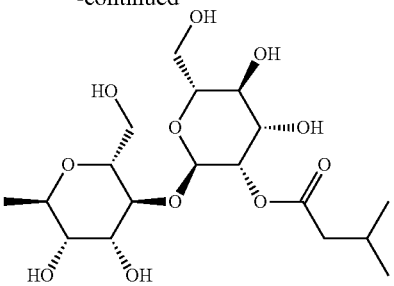

,

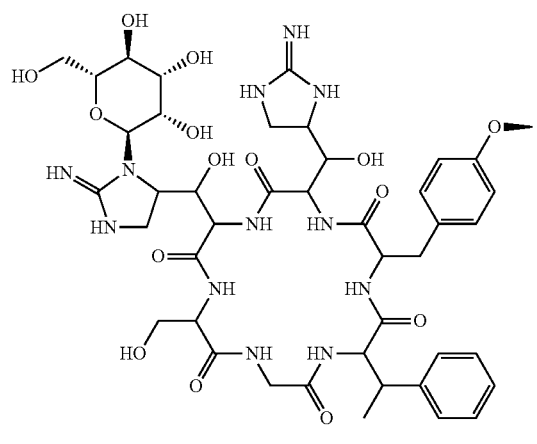

and

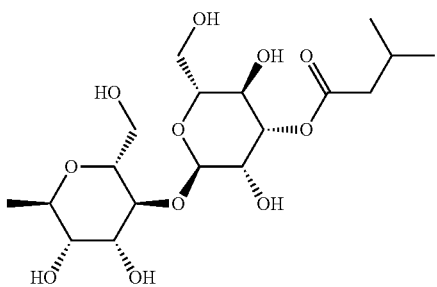

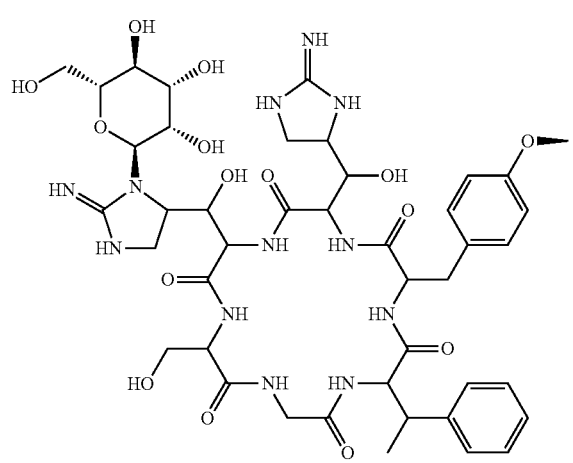

402
-continued

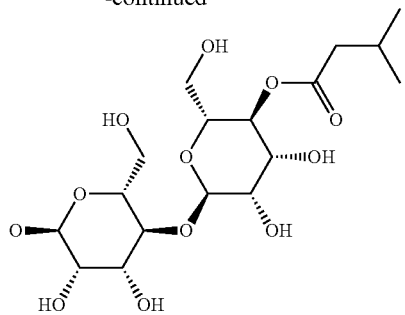

.

and which has been deposited under the Budapest Treaty with an accession number selected from NRRL 30439.

2. A biologically pure microorganism of *Streptomyces hygroscopicus* according to claim 1 wherein the accession number is NRRL 30439.

3. A biologically pure microorganism of *Streptomyces hygroscopicus* according to claim 1 wherein the accession number is NRRL 30440.

4. A biologically pure microorganism of *Streptomyces hygroscopicus* according to claim 1 wherein the accession number is NRRL 30441.

5. A biologically pure microorganism of *Streptomyces hygroscopicus* according to claim 1 wherein the accession number is NRRL 30442.

6. A biologically pure microorganism of *Streptomyces hygroscopicus* according to claim 1 wherein the accession number is NRRL 30443.

7. A biologically pure microorganism of *Streptomyces hygroscopicus* according to claim 1 wherein the accession number is NRRL 30444.

8. A biologically pure microorganism of *Streptomyces hygroscopicus* according to claim 1 wherein the accession number is NRRL 30445.

9. A biologically pure microorganism of *Streptomyces hygroscopicus* according to claim 1 wherein the accession number is NRRL 30446.

10. A biologically pure microorganism of *Streptomyces hygroscopicus* according to claim 1 wherein the accession number is NRRL 30447.

11. A biologically pure microorganism of *Streptomyces hygroscopicus* according to claim 1 wherein the accession number is NRRL 30448.

12. A biologically pure microorganism of *Streptomyces hygroscopicus* according to claim 1 wherein the accession number is NRRL 30449.

13. A biologically pure microorganism of *Streptomyces hygroscopicus* according to claim 1 wherein the accession number is NRRL 30450.

14. A biologically pure microorganism of *Streptomyces hygroscopicus* according to claim 1 wherein the accession number is NRRL 30451.

15. A biologically pure microorganism of *Streptomyces hygroscopicus* according to claim 1 wherein the accession number is NRRL 30452.

16. A biologically pure microorganism of *Streptomyces hygroscopicus* according to claim 1 wherein the accession number is NRRL 30453.

17. A biologically pure microorganism of *Streptomyces hygroscopicus* according to claim 1 wherein the accession number is NRRL 30454.

* * * * *